(12) United States Patent
Kawauchi et al.

(10) Patent No.: US 11,365,449 B2
(45) Date of Patent: Jun. 21, 2022

(54) KIT OR DEVICE FOR DETECTING EARLY STAGE PANCREATIC CANCER OR PANCREATIC CANCER PRECURSOR LESIONS AND DETECTION METHOD THEREFOR

(71) Applicants: TORAY INDUSTRIES, INC., Tokyo (JP); NATIONAL CANCER CENTER, Tokyo (JP)

(72) Inventors: Junpei Kawauchi, Kamakura (JP); Hiroko Sudo, Kamakura (JP); Satoko Kozono, Kamakura (JP); Atsushi Ochiai, Kashiwa (JP); Motohiro Kojima, Kashiwa (JP)

(73) Assignees: TORAY INDUSTRIES, INC., Tokyo (JP); NATIONAL CANCER CENTER, Tokyo (JP)

( * ) Notice: Subject to any disclaimer, the term of this patent is extended or adjusted under 35 U.S.C. 154(b) by 595 days.

(21) Appl. No.: 16/088,345

(22) PCT Filed: Mar. 31, 2017

(86) PCT No.: PCT/JP2017/013728
§ 371 (c)(1),
(2) Date: Sep. 25, 2018

(87) PCT Pub. No.: WO2017/171048
PCT Pub. Date: Oct. 5, 2017

(65) Prior Publication Data
US 2020/0115758 A1   Apr. 16, 2020

(30) Foreign Application Priority Data
Mar. 31, 2016  (JP) .............................. JP2016-073132

(51) Int. Cl.
*C12Q 1/6886* (2018.01)
*C12Q 1/6827* (2018.01)

(52) U.S. Cl.
CPC ......... *C12Q 1/6886* (2013.01); *C12Q 1/6827* (2013.01); *C12Q 2600/112* (2013.01); *C12Q 2600/118* (2013.01); *C12Q 2600/158* (2013.01); *C12Q 2600/178* (2013.01)

(58) Field of Classification Search
None
See application file for complete search history.

(56) References Cited

U.S. PATENT DOCUMENTS

| 2015/0011410 | A1 | 1/2015 | Ganepola |
| 2015/0011414 | A1 | 1/2015 | Johansen et al. |
| 2015/0184248 | A1* | 7/2015 | Tsuchiya ............ C12Q 1/6886 506/9 |
| 2017/0073764 | A1 | 3/2017 | Tahara et al. |
| 2017/0121779 | A1 | 5/2017 | Kondou et al. |
| 2017/0130273 | A1 | 5/2017 | Sudo et al. |
| 2017/0130274 | A1 | 5/2017 | Kozono et al. |
| 2017/0130275 | A1 | 5/2017 | Kondou et al. |
| 2017/0130276 | A1 | 5/2017 | Kozono |
| 2017/0130278 | A1 | 5/2017 | Sudo |
| 2017/0166975 | A1 | 6/2017 | Kondou et al. |
| 2017/0275699 | A1 | 9/2017 | Kawauchi et al. |

FOREIGN PATENT DOCUMENTS

| JP | 2015-502176 A | 1/2015 |
| JP | 2015-107091 A | 6/2015 |
| WO | WO 2014/003053 A1 | 1/2014 |
| WO | WO 2015/133477 A1 | 9/2015 |
| WO | WO 2015/153679 A1 | 10/2015 |
| WO | WO 2015/182781 A1 | 12/2015 |
| WO | WO 2015/190584 A1 | 12/2015 |
| WO | WO 2015/190586 A1 | 12/2015 |
| WO | WO 2015/190591 A1 | 12/2015 |
| WO | WO 2015/194535 A1 | 12/2015 |
| WO | WO 2015/194610 A1 | 12/2015 |
| WO | WO 2015/194615 A1 | 12/2015 |
| WO | WO 2015/194627 A1 | 12/2015 |

OTHER PUBLICATIONS

Li (Clinical Cancer Research, 19(13), pp. 3600-3610).*
Cheung et al. (Cold Spring Harbor Symposia Quant Biol, 2003, vol. LXVIII, pp. 403-407).*
Hoshikawa (Physiol Genomics, 2003, 12: 209-219).*
Li (Clinical Cancer Research, 2013, 19(13), 3600-10).*
European Search Report dated Oct. 8, 20109, for European Application No. 17775579.0.
Cote et al. "A pilot study to develop a diagnostic test for pancreatic ductal adenocarcinoma based on differential expression of select miRNA in plasma and bile", Am J. Gastroenlerol, [online], 109 (12), p. 1942-1952, Epub 2014. 10. 28, total 11 pages.
International Search Report, issued in PCT/JP2017/013728, PCT/ISA/210, dated Jun. 27, 2017.
Japan Pancreas Society, "2009 Scientific evidence based clinical practice guidelines for pancreatic cancer", CQ1 diagnosis methods, total 7 pages, http://www.suizou.org/PCMG2009/cq1/cq1-3.html.
Kiyoshi Kurokawa et al. ed., Lab Data, 2013, p. 633, 636 (Igaku-Shoin Ltd., Tokyo, Japan), total 6 pages.
Kojima et al. "MicroRNA Markers for the Diagnosis of Pancreatic and Biliary-Tract Cancers", PLoS ONE [online], 10 (2), total 26 pages.
Liu et al. "Combination of plasma microRNAs with serum CA19-9 for early detection of pancreatic cancer", Int. J. Cancer [online], 131(3), p. 683-691, Epub 2011.11.19, total 9 pages.

(Continued)

*Primary Examiner* — Sarae L Bausch
(74) *Attorney, Agent, or Firm* — Birch, Stewart, Kolasch & Birch, LLP

(57) ABSTRACT

This application provides a kit or a device for the detection of early pancreatic cancer or a pancreatic cancer precursor lesion, comprising a nucleic acid(s) capable of specifically binding to a miRNA(s) in a sample from a subject, and a method for detecting early pancreatic cancer or a pancreatic cancer precursor lesion, comprising measuring an expression level(s) of the miRNA(s) in vitro.

2 Claims, 4 Drawing Sheets

Specification includes a Sequence Listing.

(56) References Cited

OTHER PUBLICATIONS

Liu et al. "Serum MicroRNA Expression Profile as a Biomarker in the Diagnosis and Prognosis of Pancreatic Cancer", Clinical Chemistry, [online], 58 (3), p. 610-618, Epub 2011.12. 22, total 9 pages.
Miyamae et al. "Plasma microRNA profiles: identification of miR-744 as a novel diagnostic and prognostic biomarker in pancreatic cancer", 2015, British Journal of Cancer, vol. 113, (10), p. 1467-1476, total 10 pages.
Morimura et al. "Novel diagnostic value of circulating miR-18a in plasma of patients with pancreatic cancer", Br. J. Cancer [online], 105(11), p. 1733-1740, Epub 2011.11.01, total 8 pages.
Schultz et al. "MicroRNA Biomarkers in Whole Blood for Detection of Pancreatic Cancer", JAMA [online], 311 (4), p. 392-404, Jan. 22/29, 2014, total 13 pages.
Tanaka et al. "International consensus guidelines 2012 for the management of IPMN and MCN of the pancreas", Pancreatology, 12, (2012), p. 183-197, total 15 pages.
Tetsuya Mine, "Suizo (Pancreas), Journal of the Japan Pancreas Society", Japan Pancreas Society, 2007, vol. 22, p. 10-13, total 4 pages.
Working Group of the Japan Pancreas Society, International consensus guidelines 2012 for the management of IPMN and MCN of the pancreas, p. 6, 8, total 4 pages.
Written Opinion of the International Searching Authority, issued in PCT/JP2017/013728, PCT/ISA/237, dated Jun. 27, 2017.
Ganepola et al., "Novel blood-based microRNA biomarker panel for early diagnosis of pancreatic cancer," World J. Gastrointest. Oncol. (2014), vol. 6, No. 1, pp. 22-33.
Office Action dated May 21, 2021, in Republic of Korea Patent Application No. 10-2018-7027522.

\* cited by examiner

KIT OR DEVICE FOR DETECTING EARLY STAGE PANCREATIC CANCER OR PANCREATIC CANCER PRECURSOR LESIONS AND DETECTION METHOD THEREFOR

TECHNICAL FIELD

The present invention relates to a kit or a device for the detection of early pancreatic cancer or a pancreatic cancer precursor lesion, comprising a nucleic acid capable of specifically binding to a particular miRNA, which is used for examining the presence or absence of early pancreatic cancer or pancreatic cancer precursor lesion in a subject, and a method for detecting early pancreatic cancer or a pancreatic cancer precursor lesion, comprising measuring an expression level of the miRNA using the nucleic acid.

BACKGROUND ART

The pancreas serves as an exocrine gland that secretes pancreatic juice as a digestive juice and sends the juice into the digestive tract through the pancreatic duct, while also functioning as an endocrine gland that secretes hormones such as insulin and glucagon into blood.

Since the pancreas is surrounded by many organs such as the stomach, the duodenum, the small intestine, the liver, and the gallbladder, pancreatic cancer is not only difficult to detect early but has properties such as a lack of subjective symptoms, very rapid progression, and metastasis to other organs and thus has very poor prognosis as compared with other cancers. According to the 2011 statistics of cancer type-specific mortality in Japan disclosed by the Center for Cancer Control and Information Services, National Cancer Center (Tokyo, Japan), the number of pancreatic cancer deaths climbed to 28,829 people, and 5-year relative survival rates by cancer type from 2003 to 2005 were lowest in pancreatic cancer with 7.1% for males and 6.9% for females.

As described in Non-Patent Literature 1, the basic therapy of pancreatic cancer is practiced by surgery, systemic chemotherapy, radiotherapy, or a combination thereof depending on a stage of progression. Although 15 to 20% pancreatic cancer patients undergo surgery for potential complete cure, the great majority of patients who do not undergo surgery are considered to have local progression or metastasis.

The UICC (Unio Internationalis Contra Cancrum) stages of progression of pancreatic cancer are classified into stages 0, IA, IB, IIA, IIB, III, IVa, and IVb. Stages I to III occupy half or more of the number of 5-year survivals, and stages IVa and IVb occupy 70% or more of the stages of progression at the time of diagnosis. As described in Non-Patent Literature 1, the 5-year survival rate of pancreatic cancer is 45.8% for stage IA, 36.3% for stage IB, 29.4% for stage IIA, 10.6% for stage IIB, 5.9% for stage III, and 4.0% for stage IV, and the prognoses of stage III and stage IV are very poor. Therefore, early detection and treatment of pancreatic cancer are necessary.

As described in Non-Patent Literature 2, abdominal ultrasonography is very useful as convenient and minimally invasive examination in outpatient care or medical examination for the diagnosis of pancreatic cancer. However, it is often difficult to visualize pancreatic cancer having a small tumor size or a lesion on the pancreatic tail side. In ordinary medical checkup, the abnormality detection rate with pancreatic images by abdominal ultrasonography is approximately 1%, and the detection rate of pancreatic cancer is approximately 0.06% or lower. For example, CA19-9, Span-1, CA50, CA242, Dupan-2, TAG-72, and urinary fucose as carbohydrate antigens, and CEA, POA, and TPS as non-carbohydrate antigens are known as tumor markers for the detection of pancreatic cancer. As for how to use these tumor markers, a subject is suspected of having a cancer when their concentrations in blood are higher or lower than predetermined reference values. For example, as described in Non-Patent Literature 3, the reference value of CEA is set to 5 ng/mL, and the reference value of CA19-9 is set to 37 U/mL. A subject is suspected of having a cancer including pancreatic cancer when their concentrations exhibit these values or higher. However, the evaluation of tumor markers mostly examines advanced pancreatic cancer and does not show abnormal values for early pancreatic cancer in many cases. Even combinatorial use of tumor markers and abdominal ultrasonography in medical examination results in low rates of detection of pancreatic cancer. The implementation of such medical examinations for the detection of pancreatic cancer is controversial from the viewpoint of cost effectiveness.

Meanwhile, cystic diseases that occur in the pancreas are known to progress to invasive cancers through malignant transformation and can be regarded as pancreatic cancer precursor lesions. As described in Non-Patent Literature 4, the malignancy of the cystic diseases is evaluated on the basis of cyst diameters, wall thickening, diameters of the main pancreatic duct, mural nodules, stenosis of the main pancreatic duct, enlarged lymph nodes, and cystic lesions, etc. Patients with intraductal papillary-mucinous neoplasms, one type of cystic disease, have a prognosis as poor as 40.4% for malignant cancer and 30.8% for invasive cancer and are therefore recommended to receive follow-up or tumor resection even if the malignancy of the tumors is low when the tumors are detected.

As shown in Patent Literatures 1 to 5 and Non-Patent Literature 4, there are reports, albeit at a research stage, on the determination of pancreatic cancer using the expression levels of microRNAs (miRNAs), or combinations of the expression levels of miRNAs and the expression levels of additional protein markers in biological samples including blood.

Patent Literature 1 discloses a method for detecting pancreatic cancer by combining hsa-miR-125a-3p, hsa-miR-204-3p, and hsa-miR-3648 with several other miRNAs in blood.

Patent Literature 2 discloses a method for detecting pancreatic cancer by combining miRNAs such as hsa-miR-1908-5p, hsa-miR-6729-5p, and hsa-miR-5195-3p in blood.

Patent Literature 3 discloses a method for detecting pancreatic cancer by combining miR-23a-3p with tens of other miRNAs in blood.

Patent Literature 4 lists hsa-miR-1268a, hsa-miR-939-5p, and hsa-miR-642b-3p as miRNAs that have a larger expression level in the blood of pancreatic cancer patients than that in the blood of healthy subjects and discloses a method for detecting pancreatic cancer and a method for evaluating the risk of developing pancreatic cancer by combining these miRNAs with tens of other miRNAs.

Patent Literature 5 discloses a method for detecting pancreatic cancer or a pancreatic cancer precursor lesion and a method for evaluating the risk of developing pancreatic cancer by combining hsa-miR-296-5p with tens of other miRNAs in blood.

Non-Patent Literature 5 lists hsa-miR-638, hsa-miR-3196, hsa-miR-1225-3p, and the like as miRNAs that have a larger expression level in the blood of pancreatic cancer patients than that in the blood of healthy subjects and discloses a method for detecting pancreatic cancer by combining several these miRNAs.

PRIOR ART LITERATURE

Patent Literature

Patent Literature 1: JP Patent Publication (Kokai) No. 2015-107091 A (2015)
Patent Literature 2: International Publication No. WO 2015/182781
Patent Literature 3: Published U.S. Patent Application No. 2015/0011414
Patent Literature 4: JP Patent Publication (Kohyo) No. 2015-502176 A (2015)
Patent Literature 5: International Publication No. WO 2015/153679

Non-Patent Literature

Non-Patent Literature 1: Tetsuya Mine, "Suizo (Pancreas), Journal of the Japan Pancreas Society", Japan Pancreas Society, 2007, Vol. 22, p. 10-13
Non-Patent Literature 2: Japan Pancreas Society, "2009 Scientific evidence based clinical practice guidelines for pancreatic cancer" CQ1 diagnosis methods http://www-.suizou.org/PCMG2009/cq1/cq1-3.html
Non-Patent Literature 3: Kiyoshi Kurokawa et al. ed., LAB DATA, 2013, p. 633, 636 (Igaku-Shoin Ltd., Tokyo, Japan)
Non-Patent Literature 4: Working Group of the Japan Pancreas Society, International consensus guidelines 2012 for the management of IPMN and MCN of the pancreas., p. 6, 8
Non-Patent Literature 5: Miyamae M. et al., 2015, British Journal of Cancer, Vol. 113, (10) p. 1467-1476

SUMMARY OF INVENTION

Problem to be Solved by Invention

An object of the present invention is to find novel tumor markers for early pancreatic cancer or a pancreatic cancer precursor lesion and to provide a method that can effectively detect early pancreatic cancer or a pancreatic cancer precursor lesion using nucleic acids capable of specifically binding to the markers. As described in Non-Patent Literature 2, for example, CA19-9, Span-1, CA50, CA242, Dupan-2, TAG-72, and urinary fucose as carbohydrate antigens and CEA, POA, and TPS as non-carbohydrate antigens are known as tumor markers for the detection of pancreatic cancer. The pancreatic cancer detection sensitivity of these tumor markers is 70 to 80% for CA19-9, 70 to 80% for Span-1, 50 to 60% for Dupan-2, 30 to 60% for CEA, and 60% for CA50. In addition, their specificity is not much high, and their false positive rates are as high as 20 to 30%. Therefore, there may be the possibility of false detection of other cancers and/or benign tumors and/or benign diseases of the pancreas and/or peripancreatic organs, etc. Particularly, the detection sensitivity of early pancreatic cancer is generally low, and the positive rate of CA19-9 is merely ½ (52%) for pancreatic cancer having a tumor size of 2 cm or smaller. Therefore, these tumor markers are not useful for the detection of early pancreatic cancer. Furthermore, the tumor markers based on carbohydrate antigens exhibit false negatives in Lewis blood type negative cases, in which the subjects do not produce the antigens. Therefore, this examination is unsuitable for some subjects. The detection rates of intraductal papillary-mucinous neoplasms which are pancreatic cancer precursor lesions by MRI and CT are 19.9% and 1.2 to 2.6%, respectively, and are not sufficient. Thus, use of tumor markers is not recommended for the detection of pancreatic cancer precursor lesions.

As described below, there are reports, albeit at a research stage, on the determination of pancreatic cancer using the expression levels of microRNAs (miRNAs) in biological samples including blood, none of which, however, have yet been brought into practical use as a method for detecting early pancreatic cancer or a pancreatic cancer precursor lesion.

Patent Literature 1 discloses a method for detecting pancreatic cancer by combining miR-125a-3p, miR-204-3p, and miR-3648 with several other miRNAs in blood. In this literature, however, only healthy subjects were used as a negative control group for pancreatic cancer. Furthermore, the literature neither describes cancers in organs other than the pancreas or benign diseases nor describes a specific method for detecting a pancreatic cancer precursor lesion using blood.

Patent Literature 2 discloses a method for detecting pancreatic cancer by combining miRNAs such as hsa-miR-1908-5p, hsa-miR-6729-5p, and hsa-miR-5195-3p in blood. In this literature, however, only several samples from early pancreatic cancer patients were involved. Furthermore, the literature neither describes specific detection performance thereof such as accuracy, sensitivity, or specificity for early pancreatic cancer nor describes a specific method for detecting a pancreatic cancer precursor lesion using blood.

Patent Literature 3 discloses a method for detecting pancreatic cancer by combining hsa-miR-23a-3p with tens of other miRNAs in blood. This literature, however, neither describes specific detection performance thereof such as accuracy, sensitivity, or specificity for early pancreatic cancer nor describes cancers in regions other than the peripancreatic gastrointestinal upper regions as a negative control group for pancreatic cancer. Furthermore, the literature does not describe a method for detecting a pancreatic cancer precursor lesion.

Patent Literature 4 discloses a method for detecting pancreatic cancer or a pancreatic cancer precursor lesion by combining hsa-miR-1268a, hsa-miR-939-5p, and hsa-miR-642b-3p with tens of other miRNAs. This literature, however, neither describes specific detection performance thereof such as accuracy, sensitivity, or specificity for pancreatic cancer nor describes cancers in organs other than the pancreas as a negative control group for pancreatic cancer.

Patent Literature 5 discloses a method for detecting pancreatic cancer or a pancreatic cancer precursor lesion by combining hsa-miR-296-5p with tens of other miRNAs in blood. This literature, however, does not describe specific detection performance thereof such as accuracy, sensitivity, or specificity for early pancreatic cancer. In the literature, cancers in organs other than the pancreas or benign diseases were not measured as a negative control group for pancreatic cancer precursor lesions. Furthermore, the literature does not describe specific specificity.

Non-Patent Literature 5 lists hsa-miR-638, hsa-miR-3196, hsa-miR-1225-3p, and the like as miRNAs that have a larger expression level in the blood of pancreatic cancer patients than that in the blood of healthy subjects and discloses a method for detecting pancreatic cancer by combining several these miRNAs. This literature, however, does not describe cancers in organs other than pancreas as a negative control group for pancreatic cancer.

As mentioned above, the existing tumor markers exhibit low performance in the detection of early pancreatic cancer or a pancreatic cancer precursor lesion, or neither performance nor detection methods are specifically shown as to the markers at a research stage. Therefore, use of these markers might require carrying out needless extra examination due to the false detection of healthy subjects as being early pancreatic cancer or pancreatic cancer precursor lesion patients, or might waste therapeutic opportunity because of overlooking early pancreatic cancer or pancreatic cancer precursor lesion patients. In addition, the measurement of tens to hundreds of miRNAs increases examination costs and is therefore difficult to use in large-scale screening such as medical checkup. Furthermore, the collection of pancreatic tissues for measuring the tumor markers is highly invasive to patients and is not favorable. Hence, there is a demand for a highly accurate early pancreatic cancer or pancreatic cancer precursor lesion marker that is detectable from blood, which can be collected in less invasive manner, and is capable of correctly determining an early pancreatic cancer or pancreatic cancer precursor lesion patient as an early pancreatic cancer or pancreatic cancer precursor lesion patient and a healthy subject as a healthy subject. Particularly, a highly sensitive early pancreatic cancer or pancreatic cancer precursor lesion marker is desired because tumor resection based on early detection is only radical cure for pancreatic cancer.

Means for Solution of Problem

The present inventors have conducted diligent studies to attain the object and consequently completed the present invention by identifying several genes usable as markers for the detection of early pancreatic cancer or a pancreatic cancer precursor lesion from blood, which can be collected with minimal invasiveness, and finding that early pancreatic cancer or a pancreatic cancer precursor lesion can be significantly detected by using nucleic acids capable of specifically binding to any of these markers.

SUMMARY OF INVENTION

The present invention has the following features:
(1) A kit for the detection of early pancreatic cancer or a pancreatic cancer precursor lesion, comprising a nucleic acid(s) capable of specifically binding to at least one polynucleotides selected from the group consisting of the following early pancreatic cancer or pancreatic cancer precursor lesion markers: miR-6784-5p, miR-1181, miR-671-5p, miR-6857-5p, miR-4276, miR-1914-3p, miR-149-3p, miR-937-5p, miR-4675, miR-6795-5p, miR-4731-5p, miR-5090, miR-3620-5p, miR-1343-5p, miR-6717-5p, miR-6825-5p, miR-6738-5p, miR-6769a-5p, miR-4728-5p, miR-652-5p, miR-4257, miR-6785-5p, miR-7110-5p, miR-6887-5p, miR-887-3p, miR-1228-5p, miR-5572, miR-6782-5p, miR-4298, miR-6786-5p, miR-5010-5p, miR-6087, miR-6765-5p, miR-6732-5p, miR-6787-5p, miR-6737-5p, miR-128-2-5p, miR-4270, miR-6861-5p, miR-6756-5p, miR-1229-5p, miR-6891-5p, miR-6848-5p, miR-1237-5p, miR-30c-1-3p, miR-1233-5p, miR-211-3p, miR-4758-5p, miR-614, miR-6746-5p, miR-1915-5p, miR-4688, miR-3917, miR-5787, miR-4632-5p, miR-6126, miR-135a-3p, miR-8063, miR-5698, miR-6089, miR-498, miR-296-3p, miR-4419b, miR-6802-5p, miR-6829-5p, miR-6803-5p, miR-1199-5p, miR-6840-3p, miR-6752-5p, miR-6798-5p, miR-6131, miR-4667-5p, miR-6510-5p, miR-4690-5p, miR-920, miR-23b-3p, miR-4448, miR-2110, miR-4706, miR-7845-5p, miR-6808-5p, miR-4447, miR-6869-5p, miR-6794-5p, miR-6511a-5p, miR-6824-5p, miR-6766-3p, miR-6511a-5p, and miR-6749-5p.

(2) The kit according to (1), wherein miR-6784-5p is hsa-miR-6784-5p, miR-1181 is hsa-miR-1181, miR-671-5p is hsa-miR-671-5p, miR-6857-5p is hsa-miR-6857-5p, miR-4276 is hsa-miR-4276, miR-1914-3p is hsa-miR-1914-3p, miR-149-3p is hsa-miR-149-3p, miR-937-5p is hsa-miR-937-5p, miR-4675 is hsa-miR-4675, miR-6795-5p is hsa-miR-6795-5p, miR-4731-5p is hsa-miR-4731-5p, miR-5090 is hsa-miR-5090, miR-3620-5p is hsa-miR-3620-5p, miR-1343-5p is hsa-miR-1343-5p, miR-6717-5p is hsa-miR-6717-5p, miR-6825-5p is hsa-miR-6825-5p, miR-6738-5p is hsa-miR-6738-5p, miR-6769a-5p is hsa-miR-6769a-5p, miR-4728-5p is hsa-miR-4728-5p, miR-652-5p is hsa-miR-652-5p, miR-4257 is hsa-miR-4257, miR-6785-5p is hsa-miR-6785-5p, miR-7110-5p is hsa-miR-7110-5p, miR-6887-5p is hsa-miR-6887-5p, miR-887-3p is hsa-miR-887-3p, miR-1228-5p is hsa-miR-1228-5p, miR-5572 is hsa-miR-5572, miR-6782-5p is hsa-miR-6782-5p, miR-4298 is hsa-miR-4298, miR-6786-5p is hsa-miR-6786-5p, miR-5010-5p is hsa-miR-5010-5p, miR-6087 is hsa-miR-6087, miR-6765-5p is hsa-miR-6765-5p, miR-6732-5p is hsa-miR-6732-5p, miR-6787-5p is hsa-miR-6787-5p, miR-6737-5p is hsa-miR-6737-5p, miR-128-2-5p is hsa-miR-128-2-5p, miR-4270 is hsa-miR-4270, miR-6861-5p is hsa-miR-6861-5p, miR-6756-5p is hsa-miR-6756-5p, miR-1229-5p is hsa-miR-1229-5p, miR-6891-5p is hsa-miR-6891-5p, miR-6848-5p is hsa-miR-6848-5p, miR-1237-5p is hsa-miR-1237-5p, miR-30c-1-3p is hsa-miR-30c-1-3p, miR-1233-5p is hsa-miR-1233-5p, miR-211-3p is hsa-miR-211-3p, miR-4758-5p is hsa-miR-4758-5p, miR-614 is hsa-miR-614, miR-6746-5p is hsa-miR-6746-5p, miR-1915-5p is hsa-miR-1915-5p, miR-4688 is hsa-miR-4688, miR-3917 is hsa-miR-3917, miR-5787 is hsa-miR-5787, miR-4632-5p is hsa-miR-4632-5p, miR-6126 is hsa-miR-6126, miR-135a-3p is hsa-miR-135a-3p, miR-8063 is hsa-miR-8063, miR-5698 is hsa-miR-5698, miR-6089 is hsa-miR-6089, miR-498 is hsa-miR-498, miR-296-3p is hsa-miR-296-3p, miR-4419b is hsa-miR-4419b, miR-6802-5p is hsa-miR-6802-5p, miR-6829-5p is hsa-miR-6829-5p, miR-6803-5p is hsa-miR-6803-5p, miR-1199-5p is hsa-miR-1199-5p, miR-6840-3p is hsa-miR-6840-3p, miR-6752-5p is hsa-miR-6752-5p, miR-6798-5p is hsa-miR-6798-5p, miR-6131 is hsa-miR-6131, miR-4667-5p is hsa-miR-4667-5p, miR-6510-5p is hsa-miR-6510-5p, miR-4690-5p is hsa-miR-4690-5p, miR-920 is hsa-miR-920, miR-23b-3p is hsa-miR-23b-3p, miR-4448 is hsa-miR-4448, miR-2110 is hsa-miR-2110, miR-4706 is hsa-miR-4706, miR-7845-5p is hsa-miR-7845-5p, miR-6808-5p is hsa-miR-6808-5p, miR-4447 is hsa-miR-4447, miR-6869-5p is hsa-miR-6869-5p, miR-6794-5p is hsa-miR-6794-5p, miR-6511a-5p is hsa-miR-6511a-5p, miR-6824-5p is hsa-miR-6824-5p, miR-6766-3p is hsa-miR-6766-3p, miR-6511a-5p is hsa-miR-6511a-5p, and miR-6749-5p is hsa-miR-6749-5p.

(3) The kit according to (1) or (2), wherein the nucleic acid(s) is a polynucleotide(s) selected from the group consisting of the following polynucleotides (a) to (e):
(a) a polynucleotide consisting of a nucleotide sequence represented by any of SEQ ID NOs: 1 to 83, 227 to 229, 246, 248, and 250 or a nucleotide sequence derived from the nucleotide sequence by the replacement of u with t, a variant thereof, a derivative thereof, or a fragment thereof comprising 15 or more consecutive nucleotides;
(b) a polynucleotide comprising a nucleotide sequence represented by any of SEQ ID NOs: 1 to 83, 227 to 229, 246, 248, and 250;

(c) a polynucleotide consisting of a nucleotide sequence complementary to a nucleotide sequence represented by any of SEQ ID NOs: 1 to 83, 227 to 229, 246, 248, and 250 or a nucleotide sequence derived from the nucleotide sequence by the replacement of u with t, a variant thereof, a derivative thereof, or a fragment thereof comprising 15 or more consecutive nucleotides;

(d) a polynucleotide comprising a nucleotide sequence complementary to a nucleotide sequence represented by any of SEQ ID NOs: 1 to 83, 227 to 229, 246, 248, and 250 or a nucleotide sequence derived from the nucleotide sequence by the replacement of u with t; and (e) a polynucleotide hybridizing under stringent conditions to any of the polynucleotides (a) to (d).

(4) The kit according to any of (1) to (3), wherein the kit further comprises a nucleic acid(s) capable of specifically binding to at least one polynucleotide selected from the group consisting of other early pancreatic cancer or pancreatic cancer precursor lesion markers miR-1908-5p, miR-6729-5p, miR-5195-3p, miR-638, miR-6125, miR-3178, miR-3196, miR-8069, miR-4723-5p, miR-4746-3p, miR-4689, miR-6816-5p, miR-6757-5p, miR-7109-5p, miR-6724-5p, miR-1225-3p, miR-6875-5p, miR-7108-5p, miR-4508, miR-6085, miR-6779-5p, miR-642a-3p, miR-4695-5p, miR-7847-3p, miR-3197, miR-6769b-5p, miR-7641, miR-187-5p, miR-3185, miR-2861, miR-3940-5p, miR-1203, miR-615-5p, miR-4787-5p, miR-1343-3p, miR-6813-5p, miR-1225-5p, miR-602, miR-4488, miR-125a-3p, miR-5100, miR-4294, miR-1231, miR-6765-3p, miR-4442, miR-718, miR-6780b-5p, miR-6090, miR-6845-5p, miR-4741, miR-4467, miR-4707-5p, miR-4271, miR-4673, miR-3184-5p, miR-1469, miR-4640-5p, miR-663a, miR-6791-5p, miR-6826-5p, miR-4433b-3p, miR-1915-3p, miR-4417, miR-4449, miR-4707-3p, miR-3180-3p, miR-5585-3p, miR-1268a, miR-8072, miR-296-5p, miR-204-3p, miR-4454, miR-6722-3p, miR-1290, miR-3622a-5p, miR-939-5p, miR-675-5p, miR-3131, miR-4648, miR-1268b, miR-6741-5p, miR-6893-5p, miR-3162-5p, miR-642b-3p, miR-4734, miR-150-3p, miR-8089, miR-6805-3p, miR-7113-3p, miR-6850-5p, miR-6799-5p, miR-6768-5p, miR-92b-5p, miR-3679-5p, miR-4792, miR-3656, miR-92a-2-5p, miR-4466, miR-4513, miR-6781-5p, miR-4649-5p, miR-6775-5p, miR-4651, miR-3195, miR-6726-5p, miR-6872-3p, miR-371a-5p, miR-6777-5p, miR-6789-5p, miR-7975, miR-6821-5p, miR-4534, miR-619-5p, miR-7107-5p, miR-1228-3p, miR-6774-5p, miR-6805-5p, miR-23a-3p, miR-4665-5p, miR-4505, miR-4638-5p, miR-24-3p, miR-3135b, miR-4745-5p, miR-128-1-5p, miR-4476, miR-4687-3p, miR-3665, miR-6806-5p, miR-3937, miR-711, miR-3141, miR-3188, miR-4281, miR-5196-5p, miR-6880-5p, miR-3960, miR-3648, miR-6721-5p, miR-4492, miR-744-5p, miR-7704, miR-4749-5p, miR-762, miR-6836-3p, miR-6727-5p, miR-4739, miR-7977, miR-4484, miR-6515-3p, miR-373-5p, miR-4258, miR-4674, miR-3180, miR-6076, miR-1238-5p, miR-4463, miR-4486, miR-4730, miR-4286, and miR-4739.

(5) The kit according to (4), wherein miR-1908-5p is hsa-miR-1908-5p, miR-6729-5p is hsa-miR-6729-5p, miR-5195-3p is hsa-miR-5195-3p, miR-638 is hsa-miR-638, miR-6125 is hsa-miR-6125, miR-3178 is hsa-miR-3178, miR-3196 is hsa-miR-3196, miR-8069 is hsa-miR-8069, miR-4723-5p is hsa-miR-4723-5p, miR-4746-3p is hsa-miR-4746-3p, miR-4689 is hsa-miR-4689, miR-6816-5p is hsa-miR-6816-5p, miR-6757-5p is hsa-miR-6757-5p, miR-7109-5p is hsa-miR-7109-5p, miR-6724-5p is hsa-miR-6724-5p, miR-1225-3p is hsa-miR-1225-3p, miR-6875-5p is hsa-miR-6875-5p, miR-7108-5p is hsa-miR-7108-5p, miR-4508 is hsa-miR-4508, miR-6085 is hsa-miR-6085, miR-6779-5p is hsa-miR-6779-5p, miR-642a-3p is hsa-miR-642a-3p, miR-4695-5p is hsa-miR-4695-5p, miR-7847-3p is hsa-miR-7847-3p, miR-3197 is hsa-miR-3197, miR-6769b-5p is hsa-miR-6769b-5p, miR-7641 is hsa-miR-7641, miR-187-5p is hsa-miR-187-5p, miR-3185 is hsa-miR-3185, miR-2861 is hsa-miR-2861, miR-3940-5p is hsa-miR-3940-5p, miR-1203 is hsa-miR-1203, miR-615-5p is hsa-miR-615-5p, miR-4787-5p is hsa-miR-4787-5p, miR-1343-3p is hsa-miR-1343-3p, miR-6813-5p is hsa-miR-6813-5p, miR-1225-5p is hsa-miR-1225-5p, miR-602 is hsa-miR-602, miR-4488 is hsa-miR-4488, miR-125a-3p is hsa-miR-125a-3p, miR-5100 is hsa-miR-5100, miR-4294 is hsa-miR-4294, miR-1231 is hsa-miR-1231, miR-6765-3p is hsa-miR-6765-3p, miR-4442 is hsa-miR-4442, miR-718 is hsa-miR-718, miR-6780b-5p is hsa-miR-6780b-5p, miR-6090 is hsa-miR-6090, miR-6845-5p is hsa-miR-6845-5p, miR-4741 is hsa-miR-4741, miR-4467 is hsa-miR-4467, miR-4707-5p is hsa-miR-4707-5p, miR-4271 is hsa-miR-4271, miR-4673 is hsa-miR-4673, miR-3184-5p is hsa-miR-3184-5p, miR-1469 is hsa-miR-1469, miR-4640-5p is hsa-miR-4640-5p, miR-663a is hsa-miR-663a, miR-6791-5p is hsa-miR-6791-5p, miR-6826-5p is hsa-miR-6826-5p, miR-4433b-3p is hsa-miR-4433b-3p, miR-1915-3p is hsa-miR-1915-3p, miR-4417 is hsa-miR-4417, miR-4449 is hsa-miR-4449, miR-4707-3p is hsa-miR-4707-3p, miR-3180-3p is hsa-miR-3180-3p, miR-5585-3p is hsa-miR-5585-3p, miR-1268a is hsa-miR-1268a, miR-8072 is hsa-miR-8072, miR-296-5p is hsa-miR-296-5p, miR-204-3p is hsa-miR-204-3p, miR-4454 is hsa-miR-4454, miR-6722-3p is hsa-miR-6722-3p, miR-1290 is hsa-miR-1290, miR-3622a-5p is hsa-miR-3622a-5p, miR-939-5p is hsa-miR-939-5p, miR-675-5p is hsa-miR-675-5p, miR-3131 is hsa-miR-3131, miR-4648 is hsa-miR-4648, miR-1268b is hsa-miR-1268b, miR-6741-5p is hsa-miR-6741-5p, miR-6893-5p is hsa-miR-6893-5p, miR-3162-5p is hsa-miR-3162-5p, miR-642b-3p is hsa-miR-642b-3p, miR-4734 is hsa-miR-4734, miR-150-3p is hsa-miR-150-3p, miR-8089 is hsa-miR-8089, miR-6805-3p is hsa-miR-6805-3p, miR-7113-3p is hsa-miR-7113-3p, miR-6850-5p is hsa-miR-6850-5p, miR-6799-5p is hsa-miR-6799-5p, miR-6768-5p is hsa-miR-6768-5p, miR-92b-5p is hsa-miR-92b-5p, miR-3679-5p is hsa-miR-3679-5p, miR-4792 is hsa-miR-4792, miR-3656 is hsa-miR-3656, miR-92a-2-5p is hsa-miR-92a-2-5p, miR-4466 is hsa-miR-4466, miR-4513 is hsa-miR-4513, miR-6781-5p is hsa-miR-6781-5p, miR-4649-5p is hsa-miR-4649-5p, miR-6775-5p is hsa-miR-6775-5p, miR-4651 is hsa-miR-4651, miR-3195 is hsa-miR-3195, miR-6726-5p is hsa-miR-6726-5p, miR-6872-3p is hsa-miR-6872-3p, miR-371a-5p is hsa-miR-371a-5p, miR-6777-5p is hsa-miR-6777-5p, miR-6789-5p is hsa-miR-6789-5p, miR-7975 is hsa-miR-7975, miR-6821-5p is hsa-miR-6821-5p, miR-4534 is hsa-miR-4534, miR-619-5p is hsa-miR-619-5p, miR-7107-5p is hsa-miR-7107-5p, miR-1228-3p is hsa-miR-1228-3p, miR-6774-5p is hsa-miR-6774-5p, miR-6805-5p is hsa-miR-6805-5p, miR-23a-3p is hsa-miR-23a-3p, miR-4665-5p is hsa-miR-4665-5p, miR-4505 is hsa-miR-4505, miR-4638-5p is hsa-miR-4638-5p, miR-24-3p is hsa-miR-24-3p, miR-3135b is hsa-miR-3135b, miR-4745-5p is hsa-miR-4745-5p, miR-128-1-5p is hsa-miR-128-1-5p, miR-4476 is hsa-miR-4476, miR-4687-3p is hsa-miR-4687-3p, miR-3665 is hsa-miR-3665, miR-6806-5p is hsa-miR-6806-5p, miR-3937 is hsa-miR-3937, miR-711 is hsa-miR-711, miR-3141 is hsa-miR-3141, miR-3188 is hsa-miR-3188, miR-4281 is hsa-miR-4281, miR-5196-5p is hsa-miR-5196-5p, miR-6880-5p is hsa-miR-6880-5p, miR-3960 is hsa-miR-3960, miR-3648 is hsa-miR-3648, miR-6721-5p is hsa-miR-6721-5p, miR-4492 is hsamiR-4492, miR-744-5p is hsa-miR-744-5p, miR-7704 is hsa-miR-7704, miR-4749-5p is hsa-miR-4749-5p, miR-762 is hsa-miR-762, miR-6836-3p is hsa-miR-6836-3p, miR-6727-5p is hsa-miR-6727-5p, miR-4739 is hsa-miR-4739, miR-7977 is hsa-miR-7977, miR-4484 is hsa-miR-4484, miR-6515-3p is hsa-miR-6515-3p, miR-373-5p is hsa-miR-373-5p, miR-4258 is hsa-miR-4258, miR-4674 is hsa-miR-4674, miR-3180 is hsa-miR-3180, miR-6076 is hsa-miR-6076, miR-1238-5p is hsa-miR-1238-5p, miR-4463 is hsa-miR-4463, miR-4486 is hsa-miR-4486, miR-4730 is hsa-miR-4730, miR-4286 is hsa-miR-4286, and miR-4739 is hsa-miR-4739.

(6) The kit according to (4) or (5), wherein the nucleic acid(s) is a polynucleotide(s) selected from the group consisting of the following polynucleotides (f) to (j):
(f) a polynucleotide consisting of a nucleotide sequence represented by any of SEQ ID NOs: 84 to 226, 230 to 245, 247, and 249 or a nucleotide sequence derived from the nucleotide sequence by the replacement of u with t, a variant thereof, a derivative thereof, or a fragment thereof comprising 15 or more consecutive nucleotides;
(g) a polynucleotide comprising a nucleotide sequence represented by any of SEQ ID NOs: 84 to 226, 230 to 245, 247, and 249;
(h) a polynucleotide consisting of a nucleotide sequence complementary to a nucleotide sequence represented by any of SEQ ID NOs: 84 to 226, 230 to 245, 247, and 249 or a nucleotide sequence derived from the nucleotide sequence by the replacement of u with t, a variant thereof, a derivative thereof, or a fragment thereof comprising 15 or more consecutive nucleotides;
(i) a polynucleotide comprising a nucleotide sequence complementary to a nucleotide sequence represented by any of SEQ ID NOs: 84 to 226, 230 to 245, 247, and 249 or a nucleotide sequence derived from the nucleotide sequence by the replacement of u with t; and
(j) a polynucleotide hybridizing under stringent conditions to any of the polynucleotides (f) to (i).

(7) A device for the detection of early pancreatic cancer or a pancreatic cancer precursor lesion, comprising a nucleic acid(s) capable of specifically binding to at least one polynucleotide selected from early pancreatic cancer or pancreatic cancer precursor lesion markers miR-6784-5p, miR-1181, miR-671-5p, miR-6857-5p, miR-4276, miR-1914-3p, miR-149-3p, miR-937-5p, miR-4675, miR-6795-5p, miR-4731-5p, miR-5090, miR-3620-5p, miR-1343-5p, miR-6717-5p, miR-6825-5p, miR-6738-5p, miR-6769a-5p, miR-4728-5p, miR-652-5p, miR-4257, miR-6785-5p, miR-7110-5p, miR-6887-5p, miR-887-3p, miR-1228-5p, miR-5572, miR-6782-5p, miR-4298, miR-6786-5p, miR-5010-5p, miR-6087, miR-6765-5p, miR-6732-5p, miR-6787-5p, miR-6737-5p, miR-128-2-5p, miR-4270, miR-6861-5p, miR-6756-5p, miR-1229-5p, miR-6891-5p, miR-6848-5p, miR-1237-5p, miR-30c-1-3p, miR-1233-5p, miR-211-3p, miR-4758-5p, miR-614, miR-6746-5p, miR-1915-5p, miR-4688, miR-3917, miR-5787, miR-4632-5p, miR-6126, miR-135a-3p, miR-8063, miR-5698, miR-6089, miR-498, miR-296-3p, miR-4419b, miR-6802-5p, miR-6829-5p, miR-6803-5p, miR-1199-5p, miR-6840-3p, miR-6752-5p, miR-6798-5p, miR-6131, miR-4667-5p, miR-6510-5p, miR-4690-5p, miR-920, miR-23b-3p, miR-4448, miR-2110, miR-4706, miR-7845-5p, miR-6808-5p, miR-4447, miR-6869-5p, miR-6794-5p, miR-6511a-5p, miR-6824-5p, miR-6766-3p, miR-6511a-5p, and miR-6749-5p.

(8) The device according to (7), wherein miR-6784-5p is hsa-miR-6784-5p, miR-1181 is hsa-miR-1181, miR-671-5p is hsa-miR-671-5p, miR-6857-5p is hsa-miR-6857-5p, miR-4276 is hsa-miR-4276, miR-1914-3p is hsa-miR-1914-3p, miR-149-3p is hsa-miR-149-3p, miR-937-5p is hsa-miR-937-5p, miR-4675 is hsa-miR-4675, miR-6795-5p is hsa-miR-6795-5p, miR-4731-5p is hsa-miR-4731-5p, miR-5090 is hsa-miR-5090, miR-3620-5p is hsa-miR-3620-5p, miR-1343-5p is hsa-miR-1343-5p, miR-6717-5p is hsa-miR-6717-5p, miR-6825-5p is hsa-miR-6825-5p, miR-6738-5p is hsa-miR-6738-5p, miR-6769a-5p is hsa-miR-6769a-5p, miR-4728-5p is hsa-miR-4728-5p, miR-652-5p is hsa-miR-652-5p, miR-4257 is hsa-miR-4257, miR-6785-5p is hsa-miR-6785-5p, miR-7110-5p is hsa-miR-7110-5p, miR-6887-5p is hsa-miR-6887-5p, miR-887-3p is hsa-miR-887-3p, miR-1228-5p is hsa-miR-1228-5p, miR-5572 is hsa-miR-5572, miR-6782-5p is hsa-miR-6782-5p, miR-4298 is hsa-miR-4298, miR-6786-5p is hsa-miR-6786-5p, miR-5010-5p is hsa-miR-5010-5p, miR-6087 is hsa-miR-6087, miR-6765-5p is hsa-miR-6765-5p, miR-6732-5p is hsa-miR-6732-5p, miR-6787-5p is hsa-miR-6787-5p, miR-6737-5p is hsa-miR-6737-5p, miR-128-2-5p is hsa-miR-128-2-5p, miR-4270 is hsa-miR-4270, miR-6861-5p is hsa-miR-6861-5p, miR-6756-5p is hsa-miR-6756-5p, miR-1229-5p is hsa-miR-1229-5p, miR-6891-5p is hsa-miR-6891-5p, miR-6848-5p is hsa-miR-6848-5p, miR-1237-5p is hsa-miR-1237-5p, miR-30c-1-3p is hsa-miR-30c-1-3p, miR-1233-5p is hsa-miR-1233-5p, miR-211-3p is hsa-miR-211-3p, miR-4758-5p is hsa-miR-4758-5p, miR-614 is hsa-miR-614, miR-6746-5p is hsa-miR-6746-5p, miR-1915-5p is hsa-miR-1915-5p, miR-4688 is hsa-miR-4688, miR-3917 is hsa-miR-3917, miR-5787 is hsa-miR-5787, miR-4632-5p is hsa-miR-4632-5p, miR-6126 is hsa-miR-6126, miR-135a-3p is hsa-miR-135a-3p, miR-8063 is hsa-miR-8063, miR-5698 is hsa-miR-5698, miR-6089 is hsa-miR-6089, miR-498 is hsa-miR-498, miR-296-3p is hsa-miR-296-3p, miR-4419b is hsa-miR-4419b, miR-6802-5p is hsa-miR-6802-5p, miR-6829-5p is hsa-miR-6829-5p, miR-6803-5p is hsa-miR-6803-5p, miR-1199-5p is hsa-miR-1199-5p, miR-6840-3p is hsa-miR-6840-3p, miR-6752-5p is hsa-miR-6752-5p, miR-6798-5p is hsa-miR-6798-5p, miR-6131 is hsa-miR-6131, miR-4667-5p is hsa-miR-4667-5p, miR-6510-5p is hsa-miR-6510-5p, miR-4690-5p is hsa-miR-4690-5p, miR-920 is hsa-miR-920, miR-23b-3p is hsa-miR-23b-3p, miR-4448 is hsa-miR-4448, miR-2110 is hsa-miR-2110, miR-4706 is hsa-miR-4706, miR-7845-5p is hsa-miR-7845-5p, miR-6808-5p is hsa-miR-6808-5p, miR-4447 is hsa-miR-4447, miR-6869-5p is hsa-miR-6869-5p, miR-6794-5p is hsa-miR-6794-5p, miR-6511a-5p is hsa-miR-6511a-5p, miR-6824-5p is hsa-miR-6824-5p, miR-6766-3p is hsa-miR-6766-3p, miR-6511a-5p is hsa-miR-6511a-5p, and miR-6749-5p is hsa-miR-6749-5p.

(9) The device according to (7) or (8), wherein the nucleic acid(s) is a polynucleotide(s) selected from the group consisting of the following polynucleotides (a) to (e):
(a) a polynucleotide consisting of a nucleotide sequence represented by any of SEQ ID NOs: 1 to 83, 227 to 229, 246, 248, and 250 or a nucleotide sequence derived from the nucleotide sequence by the replacement of u with t, a variant thereof, a derivative thereof, or a fragment thereof comprising 15 or more consecutive nucleotides;
(b) a polynucleotide comprising a nucleotide sequence represented by any of SEQ ID NOs: 1 to 83, 227 to 229, 246, 248 and 250;
(c) a polynucleotide consisting of a nucleotide sequence complementary to a nucleotide sequence represented by any of SEQ ID NOs: 1 to 83, 227 to 229, 246, 248, and 250 or a nucleotide sequence derived from the nucleotide sequence by the replacement of u with t, a variant thereof, a derivative thereof, or a fragment thereof comprising 15 or more consecutive nucleotides;

(d) a polynucleotide comprising a nucleotide sequence complementary to a nucleotide sequence represented by any of SEQ ID NOs: 1 to 83, 227 to 229, 246, 248, and 250 or a nucleotide sequence derived from the nucleotide sequence by the replacement of u with t; and (e) a polynucleotide hybridizing under stringent conditions to any of the polynucleotides (a) to (d).

(10) The device according to any of (7) to (9), wherein the device further comprises a nucleic acid(s) capable of specifically binding to at least one polynucleotide selected from the group consisting of other early pancreatic cancer or pancreatic cancer precursor lesion markers miR-1908-5p, miR-6729-5p, miR-5195-3p, miR-638, miR-6125, miR-3178, miR-3196, miR-8069, miR-4723-5p, miR-4746-3p, miR-4689, miR-6816-5p, miR-6757-5p, miR-7109-5p, miR-6724-5p, miR-1225-3p, miR-6875-5p, miR-7108-5p, miR-4508, miR-6085, miR-6779-5p, miR-642a-3p, miR-4695-5p, miR-7847-3p, miR-3197, miR-6769b-5p, miR-7641, miR-187-5p, miR-3185, miR-2861, miR-3940-5p, miR-1203, miR-615-5p, miR-4787-5p, miR-1343-3p, miR-6813-5p, miR-1225-5p, miR-602, miR-4488, miR-125a-3p, miR-5100, miR-4294, miR-1231, miR-6765-3p, miR-4442, miR-718, miR-6780b-5p, miR-6090, miR-6845-5p, miR-4741, miR-4467, miR-4707-5p, miR-4271, miR-4673, miR-3184-5p, miR-1469, miR-4640-5p, miR-663a, miR-6791-5p, miR-6826-5p, miR-4433b-3p, miR-1915-3p, miR-4417, miR-4449, miR-4707-3p, miR-3180-3p, miR-5585-3p, miR-1268a, miR-8072, miR-296-5p, miR-204-3p, miR-4454, miR-6722-3p, miR-1290, miR-3622a-5p, miR-939-5p, miR-675-5p, miR-3131, miR-4648, miR-1268b, miR-6741-5p, miR-6893-5p, miR-3162-5p, miR-642b-3p, miR-4734, miR-150-3p, miR-8089, miR-6805-3p, miR-7113-3p, miR-6850-5p, miR-6799-5p, miR-6768-5p, miR-92b-5p, miR-3679-5p, miR-4792, miR-3656, miR-92a-2-5p, miR-4466, miR-4513, miR-6781-5p, miR-4649-5p, miR-6775-5p, miR-4651, miR-3195, miR-6726-5p, miR-6872-3p, miR-371a-5p, miR-6777-5p, miR-6789-5p, miR-7975, miR-6821-5p, miR-4534, miR-619-5p, miR-7107-5p, miR-1228-3p, miR-6774-5p, miR-6805-5p, miR-23a-3p, miR-4665-5p, miR-4505, miR-4638-5p, miR-24-3p, miR-3135b, miR-4745-5p, miR-128-1-5p, miR-4476, miR-4687-3p, miR-3665, miR-6806-5p, miR-3937, miR-711, miR-3141, miR-3188, miR-4281, miR-5196-5p, miR-6880-5p, miR-3960, miR-3648, miR-6721-5p, miR-4492, miR-744-5p, miR-7704, miR-4749-5p, miR-762, miR-6836-3p, miR-6727-5p, miR-4739, miR-7977, miR-4484, miR-6515-3p, miR-373-5p, miR-4258, miR-4674, miR-3180, miR-6076, miR-1238-5p, miR-4463, miR-4486, miR-4730, miR-4286, and miR-4739.

(11) The device according to (10), wherein miR-1908-5p is hsa-miR-1908-5p, miR-6729-5p is hsa-miR-6729-5p, miR-5195-3p is hsa-miR-5195-3p, miR-638 is hsa-miR-638, miR-6125 is hsa-miR-6125, miR-3178 is hsa-miR-3178, miR-3196 is hsa-miR-3196, miR-8069 is hsa-miR-8069, miR-4723-5p is hsa-miR-4723-5p, miR-4746-3p is hsa-miR-4746-3p, miR-4689 is hsa-miR-4689, miR-6816-5p is hsa-miR-6816-5p, miR-6757-5p is hsa-miR-6757-5p, miR-7109-5p is hsa-miR-7109-5p, miR-6724-5p is hsa-miR-6724-5p, miR-1225-3p is hsa-miR-1225-3p, miR-6875-5p is hsa-miR-6875-5p, miR-7108-5p is hsa-miR-7108-5p, miR-4508 is hsa-miR-4508, miR-6085 is hsa-miR-6085, miR-6779-5p is hsa-miR-6779-5p, miR-642a-3p is hsa-miR-642a-3p, miR-4695-5p is hsa-miR-4695-5p, miR-7847-3p is hsa-miR-7847-3p, miR-3197 is hsa-miR-3197, miR-6769b-5p is hsa-miR-6769b-5p, miR-7641 is hsa-miR-7641, miR-187-5p is hsa-miR-187-5p, miR-3185 is hsa-miR-3185, miR-2861 is hsa-miR-2861, miR-3940-5p is hsa-miR-3940-5p, miR-1203 is hsa-miR-1203, miR-615-5p is hsa-miR-615-5p, miR-4787-5p is hsa-miR-4787-5p, miR-1343-3p is hsa-miR-1343-3p, miR-6813-5p is hsa-miR-6813-5p, miR-1225-5p is hsa-miR-1225-5p, miR-602 is hsa-miR-602, miR-4488 is hsa-miR-4488, miR-125a-3p is hsa-miR-125a-3p, miR-5100 is hsa-miR-5100, miR-4294 is hsa-miR-4294, miR-1231 is hsa-miR-1231, miR-6765-3p is hsa-miR-6765-3p, miR-4442 is hsa-miR-4442, miR-718 is hsa-miR-718, miR-6780b-5p is hsa-miR-6780b-5p, miR-6090 is hsa-miR-6090, miR-6845-5p is hsa-miR-6845-5p, miR-4741 is hsa-miR-4741, miR-4467 is hsa-miR-4467, miR-4707-5p is hsa-miR-4707-5p, miR-4271 is hsa-miR-4271, miR-4673 is hsa-miR-4673, miR-3184-5p is hsa-miR-3184-5p, miR-1469 is hsa-miR-1469, miR-4640-5p is hsa-miR-4640-5p, miR-663a is hsa-miR-663a, miR-6791-5p is hsa-miR-6791-5p, miR-6826-5p is hsa-miR-6826-5p, miR-4433b-3p is hsa-miR-4433b-3p, miR-1915-3p is hsa-miR-1915-3p, miR-4417 is hsa-miR-4417, miR-4449 is hsa-miR-4449, miR-4707-3p is hsa-miR-4707-3p, miR-3180-3p is hsa-miR-3180-3p, miR-5585-3p is hsa-miR-5585-3p, miR-1268a is hsa-miR-1268a, miR-8072 is hsa-miR-8072, miR-296-5p is hsa-miR-296-5p, miR-204-3p is hsa-miR-204-3p, miR-4454 is hsa-miR-4454, miR-6722-3p is hsa-miR-6722-3p, miR-1290 is hsa-miR-1290, miR-3622a-5p is hsa-miR-3622a-5p, miR-939-5p is hsa-miR-939-5p, miR-675-5p is hsa-miR-675-5p, miR-3131 is hsa-miR-3131, miR-4648 is hsa-miR-4648, miR-1268b is hsa-miR-1268b, miR-6741-5p is hsa-miR-6741-5p, miR-6893-5p is hsa-miR-6893-5p, miR-3162-5p is hsa-miR-3162-5p, miR-642b-3p is hsa-miR-642b-3p, miR-4734 is hsa-miR-4734, miR-150-3p is hsa-miR-150-3p, miR-8089 is hsa-miR-8089, miR-6805-3p is hsa-miR-6805-3p, miR-7113-3p is hsa-miR-7113-3p, miR-6850-5p is hsa-miR-6850-5p, miR-6799-5p is hsa-miR-6799-5p, miR-6768-5p is hsa-miR-6768-5p, miR-92b-5p is hsa-miR-92b-5p, miR-3679-5p is hsa-miR-3679-5p, miR-4792 is hsa-miR-4792, miR-3656 is hsa-miR-3656, miR-92a-2-5p is hsa-miR-92a-2-5p, miR-4466 is hsa-miR-4466, miR-4513 is hsa-miR-4513, miR-6781-5p is hsa-miR-6781-5p, miR-4649-5p is hsa-miR-4649-5p, miR-6775-5p is hsa-miR-6775-5p, miR-4651 is hsa-miR-4651, miR-3195 is hsa-miR-3195, miR-6726-5p is hsa-miR-6726-5p, miR-6872-3p is hsa-miR-6872-3p, miR-371a-5p is hsa-miR-371a-5p, miR-6777-5p is hsa-miR-6777-5p, miR-6789-5p is hsa-miR-6789-5p, miR-7975 is hsa-miR-7975, miR-6821-5p is hsa-miR-6821-5p, miR-4534 is hsa-miR-4534, miR-619-5p is hsa-miR-619-5p, miR-7107-5p is hsa-miR-7107-5p, miR-1228-3p is hsa-miR-1228-3p, miR-6774-5p is hsa-miR-6774-5p, miR-6805-5p is hsa-miR-6805-5p, miR-23a-3p is hsa-miR-23a-3p, miR-4665-5p is hsa-miR-4665-5p, miR-4505 is hsa-miR-4505, miR-4638-5p is hsa-miR-4638-5p, miR-24-3p is hsa-miR-24-3p, miR-3135b is hsa-miR-3135b, miR-4745-5p is hsa-miR-4745-5p, miR-128-1-5p is hsa-miR-128-1-5p, miR-4476 is hsa-miR-4476, miR-4687-3p is hsa-miR-4687-3p, miR-3665 is hsa-miR-3665, miR-6806-5p is hsa-miR-6806-5p, miR-3937 is hsa-miR-3937, miR-711 is hsa-miR-711, miR-3141 is hsa-miR-3141, miR-3188 is hsa-miR-3188, miR-4281 is hsa-miR-4281, miR-5196-5p is hsa-miR-5196-5p, miR-6880-5p is hsa-miR-6880-5p, miR-3960 is hsa-miR-3960, miR-3648 is hsa-miR-3648, miR-6721-5p is hsa-miR-6721-5p, miR-4492 is hsa-miR-4492, miR-744-5p is hsa-miR-744-5p, miR-7704 is hsa-miR-7704, miR-4749-5p is hsa-miR-4749-5p, miR-762 is hsa-miR-762, miR-6836-3p is hsa-miR-6836-3p, miR-6727-5p is hsa-miR-6727-5p, miR-4739 is hsa-miR-4739, miR-7977 is hsa-miR-7977, miR-4484 is hsa-miR-4484, miR-6515-3p is hsa-miR-6515-3p, miR-373-5p is hsa-miR-373-5p, miR-4258 is hsa-miR-4258, miR-4674 is hsa-miR-4674, miR-3180 is hsa-miR-3180, miR-6076 is hsa-miR-6076, miR-1238-5p is hsa-miR-1238-5p, miR-4463 is hsa-miR-4463, miR-4486 is hsa-miR-4486, miR-4730 is hsa-miR-4730, miR-4286 is hsa-miR-4286, and miR-4739 is hsa-miR-4739.

(12) The device according to (10) or (11), wherein the nucleic acid(s) is a polynucleotide(s) selected from the group consisting of the following polynucleotides (f) to (j):
(f) a polynucleotide consisting of a nucleotide sequence represented by any of SEQ ID NOs: 84 to 226, 230 to 245, 247, and 249 or a nucleotide sequence derived from the nucleotide sequence by the replacement of u with t, a variant thereof, a derivative thereof, or a fragment thereof comprising 15 or more consecutive nucleotides;
(g) a polynucleotide comprising a nucleotide sequence represented by any of SEQ ID NOs: 84 to 226, 230 to 245, 247, and 249;
(h) a polynucleotide consisting of a nucleotide sequence complementary to a nucleotide sequence represented by any of SEQ ID NOs: 84 to 226, 230 to 245, 247, and 249 or a nucleotide sequence derived from the nucleotide sequence by the replacement of u with t, a variant thereof, a derivative thereof, or a fragment thereof comprising 15 or more consecutive nucleotides;
(i) a polynucleotide comprising a nucleotide sequence complementary to a nucleotide sequence represented by any of SEQ ID NOs: 84 to 226, 230 to 245, 247, and 249 or a nucleotide sequence derived from the nucleotide sequence by the replacement of u with t; and
(j) a polynucleotide hybridizing under stringent conditions to any of the polynucleotides (f) to (i).

(13) The device according to any one of (7) to (12), wherein the device is for measurement based on a hybridization technique.

(14) The device according to (13), wherein the hybridization technique is a nucleic acid array technique.

(15) A method for detecting early pancreatic cancer or a pancreatic cancer precursor lesion in a subject, comprising: measuring an expression level(s) of a target nucleic acid(s) in a sample from the subject using a kit according to any of (1) to (6) or a device according to any of (7) to (14); and evaluating in vitro whether or not the subject has early pancreatic cancer or a pancreatic cancer precursor lesion using both of the measured expression level(s) and a control expression level(s) in a sample from a healthy subject measured in the same way, to detect the presence or absence of early pancreatic cancer or a pancreatic cancer precursor lesion in the subject.

(16) A method for detecting early pancreatic cancer or a pancreatic cancer precursor lesion in a subject, comprising: measuring an expression level(s) of a target gene(s) in a sample from the subject using a kit according to any of (1) to (6) or a device according to any of (7) to (14); and assigning the expression level(s) of the target gene(s) in the sample from the subject to a discriminant (discriminant function) to evaluate the presence or absence of early pancreatic cancer or a pancreatic cancer precursor lesion, wherein the discriminant is prepared with the gene expression level(s) in a sample(s) from a subject(s) known to have early pancreatic cancer or a pancreatic cancer precursor lesion and the gene expression level(s) in a sample(s) from a healthy subject(s) as supervising samples and is capable of discriminating an early pancreatic cancer or pancreatic cancer precursor lesion patient from a healthy subject.

(17) The method according to (15) or (16), wherein the subject is a human.

(18) The method according to any one of (15) to (17), wherein the sample is blood, serum, or plasma.

Definition of Terms

The terms used herein are defined as described below.

The term "pancreatic cancer" used herein refers to invasive ductal carcinomas. Specifically, the "pancreatic cancer" includes papillary adenocarcinoma, tubular adenocarcinoma, poorly differentiated adenocarcinoma, adenosquamous carcinoma, mucinous carcinoma, anaplastic carcinoma, and the like formed in the pancreas ("Classification of Pancreatic Carcinoma", the 6th edition, revised version, 2013, Japan Pancreas Society, KANEHARA & Co., LTD. (Tokyo, Japan), p. 27-28).

The term "pancreatic cancer precursor lesion" used herein refers to exocrine neoplasms formed in the pancreas. Specifically, the "pancreatic cancer precursor lesion" includes serous cystic neoplasms (SCNs), serous cystadenoma (SCA), serous cystadenocarcinoma (SCC), mucinous cystic neoplasms (MCNs), mucinous cystadenoma (MCA), mucinous cystadenocarcinoma (MCC), intraductal papillary-mucinous neoplasms (IPMNs), intraductal papillary-mucinous adenoma (IPMA), intraductal papillary-mucinous carcinoma (IPMC), and the like ("General Rules for the Study of Pancreatic Cancer", the 6th edition, revised version, 2013, Japan Pancreas Society, KANEHARA & Co., LTD. (Tokyo, Japan), p. 24-27).

The term "stage of progression of pancreatic cancer" used herein is classified into stages 0, IA, IB, IIA, IIB, III, IVa, and IVb according to the local extent of the primary tumor, lymph node metastasis, distant metastasis, etc. ("General Rules for the Study of Pancreatic Cancer", the 6th edition, revised version, 2013, Japan Pancreas Society, KANEHARA & Co., LTD. (Tokyo, Japan), p. 55-57).

The term "early pancreatic cancer" used herein refers to pancreatic cancer of stage 0, IA, IB, IIA, or IIB.

The term "advanced pancreatic cancer" used herein refers to pancreatic cancer of stage III, IVa, or IVb.

The term "benign disease" used herein refers to a disease with a nonmalignant tumor in an organ.

Abbreviations or terms such as "nucleotide", "polynucleotide", "DNA", and "RNA" used herein abide by "Guidelines for the preparation of specification which contains nucleotide and/or amino acid sequences" (edited by Japan Patent Office) and common use in the art.

The term "polynucleotide" used herein refers to a nucleic acid including any of RNA, DNA, and RNA/DNA (chimera). The DNA includes any of cDNA, genomic DNA, and synthetic DNA. The RNA includes any of total RNA, mRNA, rRNA, miRNA, siRNA, snoRNA, snRNA, non-coding RNA and synthetic RNA. Here the "synthetic DNA" and the "synthetic RNA" refer to a DNA and an RNA artificially prepared using, for example, an automatic nucleic acid synthesizer, on the basis of predetermined nucleotide sequences (which may be any of natural and non-natural sequences). Herein, the "non-natural sequence" is intended to be used in a broad sense and includes, for example, a sequence comprising substitution, deletion, insertion, and/or addition of one or more nucleotides (i.e., a variant sequence) and a sequence comprising one or more modified nucleotides (i.e., a modified sequence), which are different from the natural sequence. Herein, the term "polynucleotide" is used interchangeably with the term "nucleic acid."

The term "fragment" used herein is a polynucleotide having a nucleotide sequence that consists of a consecutive portion of a polynucleotide and desirably has a length of 15 or more nucleotides, preferably 17 or more nucleotides, more preferably 19 or more nucleotides.

The term "gene" used herein is intended to include not only RNA and double-stranded DNA but also each single-stranded DNA such as a plus(+) strand (or a sense strand) or a complementary strand (or an antisense strand) constituting the duplex. The gene is not particularly limited by its length.

Thus, the "gene" used herein includes any of double-stranded DNA including human genomic DNA, single-stranded DNA (plus strand), single-stranded DNA having a sequence complementary to the plus strand (complementary strand) (e.g., cDNA), microRNA (miRNA), and their fragments, and their transcripts, unless otherwise specified. The "gene" includes not only a "gene" represented by a particular nucleotide sequence (or SEQ ID NO) but "nucleic acids" encoding RNAs having biological functions equivalent to RNA encoded by the gene, for example, a congener (i.e., a homolog or an ortholog), a variant (e.g., a genetic polymorph), and a derivative. Specific examples of such a "nucleic acid" encoding a congener, a variant, or a derivative can include a "nucleic acid" having a nucleotide sequence hybridizing under stringent conditions described later to a complementary sequence of a nucleotide sequence represented by any of SEQ ID NOs: 1 to 812 or a nucleotide sequence derived from the nucleotide sequence by the replacement of u with t. Regardless whether or not there is a difference in functional region, the "gene" can comprise, for example, expression control regions, coding region, exons, or introns. The "gene" may be contained in a cell or may exist alone after being released from a cell. Alternatively, the "gene" may be in a state enclosed in a vesicle called exosome.

The term "exosome" used herein refers to a vesicle that is encapsulated by lipid bilayer and secreted from a cell. The exosome is derived from a multivesicular endosome and may incorporate biomaterials such as "genes" (e.g., RNA or DNA) or proteins when released into an extracellular environment. The exosome is known to be contained in a body fluid such as blood, serum, plasma, or lymph.

The term "transcript" used herein refers to an RNA synthesized from the DNA sequence of a gene as a template. RNA polymerase binds to a site called promoter located upstream of the gene and adds ribonucleotides complementary to the nucleotide sequence of the DNA to the 3' end to synthesize an RNA. This RNA contains not only the gene itself but the whole sequence from a transcription initiation site to the end of a polyA sequence, including expression control regions, coding region, exons, or introns.

Unless otherwise specified, the term "microRNA (miRNA)" used herein is intended to mean a 15- to 25-nucleotide non-coding RNA that is transcribed as an RNA precursor having a hairpin-like structure, cleaved by a dsRNA-cleaving enzyme having RNase III cleavage activity, and integrated into a protein complex called RISC, and that is involved in the suppression of translation of mRNA. The term "miRNA" used herein includes not only a "miRNA" represented by a particular nucleotide sequence (or SEQ ID NO) but a precursor of the "miRNA" (pre-miRNA or pri-miRNA), and miRNAs having biological functions equivalent thereto, for example, a congener (i.e., a homolog or an ortholog), a variant (e.g., a genetic polymorph), and a derivative. Such a precursor, a congener, a variant, or a derivative can be specifically identified using miRBase Release 20 (http://www.mirbase.org/), and examples thereof can include a "miRNA" having a nucleotide sequence hybridizing under stringent conditions described later to a complementary sequence of any particular nucleotide sequence represented by any of SEQ ID NOs: 1 to 812. The term "miRNA" used herein may be a gene product of a miR gene. Such a gene product includes a mature miRNA (e.g., a 15- to 25-nucleotide or 19- to 25-nucleotide non-coding RNA involved in the suppression of translation of mRNA as described above) or a miRNA precursor (e.g., pre-miRNA or pri-miRNA as described above).

The term "probe" used herein includes a polynucleotide that is used for specifically detecting an RNA resulting from the expression of a gene or a polynucleotide derived from the RNA, and/or a polynucleotide complementary thereto.

The term "primer" used herein includes a polynucleotide that specifically recognizes and amplifies an RNA resulting from the expression of a gene or a polynucleotide derived from the RNA, and/or a polynucleotide complementary thereto.

In this context, the complementary polynucleotide (complementary strand or reverse strand) means a polynucleotide in a complementary relationship based on A:T (U) and G:C base pairs with the full-length sequence of a polynucleotide consisting of a nucleotide sequence defined by any of SEQ ID NOs: 1 to 812 or a nucleotide sequence derived from the nucleotide sequence by the replacement of u with t, or a partial sequence thereof (here, this full-length or partial sequence is referred to as a plus strand for the sake of convenience). The phrase "polynucleotide consisting of a nucleotide sequence complementary" to a nucleotide sequence represented by any of SEQ ID NOs: 1 to 812 or a nucleotide sequence derived from the nucleotide sequence by the replacement of u with t is also basically understood in the same way.

The term "stringent conditions" used herein refers to conditions under which a nucleic acid probe hybridizes to its target sequence to a detectably larger extent (e.g., a measurement value equal to or larger than "(a mean of background measurement values)+(a standard error of the background measurement values)×2") than that for other sequences. The stringent conditions are dependent on a sequence and differ depending on an environment where hybridization is performed. A target sequence complementary in 100% to the nucleic acid probe can be identified by controlling the stringency of hybridization and/or washing conditions. Specific examples of the "stringent conditions" will be mentioned later.

The term "Tm value" used herein means a temperature at which the double-stranded part of a polynucleotide is denatured into single strands so that the double strands and the single strands exist at a ratio of 1:1.

The term "variant" used herein means, in the case of a nucleic acid, a natural variant attributed to polymorphism, mutation, or the like; a variant containing the deletion, substitution, addition, or insertion of 1 or 2 or more (e.g., 1 to several) nucleotides in a nucleotide sequence represented by any of SEQ ID NOs: 1 to 812 or a nucleotide sequence derived from the nucleotide sequence by the replacement of u with t, or a partial sequence thereof; a variant that exhibits percent (%) identity of approximately 90% or higher, approximately 95% or higher, approximately 97% or higher, approximately 98% or higher, approximately 99% or higher to each of these nucleotide sequences or the partial sequences thereof; or a nucleic acid hybridizing under the stringent conditions defined above to a polynucleotide or an oligonucleotide comprising each of these nucleotide sequences or the partial sequences thereof.

The term "several" used herein means an integer of approximately 10, 9, 8, 7, 6, 5, 4, 3, or 2.

The variant as used herein can be prepared by use of a well-known technique such as site-directed mutagenesis or mutagenesis using PCR.

The term "percent (%) identity" used herein can be determined with or without an introduced gap, using a protein or gene search system based on BLAST or FASTA (Zheng Zhang et al., 2000, J. Comput. Biol., Vol. 7, p. 203-214; Altschul, S. F. et al., 1990, Journal of Molecular Biology, Vol. 215, p. 403-410; and Pearson, W. R. et al., 1988, Proc. Natl. Acad. Sci. U.S.A., Vol. 85, p. 2444-2448).

The term "derivative" used herein is meant to include a modified nucleic acid, for example, unlimitedly, a derivative labeled with a fluorophore or the like, a derivative containing a modified nucleotide (e.g., a nucleotide containing a group such as halogen, alkyl such as methyl, alkoxy such as methoxy, thio, or carboxymethyl, and a nucleotide that has undergone base rearrangement, double bond saturation, deamination, replacement of an oxygen molecule with a sulfur atom, etc.), PNA (peptide nucleic acid; Nielsen, P. E. et al., 1991, Science, Vol. 254, p. 1497-500), and LNA (locked nucleic acid; Obika, S. et al., 1998, Tetrahedron Lett., Vol. 39, p. 5401-5404).

As used herein, the "nucleic acid" capable of specifically binding to a polynucleotide selected from the early pancreatic cancer or pancreatic cancer precursor lesion marker miRNAs described above is a synthesized or prepared nucleic acid and specifically includes a "nucleic acid probe" or a "primer". The "nucleic acid" is utilized directly or indirectly for detecting the presence or absence of early pancreatic cancer or a pancreatic cancer precursor lesion in a subject, for diagnosing the presence or absence or the severity of early pancreatic cancer or a pancreatic cancer precursor lesion, the presence or absence or the degree of amelioration of early pancreatic cancer or a pancreatic cancer precursor lesion, or the therapeutic sensitivity of early pancreatic cancer or a pancreatic cancer precursor lesion, or for screening for a candidate substance useful in the prevention, amelioration, or treatment of early pancreatic cancer or a pancreatic cancer precursor lesion. The "nucleic acid" includes a nucleotide, an oligonucleotide, and a polynucleotide capable of specifically recognizing and binding to a transcript represented by any of SEQ ID NOs: 1 to 812 or a synthetic cDNA nucleic acid thereof in vivo, particularly in a sample such as a body fluid (e.g., blood or urine), in relation to the development of early pancreatic cancer or a pancreatic cancer precursor lesion. The nucleotide, the oligonucleotide, and the polynucleotide can be effectively used as probes for detecting the aforementioned gene expressed in vivo, in tissues, in cells, or the like on the basis of the properties described above, or as primers for amplifying the aforementioned gene expressed in vivo.

The term "detection" used herein is interchangeable with the term "examination", "measurement", "decision", or "decision support". As used herein, the term "evaluation" is meant to include diagnosing or evaluation-supporting on the basis of examination results or measurement results.

The term "subject" used herein means a mammal such as a primate including a human and a chimpanzee, a pet animal including a dog and a cat, a livestock animal including cattle, a horse, sheep, and a goat, a rodent including a mouse and a rat, and an animal that is kept in a zoo. The subject is preferably a human. The term "healthy subject" also means such a mammal without being affected with the cancer to be detected. The healthy subject is preferably a human.

The term "P" or "P value" used herein refers to a probability at which a more extreme statistic than that actually calculated from data under null hypothesis is observed in a statistical test. Thus, with smaller "P" or "P value", it is regarded that there is a more significant difference between subjects to be compared.

The term "sensitivity" used herein means a value of (the number of true positives)/(the number of true positives+the number of false negatives). High sensitivity allows early pancreatic cancer or a pancreatic cancer precursor lesion to be detected early, leading to the complete resection of cancer sites and reduction in the rate of recurrence.

The term "specificity" used herein means a value of (the number of true negatives)/(the number of true negatives+the number of false positives). High specificity prevents needless extra examination for healthy subjects misjudged as being early pancreatic cancer or pancreatic cancer precursor lesion patients, leading to reduction in burden on patients and reduction in medical expense.

The term "accuracy" used herein means a value of (the number of true positives+the number of true negatives)/(the total number of cases). The accuracy indicates the ratio of samples that are identified correctly to all samples, and serves as a primary index for evaluating detection performance.

As used herein, the "sample" that is subject to determination, detection, or diagnosis refers to a tissue and a biological material in which the expression of the gene of the present invention varies as early pancreatic cancer or pancreatic cancer precursor lesion develops, as early pancreatic cancer or pancreatic cancer precursor lesion progresses, or as therapeutic effects on early pancreatic cancer or a pancreatic cancer precursor lesion are exerted. Specifically, the "sample" refers to a pancreatic tissue, a peripancreatic vascular channel, lymph node, and organ, an organ suspected of having metastasis, the skin, a body fluid such as blood, urine, saliva, sweat, or tissue exudates, serum or plasma prepared from blood, feces, hair, and the like. The "sample" further refers to a biological sample extracted therefrom, specifically, a gene such as RNA or miRNA.

The term "hsa-miR-6784-5p gene" or "hsa-miR-6784-5p" used herein includes the hsa-miR-6784-5p gene (miRBase Accession No. MIMAT0027468) shown in SEQ ID NO: 1, a homolog or an ortholog thereof of a different organism species, and the like. The gene can be obtained by a method described in Ladewig E et al., 2012, Genome Res, Vol. 22, p. 1634-1645. Also, "hsa-mir-6784" (miRBase Accession No. MI0022629, SEQ ID NO: 251) having a hairpin-like structure is known as a precursor of "hsa-miR-6784-5p".

The term "hsa-miR-1181 gene" or "hsa-miR-1181" used herein includes the hsa-miR-1181 gene (miRBase Accession No. MIMAT0005826) shown in SEQ ID NO: 2, a homolog or an ortholog thereof of a different organism species, and the like. The gene can be obtained by a method described in Subramanian S et al., 2008, Oncogene, Vol. 27, p. 2015-2026. Also, "hsa-mir-1181" (miRBase Accession No. MI0006274, SEQ ID NO: 252) having a hairpin-like structure is known as a precursor of "hsa-miR-1181".

The term "hsa-miR-671-5p gene" or "hsa-miR-671-5p" used herein includes the hsa-miR-671-5p gene (miRBase Accession No. MIMAT0003880) shown in SEQ ID NO: 3, a homolog or an ortholog thereof of a different organism species, and the like. The gene can be obtained by a method described in Berezikov E et al., 2006, Genome Res, Vol. 16, p. 1289-1298. Also, "hsa-mir-671" (miRBase Accession No.

MI0003760, SEQ ID NO: 253) having a hairpin-like structure is known as a precursor of "hsa-miR-671-5p".

The term "hsa-miR-6857-5p gene" or "hsa-miR-6857-5p" used herein includes the hsa-miR-6857-5p gene (miRBase Accession No. MIMAT0027614) shown in SEQ ID NO: 4, a homolog or an ortholog thereof of a different organism species, and the like. The gene can be obtained by a method described in Ladewig E et al., 2012, Genome Res, Vol. 22, p. 1634-1645. Also, "hsa-mir-6857" (miRBase Accession No. MI0022703, SEQ ID NO: 254) having a hairpin-like structure is known as a precursor of "hsa-miR-6857-5p".

The term "hsa-miR-4276 gene" or "hsa-miR-4276" used herein includes the hsa-miR-4276 gene (miRBase Accession No. MIMAT0016904) shown in SEQ ID NO: 5, a homolog or an ortholog thereof of a different organism species, and the like. The gene can be obtained by a method described in Goff L A et al., 2009, PLoS One, Vol. 4, e7192. Also, "hsa-mir-4276" (miRBase Accession No. MI0015882, SEQ ID NO: 255) having a hairpin-like structure is known as a precursor of "hsa-miR-4276".

The term "hsa-miR-1914-3p gene" or "hsa-miR-1914-3p" used herein includes the hsa-miR-1914-3p gene (miRBase Accession No. MIMAT0007890) shown in SEQ ID NO: 6, a homolog or an ortholog thereof of a different organism species, and the like. The gene can be obtained by a method described in Bar M et al., 2008, Stem Cells, Vol. 26, p. 2496-2505. Also, "hsa-mir-1914" (miRBase Accession No. MI0008335, SEQ ID NO: 256) having a hairpin-like structure is known as a precursor of "hsa-miR-1914-3p".

The term "hsa-miR-149-3p gene" or "hsa-miR-149-3p" used herein includes the hsa-miR-149-3p gene (miRBase Accession No. MIMAT0004609) shown in SEQ ID NO: 7, a homolog or an ortholog thereof of a different organism species, and the like. The gene can be obtained by a method described in Lagos-Quintana M et al., 2002, Curr Biol, Vol. 12, p. 735-739. Also, "hsa-mir-149" (miRBase Accession No. MI0000478, SEQ ID NO: 257) having a hairpin-like structure is known as a precursor of "hsa-miR-149-3p".

The term "hsa-miR-937-5p gene" or "hsa-miR-937-5p" used herein includes the hsa-miR-937-5p gene (miRBase Accession No. MIMAT0022938) shown in SEQ ID NO: 8, a homolog or an ortholog thereof of a different organism species, and the like. The gene can be obtained by a method described in Lui W O et al., 2007, Cancer Res, Vol. 67, p. 6031-6043. Also, "hsa-mir-937" (miRBase Accession No. MI0005759, SEQ ID NO: 258) having a hairpin-like structure is known as a precursor of "hsa-miR-937-5p".

The term "hsa-miR-4675 gene" or "hsa-miR-4675" used herein includes the hsa-miR-4675 gene (miRBase Accession No. MIMAT0019757) shown in SEQ ID NO: 9, a homolog or an ortholog thereof of a different organism species, and the like. The gene can be obtained by a method described in Persson H et al., 2011, Cancer Res, Vol. 71, p. 78-86. Also, "hsa-mir-4675" (miRBase Accession No. MI0017306, SEQ ID NO: 259) having a hairpin-like structure is known as a precursor of "hsa-miR-4675".

The term "hsa-miR-6795-5p gene" or "hsa-miR-6795-5p" used herein includes the hsa-miR-6795-5p gene (miRBase Accession No. MIMAT0027490) shown in SEQ ID NO: 10, a homolog or an ortholog thereof of a different organism species, and the like. The gene can be obtained by a method described in Ladewig E et al., 2012, Genome Res, Vol. 22, p. 1634-1645. Also, "hsa-mir-6795" (miRBase Accession No. MI0022640, SEQ ID NO: 260) having a hairpin-like structure is known as a precursor of "hsa-miR-6795-5p".

The term "hsa-miR-4731-5p gene" or "hsa-miR-4731-5p" used herein includes the hsa-miR-4731-5p gene (miRBase Accession No. MIMAT0019853) shown in SEQ ID NO: 11, a homolog or an ortholog thereof of a different organism species, and the like. The gene can be obtained by a method described in Persson H et al., 2011, Cancer Res, Vol. 71, p. 78-86. Also, "hsa-mir-4731" (miRBase Accession No. MI0017368, SEQ ID NO: 261) having a hairpin-like structure is known as a precursor of "hsa-miR-4731-5p".

The term "hsa-miR-5090 gene" or "hsa-miR-5090" used herein includes the hsa-miR-5090 gene (miRBase Accession No. MIMAT0021082) shown in SEQ ID NO: 12, a homolog or an ortholog thereof of a different organism species, and the like. The gene can be obtained by a method described in Ding N et al., 2011, J Radiat Res, Vol. 52, p. 425-432. Also, "hsa-mir-5090" (miRBase Accession No. MI0017979, SEQ ID NO: 262) having a hairpin-like structure is known as a precursor of "hsa-miR-5090".

The term "hsa-miR-3620-5p gene" or "hsa-miR-3620-5p" used herein includes the hsa-miR-3620-5p gene (miRBase Accession No. MIMAT0022967) shown in SEQ ID NO: 13, a homolog or an ortholog thereof of a different organism species, and the like. The gene can be obtained by a method described in Witten D et al., 2010, BMC Biol, Vol. 8, p. 58. Also, "hsa-mir-3620" (miRBase Accession No. MI0016011, SEQ ID NO: 263) having a hairpin-like structure is known as a precursor of "hsa-miR-3620-5p".

The term "hsa-miR-1343-5p gene" or "hsa-miR-1343-5p" used herein includes the hsa-miR-1343-5p gene (miRBase Accession No. MIMAT0027038) shown in SEQ ID NO: 14, a homolog or an ortholog thereof of a different organism species, and the like. The gene can be obtained by a method described in Persson H et al., 2011, Cancer Res, Vol. 71, p. 78-86. Also, "hsa-mir-1343" (miRBase Accession No. MI0017320, SEQ ID NO: 264) having a hairpin-like structure is known as a precursor of "hsa-miR-1343-5p".

The term "hsa-miR-6717-5p gene" or "hsa-miR-6717-5p" used herein includes the hsa-miR-6717-5p gene (miRBase Accession No. MIMAT0025846) shown in SEQ ID NO: 15, a homolog or an ortholog thereof of a different organism species, and the like. The gene can be obtained by a method described in Li Y et al., 2012, Gene, Vol. 497, p. 330-335. Also, "hsa-mir-6717" (miRBase Accession No. MI0022551, SEQ ID NO: 265) having a hairpin-like structure is known as a precursor of "hsa-miR-6717-5p".

The term "hsa-miR-6825-5p gene" or "hsa-miR-6825-5p" used herein includes the hsa-miR-6825-5p gene (miRBase Accession No. MIMAT0027550) shown in SEQ ID NO: 16, a homolog or an ortholog thereof of a different organism species, and the like. The gene can be obtained by a method described in Ladewig E et al., 2012, Genome Res, Vol. 22, p. 1634-1645. Also, "hsa-mir-6825" (miRBase Accession No. MI0022670, SEQ ID NO: 266) having a hairpin-like structure is known as a precursor of "hsa-miR-6825-5p".

The term "hsa-miR-6738-5p gene" or "hsa-miR-6738-5p" used herein includes the hsa-miR-6738-5p gene (miRBase Accession No. MIMAT0027377) shown in SEQ ID NO: 17, a homolog or an ortholog thereof of a different organism species, and the like. The gene can be obtained by a method described in Ladewig E et al., 2012, Genome Res, Vol. 22, p. 1634-1645. Also, "hsa-mir-6738" (miRBase Accession No. MI0022583, SEQ ID NO: 267) having a hairpin-like structure is known as a precursor of "hsa-miR-6738-5p".

The term "hsa-miR-6769a-5p gene" or "hsa-miR-6769a-5p" used herein includes the hsa-miR-6769a-5p gene (miRBase Accession No. MIMAT0027438) shown in SEQ ID NO: 18, a homolog or an ortholog thereof of a different organism species, and the like. The gene can be obtained by a method described in Ladewig E et al., 2012, Genome Res, Vol. 22, p. 1634-1645. Also, "hsa-mir-6769a" (miRBase Accession No. MI0022614, SEQ ID NO: 268) having a hairpin-like structure is known as a precursor of "hsa-miR-6769a-5p".

The term "hsa-miR-4728-5p gene" or "hsa-miR-4728-5p" used herein includes the hsa-miR-4728-5p gene (miRBase Accession No. MIMAT0019849) shown in SEQ ID NO: 19, a homolog or an ortholog thereof of a different organism species, and the like. The gene can be obtained by a method described in Persson H et al., 2011, Cancer Res, Vol. 71, p. 78-86. Also, "hsa-mir-4728" (miRBase Accession No. MI0017365, SEQ ID NO: 269) having a hairpin-like structure is known as a precursor of "hsa-miR-4728-5p".

The term "hsa-miR-652-5p gene" or "hsa-miR-652-5p" used herein includes the hsa-miR-652-5p gene (miRBase Accession No. MIMAT0022709) shown in SEQ ID NO: 20, a homolog or an ortholog thereof of a different organism species, and the like. The gene can be obtained by a method described in Cummins J M et al., 2006, Proc Natl Acad Sci USA, Vol. 103, p. 3687-3692. Also, "hsa-mir-652" (miRBase Accession No. MI0003667, SEQ ID NO: 270) having a hairpin-like structure is known as a precursor of "hsa-miR-652-5p".

The term "hsa-miR-4257 gene" or "hsa-miR-4257" used herein includes the hsa-miR-4257 gene (miRBase Accession No. MIMAT0016878) shown in SEQ ID NO: 21, a homolog or an ortholog thereof of a different organism species, and the like. The gene can be obtained by a method described in Goff L A et al., 2009, PLoS One, Vol. 4, e7192. Also, "hsa-mir-4257" (miRBase Accession No. MI0015856, SEQ ID NO: 271) having a hairpin-like structure is known as a precursor of "hsa-miR-4257".

The term "hsa-miR-6785-5p gene" or "hsa-miR-6785-5p" used herein includes the hsa-miR-6785-5p gene (miRBase Accession No. MIMAT0027470) shown in SEQ ID NO: 22, a homolog or an ortholog thereof of a different organism species, and the like. The gene can be obtained by a method described in Ladewig E et al., 2012, Genome Res, Vol. 22, p. 1634-1645. Also, "hsa-mir-6785" (miRBase Accession No. MI0022630, SEQ ID NO: 272) having a hairpin-like structure is known as a precursor of "hsa-miR-6785-5p".

The term "hsa-miR-7110-5p gene" or "hsa-miR-7110-5p" used herein includes the hsa-miR-7110-5p gene (miRBase Accession No. MIMAT0028117) shown in SEQ ID NO: 23, a homolog or an ortholog thereof of a different organism species, and the like. The gene can be obtained by a method described in Ladewig E et al., 2012, Genome Res, Vol. 22, p. 1634-1645. Also, "hsa-mir-7110" (miRBase Accession No. MI0022961, SEQ ID NO: 273) having a hairpin-like structure is known as a precursor of "hsa-miR-7110-5p".

The term "hsa-miR-6887-5p gene" or "hsa-miR-6887-5p" used herein includes the hsa-miR-6887-5p gene (miRBase Accession No. MIMAT0027674) shown in SEQ ID NO: 24, a homolog or an ortholog thereof of a different organism species, and the like. The gene can be obtained by a method described in Ladewig E et al., 2012, Genome Res, Vol. 22, p. 1634-1645. Also, "hsa-mir-6887" (miRBase Accession No. MI0022734, SEQ ID NO: 274) having a hairpin-like structure is known as a precursor of "hsa-miR-6887-5p".

The term "hsa-miR-887-3p gene" or "hsa-miR-887-3p" used herein includes the hsa-miR-887-3p gene (miRBase Accession No. MIMAT0004951) shown in SEQ ID NO: 25, a homolog or an ortholog thereof of a different organism species, and the like. The gene can be obtained by a method described in Berezikov E et al., 2006, Genome Res, Vol. 16, p. 1289-1298. Also, "hsa-mir-887" (miRBase Accession No. MI0005562, SEQ ID NO: 275) having a hairpin-like structure is known as a precursor of "hsa-miR-887-3p".

The term "hsa-miR-1228-5p gene" or "hsa-miR-1228-5p" used herein includes the hsa-miR-1228-5p gene (miRBase Accession No. MIMAT0005582) shown in SEQ ID NO: 26, a homolog or an ortholog thereof of a different organism species, and the like. The gene can be obtained by a method described in Berezikov E et al., 2007, Mol Cell, Vol. 28, p. 328-336. Also, "hsa-mir-1228" (miRBase Accession No. MI0006318, SEQ ID NO: 276) having a hairpin-like structure is known as a precursor of "hsa-miR-1228-5p".

The term "hsa-miR-5572 gene" or "hsa-miR-5572" used herein includes the hsa-miR-5572 gene (miRBase Accession No. MIMAT0022260) shown in SEQ ID NO: 27, a homolog or an ortholog thereof of a different organism species, and the like. The gene can be obtained by a method described in Tandon M et al., 2012, Oral Dis, Vol. 18, p. 127-131. Also, "hsa-mir-5572" (miRBase Accession No. MI0019117, SEQ ID NO: 277) having a hairpin-like structure is known as a precursor of "hsa-miR-5572".

The term "hsa-miR-6782-5p gene" or "hsa-miR-6782-5p" used herein includes the hsa-miR-6782-5p gene (miRBase Accession No. MIMAT0027464) shown in SEQ ID NO: 28, a homolog or an ortholog thereof of a different organism species, and the like. The gene can be obtained by a method described in Ladewig E et al., 2012, Genome Res, Vol. 22, p. 1634-1645. Also, "hsa-mir-6782" (miRBase Accession No. MI0022627, SEQ ID NO: 278) having a hairpin-like structure is known as a precursor of "hsa-miR-6782-5p".

The term "hsa-miR-4298 gene" or "hsa-miR-4298" used herein includes the hsa-miR-4298 gene (miRBase Accession No. MIMAT0016852) shown in SEQ ID NO: 29, a homolog or an ortholog thereof of a different organism species, and the like. The gene can be obtained by a method described in Goff L A et al., 2009, PLoS One, Vol. 4, e7192. Also, "hsa-mir-4298" (miRBase Accession No. MI0015830, SEQ ID NO: 279) having a hairpin-like structure is known as a precursor of "hsa-miR-4298".

The term "hsa-miR-6786-5p gene" or "hsa-miR-6786-5p" used herein includes the hsa-miR-6786-5p gene (miRBase Accession No. MIMAT0027472) shown in SEQ ID NO: 30, a homolog or an ortholog thereof of a different organism species, and the like. The gene can be obtained by a method described in Ladewig E et al., 2012, Genome Res, Vol. 22, p. 1634-1645. Also, "hsa-mir-6786" (miRBase Accession No. MI0022631, SEQ ID NO: 280) having a hairpin-like structure is known as a precursor of "hsa-miR-6786-5p".

The term "hsa-miR-5010-5p gene" or "hsa-miR-5010-5p" used herein includes the hsa-miR-5010-5p gene (miRBase Accession No. MIMAT0021043) shown in SEQ ID NO: 31, a homolog or an ortholog thereof of a different organism species, and the like. The gene can be obtained by a method described in Hansen T B et al., 2011, RNA Biol, Vol. 8, p. 378-383. Also, "hsa-mir-5010" (miRBase Accession No. MI0017878, SEQ ID NO: 281) having a hairpin-like structure is known as a precursor of "hsa-miR-5010-5p".

The term "hsa-miR-6087 gene" or "hsa-miR-6087" used herein includes the hsa-miR-6087 gene (miRBase Accession No. MIMAT0023712) shown in SEQ ID NO: 32, a homolog or an ortholog thereof of a different organism species, and the like. The gene can be obtained by a method described in Yoo J K et al., 2012, Stem Cells Dev, Vol. 21, p. 2049-2057. Also, "hsa-mir-6087" (miRBase Accession No. MI0020364, SEQ ID NO: 282) having a hairpin-like structure is known as a precursor of "hsa-miR-6087".

The term "hsa-miR-6765-5p gene" or "hsa-miR-6765-5p" used herein includes the hsa-miR-6765-5p gene (miRBase Accession No. MIMAT0027430) shown in SEQ ID NO: 33, a homolog or an ortholog thereof of a different organism species, and the like. The gene can be obtained by a method described in Ladewig E et al., 2012, Genome Res, Vol. 22, p. 1634-1645. Also, "hsa-mir-6765" (miRBase Accession No. MI0022610, SEQ ID NO: 283) having a hairpin-like structure is known as a precursor of "hsa-miR-6765-5p".

The term "hsa-miR-6732-5p gene" or "hsa-miR-6732-5p" used herein includes the hsa-miR-6732-5p gene (miRBase Accession No. MIMAT0027365) shown in SEQ ID NO: 34, a homolog or an ortholog thereof of a different organism species, and the like. The gene can be obtained by a method described in Ladewig E et al., 2012, Genome Res, Vol. 22, p. 1634-1645. Also, "hsa-mir-6732" (miRBase Accession No. MI0022577, SEQ ID NO: 284) having a hairpin-like structure is known as a precursor of "hsa-miR-6732-5p".

The term "hsa-miR-6787-5p gene" or "hsa-miR-6787-5p" used herein includes the hsa-miR-6787-5p gene (miRBase Accession No. MIMAT0027474) shown in SEQ ID NO: 35, a homolog or an ortholog thereof of a different organism species, and the like. The gene can be obtained by a method described in Ladewig E et al., 2012, Genome Res, Vol. 22, p. 1634-1645. Also, "hsa-mir-6787" (miRBase Accession No. MI0022632, SEQ ID NO: 285) having a hairpin-like structure is known as a precursor of "hsa-miR-6787-5p".

The term "hsa-miR-6737-5p gene" or "hsa-miR-6737-5p" used herein includes the hsa-miR-6737-5p gene (miRBase Accession No. MIMAT0027375) shown in SEQ ID NO: 36, a homolog or an ortholog thereof of a different organism species, and the like. The gene can be obtained by a method described in Ladewig E et al., 2012, Genome Res, Vol. 22, p. 1634-1645. Also, "hsa-mir-6737" (miRBase Accession No. MI0022582, SEQ ID NO: 286) having a hairpin-like structure is known as a precursor of "hsa-miR-6737-5p".

The term "hsa-miR-128-2-5p gene" or "hsa-miR-128-2-5p" used herein includes the hsa-miR-128-2-5p gene (miRBase Accession No. MIMAT0031095) shown in SEQ ID NO: 37, a homolog or an ortholog thereof of a different organism species, and the like. The gene can be obtained by a method described in Lagos-Quintana M et al., 2002, Curr Biol, Vol. 12, p. 735-739. Also, "hsa-mir-128-2" (miRBase Accession No. MI0000727, SEQ ID NO: 287) having a hairpin-like structure is known as a precursor of "hsa-miR-128-2-5p".

The term "hsa-miR-4270 gene" or "hsa-miR-4270" used herein includes the hsa-miR-4270 gene (miRBase Accession No. MIMAT0016900) shown in SEQ ID NO: 38, a homolog or an ortholog thereof of a different organism species, and the like. The gene can be obtained by a method described in Goff L A et al., 2009, PLoS One, Vol. 4, e7192. Also, "hsa-mir-4270" (miRBase Accession No. MI0015878, SEQ ID NO: 288) having a hairpin-like structure is known as a precursor of "hsa-miR-4270".

The term "hsa-miR-6861-5p gene" or "hsa-miR-6861-5p" used herein includes the hsa-miR-6861-5p gene (miRBase Accession No. MIMAT0027623) shown in SEQ ID NO: 39, a homolog or an ortholog thereof of a different organism species, and the like. The gene can be obtained by a method described in Ladewig E et al., 2012, Genome Res, Vol. 22, p. 1634-1645. Also, "hsa-mir-6861" (miRBase Accession No. MI0022708, SEQ ID NO: 289) having a hairpin-like structure is known as a precursor of "hsa-miR-6861-5p".

The term "hsa-miR-6756-5p gene" or "hsa-miR-6756-5p" used herein includes the hsa-miR-6756-5p gene (miRBase Accession No. MIMAT0027412) shown in SEQ ID NO: 40, a homolog or an ortholog thereof of a different organism species, and the like. The gene can be obtained by a method described in Ladewig E et al., 2012, Genome Res, Vol. 22, p. 1634-1645. Also, "hsa-mir-6756" (miRBase Accession No. MI0022601, SEQ ID NO: 290) having a hairpin-like structure is known as a precursor of "hsa-miR-6756-5p".

The term "hsa-miR-1229-5p gene" or "hsa-miR-1229-5p" used herein includes the hsa-miR-1229-5p gene (miRBase Accession No. MIMAT0022942) shown in SEQ ID NO: 41, a homolog or an ortholog thereof of a different organism species, and the like. The gene can be obtained by a method described in Berezikov E et al., 2007, Mol Cell, Vol. 28, p. 328-336. Also, "hsa-mir-1229" (miRBase Accession No. MI0006319, SEQ ID NO: 291) having a hairpin-like structure is known as a precursor of "hsa-miR-1229-5p".

The term "hsa-miR-6891-5p gene" or "hsa-miR-6891-5p" used herein includes the hsa-miR-6891-5p gene (miRBase Accession No. MIMAT0027682) shown in SEQ ID NO: 42, a homolog or an ortholog thereof of a different organism species, and the like. The gene can be obtained by a method described in Ladewig E et al., 2012, Genome Res, Vol. 22, p. 1634-1645. Also, "hsa-mir-6891" (miRBase Accession No. MI0022738, SEQ ID NO: 292) having a hairpin-like structure is known as a precursor of "hsa-miR-6891-5p".

The term "hsa-miR-6848-5p gene" or "hsa-miR-6848-5p" used herein includes the hsa-miR-6848-5p gene (miRBase Accession No. MIMAT0027596) shown in SEQ ID NO: 43, a homolog or an ortholog thereof of a different organism species, and the like. The gene can be obtained by a method described in Ladewig E et al., 2012, Genome Res, Vol. 22, p. 1634-1645. Also, "hsa-mir-6848" (miRBase Accession No. MI0022694, SEQ ID NO: 293) having a hairpin-like structure is known as a precursor of "hsa-miR-6848-5p".

The term "hsa-miR-1237-5p gene" or "hsa-miR-1237-5p" used herein includes the hsa-miR-1237-5p gene (miRBase Accession No. MIMAT0022946) shown in SEQ ID NO: 44, a homolog or an ortholog thereof of a different organism species, and the like. The gene can be obtained by a method described in Berezikov E et al., 2007, Mol Cell, Vol. 28, p. 328-336. Also, "hsa-mir-1237" (miRBase Accession No. MI0006327, SEQ ID NO: 294) having a hairpin-like structure is known as a precursor of "hsa-miR-1237-5p".

The term "hsa-miR-30c-1-3p gene" or "hsa-miR-30c-1-3p" used herein includes the hsa-miR-30c-1-3p gene (miRBase Accession No. MIMAT0004674) shown in SEQ ID NO: 45, a homolog or an ortholog thereof of a different organism species, and the like. The gene can be obtained by a method described in Lagos-Quintana M et al., 2002, Curr Biol, Vol. 12, p. 735-739. Also, "hsa-mir-30c-1" (miRBase Accession No. MI0000736, SEQ ID NO: 295) having a hairpin-like structure is known as a precursor of "hsa-miR-30c-1-3p".

The term "hsa-miR-1233-5p gene" or "hsa-miR-1233-5p" used herein includes the hsa-miR-1233-5p gene (miRBase Accession No. MIMAT0022943) shown in SEQ ID NO: 46, a homolog or an ortholog thereof of a different organism species, and the like. The gene can be obtained by a method described in Berezikov E et al., 2007, Mol Cell, Vol. 28, p. 328-336. Also, "hsa-mir-1233-1 and hsa-mir-1233-2" (miRBase Accession Nos. MI0006323 and MI0015973, SEQ ID NOs: 296 and 297) having a hairpin-like structure are known as a precursor of "hsa-miR-1233-5p".

The term "hsa-miR-211-3p gene" or "hsa-miR-211-3p" used herein includes the hsa-miR-211-3p gene (miRBase Accession No. MIMAT0022694) shown in SEQ ID NO: 47, a homolog or an ortholog thereof of a different organism species, and the like. The gene can be obtained by a method described in Lim L P et al., 2003, Science, Vol. 299, p. 1540. Also, "hsa-mir-211" (miRBase Accession No. MI0000287, SEQ ID NO: 298) having a hairpin-like structure is known as a precursor of "hsa-miR-211-3p".

The term "hsa-miR-4758-5p gene" or "hsa-miR-4758-5p" used herein includes the hsa-miR-4758-5p gene (miRBase Accession No. MIMAT0019903) shown in SEQ ID NO: 48, a homolog or an ortholog thereof of a different organism species, and the like. The gene can be obtained by a method described in Persson H et al., 2011, Cancer Res, Vol. 71, p. 78-86. Also, "hsa-mir-4758" (miRBase Accession No. MI0017399, SEQ ID NO: 299) having a hairpin-like structure is known as a precursor of "hsa-miR-4758-5p".

The term "hsa-miR-614 gene" or "hsa-miR-614" used herein includes the hsa-miR-614 gene (miRBase Accession No. MIMAT0003282) shown in SEQ ID NO: 49, a homolog or an ortholog thereof of a different organism species, and the like. The gene can be obtained by a method described in Cummins J M et al., 2006, Proc Natl Acad Sci USA, VOL. 103, p. 3687-3692. Also, "hsa-mir-614" (miRBase Accession No. MI0003627, SEQ ID NO: 300) having a hairpin-like structure is known as a precursor of "hsa-miR-614".

The term "hsa-miR-6746-5p gene" or "hsa-miR-6746-5p" used herein includes the hsa-miR-6746-5p gene (miRBase Accession No. MIMAT0027392) shown in SEQ ID NO: 50, a homolog or an ortholog thereof of a different organism species, and the like. The gene can be obtained by a method described in Ladewig E et al., 2012, Genome Res, Vol. 22, p. 1634-1645. Also, "hsa-mir-6746" (miRBase Accession No. MI0022591, SEQ ID NO: 301) having a hairpin-like structure is known as a precursor of "hsa-miR-6746-5p".

The term "hsa-miR-1915-5p gene" or "hsa-miR-1915-5p" used herein includes the hsa-miR-1915-5p gene (miRBase Accession No. MIMAT0007891) shown in SEQ ID NO: 51, a homolog or an ortholog thereof of a different organism species, and the like. The gene can be obtained by a method described in Bar M et al., 2008, Stem Cells, Vol. 26, p. 2496-2505. Also, "hsa-mir-1915" (miRBase Accession No. MI0008336, SEQ ID NO: 302) having a hairpin-like structure is known as a precursor of "hsa-miR-1915-5p".

The term "hsa-miR-4688 gene" or "hsa-miR-4688" used herein includes the hsa-miR-4688 gene (miRBase Accession No. MIMAT0019777) shown in SEQ ID NO: 52, a homolog or an ortholog thereof of a different organism species, and the like. The gene can be obtained by a method described in Persson H et al., 2011, Cancer Res, Vol. 71, p. 78-86. Also, "hsa-mir-4688" (miRBase Accession No. MI0017321, SEQ ID NO: 303) having a hairpin-like structure is known as a precursor of "hsa-miR-4688".

The term "hsa-miR-3917 gene" or "hsa-miR-3917" used herein includes the hsa-miR-3917 gene (miRBase Accession No. MIMAT0018191) shown in SEQ ID NO: 53, a homolog or an ortholog thereof of a different organism species, and the like. The gene can be obtained by a method described in Creighton C J et al., 2010, PLoS One, Vol. 5, e9637. Also, "hsa-mir-3917" (miRBase Accession No. MI0016423, SEQ ID NO: 304) having a hairpin-like structure is known as a precursor of "hsa-miR-3917".

The term "hsa-miR-5787 gene" or "hsa-miR-5787" used herein includes the hsa-miR-5787 gene (miRBase Accession No. MIMAT0023252) shown in SEQ ID NO: 54, a homolog or an ortholog thereof of a different organism species, and the like. The gene can be obtained by a method described in Yoo H et al., 2011, Biochem Biophys Res Commun, Vol. 415, p. 567-572. Also, "hsa-mir-5787" (miRBase Accession No. MI0019797, SEQ ID NO: 305) having a hairpin-like structure is known as a precursor of "hsa-miR-5787".

The term "hsa-miR-4632-5p gene" or "hsa-miR-4632-5p" used herein includes the hsa-miR-4632-5p gene (miRBase Accession No. MIMAT0022977) shown in SEQ ID NO: 55, a homolog or an ortholog thereof of a different organism species, and the like. The gene can be obtained by a method described in Persson H et al., 2011, Cancer Res, Vol. 71, p. 78-86. Also, "hsa-mir-4632" (miRBase Accession No. MI0017259, SEQ ID NO: 306) having a hairpin-like structure is known as a precursor of "hsa-miR-4632-5p".

The term "hsa-miR-6126 gene" or "hsa-miR-6126" used herein includes the hsa-miR-6126 gene (miRBase Accession No. MIMAT0024599) shown in SEQ ID NO: 56, a homolog or an ortholog thereof of a different organism species, and the like. The gene can be obtained by a method described in Smith J L et al., 2012, J Virol, Vol. 86, p. 5278-5287. Also, "hsa-mir-6126" (miRBase Accession No. MI0021260, SEQ ID NO: 307) having a hairpin-like structure is known as a precursor of "hsa-miR-6126".

The term "hsa-miR-135a-3p gene" or "hsa-miR-135a-3p" used herein includes the hsa-miR-135a-3p gene (miRBase Accession No. MIMAT0004595) shown in SEQ ID NO: 57, a homolog or an ortholog thereof of a different organism species, and the like. The gene can be obtained by a method described in Lagos-Quintana M et al., 2002, Curr Biol, Vol. 12, p. 735-739. Also, "hsa-mir-135a-1" (miRBase Accession No. MI0000452, SEQ ID NO: 308) having a hairpin-like structure is known as a precursor of "hsa-miR-135a-3p".

The term "hsa-miR-8063 gene" or "hsa-miR-8063" used herein includes the hsa-miR-8063 gene (miRBase Accession No. MIMAT0030990) shown in SEQ ID NO: 58, a homolog or an ortholog thereof of a different organism species, and the like. The gene can be obtained by a method described in Wang H J et al., 2013, Shock, Vol. 39, p. 480-487. Also, "hsa-mir-8063" (miRBase Accession No. MI0025899, SEQ ID NO: 309) having a hairpin-like structure is known as a precursor of "hsa-miR-8063".

The term "hsa-miR-5698 gene" or "hsa-miR-5698" used herein includes the hsa-miR-5698 gene (miRBase Accession No. MIMAT0022491) shown in SEQ ID NO: 59, a homolog or an ortholog thereof of a different organism species, and the like. The gene can be obtained by a method described in Watahiki A et al., 2011, PLoS One, Vol. 6, e24950. Also, "hsa-mir-5698" (miRBase Accession No. MI0019305, SEQ ID NO: 310) having a hairpin-like structure is known as a precursor of "hsa-miR-5698".

The term "hsa-miR-6089 gene" or "hsa-miR-6089" used herein includes the hsa-miR-6089 gene (miRBase Accession No. MIMAT0023714) shown in SEQ ID NO: 60, a homolog or an ortholog thereof of a different organism species, and the like. The gene can be obtained by a method described in Yoo J K et al., 2012, Stem Cells Dev, Vol. 21, p. 2049-2057. Also, "hsa-mir-6089-1 and hsa-mir-6089-2" (miRBase Accession Nos. MI0020366 and MI0023563, SEQ ID NOs: 311 and 312) having a hairpin-like structure are known as a precursor of "hsa-miR-6089".

The term "hsa-miR-498 gene" or "hsa-miR-498" used herein includes the hsa-miR-498 gene (miRBase Accession No. MIMAT0002824) shown in SEQ ID NO: 61, a homolog or an ortholog thereof of a different organism species, and the like. The gene can be obtained by a method described in Bentwich I et al., 2005, Nat Genet, Vol. 37, p. 766-770. Also, "hsa-mir-498" (miRBase Accession No. MI0003142, SEQ ID NO: 313) having a hairpin-like structure is known as a precursor of "hsa-miR-498".

The term "hsa-miR-296-3p gene" or "hsa-miR-296-3p" used herein includes the hsa-miR-296-3p gene (miRBase Accession No. MIMAT0004679) shown in SEQ ID NO: 62, a homolog or an ortholog thereof of a different organism species, and the like. The gene can be obtained by a method described in Houbaviy H B et al., 2003, Dev Cell, Vol. 5, p. 351-358. Also, "hsa-mir-296" (miRBase Accession No. MI0000747, SEQ ID NO: 314) having a hairpin-like structure is known as a precursor of "hsa-miR-296-3p".

The term "hsa-miR-4419b gene" or "hsa-miR-4419b" used herein includes the hsa-miR-4419b gene (miRBase Accession No. MIMAT0019034) shown in SEQ ID NO: 63, a homolog or an ortholog thereof of a different organism species, and the like. The gene can be obtained by a method described in Jima D D et al., 2010, Blood, Vol. 116, e118-e127. Also, "hsa-mir-4419b" (miRBase Accession No. MI0016861, SEQ ID NO: 315) having a hairpin-like structure is known as a precursor of "hsa-miR-4419b".

The term "hsa-miR-6802-5p gene" or "hsa-miR-6802-5p" used herein includes the hsa-miR-6802-5p gene (miRBase Accession No. MIMAT0027504) shown in SEQ ID NO: 64, a homolog or an ortholog thereof of a different organism species, and the like. The gene can be obtained by a method described in Ladewig E et al., 2012, Genome Res, Vol. 22, p. 1634-1645. Also, "hsa-mir-6802" (miRBase Accession No. MI0022647, SEQ ID NO: 316) having a hairpin-like structure is known as a precursor of "hsa-miR-6802-5p".

The term "hsa-miR-6829-5p gene" or "hsa-miR-6829-5p" used herein includes the hsa-miR-6829-5p gene (miRBase Accession No. MIMAT0027558) shown in SEQ ID NO: 65, a homolog or an ortholog thereof of a different organism species, and the like. The gene can be obtained by a method described in Ladewig E et al., 2012, Genome Res, Vol. 22, p. 1634-1645. Also, "hsa-mir-6829" (miRBase Accession No. MI0022674, SEQ ID NO: 317) having a hairpin-like structure is known as a precursor of "hsa-miR-6829-5p".

The term "hsa-miR-6803-5p gene" or "hsa-miR-6803-5p" used herein includes the hsa-miR-6803-5p gene (miRBase Accession No. MIMAT0027506) shown in SEQ ID NO: 66, a homolog or an ortholog thereof of a different organism species, and the like. The gene can be obtained by a method described in Ladewig E et al., 2012, Genome Res, Vol. 22, p. 1634-1645. Also, "hsa-mir-6803" (miRBase Accession No. MI0022648, SEQ ID NO: 318) having a hairpin-like structure is known as a precursor of "hsa-miR-6803-5p".

The term "hsa-miR-1199-5p gene" or "hsa-miR-1199-5p" used herein includes the hsa-miR-1199-5p gene (miRBase Accession No. MIMAT0031119) shown in SEQ ID NO: 67, a homolog or an ortholog thereof of a different organism species, and the like. The gene can be obtained by a method described in Salvi A et al., 2013, Int J Oncol, Vol. 42, p. 391-402. Also, "hsa-mir-1199" (miRBase Accession No. MI0020340, SEQ ID NO: 319) having a hairpin-like structure is known as a precursor of "hsa-miR-1199-5p".

The term "hsa-miR-6840-3p gene" or "hsa-miR-6840-3p" used herein includes the hsa-miR-6840-3p gene (miRBase Accession No. MIMAT0027583) shown in SEQ ID NO: 68, a homolog or an ortholog thereof of a different organism species, and the like. The gene can be obtained by a method described in Ladewig E et al., 2012, Genome Res, Vol. 22, p. 1634-1645. Also, "hsa-mir-6840" (miRBase Accession No. MI0022686, SEQ ID NO: 320) having a hairpin-like structure is known as a precursor of "hsa-miR-6840-3p".

The term "hsa-miR-6752-5p gene" or "hsa-miR-6752-5p" used herein includes the hsa-miR-6752-5p gene (miRBase Accession No. MIMAT0027404) shown in SEQ ID NO: 69, a homolog or an ortholog thereof of a different organism species, and the like. The gene can be obtained by a method described in Ladewig E et al., 2012, Genome Res, Vol. 22, p. 1634-1645. Also, "hsa-mir-6752" (miRBase Accession No. MI0022597, SEQ ID NO: 321) having a hairpin-like structure is known as a precursor of "hsa-miR-6752-5p".

The term "hsa-miR-6798-5p gene" or "hsa-miR-6798-5p" used herein includes the hsa-miR-6798-5p gene (miRBase Accession No. MIMAT0027496) shown in SEQ ID NO: 70, a homolog or an ortholog thereof of a different organism species, and the like. The gene can be obtained by a method described in Ladewig E et al., 2012, Genome Res, Vol. 22, p. 1634-1645. Also, "hsa-mir-6798" (miRBase Accession No. MI0022643, SEQ ID NO: 322) having a hairpin-like structure is known as a precursor of "hsa-miR-6798-5p".

The term "hsa-miR-6131 gene" or "hsa-miR-6131" used herein includes the hsa-miR-6131 gene (miRBase Accession No. MIMAT0024615) shown in SEQ ID NO: 71, a homolog or an ortholog thereof of a different organism species, and the like. The gene can be obtained by a method described in Dannemann M et al., 2012, Genome Biol Evol, Vol. 4, p. 552-564. Also, "hsa-mir-6131" (miRBase Accession No. MI0021276, SEQ ID NO: 323) having a hairpin-like structure is known as a precursor of "hsa-miR-6131".

The term "hsa-miR-4667-5p gene" or "hsa-miR-4667-5p" used herein includes the hsa-miR-4667-5p gene (miRBase Accession No. MIMAT0019743) shown in SEQ ID NO: 72, a homolog or an ortholog thereof of a different organism species, and the like. The gene can be obtained by a method described in Persson H et al., 2011, Cancer Res, Vol. 71, p. 78-86. Also, "hsa-mir-4667" (miRBase Accession No. MI0017297, SEQ ID NO: 324) having a hairpin-like structure is known as a precursor of "hsa-miR-4667-5p".

The term "hsa-miR-6510-5p gene" or "hsa-miR-6510-5p" used herein includes the hsa-miR-6510-5p gene (miRBase Accession No. MIMAT0025476) shown in SEQ ID NO: 73, a homolog or an ortholog thereof of a different organism species, and the like. The gene can be obtained by a method described in Joyce C E et al., 2011, Hum Mol Genet, Vol. 20, p. 4025-4040. Also, "hsa-mir-6510" (miRBase Accession No. MI0022222, SEQ ID NO: 325) having a hairpin-like structure is known as a precursor of "hsa-miR-6510-5p".

The term "hsa-miR-4690-5p gene" or "hsa-miR-4690-5p" used herein includes the hsa-miR-4690-5p gene (miRBase Accession No. MIMAT0019779) shown in SEQ ID NO: 74, a homolog or an ortholog thereof of a different organism species, and the like. The gene can be obtained by a method described in Persson H et al., 2011, Cancer Res, Vol. 71, p. 78-86. Also, "hsa-mir-4690" (miRBase Accession No. MI0017323, SEQ ID NO: 326) having a hairpin-like structure is known as a precursor of "hsa-miR-4690-5p".

The term "hsa-miR-920 gene" or "hsa-miR-920" used herein includes the hsa-miR-920 gene (miRBase Accession No. MIMAT0004970) shown in SEQ ID NO: 75, a homolog or an ortholog thereof of a different organism species, and the like. The gene can be obtained by a method described in Novotny G W et al., 2007, Int J Androl, Vol. 30, p. 316-326. Also, "hsa-mir-920" (miRBase Accession No. MI0005712, SEQ ID NO: 327) having a hairpin-like structure is known as a precursor of "hsa-miR-920".

The term "hsa-miR-23b-3p gene" or "hsa-miR-23b-3p" used herein includes the hsa-miR-23b-3p gene (miRBase Accession No. MIMAT0000418) shown in SEQ ID NO: 76, a homolog or an ortholog thereof of a different organism species, and the like. The gene can be obtained by a method described in Lagos-Quintana M et al., 2002, Curr Biol, Vol. 12, p. 735-739. Also, "hsa-mir-23b" (miRBase Accession No. MI0000439, SEQ ID NO: 328) having a hairpin-like structure is known as a precursor of "hsa-miR-23b-3p".

The term "hsa-miR-4448 gene" or "hsa-miR-4448" used herein includes the hsa-miR-4448 gene (miRBase Accession No. MIMAT0018967) shown in SEQ ID NO: 77, a homolog or an ortholog thereof of a different organism species, and the like. The gene can be obtained by a method described in Jima D D et al., 2010, Blood, Vol. 116, e118-e127. Also, "hsa-mir-4448" (miRBase Accession No. MI0016791, SEQ ID NO: 329) having a hairpin-like structure is known as a precursor of "hsa-miR-4448".

The term "hsa-miR-2110 gene" or "hsa-miR-2110" used herein includes the hsa-miR-2110 gene (miRBase Accession No. MIMAT0010133) shown in SEQ ID NO: 78, a homolog or an ortholog thereof of a different organism species, and the like. The gene can be obtained by a method described in Zhu J Y et al., 2009, J Virol, Vol. 83, p. 3333-3341. Also, "hsa-mir-2110" (miRBase Accession No. MI0010629, SEQ ID NO: 330) having a hairpin-like structure is known as a precursor of "hsa-miR-2110".

The term "hsa-miR-4706 gene" or "hsa-miR-4706" used herein includes the hsa-miR-4706 gene (miRBase Accession No. MIMAT0019806) shown in SEQ ID NO: 79, a homolog or an ortholog thereof of a different organism species, and the like. The gene can be obtained by a method described in Persson H et al., 2011, Cancer Res, Vol. 71, p. 78-86. Also, "hsa-mir-4706" (miRBase Accession No. MI0017339, SEQ ID NO: 331) having a hairpin-like structure is known as a precursor of "hsa-miR-4706".

The term "hsa-miR-7845-5p gene" or "hsa-miR-7845-5p" used herein includes the hsa-miR-7845-5p gene (miRBase Accession No. MIMAT0030420) shown in SEQ ID NO: 80, a homolog or an ortholog thereof of a different organism species, and the like. The gene can be obtained by a method described in Ple H et al., 2012, PLoS One, Vol. 7, e50746. Also, "hsa-mir-7845" (miRBase Accession No. MI0025515, SEQ ID NO: 332) having a hairpin-like structure is known as a precursor of "hsa-miR-7845-5p".

The term "hsa-miR-6808-5p gene" or "hsa-miR-6808-5p" used herein includes the hsa-miR-6808-5p gene (miRBase Accession No. MIMAT0027516) shown in SEQ ID NO: 81, a homolog or an ortholog thereof of a different organism species, and the like. The gene can be obtained by a method described in Ladewig E et al., 2012, Genome Res, Vol. 22, p. 1634-1645. Also, "hsa-mir-6808" (miRBase Accession No. MI0022653, SEQ ID NO: 333) having a hairpin-like structure is known as a precursor of "hsa-miR-6808-5p".

The term "hsa-miR-4447 gene" or "hsa-miR-4447" used herein includes the hsa-miR-4447 gene (miRBase Accession No. MIMAT0018966) shown in SEQ ID NO: 82, a homolog or an ortholog thereof of a different organism species, and the like. The gene can be obtained by a method described in Jima D D et al., 2010, Blood, Vol. 116, e118-e127. Also, "hsa-mir-4447" (miRBase Accession No. MI0016790, SEQ ID NO: 334) having a hairpin-like structure is known as a precursor of "hsa-miR-4447".

The term "hsa-miR-6869-5p gene" or "hsa-miR-6869-5p" used herein includes the hsa-miR-6869-5p gene (miRBase Accession No. MIMAT0027638) shown in SEQ ID NO: 83, a homolog or an ortholog thereof of a different organism species, and the like. The gene can be obtained by a method described in Ladewig E et al., 2012, Genome Res, Vol. 22, p. 1634-1645. Also, "hsa-mir-6869" (miRBase Accession No. MI0022716, SEQ ID NO: 335) having a hairpin-like structure is known as a precursor of "hsa-miR-6869-5p".

The term "hsa-miR-1908-5p gene" or "hsa-miR-1908-5p" used herein includes the hsa-miR-1908-5p gene (miRBase Accession No. MIMAT0007881) shown in SEQ ID NO: 84, a homolog or an ortholog thereof of a different organism species, and the like. The gene can be obtained by a method described in Bar M et al., 2008, Stem Cells, Vol. 26, p. 2496-2505. Also, "hsa-mir-1908" (miRBase Accession No. MI0008329, SEQ ID NO: 336) having a hairpin-like structure is known as a precursor of "hsa-miR-1908-5p".

The term "hsa-miR-6729-5p gene" or "hsa-miR-6729-5p" used herein includes the hsa-miR-6729-5p gene (miRBase Accession No. MIMAT0027359) shown in SEQ ID NO: 85, a homolog or an ortholog thereof of a different organism species, and the like. The gene can be obtained by a method described in Ladewig E et al., 2012, Genome Res, Vol. 22, p. 1634-1645. Also, "hsa-mir-6729" (miRBase Accession No. MI0022574, SEQ ID NO: 337) having a hairpin-like structure is known as a precursor of "hsa-miR-6729-5p".

The term "hsa-miR-5195-3p gene" or "hsa-miR-5195-3p" used herein includes the hsa-miR-5195-3p gene (miRBase Accession No. MIMAT0021127) shown in SEQ ID NO: 86, a homolog or an ortholog thereof of a different organism species, and the like. The gene can be obtained by a method described in Schotte D et al., 2011, Leukemia, Vol. 25, p. 1389-1399. Also, "hsa-mir-5195" (miRBase Accession No. MI0018174, SEQ ID NO: 338) having a hairpin-like structure is known as a precursor of "hsa-miR-5195-3p".

The term "hsa-miR-638 gene" or "hsa-miR-638" used herein includes the hsa-miR-638 gene (miRBase Accession No. MIMAT0003308) shown in SEQ ID NO: 87, a homolog or an ortholog thereof of a different organism species, and the like. The gene can be obtained by a method described in Cummins J M et al., 2006, Proc Natl Acad Sci USA, Vol. 103, p. 3687-3692. Also, "hsa-mir-638" (miRBase Accession No. MI0003653, SEQ ID NO: 339) having a hairpin-like structure is known as a precursor of "hsa-miR-638".

The term "hsa-miR-6125 gene" or "hsa-miR-6125" used herein includes the hsa-miR-6125 gene (miRBase Accession No. MIMAT0024598) shown in SEQ ID NO: 88, a homolog or an ortholog thereof of a different organism species, and the like. The gene can be obtained by a method described in Smith J L et al., 2012, J Virol, Vol. 86, p. 5278-5287. Also, "hsa-mir-6125" (miRBase Accession No. MI0021259, SEQ ID NO: 340) having a hairpin-like structure is known as a precursor of "hsa-miR-6125".

The term "hsa-miR-3178 gene" or "hsa-miR-3178" used herein includes the hsa-miR-3178 gene (miRBase Accession No. MIMAT0015055) shown in SEQ ID NO: 89, a homolog or an ortholog thereof of a different organism species, and the like. The gene can be obtained by a method described in Stark M S et al., 2010, PLoS One, Vol. 5, e9685. Also, "hsa-mir-3178" (miRBase Accession No. MI0014212, SEQ ID NO: 341) having a hairpin-like structure is known as a precursor of "hsa-miR-3178".

The term "hsa-miR-3196 gene" or "hsa-miR-3196" used herein includes the hsa-miR-3196 gene (miRBase Accession No. MIMAT0015080) shown in SEQ ID NO: 90, a homolog or an ortholog thereof of a different organism species, and the like. The gene can be obtained by a method described in Stark M S et al., 2010, PLoS One, Vol. 5, e9685. Also, "hsa-mir-3196" (miRBase Accession No. MI0014241, SEQ ID NO: 342) having a hairpin-like structure is known as a precursor of "hsa-miR-3196".

The term "hsa-miR-8069 gene" or "hsa-miR-8069" used herein includes the hsa-miR-8069 gene (miRBase Accession No. MIMAT0030996) shown in SEQ ID NO: 91, a homolog or an ortholog thereof of a different organism species, and the like. The gene can be obtained by a method described in Wang H J et al., 2013, Shock, Vol. 39, p. 480-487. Also, "hsa-mir-8069-1 and hsa-mir-8069-2" (miRBase Accession Nos. MI0025905 and MI0031519, SEQ ID NOs: 343 and 344) having a hairpin-like structure are known as a precursor of "hsa-miR-8069".

The term "hsa-miR-4723-5p gene" or "hsa-miR-4723-5p" used herein includes the hsa-miR-4723-5p gene (miRBase Accession No. MIMAT0019838) shown in SEQ ID NO: 92, a homolog or an ortholog thereof of a different organism species, and the like. The gene can be obtained by a method described in Persson H et al., 2011, Cancer Res, Vol. 71, p. 78-86. Also, "hsa-mir-4723" (miRBase Accession No. MI0017359, SEQ ID NO: 345) having a hairpin-like structure is known as a precursor of "hsa-miR-4723-5p".

The term "hsa-miR-4746-3p gene" or "hsa-miR-4746-3p" used herein includes the hsa-miR-4746-3p gene (miRBase Accession No. MIMAT0019881) shown in SEQ ID NO: 93, a homolog or an ortholog thereof of a different organism species, and the like. The gene can be obtained by a method described in Persson H et al., 2011, Cancer Res, Vol. 71, p. 78-86. Also, "hsa-mir-4746" (miRBase Accession No. MI0017385, SEQ ID NO: 346) having a hairpin-like structure is known as a precursor of "hsa-miR-4746-3p".

The term "hsa-miR-4689 gene" or "hsa-miR-4689" used herein includes the hsa-miR-4689 gene (miRBase Accession No. MIMAT0019778) shown in SEQ ID NO: 94, a homolog or an ortholog thereof of a different organism species, and the like. The gene can be obtained by a method described in Persson H et al., 2011, Cancer Res, Vol. 71, p. 78-86. Also, "hsa-mir-4689" (miRBase Accession No. MI0017322, SEQ ID NO: 347) having a hairpin-like structure is known as a precursor of "hsa-miR-4689".

The term "hsa-miR-6816-5p gene" or "hsa-miR-6816-5p" used herein includes the hsa-miR-6816-5p gene (miRBase Accession No. MIMAT0027532) shown in SEQ ID NO: 95, a homolog or an ortholog thereof of a different organism species, and the like. The gene can be obtained by a method described in Ladewig E et al., 2012, Genome Res, Vol. 22, p. 1634-1645. Also, "hsa-mir-6816" (miRBase Accession No. MI0022661, SEQ ID NO: 348) having a hairpin-like structure is known as a precursor of "hsa-miR-6816-5p".

The term "hsa-miR-6757-5p gene" or "hsa-miR-6757-5p" used herein includes the hsa-miR-6757-5p gene (miRBase Accession No. MIMAT0027414) shown in SEQ ID NO: 96, a homolog or an ortholog thereof of a different organism species, and the like. The gene can be obtained by a method described in Ladewig E et al., 2012, Genome Res, Vol. 22, p. 1634-1645. Also, "hsa-mir-6757" (miRBase Accession No. MI0022602, SEQ ID NO: 349) having a hairpin-like structure is known as a precursor of "hsa-miR-6757-5p".

The term "hsa-miR-7109-5p gene" or "hsa-miR-7109-5p" used herein includes the hsa-miR-7109-5p gene (miRBase Accession No. MIMAT0028115) shown in SEQ ID NO: 97, a homolog or an ortholog thereof of a different organism species, and the like. The gene can be obtained by a method described in Ladewig E et al., 2012, Genome Res, Vol. 22, p. 1634-1645. Also, "hsa-mir-7109" (miRBase Accession No. MI0022960, SEQ ID NO: 350) having a hairpin-like structure is known as a precursor of "hsa-miR-7109-5p".

The term "hsa-miR-6724-5p gene" or "hsa-miR-6724-5p" used herein includes the hsa-miR-6724-5p gene (miRBase Accession No. MIMAT0025856) shown in SEQ ID NO: 98, a homolog or an ortholog thereof of a different organism species, and the like. The gene can be obtained by a method described in Li Y et al., 2012, Gene, Vol. 497, p. 330-335. Also, "hsa-mir-6724-1, hsa-mir-6724-2, hsa-mir-6724-3 and hsa-mir-6724-4" (miRBase Accession Nos. MI0022559, MI0031516, MI0031517 and MI0031518, SEQ ID NOs: 351, 352, 353 and 354) having a hairpin-like structure are known as a precursor of "hsa-miR-6724-5p".

The term "hsa-miR-1225-3p gene" or "hsa-miR-1225-3p" used herein includes the hsa-miR-1225-3p gene (miRBase Accession No. MIMAT0005573) shown in SEQ ID NO: 99, a homolog or an ortholog thereof of a different organism species, and the like. The gene can be obtained by a method described in Berezikov E et al., 2007, Mol Cell, Vol. 28, p. 328-336. Also, "hsa-mir-1225" (miRBase Accession No. MI0006311, SEQ ID NO: 355) having a hairpin-like structure is known as a precursor of "hsa-miR-1225-3p".

The term "hsa-miR-6875-5p gene" or "hsa-miR-6875-5p" used herein includes the hsa-miR-6875-5p gene (miRBase Accession No. MIMAT0027650) shown in SEQ ID NO: 100, a homolog or an ortholog thereof of a different organism species, and the like. The gene can be obtained by a method described in Ladewig E et al., 2012, Genome Res, Vol. 22, p. 1634-1645. Also, "hsa-mir-6875" (miRBase Accession No. MI0022722, SEQ ID NO: 356) having a hairpin-like structure is known as a precursor of "hsa-miR-6875-5p".

The term "hsa-miR-7108-5p gene" or "hsa-miR-7108-5p" used herein includes the hsa-miR-7108-5p gene (miRBase Accession No. MIMAT0028113) shown in SEQ ID NO: 101, a homolog or an ortholog thereof of a different organism species, and the like. The gene can be obtained by a method described in Ladewig E et al., 2012, Genome Res, Vol. 22, p. 1634-1645. Also, "hsa-mir-7108" (miRBase Accession No. MI0022959, SEQ ID NO: 357) having a hairpin-like structure is known as a precursor of "hsa-miR-7108-5p".

The term "hsa-miR-4508 gene" or "hsa-miR-4508" used herein includes the hsa-miR-4508 gene (miRBase Accession No. MIMAT0019045) shown in SEQ ID NO: 102, a homolog or an ortholog thereof of a different organism species, and the like. The gene can be obtained by a method described in Jima D D et al., 2010, Blood, Vol. 116, e118-e127. Also, "hsa-mir-4508" (miRBase Accession No. MI0016872, SEQ ID NO: 358) having a hairpin-like structure is known as a precursor of "hsa-miR-4508".

The term "hsa-miR-6085 gene" or "hsa-miR-6085" used herein includes the hsa-miR-6085 gene (miRBase Accession No. MIMAT0023710) shown in SEQ ID NO: 103, a homolog or an ortholog thereof of a different organism species, and the like. The gene can be obtained by a method described in Voellenkle C et al., 2012, RNA, Vol. 18, p. 472-484. Also, "hsa-mir-6085" (miRBase Accession No. MI0020362, SEQ ID NO: 359) having a hairpin-like structure is known as a precursor of "hsa-miR-6085".

The term "hsa-miR-6779-5p gene" or "hsa-miR-6779-5p" used herein includes the hsa-miR-6779-5p gene (miRBase Accession No. MIMAT0027458) shown in SEQ ID NO: 104, a homolog or an ortholog thereof of a different organism species, and the like. The gene can be obtained by a method described in Ladewig E et al., 2012, Genome Res, Vol. 22, p. 1634-1645. Also, "hsa-mir-6779" (miRBase Accession No. MI0022624, SEQ ID NO: 360) having a hairpin-like structure is known as a precursor of "hsa-miR-6779-5p".

The term "hsa-miR-642a-3p gene" or "hsa-miR-642a-3p" used herein includes the hsa-miR-642a-3p gene (miRBase Accession No. MIMAT0020924) shown in SEQ ID NO: 105, a homolog or an ortholog thereof of a different organism species, and the like. The gene can be obtained by a method described in Cummins J M et al., 2006, Proc Natl Acad Sci USA, Vol. 103, p. 3687-3692. Also, "hsa-mir-642a" (miRBase Accession No. MI0003657, SEQ ID NO: 361) having a hairpin-like structure is known as a precursor of "hsa-miR-642a-3p".

The term "hsa-miR-4695-5p gene" or "hsa-miR-4695-5p" used herein includes the hsa-miR-4695-5p gene (miRBase Accession No. MIMAT0019788) shown in SEQ ID NO: 106, a homolog or an ortholog thereof of a different organism species, and the like. The gene can be obtained by a method described in Persson H et al., 2011, Cancer Res, Vol. 71, p. 78-86. Also, "hsa-mir-4695" (miRBase Accession No. MI0017328, SEQ ID NO: 362) having a hairpin-like structure is known as a precursor of "hsa-miR-4695-5p".

The term "hsa-miR-7847-3p gene" or "hsa-miR-7847-3p" used herein includes the hsa-miR-7847-3p gene (miRBase Accession No. MIMAT0030422) shown in SEQ ID NO: 107, a homolog or an ortholog thereof of a different organism species, and the like. The gene can be obtained by a method described in Ple H et al., 2012, PLoS One, Vol. 7, e50746. Also, "hsa-mir-7847" (miRBase Accession No. MI0025517, SEQ ID NO: 363) having a hairpin-like structure is known as a precursor of "hsa-miR-7847-3p".

The term "hsa-miR-3197 gene" or "hsa-miR-3197" used herein includes the hsa-miR-3197 gene (miRBase Accession No. MIMAT0015082) shown in SEQ ID NO: 108, a homolog or an ortholog thereof of a different organism species, and the like. The gene can be obtained by a method described in Stark M S et al., 2010, PLoS One, Vol. 5, e9685. Also, "hsa-mir-3197" (miRBase Accession No. MI0014245, SEQ ID NO: 364) having a hairpin-like structure is known as a precursor of "hsa-miR-3197".

The term "hsa-miR-6769b-5p gene" or "hsa-miR-6769b-5p" used herein includes the hsa-miR-6769b-5p gene (miRBase Accession No. MIMAT0027620) shown in SEQ ID NO: 109, a homolog or an ortholog thereof of a different organism species, and the like. The gene can be obtained by a method described in Ladewig E et al., 2012, Genome Res, Vol. 22, p. 1634-1645. Also, "hsa-mir-6769b" (miRBase Accession No. MI0022706, SEQ ID NO: 365) having a hairpin-like structure is known as a precursor of "hsa-miR-6769b-5p".

The term "hsa-miR-7641 gene" or "hsa-miR-7641" used herein includes the hsa-miR-7641 gene (miRBase Accession No. MIMAT0029782) shown in SEQ ID NO: 110, a homolog or an ortholog thereof of a different organism species, and the like. The gene can be obtained by a method described in Yoo J K et al., 2013, Arch Pharm Res, Vol. 36, p. 353-358. Also, "hsa-mir-7641-1 and hsa-mir-7641-2" (miRBase Accession Nos. MI0024975 and MI0024976, SEQ ID NOs: 366 and 367) having a hairpin-like structure are known as a precursor of "hsa-miR-7641".

The term "hsa-miR-187-5p gene" or "hsa-miR-187-5p" used herein includes the hsa-miR-187-5p gene (miRBase Accession No. MIMAT0004561) shown in SEQ ID NO: 111, a homolog or an ortholog thereof of a different organism species, and the like. The gene can be obtained by a method described in Lim L P et al., 2003, Science, Vol. 299, p. 1540. Also, "hsa-mir-187" (miRBase Accession No. MI0000274, SEQ ID NO: 368) having a hairpin-like structure is known as a precursor of "hsa-miR-187-5p".

The term "hsa-miR-3185 gene" or "hsa-miR-3185" used herein includes the hsa-miR-3185 gene (miRBase Accession No. MIMAT0015065) shown in SEQ ID NO: 112, a homolog or an ortholog thereof of a different organism species, and the like. The gene can be obtained by a method described in Stark M S et al., 2010, PLoS One, Vol. 5, e9685. Also, "hsa-mir-3185" (miRBase Accession No. MI0014227, SEQ ID NO: 369) having a hairpin-like structure is known as a precursor of "hsa-miR-3185".

The term "hsa-miR-2861 gene" or "hsa-miR-2861" used herein includes the hsa-miR-2861 gene (miRBase Accession No. MIMAT0013802) shown in SEQ ID NO: 113, a homolog or an ortholog thereof of a different organism species, and the like. The gene can be obtained by a method described in Li H et al., 2009, J Clin Invest, Vol. 119, p. 3666-3677. Also, "hsa-mir-2861" (miRBase Accession No. MI0013006, SEQ ID NO: 370) having a hairpin-like structure is known as a precursor of "hsa-miR-2861".

The term "hsa-miR-3940-5p gene" or "hsa-miR-3940-5p" used herein includes the hsa-miR-3940-5p gene (miRBase Accession No. MIMAT0019229) shown in SEQ ID NO: 114, a homolog or an ortholog thereof of a different organism species, and the like. The gene can be obtained by a method described in Liao J Y et al., 2010, PLoS One, Vol. 5, e10563. Also, "hsa-mir-3940" (miRBase Accession No. MI0016597, SEQ ID NO: 371) having a hairpin-like structure is known as a precursor of "hsa-miR-3940-5p".

The term "hsa-miR-1203 gene" or "hsa-miR-1203" used herein includes the hsa-miR-1203 gene (miRBase Accession No. MIMAT0005866) shown in SEQ ID NO: 115, a homolog or an ortholog thereof of a different organism species, and the like. The gene can be obtained by a method described in Marton S et al., 2008, Leukemia, Vol. 22, p. 330-338. Also, "hsa-mir-1203" (miRBase Accession No. MI0006335, SEQ ID NO: 372) having a hairpin-like structure is known as a precursor of "hsa-miR-1203".

The term "hsa-miR-615-5p gene" or "hsa-miR-615-5p" used herein includes the hsa-miR-615-5p gene (miRBase Accession No. MIMAT0004804) shown in SEQ ID NO: 116, a homolog or an ortholog thereof of a different organism species, and the like. The gene can be obtained by a method described in Cummins J M et al., 2006, Proc Natl Acad Sci USA, Vol. 103, p. 3687-3692. Also, "hsa-mir-615" (miRBase Accession No. MI0003628, SEQ ID NO: 373) having a hairpin-like structure is known as a precursor of "hsa-miR-615-5p".

The term "hsa-miR-4787-5p gene" or "hsa-miR-4787-5p" used herein includes the hsa-miR-4787-5p gene (miRBase Accession No. MIMAT0019956) shown in SEQ ID NO: 117, a homolog or an ortholog thereof of a different organism species, and the like. The gene can be obtained by a method described in Persson H et al., 2011, Cancer Res, Vol. 71, p. 78-86. Also, "hsa-mir-4787" (miRBase Accession No. MI0017434, SEQ ID NO: 374) having a hairpin-like structure is known as a precursor of "hsa-miR-4787-5p".

The term "hsa-miR-1343-3p gene" or "hsa-miR-1343-3p" used herein includes the hsa-miR-1343-3p gene (miRBase Accession No. MIMAT0019776) shown in SEQ ID NO: 118, a homolog or an ortholog thereof of a different organism species, and the like. The gene can be obtained by a method described in Persson H et al., 2011, Cancer Res, Vol. 71, p. 78-86. Also, "hsa-mir-1343" (miRBase Accession No. MI0017320, SEQ ID NO: 375) having a hairpin-like structure is known as a precursor of "hsa-miR-1343-3p".

The term "hsa-miR-6813-5p gene" or "hsa-miR-6813-5p" used herein includes the hsa-miR-6813-5p gene (miRBase Accession No. MIMAT0027526) shown in SEQ ID NO: 119, a homolog or an ortholog thereof of a different organism species, and the like. The gene can be obtained by a method described in Ladewig E et al., 2012, Genome Res, Vol. 22, p. 1634-1645. Also, "hsa-mir-6813" (miRBase Accession No. MI0022658, SEQ ID NO: 376) having a hairpin-like structure is known as a precursor of "hsa-miR-6813-5p".

The term "hsa-miR-1225-5p gene" or "hsa-miR-1225-5p" used herein includes the hsa-miR-1225-5p gene (miRBase Accession No. MIMAT0005572) shown in SEQ ID NO: 120, a homolog or an ortholog thereof of a different organism species, and the like. The gene can be obtained by a method described in Berezikov E et al., 2007, Mol Cell, Vol.

28, p. 328-336. Also, "hsa-mir-1225" (miRBase Accession No. MI0006311, SEQ ID NO: 377) having a hairpin-like structure is known as a precursor of "hsa-miR-1225-5p".

The term "hsa-miR-602 gene" or "hsa-miR-602" used herein includes the hsa-miR-602 gene (miRBase Accession No. MIMAT0003270) shown in SEQ ID NO: 121, a homolog or an ortholog thereof of a different organism species, and the like. The gene can be obtained by a method described in Cummins J M et al., 2006, Proc Natl Acad Sci USA, Vol. 103, p. 3687-3692. Also, "hsa-mir-602" (miRBase Accession No. MI0003615, SEQ ID NO: 378) having a hairpin-like structure is known as a precursor of "hsa-miR-602".

The term "hsa-miR-4488 gene" or "hsa-miR-4488" used herein includes the hsa-miR-4488 gene (miRBase Accession No. MIMAT0019022) shown in SEQ ID NO: 122, a homolog or an ortholog thereof of a different organism species, and the like. The gene can be obtained by a method described in Jima D D et al., 2010, Blood, Vol. 116, e118-e127. Also, "hsa-mir-4488" (miRBase Accession No. MI0016849, SEQ ID NO: 379) having a hairpin-like structure is known as a precursor of "hsa-miR-4488".

The term "hsa-miR-125a-3p gene" or "hsa-miR-125a-3p" used herein includes the hsa-miR-125a-3p gene (miRBase Accession No. MIMAT0004602) shown in SEQ ID NO: 123, a homolog or an ortholog thereof of a different organism species, and the like. The gene can be obtained by a method described in Lagos-Quintana M et al., 2002, Curr Biol, Vol. 12, p. 735-739. Also, "hsa-mir-125a" (miRBase Accession No. MI0000469, SEQ ID NO: 380) having a hairpin-like structure is known as a precursor of "hsa-miR-125a-3p".

The term "hsa-miR-5100 gene" or "hsa-miR-5100" used herein includes the hsa-miR-5100 gene (miRBase Accession No. MIMAT0022259) shown in SEQ ID NO: 124, a homolog or an ortholog thereof of a different organism species, and the like. The gene can be obtained by a method described in Tandon M et al., 2012, Oral Dis, Vol. 18, p. 127-131. Also, "hsa-mir-5100" (miRBase Accession No. MI0019116, SEQ ID NO: 381) having a hairpin-like structure is known as a precursor of "hsa-miR-5100".

The term "hsa-miR-4294 gene" or "hsa-miR-4294" used herein includes the hsa-miR-4294 gene (miRBase Accession No. MIMAT0016849) shown in SEQ ID NO: 125, a homolog or an ortholog thereof of a different organism species, and the like. The gene can be obtained by a method described in Goff L A et al., 2009, PLoS One, Vol. 4, e7192. Also, "hsa-mir-4294" (miRBase Accession No. MI0015827, SEQ ID NO: 382) having a hairpin-like structure is known as a precursor of "hsa-miR-4294".

The term "hsa-miR-1231 gene" or "hsa-miR-1231" used herein includes the hsa-miR-1231 gene (miRBase Accession No. MIMAT0005586) shown in SEQ ID NO: 126, a homolog or an ortholog thereof of a different organism species, and the like. The gene can be obtained by a method described in Berezikov E et al., 2007, Mol Cell, Vol. 28, p. 328-336. Also, "hsa-mir-1231" (miRBase Accession No. MI0006321, SEQ ID NO: 383) having a hairpin-like structure is known as a precursor of "hsa-miR-1231".

The term "hsa-miR-6765-3p gene" or "hsa-miR-6765-3p" used herein includes the hsa-miR-6765-3p gene (miRBase Accession No. MIMAT0027431) shown in SEQ ID NO: 127, a homolog or an ortholog thereof of a different organism species, and the like. The gene can be obtained by a method described in Ladewig E et al., 2012, Genome Res, Vol. 22, p. 1634-1645. Also, "hsa-mir-6765" (miRBase Accession No. MI0022610, SEQ ID NO: 384) having a hairpin-like structure is known as a precursor of "hsa-miR-6765-3p".

The term "hsa-miR-4442 gene" or "hsa-miR-4442" used herein includes the hsa-miR-4442 gene (miRBase Accession No. MIMAT0018960) shown in SEQ ID NO: 128, a homolog or an ortholog thereof of a different organism species, and the like. The gene can be obtained by a method described in Jima D D et al., 2010, Blood, Vol. 116, e118-e127. Also, "hsa-mir-4442" (miRBase Accession No. MI0016785, SEQ ID NO: 385) having a hairpin-like structure is known as a precursor of "hsa-miR-4442".

The term "hsa-miR-718 gene" or "hsa-miR-718" used herein includes the hsa-miR-718 gene (miRBase Accession No. MIMAT0012735) shown in SEQ ID NO: 129, a homolog or an ortholog thereof of a different organism species, and the like. The gene can be obtained by a method described in Artzi S et al., 2008, BMC Bioinformatics, Vol. 9, p. 39. Also, "hsa-mir-718" (miRBase Accession No. MI0012489, SEQ ID NO: 386) having a hairpin-like structure is known as a precursor of "hsa-miR-718".

The term "hsa-miR-6780b-5p gene" or "hsa-miR-6780b-5p" used herein includes the hsa-miR-6780b-5p gene (miRBase Accession No. MIMAT0027572) shown in SEQ ID NO: 130, a homolog or an ortholog thereof of a different organism species, and the like. The gene can be obtained by a method described in Ladewig E et al., 2012, Genome Res, Vol. 22, p. 1634-1645. Also, "hsa-mir-6780b" (miRBase Accession No. MI0022681, SEQ ID NO: 387) having a hairpin-like structure is known as a precursor of "hsa-miR-6780b-5p".

The term "hsa-miR-6090 gene" or "hsa-miR-6090" used herein includes the hsa-miR-6090 gene (miRBase Accession No. MIMAT0023715) shown in SEQ ID NO: 131, a homolog or an ortholog thereof of a different organism species, and the like. The gene can be obtained by a method described in Yoo J K et al., 2012, Stem Cells Dev, Vol. 21, p. 2049-2057. Also, "hsa-mir-6090" (miRBase Accession No. MI0020367, SEQ ID NO: 388) having a hairpin-like structure is known as a precursor of "hsa-miR-6090".

The term "hsa-miR-6845-5p gene" or "hsa-miR-6845-5p" used herein includes the hsa-miR-6845-5p gene (miRBase Accession No. MIMAT0027590) shown in SEQ ID NO: 132, a homolog or an ortholog thereof of a different organism species, and the like. The gene can be obtained by a method described in Ladewig E et al., 2012, Genome Res, Vol. 22, p. 1634-1645. Also, "hsa-mir-6845" (miRBase Accession No. MI0022691, SEQ ID NO: 389) having a hairpin-like structure is known as a precursor of "hsa-miR-6845-5p".

The term "hsa-miR-4741 gene" or "hsa-miR-4741" used herein includes the hsa-miR-4741 gene (miRBase Accession No. MIMAT0019871) shown in SEQ ID NO: 133, a homolog or an ortholog thereof of a different organism species, and the like. The gene can be obtained by a method described in Persson H et al., 2011, Cancer Res, Vol. 71, p. 78-86. Also, "hsa-mir-4741" (miRBase Accession No. MI0017379, SEQ ID NO: 390) having a hairpin-like structure is known as a precursor of "hsa-miR-4741".

The term "hsa-miR-4467 gene" or "hsa-miR-4467" used herein includes the hsa-miR-4467 gene (miRBase Accession No. MIMAT0018994) shown in SEQ ID NO: 134, a homolog or an ortholog thereof of a different organism species, and the like. The gene can be obtained by a method described in Jima D D et al., 2010, Blood, Vol. 116, e118-e127. Also, "hsa-mir-4467" (miRBase Accession No.

MI0016818, SEQ ID NO: 391) having a hairpin-like structure is known as a precursor of "hsa-miR-4467".

The term "hsa-miR-4707-5p gene" or "hsa-miR-4707-5p" used herein includes the hsa-miR-4707-5p gene (miRBase Accession No. MIMAT0019807) shown in SEQ ID NO: 135, a homolog or an ortholog thereof of a different organism species, and the like. The gene can be obtained by a method described in Persson H et al., 2011, Cancer Res, Vol. 71, p. 78-86. Also, "hsa-mir-4707" (miRBase Accession No. MI0017340, SEQ ID NO: 392) having a hairpin-like structure is known as a precursor of "hsa-miR-4707-5p".

The term "hsa-miR-4271 gene" or "hsa-miR-4271" used herein includes the hsa-miR-4271 gene (miRBase Accession No. MIMAT0016901) shown in SEQ ID NO: 136, a homolog or an ortholog thereof of a different organism species, and the like. The gene can be obtained by a method described in Goff L A et al., 2009, PLoS One, Vol. 4, e7192. Also, "hsa-mir-4271" (miRBase Accession No. MI0015879, SEQ ID NO: 393) having a hairpin-like structure is known as a precursor of "hsa-miR-4271".

The term "hsa-miR-4673 gene" or "hsa-miR-4673" used herein includes the hsa-miR-4673 gene (miRBase Accession No. MIMAT0019755) shown in SEQ ID NO: 137, a homolog or an ortholog thereof of a different organism species, and the like. The gene can be obtained by a method described in Persson H et al., 2011, Cancer Res, Vol. 71, p. 78-86. Also, "hsa-mir-4673" (miRBase Accession No. MI0017304, SEQ ID NO: 394) having a hairpin-like structure is known as a precursor of "hsa-miR-4673".

The term "hsa-miR-3184-5p gene" or "hsa-miR-3184-5p" used herein includes the hsa-miR-3184-5p gene (miRBase Accession No. MIMAT0015064) shown in SEQ ID NO: 138, a homolog or an ortholog thereof of a different organism species, and the like. The gene can be obtained by a method described in Stark M S et al., 2010, PLoS One, Vol. 5, e9685. Also, "hsa-mir-3184" (miRBase Accession No. MI0014226, SEQ ID NO: 395) having a hairpin-like structure is known as a precursor of "hsa-miR-3184-5p".

The term "hsa-miR-1469 gene" or "hsa-miR-1469" used herein includes the hsa-miR-1469 gene (miRBase Accession No. MIMAT0007347) shown in SEQ ID NO: 139, a homolog or an ortholog thereof of a different organism species, and the like. The gene can be obtained by a method described in Kawaji H et al., 2008, BMC Genomics, Vol. 9, p. 157. Also, "hsa-mir-1469" (miRBase Accession No. MI0007074, SEQ ID NO: 396) having a hairpin-like structure is known as a precursor of "hsa-miR-1469".

The term "hsa-miR-4640-5p gene" or "hsa-miR-4640-5p" used herein includes the hsa-miR-4640-5p gene (miRBase Accession No. MIMAT0019699) shown in SEQ ID NO: 140, a homolog or an ortholog thereof of a different organism species, and the like. The gene can be obtained by a method described in Persson H et al., 2011, Cancer Res, Vol. 71, p. 78-86. Also, "hsa-mir-4640" (miRBase Accession No. MI0017267, SEQ ID NO: 397) having a hairpin-like structure is known as a precursor of "hsa-miR-4640-5p".

The term "hsa-miR-663a gene" or "hsa-miR-663a" used herein includes the hsa-miR-663a gene (miRBase Accession No. MIMAT0003326) shown in SEQ ID NO: 141, a homolog or an ortholog thereof of a different organism species, and the like. The gene can be obtained by a method described in Cummins J M et al., 2006, Proc Natl Acad Sci USA, Vol. 103, p. 3687-3692. Also, "hsa-mir-663a" (miRBase Accession No. MI0003672, SEQ ID NO: 398) having a hairpin-like structure is known as a precursor of "hsa-miR-663a".

The term "hsa-miR-6791-5p gene" or "hsa-miR-6791-5p" used herein includes the hsa-miR-6791-5p gene (miRBase Accession No. MIMAT0027482) shown in SEQ ID NO: 142, a homolog or an ortholog thereof of a different organism species, and the like. The gene can be obtained by a method described in Ladewig E et al., 2012, Genome Res, Vol. 22, p. 1634-1645. Also, "hsa-mir-6791" (miRBase Accession No. MI0022636, SEQ ID NO: 399) having a hairpin-like structure is known as a precursor of "hsa-miR-6791-5p".

The term "hsa-miR-6826-5p gene" or "hsa-miR-6826-5p" used herein includes the hsa-miR-6826-5p gene (miRBase Accession No. MIMAT0027552) shown in SEQ ID NO: 143, a homolog or an ortholog thereof of a different organism species, and the like. The gene can be obtained by a method described in Ladewig E et al., 2012, Genome Res, Vol. 22, p. 1634-1645. Also, "hsa-mir-6826" (miRBase Accession No. MI0022671, SEQ ID NO: 400) having a hairpin-like structure is known as a precursor of "hsa-miR-6826-5p".

The term "hsa-miR-4433b-3p gene" or "hsa-miR-4433b-3p" used herein includes the hsa-miR-4433b-3p gene (miRBase Accession No. MIMAT0030414) shown in SEQ ID NO: 144, a homolog or an ortholog thereof of a different organism species, and the like. The gene can be obtained by a method described in Ple H et al., 2012, PLoS One, Vol. 7, e50746. Also, "hsa-mir-4433b" (miRBase Accession No. MI0025511, SEQ ID NO: 401) having a hairpin-like structure is known as a precursor of "hsa-miR-4433b-3p".

The term "hsa-miR-1915-3p gene" or "hsa-miR-1915-3p" used herein includes the hsa-miR-1915-3p gene (miRBase Accession No. MIMAT0007892) shown in SEQ ID NO: 145, a homolog or an ortholog thereof of a different organism species, and the like. The gene can be obtained by a method described in Bar M et al., 2008, Stem Cells, Vol. 26, p. 2496-2505. Also, "hsa-mir-1915" (miRBase Accession No. MI0008336, SEQ ID NO: 402) having a hairpin-like structure is known as a precursor of "hsa-miR-1915-3p".

The term "hsa-miR-4417 gene" or "hsa-miR-4417" used herein includes the hsa-miR-4417 gene (miRBase Accession No. MIMAT0018929) shown in SEQ ID NO: 146, a homolog or an ortholog thereof of a different organism species, and the like. The gene can be obtained by a method described in Jima D D et al., 2010, Blood, Vol. 116, e118-e127. Also, "hsa-mir-4417" (miRBase Accession No. MI0016753, SEQ ID NO: 403) having a hairpin-like structure is known as a precursor of "hsa-miR-4417".

The term "hsa-miR-4449 gene" or "hsa-miR-4449" used herein includes the hsa-miR-4449 gene (miRBase Accession No. MIMAT0018968) shown in SEQ ID NO: 147, a homolog or an ortholog thereof of a different organism species, and the like. The gene can be obtained by a method described in Jima D D et al., 2010, Blood, Vol. 116, e118-e127. Also, "hsa-mir-4449" (miRBase Accession No. MI0016792, SEQ ID NO: 404) having a hairpin-like structure is known as a precursor of "hsa-miR-4449".

The term "hsa-miR-4707-3p gene" or "hsa-miR-4707-3p" used herein includes the hsa-miR-4707-3p gene (miRBase Accession No. MIMAT0019808) shown in SEQ ID NO: 148, a homolog or an ortholog thereof of a different organism species, and the like. The gene can be obtained by a method described in Persson H et al., 2011, Cancer Res, Vol. 71, p. 78-86. Also, "hsa-mir-4707" (miRBase Accession No. MI0017340, SEQ ID NO: 405) having a hairpin-like structure is known as a precursor of "hsa-miR-4707-3p".

The term "hsa-miR-3180-3p gene" or "hsa-miR-3180-3p" used herein includes the hsa-miR-3180-3p gene (miRBase Accession No. MIMAT0015058) shown in SEQ ID NO: 149, a homolog or an ortholog thereof of a different organism species, and the like. The gene can be obtained by a method described in Creighton C J et al., 2010, PLoS One, Vol. 5, e9637. Also, "hsa-mir-3180-1, hsa-mir-3180-2 and hsa-mir-3180-3" (miRBase Accession Nos. MI0014214, MI0014215 and MI0014217, SEQ ID NOs: 406, 407 and 408) having a hairpin-like structure are known as a precursor of "hsa-miR-3180-3p".

The term "hsa-miR-5585-3p gene" or "hsa-miR-5585-3p" used herein includes the hsa-miR-5585-3p gene (miRBase Accession No. MIMAT0022286) shown in SEQ ID NO: 150, a homolog or an ortholog thereof of a different organism species, and the like. The gene can be obtained by a method described in Friedlander M R et al., 2012, Nucleic Acids Res, Vol. 40, p. 37-52. Also, "hsa-mir-5585" (miRBase Accession No. MI0019142, SEQ ID NO: 409) having a hairpin-like structure is known as a precursor of "hsa-miR-5585-3p".

The term "hsa-miR-1268a gene" or "hsa-miR-1268a" used herein includes the hsa-miR-1268a gene (miRBase Accession No. MIMAT0005922) shown in SEQ ID NO: 151, a homolog or an ortholog thereof of a different organism species, and the like. The gene can be obtained by a method described in Morin R D et al., 2008, Genome Res, Vol. 18, p. 610-621. Also, "hsa-mir-1268a" (miRBase Accession No. MI0006405, SEQ ID NO: 410) having a hairpin-like structure is known as a precursor of "hsa-miR-1268a".

The term "hsa-miR-8072 gene" or "hsa-miR-8072" used herein includes the hsa-miR-8072 gene (miRBase Accession No. MIMAT0030999) shown in SEQ ID NO: 152, a homolog or an ortholog thereof of a different organism species, and the like. The gene can be obtained by a method described in Wang H J et al., 2013, Shock, Vol. 39, p. 480-487. Also, "hsa-mir-8072" (miRBase Accession No. MI0025908, SEQ ID NO: 411) having a hairpin-like structure is known as a precursor of "hsa-miR-8072".

The term "hsa-miR-296-5p gene" or "hsa-miR-296-5p" used herein includes the hsa-miR-296-5p gene (miRBase Accession No. MIMAT0000690) shown in SEQ ID NO: 153, a homolog or an ortholog thereof of a different organism species, and the like. The gene can be obtained by a method described in Houbaviy H B et al., 2003, Dev Cell, Vol. 5, p. 351-358. Also, "hsa-mir-296" (miRBase Accession No. MI0000747, SEQ ID NO: 412) having a hairpin-like structure is known as a precursor of "hsa-miR-296-5p".

The term "hsa-miR-204-3p gene" or "hsa-miR-204-3p" used herein includes the hsa-miR-204-3p gene (miRBase Accession No. MIMAT0022693) shown in SEQ ID NO: 154, a homolog or an ortholog thereof of a different organism species, and the like. The gene can be obtained by a method described in Lim L P et al., 2003, Science, Vol. 299, p. 1540. Also, "hsa-mir-204" (miRBase Accession No. MI0000284, SEQ ID NO: 413) having a hairpin-like structure is known as a precursor of "hsa-miR-204-3p".

The term "hsa-miR-4454 gene" or "hsa-miR-4454" used herein includes the hsa-miR-4454 gene (miRBase Accession No. MIMAT0018976) shown in SEQ ID NO: 155, a homolog or an ortholog thereof of a different organism species, and the like. The gene can be obtained by a method described in Jima D D et al., 2010, Blood, Vol. 116, e118-e127. Also, "hsa-mir-4454" (miRBase Accession No. MI0016800, SEQ ID NO: 414) having a hairpin-like structure is known as a precursor of "hsa-miR-4454".

The term "hsa-miR-6722-3p gene" or "hsa-miR-6722-3p" used herein includes the hsa-miR-6722-3p gene (miRBase Accession No. MIMAT0025854) shown in SEQ ID NO: 156, a homolog or an ortholog thereof of a different organism species, and the like. The gene can be obtained by a method described in Li Y et al., 2012, Gene, Vol. 497, p. 330-335. Also, "hsa-mir-6722" (miRBase Accession No. MI0022557, SEQ ID NO: 415) having a hairpin-like structure is known as a precursor of "hsa-miR-6722-3p".

The term "hsa-miR-1290 gene" or "hsa-miR-1290" used herein includes the hsa-miR-1290 gene (miRBase Accession No. MIMAT0005880) shown in SEQ ID NO: 157, a homolog or an ortholog thereof of a different organism species, and the like. The gene can be obtained by a method described in Morin R D et al., 2008, Genome Res, Vol. 18, p. 610-621. Also, "hsa-mir-1290" (miRBase Accession No. MI0006352, SEQ ID NO: 416) having a hairpin-like structure is known as a precursor of "hsa-miR-1290".

The term "hsa-miR-3622a-5p gene" or "hsa-miR-3622a-5p" used herein includes the hsa-miR-3622a-5p gene (miRBase Accession No. MIMAT0018003) shown in SEQ ID NO: 158, a homolog or an ortholog thereof of a different organism species, and the like. The gene can be obtained by a method described in Witten D et al., 2010, BMC Biol, Vol. 8, p. 58. Also, "hsa-mir-3622a" (miRBase Accession No. MI0016013, SEQ ID NO: 417) having a hairpin-like structure is known as a precursor of "hsa-miR-3622a-5p".

The term "hsa-miR-939-5p gene" or "hsa-miR-939-5p" used herein includes the hsa-miR-939-5p gene (miRBase Accession No. MIMAT0004982) shown in SEQ ID NO: 159, a homolog or an ortholog thereof of a different organism species, and the like. The gene can be obtained by a method described in Lui W O et al., 2007, Cancer Res, Vol. 67, p. 6031-6043. Also, "hsa-mir-939" (miRBase Accession No. MI0005761, SEQ ID NO: 418) having a hairpin-like structure is known as a precursor of "hsa-miR-939-5p".

The term "hsa-miR-675-5p gene" or "hsa-miR-675-5p" used herein includes the hsa-miR-675-5p gene (miRBase Accession No. MIMAT0004284) shown in SEQ ID NO: 160, a homolog or an ortholog thereof of a different organism species, and the like. The gene can be obtained by a method described in Cai X et al., 2007, RNA, Vol. 13, p. 313-316. Also, "hsa-mir-675" (miRBase Accession No. MI0005416, SEQ ID NO: 419) having a hairpin-like structure is known as a precursor of "hsa-miR-675-5p".

The term "hsa-miR-3131 gene" or "hsa-miR-3131" used herein includes the hsa-miR-3131 gene (miRBase Accession No. MIMAT0014996) shown in SEQ ID NO: 161, a homolog or an ortholog thereof of a different organism species, and the like. The gene can be obtained by a method described in Stark M S et al., 2010, PLoS One, Vol. 5, e9685. Also, "hsa-mir-3131" (miRBase Accession No. MI0014151, SEQ ID NO: 420) having a hairpin-like structure is known as a precursor of "hsa-miR-3131".

The term "hsa-miR-4648 gene" or "hsa-miR-4648" used herein includes the hsa-miR-4648 gene (miRBase Accession No. MIMAT0019710) shown in SEQ ID NO: 162, a homolog or an ortholog thereof of a different organism species, and the like. The gene can be obtained by a method described in Persson H et al., 2011, Cancer Res, Vol. 71, p. 78-86. Also, "hsa-mir-4648" (miRBase Accession No. MI0017275, SEQ ID NO: 421) having a hairpin-like structure is known as a precursor of "hsa-miR-4648".

The term "hsa-miR-1268b gene" or "hsa-miR-1268b" used herein includes the hsa-miR-1268b gene (miRBase Accession No. MIMAT0018925) shown in SEQ ID NO: 163, a homolog or an ortholog thereof of a different organism species, and the like. The gene can be obtained by a method described in Jima D D et al., 2010, Blood, Vol. 116, e118-e127. Also, "hsa-mir-1268b" (miRBase Accession No. MI0016748, SEQ ID NO: 422) having a hairpin-like structure is known as a precursor of "hsa-miR-1268b".

The term "hsa-miR-6741-5p gene" or "hsa-miR-6741-5p" used herein includes the hsa-miR-6741-5p gene (miRBase Accession No. MIMAT0027383) shown in SEQ ID NO: 164, a homolog or an ortholog thereof of a different organism species, and the like. The gene can be obtained by a method described in Ladewig E et al., 2012, Genome Res, Vol. 22, p. 1634-1645. Also, "hsa-mir-6741" (miRBase Accession No. MI0022586, SEQ ID NO: 423) having a hairpin-like structure is known as a precursor of "hsa-miR-6741-5p".

The term "hsa-miR-6893-5p gene" or "hsa-miR-6893-5p" used herein includes the hsa-miR-6893-5p gene (miRBase Accession No. MIMAT0027686) shown in SEQ ID NO: 165, a homolog or an ortholog thereof of a different organism species, and the like. The gene can be obtained by a method described in Ladewig E et al., 2012, Genome Res, Vol. 22, p. 1634-1645. Also, "hsa-mir-6893" (miRBase Accession No. MI0022740, SEQ ID NO: 424) having a hairpin-like structure is known as a precursor of "hsa-miR-6893-5p".

The term "hsa-miR-3162-5p gene" or "hsa-miR-3162-5p" used herein includes the hsa-miR-3162-5p gene (miRBase Accession No. MIMAT0015036) shown in SEQ ID NO: 166, a homolog or an ortholog thereof of a different organism species, and the like. The gene can be obtained by a method described in Stark M S et al., 2010, PLoS One, Vol. 5, e9685. Also, "hsa-mir-3162" (miRBase Accession No. MI0014192, SEQ ID NO: 425) having a hairpin-like structure is known as a precursor of "hsa-miR-3162-5p".

The term "hsa-miR-642b-3p gene" or "hsa-miR-642b-3p" used herein includes the hsa-miR-642b-3p gene (miRBase Accession No. MIMAT0018444) shown in SEQ ID NO: 167, a homolog or an ortholog thereof of a different organism species, and the like. The gene can be obtained by a method described in Witten D et al., 2010, BMC Biol, Vol. 8, p. 58. Also, "hsa-mir-642b" (miRBase Accession No. MI0016685, SEQ ID NO: 426) having a hairpin-like structure is known as a precursor of "hsa-miR-642b-3p".

The term "hsa-miR-4734 gene" or "hsa-miR-4734" used herein includes the hsa-miR-4734 gene (miRBase Accession No. MIMAT0019859) shown in SEQ ID NO: 168, a homolog or an ortholog thereof of a different organism species, and the like. The gene can be obtained by a method described in Persson H et al., 2011, Cancer Res, Vol. 71, p. 78-86. Also, "hsa-mir-4734" (miRBase Accession No. MI0017371, SEQ ID NO: 427) having a hairpin-like structure is known as a precursor of "hsa-miR-4734".

The term "hsa-miR-150-3p gene" or "hsa-miR-150-3p" used herein includes the hsa-miR-150-3p gene (miRBase Accession No. MIMAT0004610) shown in SEQ ID NO: 169, a homolog or an ortholog thereof of a different organism species, and the like. The gene can be obtained by a method described in Lagos-Quintana M et al., 2002, Curr Biol, Vol. 12, p. 735-739. Also, "hsa-mir-150" (miRBase Accession No. MI0000479, SEQ ID NO: 428) having a hairpin-like structure is known as a precursor of "hsa-miR-150-3p".

The term "hsa-miR-8089 gene" or "hsa-miR-8089" used herein includes the hsa-miR-8089 gene (miRBase Accession No. MIMAT0031016) shown in SEQ ID NO: 170, a homolog or an ortholog thereof of a different organism species, and the like. The gene can be obtained by a method described in Wang H J et al., 2013, Shock, Vol. 39, p. 480-487. Also, "hsa-mir-8089" (miRBase Accession No. MI0025925, SEQ ID NO: 429) having a hairpin-like structure is known as a precursor of "hsa-miR-8089".

The term "hsa-miR-6805-3p gene" or "hsa-miR-6805-3p" used herein includes the hsa-miR-6805-3p gene (miRBase Accession No. MIMAT0027511) shown in SEQ ID NO: 171, a homolog or an ortholog thereof of a different organism species, and the like. The gene can be obtained by a method described in Ladewig E et al., 2012, Genome Res, Vol. 22, p. 1634-1645. Also, "hsa-mir-6805" (miRBase Accession No. MI0022650, SEQ ID NO: 430) having a hairpin-like structure is known as a precursor of "hsa-miR-6805-3p".

The term "hsa-miR-7113-3p gene" or "hsa-miR-7113-3p" used herein includes the hsa-miR-7113-3p gene (miRBase Accession No. MIMAT0028124) shown in SEQ ID NO: 172, a homolog or an ortholog thereof of a different organism species, and the like. The gene can be obtained by a method described in Ladewig E et al., 2012, Genome Res, Vol. 22, p. 1634-1645. Also, "hsa-mir-7113" (miRBase Accession No. MI0022964, SEQ ID NO: 431) having a hairpin-like structure is known as a precursor of "hsa-miR-7113-3p".

The term "hsa-miR-6850-5p gene" or "hsa-miR-6850-5p" used herein includes the hsa-miR-6850-5p gene (miRBase Accession No. MIMAT0027600) shown in SEQ ID NO: 173, a homolog or an ortholog thereof of a different organism species, and the like. The gene can be obtained by a method described in Ladewig E et al., 2012, Genome Res, Vol. 22, p. 1634-1645. Also, "hsa-mir-6850" (miRBase Accession No. MI0022696, SEQ ID NO: 432) having a hairpin-like structure is known as a precursor of "hsa-miR-6850-5p".

The term "hsa-miR-6799-5p gene" or "hsa-miR-6799-5p" used herein includes the hsa-miR-6799-5p gene (miRBase Accession No. MIMAT0027498) shown in SEQ ID NO: 174, a homolog or an ortholog thereof of a different organism species, and the like. The gene can be obtained by a method described in Ladewig E et al., 2012, Genome Res, Vol. 22, p. 1634-1645. Also, "hsa-mir-6799" (miRBase Accession No. MI0022644, SEQ ID NO: 433) having a hairpin-like structure is known as a precursor of "hsa-miR-6799-5p".

The term "hsa-miR-6768-5p gene" or "hsa-miR-6768-5p" used herein includes the hsa-miR-6768-5p gene (miRBase Accession No. MIMAT0027436) shown in SEQ ID NO: 175, a homolog or an ortholog thereof of a different organism species, and the like. The gene can be obtained by a method described in Ladewig E et al., 2012, Genome Res, Vol. 22, p. 1634-1645. Also, "hsa-mir-6768" (miRBase Accession No. MI0022613, SEQ ID NO: 434) having a hairpin-like structure is known as a precursor of "hsa-miR-6768-5p".

The term "hsa-miR-92b-5p gene" or "hsa-miR-92b-5p" used herein includes the hsa-miR-92b-5p gene (miRBase Accession No. MIMAT0004792) shown in SEQ ID NO: 176, a homolog or an ortholog thereof of a different organism species, and the like. The gene can be obtained by a method described in Cummins J M et al., 2006, Proc Natl Acad Sci USA, Vol. 103, p. 3687-3692. Also, "hsa-mir-92b" (miRBase Accession No. MI0003560, SEQ ID NO: 435) having a hairpin-like structure is known as a precursor of "hsa-miR-92b-5p".

The term "hsa-miR-3679-5p gene" or "hsa-miR-3679-5p" used herein includes the hsa-miR-3679-5p gene (miRBase Accession No. MIMAT0018104) shown in SEQ ID NO: 177, a homolog or an ortholog thereof of a different organism species, and the like. The gene can be obtained by a method described in Creighton C J et al., 2010, PLoS One, Vol. 5, e9637. Also, "hsa-mir-3679" (miRBase Accession No. MI0016080, SEQ ID NO: 436) having a hairpin-like structure is known as a precursor of "hsa-miR-3679-5p".

The term "hsa-miR-4792 gene" or "hsa-miR-4792" used herein includes the hsa-miR-4792 gene (miRBase Accession No. MIMAT0019964) shown in SEQ ID NO: 178, a homolog or an ortholog thereof of a different organism species, and the like. The gene can be obtained by a method described in Persson H et al., 2011, Cancer Res, Vol. 71, p. 78-86. Also, "hsa-mir-4792" (miRBase Accession No. MI0017439, SEQ ID NO: 437) having a hairpin-like structure is known as a precursor of "hsa-miR-4792".

The term "hsa-miR-3656 gene" or "hsa-miR-3656" used herein includes the hsa-miR-3656 gene (miRBase Accession No. MIMAT0018076) shown in SEQ ID NO: 179, a homolog or an ortholog thereof of a different organism species, and the like. The gene can be obtained by a method described in Meiri E et al., 2010, Nucleic Acids Res, Vol. 38, p. 6234-6246. Also, "hsa-mir-3656" (miRBase Accession No. MI0016056, SEQ ID NO: 438) having a hairpin-like structure is known as a precursor of "hsa-miR-3656".

The term "hsa-miR-92a-2-5p gene" or "hsa-miR-92a-2-5p" used herein includes the hsa-miR-92a-2-5p gene (miRBase Accession No. MIMAT0004508) shown in SEQ ID NO: 180, a homolog or an ortholog thereof of a different organism species, and the like. The gene can be obtained by a method described in Mourelatos Z et al., 2002, Genes Dev, Vol. 16, p. 720-728. Also, "hsa-mir-92a-2" (miRBase Accession No. MI0000094, SEQ ID NO: 439) having a hairpin-like structure is known as a precursor of "hsa-miR-92a-2-5p".

The term "hsa-miR-4466 gene" or "hsa-miR-4466" used herein includes the hsa-miR-4466 gene (miRBase Accession No. MIMAT0018993) shown in SEQ ID NO: 181, a homolog or an ortholog thereof of a different organism species, and the like. The gene can be obtained by a method described in Jima D D et al., 2010, Blood, Vol. 116, e118-e127. Also, "hsa-mir-4466" (miRBase Accession No. MI0016817, SEQ ID NO: 440) having a hairpin-like structure is known as a precursor of "hsa-miR-4466".

The term "hsa-miR-4513 gene" or "hsa-miR-4513" used herein includes the hsa-miR-4513 gene (miRBase Accession No. MIMAT0019050) shown in SEQ ID NO: 182, a homolog or an ortholog thereof of a different organism species, and the like. The gene can be obtained by a method described in Jima D D et al., 2010, Blood, Vol. 116, e118-e127. Also, "hsa-mir-4513" (miRBase Accession No. MI0016879, SEQ ID NO: 441) having a hairpin-like structure is known as a precursor of "hsa-miR-4513".

The term "hsa-miR-6781-5p gene" or "hsa-miR-6781-5p" used herein includes the hsa-miR-6781-5p gene (miRBase Accession No. MIMAT0027462) shown in SEQ ID NO: 183, a homolog or an ortholog thereof of a different organism species, and the like. The gene can be obtained by a method described in Ladewig E et al., 2012, Genome Res, Vol. 22, p. 1634-1645. Also, "hsa-mir-6781" (miRBase Accession No. MI0022626, SEQ ID NO: 442) having a hairpin-like structure is known as a precursor of "hsa-miR-6781-5p".

The term "hsa-miR-4649-5p gene" or "hsa-miR-4649-5p" used herein includes the hsa-miR-4649-5p gene (miRBase Accession No. MIMAT0019711) shown in SEQ ID NO: 184, a homolog or an ortholog thereof of a different organism species, and the like. The gene can be obtained by a method described in Persson H et al., 2011, Cancer Res, Vol. 71, p. 78-86. Also, "hsa-mir-4649" (miRBase Accession No. MI0017276, SEQ ID NO: 443) having a hairpin-like structure is known as a precursor of "hsa-miR-4649-5p".

The term "hsa-miR-6775-5p gene" or "hsa-miR-6775-5p" used herein includes the hsa-miR-6775-5p gene (miRBase Accession No. MIMAT0027450) shown in SEQ ID NO: 185, a homolog or an ortholog thereof of a different organism species, and the like. The gene can be obtained by a method described in Ladewig E et al., 2012, Genome Res, Vol. 22, p. 1634-1645. Also, "hsa-mir-6775" (miRBase Accession No. MI0022620, SEQ ID NO: 444) having a hairpin-like structure is known as a precursor of "hsa-miR-6775-5p".

The term "hsa-miR-4651 gene" or "hsa-miR-4651" used herein includes the hsa-miR-4651 gene (miRBase Accession No. MIMAT0019715) shown in SEQ ID NO: 186, a homolog or an ortholog thereof of a different organism species, and the like. The gene can be obtained by a method described in Persson H et al., 2011, Cancer Res, Vol. 71, p. 78-86. Also, "hsa-mir-4651" (miRBase Accession No. MI0017279, SEQ ID NO: 445) having a hairpin-like structure is known as a precursor of "hsa-miR-4651".

The term "hsa-miR-3195 gene" or "hsa-miR-3195" used herein includes the hsa-miR-3195 gene (miRBase Accession No. MIMAT0015079) shown in SEQ ID NO: 187, a homolog or an ortholog thereof of a different organism species, and the like. The gene can be obtained by a method described in Stark M S et al., 2010, PLoS One, Vol. 5, e9685. Also, "hsa-mir-3195" (miRBase Accession No. MI0014240, SEQ ID NO: 446) having a hairpin-like structure is known as a precursor of "hsa-miR-3195".

The term "hsa-miR-6726-5p gene" or "hsa-miR-6726-5p" used herein includes the hsa-miR-6726-5p gene (miRBase Accession No. MIMAT0027353) shown in SEQ ID NO: 188, a homolog or an ortholog thereof of a different organism species, and the like. The gene can be obtained by a method described in Ladewig E et al., 2012, Genome Res, Vol. 22, p. 1634-1645. Also, "hsa-mir-6726" (miRBase Accession No. MI0022571, SEQ ID NO: 447) having a hairpin-like structure is known as a precursor of "hsa-miR-6726-5p".

The term "hsa-miR-6872-3p gene" or "hsa-miR-6872-3p" used herein includes the hsa-miR-6872-3p gene (miRBase Accession No. MIMAT0027645) shown in SEQ ID NO: 189, a homolog or an ortholog thereof of a different organism species, and the like. The gene can be obtained by a method described in Ladewig E et al., 2012, Genome Res, Vol. 22, p. 1634-1645. Also, "hsa-mir-6872" (miRBase Accession No. MI0022719, SEQ ID NO: 448) having a hairpin-like structure is known as a precursor of "hsa-miR-6872-3p".

The term "hsa-miR-371a-5p gene" or "hsa-miR-371a-5p" used herein includes the hsa-miR-371a-5p gene (miRBase Accession No. MIMAT0004687) shown in SEQ ID NO: 190, a homolog or an ortholog thereof of a different organism species, and the like. The gene can be obtained by a method described in Suh M R et al., 2004, Dev Biol, Vol. 270, p. 488-498. Also, "hsa-mir-371a" (miRBase Accession No. MI0000779, SEQ ID NO: 449) having a hairpin-like structure is known as a precursor of "hsa-miR-371a-5p".

The term "hsa-miR-6777-5p gene" or "hsa-miR-6777-5p" used herein includes the hsa-miR-6777-5p gene (miRBase Accession No. MIMAT0027454) shown in SEQ ID NO: 191, a homolog or an ortholog thereof of a different organism species, and the like. The gene can be obtained by a method described in Ladewig E et al., 2012, Genome Res, Vol. 22, p. 1634-1645. Also, "hsa-mir-6777" (miRBase Accession No. MI0022622, SEQ ID NO: 450) having a hairpin-like structure is known as a precursor of "hsa-miR-6777-5p".

The term "hsa-miR-6789-5p gene" or "hsa-miR-6789-5p" used herein includes the hsa-miR-6789-5p gene (miRBase Accession No. MIMAT0027478) shown in SEQ ID NO: 192, a homolog or an ortholog thereof of a different organism species, and the like. The gene can be obtained by a method described in Ladewig E et al., 2012, Genome Res, Vol. 22, p. 1634-1645. Also, "hsa-mir-6789" (miRBase Accession No. MI0022634, SEQ ID NO: 451) having a hairpin-like structure is known as a precursor of "hsa-miR-6789-5p".

The term "hsa-miR-7975 gene" or "hsa-miR-7975" used herein includes the hsa-miR-7975 gene (miRBase Accession No. MIMAT0031178) shown in SEQ ID NO: 193, a homolog or an ortholog of a different organism species, and the like. The gene can be obtained by a method described in Velthut-Meikas A et al., 2013, Mol Endocrinol, Vol. 27, p. 1128-1141. Also, "hsa-mir-7975" (miRBase Accession No. MI0025751, SEQ ID NO: 452) having a hairpin-like structure is known as a precursor of "hsa-miR-7975".

The term "hsa-miR-6821-5p gene" or "hsa-miR-6821-5p" used herein includes the hsa-miR-6821-5p gene (miRBase Accession No. MIMAT0027542) shown in SEQ ID NO: 194, a homolog or an ortholog thereof of a different organism species, and the like. The gene can be obtained by a method described in Ladewig E et al., 2012, Genome Res, Vol. 22, p. 1634-1645. Also, "hsa-mir-6821" (miRBase Accession No. MI0022666, SEQ ID NO: 453) having a hairpin-like structure is known as a precursor of "hsa-miR-6821-5p".

The term "hsa-miR-4534 gene" or "hsa-miR-4534" used herein includes the hsa-miR-4534 gene (miRBase Accession No. MIMAT0019073) shown in SEQ ID NO: 195, a homolog or an ortholog thereof of a different organism species, and the like. The gene can be obtained by a method described in Jima D D et al., 2010, Blood, Vol. 116, e118-e127. Also, "hsa-mir-4534" (miRBase Accession No. MI0016901, SEQ ID NO: 454) having a hairpin-like structure is known as a precursor of "hsa-miR-4534".

The term "hsa-miR-619-5p gene" or "hsa-miR-619-5p" used herein includes the hsa-miR-619-5p gene (miRBase Accession No. MIMAT0026622) shown in SEQ ID NO: 196, a homolog or an ortholog thereof of a different organism species, and the like. The gene can be obtained by a method described in Cummins J M et al., 2006, Proc Natl Acad Sci USA, Vol. 103, p. 3687-3692. Also, "hsa-mir-619" (miRBase Accession No. MI0003633, SEQ ID NO: 455) having a hairpin-like structure is known as a precursor of "hsa-miR-619-5p".

The term "hsa-miR-7107-5p gene" or "hsa-miR-7107-5p" used herein includes the hsa-miR-7107-5p gene (miRBase Accession No. MIMAT0028111) shown in SEQ ID NO: 197, a homolog or an ortholog thereof of a different organism species, and the like. The gene can be obtained by a method described in Ladewig E et al., 2012, Genome Res, Vol. 22, p. 1634-1645. Also, "hsa-mir-7107" (miRBase Accession No. MI0022958, SEQ ID NO: 456) having a hairpin-like structure is known as a precursor of "hsa-miR-7107-5p".

The term "hsa-miR-1228-3p gene" or "hsa-miR-1228-3p" used herein includes the hsa-miR-1228-3p gene (miRBase Accession No. MIMAT0005583) shown in SEQ ID NO: 198, a homolog or an ortholog thereof of a different organism species, and the like. The gene can be obtained by a method described in Berezikov E et al., 2007, Mol Cell, Vol. 28, p. 328-336. Also, "hsa-mir-1228" (miRBase Accession No. MI0006318, SEQ ID NO: 457) having a hairpin-like structure is known as a precursor of "hsa-miR-1228-3p".

The term "hsa-miR-6774-5p gene" or "hsa-miR-6774-5p" used herein includes the hsa-miR-6774-5p gene (miRBase Accession No. MIMAT0027448) shown in SEQ ID NO: 199, a homolog or an ortholog thereof of a different organism species, and the like. The gene can be obtained by a method described in Ladewig E et al., 2012, Genome Res, Vol. 22, p. 1634-1645. Also, "hsa-mir-6774" (miRBase Accession No. MI0022619, SEQ ID NO: 458) having a hairpin-like structure is known as a precursor of "hsa-miR-6774-5p".

The term "hsa-miR-6805-5p gene" or "hsa-miR-6805-5p" used herein includes the hsa-miR-6805-5p gene (miRBase Accession No. MIMAT0027510) shown in SEQ ID NO: 200, a homolog or an ortholog thereof of a different organism species, and the like. The gene can be obtained by a method described in Ladewig E et al., 2012, Genome Res, Vol. 22, p. 1634-1645. Also, "hsa-mir-6805" (miRBase Accession No. MI0022650, SEQ ID NO: 459) having a hairpin-like structure is known as a precursor of "hsa-miR-6805-5p".

The term "hsa-miR-23a-3p gene" or "hsa-miR-23a-3p" used herein includes the hsa-miR-23a-3p gene (miRBase Accession No. MIMAT0000078) shown in SEQ ID NO: 201, a homolog or an ortholog thereof of a different organism species, and the like. The gene can be obtained by a method described in Lagos-Quintana M et al., 2001, Science, Vol. 294, p. 853-858. Also, "hsa-mir-23a" (miRBase Accession No. MI0000079, SEQ ID NO: 460) having a hairpin-like structure is known as a precursor of "hsa-miR-23a-3p".

The term "hsa-miR-4665-5p gene" or "hsa-miR-4665-5p" used herein includes the hsa-miR-4665-5p gene (miRBase Accession No. MIMAT0019739) shown in SEQ ID NO: 202, a homolog or an ortholog thereof of a different organism species, and the like. The gene can be obtained by a method described in Persson H et al., 2011, Cancer Res, Vol. 71, p. 78-86. Also, "hsa-mir-4665" (miRBase Accession No. MI0017295, SEQ ID NO: 461) having a hairpin-like structure is known as a precursor of "hsa-miR-4665-5p".

The term "hsa-miR-4505 gene" or "hsa-miR-4505" used herein includes the hsa-miR-4505 gene (miRBase Accession No. MIMAT0019041) shown in SEQ ID NO: 203, a homolog or an ortholog thereof of a different organism species, and the like. The gene can be obtained by a method described in Jima D D et al., 2010, Blood, Vol. 116, e118-e127. Also, "hsa-mir-4505" (miRBase Accession No. MI0016868, SEQ ID NO: 462) having a hairpin-like structure is known as a precursor of "hsa-miR-4505".

The term "hsa-miR-4638-5p gene" or "hsa-miR-4638-5p" used herein includes the hsa-miR-4638-5p gene (miRBase Accession No. MIMAT0019695) shown in SEQ ID NO: 204, a homolog or an ortholog thereof of a different organism species, and the like. The gene can be obtained by a method described in Persson H et al., 2011, Cancer Res, Vol. 71, p. 78-86. Also, "hsa-mir-4638" (miRBase Accession No. MI0017265, SEQ ID NO: 463) having a hairpin-like structure is known as a precursor of "hsa-miR-4638-5p".

The term "hsa-miR-24-3p gene" or "hsa-miR-24-3p" used herein includes the hsa-miR-24-3p gene (miRBase Accession No. MIMAT0000080) shown in SEQ ID NO: 205, a homolog or an ortholog thereof of a different organism species, and the like. The gene can be obtained by a method described in Lagos-Quintana M et al., 2001, Science, Vol. 294, p. 853-858. Also, "hsa-mir-24-1 and hsamir-24-2" (miRBase Accession Nos. MI0000080 and MI0000081, SEQ ID NOs: 464 and 465) having a hairpin-like structure are known as a precursor of "hsa-miR-24-3p".

The term "hsa-miR-3135b gene" or "hsa-miR-3135b" used herein includes the hsa-miR-3135b gene (miRBase Accession No. MIMAT0018985) shown in SEQ ID NO: 206, a homolog or an ortholog thereof of a different organism species, and the like. The gene can be obtained by a method described in Jima D D et al., 2010, Blood, Vol. 116, e118-e27. Also, "hsa-mir-3135b" (miRBase Accession No. MI0016809, SEQ ID NO: 466) having a hairpin-like structure is known as a precursor of "hsa-miR-3135b".

The term "hsa-miR-4745-5p gene" or "hsa-miR-4745-5p" used herein includes the hsa-miR-4745-5p gene (miRBase Accession No. MIMAT0019878) shown in SEQ ID NO: 207, a homolog or an ortholog thereof of a different organism species, and the like. The gene can be obtained by a method described in Persson H et al., 2011, Cancer Res, Vol. 71, p. 78-86. Also, "hsa-mir-4745" (miRBase Accession No. MI0017384, SEQ ID NO: 467) having a hairpin-like structure is known as a precursor of "hsa-miR-4745-5p".

The term "hsa-miR-128-1-5p gene" or "hsa-miR-128-1-5p" used herein includes the hsa-miR-128-1-5p gene (miRBase Accession No. MIMAT0026477) shown in SEQ ID NO: 208, a homolog or an ortholog thereof of a different organism species, and the like. The gene can be obtained by a method described in Lagos-Quintana M et al., 2002, Curr Biol, Vol. 12, p. 735-739. Also, "hsa-mir-128-1" (miRBase Accession No. MI0000447, SEQ ID NO: 468) having a hairpin-like structure is known as a precursor of "hsa-miR-128-1-5p".

The term "hsa-miR-4476 gene" or "hsa-miR-4476" used herein includes the hsa-miR-4476 gene (miRBase Accession No. MIMAT0019003) shown in SEQ ID NO: 209, a homolog or an ortholog thereof of a different organism species, and the like. The gene can be obtained by a method described in Jima D D et al., 2010, Blood, Vol. 116, e118-e127. Also, "hsa-mir-4476" (miRBase Accession No. MI0016828, SEQ ID NO: 469) having a hairpin-like structure is known as a precursor of "hsa-miR-4476".

The term "hsa-miR-4687-3p gene" or "hsa-miR-4687-3p" used herein includes the hsa-miR-4687-3p gene (miRBase Accession No. MIMAT0019775) shown in SEQ ID NO: 210, a homolog or an ortholog thereof of a different organism species, and the like. The gene can be obtained by a method described in Persson H et al., 2011, Cancer Res, Vol. 71, p. 78-86. Also, "hsa-mir-4687" (miRBase Accession No. MI0017319, SEQ ID NO: 470) having a hairpin-like structure is known as a precursor of "hsa-miR-4687-3p".

The term "hsa-miR-3665 gene" or "hsa-miR-3665" used herein includes the hsa-miR-3665 gene (miRBase Accession No. MIMAT0018087) shown in SEQ ID NO: 211, a homolog or an ortholog thereof of a different organism species, and the like. The gene can be obtained by a method described in Xie X et al., 2005, Nature, Vol. 434, p. 338-345. Also, "hsa-mir-3665" (miRBase Accession No. MI0016066, SEQ ID NO: 471) having a hairpin-like structure is known as a precursor of "hsa-miR-3665".

The term "hsa-miR-6806-5p gene" or "hsa-miR-6806-5p" used herein includes the hsa-miR-6806-5p gene (miRBase Accession No. MIMAT0027512) shown in SEQ ID NO: 212, a homolog or an ortholog thereof of a different organism species, and the like. The gene can be obtained by a method described in Ladewig E et al., 2012, Genome Res, Vol. 22, p. 1634-1645. Also, "hsa-mir-6806" (miRBase Accession No. MI0022651, SEQ ID NO: 472) having a hairpin-like structure is known as a precursor of "hsa-miR-6806-5p".

The term "hsa-miR-3937 gene" or "hsa-miR-3937" used herein includes the hsa-miR-3937 gene (miRBase Accession No. MIMAT0018352) shown in SEQ ID NO: 213, a homolog or an ortholog thereof of a different organism species, and the like. The gene can be obtained by a method described in Liao J Y et al., 2010, PLoS One, Vol. 5, e10563. Also, "hsa-mir-3937" (miRBase Accession No. MI0016593, SEQ ID NO: 473) having a hairpin-like structure is known as a precursor of "hsa-miR-3937".

The term "hsa-miR-711 gene" or "hsa-miR-711" used herein includes the hsa-miR-711 gene (miRBase Accession No. MIMAT0012734) shown in SEQ ID NO: 214, a homolog or an ortholog thereof of a different organism species, and the like. The gene can be obtained by a method described in Artzi S et al., 2008, BMC Bioinformatics, Vol. 9, p. 39. Also, "hsa-mir-711" (miRBase Accession No. MI0012488, SEQ ID NO: 474) having a hairpin-like structure is known as a precursor of "hsa-miR-711"

The term "hsa-miR-3141 gene" or "hsa-miR-3141" used herein includes the hsa-miR-3141 gene (miRBase Accession No. MIMAT0015010) shown in SEQ ID NO: 215, a homolog or an ortholog thereof of a different organism species, and the like. The gene can be obtained by a method described in Stark M S et al., 2010, PLoS One, Vol. 5, e9685. Also, "hsa-mir-3141" (miRBase Accession No. MI0014165, SEQ ID NO: 475) having a hairpin-like structure is known as a precursor of "hsa-miR-3141".

The term "hsa-miR-3188 gene" or "hsa-miR-3188" used herein includes the hsa-miR-3188 gene (miRBase Accession No. MIMAT0015070) shown in SEQ ID NO: 216, a homolog or an ortholog thereof of a different organism species, and the like. The gene can be obtained by a method described in Stark M S et al., 2010, PLoS One, Vol. 5, e9685. Also, "hsa-mir-3188" (miRBase Accession No. MI0014232, SEQ ID NO: 476) having a hairpin-like structure is known as a precursor of "hsa-miR-3188".

The term "hsa-miR-4281 gene" or "hsa-miR-4281" used herein includes the hsa-miR-4281 gene (miRBase Accession No. MIMAT0016907) shown in SEQ ID NO: 217, a homolog or an ortholog thereof of a different organism species, and the like. The gene can be obtained by a method described in Goff L A et al., 2009, PLoS One, Vol. 4, e7192. Also, "hsa-mir-4281" (miRBase Accession No. MI0015885, SEQ ID NO: 477) having a hairpin-like structure is known as a precursor of "hsa-miR-4281".

The term "hsa-miR-5196-5p gene" or "hsa-miR-5196-5p" used herein includes the hsa-miR-5196-5p gene (miRBase Accession No. MIMAT0021128) shown in SEQ ID NO: 218, a homolog or an ortholog thereof of a different organism species, and the like. The gene can be obtained by a method described in Schotte D et al., 2011, Leukemia, Vol. 25, p. 1389-1399. Also, "hsa-mir-5196" (miRBase Accession No. MI0018175, SEQ ID NO: 478) having a hairpin-like structure is known as a precursor of "hsa-miR-5196-5p".

The term "hsa-miR-6880-5p gene" or "hsa-miR-6880-5p" used herein includes the hsa-miR-6880-5p gene (miRBase Accession No. MIMAT0027660) shown in SEQ ID NO: 219, a homolog or an ortholog thereof of a different organism species, and the like. The gene can be obtained by a method described in Ladewig E et al., 2012, Genome Res, Vol. 22, p. 1634-1645. Also, "hsa-mir-6880" (miRBase Accession No. MI0022727, SEQ ID NO: 479) having a hairpin-like structure is known as a precursor of "hsa-miR-6880-5p".

The term "hsa-miR-3960 gene" or "hsa-miR-3960" used herein includes the hsa-miR-3960 gene (miRBase Accession No. MIMAT0019337) shown in SEQ ID NO: 220, a homolog or an ortholog thereof of a different organism species, and the like. The gene can be obtained by a method described in Hu R et al., 2011, J Biol Chem, Vol. 286, p. 12328-12339. Also, "hsa-mir-3960" (miRBase Accession No. MI0016964, SEQ ID NO: 480) having a hairpin-like structure is known as a precursor of "hsa-miR-3960".

The term "hsa-miR-3648 gene" or "hsa-miR-3648" used herein includes the hsa-miR-3648 gene (miRBase Accession No. MIMAT0018068) shown in SEQ ID NO: 221, a homolog or an ortholog thereof of a different organism species, and the like. The gene can be obtained by a method described in Meiri E et al., 2010, Nucleic Acids Res, Vol. 38, p. 6234-6246. Also, "hsa-mir-3648-1 and hsa-miR-3648-2" (miRBase Accession Nos. MI0016048 and MI0031512, SEQ ID NOs: 481 and 482) having a hairpin-like structure are known as a precursor of "hsa-miR-3648".

The term "hsa-miR-6721-5p gene" or "hsa-miR-6721-5p" used herein includes the hsa-miR-6721-5p gene (miRBase Accession No. MIMAT0025852) shown in SEQ ID NO: 222, a homolog or an ortholog thereof of a different organism species, and the like. The gene can be obtained by a method described in Li Y et al., 2012, Gene, Vol. 497, p. 330-335. Also, "hsa-mir-6721" (miRBase Accession No. MI0022556, SEQ ID NO: 483) having a hairpin-like structure is known as a precursor of "hsa-miR-6721-5p".

The term "hsa-miR-4492 gene" or "hsa-miR-4492" used herein includes the hsa-miR-4492 gene (miRBase Accession No. MIMAT0019027) shown in SEQ ID NO: 223, a homolog or an ortholog thereof of a different organism species, and the like. The gene can be obtained by a method described in Jima D D et al., 2010, Blood, Vol. 116, e118-e127. Also, "hsa-mir-4492" (miRBase Accession No. MI0016854, SEQ ID NO: 484) having a hairpin-like structure is known as a precursor of "hsa-miR-4492".

The term "hsa-miR-744-5p gene" or "hsa-miR-744-5p" used herein includes the hsa-miR-744-5p gene (miRBase Accession No. MIMAT0004945) shown in SEQ ID NO: 224, a homolog or an ortholog thereof of a different organism species, and the like. The gene can be obtained by a method described in Berezikov E et al., 2006, Genome Res, Vol. 16, p. 1289-1298. Also, "hsa-mir-744" (miRBase Accession No. MI0005559, SEQ ID NO: 485) having a hairpin-like structure is known as a precursor of "hsa-miR-744-5p".

The term "hsa-miR-7704 gene" or "hsa-miR-7704" used herein includes the hsa-miR-7704 gene (miRBase Accession No. MIMAT0030019) shown in SEQ ID NO: 225, a homolog or an ortholog thereof of a different organism species, and the like. The gene can be obtained by a method described in Swaminathan S et al., 2013, Biochem Biophys Res Commun, Vol. 434, p. 228-234. Also, "hsa-mir-7704" (miRBase Accession No. MI0025240, SEQ ID NO: 486) having a hairpin-like structure is known as a precursor of "hsa-miR-7704".

The term "hsa-miR-4749-5p gene" or "hsa-miR-4749-5p" used herein includes the hsa-miR-4749-5p gene (miRBase Accession No. MIMAT0019885) shown in SEQ ID NO: 226, a homolog or an ortholog thereof of a different organism species, and the like. The gene can be obtained by a method described in Persson H et al., 2011, Cancer Res, Vol. 71, p. 78-86. Also, "hsa-mir-4749" (miRBase Accession No. MI0017388, SEQ ID NO: 487) having a hairpin-like structure is known as a precursor of "hsa-miR-4749-5p".

The term "hsa-miR-6794-5p gene" or "hsa-miR-6794-5p" used herein includes the hsa-miR-6794-5p gene (miRBase Accession No. MIMAT0027488) shown in SEQ ID NO: 227, a homolog or an ortholog thereof of a different organism species, and the like. The gene can be obtained by a method described in Ladewig E et al., 2012, Genome Res, Vol. 22, p. 1634-1645. Also, "hsa-mir-6794" (miRBase Accession No. MI0022639, SEQ ID NO: 488) having a hairpin-like structure is known as a precursor of "hsa-miR-6794-5p".

The term "hsa-miR-6511a-5p gene" or "hsa-miR-6511a-5p" used herein includes the hsa-miR-6511a-5p gene (miRBase Accession No. MIMAT0025478) shown in SEQ ID NO: 228, a homolog or an ortholog thereof of a different organism species, and the like. The gene can be obtained by a method described in Joyce C E et al., 2011, Hum Mol Genet, Vol. 20, p. 4025-4040. Also, "hsa-mir-6511a-1, hsa-mir-6511a-2, hsa-mir-6511a-3 and hsa-mir-6511a-4" (miRBase Accession Nos. MI0022223, MI0023564, MI0023565 and MI0023566, SEQ ID NOs: 489, 490, 491 and 492) having a hairpin-like structure are known as a precursor of "hsa-miR-6511a-5p".

The term "hsa-miR-6824-5p gene" or "hsa-miR-6824-5p" used herein includes the hsa-miR-6824-5p gene (miRBase Accession No. MIMAT0027548) shown in SEQ ID NO: 229, a homolog or an ortholog thereof of a different organism species, and the like. The gene can be obtained by a method described in Ladewig E et al., 2012, Genome Res, Vol. 22, p. 1634-1645. Also, "hsa-mir-6824" (miRBase Accession No. MI0022669, SEQ ID NO: 493) having a hairpin-like structure is known as a precursor of "hsa-miR-6824-5p".

The term "hsa-miR-762 gene" or "hsa-miR-762" used herein includes the hsa-miR-762 gene (miRBase Accession No. MIMAT0010313) shown in SEQ ID NO: 230, a homolog or an ortholog thereof of a different organism species, and the like. The gene can be obtained by a method described in Berezikov E et al., 2006, Genome Res, Vol. 16, p. 1289-1298. Also, "hsa-mir-762" (miRBase Accession No. MI0003892, SEQ ID NO: 494) having a hairpin-like structure is known as a precursor of "hsa-miR-762".

The term "hsa-miR-6836-3p gene" or "hsa-miR-6836-3p" used herein includes the hsa-miR-6836-3p gene (miRBase Accession No. MIMAT0027575) shown in SEQ ID NO: 231, a homolog or an ortholog thereof of a different organism species, and the like. The gene can be obtained by a method described in Ladewig E et al., 2012, Genome Res, Vol. 22, p. 1634-1645. Also, "hsa-mir-6836" (miRBase Accession No. MI0022682, SEQ ID NO: 495) having a hairpin-like structure is known as a precursor of "hsa-miR-6836-3p".

The term "hsa-miR-6727-5p gene" or "hsa-miR-6727-5p" used herein includes the hsa-miR-6727-5p gene (miRBase Accession No. MIMAT0027355) shown in SEQ ID NO: 232, a homolog or an ortholog thereof of a different organism species, and the like. The gene can be obtained by a method described in Ladewig E et al., 2012, Genome Res, Vol. 22, p. 1634-1645. Also, "hsa-mir-6727" (miRBase Accession No. MI0022572, SEQ ID NO: 496) having a hairpin-like structure is known as a precursor of "hsa-miR-6727-5p".

The term "hsa-miR-4739 gene" or "hsa-miR-4739" used herein includes the hsa-miR-4739 gene (miRBase Accession No. MIMAT0019868) shown in SEQ ID NO: 233, a homolog or an ortholog thereof of a different organism species, and the like. The gene can be obtained by a method described in Persson H et al., 2011, Cancer Res, Vol. 71, p. 78-86. Also, "hsa-mir-4739" (miRBase Accession No. MI0017377, SEQ ID NO: 497) having a hairpin-like structure is known as a precursor of "hsa-miR-4739".

The term "hsa-miR-7977 gene" or "hsa-miR-7977" used herein includes the hsa-miR-7977 gene (miRBase Accession No. MIMAT0031180) shown in SEQ ID NO: 234, a homolog or an ortholog thereof of a different organism species, and the like. The gene can be obtained by a method described in Velthut-Meikas A et al., 2013, Mol Endocrinol, Vol. 27, p. 1128-1141. Also, "hsa-mir-7977" (miRBase Accession No. MI0025753, SEQ ID NO: 498) having a hairpin-like structure is known as a precursor of "hsa-miR-7977".

The term "hsa-miR-4484 gene" or "hsa-miR-4484" used herein includes the hsa-miR-4484 gene (miRBase Accession No. MIMAT0019018) shown in SEQ ID NO: 235, a homolog or an ortholog thereof of a different organism species, and the like. The gene can be obtained by a method described in Jima D D et al., 2010, Blood, Vol. 116, e118-e127. Also, "hsa-mir-4484" (miRBase Accession No. MI0016845, SEQ ID NO: 499) having a hairpin-like structure is known as a precursor of "hsa-miR-4484".

The term "hsa-miR-6515-3p gene" or "hsa-miR-6515-3p" used herein includes the hsa-miR-6515-3p gene (miRBase Accession No. MIMAT0025487) shown in SEQ ID NO: 236, a homolog or an ortholog thereof of a different organism species, and the like. The gene can be obtained by a method described in Joyce C E et al., 2011, Hum Mol Genet, Vol. 20, p. 4025-4040. Also, "hsa-mir-6515" (miRBase Accession No. MI0022227, SEQ ID NO: 500) having a hairpin-like structure is known as a precursor of "hsa-miR-6515-3p".

The term "hsa-miR-373-5p gene" or "hsa-miR-373-5p" used herein includes the hsa-miR-373-5p gene (miRBase Accession No. MIMAT0000725) shown in SEQ ID NO: 237, a homolog or an ortholog thereof of a different organism species, and the like. The gene can be obtained by a method described in Suh M R et al., 2004, Dev Biol, Vol. 270, p. 488-498. Also, "hsa-mir-373" (miRBase Accession No. MI0000781, SEQ ID NO: 501) having a hairpin-like structure is known as a precursor of "hsa-miR-373-5p".

The term "hsa-miR-4258 gene" or "hsa-miR-4258" used herein includes the hsa-miR-4258 gene (miRBase Accession No. MIMAT0016879) shown in SEQ ID NO: 238, a homolog or an ortholog thereof of a different organism species, and the like. The gene can be obtained by a method described in Goff L A et al., 2009, PLoS One, Vol. 4, e7192. Also, "hsa-mir-4258" (miRBase Accession No. MI0015857, SEQ ID NO: 502) having a hairpin-like structure is known as a precursor of "hsa-miR-4258".

The term "hsa-miR-4674 gene" or "hsa-miR-4674" used herein includes the hsa-miR-4674 gene (miRBase Accession No. MIMAT0019756) shown in SEQ ID NO: 239, a homolog or an ortholog thereof of a different organism species, and the like. The gene can be obtained by a method described in Persson H et al., 2011, Cancer Res, Vol. 71, p. 78-86. Also, "hsa-mir-4674" (miRBase Accession No. MI0017305, SEQ ID NO: 503) having a hairpin-like structure is known as a precursor of "hsa-miR-4674".

The term "hsa-miR-3180 gene" or "hsa-miR-3180" used herein includes the hsa-miR-3180 gene (miRBase Accession No. MIMAT0018178) shown in SEQ ID NO: 240, a homolog or an ortholog thereof of a different organism species, and the like. The gene can be obtained by a method described in Creighton C J et al., 2010, PLoS One, Vol. 5, e9637. Also, "hsa-mir-3180-4 and hsa-mir-3180-5" (miRBase Accession Nos. MI0016408 and MI0016409, SEQ ID NOs: 504 and 505) having a hairpin-like structure are known as a precursor of "hsa-miR-3180".

The term "hsa-miR-6076 gene" or "hsa-miR-6076" used herein includes the hsa-miR-6076 gene (miRBase Accession No. MIMAT0023701) shown in SEQ ID NO: 241, a homolog or an ortholog thereof of a different organism species, and the like. The gene can be obtained by a method described in Voellenkle C et al., 2012, RNA, VOL. 18, p. 472-484. Also, "hsa-mir-6076" (miRBase Accession No. MI0020353, SEQ ID NO: 506) having a hairpin-like structure is known as a precursor of "hsa-miR-6076".

The term "hsa-miR-1238-5p gene" or "hsa-miR-1238-5p" used herein includes the hsa-miR-1238-5p gene (miRBase Accession No. MIMAT0022947) shown in SEQ ID NO: 242, a homolog or an ortholog thereof of a different organism species, and the like. The gene can be obtained by a method described in Berezikov E et al., 2007, Mol Cell, Vol. 28, p. 328-336. Also, "hsa-mir-1238" (miRBase Accession No. MI0006328, SEQ ID NO: 507) having a hairpin-like structure is known as a precursor of "hsa-miR-1238-5p".

The term "hsa-miR-4463 gene" or "hsa-miR-4463" used herein includes the hsa-miR-4463 gene (miRBase Accession No. MIMAT0018987) shown in SEQ ID NO: 243, a homolog or an ortholog thereof of a different organism species, and the like. The gene can be obtained by a method described in Jima D D et al., 2010, Blood, Vol. 116, e118-e127. Also, "hsa-mir-4463" (miRBase Accession No. MI0016811, SEQ ID NO: 508) having a hairpin-like structure is known as a precursor of "hsa-miR-4463".

The term "hsa-miR-4486 gene" or "hsa-miR-4486" used herein includes the hsa-miR-4486 gene (miRBase Accession No. MIMAT0019020) shown in SEQ ID NO: 244, a homolog or an ortholog thereof of a different organism species, and the like. The gene can be obtained by a method described in Jima D D et al., 2010, Blood, Vol. 116, e118-e127. Also, "hsa-mir-4486" (miRBase Accession No. MI0016847, SEQ ID NO: 509) having a hairpin-like structure is known as a precursor of "hsa-miR-4486".

The term "hsa-miR-4730 gene" or "hsa-miR-4730" used herein includes the hsa-miR-4730 gene (miRBase Accession No. MIMAT0019852) shown in SEQ ID NO: 245, a homolog or an ortholog thereof of a different organism species, and the like. The gene can be obtained by a method described in Persson H et al., 2011, Cancer Res, Vol. 71, p. 78-86. Also, "hsa-mir-4730" (miRBase Accession No. MI0017367, SEQ ID NO: 510) having a hairpin-like structure is known as a precursor of "hsa-miR-4730".

The term "hsa-miR-6766-3p gene" or "hsa-miR-6766-3p" used herein includes the hsa-miR-6766-3p gene (miRBase Accession No. MIMAT0027433) shown in SEQ ID NO: 246, a homolog or an ortholog thereof of a different organism species, and the like. The gene can be obtained by a method described in Ladewig E et al., 2012, Genome Res, Vol. 22, p. 1634-1645. Also, "hsa-mir-6766" (miRBase Accession No. MI0022611, SEQ ID NO: 511) having a hairpin-like structure is known as a precursor of "hsa-miR-6766-3p".

The term "hsa-miR-4286 gene" or "hsa-miR-4286" used herein includes the hsa-miR-4286 gene (miRBase Accession No. MIMAT0016916) shown in SEQ ID NO: 247, a homolog or an ortholog thereof of a different organism species, and the like. The gene can be obtained by a method described in Goff L A et al., 2009, PLoS One, Vol. 4, e7192. Also, "hsa-mir-4286" (miRBase Accession No. MI0015894, SEQ ID NO: 512) having a hairpin-like structure is known as a precursor of "hsa-miR-4286".

The term "hsa-miR-6511a-5p gene" or "hsa-miR-6511a-5p" used herein includes the hsa-miR-6511a-5p gene (miRBase Accession No. MIMAT0025478) shown in SEQ ID NO: 248, a homolog or an ortholog thereof of a different organism species, and the like. The gene can be obtained by a method described in Joyce C E et al., 2011, Hum Mol Genet, Vol. 20, p. 4025-4040. Also, "hsa-mir-6511a-1, hsa-mir-6511a-2, hsa-mir-6511a-3 and hsa-mir-6511a-4" (miRBase Accession Nos. MI0022223, MI0023564, MI0023565 and MI0023566, SEQ ID NOs: 513, 514, 515 and 516) having a hairpin-like structure are known as a precursor of "hsa-miR-6511a-5p".

The term "hsa-miR-4739 gene" or "hsa-miR-4739" used herein includes the hsa-miR-4739 gene (miRBase Accession No. MIMAT0019868) shown in SEQ ID NO: 249, a homolog or an ortholog thereof of a different organism species, and the like. The gene can be obtained by a method described in Persson H et al., 2011, Cancer Res, Vol. 71, p. 78-86. Also, "hsa-mir-4739" (miRBase Accession No. MI0017377, SEQ ID NO: 517) having a hairpin-like structure is known as a precursor of "hsa-miR-4739".

The term "hsa-miR-6749-5p gene" or "hsa-miR-6749-5p" used herein includes the hsa-miR-6749-5p gene (miRBase Accession No. MIMAT0027398) shown in SEQ ID NO: 250, a homolog or an ortholog thereof of a different organism species, and the like. The gene can be obtained by a method described in Ladewig E et al., 2012, Genome Res, Vol. 22, p. 1634-1645. Also, "hsa-mir-6749" (miRBase Accession No. MI0022594, SEQ ID NO: 518) having a hairpin-like structure is known as a precursor of "hsa-miR-6749-5p".

A mature miRNA may become a variant, due to a cleavage whereby the resulting sequence is shorter or longer by one to several flanking nucleotides, or due to substitution of nucleotides, when cut out as the mature miRNA from its RNA precursor having a hairpin-like structure. This variant is called isomiR (Morin R D. et al., 2008, Genome Res., Vol. 18, p. 610-621). The miRBase Release 20 shows the nucleotide sequences represented by SEQ ID NOs: 1 to 250 as well as a large number of the nucleotide sequence variants and fragments represented by SEQ ID NOs: 519 to 812, called isomiRs. These variants can also be obtained as miRNAs having a nucleotide sequence represented by any of SEQ ID NOs: 1 to 250. Specifically, among the variants of polynucleotides consisting of the nucleotide sequence represented by any of SEQ ID NOs: 2, 3, 6, 7, 8, 11, 12, 13, 15, 19, 20, 25, 26, 27, 29, 31, 32, 37, 44, 45, 46, 47, 48, 49, 51, 52, 53, 54, 55, 56, 57, 59, 60, 61, 62, 63, 71, 72, 73, 74, 76, 77, 78, 79, 83, 84, 86, 87, 88, 89, 90, 92, 94, 98, 102, 105, 106, 108, 111, 112, 113, 114, 116, 117, 118, 122, 123, 124, 128, 129, 133, 134, 135, 136, 137, 140, 141, 145, 146, 147, 148, 149, 150, 151, 153, 154, 155, 157, 158, 159, 160, 161, 162, 163, 166, 167, 168, 169, 176, 177, 178, 179, 180, 181, 182, 184, 186, 187, 190, 193, 196, 198, 201, 202, 203, 204, 205, 206, 207, 208, 209, 210, 211, 214, 215, 216, 217, 218, 220, 221, 222, 223, 224, 226, 228, 233, 235, 236, 237, 239, 240, 243, 244, 245, 247, 248, and 249 or a nucleotide sequence derived from the nucleotide sequence by the replacement of u with t according to the present invention, examples of the longest variants registered in miRBase Release 20 include polynucleotides represented by SEQ ID NOs: 519, 521, 523, 525, 527, 529, 531, 533, 535, 537, 539, 541, 543, 545, 547, 549, 551, 553, 555, 557, 559, 561, 563, 565, 567, 569, 571, 573, 575, 577, 579, 581, 583, 585, 587, 589, 591, 593, 595, 597, 599, 601, 603, 605, 607, 609, 611, 613, 615, 617, 619, 621, 623, 625, 627, 629, 631, 633, 635, 637, 639, 641, 643, 645, 647, 649, 651, 653, 655, 657, 659, 661, 663, 665, 667, 669, 671, 673, 675, 677, 679, 681, 683, 685, 687, 689, 691, 693, 695, 697, 699, 701, 703, 705, 707, 709, 711, 713, 715, 717, 719, 721, 723, 725, 727, 729, 731, 733, 735, 737, 739, 741, 743, 745, 747, 749, 751, 753, 755, 757, 759, 761, 763, 765, 767, 769, 771, 773, 775, 777, 779, 781, 783, 785, 787, 789, 791, 793, 795, 797, 799, 801, 803, 805, 807, 809, and 811, respectively. Also, among the variants of polynucleotides consisting of a nucleotide sequence represented by any of SEQ ID NOs: 2, 3, 6, 7, 8, 11, 12, 13, 15, 19, 20, 25, 26, 27, 29, 31, 32, 37, 44, 45, 46, 47, 48, 49, 51, 52, 53, 54, 55, 56, 57, 59, 60, 61, 62, 63, 71, 72, 73, 74, 76, 77, 78, 79, 83, 84, 86, 87, 88, 89, 90, 92, 94, 98, 102, 105, 106, 108, 111, 112, 113, 114, 116, 117, 118, 122, 123, 124, 128, 129, 133, 134, 135, 136, 137, 140, 141, 145, 146, 147, 148, 149, 150, 151, 153, 154, 155, 157, 158, 159, 160, 161, 162, 163, 166, 167, 168, 169, 176, 177, 178, 179, 180, 181, 182, 184, 186, 187, 190, 193, 196, 198, 201, 202, 203, 204, 205, 206, 207, 208, 209, 210, 211, 214, 215, 216, 217, 218, 220, 221, 222, 223, 224, 226, 228, 233, 235, 236, 237, 239, 240, 243, 244, 245, 247, 248, and 249 or a nucleotide sequence derived from the nucleotide sequence by the replacement of u with t according to the present invention, examples of shortest variants registered in the miRBase Release 20 include polynucleotides having sequences represented by SEQ ID NOs: 520, 522, 524, 526, 528, 530, 532, 534, 536, 538, 540, 542, 544, 546, 548, 550, 552, 554, 556, 558, 560, 562, 564, 566, 568, 570, 572, 574, 576, 578, 580, 582, 584, 586, 588, 590, 592, 594, 596, 598, 600, 602, 604, 606, 608, 610, 612, 614, 616, 618, 620, 622, 624, 626, 628, 630, 632, 634, 636, 638, 640, 642, 644, 646, 648, 650, 652, 654, 656, 658, 660, 662, 664, 666, 668, 670, 672, 674, 676, 678, 680, 682, 684, 686, 688, 690, 692, 694, 696, 698, 700, 702, 704, 706, 708, 710, 712, 714, 716, 718, 720, 722, 724, 726, 728, 730, 732, 734, 736, 738, 740, 742, 744, 746, 748, 750, 752, 754, 756, 758, 760, 762, 764, 766, 768, 770, 772, 774, 776, 778, 780, 782, 784, 786, 788, 790, 792, 794, 796, 798, 800, 802, 804, 806, 808, 810, and 812, respectively. In addition to these variants and fragments, examples thereof include a large number of isomiR polynucleotides of SEQ ID NOs: 2, 3, 6, 7, 8, 11, 12, 13, 15, 19, 20, 25, 26, 27, 29, 31, 32, 37, 44, 45, 46, 47, 48, 49, 51, 52, 53, 54, 55, 56, 57, 59, 60, 61, 62, 63, 71, 72, 73, 74, 76, 77, 78, 79, 83, 84, 86, 87, 88, 89, 90, 92, 94, 98, 102, 105, 106, 108, 111, 112, 113, 114, 116, 117, 118, 122, 123, 124, 128, 129, 133, 134, 135, 136, 137, 140, 141, 145, 146, 147, 148, 149, 150, 151, 153, 154, 155, 157, 158, 159, 160, 161, 162, 163, 166, 167, 168, 169, 176, 177, 178, 179, 180, 181, 182, 184, 186, 187, 190, 193, 196, 198, 201, 202, 203, 204, 205, 206, 207, 208, 209, 210, 211, 214, 215, 216, 217, 218, 220, 221, 222, 223, 224, 226, 228, 233, 235, 236, 237, 239, 240, 243, 244, 245, 247, 248, and 249 registered in the miRBase. Examples of the polynucleotide comprising a nucleotide sequence represented by any of SEQ ID NOs: 1 to 250 include a polynucleotide represented by any of SEQ ID NOs: 251 to 518, which are their respective precursors.

The names and miRBase Accession Nos. (registration numbers) of the genes represented by SEQ ID NOs: 1 to 812 are shown in Table 1.

As used herein, the term "capable of specifically binding" means that the nucleic acid probe or the primer used in the present invention binds to a particular target nucleic acid and cannot substantially bind to other nucleic acids.

TABLE 1

| SEQ ID NO: | Gene name | miRBase registration No. |
|---|---|---|
| 1 | hsa-miR-6784-5p | MIMAT0027468 |
| 2 | hsa-miR-1181 | MIMAT0005826 |
| 3 | hsa-miR-671-5p | MIMAT0003880 |
| 4 | hsa-miR-6857-5p | MIMAT0027614 |
| 5 | hsa-miR-4276 | MIMAT0016904 |
| 6 | hsa-miR-1914-3p | MIMAT0007890 |
| 7 | hsa-miR-149-3p | MIMAT0004609 |
| 8 | hsa-miR-937-5p | MIMAT0022938 |
| 9 | hsa-miR-4675 | MIMAT0019757 |
| 10 | hsa-miR-6795-5p | MIMAT0027490 |
| 11 | hsa-miR-4731-5p | MIMAT0019853 |
| 12 | hsa-miR-5090 | MIMAT0021082 |
| 13 | hsa-miR-3620-5p | MIMAT0022967 |
| 14 | hsa-miR-1343-5p | MIMAT0027038 |
| 15 | hsa-miR-6717-5p | MIMAT0025846 |
| 16 | hsa-miR-6825-5p | MIMAT0027550 |
| 17 | hsa-miR-6738-5p | MIMAT0027377 |
| 18 | hsa-miR-6769a-5p | MIMAT0027438 |
| 19 | hsa-miR-4728-5p | MIMAT0019849 |
| 20 | hsa-miR-652-5p | MIMAT0022709 |
| 21 | hsa-miR-4257 | MIMAT0016878 |
| 22 | hsa-miR-6785-5p | MIMAT0027470 |
| 23 | hsa-miR-7110-5p | MIMAT0028117 |
| 24 | hsa-miR-6887-5p | MIMAT0027674 |
| 25 | hsa-miR-887-3p | MIMAT0004951 |
| 26 | hsa-miR-1228-5p | MIMAT0005582 |
| 27 | hsa-miR-5572 | MIMAT0022260 |
| 28 | hsa-miR-6782-5p | MIMAT0027464 |
| 29 | hsa-miR-4298 | MIMAT0016852 |
| 30 | hsa-miR-6786-5p | MIMAT0027472 |
| 31 | hsa-miR-5010-5p | MIMAT0021043 |
| 32 | hsa-miR-6087 | MIMAT0023712 |
| 33 | hsa-miR-6765-5p | MIMAT0027430 |
| 34 | hsa-miR-6732-5p | MIMAT0027365 |
| 35 | hsa-miR-6787-5p | MIMAT0027474 |
| 36 | hsa-miR-6737-5p | MIMAT0027375 |
| 37 | hsa-miR-128-2-5p | MIMAT0031095 |
| 38 | hsa-miR-4270 | MIMAT0016900 |
| 39 | hsa-miR-6861-5p | MIMAT0027623 |
| 40 | hsa-miR-6756-5p | MIMAT0027412 |
| 41 | hsa-miR-1229-5p | MIMAT0022942 |
| 42 | hsa-miR-6891-5p | MIMAT0027682 |
| 43 | hsa-miR-6848-5p | MIMAT0027596 |
| 44 | hsa-miR-1237-5p | MIMAT0022946 |
| 45 | hsa-miR-30c-1-3p | MIMAT0004674 |
| 46 | hsa-miR-1233-5p | MIMAT0022943 |
| 47 | hsa-miR-211-3p | MIMAT0022694 |
| 48 | hsa-miR-4758-5p | MIMAT0019903 |
| 49 | hsa-miR-614 | MIMAT0003282 |
| 50 | hsa-miR-6746-5p | MIMAT0027392 |
| 51 | hsa-miR-1915-5p | MIMAT0007891 |
| 52 | hsa-miR-4688 | MIMAT0019777 |
| 53 | hsa-miR-3917 | MIMAT0018191 |
| 54 | hsa-miR-5787 | MIMAT0023252 |
| 55 | hsa-miR-4632-5p | MIMAT0022977 |
| 56 | hsa-miR-6126 | MIMAT0024599 |
| 57 | hsa-miR-135a-3p | MIMAT0004595 |
| 58 | hsa-miR-8063 | MIMAT0030990 |
| 59 | hsa-miR-5698 | MIMAT0022491 |
| 60 | hsa-miR-6089 | MIMAT0023714 |
| 61 | hsa-miR-498 | MIMAT0002824 |
| 62 | hsa-miR-296-3p | MIMAT0004679 |
| 63 | hsa-miR-4419b | MIMAT0019034 |
| 64 | hsa-miR-6802-5p | MIMAT0027504 |
| 65 | hsa-miR-6829-5p | MIMAT0027558 |
| 66 | hsa-miR-6803-5p | MIMAT0027506 |
| 67 | hsa-miR-1199-5p | MIMAT0031119 |
| 68 | hsa-miR-6840-3p | MIMAT0027583 |
| 69 | hsa-miR-6752-5p | MIMAT0027404 |
| 70 | hsa-miR-6798-5p | MIMAT0027496 |
| 71 | hsa-miR-6131 | MIMAT0024615 |
| 72 | hsa-miR-4667-5p | MIMAT0019743 |
| 73 | hsa-miR-6510-5p | MIMAT0025476 |
| 74 | hsa-miR-4690-5p | MIMAT0019779 |
| 75 | hsa-miR-920 | MIMAT0004970 |
| 76 | hsa-miR-23b-3p | MIMAT0000418 |
| 77 | hsa-miR-4448 | MIMAT0018967 |
| 78 | hsa-miR-2110 | MIMAT0010133 |
| 79 | hsa-miR-4706 | MIMAT0019806 |
| 80 | hsa-miR-7845-5p | MIMAT0030420 |
| 81 | hsa-miR-6808-5p | MIMAT0027516 |
| 82 | hsa-miR-4447 | MIMAT0018966 |
| 83 | hsa-miR-6869-5p | MIMAT0027638 |
| 84 | hsa-miR-1908-5p | MIMAT0007881 |
| 85 | hsa-miR-6729-5p | MIMAT0027359 |
| 86 | hsa-miR-5195-3p | MIMAT0021127 |
| 87 | hsa-miR-638 | MIMAT0003308 |
| 88 | hsa-miR-6125 | MIMAT0024598 |
| 89 | hsa-miR-3178 | MIMAT0015055 |
| 90 | hsa-miR-3196 | MIMAT0015080 |
| 91 | hsa-miR-8069 | MIMAT0030996 |
| 92 | hsa-miR-4723-5p | MIMAT0019838 |
| 93 | hsa-miR-4746-3p | MIMAT0019881 |
| 94 | hsa-miR-4689 | MIMAT0019778 |
| 95 | hsa-miR-6816-5p | MIMAT0027532 |
| 96 | hsa-miR-6757-5p | MIMAT0027414 |
| 97 | hsa-miR-7109-5p | MIMAT0028115 |
| 98 | hsa-miR-6724-5p | MIMAT0025856 |
| 99 | hsa-miR-1225-3p | MIMAT0005573 |
| 100 | hsa-miR-6875-5p | MIMAT0027650 |
| 101 | hsa-miR-7108-5p | MIMAT0028113 |
| 102 | hsa-miR-4508 | MIMAT0019045 |
| 103 | hsa-miR-6085 | MIMAT0023710 |
| 104 | hsa-miR-6779-5p | MIMAT0027458 |
| 105 | hsa-miR-642a-3p | MIMAT0020924 |
| 106 | hsa-miR-4695-5p | MIMAT0019788 |
| 107 | hsa-miR-7847-3p | MIMAT0030422 |
| 108 | hsa-miR-3197 | MIMAT0015082 |
| 109 | hsa-miR-6769b-5p | MIMAT0027620 |
| 110 | hsa-miR-7641 | MIMAT0029782 |
| 111 | hsa-miR-187-5p | MIMAT0004561 |
| 112 | hsa-miR-3185 | MIMAT0015065 |
| 113 | hsa-miR-2861 | MIMAT0013802 |
| 114 | hsa-miR-3940-5p | MIMAT0019229 |
| 115 | hsa-miR-1203 | MIMAT0005866 |
| 116 | hsa-miR-615-5p | MIMAT0004804 |
| 117 | hsa-miR-4787-5p | MIMAT0019956 |
| 118 | hsa-miR-1343-3p | MIMAT0019776 |
| 119 | hsa-miR-6813-5p | MIMAT0027526 |
| 120 | hsa-miR-1225-5p | MIMAT0005572 |
| 121 | hsa-miR-602 | MIMAT0003270 |
| 122 | hsa-miR-4488 | MIMAT0019022 |
| 123 | hsa-miR-125a-3p | MIMAT0004602 |
| 124 | hsa-miR-5100 | MIMAT0022259 |
| 125 | hsa-miR-4294 | MIMAT0016849 |
| 126 | hsa-miR-1231 | MIMAT0005586 |
| 127 | hsa-miR-6765-3p | MIMAT0027431 |
| 128 | hsa-miR-4442 | MIMAT0018960 |
| 129 | hsa-miR-718 | MIMAT0012735 |
| 130 | hsa-miR-6780b-5p | MIMAT0027572 |
| 131 | hsa-miR-6090 | MIMAT0023715 |
| 132 | hsa-miR-6845-5p | MIMAT0027590 |
| 133 | hsa-miR-4741 | MIMAT0019871 |
| 134 | hsa-miR-4467 | MIMAT0018994 |
| 135 | hsa-miR-4707-5p | MIMAT0019807 |
| 136 | hsa-miR-4271 | MIMAT0016901 |
| 137 | hsa-miR-4673 | MIMAT0019755 |
| 138 | hsa-miR-3184-5p | MIMAT0015064 |
| 139 | hsa-miR-1469 | MIMAT0007347 |
| 140 | hsa-miR-4640-5p | MIMAT0019699 |
| 141 | hsa-miR-663a | MIMAT0003326 |
| 142 | hsa-miR-6791-5p | MIMAT0027482 |
| 143 | hsa-miR-6826-5p | MIMAT0027552 |
| 144 | hsa-miR-4433b-3p | MIMAT0030414 |
| 145 | hsa-miR-1915-3p | MIMAT0007892 |
| 146 | hsa-miR-4417 | MIMAT0018929 |
| 147 | hsa-miR-4449 | MIMAT0018968 |
| 148 | hsa-miR-4707-3p | MIMAT0019808 |
| 149 | hsa-miR-3180-3p | MIMAT0015058 |
| 150 | hsa-miR-5585-3p | MIMAT0022286 |
| 151 | hsa-miR-1268a | MIMAT0005922 |
| 152 | hsa-miR-8072 | MIMAT0030999 |
| 153 | hsa-miR-296-5p | MIMAT0000690 |
| 154 | hsa-miR-204-3p | MIMAT0022693 |

TABLE 1-continued

| SEQ ID NO: | Gene name | miRBase registration No. |
|---|---|---|
| 155 | hsa-miR-4454 | MIMAT0018976 |
| 156 | hsa-miR-6722-3p | MIMAT0025854 |
| 157 | hsa-miR-1290 | MIMAT0005880 |
| 158 | hsa-miR-3622a-5p | MIMAT0018003 |
| 159 | hsa-miR-939-5p | MIMAT0004982 |
| 160 | hsa-miR-675-5p | MIMAT0004284 |
| 161 | hsa-miR-3131 | MIMAT0014996 |
| 162 | hsa-miR-4648 | MIMAT0019710 |
| 163 | hsa-miR-1268b | MIMAT0018925 |
| 164 | hsa-miR-6741-5p | MIMAT0027383 |
| 165 | hsa-miR-6893-5p | MIMAT0027686 |
| 166 | hsa-miR-3162-5p | MIMAT0015036 |
| 167 | hsa-miR-642b-3p | MIMAT0018444 |
| 168 | hsa-miR-4734 | MIMAT0019859 |
| 169 | hsa-miR-150-3p | MIMAT0004610 |
| 170 | hsa-miR-8089 | MIMAT0031016 |
| 171 | hsa-miR-6805-3p | MIMAT0027511 |
| 172 | hsa-miR-7113-3p | MIMAT0028124 |
| 173 | hsa-miR-6850-5p | MIMAT0027600 |
| 174 | hsa-miR-6799-5p | MIMAT0027498 |
| 175 | hsa-miR-6768-5p | MIMAT0027436 |
| 176 | hsa-miR-92b-5p | MIMAT0004792 |
| 177 | hsa-miR-3679-5p | MIMAT0018104 |
| 178 | hsa-miR-4792 | MIMAT0019964 |
| 179 | hsa-miR-3656 | MIMAT0018076 |
| 180 | hsa-miR-92a-2-5p | MIMAT0004508 |
| 181 | hsa-miR-4466 | MIMAT0018993 |
| 182 | hsa-miR-4513 | MIMAT0019050 |
| 183 | hsa-miR-6781-5p | MIMAT0027462 |
| 184 | hsa-miR-4649-5p | MIMAT0019711 |
| 185 | hsa-miR-6775-5p | MIMAT0027450 |
| 186 | hsa-miR-4651 | MIMAT0019715 |
| 187 | hsa-miR-3195 | MIMAT0015079 |
| 188 | hsa-miR-6726-5p | MIMAT0027353 |
| 189 | hsa-miR-6872-3p | MIMAT0027645 |
| 190 | hsa-miR-371a-5p | MIMAT0004687 |
| 191 | hsa-miR-6777-5p | MIMAT0027454 |
| 192 | hsa-miR-6789-5p | MIMAT0027478 |
| 193 | hsa-miR-7975 | MIMAT0031178 |
| 194 | hsa-miR-6821-5p | MIMAT0027542 |
| 195 | hsa-miR-4534 | MIMAT0019073 |
| 196 | hsa-miR-619-5p | MIMAT0026622 |
| 197 | hsa-miR-7107-5p | MIMAT0028111 |
| 198 | hsa-miR-1228-3p | MIMAT0005583 |
| 199 | hsa-miR-6774-5p | MIMAT0027448 |
| 200 | hsa-miR-6805-5p | MIMAT0027510 |
| 201 | hsa-miR-23a-3p | MIMAT0000078 |
| 202 | hsa-miR-4665-5p | MIMAT0019739 |
| 203 | hsa-miR-4505 | MIMAT0019041 |
| 204 | hsa-miR-4638-5p | MIMAT0019695 |
| 205 | hsa-miR-24-3p | MIMAT0000080 |
| 206 | hsa-miR-3135b | MIMAT0018985 |
| 207 | hsa-miR-4745-5p | MIMAT0019878 |
| 208 | hsa-miR-128-1-5p | MIMAT0026477 |
| 209 | hsa-miR-4476 | MIMAT0019003 |
| 210 | hsa-miR-4687-3p | MIMAT0019775 |
| 211 | hsa-miR-3665 | MIMAT0018087 |
| 212 | hsa-miR-6806-5p | MIMAT0027512 |
| 213 | hsa-miR-3937 | MIMAT0018352 |
| 214 | hsa-miR-711 | MIMAT0012734 |
| 215 | hsa-miR-3141 | MIMAT0015010 |
| 216 | hsa-miR-3188 | MIMAT0015070 |
| 217 | hsa-miR-4281 | MIMAT0016907 |
| 218 | hsa-miR-5196-5p | MIMAT0021128 |
| 219 | hsa-miR-6880-5p | MIMAT0027660 |
| 220 | hsa-miR-3960 | MIMAT0019337 |
| 221 | hsa-miR-3648 | MIMAT0018068 |
| 222 | hsa-miR-6721-5p | MIMAT0025852 |
| 223 | hsa-miR-4492 | MIMAT0019027 |
| 224 | hsa-miR-744-5p | MIMAT0004945 |
| 225 | hsa-miR-7704 | MIMAT0030019 |
| 226 | hsa-miR-4749-5p | MIMAT0019885 |
| 227 | hsa-miR-6794-5p | MIMAT0027488 |
| 228 | hsa-miR-6511a-5p | MIMAT0025478 |
| 229 | hsa-miR-6824-5p | MIMAT0027548 |
| 230 | hsa-miR-762 | MIMAT0010313 |
| 231 | hsa-miR-6836-3p | MIMAT0027575 |
| 232 | hsa-miR-6727-5p | MIMAT0027355 |
| 233 | hsa-miR-4739 | MIMAT0019868 |
| 234 | hsa-miR-7977 | MIMAT0031180 |
| 235 | hsa-miR-4484 | MIMAT0019018 |
| 236 | hsa-miR-6515-3p | MIMAT0025487 |
| 237 | hsa-miR-373-5p | MIMAT0000725 |
| 238 | hsa-miR-4258 | MIMAT0016879 |
| 239 | hsa-miR-4674 | MIMAT0019756 |
| 240 | hsa-miR-3180 | MIMAT0018178 |
| 241 | hsa-miR-6076 | MIMAT0023701 |
| 242 | hsa-miR-1238-5p | MIMAT0022947 |
| 243 | hsa-miR-4463 | MIMAT0018987 |
| 244 | hsa-miR-4486 | MIMAT0019020 |
| 245 | hsa-miR-4730 | MIMAT0019852 |
| 246 | hsa-miR-6766-3p | MIMAT0027433 |
| 247 | hsa-miR-4286 | MIMAT0016916 |
| 248 | hsa-miR-6511a-5p | MIMAT0025478 |
| 249 | hsa-miR-4739 | MIMAT0019868 |
| 250 | hsa-miR-6749-5p | MIMAT0027398 |
| 251 | hsa-mir-6784 | MI0022629 |
| 252 | hsa-mir-1181 | MI0006274 |
| 253 | hsa-mir-671 | MI0003760 |
| 254 | hsa-mir-6857 | MI0022703 |
| 255 | hsa-mir-4276 | MI0015882 |
| 256 | hsa-mir-1914 | MI0008335 |
| 257 | hsa-mir-149 | MI0000478 |
| 258 | hsa-mir-937 | MI0005759 |
| 259 | hsa-mir-4675 | MI0017306 |
| 260 | hsa-mir-6795 | MI0022640 |
| 261 | hsa-mir-4731 | MI0017368 |
| 262 | hsa-mir-5090 | MI0017979 |
| 263 | hsa-mir-3620 | MI0016011 |
| 264 | hsa-mir-1343 | MI0017320 |
| 265 | hsa-mir-6717 | MI0022551 |
| 266 | hsa-mir-6825 | MI0022670 |
| 267 | hsa-mir-6738 | MI0022583 |
| 268 | hsa-mir-6769a | MI0022614 |
| 269 | hsa-mir-4728 | MI0017365 |
| 270 | hsa-mir-652 | MI0003667 |
| 271 | hsa-mir-4257 | MI0015856 |
| 272 | hsa-mir-6785 | MI0022630 |
| 273 | hsa-mir-7110 | MI0022961 |
| 274 | hsa-mir-6887 | MI0022734 |
| 275 | hsa-mir-887 | MI0005562 |
| 276 | hsa-mir-1228 | MI0006318 |
| 277 | hsa-mir-5572 | MI0019117 |
| 278 | hsa-mir-6782 | MI0022627 |
| 279 | hsa-mir-4298 | MI0015830 |
| 280 | hsa-mir-6786 | MI0022631 |
| 281 | hsa-mir-5010 | MI0017878 |
| 282 | hsa-mir-6087 | MI0020364 |
| 283 | hsa-mir-6765 | MI0022610 |
| 284 | hsa-mir-6732 | MI0022577 |
| 285 | hsa-mir-6787 | MI0022632 |
| 286 | hsa-mir-6737 | MI0022582 |
| 287 | hsa-mir-128-2 | MI0000727 |
| 288 | hsa-mir-4270 | MI0015878 |
| 289 | hsa-mir-6861 | MI0022708 |
| 290 | hsa-mir-6756 | MI0022601 |
| 291 | hsa-mir-1229 | MI0006319 |
| 292 | hsa-mir-6891 | MI0022738 |
| 293 | hsa-mir-6848 | MI0022694 |
| 294 | hsa-mir-1237 | MI0006327 |
| 295 | hsa-mir-30c-1 | MI0000736 |
| 296 | hsa-mir-1233-1 | MI0006323 |
| 297 | hsa-mir-1233-2 | MI0015973 |
| 298 | hsa-mir-211 | MI0000287 |
| 299 | hsa-mir-4758 | MI0017399 |
| 300 | hsa-mir-614 | MI0003627 |
| 301 | hsa-mir-6746 | MI0022591 |
| 302 | hsa-mir-1915 | MI0008336 |
| 303 | hsa-mir-4688 | MI0017321 |
| 304 | hsa-mir-3917 | MI0016423 |
| 305 | hsa-mir-5787 | MI0019797 |
| 306 | hsa-mir-4632 | MI0017259 |
| 307 | hsa-mir-6126 | MI0021260 |
| 308 | hsa-mir-135a-1 | MI0000452 |

TABLE 1-continued

| SEQ ID NO: | Gene name | miRBase registration No. |
|---|---|---|
| 309 | hsa-mir-8063 | MI0025899 |
| 310 | hsa-mir-5698 | MI0019305 |
| 311 | hsa-mir-6089-1 | MI0020366 |
| 312 | hsa-mir-6089-2 | MI0023563 |
| 313 | hsa-mir-498 | MI0003142 |
| 314 | hsa-mir-296 | MI0000747 |
| 315 | hsa-mir-4419b | MI0016861 |
| 316 | hsa-mir-6802 | MI0022647 |
| 317 | hsa-mir-6829 | MI0022674 |
| 318 | hsa-mir-6803 | MI0022648 |
| 319 | hsa-mir-1199 | MI0020340 |
| 320 | hsa-mir-6840 | MI0022686 |
| 321 | hsa-mir-6752 | MI0022597 |
| 322 | hsa-mir-6798 | MI0022643 |
| 323 | hsa-mir-6131 | MI0021276 |
| 324 | hsa-mir-4667 | MI0017297 |
| 325 | hsa-mir-6510 | MI0022222 |
| 326 | hsa-mir-4690 | MI0017323 |
| 327 | hsa-mir-920 | MI0005712 |
| 328 | hsa-mir-23b | MI0000439 |
| 329 | hsa-mir-4448 | MI0016791 |
| 330 | hsa-mir-2110 | MI0010629 |
| 331 | hsa-mir-4706 | MI0017339 |
| 332 | hsa-mir-7845 | MI0025515 |
| 333 | hsa-mir-6808 | MI0022653 |
| 334 | hsa-mir-4447 | MI0016790 |
| 335 | hsa-mir-6869 | MI0022716 |
| 336 | hsa-mir-1908 | MI0008329 |
| 337 | hsa-mir-6729 | MI0022574 |
| 338 | hsa-mir-5195 | MI0018174 |
| 339 | hsa-mir-638 | MI0003653 |
| 340 | hsa-mir-6125 | MI0021259 |
| 341 | hsa-mir-3178 | MI0014212 |
| 342 | hsa-mir-3196 | MI0014241 |
| 343 | hsa-mir-8069-1 | MI0025905 |
| 344 | hsa-mir-8069-2 | MI0031519 |
| 345 | hsa-mir-4723 | MI0017359 |
| 346 | hsa-mir-4746 | MI0017385 |
| 347 | hsa-mir-4689 | MI0017322 |
| 348 | hsa-mir-6816 | MI0022661 |
| 349 | hsa-mir-6757 | MI0022602 |
| 350 | hsa-mir-7109 | MI0022960 |
| 351 | hsa-mir-6724-1 | MI0022559 |
| 352 | hsa-mir-6724-2 | MI0031516 |
| 353 | hsa-mir-6724-3 | MI0031517 |
| 354 | hsa-mir-6724-4 | MI0031518 |
| 355 | hsa-mir-1225 | MI0006311 |
| 356 | hsa-mir-6875 | MI0022722 |
| 357 | hsa-mir-7108 | MI0022959 |
| 358 | hsa-mir-4508 | MI0016872 |
| 359 | hsa-mir-6085 | MI0020362 |
| 360 | hsa-mir-6779 | MI0022624 |
| 361 | hsa-mir-642a | MI0003657 |
| 362 | hsa-mir-4695 | MI0017328 |
| 363 | hsa-mir-7847 | MI0025517 |
| 364 | hsa-mir-3197 | MI0014245 |
| 365 | hsa-mir-6769b | MI0022706 |
| 366 | hsa-mir-7641-1 | MI0024975 |
| 367 | hsa-mir-7641-2 | MI0024976 |
| 368 | hsa-mir-187 | MI0000274 |
| 369 | hsa-mir-3185 | MI0014227 |
| 370 | hsa-mir-2861 | MI0013006 |
| 371 | hsa-mir-3940 | MI0016597 |
| 372 | hsa-mir-1203 | MI0006335 |
| 373 | hsa-mir-615 | MI0003628 |
| 374 | hsa-mir-4787 | MI0017434 |
| 375 | hsa-mir-1343 | MI0017320 |
| 376 | hsa-mir-6813 | MI0022658 |
| 377 | hsa-mir-1225 | MI0006311 |
| 378 | hsa-mir-602 | MI0003615 |
| 379 | hsa-mir-4488 | MI0016849 |
| 380 | hsa-mir-125a | MI0000469 |
| 381 | hsa-mir-5100 | MI0019116 |
| 382 | hsa-mir-4294 | MI0015827 |
| 383 | hsa-mir-1231 | MI0006321 |
| 384 | hsa-mir-6765 | MI0022610 |
| 385 | hsa-mir-4442 | MI0016785 |
| 386 | hsa-mir-718 | MI0012489 |
| 387 | hsa-mir-6780b | MI0022681 |
| 388 | hsa-mir-6090 | MI0020367 |
| 389 | hsa-mir-6845 | MI0022691 |
| 390 | hsa-mir-4741 | MI0017379 |
| 391 | hsa-mir-4467 | MI0016818 |
| 392 | hsa-mir-4707 | MI0017340 |
| 393 | hsa-mir-4271 | MI0015879 |
| 394 | hsa-mir-4673 | MI0017304 |
| 395 | hsa-mir-3184 | MI0014226 |
| 396 | hsa-mir-1469 | MI0007074 |
| 397 | hsa-mir-4640 | MI0017267 |
| 398 | hsa-mir-663a | MI0003672 |
| 399 | hsa-mir-6791 | MI0022636 |
| 400 | hsa-mir-6826 | MI0022671 |
| 401 | hsa-mir-4433b | MI0025511 |
| 402 | hsa-mir-1915 | MI0008336 |
| 403 | hsa-mir-4417 | MI0016753 |
| 404 | hsa-mir-4449 | MI0016792 |
| 405 | hsa-mir-4707 | MI0017340 |
| 406 | hsa-mir-3180-1 | MI0014214 |
| 407 | hsa-mir-3180-2 | MI0014215 |
| 408 | hsa-mir-3180-3 | MI0014217 |
| 409 | hsa-mir-5585 | MI0019142 |
| 410 | hsa-mir-1268a | MI0006405 |
| 411 | hsa-mir-8072 | MI0025908 |
| 412 | hsa-mir-296 | MI0000747 |
| 413 | hsa-mir-204 | MI0000284 |
| 414 | hsa-mir-4454 | MI0016800 |
| 415 | hsa-mir-6722 | MI0022557 |
| 416 | hsa-mir-1290 | MI0006352 |
| 417 | hsa-mir-3622a | MI0016013 |
| 418 | hsa-mir-939 | MI0005761 |
| 419 | hsa-mir-675 | MI0005416 |
| 420 | hsa-mir-3131 | MI0014151 |
| 421 | hsa-mir-4648 | MI0017275 |
| 422 | hsa-mir-1268b | MI0016748 |
| 423 | hsa-mir-6741 | MI0022586 |
| 424 | hsa-mir-6893 | MI0022740 |
| 425 | hsa-mir-3162 | MI0014192 |
| 426 | hsa-mir-642b | MI0016685 |
| 427 | hsa-mir-4734 | MI0017371 |
| 428 | hsa-mir-150 | MI0000479 |
| 429 | hsa-mir-8089 | MI0025925 |
| 430 | hsa-mir-6805 | MI0022650 |
| 431 | hsa-mir-7113 | MI0022964 |
| 432 | hsa-mir-6850 | MI0022696 |
| 433 | hsa-mir-6799 | MI0022644 |
| 434 | hsa-mir-6768 | MI0022613 |
| 435 | hsa-mir-92b | MI0003560 |
| 436 | hsa-mir-3679 | MI0016080 |
| 437 | hsa-mir-4792 | MI0017439 |
| 438 | hsa-mir-3656 | MI0016056 |
| 439 | hsa-mir-92a-2 | MI0000094 |
| 440 | hsa-mir-4466 | MI0016817 |
| 441 | hsa-mir-4513 | MI0016879 |
| 442 | hsa-mir-6781 | MI0022626 |
| 443 | hsa-mir-4649 | MI0017276 |
| 444 | hsa-mir-6775 | MI0022620 |
| 445 | hsa-mir-4651 | MI0017279 |
| 446 | hsa-mir-3195 | MI0014240 |
| 447 | hsa-mir-6726 | MI0022571 |
| 448 | hsa-mir-6872 | MI0022719 |
| 449 | hsa-mir-371a | MI0000779 |
| 450 | hsa-mir-6777 | MI0022622 |
| 451 | hsa-mir-6789 | MI0022634 |
| 452 | hsa-mir-7975 | MI0025751 |
| 453 | hsa-mir-6821 | MI0022666 |
| 454 | hsa-mir-4534 | MI0016901 |
| 455 | hsa-mir-619 | MI0003633 |
| 456 | hsa-mir-7107 | MI0022958 |
| 457 | hsa-mir-1228 | MI0006318 |
| 458 | hsa-mir-6774 | MI0022619 |
| 459 | hsa-mir-6805 | MI0022650 |
| 460 | hsa-mir-23a | MI0000079 |
| 461 | hsa-mir-4665 | MI0017295 |
| 462 | hsa-mir-4505 | MI0016868 |

TABLE 1-continued

| SEQ ID NO: | Gene name | miRBase registration No. |
|---|---|---|
| 463 | hsa-mir-4638 | MI0017265 |
| 464 | hsa-mir-24-1 | MI0000080 |
| 465 | hsa-mir-24-2 | MI0000081 |
| 466 | hsa-mir-3135b | MI0016809 |
| 467 | hsa-mir-4745 | MI0017384 |
| 468 | hsa-mir-128-1 | MI0000447 |
| 469 | hsa-mir-4476 | MI0016828 |
| 470 | hsa-mir-4687 | MI0017319 |
| 471 | hsa-mir-3665 | MI0016066 |
| 472 | hsa-mir-6806 | MI0022651 |
| 473 | hsa-mir-3937 | MI0016593 |
| 474 | hsa-mir-711 | MI0012488 |
| 475 | hsa-mir-3141 | MI0014165 |
| 476 | hsa-mir-3188 | MI0014232 |
| 477 | hsa-mir-4281 | MI0015885 |
| 478 | hsa-mir-5196 | MI0018175 |
| 479 | hsa-mir-6880 | MI0022727 |
| 480 | hsa-mir-3960 | MI0016964 |
| 481 | hsa-mir-3648-1 | MI0016048 |
| 482 | hsa-mir-3648-2 | MI0031512 |
| 483 | hsa-mir-6721 | MI0022556 |
| 484 | hsa-mir-4492 | MI0016854 |
| 485 | hsa-mir-744 | MI0005559 |
| 486 | hsa-mir-7704 | MI0025240 |
| 487 | hsa-mir-4749 | MI0017388 |
| 488 | hsa-mir-6794 | MI0022639 |
| 489 | hsa-mir-6511a-1 | MI0022223 |
| 490 | hsa-mir-6511a-2 | MI0023564 |
| 491 | hsa-mir-6511a-3 | MI0023565 |
| 492 | hsa-mir-6511a-4 | MI0023566 |
| 493 | hsa-mir-6824 | MI0022669 |
| 494 | hsa-mir-762 | MI0003892 |
| 495 | hsa-mir-6836 | MI0022682 |
| 496 | hsa-mir-6727 | MI0022572 |
| 497 | hsa-mir-4739 | MI0017377 |
| 498 | hsa-mir-7977 | MI0025753 |
| 499 | hsa-mir-4484 | MI0016845 |
| 500 | hsa-mir-6515 | MI0022227 |
| 501 | hsa-mir-373 | MI0000781 |
| 502 | hsa-mir-4258 | MI0015857 |
| 503 | hsa-mir-4674 | MI0017305 |
| 504 | hsa-mir-3180-4 | MI0016408 |
| 505 | hsa-mir-3180-5 | MI0016409 |
| 506 | hsa-mir-6076 | MI0020353 |
| 507 | hsa-mir-1238 | MI0006328 |
| 508 | hsa-mir-4463 | MI0016811 |
| 509 | hsa-mir-4486 | MI0016847 |
| 510 | hsa-mir-4730 | MI0017367 |
| 511 | hsa-mir-6766 | MI0022611 |
| 512 | hsa-mir-4286 | MI0015894 |
| 513 | hsa-mir-6511a-1 | MI0022223 |
| 514 | hsa-mir-6511a-2 | MI0023564 |
| 515 | hsa-mir-6511a-3 | MI0023565 |
| 516 | hsa-mir-6511a-4 | MI0023566 |
| 517 | hsa-mir-4739 | MI0017377 |
| 518 | hsa-mir-6749 | MI0022594 |
| 519 | isomiR example 1 of SEQ ID NO: 2 | — |
| 520 | isomiR example 2 of SEQ ID NO: 2 | — |
| 521 | isomiR example 1 of SEQ ID NO: 3 | — |
| 522 | isomiR example 2 of SEQ ID NO: 3 | — |
| 523 | isomiR example 1 of SEQ ID NO: 6 | — |
| 524 | isomiR example 2 of SEQ ID NO: 6 | — |
| 525 | isomiR example 1 of SEQ ID NO: 7 | — |
| 526 | isomiR example 2 of SEQ ID NO: 7 | — |
| 527 | isomiR example 1 of SEQ ID NO: 8 | — |
| 528 | isomiR example 2 of SEQ ID NO: 8 | — |
| 529 | isomiR example 1 of SEQ ID NO: 11 | — |
| 530 | isomiR example 2 of SEQ ID NO: 11 | — |
| 531 | isomiR example 1 of SEQ ID NO: 12 | — |
| 532 | isomiR example 2 of SEQ ID NO: 12 | — |
| 533 | isomiR example 1 of SEQ ID NO: 13 | — |
| 534 | isomiR example 2 of SEQ ID NO: 13 | — |
| 535 | isomiR example 1 of SEQ ID NO: 15 | — |
| 536 | isomiR example 2 of SEQ ID NO: 15 | — |
| 537 | isomiR example 1 of SEQ ID NO: 19 | — |
| 538 | isomiR example 2 of SEQ ID NO: 19 | — |
| 539 | isomiR example 1 of SEQ ID NO: 20 | — |
| 540 | isomiR example 2 of SEQ ID NO: 20 | — |
| 541 | isomiR example 1 of SEQ ID NO: 25 | — |
| 542 | isomiR example 2 of SEQ ID NO: 25 | — |
| 543 | isomiR example 1 of SEQ ID NO: 26 | — |
| 544 | isomiR example 2 of SEQ ID NO: 26 | — |
| 545 | isomiR example 1 of SEQ ID NO: 27 | — |
| 546 | isomiR example 2 of SEQ ID NO: 27 | — |
| 547 | isomiR example 1 of SEQ ID NO: 29 | — |
| 548 | isomiR example 2 of SEQ ID NO: 29 | — |
| 549 | isomiR example 1 of SEQ ID NO: 31 | — |
| 550 | isomiR example 2 of SEQ ID NO: 31 | — |
| 551 | isomiR example 1 of SEQ ID NO: 32 | — |
| 552 | isomiR example 2 of SEQ ID NO: 32 | — |
| 553 | isomiR example 1 of SEQ ID NO: 37 | — |
| 554 | isomiR example 2 of SEQ ID NO: 37 | — |
| 555 | isomiR example 1 of SEQ ID NO: 44 | — |
| 556 | isomiR example 2 of SEQ ID NO: 44 | — |
| 557 | isomiR example 1 of SEQ ID NO: 45 | — |
| 558 | isomiR example 2 of SEQ ID NO: 45 | — |
| 559 | isomiR example 1 of SEQ ID NO: 46 | — |
| 560 | isomiR example 2 of SEQ ID NO: 46 | — |
| 561 | isomiR example 1 of SEQ ID NO: 47 | — |
| 562 | isomiR example 2 of SEQ ID NO: 47 | — |
| 563 | isomiR example 1 of SEQ ID NO: 48 | — |
| 564 | isomiR example 2 of SEQ ID NO: 48 | — |
| 565 | isomiR example 1 of SEQ ID NO: 49 | — |
| 566 | isomiR example 2 of SEQ ID NO: 49 | — |
| 567 | isomiR example 1 of SEQ ID NO: 51 | — |
| 568 | isomiR example 2 of SEQ ID NO: 51 | — |
| 569 | isomiR example 1 of SEQ ID NO: 52 | — |
| 570 | isomiR example 2 of SEQ ID NO: 52 | — |
| 571 | isomiR example 1 of SEQ ID NO: 53 | — |
| 572 | isomiR example 2 of SEQ ID NO: 53 | — |
| 573 | isomiR example 1 of SEQ ID NO: 54 | — |
| 574 | isomiR example 2 of SEQ ID NO: 54 | — |
| 575 | isomiR example 1 of SEQ ID NO: 55 | — |
| 576 | isomiR example 2 of SEQ ID NO: 55 | — |
| 577 | isomiR example 1 of SEQ ID NO: 56 | — |
| 578 | isomiR example 2 of SEQ ID NO: 56 | — |
| 579 | isomiR example 1 of SEQ ID NO: 57 | — |
| 580 | isomiR example 2 of SEQ ID NO: 57 | — |
| 581 | isomiR example 1 of SEQ ID NO: 59 | — |
| 582 | isomiR example 2 of SEQ ID NO: 59 | — |
| 583 | isomiR example 1 of SEQ ID NO: 60 | — |
| 584 | isomiR example 2 of SEQ ID NO: 60 | — |
| 585 | isomiR example 1 of SEQ ID NO: 61 | — |
| 586 | isomiR example 2 of SEQ ID NO: 61 | — |
| 587 | isomiR example 1 of SEQ ID NO: 62 | — |
| 588 | isomiR example 2 of SEQ ID NO: 62 | — |
| 589 | isomiR example 1 of SEQ ID NO: 63 | — |
| 590 | isomiR example 2 of SEQ ID NO: 63 | — |
| 591 | isomiR example 1 of SEQ ID NO: 71 | — |
| 592 | isomiR example 2 of SEQ ID NO: 71 | — |
| 593 | isomiR example 1 of SEQ ID NO: 72 | — |
| 594 | isomiR example 2 of SEQ ID NO: 72 | — |
| 595 | isomiR example 1 of SEQ ID NO: 73 | — |
| 596 | isomiR example 2 of SEQ ID NO: 73 | — |
| 597 | isomiR example 1 of SEQ ID NO: 74 | — |
| 598 | isomiR example 2 of SEQ ID NO: 74 | — |
| 599 | isomiR example 1 of SEQ ID NO: 76 | — |
| 600 | isomiR example 2 of SEQ ID NO: 76 | — |
| 601 | isomiR example 1 of SEQ ID NO: 77 | — |
| 602 | isomiR example 2 of SEQ ID NO: 77 | — |
| 603 | isomiR example 1 of SEQ ID NO: 78 | — |
| 604 | isomiR example 2 of SEQ ID NO: 78 | — |
| 605 | isomiR example 1 of SEQ ID NO: 79 | — |
| 606 | isomiR example 2 of SEQ ID NO: 79 | — |
| 607 | isomiR example 1 of SEQ ID NO: 83 | — |
| 608 | isomiR example 2 of SEQ ID NO: 83 | — |
| 609 | isomiR example 1 of SEQ ID NO: 84 | — |
| 610 | isomiR example 2 of SEQ ID NO: 84 | — |
| 611 | isomiR example 1 of SEQ ID NO: 86 | — |
| 612 | isomiR example 2 of SEQ ID NO: 86 | — |
| 613 | isomiR example 1 of SEQ ID NO: 87 | — |
| 614 | isomiR example 2 of SEQ ID NO: 87 | — |
| 615 | isomiR example 1 of SEQ ID NO: 88 | — |
| 616 | isomiR example 2 of SEQ ID NO: 88 | — |

TABLE 1-continued

| SEQ ID NO: | Gene name | miRBase registration No. |
|---|---|---|
| 617 | isomiR example 1 of SEQ ID NO: 89 | — |
| 618 | isomiR example 2 of SEQ ID NO: 89 | — |
| 619 | isomiR example 1 of SEQ ID NO: 90 | — |
| 620 | isomiR example 2 of SEQ ID NO: 90 | — |
| 621 | isomiR example 1 of SEQ ID NO: 92 | — |
| 622 | isomiR example 2 of SEQ ID NO: 92 | — |
| 623 | isomiR example 1 of SEQ ID NO: 94 | — |
| 624 | isomiR example 2 of SEQ ID NO: 94 | — |
| 625 | isomiR example 1 of SEQ ID NO: 98 | — |
| 626 | isomiR example 2 of SEQ ID NO: 98 | — |
| 627 | isomiR example 1 of SEQ ID NO: 102 | — |
| 628 | isomiR example 2 of SEQ ID NO: 102 | — |
| 629 | isomiR example 1 of SEQ ID NO: 105 | — |
| 630 | isomiR example 2 of SEQ ID NO: 105 | — |
| 631 | isomiR example 1 of SEQ ID NO: 106 | — |
| 632 | isomiR example 2 of SEQ ID NO: 106 | — |
| 633 | isomiR example 1 of SEQ ID NO: 108 | — |
| 634 | isomiR example 2 of SEQ ID NO: 108 | — |
| 635 | isomiR example 1 of SEQ ID NO: 111 | — |
| 636 | isomiR example 2 of SEQ ID NO: 111 | — |
| 637 | isomiR example 1 of SEQ ID NO: 112 | — |
| 638 | isomiR example 2 of SEQ ID NO: 112 | — |
| 639 | isomiR example 1 of SEQ ID NO: 113 | — |
| 640 | isomiR example 2 of SEQ ID NO: 113 | — |
| 641 | isomiR example 1 of SEQ ID NO: 114 | — |
| 642 | isomiR example 2 of SEQ ID NO: 114 | — |
| 643 | isomiR example 1 of SEQ ID NO: 116 | — |
| 644 | isomiR example 2 of SEQ ID NO: 116 | — |
| 645 | isomiR example 1 of SEQ ID NO: 117 | — |
| 646 | isomiR example 2 of SEQ ID NO: 117 | — |
| 647 | isomiR example 1 of SEQ ID NO: 118 | — |
| 648 | isomiR example 2 of SEQ ID NO: 118 | — |
| 649 | isomiR example 1 of SEQ ID NO: 122 | — |
| 650 | isomiR example 2 of SEQ ID NO: 122 | — |
| 651 | isomiR example 1 of SEQ ID NO: 123 | — |
| 652 | isomiR example 2 of SEQ ID NO: 123 | — |
| 653 | isomiR example 1 of SEQ ID NO: 124 | — |
| 654 | isomiR example 2 of SEQ ID NO: 124 | — |
| 655 | isomiR example 1 of SEQ ID NO: 128 | — |
| 656 | isomiR example 2 of SEQ ID NO: 128 | — |
| 657 | isomiR example 1 of SEQ ID NO: 129 | — |
| 658 | isomiR example 2 of SEQ ID NO: 129 | — |
| 659 | isomiR example 1 of SEQ ID NO: 133 | — |
| 660 | isomiR example 2 of SEQ ID NO: 133 | — |
| 661 | isomiR example 1 of SEQ ID NO: 134 | — |
| 662 | isomiR example 2 of SEQ ID NO: 134 | — |
| 663 | isomiR example 1 of SEQ ID NO: 135 | — |
| 664 | isomiR example 2 of SEQ ID NO: 135 | — |
| 665 | isomiR example 1 of SEQ ID NO: 136 | — |
| 666 | isomiR example 2 of SEQ ID NO: 136 | — |
| 667 | isomiR example 1 of SEQ ID NO: 137 | — |
| 668 | isomiR example 2 of SEQ ID NO: 137 | — |
| 669 | isomiR example 1 of SEQ ID NO: 140 | — |
| 670 | isomiR example 2 of SEQ ID NO: 140 | — |
| 671 | isomiR example 1 of SEQ ID NO: 141 | — |
| 672 | isomiR example 2 of SEQ ID NO: 141 | — |
| 673 | isomiR example 1 of SEQ ID NO: 145 | — |
| 674 | isomiR example 2 of SEQ ID NO: 145 | — |
| 675 | isomiR example 1 of SEQ ID NO: 146 | — |
| 676 | isomiR example 2 of SEQ ID NO: 146 | — |
| 677 | isomiR example 1 of SEQ ID NO: 147 | — |
| 678 | isomiR example 2 of SEQ ID NO: 147 | — |
| 679 | isomiR example 1 of SEQ ID NO: 148 | — |
| 680 | isomiR example 2 of SEQ ID NO: 148 | — |
| 681 | isomiR example 1 of SEQ ID NO: 149 | — |
| 682 | isomiR example 2 of SEQ ID NO: 149 | — |
| 683 | isomiR example 1 of SEQ ID NO: 150 | — |
| 684 | isomiR example 2 of SEQ ID NO: 150 | — |
| 685 | isomiR example 1 of SEQ ID NO: 151 | — |
| 686 | isomiR example 2 of SEQ ID NO: 151 | — |
| 687 | isomiR example 1 of SEQ ID NO: 153 | — |
| 688 | isomiR example 2 of SEQ ID NO: 153 | — |
| 689 | isomiR example 1 of SEQ ID NO: 154 | — |
| 690 | isomiR example 2 of SEQ ID NO: 154 | — |
| 691 | isomiR example 1 of SEQ ID NO: 155 | — |
| 692 | isomiR example 2 of SEQ ID NO: 155 | — |
| 693 | isomiR example 1 of SEQ ID NO: 157 | — |
| 694 | isomiR example 2 of SEQ ID NO: 157 | — |
| 695 | isomiR example 1 of SEQ ID NO: 158 | — |
| 696 | isomiR example 2 of SEQ ID NO: 158 | — |
| 697 | isomiR example 1 of SEQ ID NO: 159 | — |
| 698 | isomiR example 2 of SEQ ID NO: 159 | — |
| 699 | isomiR example 1 of SEQ ID NO: 160 | — |
| 700 | isomiR example 2 of SEQ ID NO: 160 | — |
| 701 | isomiR example 1 of SEQ ID NO: 161 | — |
| 702 | isomiR example 2 of SEQ ID NO: 161 | — |
| 703 | isomiR example 1 of SEQ ID NO: 162 | — |
| 704 | isomiR example 2 of SEQ ID NO: 162 | — |
| 705 | isomiR example 1 of SEQ ID NO: 163 | — |
| 706 | isomiR example 2 of SEQ ID NO: 163 | — |
| 707 | isomiR example 1 of SEQ ID NO: 166 | — |
| 708 | isomiR example 2 of SEQ ID NO: 166 | — |
| 709 | isomiR example 1 of SEQ ID NO: 167 | — |
| 710 | isomiR example 2 of SEQ ID NO: 167 | — |
| 711 | isomiR example 1 of SEQ ID NO: 168 | — |
| 712 | isomiR example 2 of SEQ ID NO: 168 | — |
| 713 | isomiR example 1 of SEQ ID NO: 169 | — |
| 714 | isomiR example 2 of SEQ ID NO: 169 | — |
| 715 | isomiR example 1 of SEQ ID NO: 176 | — |
| 716 | isomiR example 2 of SEQ ID NO: 176 | — |
| 717 | isomiR example 1 of SEQ ID NO: 177 | — |
| 718 | isomiR example 2 of SEQ ID NO: 177 | — |
| 719 | isomiR example 1 of SEQ ID NO: 178 | — |
| 720 | isomiR example 2 of SEQ ID NO: 178 | — |
| 721 | isomiR example 1 of SEQ ID NO: 179 | — |
| 722 | isomiR example 2 of SEQ ID NO: 179 | — |
| 723 | isomiR example 1 of SEQ ID NO: 180 | — |
| 724 | isomiR example 2 of SEQ ID NO: 180 | — |
| 725 | isomiR example 1 of SEQ ID NO: 181 | — |
| 726 | isomiR example 2 of SEQ ID NO: 181 | — |
| 727 | isomiR example 1 of SEQ ID NO: 182 | — |
| 728 | isomiR example 2 of SEQ ID NO: 182 | — |
| 729 | isomiR example 1 of SEQ ID NO: 184 | — |
| 730 | isomiR example 2 of SEQ ID NO: 184 | — |
| 731 | isomiR example 1 of SEQ ID NO: 186 | — |
| 732 | isomiR example 2 of SEQ ID NO: 186 | — |
| 733 | isomiR example 1 of SEQ ID NO: 187 | — |
| 734 | isomiR example 2 of SEQ ID NO: 187 | — |
| 735 | isomiR example 1 of SEQ ID NO: 190 | — |
| 736 | isomiR example 2 of SEQ ID NO: 190 | — |
| 737 | isomiR example 1 of SEQ ID NO: 193 | — |
| 738 | isomiR example 2 of SEQ ID NO: 193 | — |
| 739 | isomiR example 1 of SEQ ID NO: 196 | — |
| 740 | isomiR example 2 of SEQ ID NO: 196 | — |
| 741 | isomiR example 1 of SEQ ID NO: 198 | — |
| 742 | isomiR example 2 of SEQ ID NO: 198 | — |
| 743 | isomiR example 1 of SEQ ID NO: 201 | — |
| 744 | isomiR example 2 of SEQ ID NO: 201 | — |
| 745 | isomiR example 1 of SEQ ID NO: 202 | — |
| 746 | isomiR example 2 of SEQ ID NO: 202 | — |
| 747 | isomiR example 1 of SEQ ID NO: 203 | — |
| 748 | isomiR example 2 of SEQ ID NO: 203 | — |
| 749 | isomiR example 1 of SEQ ID NO: 204 | — |
| 750 | isomiR example 2 of SEQ ID NO: 204 | — |
| 751 | isomiR example 1 of SEQ ID NO: 205 | — |
| 752 | isomiR example 2 of SEQ ID NO: 205 | — |
| 753 | isomiR example 1 of SEQ ID NO: 206 | — |
| 754 | isomiR example 2 of SEQ ID NO: 206 | — |
| 755 | isomiR example 1 of SEQ ID NO: 207 | — |
| 756 | isomiR example 2 of SEQ ID NO: 207 | — |
| 757 | isomiR example 1 of SEQ ID NO: 208 | — |
| 758 | isomiR example 2 of SEQ ID NO: 208 | — |
| 759 | isomiR example 1 of SEQ ID NO: 209 | — |
| 760 | isomiR example 2 of SEQ ID NO: 209 | — |
| 761 | isomiR example 1 of SEQ ID NO: 210 | — |
| 762 | isomiR example 2 of SEQ ID NO: 210 | — |
| 763 | isomiR example 1 of SEQ ID NO: 211 | — |
| 764 | isomiR example 2 of SEQ ID NO: 211 | — |
| 765 | isomiR example 1 of SEQ ID NO: 214 | — |
| 766 | isomiR example 2 of SEQ ID NO: 214 | — |
| 767 | isomiR example 1 of SEQ ID NO: 215 | — |
| 768 | isomiR example 2 of SEQ ID NO: 215 | — |
| 769 | isomiR example 1 of SEQ ID NO: 216 | — |
| 770 | isomiR example 2 of SEQ ID NO: 216 | — |

TABLE 1-continued

| SEQ ID NO: | Gene name | miRBase registration No. |
|---|---|---|
| 771 | isomiR example 1 of SEQ ID NO: 217 | — |
| 772 | isomiR example 2 of SEQ ID NO: 217 | — |
| 773 | isomiR example 1 of SEQ ID NO: 218 | — |
| 774 | isomiR example 2 of SEQ ID NO: 218 | — |
| 775 | isomiR example 1 of SEQ ID NO: 220 | — |
| 776 | isomiR example 2 of SEQ ID NO: 220 | — |
| 777 | isomiR example 1 of SEQ ID NO: 221 | — |
| 778 | isomiR example 2 of SEQ ID NO: 221 | — |
| 779 | isomiR example 1 of SEQ ID NO: 222 | — |
| 780 | isomiR example 2 of SEQ ID NO: 222 | — |
| 781 | isomiR example 1 of SEQ ID NO: 223 | — |
| 782 | isomiR example 2 of SEQ ID NO: 223 | — |
| 783 | isomiR example 1 of SEQ ID NO: 224 | — |
| 784 | isomiR example 2 of SEQ ID NO: 224 | — |
| 785 | isomiR example 1 of SEQ ID NO: 226 | — |
| 786 | isomiR example 2 of SEQ ID NO: 226 | — |
| 787 | isomiR example 1 of SEQ ID NO: 228 | — |
| 788 | isomiR example 2 of SEQ ID NO: 228 | — |
| 789 | isomiR example 1 of SEQ ID NO: 233 | — |
| 790 | isomiR example 2 of SEQ ID NO: 233 | — |
| 791 | isomiR example 1 of SEQ ID NO: 235 | — |
| 792 | isomiR example 2 of SEQ ID NO: 235 | — |
| 793 | isomiR example 1 of SEQ ID NO: 236 | — |
| 794 | isomiR example 2 of SEQ ID NO: 236 | — |
| 795 | isomiR example 1 of SEQ ID NO: 237 | — |
| 796 | isomiR example 2 of SEQ ID NO: 237 | — |
| 797 | isomiR example 1 of SEQ ID NO: 239 | — |
| 798 | isomiR example 2 of SEQ ID NO: 239 | — |
| 799 | isomiR example 1 of SEQ ID NO: 240 | — |
| 800 | isomiR example 2 of SEQ ID NO: 240 | — |
| 801 | isomiR example 1 of SEQ ID NO: 243 | — |
| 802 | isomiR example 2 of SEQ ID NO: 243 | — |
| 803 | isomiR example 1 of SEQ ID NO: 244 | — |
| 804 | isomiR example 2 of SEQ ID NO: 244 | — |
| 805 | isomiR example 1 of SEQ ID NO: 245 | — |
| 806 | isomiR example 2 of SEQ ID NO: 245 | — |
| 807 | isomiR example 1 of SEQ ID NO: 247 | — |
| 808 | isomiR example 2 of SEQ ID NO: 247 | — |
| 809 | isomiR example 1 of SEQ ID NO: 248 | — |
| 810 | isomiR example 2 of SEQ ID NO: 248 | — |
| 811 | isomiR example 1 of SEQ ID NO: 249 | — |
| 812 | isomiR example 2 of SEQ ID NO: 249 | — |
| 813 | hsa-miR-145-5p | MIMAT0000437 |
| 814 | hsa-let-7f-5p | MIMAT0000067 |
| 815 | hsa-miR-146a-5p | MIMAT0000449 |
| 816 | hsa-let-7d-5p | MIMAT0000065 |
| 817 | hsa-let-7a-5p | MIMAT0000062 |

The present specification incorporates the contents disclosed in Japanese Patent Application No. 2016-073132 (filing date: Mar. 31, 2016) to which the present application claims priorities.

Advantageous Effect of Invention

According to the present invention, early pancreatic cancer or pancreatic cancer precursor lesion can be detected easily and in high accuracy.

For example, the presence or absence of early pancreatic cancer or a pancreatic cancer precursor lesion in patients can be easily detected by using, as indicators, the determined expression levels of several miRNAs in blood, serum, and/or plasma of the patients, which can be collected with minimal invasiveness.

MODES FOR CARRYING OUT THE INVENTION

Figure 1:
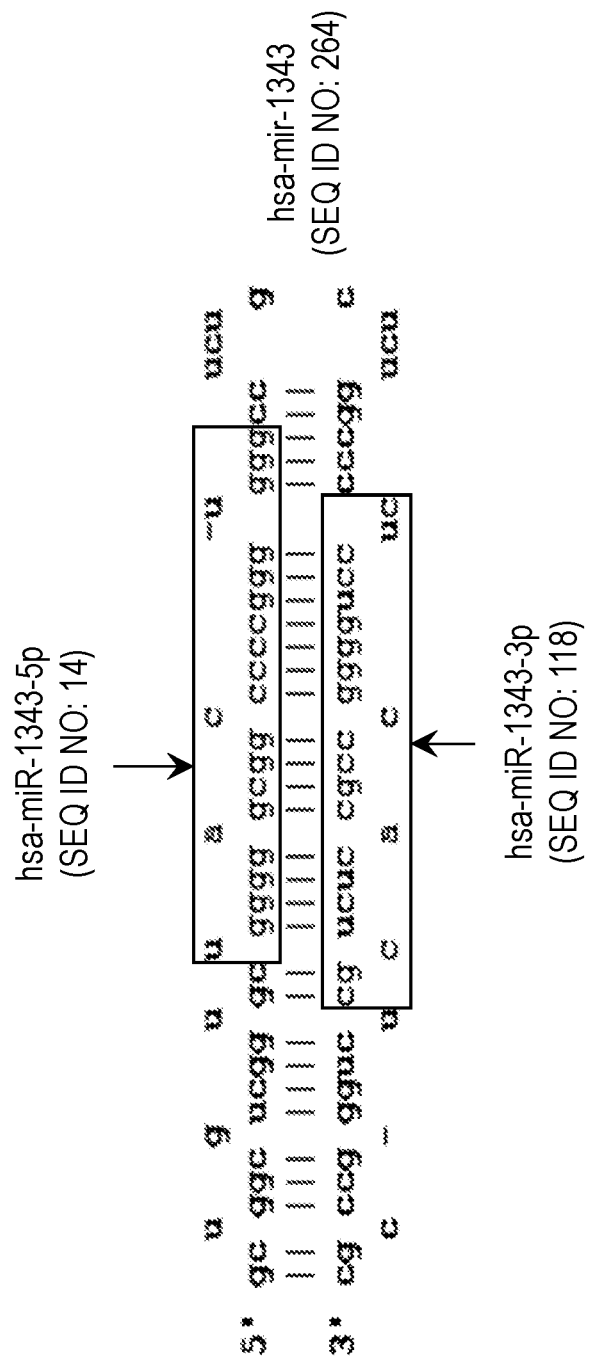
FIG. 1 This figure shows the relationship between the nucleotide sequences of hsa-miR-1343-3p represented by SEQ ID NO: 118 and hsa-miR-1343-5p represented by SEQ ID NO: 14, which are produced from hsa-mir-1343 represented by SEQ ID NO: 264 as a precursor.

Hereinafter, the present invention will be further described in detail.

1. Target Nucleic Acid for Early Pancreatic Cancer or Pancreatic Cancer Precursor Lesion Primary target nucleic acids, as early pancreatic cancer or pancreatic cancer precursor lesion markers, for detecting the presence and/or absence of early pancreatic cancer or a pancreatic cancer precursor lesion or early pancreatic cancer or pancreatic cancer precursor lesion cells using the nucleic acid probes or the primers for the detection of early pancreatic cancer or a pancreatic cancer precursor lesion defined above according to the present invention comprise at least one miRNA selected from the group consisting of the following miRNAs: hsa-miR-6784-5p, hsa-miR-1181, hsa-miR-671-5p, hsa-miR-6857-5p, hsa-miR-4276, hsa-miR-1914-3p, hsa-miR-149-3p, hsa-miR-937-5p, hsa-miR-4675, hsa-miR-6795-5p, hsa-miR-4731-5p, hsa-miR-5090, hsa-miR-3620-5p, hsa-miR-1343-5p, hsa-miR-6717-5p, hsa-miR-6825-5p, hsa-miR-6738-5p, hsa-miR-6769a-5p, hsa-miR-4728-5p, hsa-miR-652-5p, hsa-miR-4257, hsa-miR-6785-5p, hsa-miR-7110-5p, hsa-miR-6887-5p, hsa-miR-887-3p, hsa-miR-1228-5p, hsa-miR-5572, hsa-miR-6782-5p, hsa-miR-4298, hsa-miR-6786-5p, hsa-miR-5010-5p, hsa-miR-6087, hsa-miR-6765-5p, hsa-miR-6732-5p, hsa-miR-6787-5p, hsa-miR-6737-5p, hsa-miR-128-2-5p, hsa-miR-4270, hsa-miR-6861-5p, hsa-miR-6756-5p, hsa-miR-1229-5p, hsa-miR-6891-5p, hsa-miR-6848-5p, hsa-miR-1237-5p, hsa-miR-30c-1-3p, hsa-miR-1233-5p, hsa-miR-211-3p, hsa-miR-4758-5p, hsa-miR-614, hsa-miR-6746-5p, hsa-miR-1915-5p, hsa-miR-4688, hsa-miR-3917, hsa-miR-5787, hsa-miR-4632-5p, hsa-miR-6126, hsa-miR-135a-3p, hsa-miR-8063, hsa-miR-5698, hsa-miR-6089, hsa-miR-498, hsa-miR-296-3p, hsa-miR-4419b, hsa-miR-6802-5p, hsa-miR-6829-5p, hsa-miR-6803-5p, hsa-miR-1199-5p, hsa-miR-6840-3p, hsa-miR-6752-5p, hsa-miR-6798-5p, hsa-miR-6131, hsa-miR-4667-5p, hsa-miR-6510-5p, hsa-miR-4690-5p, hsa-miR-920, hsa-miR-23b-3p, hsa-miR-4448, hsa-miR-2110, hsa-miR-4706, hsa-miR-7845-5p, hsa-miR-6808-5p, hsa-miR-4447, hsa-miR-6869-5p, hsa-miR-6794-5p, hsa-miR-6511a-5p, hsa-miR-6824-5p, hsa-miR-6766-3p, hsa-miR-6511a-5p, and hsa-miR-6749-5p.

Furthermore, at least one miRNA selected from the group consisting of the following other early pancreatic cancer or pancreatic cancer precursor lesion markers that can be combined with these miRNAs, i.e., hsa-miR-1908-5p, hsa-miR-6729-5p, hsa-miR-5195-3p, hsa-miR-638, hsa-miR-6125, hsa-miR-3178, hsa-miR-3196, hsa-miR-8069, hsa-miR-4723-5p, hsa-miR-4746-3p, hsa-miR-4689, hsa-miR-6816-5p, hsa-miR-6757-5p, hsa-miR-7109-5p, hsa-miR-6724-5p, hsa-miR-1225-3p, hsa-miR-6875-5p, hsa-miR-7108-5p, hsa-miR-4508, hsa-miR-6085, hsa-miR-6779-5p, hsa-miR-642a-3p, hsa-miR-4695-5p, hsa-miR-7847-3p, hsa-miR-3197, hsa-miR-6769b-5p, hsa-miR-7641, hsa-miR-187-5p, hsa-miR-3185, hsa-miR-2861, hsa-miR-3940-5p, hsa-miR-1203, hsa-miR-615-5p, hsa-miR-4787-5p, hsa-miR-1343-3p, hsa-miR-6813-5p, hsa-miR-1225-5p, hsa-miR-602, hsa-miR-4488, hsa-miR-125a-3p, hsa-miR-5100, hsa-miR-4294, hsa-miR-1231, hsa-miR-6765-3p, hsa-miR-4442, hsa-miR-718, hsa-miR-6780b-5p, hsa-miR-6090, hsa-miR-6845-5p, hsa-miR-4741, hsa-miR-4467, hsa-miR-4707-5p, hsa-miR-4271, hsa-miR-4673, hsa-miR-3184-5p, hsa-miR-1469, hsa-miR-4640-5p, hsa-miR-663a, hsa-miR-6791-5p, hsa-miR-6826-5p, hsa-miR-4433b-3p, hsa-miR-1915-3p, hsa-miR-4417, hsa-miR-4449, hsa-miR-4707-3p, hsa-miR-3180-3p, hsa-miR-5585-3p, hsa-miR-1268a, hsa-miR-8072, hsa-miR-296-5p, hsa-miR-204-3p, hsa-miR-4454, hsa-miR-6722-3p, hsa-miR-1290, hsa-miR-3622a-5p, hsa-miR-939-5p, hsa-miR-675-5p, hsa-miR-3131, hsa-miR-4648, hsa-miR-1268b, hsa-miR-6741-5p, hsa-miR-6893-5p, hsa-miR-3162-5p, hsa-miR-642b-3p, hsa-miR-4734, hsa-miR-150-3p, hsa-miR-8089, hsa-miR-6805-3p, hsa-miR-7113-3p, hsa-miR-6850-5p, hsa-miR-6799-5p, hsa-miR-6768-5p, hsa-miR-92b-5p, hsa-miR-3679-5p, hsa-miR-4792, hsa-miR-3656, hsa-miR-92a-2-5p, hsa-miR-4466, hsa-miR-4513, hsa-miR-6781-5p, hsa-miR-4649-5p, hsa-miR-6775-5p, hsa-miR-4651, hsa-miR-3195, hsa-miR-6726-5p, hsa-miR-6872-3p, hsa-miR-371a-5p, hsa-miR-6777-5p, hsa-miR-6789-5p, hsa-miR-7975, hsa-miR-6821-5p, hsa-miR-4534, hsa-miR-619-5p, hsa-miR-7107-5p, hsa-miR-1228-3p, hsa-miR-6774-5p, hsa-miR-6805-5p, hsa-miR-23a-3p, hsa-miR-4665-5p, hsa-miR-4505, hsa-miR-4638-5p, hsa-miR-24-3p, hsa-miR-3135b, hsa-miR-4745-5p, hsa-miR-128-1-5p, hsa-miR-4476, hsa-miR-4687-3p, hsa-miR-3665, hsa-miR-6806-5p, hsa-miR-3937, hsa-miR-711, hsa-miR-3141, hsa-miR-3188, hsa-miR-4281, hsa-miR-5196-5p, hsa-miR-6880-5p, hsa-miR-3960, hsa-miR-3648, hsa-miR-6721-5p, hsa-miR-4492, hsa-miR-744-5p, hsa-miR-7704, hsa-miR-4749-5p, hsa-miR-762, hsa-miR-6836-3p, hsa-miR-6727-5p, hsa-miR-4739, hsa-miR-7977, hsa-miR-4484, hsa-miR-6515-3p, hsa-miR-373-5p, hsa-miR-4258, hsa-miR-4674, hsa-miR-3180, hsa-miR-6076, hsa-miR-1238-5p, hsa-miR-4463, hsa-miR-4486, hsa-miR-4730, hsa-miR-4286, and hsa-miR-4739 can also be preferably used as target nucleic acids.

These miRNAs include, for example, a human gene comprising a nucleotide sequence represented by any of SEQ ID NOs: 1 to 250 (i.e., hsa-miR-6784-5p, hsa-miR-1181, hsa-miR-671-5p, hsa-miR-6857-5p, hsa-miR-4276, hsa-miR-1914-3p, hsa-miR-149-3p, hsa-miR-937-5p, hsa-miR-4675, hsa-miR-6795-5p, hsa-miR-4731-5p, hsa-miR-5090, hsa-miR-3620-5p, hsa-miR-1343-5p, hsa-miR-6717-5p, hsa-miR-6825-5p, hsa-miR-6738-5p, hsa-miR-6769a-5p, hsa-miR-4728-5p, hsa-miR-652-5p, hsa-miR-4257, hsa-miR-6785-5p, hsa-miR-7110-5p, hsa-miR-6887-5p, hsa-miR-887-3p, hsa-miR-1228-5p, hsa-miR-5572, hsa-miR-6782-5p, hsa-miR-4298, hsa-miR-6786-5p, hsa-miR-5010-5p, hsa-miR-6087, hsa-miR-6765-5p, hsa-miR-6732-5p, hsa-miR-6787-5p, hsa-miR-6737-5p, hsa-miR-128-2-5p, hsa-miR-4270, hsa-miR-6861-5p, hsa-miR-6756-5p, hsa-miR-1229-5p, hsa-miR-6891-5p, hsa-miR-6848-5p, hsa-miR-1237-5p, hsa-miR-30c-1-3p, hsa-miR-1233-5p, hsamiR-211-3p, hsa-miR-4758-5p, hsa-miR-614, hsa-miR-6746-5p, hsa-miR-1915-5p, hsa-miR-4688, hsa-miR-3917, hsa-miR-5787, hsa-miR-4632-5p, hsa-miR-6126, hsa-miR-135a-3p, hsa-miR-8063, hsa-miR-5698, hsa-miR-6089, hsa-miR-498, hsa-miR-296-3p, hsa-miR-4419b, hsa-miR-6802-5p, hsa-miR-6829-5p, hsa-miR-6803-5p, hsa-miR-1199-5p, hsa-miR-6840-3p, hsa-miR-6752-5p, hsa-miR-6798-5p, hsa-miR-6131, hsa-miR-4667-5p, hsa-miR-6510-5p, hsa-miR-4690-5p, hsa-miR-920, hsa-miR-23b-3p, hsa-miR-4448, hsa-miR-2110, hsa-miR-4706, hsa-miR-7845-5p, hsa-miR-6808-5p, hsa-miR-4447, hsa-miR-6869-5p, hsa-miR-1908-5p, hsa-miR-6729-5p, hsa-miR-5195-3p, hsa-miR-638, hsa-miR-6125, hsa-miR-3178, hsa-miR-3196, hsa-miR-8069, hsa-miR-4723-5p, hsa-miR-4746-3p, hsa-miR-4689, hsa-miR-6816-5p, hsa-miR-6757-5p, hsa-miR-7109-5p, hsa-miR-6724-5p, hsa-miR-1225-3p, hsa-miR-6875-5p, hsa-miR-7108-5p, hsa-miR-4508, hsa-miR-6085, hsa-miR-6779-5p, hsa-miR-642a-3p, hsa-miR-4695-5p, hsa-miR-7847-3p, hsa-miR-3197, hsa-miR-6769b-5p, hsa-miR-7641, hsa-miR-187-5p, hsa-miR-3185, hsa-miR-2861, hsa-miR-3940-5p, hsa-miR-1203, hsa-miR-615-5p, hsa-miR-4787-5p, hsa-miR-1343-3p, hsa-miR-6813-5p, hsa-miR-1225-5p, hsa-miR-602, hsa-miR-4488, hsa-miR-125a-3p, hsa-miR-5100, hsa-miR-4294, hsa-miR-1231, hsa-miR-6765-3p, hsa-miR-4442, hsa-miR-718, hsa-miR-6780b-5p, hsa-miR-6090, hsa-miR-6845-5p, hsa-miR-4741, hsa-miR-4467, hsa-miR-4707-5p, hsa-miR-4271, hsa-miR-4673, hsa-miR-3184-5p, hsa-miR-1469, hsa-miR-4640-5p, hsa-miR-663a, hsa-miR-6791-5p, hsa-miR-6826-5p, hsa-miR-4433b-3p, hsa-miR-1915-3p, hsa-miR-4417, hsa-miR-4449, hsa-miR-4707-3p, hsa-miR-3180-3p, hsa-miR-5585-3p, hsa-miR-1268a, hsa-miR-8072, hsa-miR-296-5p, hsa-miR-204-3p, hsa-miR-4454, hsa-miR-6722-3p, hsa-miR-1290, hsa-miR-3622a-5p, hsa-miR-939-5p, hsa-miR-675-5p, hsa-miR-3131, hsa-miR-4648, hsa-miR-1268b, hsa-miR-6741-5p, hsa-miR-6893-5p, hsa-miR-3162-5p, hsa-miR-642b-3p, hsa-miR-4734, hsa-miR-150-3p, hsa-miR-8089, hsa-miR-6805-3p, hsa-miR-7113-3p, hsa-miR-6850-5p, hsa-miR-6799-5p, hsa-miR-6768-5p, hsa-miR-92b-5p, hsa-miR-3679-5p, hsa-miR-4792, hsa-miR-3656, hsa-miR-92a-2-5p, hsa-miR-4466, hsa-miR-4513, hsa-miR-6781-5p, hsa-miR-4649-5p, hsa-miR-6775-5p, hsa-miR-4651, hsa-miR-3195, hsa-miR-6726-5p, hsa-miR-6872-3p, hsa-miR-371a-5p, hsa-miR-6777-5p, hsa-miR-6789-5p, hsa-miR-7975, hsa-miR-6821-5p, hsa-miR-4534, hsa-miR-619-5p, hsa-miR-7107-5p, hsa-miR-1228-3p, hsa-miR-6774-5p, hsa-miR-6805-5p, hsa-miR-23a-3p, hsa-miR-4665-5p, hsa-miR-4505, hsa-miR-4638-5p, hsa-miR-24-3p, hsa-miR-3135b, hsa-miR-4745-5p, hsa-miR-128-1-5p, hsa-miR-4476, hsa-miR-4687-3p, hsa-miR-3665, hsa-miR-6806-5p, hsa-miR-3937, hsa-miR-711, hsa-miR-3141, hsa-miR-3188, hsa-miR-4281, hsa-miR-5196-5p, hsa-miR-6880-5p, hsa-miR-3960, hsa-miR-3648, hsa-miR-6721-5p, hsa-miR-4492, hsa-miR-744-5p, hsa-miR-7704, hsa-miR-4749-5p, hsa-miR-6794-5p, hsa-miR-6511a-5p, hsa-miR-6824-5p, hsa-miR-762, hsa-miR-6836-3p, hsa-miR-6727-5p, hsa-miR-4739, hsa-miR-7977, hsa-miR-4484, hsa-miR-6515-3p, hsa-miR-373-5p, hsa-miR-4258, hsa-miR-4674, hsa-miR-3180, hsa-miR-6076, hsa-miR-1238-5p, hsa-miR-4463, hsa-miR-4486, hsa-miR-4730, hsa-miR-6766-3p, hsa-miR-4286, hsa-miR-6511a-5p, hsa-miR-4739, and hsa-miR-6749-5p, respectively), a congener, a transcript thereof, or/and a variant or a derivative thereof. In this context, the gene, the congener, the transcript, the variant, and the derivative are as defined above.

The target nucleic acid is preferably a human gene comprising a nucleotide sequence represented by any of SEQ ID NOs: 1 to 812 or a transcript thereof, more preferably the transcript, i.e., a miRNA or its precursor RNA (pri-miRNA or pre-miRNA).

The first target gene is the hsa-miR-6784-5p gene, a congener thereof, a transcript thereof, or a variant or a derivative thereof. None of the previously known reports show that change in the expression of the gene or the transcript thereof can serve as a marker for early pancreatic cancer or a pancreatic cancer precursor lesion.

The second target gene is the hsa-miR-1181 gene, a congener thereof, a transcript thereof, or a variant or a derivative thereof. None of the previously known reports show that change in the expression of the gene or the transcript thereof can serve as a marker for early pancreatic cancer or a pancreatic cancer precursor lesion.

The third target gene is the hsa-miR-671-5p gene, a congener thereof, a transcript thereof, or a variant or a derivative thereof. None of the previously known reports show that change in the expression of the gene or the transcript thereof can serve as a marker for early pancreatic cancer or a pancreatic cancer precursor lesion.

The fourth target gene is the hsa-miR-6857-5p gene, a congener thereof, a transcript thereof, or a variant or a derivative thereof. None of the previously known reports show that change in the expression of the gene or the transcript thereof can serve as a marker for early pancreatic cancer or a pancreatic cancer precursor lesion.

The fifth target gene is the hsa-miR-4276 gene, a congener thereof, a transcript thereof, or a variant or a derivative thereof. None of the previously known reports show that change in the expression of the gene or the transcript thereof can serve as a marker for early pancreatic cancer or a pancreatic cancer precursor lesion.

The sixth target gene is the hsa-miR-1914-3p gene, a congener thereof, a transcript thereof, or a variant or a derivative thereof. None of the previously known reports show that change in the expression of the gene or the transcript thereof can serve as a marker for early pancreatic cancer or a pancreatic cancer precursor lesion.

The seventh target gene is the hsa-miR-149-3p gene, a congener thereof, a transcript thereof, or a variant or a derivative thereof. None of the previously known reports show that change in the expression of the gene or the transcript thereof can serve as a marker for early pancreatic cancer or a pancreatic cancer precursor lesion.

The eighth target gene is the hsa-miR-937-5p gene, a congener thereof, a transcript thereof, or a variant or a derivative thereof. None of the previously known reports show that change in the expression of the gene or the transcript thereof can serve as a marker for early pancreatic cancer or a pancreatic cancer precursor lesion.

The ninth target gene is the hsa-miR-4675 gene, a congener thereof, a transcript thereof, or a variant or a derivative thereof. None of the previously known reports show that change in the expression of the gene or the transcript thereof can serve as a marker for early pancreatic cancer or a pancreatic cancer precursor lesion.

The 10th target gene is the hsa-miR-6795-5p gene, a congener thereof, a transcript thereof, or a variant or a derivative thereof. None of the previously known reports show that change in the expression of the gene or the transcript thereof can serve as a marker for early pancreatic cancer or a pancreatic cancer precursor lesion.

The 11th target gene is the hsa-miR-4731-5p gene, a congener thereof, a transcript thereof, or a variant or a derivative thereof. None of the previously known reports show that change in the expression of the gene or the transcript thereof can serve as a marker for early pancreatic cancer or a pancreatic cancer precursor lesion.

The 12th target gene is the hsa-miR-5090 gene, a congener thereof, a transcript thereof, or a variant or a derivative thereof. None of the previously known reports show that change in the expression of the gene or the transcript thereof can serve as a marker for early pancreatic cancer or a pancreatic cancer precursor lesion.

The 13th target gene is the hsa-miR-3620-5p gene, a congener thereof, a transcript thereof, or a variant or a derivative thereof. None of the previously known reports show that change in the expression of the gene or the transcript thereof can serve as a marker for early pancreatic cancer or a pancreatic cancer precursor lesion.

The 14th target gene is the hsa-miR-1343-5p gene, a congener thereof, a transcript thereof, or a variant or a derivative thereof. None of the previously known reports show that change in the expression of the gene or the transcript thereof can serve as a marker for early pancreatic cancer or a pancreatic cancer precursor lesion.

The 15th target gene is the hsa-miR-6717-5p gene, a congener thereof, a transcript thereof, or a variant or a derivative thereof. None of the previously known reports show that change in the expression of the gene or the transcript thereof can serve as a marker for early pancreatic cancer or a pancreatic cancer precursor lesion.

The 16th target gene is the hsa-miR-6825-5p gene, a congener thereof, a transcript thereof, or a variant or a derivative thereof. None of the previously known reports show that change in the expression of the gene or the transcript thereof can serve as a marker for early pancreatic cancer or a pancreatic cancer precursor lesion.

The 17th target gene is the hsa-miR-6738-5p gene, a congener thereof, a transcript thereof, or a variant or a derivative thereof. None of the previously known reports show that change in the expression of the gene or the transcript thereof can serve as a marker for early pancreatic cancer or a pancreatic cancer precursor lesion.

The 18th target gene is the hsa-miR-6769a-5p gene, a congener thereof, a transcript thereof, or a variant or a derivative thereof. None of the previously known reports show that change in the expression of the gene or the transcript thereof can serve as a marker for early pancreatic cancer or a pancreatic cancer precursor lesion.

The 19th target gene is the hsa-miR-4728-5p gene, a congener thereof, a transcript thereof, or a variant or a derivative thereof. None of the previously known reports show that change in the expression of the gene or the transcript thereof can serve as a marker for early pancreatic cancer or a pancreatic cancer precursor lesion.

The 20th target gene is the hsa-miR-652-5p gene, a congener thereof, a transcript thereof, or a variant or a derivative thereof. None of the previously known reports show that change in the expression of the gene or the transcript thereof can serve as a marker for early pancreatic cancer or a pancreatic cancer precursor lesion.

The 21st target gene is the hsa-miR-4257 gene, a congener thereof, a transcript thereof, or a variant or a derivative thereof. None of the previously known reports show that change in the expression of the gene or the transcript thereof can serve as a marker for early pancreatic cancer or a pancreatic cancer precursor lesion.

The 22nd target gene is the hsa-miR-6785-5p gene, a congener thereof, a transcript thereof, or a variant or a derivative thereof. None of the previously known reports show that change in the expression of the gene or the transcript thereof can serve as a marker for early pancreatic cancer or a pancreatic cancer precursor lesion.

The 23rd target gene is the hsa-miR-7110-5p gene, a congener thereof, a transcript thereof, or a variant or a derivative thereof. None of the previously known reports show that change in the expression of the gene or the transcript thereof can serve as a marker for early pancreatic cancer or a pancreatic cancer precursor lesion.

The 24th target gene is the hsa-miR-6887-5p gene, a congener thereof, a transcript thereof, or a variant or a derivative thereof. None of the previously known reports show that change in the expression of the gene or the transcript thereof can serve as a marker for early pancreatic cancer or a pancreatic cancer precursor lesion.

The 25th target gene is the hsa-miR-887-3p gene, a congener thereof, a transcript thereof, or a variant or a derivative thereof. None of the previously known reports show that change in the expression of the gene or the transcript thereof can serve as a marker for early pancreatic cancer or a pancreatic cancer precursor lesion.

The 26th target gene is the hsa-miR-1228-5p gene, a congener thereof, a transcript thereof, or a variant or a derivative thereof. None of the previously known reports show that change in the expression of the gene or the transcript thereof can serve as a marker for early pancreatic cancer or a pancreatic cancer precursor lesion.

The 27th target gene is the hsa-miR-5572 gene, a congener thereof, a transcript thereof, or a variant or a derivative thereof. None of the previously known reports show that change in the expression of the gene or the transcript thereof can serve as a marker for early pancreatic cancer or a pancreatic cancer precursor lesion.

The 28th target gene is the hsa-miR-6782-5p gene, a congener thereof, a transcript thereof, or a variant or a derivative thereof. None of the previously known reports show that change in the expression of the gene or the transcript thereof can serve as a marker for early pancreatic cancer or a pancreatic cancer precursor lesion.

The 29th target gene is the hsa-miR-4298 gene, a congener thereof, a transcript thereof, or a variant or a derivative thereof. None of the previously known reports show that change in the expression of the gene or the transcript thereof can serve as a marker for early pancreatic cancer or a pancreatic cancer precursor lesion.

The 30th target gene is the hsa-miR-6786-5p gene, a congener thereof, a transcript thereof, or a variant or a derivative thereof. None of the previously known reports show that change in the expression of the gene or the transcript thereof can serve as a marker for early pancreatic cancer or a pancreatic cancer precursor lesion.

The 31st target gene is the hsa-miR-5010-5p gene, a congener thereof, a transcript thereof, or a variant or a derivative thereof. None of the previously known reports show that change in the expression of the gene or the transcript thereof can serve as a marker for early pancreatic cancer or a pancreatic cancer precursor lesion.

The 32nd target gene is the hsa-miR-6087 gene, a congener thereof, a transcript thereof, or a variant or a derivative thereof. None of the previously known reports show that change in the expression of the gene or the transcript thereof can serve as a marker for early pancreatic cancer or a pancreatic cancer precursor lesion.

The 33rd target gene is the hsa-miR-6765-5p gene, a congener thereof, a transcript thereof, or a variant or a derivative thereof. None of the previously known reports show that change in the expression of the gene or the transcript thereof can serve as a marker for early pancreatic cancer or a pancreatic cancer precursor lesion.

The 34th target gene is the hsa-miR-6732-5p gene, a congener thereof, a transcript thereof, or a variant or a derivative thereof. None of the previously known reports show that change in the expression of the gene or the transcript thereof can serve as a marker for early pancreatic cancer or a pancreatic cancer precursor lesion.

The 35th target gene is the hsa-miR-6787-5p gene, a congener thereof, a transcript thereof, or a variant or a derivative thereof. None of the previously known reports show that change in the expression of the gene or the transcript thereof can serve as a marker for early pancreatic cancer or a pancreatic cancer precursor lesion.

The 36th target gene is the hsa-miR-6737-5p gene, a congener thereof, a transcript thereof, or a variant or a derivative thereof. None of the previously known reports show that change in the expression of the gene or the transcript thereof can serve as a marker for early pancreatic cancer or a pancreatic cancer precursor lesion.

The 37th target gene is the hsa-miR-128-2-5p gene, a congener thereof, a transcript thereof, or a variant or a derivative thereof. None of the previously known reports show that change in the expression of the gene or the transcript thereof can serve as a marker for early pancreatic cancer or a pancreatic cancer precursor lesion.

The 38th target gene is the hsa-miR-4270 gene, a congener thereof, a transcript thereof, or a variant or a derivative thereof. None of the previously known reports show that change in the expression of the gene or the transcript thereof can serve as a marker for early pancreatic cancer or a pancreatic cancer precursor lesion.

The 39th target gene is the hsa-miR-6861-5p gene, a congener thereof, a transcript thereof, or a variant or a derivative thereof. None of the previously known reports show that change in the expression of the gene or the transcript thereof can serve as a marker for early pancreatic cancer or a pancreatic cancer precursor lesion.

The 40th target gene is the hsa-miR-6756-5p gene, a congener thereof, a transcript thereof, or a variant or a derivative thereof. None of the previously known reports show that change in the expression of the gene or the transcript thereof can serve as a marker for early pancreatic cancer or a pancreatic cancer precursor lesion.

The 41st target gene is the hsa-miR-1229-5p gene, a congener thereof, a transcript thereof, or a variant or a derivative thereof. None of the previously known reports show that change in the expression of the gene or the transcript thereof can serve as a marker for early pancreatic cancer or a pancreatic cancer precursor lesion.

The 42nd target gene is the hsa-miR-6891-5p gene, a congener thereof, a transcript thereof, or a variant or a derivative thereof. None of the previously known reports show that change in the expression of the gene or the transcript thereof can serve as a marker for early pancreatic cancer or a pancreatic cancer precursor lesion.

The 43rd target gene is the hsa-miR-6848-5p gene, a congener thereof, a transcript thereof, or a variant or a derivative thereof. None of the previously known reports show that change in the expression of the gene or the transcript thereof can serve as a marker for early pancreatic cancer or a pancreatic cancer precursor lesion.

The 44th target gene is the hsa-miR-1237-5p gene, a congener thereof, a transcript thereof, or a variant or a derivative thereof. None of the previously known reports show that change in the expression of the gene or the transcript thereof can serve as a marker for early pancreatic cancer or a pancreatic cancer precursor lesion.

The 45th target gene is the hsa-miR-30c-1-3p gene, a congener thereof, a transcript thereof, or a variant or a derivative thereof. None of the previously known reports show that change in the expression of the gene or the transcript thereof can serve as a marker for early pancreatic cancer or a pancreatic cancer precursor lesion.

The 46th target gene is the hsa-miR-1233-5p gene, a congener thereof, a transcript thereof, or a variant or a derivative thereof. None of the previously known reports show that change in the expression of the gene or the transcript thereof can serve as a marker for early pancreatic cancer or a pancreatic cancer precursor lesion.

The 47th target gene is the hsa-miR-211-3p gene, a congener thereof, a transcript thereof, or a variant or a derivative thereof. None of the previously known reports show that change in the expression of the gene or the transcript thereof can serve as a marker for early pancreatic cancer or a pancreatic cancer precursor lesion.

The 48th target gene is the hsa-miR-4758-5p gene, a congener thereof, a transcript thereof, or a variant or a derivative thereof. None of the previously known reports show that change in the expression of the gene or the transcript thereof can serve as a marker for early pancreatic cancer or a pancreatic cancer precursor lesion.

The 49th target gene is the hsa-miR-614 gene, a congener thereof, a transcript thereof, or a variant or a derivative thereof. None of the previously known reports show that change in the expression of the gene or the transcript thereof can serve as a marker for early pancreatic cancer or a pancreatic cancer precursor lesion.

The 50th target gene is the hsa-miR-6746-5p gene, a congener thereof, a transcript thereof, or a variant or a derivative thereof. None of the previously known reports show that change in the expression of the gene or the transcript thereof can serve as a marker for early pancreatic cancer or a pancreatic cancer precursor lesion.

The 51st target gene is the hsa-miR-1915-5p gene, a congener thereof, a transcript thereof, or a variant or a derivative thereof. None of the previously known reports show that change in the expression of the gene or the transcript thereof can serve as a marker for early pancreatic cancer or a pancreatic cancer precursor lesion.

The 52nd target gene is the hsa-miR-4688 gene, a congener thereof, a transcript thereof, or a variant or a derivative thereof. None of the previously known reports show that change in the expression of the gene or the transcript thereof can serve as a marker for early pancreatic cancer or a pancreatic cancer precursor lesion.

The 53rd target gene is the hsa-miR-3917 gene, a congener thereof, a transcript thereof, or a variant or a derivative thereof. None of the previously known reports show that change in the expression of the gene or the transcript thereof can serve as a marker for early pancreatic cancer or a pancreatic cancer precursor lesion.

The 54th target gene is the hsa-miR-5787 gene, a congener thereof, a transcript thereof, or a variant or a derivative thereof. None of the previously known reports show that change in the expression of the gene or the transcript thereof can serve as a marker for early pancreatic cancer or a pancreatic cancer precursor lesion.

The 55th target gene is the hsa-miR-4632-5p gene, a congener thereof, a transcript thereof, or a variant or a derivative thereof. None of the previously known reports show that change in the expression of the gene or the transcript thereof can serve as a marker for early pancreatic cancer or a pancreatic cancer precursor lesion.

The 56th target gene is the hsa-miR-6126 gene, a congener thereof, a transcript thereof, or a variant or a derivative thereof. None of the previously known reports show that change in the expression of the gene or the transcript thereof can serve as a marker for early pancreatic cancer or a pancreatic cancer precursor lesion.

The 57th target gene is the hsa-miR-135a-3p gene, a congener thereof, a transcript thereof, or a variant or a derivative thereof. None of the previously known reports show that change in the expression of the gene or the transcript thereof can serve as a marker for early pancreatic cancer or a pancreatic cancer precursor lesion.

The 58th target gene is the hsa-miR-8063 gene, a congener thereof, a transcript thereof, or a variant or a derivative thereof. None of the previously known reports show that change in the expression of the gene or the transcript thereof can serve as a marker for early pancreatic cancer or a pancreatic cancer precursor lesion.

The 59th target gene is the hsa-miR-5698 gene, a congener thereof, a transcript thereof, or a variant or a derivative thereof. None of the previously known reports show that change in the expression of the gene or the transcript thereof can serve as a marker for early pancreatic cancer or a pancreatic cancer precursor lesion.

The 60th target gene is the hsa-miR-6089 gene, a congener thereof, a transcript thereof, or a variant or a derivative thereof. None of the previously known reports show that change in the expression of the gene or the transcript thereof can serve as a marker for early pancreatic cancer or a pancreatic cancer precursor lesion.

The 61st target gene is the hsa-miR-498 gene, a congener thereof, a transcript thereof, or a variant or a derivative thereof. None of the previously known reports show that change in the expression of the gene or the transcript thereof can serve as a marker for early pancreatic cancer or a pancreatic cancer precursor lesion.

The 62nd target gene is the hsa-miR-296-3p gene, a congener thereof, a transcript thereof, or a variant or a derivative thereof. None of the previously known reports show that change in the expression of the gene or the transcript thereof can serve as a marker for early pancreatic cancer or a pancreatic cancer precursor lesion.

The 63rd target gene is the hsa-miR-4419b gene, a congener thereof, a transcript thereof, or a variant or a derivative thereof. None of the previously known reports show that change in the expression of the gene or the transcript thereof can serve as a marker for early pancreatic cancer or a pancreatic cancer precursor lesion.

The 64th target gene is the hsa-miR-6802-5p gene, a congener thereof, a transcript thereof, or a variant or a derivative thereof. None of the previously known reports show that change in the expression of the gene or the transcript thereof can serve as a marker for early pancreatic cancer or a pancreatic cancer precursor lesion.

The 65th target gene is the hsa-miR-6829-5p gene, a congener thereof, a transcript thereof, or a variant or a derivative thereof. None of the previously known reports show that change in the expression of the gene or the transcript thereof can serve as a marker for early pancreatic cancer or a pancreatic cancer precursor lesion.

The 66th target gene is the hsa-miR-6803-5p gene, a congener thereof, a transcript thereof, or a variant or a derivative thereof. None of the previously known reports show that change in the expression of the gene or the transcript thereof can serve as a marker for early pancreatic cancer or a pancreatic cancer precursor lesion.

The 67th target gene is the hsa-miR-1199-5p gene, a congener thereof, a transcript thereof, or a variant or a derivative thereof. None of the previously known reports show that change in the expression of the gene or the transcript thereof can serve as a marker for early pancreatic cancer or a pancreatic cancer precursor lesion.

The 68th target gene is the hsa-miR-6840-3p gene, a congener thereof, a transcript thereof, or a variant or a derivative thereof. None of the previously known reports show that change in the expression of the gene or the transcript thereof can serve as a marker for early pancreatic cancer or a pancreatic cancer precursor lesion.

The 69th target gene is the hsa-miR-6752-5p gene, a congener thereof, a transcript thereof, or a variant or a derivative thereof. None of the previously known reports show that change in the expression of the gene or the transcript thereof can serve as a marker for early pancreatic cancer or a pancreatic cancer precursor lesion.

The 70th target gene is the hsa-miR-6798-5p gene, a congener thereof, a transcript thereof, or a variant or a derivative thereof. None of the previously known reports show that change in the expression of the gene or the transcript thereof can serve as a marker for early pancreatic cancer or a pancreatic cancer precursor lesion.

The 71st target gene is the hsa-miR-6131 gene, a congener thereof, a transcript thereof, or a variant or a derivative thereof. None of the previously known reports show that change in the expression of the gene or the transcript thereof can serve as a marker for early pancreatic cancer or a pancreatic cancer precursor lesion.

The 72nd target gene is the hsa-miR-4667-5p gene, a congener thereof, a transcript thereof, or a variant or a derivative thereof. None of the previously known reports show that change in the expression of the gene or the transcript thereof can serve as a marker for early pancreatic cancer or a pancreatic cancer precursor lesion.

The 73rd target gene is the hsa-miR-6510-5p gene, a congener thereof, a transcript thereof, or a variant or a derivative thereof. None of the previously known reports show that change in the expression of the gene or the transcript thereof can serve as a marker for early pancreatic cancer or a pancreatic cancer precursor lesion.

The 74th target gene is the hsa-miR-4690-5p gene, a congener thereof, a transcript thereof, or a variant or a derivative thereof. None of the previously known reports show that change in the expression of the gene or the transcript thereof can serve as a marker for early pancreatic cancer or a pancreatic cancer precursor lesion.

The 75th target gene is the hsa-miR-920 gene, a congener thereof, a transcript thereof, or a variant or a derivative thereof. None of the previously known reports show that change in the expression of the gene or the transcript thereof can serve as a marker for early pancreatic cancer or a pancreatic cancer precursor lesion.

The 76th target gene is the hsa-miR-23b-3p gene, a congener thereof, a transcript thereof, or a variant or a derivative thereof. None of the previously known reports show that change in the expression of the gene or the transcript thereof can serve as a marker for early pancreatic cancer or a pancreatic cancer precursor lesion.

The 77th target gene is the hsa-miR-4448 gene, a congener thereof, a transcript thereof, or a variant or a derivative thereof. None of the previously known reports show that change in the expression of the gene or the transcript thereof can serve as a marker for early pancreatic cancer or a pancreatic cancer precursor lesion.

The 78th target gene is the hsa-miR-2110 gene, a congener thereof, a transcript thereof, or a variant or a derivative thereof. None of the previously known reports show that change in the expression of the gene or the transcript thereof can serve as a marker for early pancreatic cancer or a pancreatic cancer precursor lesion.

The 79th target gene is the hsa-miR-4706 gene, a congener thereof, a transcript thereof, or a variant or a derivative thereof. None of the previously known reports show that change in the expression of the gene or the transcript thereof can serve as a marker for early pancreatic cancer or a pancreatic cancer precursor lesion.

The 80th target gene is the hsa-miR-7845-5p gene, a congener thereof, a transcript thereof, or a variant or a derivative thereof. None of the previously known reports show that change in the expression of the gene or the transcript thereof can serve as a marker for early pancreatic cancer or a pancreatic cancer precursor lesion.

The 81st target gene is the hsa-miR-6808-5p gene, a congener thereof, a transcript thereof, or a variant or a derivative thereof. None of the previously known reports show that change in the expression of the gene or the transcript thereof can serve as a marker for early pancreatic cancer or a pancreatic cancer precursor lesion.

The 82nd target gene is the hsa-miR-4447 gene, a congener thereof, a transcript thereof, or a variant or a derivative thereof. None of the previously known reports show that change in the expression of the gene or the transcript thereof can serve as a marker for early pancreatic cancer or a pancreatic cancer precursor lesion.

The 83rd target gene is the hsa-miR-6869-5p gene, a congener thereof, a transcript thereof, or a variant or a derivative thereof. None of the previously known reports show that change in the expression of the gene or the transcript thereof can serve as a marker for early pancreatic cancer or a pancreatic cancer precursor lesion.

The 84th target gene is the hsa-miR-1908-5p gene, a congener thereof, a transcript thereof, or a variant or a derivative thereof. The previously known report shows that change in the expression of the gene or the transcript thereof can serve as a marker for pancreatic cancer (Patent Literature 2 described above).

The 85th target gene is the hsa-miR-6729-5p gene, a congener thereof, a transcript thereof, or a variant or a derivative thereof. The previously known report shows that change in the expression of the gene or the transcript thereof can serve as a marker for pancreatic cancer (Patent Literature 2 described above).

The 86th target gene is the hsa-miR-5195-3p gene, a congener thereof, a transcript thereof, or a variant or a derivative thereof. The previously known report shows that change in the expression of the gene or the transcript thereof can serve as a marker for pancreatic cancer (Patent Literature 2 described above).

The 87th target gene is the hsa-miR-638 gene, a congener thereof, a transcript thereof, or a variant or a derivative thereof. The previously known report shows that change in the expression of the gene or the transcript thereof can serve as a marker for pancreatic cancer (Non-Patent Literature 5 described above).

The 88th target gene is the hsa-miR-6125 gene, a congener thereof, a transcript thereof, or a variant or a derivative thereof. The previously known report shows that change in the expression of the gene or the transcript thereof can serve as a marker for pancreatic cancer (Patent Literature 2 described above).

The 89th target gene is the hsa-miR-3178 gene, a congener thereof, a transcript thereof, or a variant or a derivative thereof. The previously known report shows that change in the expression of the gene or the transcript thereof can serve as a marker for pancreatic cancer (Patent Literature 2 described above).

The 90th target gene is the hsa-miR-3196 gene, a congener thereof, a transcript thereof, or a variant or a derivative thereof. The previously known report shows that change in the expression of the gene or the transcript thereof can serve as a marker for pancreatic cancer (Non-Patent Literature 5 described above).

The 91st target gene is the hsa-miR-8069 gene, a congener thereof, a transcript thereof, or a variant or a derivative thereof. The previously known report shows that change in the expression of the gene or the transcript thereof can serve as a marker for pancreatic cancer (Patent Literature 2 described above).

The 92nd target gene is the hsa-miR-4723-5p gene, a congener thereof, a transcript thereof, or a variant or a derivative thereof. The previously known report shows that change in the expression of the gene or the transcript thereof can serve as a marker for pancreatic cancer (Patent Literature 2 described above).

The 93rd target gene is the hsa-miR-4746-3p gene, a congener thereof, a transcript thereof, or a variant or a derivative thereof. The previously known report shows that change in the expression of the gene or the transcript thereof can serve as a marker for pancreatic cancer (Patent Literature 2 described above).

The 94th target gene is the hsa-miR-4689 gene, a congener thereof, a transcript thereof, or a variant or a derivative thereof. The previously known report shows that change in the expression of the gene or the transcript thereof can serve as a marker for pancreatic cancer (Patent Literature 2 described above).

The 95th target gene is the hsa-miR-6816-5p gene, a congener thereof, a transcript thereof, or a variant or a derivative thereof. The previously known report shows that change in the expression of the gene or the transcript thereof can serve as a marker for pancreatic cancer (Patent Literature 2 described above).

The 96th target gene is the hsa-miR-6757-5p gene, a congener thereof, a transcript thereof, or a variant or a derivative thereof. The previously known report shows that change in the expression of the gene or the transcript thereof can serve as a marker for pancreatic cancer (Patent Literature 2 described above).

The 97th target gene is the hsa-miR-7109-5p gene, a congener thereof, a transcript thereof, or a variant or a derivative thereof. The previously known report shows that change in the expression of the gene or the transcript thereof can serve as a marker for pancreatic cancer (Patent Literature 2 described above).

The 98th target gene is the hsa-miR-6724-5p gene, a congener thereof, a transcript thereof, or a variant or a derivative thereof. The previously known report shows that change in the expression of the gene or the transcript thereof can serve as a marker for pancreatic cancer (Patent Literature 2 described above).

The 99th target gene is the hsa-miR-1225-3p gene, a congener thereof, a transcript thereof, or a variant or a derivative thereof. The previously known report shows that change in the expression of the gene or the transcript thereof can serve as a marker for pancreatic cancer (Non-Patent Literature 5 described above).

The 100th target gene is the hsa-miR-6875-5p gene, a congener thereof, a transcript thereof, or a variant or a derivative thereof. The previously known report shows that change in the expression of the gene or the transcript thereof can serve as a marker for pancreatic cancer (Patent Literature 2 described above).

The 101st target gene is the hsa-miR-7108-5p gene, a congener thereof, a transcript thereof, or a variant or a derivative thereof. The previously known report shows that change in the expression of the gene or the transcript thereof can serve as a marker for pancreatic cancer (Patent Literature 2 described above).

The 102nd target gene is the hsa-miR-4508 gene, a congener thereof, a transcript thereof, or a variant or a derivative thereof. The previously known report shows that change in the expression of the gene or the transcript thereof can serve as a marker for pancreatic cancer (Patent Literature 2 described above).

The 103rd target gene is the hsa-miR-6085 gene, a congener thereof, a transcript thereof, or a variant or a derivative thereof. The previously known report shows that change in the expression of the gene or the transcript thereof can serve as a marker for pancreatic cancer (Patent Literature 2 described above).

The 104th target gene is the hsa-miR-6779-5p gene, a congener thereof, a transcript thereof, or a variant or a derivative thereof. The previously known report shows that change in the expression of the gene or the transcript thereof can serve as a marker for pancreatic cancer (Patent Literature 2 described above).

The 105th target gene is the hsa-miR-642a-3p gene, a congener thereof, a transcript thereof, or a variant or a derivative thereof. The previously known report shows that change in the expression of the gene or the transcript thereof can serve as a marker for pancreatic cancer (Patent Literature 2 described above).

The 106th target gene is the hsa-miR-4695-5p gene, a congener thereof, a transcript thereof, or a variant or a derivative thereof. The previously known report shows that change in the expression of the gene or the transcript thereof can serve as a marker for pancreatic cancer (Non-Patent Literature 5 described above).

The 107th target gene is the hsa-miR-7847-3p gene, a congener thereof, a transcript thereof, or a variant or a derivative thereof. The previously known report shows that change in the expression of the gene or the transcript thereof can serve as a marker for pancreatic cancer (Patent Literature 2 described above).

The 108th target gene is the hsa-miR-3197 gene, a congener thereof, a transcript thereof, or a variant or a derivative thereof. The previously known report shows that change in the expression of the gene or the transcript thereof can serve as a marker for pancreatic cancer (Non-Patent Literature 5 described above).

The 109th target gene is the hsa-miR-6769b-5p gene, a congener thereof, a transcript thereof, or a variant or a derivative thereof. The previously known report shows that change in the expression of the gene or the transcript thereof can serve as a marker for pancreatic cancer (Patent Literature 2 described above).

The 110th target gene is the hsa-miR-7641 gene, a congener thereof, a transcript thereof, or a variant or a derivative thereof. The previously known report shows that change in the expression of the gene or the transcript thereof can serve as a marker for pancreatic cancer (Patent Literature 2 described above).

The 111th target gene is the hsa-miR-187-5p gene, a congener thereof, a transcript thereof, or a variant or a derivative thereof. The previously known report shows that change in the expression of the gene or the transcript thereof can serve as a marker for pancreatic cancer (Patent Literature 2 described above).

The 112th target gene is the hsa-miR-3185 gene, a congener thereof, a transcript thereof, or a variant or a derivative thereof. The previously known report shows that change in the expression of the gene or the transcript thereof can serve as a marker for pancreatic cancer (Patent Literature 2 described above).

The 113th target gene is the hsa-miR-2861 gene, a congener thereof, a transcript thereof, or a variant or a derivative thereof. The previously known report shows that change in the expression of the gene or the transcript thereof can serve as a marker for pancreatic cancer (Patent Literature 2 described above).

The 114th target gene is the hsa-miR-3940-5p gene, a congener thereof, a transcript thereof, or a variant or a derivative thereof. The previously known report shows that change in the expression of the gene or the transcript thereof can serve as a marker for pancreatic cancer (Patent Literature 2 described above).

The 115th target gene is the hsa-miR-1203 gene, a congener thereof, a transcript thereof, or a variant or a derivative thereof. The previously known report shows that change in the expression of the gene or the transcript thereof can serve as a marker for pancreatic cancer (Patent Literature 2 described above).

The 116th target gene is the hsa-miR-615-5p gene, a congener thereof, a transcript thereof, or a variant or a derivative thereof. The previously known report shows that change in the expression of the gene or the transcript thereof can serve as a marker for pancreatic cancer (Patent Literature 2 described above).

The 117th target gene is the hsa-miR-4787-5p gene, a congener thereof, a transcript thereof, or a variant or a derivative thereof. The previously known report shows that change in the expression of the gene or the transcript thereof can serve as a marker for pancreatic cancer (Non-Patent Literature 5 described above).

The 118th target gene is the hsa-miR-1343-3p gene, a congener thereof, a transcript thereof, or a variant or a derivative thereof. The previously known report shows that change in the expression of the gene or the transcript thereof can serve as a marker for pancreatic cancer (Patent Literature 2 described above).

The 119th target gene is the hsa-miR-6813-5p gene, a congener thereof, a transcript thereof, or a variant or a derivative thereof. The previously known report shows that change in the expression of the gene or the transcript thereof can serve as a marker for pancreatic cancer (Patent Literature 2 described above).

The 120th target gene is the hsa-miR-1225-5p gene, a congener thereof, a transcript thereof, or a variant or a derivative thereof. The previously known report shows that change in the expression of the gene or the transcript thereof can serve as a marker for pancreatic cancer (Non-Patent Literature 5 described above).

The 121st target gene is the hsa-miR-602 gene, a congener thereof, a transcript thereof, or a variant or a derivative thereof. The previously known report shows that change in the expression of the gene or the transcript thereof can serve as a marker for pancreatic cancer (Patent Literature 2 described above).

The 122nd target gene is the hsa-miR-4488 gene, a congener thereof, a transcript thereof, or a variant or a derivative thereof. The previously known report shows that change in the expression of the gene or the transcript thereof can serve as a marker for pancreatic cancer (Non-Patent Literature 5 described above).

The 123rd target gene is the hsa-miR-125a-3p gene, a congener thereof, a transcript thereof, or a variant or a derivative thereof. The previously known report shows that change in the expression of the gene or the transcript thereof can serve as a marker for pancreatic cancer (Patent Literature 2 described above).

The 124th target gene is the hsa-miR-5100 gene, a congener thereof, a transcript thereof, or a variant or a derivative thereof. The previously known report shows that change in the expression of the gene or the transcript thereof can serve as a marker for pancreatic cancer (Patent Literature 2 described above).

The 125th target gene is the hsa-miR-4294 gene, a congener thereof, a transcript thereof, or a variant or a derivative thereof. The previously known report shows that change in the expression of the gene or the transcript thereof can serve as a marker for pancreatic cancer (Patent Literature 2 described above).

The 126th target gene is the hsa-miR-1231 gene, a congener thereof, a transcript thereof, or a variant or a derivative thereof. The previously known report shows that change in the expression of the gene or the transcript thereof can serve as a marker for pancreatic cancer (Patent Literature 2 described above).

The 127th target gene is the hsa-miR-6765-3p gene, a congener thereof, a transcript thereof, or a variant or a derivative thereof. The previously known report shows that change in the expression of the gene or the transcript thereof can serve as a marker for pancreatic cancer (Patent Literature 2 described above).

The 128th target gene is the hsa-miR-4442 gene, a congener thereof, a transcript thereof, or a variant or a derivative thereof. The previously known report shows that change in the expression of the gene or the transcript thereof can serve as a marker for pancreatic cancer (Patent Literature 2 described above).

The 129th target gene is the hsa-miR-718 gene, a congener thereof, a transcript thereof, or a variant or a derivative thereof. The previously known report shows that change in the expression of the gene or the transcript thereof can serve as a marker for pancreatic cancer (Patent Literature 2 described above).

The 130th target gene is the hsa-miR-6780b-5p gene, a congener thereof, a transcript thereof, or a variant or a derivative thereof. The previously known report shows that change in the expression of the gene or the transcript thereof can serve as a marker for pancreatic cancer (Patent Literature 2 described above).

The 131st target gene is the hsa-miR-6090 gene, a congener thereof, a transcript thereof, or a variant or a derivative thereof. The previously known report shows that change in the expression of the gene or the transcript thereof can serve as a marker for pancreatic cancer (Patent Literature 2 described above).

The 132nd target gene is the hsa-miR-6845-5p gene, a congener thereof, a transcript thereof, or a variant or a derivative thereof. The previously known report shows that change in the expression of the gene or the transcript thereof can serve as a marker for pancreatic cancer (Patent Literature 2 described above).

The 133rd target gene is the hsa-miR-4741 gene, a congener thereof, a transcript thereof, or a variant or a derivative thereof. The previously known report shows that change in the expression of the gene or the transcript thereof can serve as a marker for pancreatic cancer (Patent Literature 2 described above).

The 134th target gene is the hsa-miR-4467 gene, a congener thereof, a transcript thereof, or a variant or a derivative thereof. The previously known report shows that change in the expression of the gene or the transcript thereof can serve as a marker for pancreatic cancer (Patent Literature 2 described above).

The 135th target gene is the hsa-miR-4707-5p gene, a congener thereof, a transcript thereof, or a variant or a derivative thereof. The previously known report shows that change in the expression of the gene or the transcript thereof can serve as a marker for pancreatic cancer (Patent Literature 2 described above).

The 136th target gene is the hsa-miR-4271 gene, a congener thereof, a transcript thereof, or a variant or a derivative thereof. The previously known report shows that change in the expression of the gene or the transcript thereof can serve as a marker for pancreatic cancer (Patent Literature 2 described above).

The 137th target gene is the hsa-miR-4673 gene, a congener thereof, a transcript thereof, or a variant or a derivative thereof. The previously known report shows that change in the expression of the gene or the transcript thereof can serve as a marker for pancreatic cancer (Patent Literature 2 described above).

The 138th target gene is the hsa-miR-3184-5p gene, a congener thereof, a transcript thereof, or a variant or a derivative thereof. The previously known report shows that change in the expression of the gene or the transcript thereof can serve as a marker for pancreatic cancer (Patent Literature 2 described above).

The 139th target gene is the hsa-miR-1469 gene, a congener thereof, a transcript thereof, or a variant or a derivative thereof. The previously known report shows that change in the expression of the gene or the transcript thereof can serve as a marker for pancreatic cancer (Patent Literature 2 described above).

The 140th target gene is the hsa-miR-4640-5p gene, a congener thereof, a transcript thereof, or a variant or a derivative thereof. The previously known report shows that change in the expression of the gene or the transcript thereof can serve as a marker for pancreatic cancer (Non-Patent Literature 5 described above).

The 141st target gene is the hsa-miR-663a gene, a congener thereof, a transcript thereof, or a variant or a derivative thereof. The previously known report shows that change in the expression of the gene or the transcript thereof can serve as a marker for pancreatic cancer (Patent Literature 2 described above).

The 142nd target gene is the hsa-miR-6791-5p gene, a congener thereof, a transcript thereof, or a variant or a derivative thereof. The previously known report shows that change in the expression of the gene or the transcript thereof can serve as a marker for pancreatic cancer (Patent Literature 2 described above).

The 143rd target gene is the hsa-miR-6826-5p gene, a congener thereof, a transcript thereof, or a variant or a derivative thereof. The previously known report shows that change in the expression of the gene or the transcript thereof can serve as a marker for pancreatic cancer (Patent Literature 2 described above).

The 144th target gene is the hsa-miR-4433b-3p gene, a congener thereof, a transcript thereof, or a variant or a derivative thereof. The previously known report shows that change in the expression of the gene or the transcript thereof can serve as a marker for pancreatic cancer (Patent Literature 2 described above).

The 145th target gene is the hsa-miR-1915-3p gene, a congener thereof, a transcript thereof, or a variant or a derivative thereof. The previously known report shows that change in the expression of the gene or the transcript thereof can serve as a marker for pancreatic cancer (Patent Literature 2 described above).

The 146th target gene is the hsa-miR-4417 gene, a congener thereof, a transcript thereof, or a variant or a derivative thereof. The previously known report shows that change in the expression of the gene or the transcript thereof can serve as a marker for pancreatic cancer (Patent Literature 2 described above).

The 147th target gene is the hsa-miR-4449 gene, a congener thereof, a transcript thereof, or a variant or a derivative thereof. The previously known report shows that change in the expression of the gene or the transcript thereof can serve as a marker for pancreatic cancer (Patent Literature 2 described above).

The 148th target gene is the hsa-miR-4707-3p gene, a congener thereof, a transcript thereof, or a variant or a derivative thereof. The previously known report shows that change in the expression of the gene or the transcript thereof can serve as a marker for pancreatic cancer (Non-Patent Literature 5 described above).

The 149th target gene is the hsa-miR-3180-3p gene, a congener thereof, a transcript thereof, or a variant or a derivative thereof. The previously known report shows that change in the expression of the gene or the transcript thereof can serve as a marker for pancreatic cancer (Non-Patent Literature 5 described above).

The 150th target gene is the hsa-miR-5585-3p gene, a congener thereof, a transcript thereof, or a variant or a derivative thereof. The previously known report shows that change in the expression of the gene or the transcript thereof can serve as a marker for pancreatic cancer (Patent Literature 2 described above).

The 151st target gene is the hsa-miR-1268a gene, a congener thereof, a transcript thereof, or a variant or a derivative thereof. The previously known report shows that change in the expression of the gene or the transcript thereof can serve as a marker for early pancreatic cancer or a pancreatic cancer precursor lesion (Patent Literature 4 described above).

The 152nd target gene is the hsa-miR-8072 gene, a congener thereof, a transcript thereof, or a variant or a derivative thereof. The previously known report shows that change in the expression of the gene or the transcript thereof can serve as a marker for pancreatic cancer (Patent Literature 2 described above).

The 153rd target gene is the hsa-miR-296-5p gene, a congener thereof, a transcript thereof, or a variant or a derivative thereof. The previously known report shows that change in the expression of the gene or the transcript thereof can serve as a marker for early pancreatic cancer or a pancreatic cancer precursor lesion (Patent Literature 5 described above).

The 154th target gene is the hsa-miR-204-3p gene, a congener thereof, a transcript thereof, or a variant or a derivative thereof. The previously known report shows that change in the expression of the gene or the transcript thereof can serve as a marker for pancreatic cancer (Patent Literature 2 described above).

The 155th target gene is the hsa-miR-4454 gene, a congener thereof, a transcript thereof, or a variant or a derivative thereof. The previously known report shows that change in the expression of the gene or the transcript thereof can serve as a marker for pancreatic cancer (Patent Literature 2 described above).

The 156th target gene is the hsa-miR-6722-3p gene, a congener thereof, a transcript thereof, or a variant or a derivative thereof. The previously known report shows that change in the expression of the gene or the transcript thereof can serve as a marker for pancreatic cancer (Patent Literature 2 described above).

The 157th target gene is the hsa-miR-1290 gene, a congener thereof, a transcript thereof, or a variant or a derivative thereof. The previously known report shows that change in the expression of the gene or the transcript thereof can serve as a marker for pancreatic cancer (Patent Literature 2 described above).

The 158th target gene is the hsa-miR-3622a-5p gene, a congener thereof, a transcript thereof, or a variant or a derivative thereof. The previously known report shows that change in the expression of the gene or the transcript thereof can serve as a marker for pancreatic cancer (Patent Literature 2 described above).

The 159th target gene is the hsa-miR-939-5p gene, a congener thereof, a transcript thereof, or a variant or a derivative thereof. The previously known report shows that change in the expression of the gene or the transcript thereof can serve as a marker for early pancreatic cancer or a pancreatic cancer precursor lesion (Patent Literature 4 described above).

The 160th target gene is the hsa-miR-675-5p gene, a congener thereof, a transcript thereof, or a variant or a derivative thereof. The previously known report shows that change in the expression of the gene or the transcript thereof can serve as a marker for pancreatic cancer (Non-Patent Literature 5 described above).

The 161st target gene is the hsa-miR-3131 gene, a congener thereof, a transcript thereof, or a variant or a derivative thereof. The previously known report shows that change in the expression of the gene or the transcript thereof can serve as a marker for pancreatic cancer (Patent Literature 2 described above).

The 162nd target gene is the hsa-miR-4648 gene, a congener thereof, a transcript thereof, or a variant or a derivative thereof. The previously known report shows that change in the expression of the gene or the transcript thereof can serve as a marker for pancreatic cancer (Patent Literature 2 described above).

The 163rd target gene is the hsa-miR-1268b gene, a congener thereof, a transcript thereof, or a variant or a derivative thereof. The previously known report shows that change in the expression of the gene or the transcript thereof can serve as a marker for pancreatic cancer (Non-Patent Literature 5 described above).

The 164th target gene is the hsa-miR-6741-5p gene, a congener thereof, a transcript thereof, or a variant or a derivative thereof. The previously known report shows that change in the expression of the gene or the transcript thereof can serve as a marker for pancreatic cancer (Patent Literature 2 described above).

The 165th target gene is the hsa-miR-6893-5p gene, a congener thereof, a transcript thereof, or a variant or a derivative thereof. The previously known report shows that change in the expression of the gene or the transcript thereof can serve as a marker for pancreatic cancer (Patent Literature 2 described above).

The 166th target gene is the hsa-miR-3162-5p gene, a congener thereof, a transcript thereof, or a variant or a derivative thereof. The previously known report shows that change in the expression of the gene or the transcript thereof can serve as a marker for pancreatic cancer (Patent Literature 2 described above).

The 167th target gene is the hsa-miR-642b-3p gene, a congener thereof, a transcript thereof, or a variant or a derivative thereof. The previously known report shows that change in the expression of the gene or the transcript thereof can serve as a marker for early pancreatic cancer or a pancreatic cancer precursor lesion (Patent Literature 4 described above).

The 168th target gene is the hsa-miR-4734 gene, a congener thereof, a transcript thereof, or a variant or a derivative thereof. The previously known report shows that change in the expression of the gene or the transcript thereof can serve as a marker for pancreatic cancer (Patent Literature 2 described above).

The 169th target gene is the hsa-miR-150-3p gene, a congener thereof, a transcript thereof, or a variant or a derivative thereof. The previously known report shows that change in the expression of the gene or the transcript thereof can serve as a marker for pancreatic cancer (Patent Literature 2 described above).

The 170th target gene is the hsa-miR-8089 gene, a congener thereof, a transcript thereof, or a variant or a derivative thereof. The previously known report shows that change in the expression of the gene or the transcript thereof can serve as a marker for pancreatic cancer (Patent Literature 2 described above).

The 171st target gene is the hsa-miR-6805-3p gene, a congener thereof, a transcript thereof, or a variant or a derivative thereof. The previously known report shows that change in the expression of the gene or the transcript thereof can serve as a marker for pancreatic cancer (Patent Literature 2 described above).

The 172nd target gene is the hsa-miR-7113-3p gene, a congener thereof, a transcript thereof, or a variant or a derivative thereof. The previously known report shows that change in the expression of the gene or the transcript thereof can serve as a marker for pancreatic cancer (Patent Literature 2 described above).

The 173rd target gene is the hsa-miR-6850-5p gene, a congener thereof, a transcript thereof, or a variant or a derivative thereof. The previously known report shows that change in the expression of the gene or the transcript thereof can serve as a marker for pancreatic cancer (Patent Literature 2 described above).

The 174th target gene is the hsa-miR-6799-5p gene, a congener thereof, a transcript thereof, or a variant or a derivative thereof. The previously known report shows that change in the expression of the gene or the transcript thereof can serve as a marker for pancreatic cancer (Patent Literature 2 described above).

The 175th target gene is the hsa-miR-6768-5p gene, a congener thereof, a transcript thereof, or a variant or a derivative thereof. The previously known report shows that change in the expression of the gene or the transcript thereof can serve as a marker for pancreatic cancer (Patent Literature 2 described above).

The 176th target gene is the hsa-miR-92b-5p gene, a congener thereof, a transcript thereof, or a variant or a derivative thereof. The previously known report shows that change in the expression of the gene or the transcript thereof can serve as a marker for pancreatic cancer (Patent Literature 2 described above).

The 177th target gene is the hsa-miR-3679-5p gene, a congener thereof, a transcript thereof, or a variant or a derivative thereof. The previously known report shows that change in the expression of the gene or the transcript thereof can serve as a marker for pancreatic cancer (Non-Patent Literature 5 described above).

The 178th target gene is the hsa-miR-4792 gene, a congener thereof, a transcript thereof, or a variant or a derivative thereof. The previously known report shows that change in the expression of the gene or the transcript thereof can serve as a marker for pancreatic cancer (Patent Literature 2 described above).

The 179th target gene is the hsa-miR-3656 gene, a congener thereof, a transcript thereof, or a variant or a derivative thereof. The previously known report shows that change in the expression of the gene or the transcript thereof can serve as a marker for pancreatic cancer (Patent Literature 2 described above).

The 180th target gene is the hsa-miR-92a-2-5p gene, a congener thereof, a transcript thereof, or a variant or a derivative thereof. The previously known report shows that change in the expression of the gene or the transcript thereof can serve as a marker for pancreatic cancer (Patent Literature 2 described above).

The 181st target gene is the hsa-miR-4466 gene, a congener thereof, a transcript thereof, or a variant or a derivative thereof. The previously known report shows that change in the expression of the gene or the transcript thereof can serve as a marker for pancreatic cancer (Non-Patent Literature 5 described above).

The 182nd target gene is the hsa-miR-4513 gene, a congener thereof, a transcript thereof, or a variant or a derivative thereof. The previously known report shows that change in the expression of the gene or the transcript thereof can serve as a marker for pancreatic cancer (Patent Literature 2 described above).

The 183rd target gene is the hsa-miR-6781-5p gene, a congener thereof, a transcript thereof, or a variant or a derivative thereof. The previously known report shows that change in the expression of the gene or the transcript thereof can serve as a marker for pancreatic cancer (Patent Literature 2 described above).

The 184th target gene is the hsa-miR-4649-5p gene, a congener thereof, a transcript thereof, or a variant or a derivative thereof. The previously known report shows that change in the expression of the gene or the transcript thereof can serve as a marker for pancreatic cancer (Patent Literature 2 described above).

The 185th target gene is the hsa-miR-6775-5p gene, a congener thereof, a transcript thereof, or a variant or a derivative thereof. The previously known report shows that change in the expression of the gene or the transcript thereof can serve as a marker for pancreatic cancer (Patent Literature 2 described above).

The 186th target gene is the hsa-miR-4651 gene, a congener thereof, a transcript thereof, or a variant or a derivative thereof. The previously known report shows that change in the expression of the gene or the transcript thereof can serve as a marker for pancreatic cancer (Patent Literature 2 described above).

The 187th target gene is the hsa-miR-3195 gene, a congener thereof, a transcript thereof, or a variant or a derivative thereof. The previously known report shows that change in the expression of the gene or the transcript thereof can serve as a marker for pancreatic cancer (Non-Patent Literature 5 described above).

The 188th target gene is the hsa-miR-6726-5p gene, a congener thereof, a transcript thereof, or a variant or a derivative thereof. The previously known report shows that change in the expression of the gene or the transcript thereof can serve as a marker for pancreatic cancer (Patent Literature 2 described above).

The 189th target gene is the hsa-miR-6872-3p gene, a congener thereof, a transcript thereof, or a variant or a derivative thereof. The previously known report shows that change in the expression of the gene or the transcript thereof can serve as a marker for pancreatic cancer (Patent Literature 2 described above).

The 190th target gene is the hsa-miR-371a-5p gene, a congener thereof, a transcript thereof, or a variant or a derivative thereof. The previously known report shows that change in the expression of the gene or the transcript thereof can serve as a marker for pancreatic cancer (Patent Literature 2 described above).

The 191st target gene is the hsa-miR-6777-5p gene, a congener thereof, a transcript thereof, or a variant or a derivative thereof. The previously known report shows that change in the expression of the gene or the transcript thereof can serve as a marker for pancreatic cancer (Patent Literature 2 described above).

The 192nd target gene is the hsa-miR-6789-5p gene, a congener thereof, a transcript thereof, or a variant or a derivative thereof. The previously known report shows that change in the expression of the gene or the transcript thereof can serve as a marker for pancreatic cancer (Patent Literature 2 described above).

The 193rd target gene is the hsa-miR-7975 gene, a congener thereof, a transcript thereof, or a variant or a derivative thereof. The previously known report shows that change in the expression of the gene or the transcript thereof can serve as a marker for pancreatic cancer (Patent Literature 2 described above).

The 194th target gene is the hsa-miR-6821-5p gene, a congener thereof, a transcript thereof, or a variant or a derivative thereof. The previously known report shows that change in the expression of the gene or the transcript thereof can serve as a marker for pancreatic cancer (Patent Literature 2 described above).

The 195th target gene is the hsa-miR-4534 gene, a congener thereof, a transcript thereof, or a variant or a derivative thereof. The previously known report shows that change in the expression of the gene or the transcript thereof can serve as a marker for pancreatic cancer (Patent Literature 2 described above).

The 196th target gene is the hsa-miR-619-5p gene, a congener thereof, a transcript thereof, or a variant or a derivative thereof. The previously known report shows that change in the expression of the gene or the transcript thereof can serve as a marker for pancreatic cancer (Patent Literature 2 described above).

The 197th target gene is the hsa-miR-7107-5p gene, a congener thereof, a transcript thereof, or a variant or a derivative thereof. The previously known report shows that change in the expression of the gene or the transcript thereof can serve as a marker for pancreatic cancer (Patent Literature 2 described above).

The 198th target gene is the hsa-miR-1228-3p gene, a congener thereof, a transcript thereof, or a variant or a derivative thereof. The previously known report shows that change in the expression of the gene or the transcript thereof can serve as a marker for pancreatic cancer (Patent Literature 2 described above).

The 199th target gene is the hsa-miR-6774-5p gene, a congener thereof, a transcript thereof, or a variant or a derivative thereof. The previously known report shows that change in the expression of the gene or the transcript thereof can serve as a marker for pancreatic cancer (Patent Literature 2 described above).

The 200th target gene is the hsa-miR-6805-5p gene, a congener thereof, a transcript thereof, or a variant or a derivative thereof. The previously known report shows that change in the expression of the gene or the transcript thereof can serve as a marker for pancreatic cancer (Patent Literature 2 described above).

The 201st target gene is the hsa-miR-23a-3p gene, a congener thereof, a transcript thereof, or a variant or a derivative thereof. The previously known report shows that change in the expression of the gene or the transcript thereof can serve as a marker for pancreatic cancer (Patent Literature 3 described above).

The 202nd target gene is the hsa-miR-4665-5p gene, a congener thereof, a transcript thereof, or a variant or a derivative thereof. The previously known report shows that change in the expression of the gene or the transcript thereof can serve as a marker for pancreatic cancer (Patent Literature 2 described above).

The 203rd target gene is the hsa-miR-4505 gene, a congener thereof, a transcript thereof, or a variant or a derivative thereof. The previously known report shows that change in the expression of the gene or the transcript thereof can serve as a marker for pancreatic cancer (Patent Literature 2 described above).

The 204th target gene is the hsa-miR-4638-5p gene, a congener thereof, a transcript thereof, or a variant or a derivative thereof. The previously known report shows that change in the expression of the gene or the transcript thereof can serve as a marker for pancreatic cancer (Patent Literature 2 described above).

The 205th target gene is the hsa-miR-24-3p gene, a congener thereof, a transcript thereof, or a variant or a derivative thereof. The previously known report shows that change in the expression of the gene or the transcript thereof can serve as a marker for pancreatic cancer (Patent Literature 2 described above).

The 206th target gene is the hsa-miR-3135b gene, a congener thereof, a transcript thereof, or a variant or a derivative thereof. The previously known report shows that change in the expression of the gene or the transcript thereof can serve as a marker for pancreatic cancer (Patent Literature 2 described above).

The 207th target gene is the hsa-miR-4745-5p gene, a congener thereof, a transcript thereof, or a variant or a derivative thereof. The previously known report shows that change in the expression of the gene or the transcript thereof can serve as a marker for pancreatic cancer (Non-Patent Literature 5 described above).

The 208th target gene is the hsa-miR-128-1-5p gene, a congener thereof, a transcript thereof, or a variant or a derivative thereof. The previously known report shows that change in the expression of the gene or the transcript thereof can serve as a marker for pancreatic cancer (Patent Literature 2 described above).

The 209th target gene is the hsa-miR-4476 gene, a congener thereof, a transcript thereof, or a variant or a derivative thereof. The previously known report shows that change in the expression of the gene or the transcript thereof can serve as a marker for pancreatic cancer (Patent Literature 2 described above).

The 210th target gene is the hsa-miR-4687-3p gene, a congener thereof, a transcript thereof, or a variant or a derivative thereof. The previously known report shows that change in the expression of the gene or the transcript thereof can serve as a marker for pancreatic cancer (Patent Literature 2 described above).

The 211th target gene is the hsa-miR-3665 gene, a congener thereof, a transcript thereof, or a variant or a derivative thereof. The previously known report shows that change in the expression of the gene or the transcript thereof can serve as a marker for pancreatic cancer (Non-Patent Literature 5 described above).

The 212th target gene is the hsa-miR-6806-5p gene, a congener thereof, a transcript thereof, or a variant or a derivative thereof. The previously known report shows that change in the expression of the gene or the transcript thereof can serve as a marker for pancreatic cancer (Patent Literature 2 described above).

The 213th target gene is the hsa-miR-3937 gene, a congener thereof, a transcript thereof, or a variant or a derivative thereof. The previously known report shows that change in the expression of the gene or the transcript thereof can serve as a marker for pancreatic cancer (Non-Patent Literature 5 described above).

The 214th target gene is the hsa-miR-711 gene, a congener thereof, a transcript thereof, or a variant or a derivative thereof. The previously known report shows that change in the expression of the gene or the transcript thereof can serve as a marker for pancreatic cancer (Non-Patent Literature 5 described above).

The 215th target gene is the hsa-miR-3141 gene, a congener thereof, a transcript thereof, or a variant or a derivative thereof. The previously known report shows that change in the expression of the gene or the transcript thereof can serve as a marker for pancreatic cancer (Non-Patent Literature 5 described above).

The 216th target gene is the hsa-miR-3188 gene, a congener thereof, a transcript thereof, or a variant or a derivative thereof. The previously known report shows that change in the expression of the gene or the transcript thereof can serve as a marker for pancreatic cancer (Patent Literature 2 described above).

The 217th target gene is the hsa-miR-4281 gene, a congener thereof, a transcript thereof, or a variant or a derivative thereof. The previously known report shows that change in the expression of the gene or the transcript thereof can serve as a marker for pancreatic cancer (Patent Literature 2 described above).

The 218th target gene is the hsa-miR-5196-5p gene, a congener thereof, a transcript thereof, or a variant or a derivative thereof. The previously known report shows that change in the expression of the gene or the transcript thereof can serve as a marker for pancreatic cancer (Patent Literature 2 described above).

The 219th target gene is the hsa-miR-6880-5p gene, a congener thereof, a transcript thereof, or a variant or a derivative thereof. The previously known report shows that change in the expression of the gene or the transcript thereof can serve as a marker for pancreatic cancer (Patent Literature 2 described above).

The 220th target gene is the hsa-miR-3960 gene, a congener thereof, a transcript thereof, or a variant or a derivative thereof. The previously known report shows that change in the expression of the gene or the transcript thereof can serve as a marker for pancreatic cancer (Non-Patent Literature 5 described above).

The 221st target gene is the hsa-miR-3648 gene, a congener thereof, a transcript thereof, or a variant or a derivative thereof. The previously known report shows that change in the expression of the gene or the transcript thereof can serve as a marker for pancreatic cancer (Patent Literature 1 described above).

The 222nd target gene is the hsa-miR-6721-5p gene, a congener thereof, a transcript thereof, or a variant or a derivative thereof. The previously known report shows that change in the expression of the gene or the transcript thereof can serve as a marker for pancreatic cancer (Patent Literature 2 described above).

The 223rd target gene is the hsa-miR-4492 gene, a congener thereof, a transcript thereof, or a variant or a derivative thereof. The previously known report shows that change in the expression of the gene or the transcript thereof can serve as a marker for pancreatic cancer (Non-Patent Literature 5 described above).

The 224th target gene is the hsa-miR-744-5p gene, a congener thereof, a transcript thereof, or a variant or a derivative thereof. The previously known report shows that change in the expression of the gene or the transcript thereof can serve as a marker for pancreatic cancer (Non-Patent Literature 5 described above).

The 225th target gene is the hsa-miR-7704 gene, a congener thereof, a transcript thereof, or a variant or a derivative thereof. The previously known report shows that change in the expression of the gene or the transcript thereof can serve as a marker for pancreatic cancer (Patent Literature 2 described above).

The 226th target gene is the hsa-miR-4749-5p gene, a congener thereof, a transcript thereof, or a variant or a derivative thereof. The previously known report shows that change in the expression of the gene or the transcript thereof can serve as a marker for pancreatic cancer (Non-Patent Literature 5 described above).

The 227th target gene is the hsa-miR-6794-5p gene, a congener thereof, a transcript thereof, or a variant or a derivative thereof. None of the previously known report shows that change in the expression of the gene or the transcript thereof can serve as a marker for pancreatic cancer.

The 228th target gene is the hsa-miR-6511a-5p gene, a congener thereof, a transcript thereof, or a variant or a derivative thereof. None of the previously known report shows that change in the expression of the gene or the transcript thereof can serve as a marker for pancreatic cancer.

The 229th target gene is the hsa-miR-6824-5p gene, a congener thereof, a transcript thereof, or a variant or a derivative thereof. None of the previously known report shows that change in the expression of the gene or the transcript thereof can serve as a marker for pancreatic cancer.

The 230th target gene is the hsa-miR-762 gene, a congener thereof, a transcript thereof, or a variant or a derivative thereof. The previously known report shows that change in the expression of the gene or the transcript thereof can serve as a marker for pancreatic cancer (Non-Patent Literature 5 described above).

The 231st target gene is the hsa-miR-6836-3p gene, a congener thereof, a transcript thereof, or a variant or a derivative thereof. The previously known report shows that change in the expression of the gene or the transcript thereof can serve as a marker for pancreatic cancer (Patent Literature 2 described above).

The 232nd target gene is the hsa-miR-6727-5p gene, a congener thereof, a transcript thereof, or a variant or a derivative thereof. The previously known report shows that change in the expression of the gene or the transcript thereof can serve as a marker for pancreatic cancer (Patent Literature 2 described above).

The 233rd target gene is the hsa-miR-4739 gene, a congener thereof, a transcript thereof, or a variant or a derivative thereof. The previously known report shows that change in the expression of the gene or the transcript thereof can serve as a marker for pancreatic cancer (Non-Patent Literature 5 described above).

The 234th target gene is the hsa-miR-7977 gene, a congener thereof, a transcript thereof, or a variant or a derivative thereof. The previously known report shows that change in the expression of the gene or the transcript thereof can serve as a marker for pancreatic cancer (Patent Literature 2 described above).

The 235th target gene is the hsa-miR-4484 gene, a congener thereof, a transcript thereof, or a variant or a derivative thereof. The previously known report shows that change in the expression of the gene or the transcript thereof can serve as a marker for pancreatic cancer (Patent Literature 2 described above).

The 236th target gene is the hsa-miR-6515-3p gene, a congener thereof, a transcript thereof, or a variant or a derivative thereof. The previously known report shows that change in the expression of the gene or the transcript thereof can serve as a marker for pancreatic cancer (Patent Literature 2 described above).

The 237th target gene is the hsa-miR-373-5p gene, a congener thereof, a transcript thereof, or a variant or a derivative thereof. The previously known report shows that change in the expression of the gene or the transcript thereof can serve as a marker for pancreatic cancer (Non-Patent Literature 5 described above).

The 238th target gene is the hsa-miR-4258 gene, a congener thereof, a transcript thereof, or a variant or a derivative thereof. The previously known report shows that change in the expression of the gene or the transcript thereof can serve as a marker for pancreatic cancer (Patent Literature 2 described above).

The 239th target gene is the hsa-miR-4674 gene, a congener thereof, a transcript thereof, or a variant or a derivative thereof. The previously known report shows that change in the expression of the gene or the transcript thereof can serve as a marker for pancreatic cancer (Patent Literature 2 described above).

The 240th target gene is the hsa-miR-3180 gene, a congener thereof, a transcript thereof, or a variant or a derivative thereof. The previously known report shows that change in the expression of the gene or the transcript thereof can serve as a marker for pancreatic cancer (Non-Patent Literature 5 described above).

The 241st target gene is the hsa-miR-6076 gene, a congener thereof, a transcript thereof, or a variant or a derivative thereof. The previously known report shows that change in the expression of the gene or the transcript thereof can serve as a marker for pancreatic cancer (Patent Literature 2 described above).

The 242nd target gene is the hsa-miR-1238-5p gene, a congener thereof, a transcript thereof, or a variant or a derivative thereof. The previously known report shows that change in the expression of the gene or the transcript thereof can serve as a marker for pancreatic cancer (Patent Literature 2 described above).

The 243rd target gene is the hsa-miR-4463 gene, a congener thereof, a transcript thereof, or a variant or a derivative thereof. The previously known report shows that change in the expression of the gene or the transcript thereof can serve as a marker for pancreatic cancer (Non-Patent Literature 5 described above).

The 244th target gene is the hsa-miR-4486 gene, a congener thereof, a transcript thereof, or a variant or a derivative thereof. The previously known report shows that change in the expression of the gene or the transcript thereof can serve as a marker for pancreatic cancer (Patent Literature 2 described above).

The 245th target gene is the hsa-miR-4730 gene, a congener thereof, a transcript thereof, or a variant or a derivative thereof. The previously known report shows that change in the expression of the gene or the transcript thereof can serve as a marker for pancreatic cancer (Non-Patent Literature 5 described above).

The 246th target gene is the hsa-miR-6766-3p gene, a congener thereof, a transcript thereof, or a variant or a derivative thereof. None of the previously known report shows that change in the expression of the gene or the transcript thereof can serve as a marker for pancreatic cancer.

The 247th target gene is the hsa-miR-4286 gene, a congener thereof, a transcript thereof, or a variant or a derivative thereof. The previously known report shows that change in the expression of the gene or the transcript thereof can serve as a marker for pancreatic cancer (Patent Literature 2 described above).

The 248th target gene is the hsa-miR-6511a-5p gene, a congener thereof, a transcript thereof, or a variant or a derivative thereof. None of the previously known report shows that change in the expression of the gene or the transcript thereof can serve as a marker for pancreatic cancer.

The 249th target gene is the hsa-miR-4739 gene, a congener thereof, a transcript thereof, or a variant or a derivative thereof. The previously known report shows that change in the expression of the gene or the transcript thereof can serve as a marker for pancreatic cancer (Non-Patent Literature 5 described above).

The 250th target gene is the hsa-miR-6749-5p gene, a congener thereof, a transcript thereof, or a variant or a derivative thereof. None of the previously known report shows that change in the expression of the gene or the transcript thereof can serve as a marker for pancreatic cancer.

2. Nucleic Acid Probe or Primer for Detection of Early Pancreatic Cancer or a Pancreatic Cancer Precursor Lesion In the present invention, a nucleic acid capable of specifically binding to any of the target nucleic acids as the early pancreatic cancer or pancreatic cancer precursor lesion markers described above can be used as a nucleic acid, for example, a nucleic acid probe or a primer, for the detection or diagnosis of early pancreatic cancer or a pancreatic cancer precursor lesion.

In the present invention, the nucleic acid probes or the primers that can be used for detecting early pancreatic cancer or a pancreatic cancer precursor lesion or for diagnosing early pancreatic cancer or a pancreatic cancer precursor lesion enable qualitative and/or quantitative measurement of the presence, expression level, or existing amount (abundance) of: any of human-derived hsa-miR-6784-5p, hsa-miR-1181, hsa-miR-671-5p, hsa-miR-6857-5p, hsa-miR-4276, hsa-miR-1914-3p, hsa-miR-149-3p, hsa-miR-937-5p, hsa-miR-4675, hsa-miR-6795-5p, hsa-miR-4731-5p, hsa-miR-5090, hsa-miR-3620-5p, hsa-miR-1343-5p, hsa-miR-6717-5p, hsa-miR-6825-5p, hsa-miR-6738-5p, hsa-miR-6769a-5p, hsa-miR-4728-5p, hsa-miR-652-5p, hsa-miR-4257, hsa-miR-6785-5p, hsa-miR-7110-5p, hsa-miR-6887-5p, hsa-miR-887-3p, hsa-miR-1228-5p, hsa-miR-5572, hsa-miR-6782-5p, hsa-miR-4298, hsa-miR-6786-5p, hsa-miR-5010-5p, hsa-miR-6087, hsa-miR-6765-5p, hsa-miR-6732-5p, hsa-miR-6787-5p, hsa-miR-6737-5p, hsa-miR-128-2-5p, hsa-miR-4270, hsa-miR-6861-5p, hsa-miR-6756-5p, hsa-miR-1229-5p, hsa-miR-6891-5p, hsa-miR-6848-5p, hsa-miR-1237-5p, hsa-miR-30c-1-3p, hsa-miR-1233-5p, hsa-miR-211-3p, hsa-miR-4758-5p, hsa-miR-614, hsa-miR-6746-5p, hsa-miR-1915-5p, hsa-miR-4688, hsa-miR-3917, hsa-miR-5787, hsa-miR-4632-5p, hsa-miR-6126, hsa-miR-135a-3p, hsa-miR-8063, hsa-miR-5698, hsa-miR-6089, hsa-miR-498, hsa-miR-296-3p, hsa-miR-4419b, hsa-miR-6802-5p, hsa-miR-6829-5p, hsa-miR-6803-5p, hsa-miR-1199-5p, hsa-miR-6840-3p, hsa-miR-6752-5p, hsa-miR-6798-5p, hsa-miR-6131, hsa-miR-4667-5p, hsa-miR-6510-5p, hsa-miR-4690-5p, hsa-miR-920, hsa-miR-23b-3p, hsa-miR-4448, hsa-miR-2110, hsa-miR-4706, hsa-miR-7845-5p, hsa-miR-6808-5p, hsa-miR-4447, hsa-miR-6869-5p, hsa-miR-6794-5p, hsa-miR-6511a-5p, hsa-miR-6824-5p, hsa-miR-6766-3p, hsa-miR-6511a-5p, and hsa-miR-6749-5p, as target nucleic acids for early pancreatic cancer or a pancreatic cancer precursor lesion, or a combination thereof; and hsa-miR-1908-5p, hsa-miR-6729-5p, hsa-miR-5195-3p, hsa-miR-638, hsa-miR-6125, hsa-miR-3178, hsa-miR-3196, hsa-miR-8069, hsa-miR-4723-5p, hsa-miR-4746-3p, hsa-miR-4689, hsa-miR-6816-5p, hsa-miR-6757-5p, hsa-miR-7109-5p, hsa-miR-6724-5p, hsa-miR-1225-3p, hsa-miR-6875-5p, hsa-miR-7108-5p, hsa-miR-4508, hsa-miR-6085, hsa-miR-6779-5p, hsa-miR-642a-3p, hsa-miR-4695-5p, hsa-miR-7847-3p, hsa-miR-3197, hsa-miR-6769b-5p, hsa-miR-7641, hsa-miR-187-5p, hsa-miR-3185, hsa-miR-2861, hsa-miR-3940-5p, hsa-miR-1203, hsa-miR-615-5p, hsa-miR-4787-5p, hsa-miR-1343-3p, hsa-miR-6813-5p, hsa-miR-1225-5p, hsa-miR-602, hsa-miR-4488, hsa-miR-125a-3p, hsa-miR-5100, hsa-miR-4294, hsa-miR-1231, hsa-miR-6765-3p, hsa-miR-4442, hsa-miR-718, hsa-miR-6780b-5p, hsa-miR-6090, hsa-miR-6845-5p, hsa-miR-4741, hsa-miR-4467, hsa-miR-4707-5p, hsa-miR-4271, hsa-miR-4673, hsa-miR-3184-5p, hsa-miR-1469, hsa-miR-4640-5p, hsa-miR-663a, hsa-miR-6791-5p, hsa-miR-6826-5p, hsa-miR-4433b-3p, hsa-miR-1915-3p, hsa-miR-4417, hsa-miR-4449, hsa-miR-4707-3p, hsa-miR-3180-3p, hsa-miR-5585-3p, hsa-miR-1268a, hsa-miR-8072, hsa-miR-296-5p, hsa-miR-204-3p, hsa-miR-4454, hsa-miR-6722-3p, hsa-miR-1290, hsa-miR-3622a-5p, hsa-miR-939-5p, hsa-miR-675-5p, hsa-miR-3131, hsa-miR-4648, hsa-miR-1268b, hsa-miR-6741-5p, hsa-miR-6893-5p, hsa-miR-3162-5p, hsa-miR-642b-3p, hsa-miR-4734, hsa-miR-150-3p, hsa-miR-8089, hsa-miR-6805-3p, hsa-miR-7113-3p, hsa-miR-6850-5p, hsa-miR-6799-5p, hsa-miR-6768-5p, hsa-miR-92b-5p, hsa-miR-3679-5p, hsa-miR-4792, hsa-miR-3656, hsa-miR-92a-2-5p, hsa-miR-4466, hsa-miR-4513, hsa-miR-6781-5p, hsa-miR-4649-5p, hsa-miR-6775-5p, hsa-miR-4651, hsa-miR-3195, hsa-miR-6726-5p, hsa-miR-6872-3p, hsa-miR-371a-5p, hsa-miR-6777-5p, hsa-miR-6789-5p, hsa-miR-7975, hsa-miR-6821-5p, hsa-miR-4534, hsa-miR-619-5p, hsa-miR-7107-5p, hsa-miR-1228-3p, hsa-miR-6774-5p, hsa-miR-6805-3p, hsa-miR-23a-3p, hsa-miR-4665-5p, hsa-miR-4505, hsa-miR-4638-5p, hsa-miR-24-3p, hsa-miR-3135b, hsa-miR-4745-5p, hsa-miR-128-1-5p, hsa-miR-4476, hsa-miR-4687-3p, hsa-miR-3665, hsa-miR-6806-5p, hsa-miR-3937, hsa-miR-711, hsa-miR-3141, hsa-miR-3188, hsa-miR-4281, hsa-miR-5196-5p, hsa-miR-6880-5p, hsa-miR-3960, hsa-miR-3648, hsa-miR-6721-5p, hsa-miR-4492, hsa-miR-744-5p, hsa-miR-7704, hsa-miR-4749-5p, hsa-miR-762, hsa-miR-6836-3p, hsa-miR-6727-5p, hsa-miR-4739, hsa-miR-7977, hsa-miR-4484, hsa-miR-6515-3p, hsa-miR-373-5p, hsa-miR-4258, hsa-miR-4674, hsa-miR-3180, hsa-miR-6076, hsa-miR-1238-5p, hsa-miR-4463, hsa-miR-4486, hsa-miR-4730, hsa-miR-4286, and hsa-miR-4739, which can be further optionally combined therewith or a combination thereof; congeners thereof: transcripts thereof: or variants or derivatives thereof.

The expression levels of the target nucleic acids described above are increased or decreased (hereinafter, referred to as "increased/decreased") depending on the identities of the target nucleic acids in subjects having early pancreatic cancer or a pancreatic cancer precursor lesion as compared with healthy subjects. For example, Table 2 illustrates change in the expression levels of target miRNAs corresponding to SEQ ID NOs: 1 to 226 in the blood (serum) of pancreatic cancer precursor lesion patients (humans) relative to healthy subjects. As shown in Table 2, the expression levels of the target miRNAs are increased or decreased depending on the identities of the target miRNAs. In the present invention, any of the target miRNAs selected this time and described herein can be used for the detection and determination of early pancreatic cancer or a pancreatic cancer precursor lesion in a subject.

Accordingly, the present invention can be effectively used for measuring expression levels of the target nucleic acids in body fluids from subjects (e.g., humans) suspected of having early pancreatic cancer or a pancreatic cancer precursor lesion and body fluids from healthy subjects and thereby detecting early pancreatic cancer or a pancreatic cancer precursor lesion with high accuracy through the comparison thereof. The present invention can also be effectively used for measuring expression levels of the target nucleic acids in body fluids from subjects (e.g., humans) suspected of having early pancreatic cancer or a pancreatic cancer precursor lesion and body fluids from advanced pancreatic cancer patients, bile duct cancer patients, breast cancer patients, prostate cancer patients, colorectal cancer patients, stomach cancer patients, esophageal cancer patients, liver cancer patients, benign pancreatic disease patients, or benign prostatic disease patients, or a combination thereof and thereby specifically discriminating early pancreatic cancer or a pancreatic cancer precursor lesion from other cancers, benign diseases or the like, with high accuracy through the comparison thereof.

The nucleic acid probe or the primer that can be used in the present invention is a nucleic acid probe(s) capable of specifically binding to a polynucleotide(s) consisting of a nucleotide sequence(s) represented by at least one, at least two, at least three, at least four, or at least five of SEQ ID NOs: 1 to 83, 227 to 229, 246, 248, and 250, or a primer(s) for amplifying a polynucleotide(s) consisting of a nucleotide sequence(s) represented by at least one, at least two, at least three, at least four, or at least five of SEQ ID NOs: 1 to 83, 227 to 229, 246, 248, and 250.

The nucleic acid probe or the primer that can be used in the present invention may further comprise a nucleic acid probe(s) capable of specifically binding to a polynucleotide(s) consisting of a nucleotide sequence(s) represented by at least one, at least two, at least three, at least four, or at least five of SEQ ID NOs: 84 to 226, 230 to 245, 247, and 249, or a primer(s) for amplifying a polynucleotide(s) consisting of a nucleotide sequence(s) represented by at least one, at least two, at least three, at least four, or at least five of SEQ ID NOs: 84 to 226, 230 to 245, 247, and 249.

Specifically, these nucleic acid probes or primers comprise a combination of one or more polynucleotides selected from: a group of polynucleotides comprising nucleotide sequences represented by any of SEQ ID NOs: 1 to 250 or nucleotide sequences derived from the nucleotide sequences by the replacement of u with t, and a group of complementary polynucleotides thereof; a group of polynucleotides respectively hybridizing under stringent conditions (mentioned later) to DNAs consisting of nucleotide sequences complementary to these nucleotide sequences, and a group of complementary polynucleotides thereof; and a group of polynucleotides comprising 15 or more, preferably 17 or more consecutive nucleotides from the nucleotide sequences of these polynucleotide groups. In this respect, the target miRNA used in the present invention also includes, for example, precursor miRNAs as shown in SEQ ID NOs: 251 to 518 and isomiRNAs as shown in SEQ ID NOs: 519 to 812 in Table 1. The isomiRNAs include those having the number of nucleotides as short as approximately 15, those having the number of nucleotides as long as approximately 29, those having mutation such as substitution, and the like. Hence, in the present invention, the nucleic acid probes or the primers also include nucleic acid probes or primers for enabling measurement of the expression of precursor miRNAs and target isomiRNAs. These polynucleotides can be used as nucleic acid probes and primers for detecting the early pancreatic cancer or pancreatic cancer precursor lesion markers as target nucleic acids.

More specifically, examples of the nucleic acid probes or the primers that can be used in the present invention include at least one (i.e., one or more) polynucleotide selected from the group consisting of the following polynucleotides (a) to (e):
(a) a polynucleotide consisting of a nucleotide sequence represented by any of SEQ ID NOs: 1 to 83, 227 to 229, 246, 248, and 250 or a nucleotide sequence derived from the nucleotide sequence by the replacement of u with t, a variant thereof, a derivative thereof, or a fragment thereof comprising 15 or more consecutive nucleotides;
(b) a polynucleotide comprising a nucleotide sequence represented by any of SEQ ID NOs: 1 to 83, 227 to 229, 246, 248, and 250;
(c) a polynucleotide consisting of a nucleotide sequence complementary to a nucleotide sequence represented by any of SEQ ID NOs: 1 to 83, 227 to 229, 246, 248, and 250 or a nucleotide sequence derived from the nucleotide sequence by the replacement of u with t, a variant thereof, a derivative thereof, or a fragment thereof comprising 15 or more consecutive nucleotides;
(d) a polynucleotide comprising a nucleotide sequence complementary to a nucleotide sequence represented by any of SEQ ID NOs: 1 to 83, 227 to 229, 246, 248, and 250 or a nucleotide sequence derived from the nucleotide sequence by the replacement of u with t; and
(e) a polynucleotide hybridizing under stringent conditions to any of the polynucleotides (a) to (d).

In addition to at least one (i.e., one or more) polynucleotides selected from any of the polynucleotides (a) to (e), the nucleic acid probes or the primers that can be used in the present invention may further comprise at least one (i.e., one or more) polynucleotides of the following polynucleotides (f) to (j):

(f) a polynucleotide consisting of a nucleotide sequence represented by any of SEQ ID NOs: 84 to 226, 230 to 245, 247, and 249 or a nucleotide sequence derived from the nucleotide sequence by the replacement of u with t, a variant thereof, a derivative thereof, or a fragment thereof comprising 15 or more consecutive nucleotides;
(g) a polynucleotide comprising a nucleotide sequence represented by any of SEQ ID NOs: 84 to 226, 230 to 245, 247, and 249;
(h) a polynucleotide consisting of a nucleotide sequence complementary to a nucleotide sequence represented by any of SEQ ID NOs: 84 to 226, 230 to 245, 247, and 249 or a nucleotide sequence derived from the nucleotide sequence by the replacement of u with t, a variant thereof, a derivative thereof, or a fragment thereof comprising 15 or more consecutive nucleotides;
(i) a polynucleotide comprising a nucleotide sequence complementary to a nucleotide sequence represented by any of SEQ ID NOs: 84 to 226, 230 to 245, 247, and 249 or a nucleotide sequence derived from the nucleotide sequence by the replacement of u with t; and
(j) a polynucleotide hybridizing under stringent conditions to any of the polynucleotides (f) to (i).

For the above-mentioned polynucleotides, the "fragment thereof comprising 15 or more consecutive nucleotides" is derived from the nucleotide sequence of each polynucleotide, and can comprise, but is not limited to, the number of nucleotides in the range of, for example, from 15 consecutive nucleotides to less than the total number of nucleotides of the sequence, from 17 consecutive nucleotides to less than the total number of nucleotides of the sequence, from 19 consecutive nucleotides to less than the total number of nucleotides of the sequence, or the like.

These polynucleotides or fragments thereof used in the present invention may each be DNA or RNA.

The polynucleotides that can be used in the present invention can be prepared by use of a general technique such as a DNA recombination technique, a PCR method, or a method using an automatic DNA/RNA synthesizer.

The DNA recombination technique and the PCR method may employ techniques described in, for example, Ausubel et al., Current Protocols in Molecular Biology, John Willey & Sons, US (1993); and Sambrook et al., Molecular Cloning—A Laboratory Manual, Cold Spring Harbor Laboratory Press, US (1989).

The human-derived hsa-miR-6784-5p, hsa-miR-1181, hsa-miR-671-5p, hsa-miR-6857-5p, hsa-miR-4276, hsa-miR-1914-3p, hsa-miR-149-3p, hsa-miR-937-5p, hsa-miR-4675, hsa-miR-6795-5p, hsa-miR-4731-5p, hsa-miR-5090, hsa-miR-3620-5p, hsa-miR-1343-5p, hsa-miR-6717-5p, hsa-miR-6825-5p, hsa-miR-6738-5p, hsa-miR-6769a-5p, hsa-miR-4728-5p, hsa-miR-652-5p, hsa-miR-4257, hsa-miR-6785-5p, hsa-miR-7110-5p, hsa-miR-6887-5p, hsa-miR-887-3p, hsa-miR-1228-5p, hsa-miR-5572, hsa-miR-6782-5p, hsa-miR-4298, hsa-miR-6786-5p, hsa-miR-5010-5p, hsa-miR-6087, hsa-miR-6765-5p, hsa-miR-6732-5p, hsa-miR-6787-5p, hsa-miR-6737-5p, hsa-miR-128-2-5p, hsa-miR-4270, hsa-miR-6861-5p, hsa-miR-6756-5p, hsa-miR-1229-5p, hsa-miR-6891-5p, hsa-miR-6848-5p, hsa-miR-1237-5p, hsa-miR-30c-1-3p, hsa-miR-1233-5p, hsa-miR-211-3p, hsa-miR-4758-5p, hsa-miR-614, hsa-miR-6746-5p, hsa-miR-1915-5p, hsa-miR-4688, hsa-miR-3917, hsa-miR-5787, hsa-miR-4632-5p, hsa-miR-6126, hsa-miR-135a-3p, hsa-miR-8063, hsa-miR-5698, hsa-miR-6089, hsa-miR-498, hsa-miR-296-3p, hsa-miR-4419b, hsa-miR-6802-5p, hsa-miR-6829-5p, hsa-miR-6803-5p, hsa-miR-1199-5p, hsa-miR-6840-3p, hsa-miR-6752-5p, hsa-miR-6798-5p, hsa-miR-6131, hsa-miR-4667-5p, hsa-miR-6510-5p, hsa-miR-4690-5p, hsa-miR-920, hsa-miR-23b-3p, hsa-miR-4448, hsa-miR-2110, hsa-miR-4706, hsa-miR-7845-5p, hsa-miR-6808-5p, hsa-miR-4447, hsa-miR-6869-5p, hsa-miR-1908-5p, hsa-miR-6729-5p, hsa-miR-5195-3p, hsa-miR-638, hsa-miR-6125, hsa-miR-3178, hsa-miR-3196, hsa-miR-8069, hsa-miR-4723-5p, hsa-miR-4746-3p, hsa-miR-4689, hsa-miR-6816-5p, hsa-miR-6757-5p, hsa-miR-7109-5p, hsa-miR-6724-5p, hsa-miR-1225-3p, hsa-miR-6875-5p, hsa-miR-7108-5p, hsa-miR-4508, hsa-miR-6085, hsa-miR-6779-5p, hsa-miR-642a-3p, hsa-miR-4695-5p, hsa-miR-7847-3p, hsa-miR-3197, hsa-miR-6769b-5p, hsa-miR-7641, hsa-miR-187-5p, hsa-miR-3185, hsa-miR-2861, hsa-miR-3940-5p, hsa-miR-1203, hsa-miR-615-5p, hsa-miR-4787-5p, hsa-miR-1343-3p, hsa-miR-6813-5p, hsa-miR-1225-5p, hsa-miR-602, hsa-miR-4488, hsa-miR-125a-3p, hsa-miR-5100, hsa-miR-4294, hsa-miR-1231, hsa-miR-6765-3p, hsa-miR-4442, hsa-miR-718, hsa-miR-6780b-5p, hsa-miR-6090, hsa-miR-6845-5p, hsa-miR-4741, hsa-miR-4467, hsa-miR-4707-5p, hsa-miR-4271, hsa-miR-4673, hsa-miR-3184-5p, hsa-miR-1469, hsa-miR-4640-5p, hsa-miR-663a, hsa-miR-6791-5p, hsa-miR-6826-5p, hsa-miR-4433b-3p, hsa-miR-1915-3p, hsa-miR-4417, hsa-miR-4449, hsa-miR-4707-3p, hsa-miR-3180-3p, hsa-miR-5585-3p, hsa-miR-1268a, hsa-miR-8072, hsa-miR-296-5p, hsa-miR-204-3p, hsa-miR-4454, hsa-miR-6722-3p, hsa-miR-1290, hsa-miR-3622a-5p, hsa-miR-939-5p, hsa-miR-675-5p, hsa-miR-3131, hsa-miR-4648, hsa-miR-1268b, hsa-miR-6741-5p, hsa-miR-6893-5p, hsa-miR-3162-5p, hsa-miR-642b-3p, hsa-miR-4734, hsa-miR-150-3p, hsa-miR-8089, hsa-miR-6805-3p, hsa-miR-7113-3p, hsa-miR-6850-5p, hsa-miR-6799-5p, hsa-miR-6768-5p, hsa-miR-92b-5p, hsa-miR-3679-5p, hsa-miR-4792, hsa-miR-3656, hsa-miR-92a-2-5p, hsa-miR-4466, hsa-miR-4513, hsa-miR-6781-5p, hsa-miR-4649-5p, hsa-miR-6775-5p, hsa-miR-4651, hsa-miR-3195, hsa-miR-6726-5p, hsa-miR-6872-3p, hsa-miR-371a-5p, hsa-miR-6777-5p, hsa-miR-6789-5p, hsa-miR-7975, hsa-miR-6821-5p, hsa-miR-4534, hsa-miR-619-5p, hsa-miR-7107-5p, hsa-miR-1228-3p, hsa-miR-6774-5p, hsa-miR-6805-5p, hsa-miR-23a-3p, hsa-miR-4665-5p, hsa-miR-4505, hsa-miR-4638-5p, hsa-miR-24-3p, hsa-miR-3135b, hsa-miR-4745-5p, hsa-miR-128-1-5p, hsa-miR-4476, hsa-miR-4687-3p, hsa-miR-3665, hsa-miR-6806-5p, hsa-miR-3937, hsa-miR-711, hsa-miR-3141, hsa-miR-3188, hsa-miR-4281, hsa-miR-5196-5p, hsa-miR-6880-5p, hsa-miR-3960, hsa-miR-3648, hsa-miR-6721-5p, hsa-miR-4492, hsa-miR-744-5p, hsa-miR-7704, hsa-miR-4749-5p, hsa-miR-6794-5p, hsa-miR-6511a-5p, hsa-miR-6824-5p, hsa-miR-762, hsa-miR-6836-3p, hsa-miR-6727-5p, hsa-miR-4739, hsa-miR-7977, hsa-miR-4484, hsa-miR-6515-3p, hsa-miR-373-5p, hsa-miR-4258, hsa-miR-4674, hsa-miR-3180, hsa-miR-6076, hsa-miR-1238-5p, hsa-miR-4463, hsa-miR-4486, hsa-miR-4730, hsa-miR-6766-3p, hsa-miR-4286, hsa-miR-6511a-5p, hsa-miR-4739, and hsa-miR-6749-5p represented by SEQ ID NOs: 1 to 250 are known in the art, and their obtainment methods are also known as mentioned above. Therefore, each polynucleotide that can be used as a nucleic acid probe or a primer in the present invention can be prepared by cloning the gene.

Such nucleic acid probes or primers can be chemically synthesized using an automatic DNA synthesizer. In general, the phosphoramidite method is used in this synthesis, and single-stranded DNA up to approximately 100 nucleotides can be automatically synthesized by this method. The automatic DNA synthesizer is commercially available from, for example, Polygen GmbH, ABI, or Applied Biosystems, Inc.

Alternatively, the polynucleotides of the present invention can also be prepared by cDNA cloning methods. The cDNA cloning technique may employ, for example, microRNA Cloning Kit Wako.

In this context, the sequences of the nucleic acid probes and the primers for detecting the polynucleotide consisting of a nucleotide sequence represented by any of SEQ ID NOs: 1 to 250 do not exist as miRNAs or precursors thereof in the living body or in vivo. For example, the nucleotide sequences represented by SEQ ID NO: 14 and SEQ ID NO: 118 are produced from the precursor represented by SEQ ID NO: 264. This precursor has a hairpin-like structure as shown in FIG. 1, and the nucleotide sequences represented by SEQ ID NO: 14 and SEQ ID NO: 118 have mismatch sequences with each other. As such, a nucleotide sequence completely complementary to the nucleotide sequence represented by SEQ ID NO: 14 or SEQ ID NO: 118 does not naturally occur in vivo. Therefore, the nucleic acid probes and the primers for detecting the nucleotide sequence represented by any of SEQ ID NOs: 1 to 250 have artificial nucleotide sequences that do not exist in the living body or in vivo.

3. Kit or Device for Detection of Early Pancreatic Cancer or a Pancreatic Cancer Precursor Lesion The present invention also provides a kit or a device for the detection of early pancreatic cancer or a pancreatic cancer precursor lesion, comprising one or more polynucleotides (which may include a variant, a fragment, or a derivative thereof) that can be used as nucleic acid probes or primers in the present invention for measuring target nucleic acids as early pancreatic cancer or pancreatic cancer precursor lesion markers.

The target nucleic acids as early pancreatic cancer or pancreatic cancer precursor lesion markers according to the present invention are at least one nucleic acid selected from the following group A:

Group A:

hsa-miR-6784-5p, hsa-miR-1181, hsa-miR-671-5p, hsa-miR-6857-5p, hsa-miR-4276, hsa-miR-1914-3p, hsa-miR-149-3p, hsa-miR-937-5p, hsa-miR-4675, hsa-miR-6795-5p, hsa-miR-4731-5p, hsa-miR-5090, hsa-miR-3620-5p, hsa-miR-1343-5p, hsa-miR-6717-5p, hsa-miR-6825-5p, hsa-miR-6738-5p, hsa-miR-6769a-5p, hsa-miR-4728-5p, hsa-miR-652-5p, hsa-miR-4257, hsa-miR-6785-5p, hsa-miR-7110-5p, hsa-miR-6887-5p, hsa-miR-887-3p, hsa-miR-1228-5p, hsa-miR-5572, hsa-miR-6782-5p, hsa-miR-4298, hsa-miR-6786-5p, hsa-miR-5010-5p, hsa-miR-6087, hsa-miR-6765-5p, hsa-miR-6732-5p, hsa-miR-6787-5p, hsa-miR-6737-5p, hsa-miR-128-2-5p, hsa-miR-4270, hsa-miR-6861-5p, hsa-miR-6756-5p, hsa-miR-1229-5p, hsa-miR-6891-5p, hsa-miR-6848-5p, hsa-miR-1237-5p, hsa-miR-30c-1-3p, hsa-miR-1233-5p, hsa-miR-211-3p, hsa-miR-4758-5p, hsa-miR-614, hsa-miR-6746-5p, hsa-miR-1915-5p, hsa-miR-4688, hsa-miR-3917, hsa-miR-5787, hsa-miR-4632-5p, hsa-miR-6126, hsa-miR-135a-3p, hsa-miR-8063, hsa-miR-5698, hsa-miR-6089, hsa-miR-498, hsa-miR-296-3p, hsa-miR-4419b, hsa-miR-6802-5p, hsa-miR-6829-5p, hsa-miR-6803-5p, hsa-miR-1199-5p, hsa-miR-6840-3p, hsa-miR-6752-5p, hsa-miR-6798-5p, hsa-miR-6131, hsa-miR-4667-5p, hsa-miR-6510-5p, hsa-miR-4690-5p, hsa-miR-920, hsa-miR-23b-3p, hsa-miR-4448, hsa-miR-2110, hsa-miR-4706, hsa-miR-7845-5p, hsa-miR-6808-5p, hsa-miR-4447, hsa-miR-6869-5p, hsa-miR-6794-5p, hsa-miR-6511a-5p, hsa-miR-6824-5p, hsa-miR-6766-3p, hsa-miR-6511a-5p, and hsa-miR-6749-5p.

Additional target nucleic acids that may be optionally used in the measurement are at least one nucleic acid selected from the following group B:

Group B:

hsa-miR-1908-5p, hsa-miR-6729-5p, hsa-miR-5195-3p, hsa-miR-638, hsa-miR-6125, hsa-miR-3178, hsa-miR-3196, hsa-miR-8069, hsa-miR-4723-5p, hsa-miR-4746-3p, hsa-miR-4689, hsa-miR-6816-5p, hsa-miR-6757-5p, hsa-miR-7109-5p, hsa-miR-6724-5p, hsa-miR-1225-3p, hsa-miR-6875-5p, hsa-miR-7108-5p, hsa-miR-4508, hsa-miR-6085, hsa-miR-6779-5p, hsa-miR-642a-3p, hsa-miR-4695-5p, hsa-miR-7847-3p, hsa-miR-3197, hsa-miR-6769b-5p, hsa-miR-7641, hsa-miR-187-5p, hsa-miR-3185, hsa-miR-2861, hsa-miR-3940-5p, hsa-miR-1203, hsa-miR-615-5p, hsa-miR-4787-5p, hsa-miR-1343-3p, hsa-miR-6813-5p, hsa-miR-1225-5p, hsa-miR-602, hsa-miR-4488, hsa-miR-125a-3p, hsa-miR-5100, hsa-miR-4294, hsa-miR-1231, hsa-miR-6765-3p, hsa-miR-4442, hsa-miR-718, hsa-miR-6780b-5p, hsa-miR-6090, hsa-miR-6845-5p, hsa-miR-4741, hsa-miR-4467, hsa-miR-4707-5p, hsa-miR-4271, hsa-miR-4673, hsa-miR-3184-5p, hsa-miR-1469, hsa-miR-4640-5p, hsa-miR-663a, hsa-miR-6791-5p, hsa-miR-6826-5p, hsa-miR-4433b-3p, hsa-miR-1915-3p, hsa-miR-4417, hsa-miR-4449, hsa-miR-4707-3p, hsa-miR-3180-3p, hsa-miR-5585-3p, hsa-miR-1268a, hsa-miR-8072, hsa-miR-296-5p, hsa-miR-204-3p, hsa-miR-4454, hsa-miR-6722-3p, hsa-miR-1290, hsa-miR-3622a-5p, hsa-miR-939-5p, hsa-miR-675-5p, hsa-miR-3131, hsa-miR-4648, hsa-miR-1268b, hsa-miR-6741-5p, hsa-miR-6893-5p, hsa-miR-3162-5p, hsa-miR-642b-3p, hsa-miR-4734, hsa-miR-150-3p, hsa-miR-8089, hsa-miR-6805-3p, hsa-miR-7113-3p, hsa-miR-6850-5p, hsa-miR-6799-5p, hsa-miR-6768-5p, hsa-miR-92b-5p, hsa-miR-3679-5p, hsa-miR-4792, hsa-miR-3656, hsa-miR-92a-2-5p, hsa-miR-4466, hsa-miR-4513, hsa-miR-6781-5p, hsa-miR-4649-5p, hsa-miR-6775-5p, hsa-miR-4651, hsa-miR-3195, hsa-miR-6726-5p, hsa-miR-6872-3p, hsa-miR-371a-5p, hsa-miR-6777-5p, hsa-miR-6789-5p, hsa-miR-7975, hsa-miR-6821-5p, hsa-miR-4534, hsa-miR-619-5p, hsa-miR-7107-5p, hsa-miR-1228-3p, hsa-miR-6774-5p, hsa-miR-6805-5p, hsa-miR-23a-3p, hsa-miR-4665-5p, hsa-miR-4505, hsa-miR-4638-5p, hsa-miR-24-3p, hsa-miR-3135b, hsa-miR-4745-5p, hsa-miR-128-1-5p, hsa-miR-4476, hsa-miR-4687-3p, hsa-miR-3665, hsa-miR-6806-5p, hsa-miR-3937, hsa-miR-711, hsa-miR-3141, hsa-miR-3188, hsa-miR-4281, hsa-miR-5196-5p, hsa-miR-6880-5p, hsa-miR-3960, hsa-miR-3648, hsa-miR-6721-5p, hsa-miR-4492, hsa-miR-744-5p, hsa-miR-7704, hsa-miR-4749-5p, hsa-miR-762, hsa-miR-6836-3p, hsa-miR-6727-5p, hsa-miR-4739, hsa-miR-7977, hsa-miR-4484, hsa-miR-6515-3p, hsa-miR-373-5p, hsa-miR-4258, hsa-miR-4674, hsa-miR-3180, hsa-miR-6076, hsa-miR-1238-5p, hsa-miR-4463, hsa-miR-4486, hsa-miR-4730, hsa-miR-4286, and hsa-miR-4739.

The kit or the device of the present invention comprises nucleic acid capable of specifically binding to any of the target nucleic acids as the early pancreatic cancer or pancreatic cancer precursor lesion markers described above, preferably at least one (or one or more) polynucleotide selected from the polynucleotides described in the preceding Section 2, or a variant thereof.

Specifically, the kit or the device of the present invention can comprise at least one (or one or more) polynucleotides comprising (or consisting of) a nucleotide sequence represented by any of SEQ ID NOs: 1 to 83, 227 to 229, 246, 248, and 250 or a nucleotide sequence derived from the nucleotide sequence by the replacement of u with t, polynucleotide(s) comprising (or consisting of) a complementary sequence thereof, a polynucleotide(s) hybridizing under stringent conditions to any of these polynucleotides, or a variant(s) or a fragment(s) comprising 15 or more consecutive nucleotides of any of these polynucleotide sequences.

The kit or the device of the present invention can further comprise one or more, two or more, three or more, four or more, or five or more polynucleotides comprising (or consisting of) a nucleotide sequence represented by any of SEQ ID NOs: 84 to 226, 230 to 245, 247, and 249 or a nucleotide sequence derived from the nucleotide sequence by the replacement of u with t, a polynucleotide(s) comprising (or consisting of) a complementary sequence thereof, a polynucleotide(s) hybridizing under stringent conditions to any of these polynucleotides, a variant(s) or a fragment(s) comprising 15 or more, 17 or more, or 19 or more consecutive nucleotides of any of these polynucleotide sequences.

The fragment or fragments that can be comprised in the kit or the device of the present invention is/are, for example, one or more, two or more, three or more, four or more, or five or more polynucleotides selected from the group consisting of the following polynucleotides (1) and (2):

(1) a polynucleotide comprising 15 or more, 17 or more, or 19 or more consecutive nucleotides that are from a nucleotide sequence derived from a nucleotide sequence represented by any of SEQ ID NOs: 1 to 83, 227 to 229, 246, 248, and 250 by the replacement of u with t, or a complementary sequence thereof; and (2) a polynucleotide comprising 15 or more, 17 or more, or 19 or more consecutive nucleotides that are from a nucleotide sequence derived from a nucleotide sequence represented by any of SEQ ID NOs: 84 to 226, 230 to 245, 247, and 249 by the replacement of u with t, or a complementary sequence thereof.

In a preferred embodiment, the polynucleotide is a polynucleotide consisting of a nucleotide sequence represented by any of SEQ ID NOs: 1 to 83, 227 to 229, 246, 248, and 250 or a nucleotide sequence derived from the nucleotide sequence by the replacement of u with t, a polynucleotide consisting of a complementary sequence thereof, a polynucleotide hybridizing under stringent conditions to any of these polynucleotides, or a variant thereof comprising 15 or more, 17 or more, or 19 or more consecutive nucleotides.

In a preferred embodiment, the polynucleotide is a polynucleotide consisting of a nucleotide sequence represented by any of SEQ ID NOs: 84 to 226, 230 to 245, 247, and 249 or a nucleotide sequence derived from the nucleotide sequence by the replacement of u with t, a polynucleotide consisting of a complementary sequence thereof, a polynucleotide hybridizing under stringent conditions to any of these polynucleotides, or a variant thereof comprising 15 or more, 17 or more, or 19 or more consecutive nucleotides.

In a preferred embodiment, the fragment can be a polynucleotide comprising 15 or more, 17 or more, or 19 or more consecutive nucleotides.

In the present invention, the size of the polynucleotide fragment is the number of nucleotides in the range from, for example, 15 consecutive nucleotides to less than the total number of nucleotides of the sequence, from 17 consecutive nucleotides to less than the total number of nucleotides of the sequence, or from 19 consecutive nucleotides to less than the total number of nucleotides of the sequence, in the nucleotide sequence of each polynucleotide.

Specific examples of the aforementioned combination constituting the kit or the device of the present invention can include the above-mentioned polynucleotides relating to the combinations of SEQ ID NOs shown in Table 1 (i.e., SEQ ID NOs: 1 to 250 corresponding to the miRNA markers in Table 1). However, these are given merely for illustrative purposes, and all of various possible combinations with polynucleotides capable of specifically binding to other miRNA markers in Table 1 (corresponding to SEQ ID NOs: 251 to 812) are included in the present invention.

The combination constituting the kit or the device for discriminating an early pancreatic cancer or pancreatic cancer precursor lesion patient from a healthy subject according to the present invention may be, for example, a combination of two or more, three or more, four or more, or five or more polynucleotides consisting of the nucleotide sequences represented by SEQ ID NOs shown in Table 1. Usually, a combination of even two of these polynucleotides can produce adequate performance.

The specific combination of two polynucleotides that consist of the above-mentioned nucleotide sequences or the complementary sequences thereof for discriminating an early pancreatic cancer or pancreatic cancer precursor lesion patient from a healthy subject is preferably a combination comprising at least one (one or more) polynucleotides of the newly found polynucleotides consisting of the nucleotide sequences represented by SEQ ID NOs: 1 to 83, 227 to 229, 246, 248, and 250, among the combinations constituted by two polynucleotides of the polynucleotides consisting of the nucleotide sequences represented by SEQ ID NOs: 1 to 250.

The combination of two polynucleotides that consist of the above-mentioned nucleotide sequences or the complementary sequences thereof for discriminating an early pancreatic cancer or pancreatic cancer precursor lesion patient from a healthy subject is preferably a combination of a plurality of polynucleotides comprising at least one polynucleotide selected from the group consisting of polynucleotides consisting of the nucleotide sequences represented unlimitedly, for example, by SEQ ID NOs: 2, 3, 18, 12, 20, 1, 15, 50, 63, 72, 5, 24, 10, 52, 9, 11, 19, 39, 61, 7, 17, 22, 26, 74, 21, and 28 or complementary sequences thereof, with any of the polynucleotides of the other SEQ ID NOs.

Non-limiting examples of the combination comprising a polynucleotide consisting of the nucleotide sequence represented by SEQ ID NO: 2 or a complementary sequence thereof among the combinations constituted by two polynucleotides of the polynucleotides consisting of the nucleotide sequences represented by SEQ ID NOs: 1 to 250 for discriminating an early pancreatic cancer or pancreatic cancer precursor lesion patient from a healthy subject are listed below:

(1) a combination of SEQ ID NOs: 2 and 18 (markers: hsa-miR-1181 and hsa-miR-6769a-5p);
(2) a combination of SEQ ID NOs: 2 and 53 (markers: hsa-miR-1181 and hsa-miR-3917);
(3) a combination of SEQ ID NOs: 2 and 20 (markers: hsa-miR-1181 and hsa-miR-652-5p);
(4) a combination of SEQ ID NOs: 2 and 3 (markers: hsa-miR-1181 and hsa-miR-671-5p); and
(5) a combination of SEQ ID NOs: 2 and 50 (markers: hsa-miR-1181 and hsa-miR-6746-5p).

Non-limiting examples of the combination comprising a polynucleotide consisting of the nucleotide sequence represented by SEQ ID NO: 3 or a complementary sequence thereof among the combinations constituted by two polynucleotides of the polynucleotides consisting of the nucleotide sequences represented by SEQ ID NOs: 1 to 250 for discriminating an early pancreatic cancer or pancreatic cancer precursor lesion patient from a healthy subject are listed below:

(1) a combination of SEQ ID NOs: 85 and 3 (markers: hsa-miR-6729-5p and hsa-miR-671-5p);
(2) a combination of SEQ ID NOs: 84 and 3 (markers: hsa-miR-1908-5p and hsa-miR-671-5p);
(3) a combination of SEQ ID NOs: 90 and 3 (markers: hsa-miR-3196 and hsa-miR-671-5p);
(4) a combination of SEQ ID NOs: 87 and 3 (markers: hsa-miR-638 and hsa-miR-671-5p); and
(5) a combination of SEQ ID NOs: 3 and 137 (markers: hsa-miR-671-5p and hsa-miR-4673).

Non-limiting examples of the combination comprising a polynucleotide consisting of the nucleotide sequence represented by SEQ ID NO: 18 or a complementary sequence thereof among the combinations constituted by two polynucleotides of the polynucleotides consisting of the nucleotide sequences represented by SEQ ID NOs: 1 to 250 for discriminating an early pancreatic cancer or pancreatic cancer precursor lesion patient from a healthy subject are listed below:

(1) a combination of SEQ ID NOs: 90 and 18 (markers: hsa-miR-3196 and hsa-miR-6769a-5p);
(2) a combination of SEQ ID NOs: 87 and 18 (markers: hsa-miR-638 and hsa-miR-6769a-5p);
(3) a combination of SEQ ID NOs: 89 and 18 (markers: hsa-miR-3178 and hsa-miR-6769a-5p);
(4) a combination of SEQ ID NOs: 18 and 137 (markers: hsa-miR-6769a-5p and hsa-miR-4673); and
(5) a combination of SEQ ID NOs: 84 and 18 (markers: hsa-miR-1908-5p and hsa-miR-6769a-5p).

Non-limiting examples of the combination comprising a polynucleotide consisting of the nucleotide sequence represented by SEQ ID NO: 12 or a complementary sequence thereof among the combinations constituted by two polynucleotides of the polynucleotides consisting of the nucleotide sequences represented by SEQ ID NOs: 1 to 250 for discriminating an early pancreatic cancer or pancreatic cancer precursor lesion patient from a healthy subject are listed below:

(1) a combination of SEQ ID NOs: 86 and 12 (markers: hsa-miR-5195-3p and hsa-miR-5090);
(2) a combination of SEQ ID NOs: 109 and 12 (markers: hsa-miR-6769b-5p and hsa-miR-5090);
(3) a combination of SEQ ID NOs: 85 and 12 (markers: hsa-miR-6729-5p and hsa-miR-5090);
(4) a combination of SEQ ID NOs: 88 and 12 (markers: hsa-miR-6125 and hsa-miR-5090); and
(5) a combination of SEQ ID NOs: 105 and 12 (markers: hsa-miR-642a-3p and hsa-miR-5090).

Non-limiting examples of the combination comprising a polynucleotide consisting of the nucleotide sequence represented by SEQ ID NO: 20 or a complementary sequence thereof among the combinations constituted by two polynucleotides of the polynucleotides consisting of the nucleotide sequences represented by SEQ ID NOs: 1 to 250 for discriminating an early pancreatic cancer or pancreatic cancer precursor lesion patient from a healthy subject are listed below:

(1) a combination of SEQ ID NOs: 85 and 20 (markers: hsa-miR-6729-5p and hsa-miR-652-5p);
(2) a combination of SEQ ID NOs: 84 and 20 (markers: hsa-miR-1908-5p and hsa-miR-652-5p);
(3) a combination of SEQ ID NOs: 106 and 20 (markers: hsa-miR-4695-5p and hsa-miR-652-5p);
(4) a combination of SEQ ID NOs: 90 and 20 (markers: hsa-miR-3196 and hsa-miR-652-5p); and
(5) a combination of SEQ ID NOs: 87 and 20 (markers: hsa-miR-638 and hsa-miR-652-5p).

Non-limiting examples of the combination comprising a polynucleotide consisting of the nucleotide sequence represented by SEQ ID NO: 1 or a complementary sequence thereof among the combinations constituted by two polynucleotides of the polynucleotides consisting of the nucleotide sequences represented by SEQ ID NOs: 1 to 250 for discriminating an early pancreatic cancer or pancreatic cancer precursor lesion patient from a healthy subject are listed below:

(1) a combination of SEQ ID NOs: 85 and 1 (markers: hsa-miR-6729-5p and hsa-miR-6784-5p);
(2) a combination of SEQ ID NOs: 87 and 1 (markers: hsa-miR-638 and hsa-miR-6784-5p);
(3) a combination of SEQ ID NOs: 88 and 1 (markers: hsa-miR-6125 and hsa-miR-6784-5p);
(4) a combination of SEQ ID NOs: 86 and 1 (markers: hsa-miR-5195-3p and hsa-miR-6784-5p); and
(5) a combination of SEQ ID NOs: 1 and 3 (markers: hsa-miR-6784-5p and hsa-miR-671-5p).

Non-limiting examples of the combination comprising a polynucleotide consisting of the nucleotide sequence represented by SEQ ID NO: 15 or a complementary sequence thereof among the combinations constituted by two polynucleotides of the polynucleotides consisting of the nucleotide sequences represented by SEQ ID NOs: 1 to 250 for discriminating an early pancreatic cancer or pancreatic cancer precursor lesion patient from a healthy subject are listed below:

(1) a combination of SEQ ID NOs: 87 and 15 (markers: hsa-miR-638 and hsa-miR-6717-5p);
(2) a combination of SEQ ID NOs: 85 and 15 (markers: hsa-miR-6729-5p and hsa-miR-6717-5p);
(3) a combination of SEQ ID NOs: 2 and 15 (markers: hsa-miR-1181 and hsa-miR-6717-5p);
(4) a combination of SEQ ID NOs: 88 and 15 (markers: hsa-miR-6125 and hsa-miR-6717-5p); and
(5) a combination of SEQ ID NOs: 15 and 137 (markers: hsa-miR-6717-5p and hsa-miR-4673).

Non-limiting examples of the combination comprising a polynucleotide consisting of the nucleotide sequence represented by SEQ ID NO: 50 or a complementary sequence thereof among the combinations constituted by two polynucleotides of the polynucleotides consisting of the nucleotide sequences represented by SEQ ID NOs: 1 to 250 for discriminating an early pancreatic cancer or pancreatic cancer precursor lesion patient from a healthy subject are listed below:

(1) a combination of SEQ ID NOs: 85 and 50 (markers: hsa-miR-6729-5p and hsa-miR-6746-5p);
(2) a combination of SEQ ID NOs: 87 and 50 (markers: hsa-miR-638 and hsa-miR-6746-5p);
(3) a combination of SEQ ID NOs: 84 and 50 (markers: hsa-miR-1908-5p and hsa-miR-6746-5p);
(4) a combination of SEQ ID NOs: 106 and 50 (markers: hsa-miR-4695-5p and hsa-miR-6746-5p); and
(5) a combination of SEQ ID NOs: 90 and 50 (markers: hsa-miR-3196 and hsa-miR-6746-5p).

Non-limiting examples of the combination comprising a polynucleotide consisting of the nucleotide sequence represented by SEQ ID NO: 63 or a complementary sequence thereof among the combinations constituted by two polynucleotides of the polynucleotides consisting of the nucleotide sequences represented by SEQ ID NOs: 1 to 250 for discriminating an early pancreatic cancer or pancreatic cancer precursor lesion patient from a healthy subject are listed below:

(1) a combination of SEQ ID NOs: 2 and 63 (markers: hsa-miR-1181 and hsa-miR-4419b);
(2) a combination of SEQ ID NOs: 85 and 63 (markers: hsa-miR-6729-5p and hsa-miR-4419b);
(3) a combination of SEQ ID NOs: 90 and 63 (markers: hsa-miR-3196 and hsa-miR-4419b);
(4) a combination of SEQ ID NOs: 84 and 63 (markers: hsa-miR-1908-5p and hsa-miR-4419b); and
(5) a combination of SEQ ID NOs: 87 and 63 (markers: hsa-miR-638 and hsa-miR-4419b).

Non-limiting examples of the combination comprising a polynucleotide consisting of the nucleotide sequence represented by SEQ ID NO: 72 or a complementary sequence thereof among the combinations constituted by two polynucleotides of the polynucleotides consisting of the nucleotide sequences represented by SEQ ID NOs: 1 to 250 for discriminating an early pancreatic cancer or pancreatic cancer precursor lesion patient from a healthy subject are listed below:

(1) a combination of SEQ ID NOs: 84 and 72 (markers: hsa-miR-1908-5p and hsa-miR-4667-5p);
(2) a combination of SEQ ID NOs: 85 and 72 (markers: hsa-miR-6729-5p and hsa-miR-4667-5p);
(3) a combination of SEQ ID NOs: 88 and 72 (markers: hsa-miR-6125 and hsa-miR-4667-5p);
(4) a combination of SEQ ID NOs: 87 and 72 (markers: hsa-miR-638 and hsa-miR-4667-5p); and
(5) a combination of SEQ ID NOs: 93 and 72 (markers: hsa-miR-4746-3p and hsa-miR-4667-5p).

Non-limiting examples of the combination comprising a polynucleotide consisting of the nucleotide sequence represented by SEQ ID NO: 5 or a complementary sequence thereof among the combinations constituted by two polynucleotides of the polynucleotides consisting of the nucleotide sequences represented by SEQ ID NOs: 1 to 250 for discriminating an early pancreatic cancer or pancreatic cancer precursor lesion patient from a healthy subject are listed below:

(1) a combination of SEQ ID NOs: 94 and 5 (markers: hsa-miR-4689 and hsa-miR-4276);
(2) a combination of SEQ ID NOs: 85 and 5 (markers: hsa-miR-6729-5p and hsa-miR-4276);
(3) a combination of SEQ ID NOs: 87 and 5 (markers: hsa-miR-638 and hsa-miR-4276);
(4) a combination of SEQ ID NOs: 5 and 107 (markers: hsa-miR-4276 and hsa-miR-7847-3p); and
(5) a combination of SEQ ID NOs: 84 and 5 (markers: hsa-miR-1908-5p and hsa-miR-4276).

Non-limiting examples of the combination comprising a polynucleotide consisting of the nucleotide sequence represented by SEQ ID NO: 24 or a complementary sequence thereof among the combinations constituted by two polynucleotides of the polynucleotides consisting of the nucleotide sequences represented by SEQ ID NOs: 1 to 250 for discriminating an early pancreatic cancer or pancreatic cancer precursor lesion patient from a healthy subject are listed below:

(1) a combination of SEQ ID NOs: 85 and 24 (markers: hsa-miR-6729-5p and hsa-miR-6887-5p);
(2) a combination of SEQ ID NOs: 87 and 24 (markers: hsa-miR-638 and hsa-miR-6887-5p);
(3) a combination of SEQ ID NOs: 89 and 24 (markers: hsa-miR-3178 and hsa-miR-6887-5p);
(4) a combination of SEQ ID NOs: 90 and 24 (markers: hsa-miR-3196 and hsa-miR-6887-5p); and
(5) a combination of SEQ ID NOs: 102 and 24 (markers: hsa-miR-4508 and hsa-miR-6887-5p).

Non-limiting examples of the combination comprising a polynucleotide consisting of the nucleotide sequence represented by SEQ ID NO: 10 or a complementary sequence thereof among the combinations constituted by two polynucleotides of the polynucleotides consisting of the nucleotide sequences represented by SEQ ID NOs: 1 to 250 for discriminating an early pancreatic cancer or pancreatic cancer precursor lesion patient from a healthy subject are listed below:

(1) a combination of SEQ ID NOs: 85 and 10 (markers: hsa-miR-6729-5p and hsa-miR-6795-5p);
(2) a combination of SEQ ID NOs: 87 and 10 (markers: hsa-miR-638 and hsa-miR-6795-5p);
(3) a combination of SEQ ID NOs: 90 and 10 (markers: hsa-miR-3196 and hsa-miR-6795-5p);
(4) a combination of SEQ ID NOs: 88 and 10 (markers: hsa-miR-6125 and hsa-miR-6795-5p); and
(5) a combination of SEQ ID NOs: 2 and 10 (markers: hsa-miR-1181 and hsa-miR-6795-5p).

Non-limiting examples of the combination comprising a polynucleotide consisting of the nucleotide sequence represented by SEQ ID NO: 52 or a complementary sequence thereof among the combinations constituted by two polynucleotides of the polynucleotides consisting of the nucleotide sequences represented by SEQ ID NOs: 1 to 250 for discriminating an early pancreatic cancer or pancreatic cancer precursor lesion patient from a healthy subject are listed below:

(1) a combination of SEQ ID NOs: 85 and 52 (markers: hsa-miR-6729-5p and hsa-miR-4688);
(2) a combination of SEQ ID NOs: 88 and 52 (markers: hsa-miR-6125 and hsa-miR-4688);
(3) a combination of SEQ ID NOs: 87 and 52 (markers: hsa-miR-638 and hsa-miR-4688);
(4) a combination of SEQ ID NOs: 98 and 52 (markers: hsa-miR-6724-5p and hsa-miR-4688); and
(5) a combination of SEQ ID NOs: 84 and 52 (markers: hsa-miR-1908-5p and hsa-miR-4688).

Non-limiting examples of the combination comprising a polynucleotide consisting of the nucleotide sequence represented by SEQ ID NO: 9 or a complementary sequence thereof among the combinations constituted by two polynucleotides of the polynucleotides consisting of the nucleotide sequences represented by SEQ ID NOs: 1 to 250 for discriminating an early pancreatic cancer or pancreatic cancer precursor lesion patient from a healthy subject are listed below:

(1) a combination of SEQ ID NOs: 87 and 9 (markers: hsa-miR-638 and hsa-miR-4675);
(2) a combination of SEQ ID NOs: 89 and 9 (markers: hsa-miR-3178 and hsa-miR-4675);
(3) a combination of SEQ ID NOs: 85 and 9 (markers: hsa-miR-6729-5p and hsa-miR-4675);
(4) a combination of SEQ ID NOs: 117 and 9 (markers: hsa-miR-4787-5p and hsa-miR-4675); and
(5) a combination of SEQ ID NOs: 88 and 9 (markers: hsa-miR-6125 and hsa-miR-4675).

Non-limiting examples of the combination comprising a polynucleotide consisting of the nucleotide sequence represented by SEQ ID NO: 11 or a complementary sequence thereof among the combinations constituted by two polynucleotides of the polynucleotides consisting of the nucleotide sequences represented by SEQ ID NOs: 1 to 250 for discriminating an early pancreatic cancer or pancreatic cancer precursor lesion patient from a healthy subject are listed below:

(1) a combination of SEQ ID NOs: 87 and 11 (markers: hsa-miR-638 and hsa-miR-4731-5p);
(2) a combination of SEQ ID NOs: 85 and 11 (markers: hsa-miR-6729-5p and hsa-miR-4731-5p);
(3) a combination of SEQ ID NOs: 89 and 11 (markers: hsa-miR-3178 and hsa-miR-4731-5p);
(4) a combination of SEQ ID NOs: 102 and 11 (markers: hsa-miR-4508 and hsa-miR-4731-5p); and
(5) a combination of SEQ ID NOs: 84 and 11 (markers: hsa-miR-1908-5p and hsa-miR-4731-5p).

Non-limiting examples of the combination comprising a polynucleotide consisting of the nucleotide sequence represented by SEQ ID NO: 19 or a complementary sequence thereof among the combinations constituted by two polynucleotides of the polynucleotides consisting of the nucleotide sequences represented by SEQ ID NOs: 1 to 250 for discriminating an early pancreatic cancer or pancreatic cancer precursor lesion patient from a healthy subject are listed below:

(1) a combination of SEQ ID NOs: 85 and 19 (markers: hsa-miR-6729-5p and hsa-miR-4728-5p);
(2) a combination of SEQ ID NOs: 87 and 19 (markers: hsa-miR-638 and hsa-miR-4728-5p);
(3) a combination of SEQ ID NOs: 88 and 19 (markers: hsa-miR-6125 and hsa-miR-4728-5p);
(4) a combination of SEQ ID NOs: 89 and 19 (markers: hsa-miR-3178 and hsa-miR-4728-5p); and
(5) a combination of SEQ ID NOs: 106 and 19 (markers: hsa-miR-4695-5p and hsa-miR-4728-5p).

Non-limiting examples of the combination comprising a polynucleotide consisting of the nucleotide sequence represented by SEQ ID NO: 39 or a complementary sequence thereof among the combinations constituted by two polynucleotides of the polynucleotides consisting of the nucleotide sequences represented by SEQ ID NOs: 1 to 250 for discriminating an early pancreatic cancer or pancreatic cancer precursor lesion patient from a healthy subject are listed below:

(1) a combination of SEQ ID NOs: 87 and 39 (markers: hsa-miR-638 and hsa-miR-6861-5p);
(2) a combination of SEQ ID NOs: 85 and 39 (markers: hsa-miR-6729-5p and hsa-miR-6861-5p);
(3) a combination of SEQ ID NOs: 88 and 39 (markers: hsa-miR-6125 and hsa-miR-6861-5p);
(4) a combination of SEQ ID NOs: 84 and 39 (markers: hsa-miR-1908-5p and hsa-miR-6861-5p); and
(5) a combination of SEQ ID NOs: 2 and 39 (markers: hsa-miR-1181 and hsa-miR-6861-5p).

Non-limiting examples of the combination comprising a polynucleotide consisting of the nucleotide sequence represented by SEQ ID NO: 61 or a complementary sequence thereof among the combinations constituted by two polynucleotides of the polynucleotides consisting of the nucleotide sequences represented by SEQ ID NOs: 1 to 250 for discriminating an early pancreatic cancer or pancreatic cancer precursor lesion patient from a healthy subject are listed below:

(1) a combination of SEQ ID NOs: 87 and 61 (markers: hsa-miR-638 and hsa-miR-498);
(2) a combination of SEQ ID NOs: 85 and 61 (markers: hsa-miR-6729-5p and hsa-miR-498);
(3) a combination of SEQ ID NOs: 88 and 61 (markers: hsa-miR-6125 and hsa-miR-498);
(4) a combination of SEQ ID NOs: 108 and 61 (markers: hsa-miR-3197 and hsa-miR-498); and
(5) a combination of SEQ ID NOs: 93 and 61 (markers: hsa-miR-4746-3p and hsa-miR-498).

Non-limiting examples of the combination comprising a polynucleotide consisting of the nucleotide sequence represented by SEQ ID NO: 7 or a complementary sequence thereof among the combinations constituted by two polynucleotides of the polynucleotides consisting of the nucleotide sequences represented by SEQ ID NOs: 1 to 250 for discriminating an early pancreatic cancer or pancreatic cancer precursor lesion patient from a healthy subject are listed below:

(1) a combination of SEQ ID NOs: 88 and 7 (markers: hsa-miR-6125 and hsa-miR-149-3p);
(2) a combination of SEQ ID NOs: 85 and 7 (markers: hsa-miR-6729-5p and hsa-miR-149-3p);
(3) a combination of SEQ ID NOs: 87 and 7 (markers: hsa-miR-638 and hsa-miR-149-3p);
(4) a combination of SEQ ID NOs: 86 and 7 (markers: hsa-miR-5195-3p and hsa-miR-149-3p); and
(5) a combination of SEQ ID NOs: 91 and 7 (markers: hsa-miR-8069 and hsa-miR-149-3p).

Non-limiting examples of the combination comprising a polynucleotide consisting of the nucleotide sequence represented by SEQ ID NO: 17 or a complementary sequence thereof among the combinations constituted by two polynucleotides of the polynucleotides consisting of the nucleotide sequences represented by SEQ ID NOs: 1 to 250 for discriminating an early pancreatic cancer or pancreatic cancer precursor lesion patient from a healthy subject are listed below:

(1) a combination of SEQ ID NOs: 85 and 17 (markers: hsa-miR-6729-5p and hsa-miR-6738-5p);
(2) a combination of SEQ ID NOs: 87 and 17 (markers: hsa-miR-638 and hsa-miR-6738-5p);
(3) a combination of SEQ ID NOs: 89 and 17 (markers: hsa-miR-3178 and hsa-miR-6738-5p);
(4) a combination of SEQ ID NOs: 102 and 17 (markers: hsa-miR-4508 and hsa-miR-6738-5p); and
(5) a combination of SEQ ID NOs: 84 and 17 (markers: hsa-miR-1908-5p and hsa-miR-6738-5p).

Non-limiting examples of the combination comprising a polynucleotide consisting of the nucleotide sequence represented by SEQ ID NO: 22 or a complementary sequence thereof among the combinations constituted by two polynucleotides of the polynucleotides consisting of the nucleotide sequences represented by SEQ ID NOs: 1 to 250 for discriminating an early pancreatic cancer or pancreatic cancer precursor lesion patient from a healthy subject are listed below:

(1) a combination of SEQ ID NOs: 85 and 22 (markers: hsa-miR-6729-5p and hsa-miR-6785-5p);
(2) a combination of SEQ ID NOs: 87 and 22 (markers: hsa-miR-638 and hsa-miR-6785-5p);
(3) a combination of SEQ ID NOs: 102 and 22 (markers: hsa-miR-4508 and hsa-miR-6785-5p);
(4) a combination of SEQ ID NOs: 89 and 22 (markers: hsa-miR-3178 and hsa-miR-6785-5p); and
(5) a combination of SEQ ID NOs: 117 and 22 (markers: hsa-miR-4787-5p and hsa-miR-6785-5p).

Non-limiting examples of the combination comprising a polynucleotide consisting of the nucleotide sequence represented by SEQ ID NO: 26 or a complementary sequence thereof among the combinations constituted by two polynucleotides of the polynucleotides consisting of the nucleotide sequences represented by SEQ ID NOs: 1 to 250 for discriminating an early pancreatic cancer or pancreatic cancer precursor lesion patient from a healthy subject are listed below:

(1) a combination of SEQ ID NOs: 85 and 26 (markers: hsa-miR-6729-5p and hsa-miR-1228-5p);
(2) a combination of SEQ ID NOs: 87 and 26 (markers: hsa-miR-638 and hsa-miR-1228-5p);
(3) a combination of SEQ ID NOs: 88 and 26 (markers: hsa-miR-6125 and hsa-miR-1228-5p);
(4) a combination of SEQ ID NOs: 84 and 26 (markers: hsa-miR-1908-5p and hsa-miR-1228-5p); and
(5) a combination of SEQ ID NOs: 94 and 26 (markers: hsa-miR-4689 and hsa-miR-1228-5p).

Non-limiting examples of the combination comprising a polynucleotide consisting of the nucleotide sequence represented by SEQ ID NO: 74 or a complementary sequence thereof among the combinations constituted by two polynucleotides of the polynucleotides consisting of the nucleotide sequences represented by SEQ ID NOs: 1 to 250 for discriminating an early pancreatic cancer or pancreatic cancer precursor lesion patient from a healthy subject are listed below:

(1) a combination of SEQ ID NOs: 85 and 74 (markers: hsa-miR-6729-5p and hsa-miR-4690-5p);
(2) a combination of SEQ ID NOs: 2 and 74 (markers: hsa-miR-1181 and hsa-miR-4690-5p);
(3) a combination of SEQ ID NOs: 87 and 74 (markers: hsa-miR-638 and hsa-miR-4690-5p);
(4) a combination of SEQ ID NOs: 84 and 74 (markers: hsa-miR-1908-5p and hsa-miR-4690-5p); and
(5) a combination of SEQ ID NOs: 88 and 74 (markers: hsa-miR-6125 and hsa-miR-4690-5p).

Non-limiting examples of the combination comprising a polynucleotide consisting of the nucleotide sequence represented by SEQ ID NO: 21 or a complementary sequence thereof among the combinations constituted by two polynucleotides of the polynucleotides consisting of the nucleotide sequences represented by SEQ ID NOs: 1 to 250 for discriminating an early pancreatic cancer or pancreatic cancer precursor lesion patient from a healthy subject are listed below:

(1) a combination of SEQ ID NOs: 90 and 21 (markers: hsa-miR-3196 and hsa-miR-4257);
(2) a combination of SEQ ID NOs: 2 and 21 (markers: hsa-miR-1181 and hsa-miR-4257);
(3) a combination of SEQ ID NOs: 106 and 21 (markers: hsa-miR-4695-5p and hsa-miR-4257);
(4) a combination of SEQ ID NOs: 84 and 21 (markers: hsa-miR-1908-5p and hsa-miR-4257); and
(5) a combination of SEQ ID NOs: 85 and 21 (markers: hsa-miR-6729-5p and hsa-miR-4257).

Non-limiting examples of the combination comprising a polynucleotide consisting of the nucleotide sequence represented by SEQ ID NO: 28 or a complementary sequence thereof among the combinations constituted by two polynucleotides of the polynucleotides consisting of the nucleotide sequences represented by SEQ ID NOs: 1 to 250 for discriminating an early pancreatic cancer or pancreatic cancer precursor lesion patient from a healthy subject are listed below:

(1) a combination of SEQ ID NOs: 85 and 28 (markers: hsa-miR-6729-5p and hsa-miR-6782-5p);
(2) a combination of SEQ ID NOs: 84 and 28 (markers: hsa-miR-1908-5p and hsa-miR-6782-5p);
(3) a combination of SEQ ID NOs: 86 and 28 (markers: hsa-miR-5195-3p and hsa-miR-6782-5p);
(4) a combination of SEQ ID NOs: 87 and 28 (markers: hsa-miR-638 and hsa-miR-6782-5p); and
(5) a combination of SEQ ID NOs: 93 and 28 (markers: hsa-miR-4746-3p and hsa-miR-6782-5p).

The combination of polynucleotides with cancer type specificity capable of discriminating an early pancreatic cancer or pancreatic cancer precursor lesion patient not only from a healthy subject but also from patients with other cancers is preferably unlimitedly, for example, a combination of multiple polynucleotides comprising: at least one polynucleotide selected from the group consisting of polynucleotides consisting of the nucleotide sequences represented by SEQ ID NOs: 119, 12, 28, 105, 137, 121, 109, 87, 5, 140, 106, 2, 175, 90, 237, 247, 103, 97, 124, 92, 100, 32, 1, 246, 84, 13, 85, 153, 111, 86, 141, 54, and 24 or complementary sequences thereof (hereinafter, this group is referred to as "cancer type-specific polynucleotide group 1"); and any of the polynucleotides of the other SEQ ID NOs.

The combination of polynucleotides with cancer type specificity capable of discriminating an early pancreatic cancer or pancreatic cancer precursor lesion patient not only from a healthy subject but also from patients with other cancers is more preferably a combination of multiple polynucleotides selected from the cancer type-specific polynucleotide group 1.

The combination of polynucleotides with cancer type specificity capable of discriminating an early pancreatic cancer or pancreatic cancer precursor lesion patient not only from a healthy subject but also from patients with other cancers is more preferably, for example, a combination of polynucleotides comprising at least one polynucleotides selected from the group consisting of polynucleotides consisting of the nucleotide sequences represented by, for example, SEQ ID NOs: 119, 12, 28, 105, 137, 121, 109, 87, 5, 140, 106, 2, 175, 90, 237, and 247 or complementary sequences thereof (hereinafter, this group is referred to as "cancer type-specific polynucleotide group 2") included in the cancer type-specific polynucleotide group 1, among the combinations of multiple polynucleotides selected from the cancer type-specific polynucleotide group 1. The number of the polynucleotides with cancer type specificity may be 1, 2, 3, 4, 5, 6, 7, 8, 9, 10 or more in the combination and is more preferably 5 or more in the combination. Usually, the combination of 5 polynucleotides of these polynucleotides can produce sufficient performance (such as accuracy, sensitivity, or specificity).

Non-limiting examples of the combination of the polynucleotides consisting of the nucleotide sequences represented by SEQ ID NO: 12 or complementary sequences thereof, with polynucleotides consisting of nucleotide sequences represented by SEQ ID NOs of five polynucleotides selected from the cancer type-specific polynucleotide group 1 or complementary sequences thereof are further listed below:

(1) a combination of SEQ ID NOs: 12, 137, 119, 105, and 237 (markers: hsa-miR-5090, hsa-miR-4673, hsa-miR-6813-5p, hsa-miR-642a-3p, and hsa-miR-373-5p);

(2) a combination of SEQ ID NOs: 87, 12, 137, 119, and 105 (markers: hsa-miR-638, hsa-miR-5090, hsa-miR-4673, hsa-miR-6813-5p, and hsa-miR-642a-3p);

(3) a combination of SEQ ID NOs: 12, 103, 137, 105, and 247 (markers: hsa-miR-5090, hsa-miR-6085, hsa-miR-4673, hsa-miR-642a-3p, and hsa-miR-4286);

(4) a combination of SEQ ID NOs: 12, 137, 119, 92, and 105 (markers: hsa-miR-5090, hsa-miR-4673, hsa-miR-6813-5p, hsa-miR-4723-5p, and hsa-miR-642a-3p);

(5) a combination of SEQ ID NOs: 12, 137, 119, 105, and 121 (markers: hsa-miR-5090, hsa-miR-4673, hsa-miR-6813-5p, hsa-miR-642a-3p, and hsa-miR-602);

(6) a combination of SEQ ID NOs: 12, 137, 1, 119, and 105 (markers: hsa-miR-5090, hsa-miR-4673, hsa-miR-6784-5p, hsa-miR-6813-5p, and hsa-miR-642a-3p);

(7) a combination of SEQ ID NOs: 12, 137, 119, 124, and 105 (markers: hsa-miR-5090, hsa-miR-4673, hsa-miR-6813-5p, hsa-miR-5100, and hsa-miR-642a-3p);

(8) a combination of SEQ ID NOs: 12, 137, 119, 105, and 32 (markers: hsa-miR-5090, hsa-miR-4673, hsa-miR-6813-5p, hsa-miR-642a-3p, and hsa-miR-6087);

(9) a combination of SEQ ID NOs: 12, 137, 119, 105, and 100 (markers: hsa-miR-5090, hsa-miR-4673, hsa-miR-6813-5p, hsa-miR-642a-3p, and hsa-miR-6875-5p);

(10) a combination of SEQ ID NOs: 12, 137, 119, 105, and 86 (markers: hsa-miR-5090, hsa-miR-4673, hsa-miR-6813-5p, hsa-miR-642a-3p, and hsa-miR-5195-3p);

(11) a combination of SEQ ID NOs: 12, 137, 119, 105, and 153 (markers: hsa-miR-5090, hsa-miR-4673, hsa-miR-6813-5p, hsa-miR-642a-3p, and hsa-miR-296-5p);

(12) a combination of SEQ ID NOs: 12, 137, 119, 105, and 141 (markers: hsa-miR-5090, hsa-miR-4673, hsa-miR-6813-5p, hsa-miR-642a-3p, and hsa-miR-663a);

(13) a combination of SEQ ID NOs: 12, 137, 105, 246, and 153 (markers: hsa-miR-5090, hsa-miR-4673, hsa-miR-642a-3p, hsa-miR-6766-3p, and hsa-miR-296-5p);

(14) a combination of SEQ ID NOs: 12, 97, 137, 105, and 153 (markers: hsa-miR-5090, hsa-miR-7109-5p, hsa-miR-4673, hsa-miR-642a-3p, and hsa-miR-296-5p);

(15) a combination of SEQ ID NOs: 12, 103, 137, 119, and 105 (markers: hsa-miR-5090, hsa-miR-6085, hsa-miR-4673, hsa-miR-6813-5p, and hsa-miR-642a-3p);

(16) a combination of SEQ ID NOs: 12, 137, 119, 105, and 246 (markers: hsa-miR-5090, hsa-miR-4673, hsa-miR-6813-5p, hsa-miR-642a-3p, and hsa-miR-6766-3p);

(17) a combination of SEQ ID NOs: 12, 137, 92, 105, and 247 (markers: hsa-miR-5090, hsa-miR-4673, hsa-miR-4723-5p, hsa-miR-642a-3p, and hsa-miR-4286);

(18) a combination of SEQ ID NOs: 12, 137, 124, 105, and 153 (markers: hsa-miR-5090, hsa-miR-4673, hsa-miR-5100, hsa-miR-642a-3p, and hsa-miR-296-5p);

(19) a combination of SEQ ID NOs: 12, 137, 105, 32, and 153 (markers: hsa-miR-5090, hsa-miR-4673, hsa-miR-642a-3p, hsa-miR-6087, and hsa-miR-296-5p);

(20) a combination of SEQ ID NOs: 12, 137, 105, 13, and 121 (markers: hsa-miR-5090, hsa-miR-4673, hsa-miR-642a-3p, hsa-miR-3620-5p, and hsa-miR-602);

(21) a combination of SEQ ID NOs: 106, 12, 137, 119, and 105 (markers: hsa-miR-4695-5p, hsa-miR-5090, hsa-miR-4673, hsa-miR-6813-5p, and hsa-miR-642a-3p);

(22) a combination of SEQ ID NOs: 12, 137, 119, 105, and 13 (markers: hsa-miR-5090, hsa-miR-4673, hsa-miR-6813-5p, hsa-miR-642a-3p, and hsa-miR-3620-5p);

(23) a combination of SEQ ID NOs: 12, 137, 119, 105, and 140 (markers: hsa-miR-5090, hsa-miR-4673, hsa-miR-6813-5p, hsa-miR-642a-3p, and hsa-miR-4640-5p);

(24) a combination of SEQ ID NOs: 12, 137, 119, 105, and 247 (markers: hsa-miR-5090, hsa-miR-4673, hsa-miR-6813-5p, hsa-miR-642a-3p, and hsa-miR-4286);

(25) a combination of SEQ ID NOs: 12, 137, 119, 105, and 109 (markers: hsa-miR-5090, hsa-miR-4673, hsa-miR-6813-5p, hsa-miR-642a-3p, and hsa-miR-6769b-5p);

(26) a combination of SEQ ID NOs: 12, 137, 105, 109, and 121 (markers: hsa-miR-5090, hsa-miR-4673, hsa-miR-642a-3p, hsa-miR-6769b-5p, and hsa-miR-602);

(27) a combination of SEQ ID NOs: 12, 103, 137, 105, and 121 (markers: hsa-miR-5090, hsa-miR-6085, hsa-miR-4673, hsa-miR-642a-3p, and hsa-miR-602);

(28) a combination of SEQ ID NOs: 12, 137, 105, 32, and 121 (markers: hsa-miR-5090, hsa-miR-4673, hsa-miR-642a-3p, hsa-miR-6087, and hsa-miR-602);

(29) a combination of SEQ ID NOs: 12, 137, 124, 105, and 247 (markers: hsa-miR-5090, hsa-miR-4673, hsa-miR-5100, hsa-miR-642a-3p, and hsa-miR-4286);

(30) a combination of SEQ ID NOs: 12, 137, 105, 246, and 247 (markers: hsa-miR-5090, hsa-miR-4673, hsa-miR-642a-3p, hsa-miR-6766-3p, and hsa-miR-4286);

(31) a combination of SEQ ID NOs: 12, 137, 105, 153, and 247 (markers: hsa-miR-5090, hsa-miR-4673, hsa-miR-642a-3p, hsa-miR-296-5p, and hsa-miR-4286);

(32) a combination of SEQ ID NOs: 12, 137, 105, 247, and 141 (markers: hsa-miR-5090, hsa-miR-4673, hsa-miR-642a-3p, hsa-miR-4286, and hsa-miR-663a);

(33) a combination of SEQ ID NOs: 12, 137, 105, and 247 (markers: hsa-miR-5090, hsa-miR-4673, hsa-miR-642a-3p, and hsa-miR-4286);

(34) a combination of SEQ ID NOs: 12, 137, 105, 140, and 247 (markers: hsa-miR-5090, hsa-miR-4673, hsa-miR-642a-3p, hsa-miR-4640-5p, and hsa-miR-4286);

(35) a combination of SEQ ID NOs: 12, 119, 124, 105, and 140 (markers: hsa-miR-5090, hsa-miR-6813-5p, hsa-miR-5100, hsa-miR-642a-3p, and hsa-miR-4640-5p);

(36) a combination of SEQ ID NOs: 12, 119, 105, 100, and 140 (markers: hsa-miR-5090, hsa-miR-6813-5p, hsa-miR-642a-3p, hsa-miR-6875-5p, and hsa-miR-4640-5p);

(37) a combination of SEQ ID NOs: 90, 12, 119, 105, and 140 (markers: hsa-miR-3196, hsa-miR-5090, hsa-miR-6813-5p, hsa-miR-642a-3p, and hsa-miR-4640-5p);

(38) a combination of SEQ ID NOs: 90, 12, 137, 119, and 105 (markers: hsa-miR-3196, hsa-miR-5090, hsa-miR-4673, hsa-miR-6813-5p, and hsa-miR-642a-3p);

(39) a combination of SEQ ID NOs: 90, 12, 137, 105, and 32 (markers: hsa-miR-3196, hsa-miR-5090, hsa-miR-4673, hsa-miR-642a-3p, and hsa-miR-6087);

(40) a combination of SEQ ID NOs: 90, 12, 137, 105, and 153 (markers: hsa-miR-3196, hsa-miR-5090, hsa-miR-4673, hsa-miR-642a-3p, and hsa-miR-296-5p);

(41) a combination of SEQ ID NOs: 90, 12, 119, 105, and 100 (markers: hsa-miR-3196, hsa-miR-5090, hsa-miR-6813-5p, hsa-miR-642a-3p, and hsa-miR-6875-5p);

(42) a combination of SEQ ID NOs: 90, 12, 119, 109, and 140 (markers: hsa-miR-3196, hsa-miR-5090, hsa-miR-6813-5p, hsa-miR-6769b-5p, and hsa-miR-4640-5p);

(43) a combination of SEQ ID NOs: 87, 12, 137, 105, and 247 (markers: hsa-miR-638, hsa-miR-5090, hsa-miR-4673, hsa-miR-642a-3p, and hsa-miR-4286);

(44) a combination of SEQ ID NOs: 90, 12, 109, 140, and 237 (markers: hsa-miR-3196, hsa-miR-5090, hsa-miR-6769b-5p, hsa-miR-4640-5p, and hsa-miR-373-5p);

(45) a combination of SEQ ID NOs: 12, 137, 105, 109, and 153 (markers: hsa-miR-5090, hsa-miR-4673, hsa-miR-642a-3p, hsa-miR-6769b-5p, and hsa-miR-296-5p);

(46) a combination of SEQ ID NOs: 12, 137, 105, 109, and 247 (markers: hsa-miR-5090, hsa-miR-4673, hsa-miR-642a-3p, hsa-miR-6769b-5p, and hsa-miR-4286);

(47) a combination of SEQ ID NOs: 12, 137, 109, 140, and 247 (markers: hsa-miR-5090, hsa-miR-4673, hsa-miR-6769b-5p, hsa-miR-4640-5p, and hsa-miR-4286);

(48) a combination of SEQ ID NOs: 12, 137, 109, 121, and 237 (markers: hsa-miR-5090, hsa-miR-4673, hsa-miR-6769b-5p, hsa-miR-602, and hsa-miR-373-5p);

(49) a combination of SEQ ID NOs: 12, 137, 119, 105, and 175 (markers: hsa-miR-5090, hsa-miR-4673, hsa-miR-6813-5p, hsa-miR-642a-3p, and hsa-miR-6768-5p);

(50) a combination of SEQ ID NOs: 12, 137, 109, 175, and 121 (markers: hsa-miR-5090, hsa-miR-4673, hsa-miR-6769b-5p, hsa-miR-6768-5p, and hsa-miR-602);

(51) a combination of SEQ ID NOs: 87, 12, 119, 105, and 175 (markers: hsa-miR-638, hsa-miR-5090, hsa-miR-6813-5p, hsa-miR-642a-3p, and hsa-miR-6768-5p);

(52) a combination of SEQ ID NOs: 12, 137, 119, 105, and 111 (markers: hsa-miR-5090, hsa-miR-4673, hsa-miR-6813-5p, hsa-miR-642a-3p, and hsa-miR-187-5p);

(53) a combination of SEQ ID NOs: 12, 137, 119, 105, and 24 (markers: hsa-miR-5090, hsa-miR-4673, hsa-miR-6813-5p, hsa-miR-642a-3p, and hsa-miR-6887-5p);

(54) a combination of SEQ ID NOs: 12, 137, 105, 32, and 247 (markers: hsa-miR-5090, hsa-miR-4673, hsa-miR-642a-3p, hsa-miR-6087, and hsa-miR-4286);

(55) a combination of SEQ ID NOs: 90, 12, 137, 105, and 237 (markers: hsa-miR-3196, hsa-miR-5090, hsa-miR-4673, hsa-miR-642a-3p, and hsa-miR-373-5p);

(56) a combination of SEQ ID NOs: 12, 84, 137, 119, and 105 (markers: hsa-miR-5090, hsa-miR-1908-5p, hsa-miR-4673, hsa-miR-6813-5p, and hsa-miR-642a-3p);

(57) a combination of SEQ ID NOs: 12, 97, 137, 105, and 247 (markers: hsa-miR-5090, hsa-miR-7109-5p, hsa-miR-4673, hsa-miR-642a-3p, and hsa-miR-4286);

(58) a combination of SEQ ID NOs: 87, 12, 137, 105, and 237 (markers: hsa-miR-638, hsa-miR-5090, hsa-miR-4673, hsa-miR-642a-3p, and hsa-miR-373-5p);

(59) a combination of SEQ ID NOs: 87, 12, 100, 109, and 237 (markers: hsa-miR-638, hsa-miR-5090, hsa-miR-6875-5p, hsa-miR-6769b-5p, and hsa-miR-373-5p);

(60) a combination of SEQ ID NOs: 87, 12, 100, 109, and 237 (markers: hsa-miR-638, hsa-miR-5090, hsa-miR-6875-5p, hsa-miR-6769b-5p, and hsa-miR-373-5p);

(61) a combination of SEQ ID NOs: 106, 12, 137, 105, and 86 (markers: hsa-miR-4695-5p, hsa-miR-5090, hsa-miR-4673, hsa-miR-642a-3p, and hsa-miR-5195-3p);

(62) a combination of SEQ ID NOs: 106, 12, 137, 105, and 247 (markers: hsa-miR-4695-5p, hsa-miR-5090, hsa-miR-4673, hsa-miR-642a-3p, and hsa-miR-4286);

(63) a combination of SEQ ID NOs: 106, 12, 119, 105, and 100 (markers: hsa-miR-4695-5p, hsa-miR-5090, hsa-miR-6813-5p, hsa-miR-642a-3p, and hsa-miR-6875-5p); and

(64) a combination of SEQ ID NOs: 106, 12, 137, 105, and 121 (markers: hsa-miR-4695-5p, hsa-miR-5090, hsa-miR-4673, hsa-miR-642a-3p, and hsa-miR-602).

Non-limiting examples of the combination of the polynucleotides consisting of the nucleotide sequences represented by SEQ ID NO: 28 or complementary sequences thereof, with polynucleotides consisting of nucleotide sequences represented by SEQ ID NOs of five polynucleotides selected from the cancer type-specific polynucleotide group 1 or complementary sequences thereof are further listed below:

(1) a combination of SEQ ID NOs: 137, 119, 105, 28, and 237 (markers: hsa-miR-4673, hsa-miR-6813-5p, hsa-miR-642a-3p, hsa-miR-6782-5p, and hsa-miR-373-5p);

(2) a combination of SEQ ID NOs: 87, 106, 119, 28, and 121 (markers: hsa-miR-638, hsa-miR-4695-5p, hsa-miR-6813-5p, hsa-miR-6782-5p, and hsa-miR-602);

(3) a combination of SEQ ID NOs: 106, 137, 119, 28, and 121 (markers: hsa-miR-4695-5p, hsa-miR-4673, hsa-miR-6813-5p, hsa-miR-6782-5p, and hsa-miR-602); and (4) a combination of SEQ ID NOs: 90, 119, 105, 28, and 237 (markers: hsa-miR-3196, hsa-miR-6813-5p, hsa-miR-642a-3p, hsa-miR-6782-5p, and hsa-miR-373-5p).

Non-limiting examples of the combination of the polynucleotides consisting of the nucleotide sequences represented by SEQ ID NO: 5 or complementary sequences thereof, with polynucleotides consisting of nucleotide sequences represented by SEQ ID NOs of five polynucleotides selected from the cancer type-specific polynucleotide group 1 or complementary sequences thereof are further listed below:

(1) a combination of SEQ ID NOs: 90, 5, 137, 119, and 105 (markers: hsa-miR-3196, hsa-miR-4276, hsa-miR-4673, hsa-miR-6813-5p, and hsa-miR-642a-3p);

(2) a combination of SEQ ID NOs: 5, 137, 119, 105, and 237 (markers: hsa-miR-4276, hsa-miR-4673, hsa-miR-6813-5p, hsa-miR-642a-3p, and hsa-miR-373-5p); and (3) a combination of SEQ ID NOs: 5, 137, 119, 105, and 32 (markers: hsa-miR-4276, hsa-miR-4673, hsa-miR-6813-5p, hsa-miR-642a-3p, and hsa-miR-6087).

Non-limiting examples of the combination of the polynucleotides consisting of the nucleotide sequences represented by SEQ ID NO: 2 or complementary sequences thereof, with polynucleotides consisting of nucleotide sequences represented by SEQ ID NOs of five polynucleotides selected from the cancer type-specific polynucleotide group 1 or complementary sequences thereof are further listed below:

(1) a combination of SEQ ID NOs: 2, 137, 119, 105, and 237 (markers: hsa-miR-1181, hsa-miR-4673, hsa-miR-6813-5p, hsa-miR-642a-3p, and hsa-miR-373-5p);

(2) a combination of SEQ ID NOs: 2, 87, 137, 119, and 105 (markers: hsa-miR-1181, hsa-miR-638, hsa-miR-4673, hsa-miR-6813-5p, and hsa-miR-642a-3p);

(3) a combination of SEQ ID NOs: 2, 137, 119, 105, and 13 (markers: hsa-miR-1181, hsa-miR-4673, hsa-miR-6813-5p, hsa-miR-642a-3p, and hsa-miR-3620-5p);

(4) a combination of SEQ ID NOs: 2, 137, 119, 105, and 121 (markers: hsa-miR-1181, hsa-miR-4673, hsa-miR-6813-5p, hsa-miR-642a-3p, and hsa-miR-602);

(5) a combination of SEQ ID NOs: 2, 137, 119, 105, and 247 (markers: hsa-miR-1181, hsa-miR-4673, hsa-miR-6813-5p, hsa-miR-642a-3p, and hsa-miR-4286);

(6) a combination of SEQ ID NOs: 2, 87, 119, 109, and 247 (markers: hsa-miR-1181, hsa-miR-638, hsa-miR-6813-5p, hsa-miR-6769b-5p, and hsa-miR-4286);

(7) a combination of SEQ ID NOs: 2, 90, 137, 119, and 105 (markers: hsa-miR-1181, hsa-miR-3196, hsa-miR-4673, hsa-miR-6813-5p, and hsa-miR-642a-3p);

(8) a combination of SEQ ID NOs: 2, 137, 119, 105, and 140 (markers: hsa-miR-1181, hsa-miR-4673, hsa-miR-6813-5p, hsa-miR-642a-3p, and hsa-miR-4640-5p); and (9) a combination of SEQ ID NOs: 2, 87, 119, 105, and 237 (markers: hsa-miR-1181, hsa-miR-638, hsa-miR-6813-5p, hsa-miR-642a-3p, and hsa-miR-373-5p).

Non-limiting examples of the combination of the polynucleotides consisting of the nucleotide sequences represented by SEQ ID NOs: 12 and 28 or complementary sequences thereof, with polynucleotides consisting of nucleotide sequences represented by SEQ ID NOs of five polynucleotides selected from the cancer type-specific polynucleotide group 1 or complementary sequences thereof are further listed below:

(1) a combination of SEQ ID NOs: 12, 137, 105, 28, and 247 (markers: hsa-miR-5090, hsa-miR-4673, hsa-miR-642a-3p, hsa-miR-6782-5p, and hsa-miR-4286);

(2) a combination of SEQ ID NOs: 12, 137, 119, 105, and 28 (markers: hsa-miR-5090, hsa-miR-4673, hsa-miR-6813-5p, hsa-miR-642a-3p, and hsa-miR-6782-5p);

(3) a combination of SEQ ID NOs: 12, 103, 137, 105, and 28 (markers: hsa-miR-5090, hsa-miR-6085, hsa-miR-4673, hsa-miR-642a-3p, and hsa-miR-6782-5p);

(4) a combination of SEQ ID NOs: 12, 84, 28, 140, and 121 (markers: hsa-miR-5090, hsa-miR-1908-5p, hsa-miR-6782-5p, hsa-miR-4640-5p, and hsa-miR-602);

(5) a combination of SEQ ID NOs: 12, 137, 28, 109, and 121 (markers: hsa-miR-5090, hsa-miR-4673, hsa-miR-6782-5p, hsa-miR-6769b-5p, and hsa-miR-602);

(6) a combination of SEQ ID NOs: 12, 1, 28, 121, and 247 (markers: hsa-miR-5090, hsa-miR-6784-5p, hsa-miR-6782-5p, hsa-miR-602, and hsa-miR-4286);

(7) a combination of SEQ ID NOs: 12, 119, 28, 100, and 121 (markers: hsa-miR-5090, hsa-miR-6813-5p, hsa-miR-6782-5p, hsa-miR-6875-5p, and hsa-miR-602);

(8) a combination of SEQ ID NOs: 12, 92, 28, 100, and 247 (markers: hsa-miR-5090, hsa-miR-4723-5p, hsa-miR-6782-5p, hsa-miR-6875-5p, and hsa-miR-4286);

(9) a combination of SEQ ID NOs: 12, 28, 100, 140, and 247 (markers: hsa-miR-5090, hsa-miR-6782-5p, hsa-miR-6875-5p, hsa-miR-4640-5p, and hsa-miR-4286);

(10) a combination of SEQ ID NOs: 12, 137, 28, 109, and 247 (markers: hsa-miR-5090, hsa-miR-4673, hsa-miR-6782-5p, hsa-miR-6769b-5p, and hsa-miR-4286);

(11) a combination of SEQ ID NOs: 12, 84, 28, 109, and 121 (markers: hsa-miR-5090, hsa-miR-1908-5p, hsa-miR-6782-5p, hsa-miR-6769b-5p, and hsa-miR-602);

(12) a combination of SEQ ID NOs: 12, 103, 1, 28, and 121 (markers: hsa-miR-5090, hsa-miR-6085, hsa-miR-6784-5p, hsa-miR-6782-5p, and hsa-miR-602);

(13) a combination of SEQ ID NOs: 12, 1, 28, 32, and 121 (markers: hsa-miR-5090, hsa-miR-6784-5p, hsa-miR-6782-5p, hsa-miR-6087, and hsa-miR-602);

(14) a combination of SEQ ID NOs: 12, 1, 28, 100, and 121 (markers: hsa-miR-5090, hsa-miR-6784-5p, hsa-miR-6782-5p, hsa-miR-6875-5p, and hsa-miR-602); and

(15) a combination of SEQ ID NOs: 12, 1, 28, 175, and 121 (markers: hsa-miR-5090, hsa-miR-6784-5p, hsa-miR-6782-5p, hsa-miR-6768-5p, and hsa-miR-602).

Non-limiting examples of the combination of the polynucleotides consisting of the nucleotide sequences represented by SEQ ID NOs: 12 and 5 or complementary sequences thereof, with polynucleotides consisting of nucleotide sequences represented by SEQ ID NOs of five polynucleotides selected from the cancer type-specific polynucleotide group 1 or complementary sequences thereof are further listed below:

(1) a combination of SEQ ID NOs: 5, 12, 137, 119, and 105 (markers: hsa-miR-4276, hsa-miR-5090, hsa-miR-4673, hsa-miR-6813-5p, and hsa-miR-642a-3p);

(2) a combination of SEQ ID NOs: 90, 5, 12, 119, and 105 (markers: hsa-miR-3196, hsa-miR-4276, hsa-miR-5090, hsa-miR-6813-5p, and hsa-miR-642a-3p);

(3) a combination of SEQ ID NOs: 5, 12, 137, 105, and 121 (markers: hsa-miR-4276, hsa-miR-5090, hsa-miR-4673, hsa-miR-642a-3p, and hsa-miR-602);

(4) a combination of SEQ ID NOs: 5, 12, 119, 92, and 121 (markers: hsa-miR-4276, hsa-miR-5090, hsa-miR-6813-5p, hsa-miR-4723-5p, and hsa-miR-602);

(5) a combination of SEQ ID NOs: 90, 5, 12, 109, and 247 (markers: hsa-miR-3196, hsa-miR-4276, hsa-miR-5090, hsa-miR-6769b-5p, and hsa-miR-4286);

(6) a combination of SEQ ID NOs: 5, 12, 137, 109, and 121 (markers: hsa-miR-4276, hsa-miR-5090, hsa-miR-6769b-5p, and hsa-miR-602);

(7) a combination of SEQ ID NOs: 5, 12, 137, 109, and 247 (markers: hsa-miR-4276, hsa-miR-5090, hsa-miR-4673, hsa-miR-6769b-5p, and hsa-miR-4286);

(8) a combination of SEQ ID NOs: 90, 5, 106, 12, and 109 (markers: hsa-miR-3196, hsa-miR-4276, hsa-miR-4695-5p, hsa-miR-5090, and hsa-miR-6769b-5p);

(9) a combination of SEQ ID NOs: 90, 5, 12, 137, and 105 (markers: hsa-miR-3196, hsa-miR-4276, hsa-miR-5090, hsa-miR-4673, and hsa-miR-642a-3p);

(10) a combination of SEQ ID NOs: 90, 5, 12, 119, and 109 (markers: hsa-miR-3196, hsa-miR-4276, hsa-miR-5090, hsa-miR-6813-5p, and hsa-miR-6769b-5p);

(11) a combination of SEQ ID NOs: 90, 5, 12, 105, and 109 (markers: hsa-miR-3196, hsa-miR-4276, hsa-miR-5090, hsa-miR-642a-3p, and hsa-miR-6769b-5p);

(12) a combination of SEQ ID NOs: 5, 12, 137, 105, and 153 (markers: hsa-miR-4276, hsa-miR-5090, hsa-miR-4673, hsa-miR-642a-3p, and hsa-miR-296-5p);

(13) a combination of SEQ ID NOs: 5, 12, 119, 105, and 54 (markers: hsa-miR-4276, hsa-miR-5090, hsa-miR-6813-5p, hsa-miR-642a-3p, and hsa-miR-5787);

(14) a combination of SEQ ID NOs: 87, 5, 106, 12, and 109 (markers: hsa-miR-638, hsa-miR-4276, hsa-miR-4695-5p, hsa-miR-5090, and hsa-miR-6769b-5p);

(15) a combination of SEQ ID NOs: 87, 5, 12, 137, and 105 (markers: hsa-miR-638, hsa-miR-4276, hsa-miR-5090, hsa-miR-4673, and hsa-miR-642a-3p);

(16) a combination of SEQ ID NOs: 90, 5, 12, 1, and 105 (markers: hsa-miR-3196, hsa-miR-4276, hsa-miR-5090, hsa-miR-6784-5p, and hsa-miR-642a-3p);

(17) a combination of SEQ ID NOs: 90, 5, 12, 109, and 86 (markers: hsa-miR-3196, hsa-miR-4276, hsa-miR-5090, hsa-miR-6769b-5p, and hsa-miR-5195-3p);

(18) a combination of SEQ ID NOs: 5, 12, 137, 105, and 247 (markers: hsa-miR-4276, hsa-miR-5090, hsa-miR-4673, hsa-miR-642a-3p, and hsa-miR-4286);

(19) a combination of SEQ ID NOs: 90, 5, 12, 109, and 175 (markers: hsa-miR-3196, hsa-miR-4276, hsa-miR-5090, hsa-miR-6769b-5p, and hsa-miR-6768-5p); and

(20) a combination of SEQ ID NOs: 5, 12, 100, 109, and 121 (markers: hsa-miR-4276, hsa-miR-5090, hsa-miR-6875-5p, hsa-miR-6769b-5p, and hsa-miR-602).

Non-limiting examples of the combination of the polynucleotides consisting of the nucleotide sequences represented by SEQ ID NOs: 12 and 2 or complementary sequences thereof, with polynucleotides consisting of nucleotide sequences represented by SEQ ID NOs of five polynucleotides selected from the cancer type-specific polynucleotide group 1 or complementary sequences thereof are further listed below:

(1) a combination of SEQ ID NOs: 2, 12, 137, 119, and 105 (markers: hsa-miR-1181, hsa-miR-5090, hsa-miR-4673, hsa-miR-6813-5p, and hsa-miR-642a-3p);

(2) a combination of SEQ ID NOs: 2, 12, 137, 105, and 153 (markers: hsa-miR-1181, hsa-miR-5090, hsa-miR-4673, hsa-miR-642a-3p, and hsa-miR-296-5p);

(3) a combination of SEQ ID NOs: 2, 12, 137, 105, and 121 (markers: hsa-miR-1181, hsa-miR-5090, hsa-miR-4673, hsa-miR-642a-3p, and hsa-miR-602);

(4) a combination of SEQ ID NOs: 2, 12, 109, 121, and 247 (markers: hsa-miR-1181, hsa-miR-5090, hsa-miR-6769b-5p, hsa-miR-602, and hsa-miR-4286);

(5) a combination of SEQ ID NOs: 2, 90, 12, 119, and 105 (markers: hsa-miR-1181, hsa-miR-3196, hsa-miR-5090, hsa-miR-6813-5p, and hsa-miR-642a-3p);

(6) a combination of SEQ ID NOs: 2, 90, 12, 109, and 140 (markers: hsa-miR-1181, hsa-miR-3196, hsa-miR-5090, hsa-miR-6769b-5p, and hsa-miR-4640-5p);

(7) a combination of SEQ ID NOs: 2, 12, 100, 109, and 121 (markers: hsa-miR-1181, hsa-miR-5090, hsa-miR-6875-5p, hsa-miR-6769b-5p, and hsa-miR-602);

(8) a combination of SEQ ID NOs: 2, 12, 109, 175, and 121 (markers: hsa-miR-1181, hsa-miR-5090, hsa-miR-6769b-5p, hsa-miR-6768-5p, and hsa-miR-602);

(9) a combination of SEQ ID NOs: 2, 12, 97, 105, and 247 (markers: hsa-miR-1181, hsa-miR-5090, hsa-miR-7109-5p, hsa-miR-642a-3p, and hsa-miR-4286);

(10) a combination of SEQ ID NOs: 2, 12, 137, 105, and 247 (markers: hsa-miR-1181, hsa-miR-5090, hsa-miR-4673, hsa-miR-642a-3p, and hsa-miR-4286); and

(11) a combination of SEQ ID NOs: 2, 12, 137, 109, and 121 (markers: hsa-miR-1181, hsa-miR-5090, hsa-miR-4673, hsa-miR-6769b-5p, and hsa-miR-602).

Non-limiting examples of the combination of the polynucleotides consisting of the nucleotide sequences represented by SEQ ID NOs: 5 and 2 or complementary sequences thereof, with polynucleotides consisting of nucleotide sequences represented by SEQ ID NOs of five polynucleotides selected from the cancer type-specific polynucleotide group 1 or complementary sequences thereof are further listed below:

(1) a combination of SEQ ID NOs: 2, 90, 5, 119, and 105 (markers: hsa-miR-1181, hsa-miR-3196, hsa-miR-4276, hsa-miR-6813-5p, and hsa-miR-642a-3p);

(2) a combination of SEQ ID NOs: 2, 5, 119, 109, and 121 (markers: hsa-miR-1181, hsa-miR-4276, hsa-miR-6813-5p, hsa-miR-6769b-5p, and hsa-miR-602); and (3) a combination of SEQ ID NOs: 2, 5, 119, 86, and 121 (markers: hsa-miR-1181, hsa-miR-4276, hsa-miR-6813-5p, hsa-miR-5195-3p, and hsa-miR-602).

Non-limiting examples of the combination of the polynucleotides consisting of the nucleotide sequences represented by SEQ ID NOs: 12, 28, and 5 or complementary sequences thereof, with polynucleotides consisting of nucleotide sequences represented by SEQ ID NOs of five polynucleotides selected from the cancer type-specific polynucleotide group 1 or complementary sequences thereof are further listed below:

(1) a combination of SEQ ID NOs: 5, 12, 1, 28, and 121 (markers: hsa-miR-4276, hsa-miR-5090, hsa-miR-6784-5p, hsa-miR-6782-5p, and hsa-miR-602).

The kit or the device of the present invention can also comprise a known polynucleotide(s) that enables detection of early pancreatic cancer or a pancreatic cancer precursor lesion, or a polynucleotide(s) that will be found in the future, in addition to the polynucleotide(s) (which may include a variant(s), a fragment(s), or a derivative(s)) as described above according to the present invention.

The kit of the present invention can also comprise an antibody for measuring a marker or markers for examination of early pancreatic cancer or pancreatic cancer precursor lesion known in the art, such as CEA, CA19-9, SPan-1, DUPAN-2, CA50, CA242, TAG-72, urinary fucose, POA, and TPS, in addition to the polynucleotide(s) according to the present invention as described above, and a variant or variants thereof or a fragment or fragments thereof.

These polynucleotides and variants thereof or fragments thereof contained in the kit of the present invention may be packaged in different containers either individually or in any combination.

The kit of the present invention may comprise a kit for extracting nucleic acids (e.g., total RNA) from body fluids, cells, or tissues, a fluorescent material for labeling, an enzyme and a medium for nucleic acid amplification, an instruction manual, etc.

The device of the present invention is a device for cancer marker measurement in which nucleic acids such as the polynucleotides according to the present invention described above, variants thereof, derivatives thereof, or fragments thereof are linked or attached to, for example, a solid phase. Examples of the material for the solid phase include plastics, paper, glass, and silicon. The material for the solid phase is preferably a plastic from the viewpoint of easy processability. The solid phase has any shape and is, for example, square, round, reed-shaped, or film-shaped. The device of the present invention includes, for example, a device for measurement by a hybridization technique. Specific examples thereof include blotting devices and nucleic acid arrays (e.g., microarrays, DNA chips, and RNA chips).

The nucleic acid array technique is a technique which involves linking or attaching the nucleic acids one by one by use of a method [e.g., a method of spotting the nucleic acids using a high-density dispenser called spotter or arrayer onto the surface of the solid phase surface-treated, if necessary, by L-lysine coating or the introduction of a functional group such as an amino group or a carboxyl group, a method of spraying the nucleic acids onto the solid phase using an inkjet which injects very small liquid droplets by a piezoelectric element or the like from a nozzle, or a method of sequentially synthesizing nucleotides on the solid phase] to prepare an array such as a chip and measuring target nucleic acids through the use of hybridization using this array.

The kit or the device of the present invention comprises nucleic acids capable of specifically binding to the polynucleotides of at least one, preferably at least two, more preferably at least three, most preferably at least five to all of the early pancreatic cancer or pancreatic cancer precursor lesion marker miRNAs, respectively, of the group 1 described above. The kit or the device of the present invention can optionally further comprise nucleic acids capable of specifically binding to the polynucleotides of at least one, preferably at least two, more preferably at least three, most preferably at least five to all of the early pancreatic cancer or pancreatic cancer precursor lesion marker miRNAs, respectively, of the group 2 described above.

The kit or the device of the present invention can be used for detecting early pancreatic cancer or a pancreatic cancer precursor lesion as described in Section 4 below.

4. Method for Detecting Early Pancreatic Cancer or Pancreatic Cancer Precursor Lesion The present invention further provides a method for detecting early pancreatic cancer or a pancreatic cancer precursor lesion in a subject, comprising using the kit or the device of the present invention (comprising the above-mentioned nucleic acid(s) that can be used in the present invention) as described in Section 3 above to measure an expression level of at least one early pancreatic cancer or pancreatic cancer precursor lesion-derived gene selected from the following group of miRNAs, i.e., miR-6784-5p, miR-1181, miR-671-5p, miR-6857-5p, miR-4276, miR-1914-3p, miR-149-3p, miR-937-5p, miR-4675, miR-6795-5p, miR-4731-5p, miR-5090, miR-3620-5p, miR-1343-5p, miR-6717-5p, miR-6825-5p, miR-6738-5p, miR-6769a-5p, miR-4728-5p, miR-652-5p, miR-4257, miR-6785-5p, miR-7110-5p, miR-6887-5p, miR-887-3p, miR-1228-5p, miR-5572, miR-6782-5p, miR-4298, miR-6786-5p, miR-5010-5p, miR-6087, miR-6765-5p, miR-6732-5p, miR-6787-5p, miR-6737-5p, miR-128-2-5p, miR-4270, miR-6861-5p, miR-6756-5p, miR-1229-5p, miR-6891-5p, miR-6848-5p, miR-1237-5p, miR-30c-1-3p, miR-1233-5p, miR-211-3p, miR-4758-5p, miR-614, miR-6746-5p, miR-1915-5p, miR-4688, miR-3917, miR-5787, miR-4632-5p, miR-6126, miR-135a-3p, miR-8063, miR-5698, miR-6089, miR-498, miR-296-3p, miR-4419b, miR-6802-5p, miR-6829-5p, miR-6803-5p, miR-1199-5p, miR-6840-3p, miR-6752-5p, miR-6798-5p, miR-6131, miR-4667-5p, miR-6510-5p, miR-4690-5p, miR-920, miR-23b-3p, miR-4448, miR-2110, miR-4706, miR-7845-5p, miR-6808-5p, miR-4447, miR-6869-5p, miR-6794-5p, miR-6511a-5p, miR-6824-5p, miR-6766-3p, miR-6511a-5p, and miR-6749-5p, and optionally an expression level of at least one early pancreatic cancer or pancreatic cancer precursor lesion-derived gene selected from the following group of miRNAs, i.e., miR-1908-5p, miR-6729-5p, miR-5195-3p, miR-638, miR-6125, miR-3178, miR-3196, miR-8069, miR-4723-5p, miR-4746-3p, miR-4689, miR-6816-5p, miR-6757-5p, miR-7109-5p, miR-6724-5p, miR-1225-3p, miR-6875-5p, miR-7108-5p, miR-4508, miR-6085, miR-6779-5p, miR-642a-3p, miR-4695-5p, miR-7847-3p, miR-3197, miR-6769b-5p, miR-7641, miR-187-5p, miR-3185, miR-2861, miR-3940-5p, miR-1203, miR-615-5p, miR-4787-5p, miR-1343-3p, miR-6813-5p, miR-1225-5p, miR-602, miR-4488, miR-125a-3p, miR-5100, miR-4294, miR-1231, miR-6765-3p, miR-4442, miR-718, miR-6780b-5p, miR-6090, miR-6845-5p, miR-4741, miR-4467, miR-4707-5p, miR-4271, miR-4673, miR-3184-5p, miR-1469, miR-4640-5p, miR-663a, miR-6791-5p, miR-6826-5p, miR-4433b-3p, miR-1915-3p, miR-4417, miR-4449, miR-4707-3p, miR-3180-3p, miR-5585-3p, miR-1268a, miR-8072, miR-296-5p, miR-204-3p, miR-4454, miR-6722-3p, miR-1290, miR-3622a-5p, miR-939-5p, miR-675-5p, miR-3131, miR-4648, miR-1268b, miR-6741-5p, miR-6893-5p, miR-3162-5p, miR-642b-3p, miR-4734, miR-150-3p, miR-8089, miR-6805-3p, miR-7113-3p, miR-6850-5p, miR-6799-5p, miR-6768-5p, miR-92b-5p, miR-3679-5p, miR-4792, miR-3656, miR-92a-2-5p, miR-4466, miR-4513, miR-6781-5p, miR-4649-5p, miR-6775-5p, miR-4651, miR-3195, miR-6726-5p, miR-6872-3p, miR-371a-5p, miR-6777-5p, miR-6789-5p, miR-7975, miR-6821-5p, miR-4534, miR-619-5p, miR-7107-5p, miR-1228-3p, miR-6774-5p, miR-6805-5p, miR-23a-3p, miR-4665-5p, miR-4505, miR-4638-5p, miR-24-3p, miR-3135b, miR-4745-5p, miR-128-1-5p, miR-4476, miR-4687-3p, miR-3665, miR-6806-5p, miR-3937, miR-711, miR-3141, miR-3188, miR-4281, miR-5196-5p, miR-6880-5p, miR-3960, miR-3648, miR-6721-5p, miR-4492, miR-744-5p, miR-7704, miR-4749-5p, miR-762, miR-6836-3p, miR-6727-5p, miR-4739, miR-7977, miR-4484, miR-6515-3p, miR-373-5p, miR-4258, miR-4674, miR-3180, miR-6076, miR-1238-5p, miR-4463, miR-4486, miR-4730, miR-4286, and miR-4739 in a sample such as blood, serum, or plasma in vitro; and comparing, for example, the expression levels having statistically significant difference using the expression level(s) thus measured and a control expression level(s) in a healthy subject(s) (including a non-pancreatic cancer patient(s) and a non-pancreatic cancer precursor lesion patient(s)) measured in the same way, or evaluating in vitro whether the subject has early pancreatic cancer or a pancreatic cancer precursor lesion on the basis of a discriminant score determined from the expression level(s) of the gene(s) in the sample and a discriminant (see below), to detect the presence or absence of early pancreatic cancer or a pancreatic cancer precursor lesion in the subject.

This method of the present invention enables a minimally invasive, early diagnosis of the cancer with high sensitivity and high specificity and thereby brings about early treatment and improved prognosis. In addition, exacerbation of the disease or the effectiveness of surgical, radiotherapeutic, and chemotherapeutic treatments can be monitored.

The method for extracting the early pancreatic cancer or pancreatic cancer precursor lesion-derived gene(s) from the sample such as blood, serum, or plasma according to the present invention is particularly preferably prepared by the addition of a reagent for RNA extraction in 3D-Gene® RNA extraction reagent from liquid sample kit (Toray Industries, Inc.). A general acidic phenol method (acid guanidinium-phenol-chloroform (AGPC) method) may be used, or Trizol® (Life Technologies Corp.) may be used. The pancreatic cancer or pancreatic cancer precursor lesion-derived gene(s) may be prepared by the addition of a reagent for RNA extraction containing acidic phenol, such as Trizol (Life Technologies Corp.) or Isogen (Nippon Gene Co., Ltd., Japan). Alternatively, a kit such as miRNeasy® Mini Kit (Qiagen N.V.) may be used, though the method is not limited thereto.

The present invention also provides use of the kit or the device of the present invention for detecting in vitro an expression product(s) of an early pancreatic cancer or pancreatic cancer precursor lesion-derived miRNA gene(s) in a sample derived from a subject.

In the method of the present invention, the kit or the device described above comprises a single polynucleotide or any possible combination of polynucleotides that can be used in the present invention as described above.

In the detection or (genetic) diagnosis of early pancreatic cancer or a pancreatic cancer precursor lesion according to the present invention, each polynucleotide contained in the kit or the device of the present invention can be used as a probe or a primer. In the case of using the polynucleotide as a primer, TaqMan® MicroRNA Assays from Life Technologies Corp., miScript PCR System from Qiagen N.V., or the like can be used, though the method is not limited thereto.

The polynucleotide contained in the kit or the device of the present invention can be used as a primer or a probe according to a routine method in a method known in the art for specifically detecting a particular gene, for example, a hybridization technique such as Northern blot, Southern blot, in situ hybridization, Northern hybridization, or Southern hybridization, a polynucleotide sequencing technique using a sequencer or the like, or a quantitative amplification technique such as quantitative RT-PCR. A body fluid such as blood, serum, plasma, or urine from a subject is collected as a sample to be assayed according to the type of the detection method used. Alternatively, total RNA prepared from such a body fluid by the method described above may be used, and various polynucleotides including cDNA prepared from the RNA may be used.

The kit or the device of the present invention is useful for the diagnosis of early pancreatic cancer or a pancreatic cancer precursor lesion or the detection of the presence or absence of early pancreatic cancer or a pancreatic cancer precursor lesion. Specifically, the detection of early pancreatic cancer or a pancreatic cancer precursor lesion using the kit or the device can be performed by detecting in vitro an expression level(s) of a gene(s) using the nucleic acid probe(s) or the primer(s) contained in the kit or the device, in a sample such as blood, serum, plasma, or urine from a subject suspected of having early pancreatic cancer or a pancreatic cancer precursor lesion. The subject suspected of having early pancreatic cancer or a pancreatic cancer precursor lesion can be evaluated as having early pancreatic cancer or a pancreatic cancer precursor lesion when the expression level(s) of a target miRNA marker(s) measured using polynucleotide(s) (including a variant(s), a fragment(s), and a derivative(s) thereof) consisting of a nucleotide sequence(s) represented by at least one (one or more) of SEQ ID NOs: 1 to 83, 227 to 229, 246, 248, and 250 or a complementary sequence(s) thereof, and optionally a nucleotide sequence(s) represented by one or more of SEQ ID NOs: 84 to 226, 230 to 245, 247, and 249 or a complementary sequence(s) thereof, in the sample such as blood, serum, plasma, or urine of the subject, has a statistically significant difference compared to an expression level(s) thereof in the sample such as blood, serum, or plasma, or urine of a healthy subject.

The method of the present invention can be combined with a diagnostic imaging method such as abdominal ultrasonography, CT scanning, endoscopic retrograde cholangiopancreatography, or endoscopic ultrasonography. The method of the present invention is capable of specifically detecting early pancreatic cancer or a pancreatic cancer precursor lesion and can substantially discriminate early pancreatic cancer or a pancreatic cancer precursor lesion from the other cancers. Alternatively, these cancers can be discriminated therefrom by combination with an additional diagnostic method such as the diagnostic imaging method as described above.

The method for detecting the absence of early pancreatic cancer or a pancreatic cancer precursor lesion or the presence of early pancreatic cancer or a pancreatic cancer precursor lesion in a sample from a subject using the kit or the device of the present invention comprises collecting a body fluid such as blood, serum, plasma, or urine of the subject, and measuring the expression level(s) of the target gene(s) (or the target nucleic acid(s)) contained therein using one or more polynucleotides (including a variant(s), a fragment(s), or a derivative(s)) selected from the groups of polynucleotides of the present invention, to evaluate the presence or absence of early pancreatic cancer or a pancreatic cancer precursor lesion or to detect early pancreatic cancer or a pancreatic cancer precursor lesion. The method for detecting early pancreatic cancer or a pancreatic cancer precursor lesion according to the present invention can also be used for evaluating or diagnosing, for example, the presence or absence of amelioration of the disease or the degree of amelioration thereof in an early pancreatic cancer or pancreatic cancer precursor lesion patient in the case that a pancreatic cancer-related therapeutic drug known or under development (non-limiting examples thereof include TS-1 (three-component combination drug of tegafur/gimeracil/oteracil potassium), Gemzar (gemcitabine hydrochloride), Tarceva (erlotinib hydrochloride), 5-FU (fluorouracil), levofolinate, irinotecan, oxaliplatin, Abraxane (nab-paclitaxel), and combinations thereof) is administered to the patient for the purpose of treating or ameliorating the disease.

The method of the present invention can comprise, for example, the following steps (a), (b), and (c):

(a) a step of contacting in vitro a sample from a subject with a polynucleotide(s) contained in the kit or the device of the present invention;

(b) a step of measuring an expression level(s) of the target nucleic acid(s) in the sample using the polynucleotide(s) as a nucleic acid probe(s) or primer(s); and (c) a step of evaluating whether or not the subject has early pancreatic cancer or a pancreatic cancer precursor lesion (cells) on the basis of the measurement results in the step (b) to detect the presence or absence of early pancreatic cancer or a pancreatic cancer precursor lesion (cells) in the subject.

In the step (a), blood, serum, or plasma can be used as a preferred sample.

In the step (b), the measurement of the expression level(s) can be performed by a technique, for example, a hybridization technique such as a nucleic acid array method, a polynucleotide sequencing technique using a sequencer or the like, or a quantitative amplification technique such as quantitative RT-PCR.

In the step (c), the subject can be evaluated as having early pancreatic cancer or a pancreatic cancer precursor lesion on the basis of a discriminant score prepared from the expression level(s) of the target nucleic acid(s) in the sample from the subject and a discriminant (mentioned later) in the case that the expression level(s) of the target nucleic acid(s) in the sample from the subject is statistically significantly different from that in a sample(s) derived from a healthy subject(s) or benign pancreatic disease subject(s) (this expression level(s) is also referred to as "reference" or "control").

Specifically, the present invention provides a method for detecting early pancreatic cancer or a pancreatic cancer precursor lesion in a subject, comprising: measuring an expression level(s) of a target nucleic acid(s) in a sample of the subject using a nucleic acid(s) capable of specifically binding to at least one (one or more), preferably at least two, at least three, at least four, or at least five polynucleotides selected from the following miRNAs: miR-6784-5p, miR-1181, miR-671-5p, miR-6857-5p, miR-4276, miR-1914-3p, miR-149-3p, miR-937-5p, miR-4675, miR-6795-5p, miR-4731-5p, miR-5090, miR-3620-5p, miR-1343-5p, miR-6717-5p, miR-6825-5p, miR-6738-5p, miR-6769a-5p, miR-4728-5p, miR-652-5p, miR-4257, miR-6785-5p, miR-7110-5p, miR-6887-5p, miR-887-3p, miR-1228-5p, miR-5572, miR-6782-5p, miR-4298, miR-6786-5p, miR-5010-5p, miR-6087, miR-6765-5p, miR-6732-5p, miR-6787-5p, miR-6737-5p, miR-128-2-5p, miR-4270, miR-6861-5p, miR-6756-5p, miR-1229-5p, miR-6891-5p, miR-6848-5p, miR-1237-5p, miR-30c-1-3p, miR-1233-5p, miR-211-3p, miR-4758-5p, miR-614, miR-6746-5p, miR-1915-5p, miR-4688, miR-3917, miR-5787, miR-4632-5p, miR-6126, miR-135a-3p, miR-8063, miR-5698, miR-6089, miR-498, miR-296-3p, miR-4419b, miR-6802-5p, miR-6829-5p, miR-6803-5p, miR-1199-5p, miR-6840-3p, miR-6752-5p, miR-6798-5p, miR-6131, miR-4667-5p, miR-6510-5p, miR-4690-5p, miR-920, miR-23b-3p, miR-4448, miR-2110, miR-4706, miR-7845-5p, miR-6808-5p, miR-4447, miR-6869-5p, miR-6794-5p, miR-6511a-5p, miR-6824-5p, miR-6766-3p, miR-6511a-5p, and miR-6749-5p; and evaluating in vitro whether or not the subject has early pancreatic cancer or a pancreatic cancer precursor lesion using the above-measured expression levels and control expression levels of a healthy subject(s) measured in the same way as above, to detect the presence or absence of early pancreatic cancer or a pancreatic cancer precursor lesion in the subject.

As used herein, the term "evaluation" may be physician's judgement or is evaluation support based on results of in vitro examination without physician's judgment.

As described above, in the method of the present invention, specifically, miR-6784-5p is hsa-miR-6784-5p, miR-1181 is hsa-miR-1181, miR-671-5p is hsa-miR-671-5p, miR-6857-5p is hsa-miR-6857-5p, miR-4276 is hsa-miR-4276, miR-1914-3p is hsa-miR-1914-3p, miR-149-3p is hsa-miR-149-3p, miR-937-5p is hsa-miR-937-5p, miR-4675 is hsa-miR-4675, miR-6795-5p is hsa-miR-6795-5p, miR-4731-5p is hsa-miR-4731-5p, miR-5090 is hsa-miR-5090, miR-3620-5p is hsa-miR-3620-5p, miR-1343-5p is hsa-miR-1343-5p, miR-6717-5p is hsa-miR-6717-5p, miR-6825-5p is hsa-miR-6825-5p, miR-6738-5p is hsa-miR-6738-5p, miR-6769a-5p is hsa-miR-6769a-5p, miR-4728-5p is hsa-miR-4728-5p, miR-652-5p is hsa-miR-652-5p, miR-4257 is hsa-miR-4257, miR-6785-5p is hsa-miR-6785-5p, miR-7110-5p is hsa-miR-7110-5p, miR-6887-5p is hsa-miR-6887-5p, miR-887-3p is hsa-miR-887-3p, miR-1228-5p is hsa-miR-1228-5p, miR-5572 is hsa-miR-5572, miR-6782-5p is hsa-miR-6782-5p, miR-4298 is hsa-miR-4298, miR-6786-5p is hsa-miR-6786-5p, miR-5010-5p is hsa-miR-5010-5p, miR-6087 is hsa-miR-6087, miR-6765-5p is hsa-miR-6765-5p, miR-6732-5p is hsa-miR-6732-5p, miR-6787-5p is hsa-miR-6787-5p, miR-6737-5p is hsa-miR-6737-5p, miR-128-2-5p is hsa-miR-128-2-5p, miR-4270 is hsa-miR-4270, miR-6861-5p is hsa-miR-6861-5p, miR-6756-5p is hsa-miR-6756-5p, miR-1229-5p is hsa-miR-1229-5p, miR-6891-5p is hsa-miR-6891-5p, miR-6848-5p is hsa-miR-6848-5p, miR-1237-5p is hsa-miR-1237-5p, miR-30c-1-3p is hsa-miR-30c-1-3p, miR-1233-5p is hsa-miR-1233-5p, miR-211-3p is hsa-miR-211-3p, miR-4758-5p is hsa-miR-4758-5p, miR-614 is hsa-miR-614, miR-6746-5p is hsa-miR-6746-5p, miR-1915-5p is hsa-miR-1915-5p, miR-4688 is hsa-miR-4688, miR-3917 is hsa-miR-3917, miR-5787 is hsa-miR-5787, miR-4632-5p is hsa-miR-4632-5p, miR-6126 is hsa-miR-6126, miR-135a-3p is hsa-miR-135a-3p, miR-8063 is hsa-miR-8063, miR-5698 is hsa-miR-5698, miR-6089 is hsa-miR-6089, miR-498 is hsa-miR-498, miR-296-3p is hsa-miR-296-3p, miR-4419b is hsa-miR-4419b, miR-6802-5p is hsa-miR-6802-5p, miR-6829-5p is hsa-miR-6829-5p, miR-6803-5p is hsa-miR-6803-5p, miR-1199-5p is hsa-miR-1199-5p, miR-6840-3p is hsa-miR-6840-3p, miR-6752-5p is hsa-miR-6752-5p, miR-6798-5p is hsa-miR-6798-5p, miR-6131 is hsa-miR-6131, miR-4667-5p is hsa-miR-4667-5p, miR-6510-5p is hsa-miR-6510-5p, miR-4690-5p is hsa-miR-4690-5p, miR-920 is hsa-miR-920, miR-23b-3p is hsa-miR-23b-3p, miR-4448 is hsa-miR-4448, miR-2110 is hsa-miR-2110, miR-4706 is hsa-miR-4706, miR-7845-5p is hsa-miR-7845-5p, miR-6808-5p is hsa-miR-6808-5p, miR-4447 is hsa-miR-4447, miR-6869-5p is hsa-miR-6869-5p, miR-6794-5p is hsa-miR-6794-5p, miR-6511a-5p is hsa-miR-6511a-5p, miR-6824-5p is hsa-miR-6824-5p, miR-6766-3p is hsa-miR-6766-3p, miR-6511a-5p is hsa-miR-6511a-5p, and miR-6749-5p is hsa-miR-6749-5p.

In the method of the present invention, specifically, the nucleic acid(s) (specifically, probe(s) or primer(s)) is selected from the group consisting of the following polynucleotides (a) to (e):

(a) a polynucleotide consisting of a nucleotide sequence represented by any of SEQ ID NOs: 1 to 83, 227 to 229, 246, 248, and 250 or a nucleotide sequence derived from the nucleotide sequence by the replacement of u with t, a variant thereof, a derivative thereof, or a fragment thereof comprising 15 or more consecutive nucleotides;

(b) a polynucleotide comprising a nucleotide sequence represented by any of SEQ ID NOs: 1 to 83, 227 to 229, 246, 248, and 250;

(c) a polynucleotide consisting of a nucleotide sequence complementary to a nucleotide sequence represented by any of SEQ ID NOs: 1 to 83, 227 to 229, 246, 248, and 250 or a nucleotide sequence derived from the nucleotide sequence by the replacement of u with t, a variant thereof, a derivative thereof, or a fragment thereof comprising 15 or more consecutive nucleotides;

(d) a polynucleotide comprising a nucleotide sequence complementary to a nucleotide sequence represented by any of SEQ ID NOs: 1 to 83, 227 to 229, 246, 248, and 250 or a nucleotide sequence derived from the nucleotide sequence by the replacement of u with t; and (e) a polynucleotide hybridizing under stringent conditions to any of the polynucleotides (a) to (d).

The nucleic acid(s) used in the method of the present invention can further comprise a nucleic acid(s) capable of specifically binding to at least one (one or more) polynucleotides selected from the following miRNAs: miR-1908-5p, miR-6729-5p, miR-5195-3p, miR-638, miR-6125, miR-3178, miR-3196, miR-8069, miR-4723-5p, miR-4746-3p, miR-4689, miR-6816-5p, miR-6757-5p, miR-7109-5p, miR-6724-5p, miR-1225-3p, miR-6875-5p, miR-7108-5p, miR-4508, miR-6085, miR-6779-5p, miR-642a-3p, miR-4695-5p, miR-7847-3p, miR-3197, miR-6769b-5p, miR-7641, miR-187-5p, miR-3185, miR-2861, miR-3940-5p, miR-1203, miR-615-5p, miR-4787-5p, miR-1343-3p, miR-6813-5p, miR-1225-5p, miR-602, miR-4488, miR-125a-3p, miR-5100, miR-4294, miR-1231, miR-6765-3p, miR-4442, miR-718, miR-6780b-5p, miR-6090, miR-6845-5p, miR-4741, miR-4467, miR-4707-5p, miR-4271, miR-4673, miR-3184-5p, miR-1469, miR-4640-5p, miR-663a, miR-6791-5p, miR-6826-5p, miR-4433b-3p, miR-1915-3p, miR-4417, miR-4449, miR-4707-3p, miR-3180-3p, miR-5585-3p, miR-1268a, miR-8072, miR-296-5p, miR-204-3p, miR-4454, miR-6722-3p, miR-1290, miR-3622a-5p, miR-939-5p, miR-675-5p, miR-3131, miR-4648, miR-1268b, miR-6741-5p, miR-6893-5p, miR-3162-5p, miR-642b-3p, miR-4734, miR-150-3p, miR-8089, miR-6805-3p, miR-7113-3p, miR-6850-5p, miR-6799-5p, miR-6768-5p, miR-92b-5p, miR-3679-5p, miR-4792, miR-3656, miR-92a-2-5p, miR-4466, miR-4513, miR-6781-5p, miR-4649-5p, miR-6775-5p, miR-4651, miR-3195, miR-6726-5p, miR-6872-3p, miR-371a-5p, miR-6777-5p, miR-6789-5p, miR-7975, miR-6821-5p, miR-4534, miR-619-5p, miR-7107-5p, miR-1228-3p, miR-6774-5p, miR-6805-5p, miR-23a-3p, miR-4665-5p, miR-4505, miR-4638-5p, miR-24-3p, miR-3135b, miR-4745-5p, miR-128-1-5p, miR-4476, miR-4687-3p, miR-3665, miR-6806-5p, miR-3937, miR-711, miR-3141, miR-3188, miR-4281, miR-5196-5p, miR-6880-5p, miR-3960, miR-3648, miR-6721-5p, miR-4492, miR-744-5p, miR-7704, miR-4749-5p, miR-762, miR-6836-3p, miR-6727-5p, miR-4739, miR-7977, miR-4484, miR-6515-3p, miR-373-5p, miR-4258, miR-4674, miR-3180, miR-6076, miR-1238-5p, miR-4463, miR-4486, miR-4730, miR-4286, and miR-4739.

Specifically, miR-1908-5p is hsa-miR-1908-5p, miR-6729-5p is hsa-miR-6729-5p, miR-5195-3p is hsa-miR-5195-3p, miR-638 is hsa-miR-638, miR-6125 is hsa-miR-6125, miR-3178 is hsa-miR-3178, miR-3196 is hsa-miR-3196, miR-8069 is hsa-miR-8069, miR-4723-5p is hsa-miR-4723-5p, miR-4746-3p is hsa-miR-4746-3p, miR-4689 is hsa-miR-4689, miR-6816-5p is hsa-miR-6816-5p, miR-6757-5p is hsa-miR-6757-5p, miR-7109-5p is hsa-miR-7109-5p, miR-6724-5p is hsa-miR-6724-5p, miR-1225-3p is hsa-miR-1225-3p, miR-6875-5p is hsa-miR-6875-5p, miR-7108-5p is hsa-miR-7108-5p, miR-4508 is hsa-miR-4508, miR-6085 is hsa-miR-6085, miR-6779-5p is hsa-miR-6779-5p, miR-642a-3p is hsa-miR-642a-3p, miR-4695-5p is hsa-miR-4695-5p, miR-7847-3p is hsa-miR-7847-3p, miR-3197 is hsa-miR-3197, miR-6769b-5p is hsa-miR-6769b-5p, miR-7641 is hsa-miR-7641, miR-187-5p is hsa-miR-187-5p, miR-3185 is hsa-miR-3185, miR-2861 is hsa-miR-2861, miR-3940-5p is hsa-miR-3940-5p, miR-1203 is hsa-miR-1203, miR-615-5p is hsa-miR-615-5p, miR-4787-5p is hsa-miR-4787-5p, miR-1343-3p is hsa-miR-1343-3p, miR-6813-5p is hsa-miR-6813-5p, miR-1225-5p is hsa-miR-1225-5p, miR-602 is hsa-miR-602, miR-4488 is hsa-miR-4488, miR-125a-3p is hsa-miR-125a-3p, miR-5100 is hsa-miR-5100, miR-4294 is hsa-miR-4294, miR-1231 is hsa-miR-1231, miR-6765-3p is hsa-miR-6765-3p, miR-4442 is hsa-miR-4442, miR-718 is hsa-miR-718, miR-6780b-5p is hsa-miR-6780b-5p, miR-6090 is hsa-miR-6090, miR-6845-5p is hsa-miR-6845-5p, miR-4741 is hsa-miR-4741, miR-4467 is hsa-miR-4467, miR-4707-5p is hsa-miR-4707-5p, miR-4271 is hsa-miR-4271, miR-4673 is hsa-miR-4673, miR-3184-5p is hsa-miR-3184-5p, miR-1469 is hsa-miR-1469, miR-4640-5p is hsa-miR-4640-5p, miR-663a is hsa-miR-663a, miR-6791-5p is hsa-miR-6791-5p, miR-6826-5p is hsa-miR-6826-5p, miR-4433b-3p is hsa-miR-4433b-3p, miR-1915-3p is hsa-miR-1915-3p, miR-4417 is hsa-miR-4417, miR-4449 is hsa-miR-4449, miR-4707-3p is hsa-miR-4707-3p, miR-3180-3p is hsa-miR-3180-3p, miR-5585-3p is hsa-miR-5585-3p, miR-1268a is hsa-miR-1268a, miR-8072 is hsa-miR-8072, miR-296-5p is hsa-miR-296-5p, miR-204-3p is hsa-miR-204-3p, miR-4454 is hsa-miR-4454, miR-6722-3p is hsa-miR-6722-3p, miR-1290 is hsa-miR-1290, miR-3622a-5p is hsa-miR-3622a-5p, miR-939-5p is hsa-miR-939-5p, miR-675-5p is hsa-miR-675-5p, miR-3131 is hsa-miR-3131, miR-4648 is hsa-miR-4648, miR-1268b is hsa-miR-1268b, miR-6741-5p is hsa-miR-6741-5p, miR-6893-5p is hsa-miR-6893-5p, miR-3162-5p is hsa-miR-3162-5p, miR-642b-3p is hsa-miR-642b-3p, miR-4734 is hsa-miR-4734, miR-150-3p is hsa-miR-150-3p, miR-8089 is hsa-miR-8089, miR-6805-3p is hsa-miR-6805-3p, miR-7113-3p is hsa-miR-7113-3p, miR-6850-5p is hsa-miR-6850-5p, miR-6799-5p is hsa-miR-6799-5p, miR-6768-5p is hsa-miR-6768-5p, miR-92b-5p is hsa-miR-92b-5p, miR-3679-5p is hsa-miR-3679-5p, miR-4792 is hsa-miR-4792, miR-3656 is hsa-miR-3656, miR-92a-2-5p is hsa-miR-92a-2-5p, miR-4466 is hsa-miR-4466, miR-4513 is hsa-miR-4513, miR-6781-5p is hsa-miR-6781-5p, miR-4649-5p is hsa-miR-4649-5p, miR-6775-5p is hsa-miR-6775-5p, miR-4651 is hsa-miR-4651, miR-3195 is hsa-miR-3195, miR-6726-5p is hsa-miR-6726-5p, miR-6872-3p is hsa-miR-6872-3p, miR-371a-5p is hsa-miR-371a-5p, miR-6777-5p is hsa-miR-6777-5p, miR-6789-5p is hsa-miR-6789-5p, miR-7975 is hsa-miR-7975, miR-6821-5p is hsa-miR-6821-5p, miR-4534 is hsa-miR-4534, miR-619-5p is hsa-miR-619-5p, miR-7107-5p is hsa-miR-7107-5p, miR-1228-3p is hsa-miR-1228-3p, miR-6774-5p is hsa-miR-6774-5p, miR-6805-5p is hsa-miR-6805-5p, miR-23a-3p is hsa-miR-23a-3p, miR-4665-5p is hsa-miR-4665-5p, miR-4505 is hsa-miR-4505, miR-4638-5p is hsa-miR-4638-5p, miR-24-3p is hsa-miR-24-3p, miR-3135b is hsa-miR-3135b, miR-4745-5p is hsa-miR-4745-5p, miR-128-1-5p is hsa-miR-128-1-5p, miR-4476 is hsa-miR-4476, miR-4687-3p is hsa-miR-4687-3p, miR-3665 is hsa-miR-3665, miR-6806-5p is hsa-miR-6806-5p, miR-3937 is hsa-miR-3937, miR-711 is hsa-miR-711, miR-3141 is hsa-miR-3141, miR-3188 is hsa-miR-3188, miR-4281 is hsa-miR-4281, miR-5196-5p is hsa-miR-5196-5p, miR-6880-5p is hsa-miR-6880-5p, miR-3960 is hsa-miR-3960, miR-3648 is hsa-miR-3648, miR-6721-5p is hsa-miR-6721-5p, miR-4492 is hsa-miR-4492, miR-744-5p is hsa-miR-744-5p, miR-7704 is hsa-miR-7704, miR-4749-5p is hsa-miR-4749-5p, miR-762 is hsa-miR-762, miR-6836-3p is hsa-miR-6836-3p, miR-6727-5p is hsa-miR-6727-5p, miR-4739 is hsa-miR-4739, miR-7977 is hsa-miR-7977, miR-4484 is hsa-miR-4484, miR-6515-3p is hsa-miR-6515-3p, miR-373-5p is hsa-miR-373-5p, miR-4258 is hsa-miR-4258, miR-4674 is hsa-miR-4674, miR-3180 is hsa-miR-3180, miR-6076 is hsa-miR-6076, miR-1238-5p is hsa-miR-1238-5p, miR-4463 is hsa-miR-4463, miR-4486 is hsa-miR-4486, miR-4730 is hsa-miR-4730, miR-4286 is hsa-miR-4286, and miR-4739 is hsa-miR-4739.

Specifically, the nucleic acid(s) is further selected from the group consisting of the following polynucleotides (f) to (j):
(f) a polynucleotide consisting of a nucleotide sequence represented by any of SEQ ID NOs: 84 to 226, 230 to 245, 247, and 249 or a nucleotide sequence derived from the nucleotide sequence by the replacement of u with t, a variant thereof, a derivative thereof, or a fragment thereof comprising 15 or more consecutive nucleotides;

(g) a polynucleotide comprising a nucleotide sequence represented by any of SEQ ID NOs: 84 to 226, 230 to 245, 247, and 249;

(h) a polynucleotide consisting of a nucleotide sequence complementary to a nucleotide sequence represented by any of SEQ ID NOs: 84 to 226, 230 to 245, 247, and 249 or a nucleotide sequence derived from the nucleotide sequence by the replacement of u with t, a variant thereof, a derivative thereof, or a fragment thereof comprising 15 or more consecutive nucleotides;

(i) a polynucleotide comprising a nucleotide sequence complementary to a nucleotide sequence represented by any of SEQ ID NOs: 84 to 226, 230 to 245, 247, and 249 or a nucleotide sequence derived from the nucleotide sequence by the replacement of u with t; and (j) a polynucleotide hybridizing under stringent conditions to any of the polynucleotides (f) to (i).

Examples of the sample used in the method of the present invention can include samples prepared from living tissues (preferably pancreatic tissues) or body fluids such as blood, serum, plasma, and urine from subjects. Specifically, for example, an RNA-containing sample prepared from the tissue, a polynucleotide-containing sample further prepared therefrom, a body fluid such as blood, serum, plasma, or urine, a portion or the whole of a living tissue collected from the subject by biopsy or the like, or a living tissue excised by surgery can be used, and the sample for measurement can be prepared therefrom.

The "subject" used herein refers to a mammal, for example, a primate such as a human or a monkey, a rodent such as a mouse or a rat, a pet animal such as a dog or a cat, an athletic animal such as a horse, and an animal that is kept in a zoo without any limitation, and is preferably a human.

The steps of the method of the present invention can be changed according to the type of the sample to be assayed.

In the case of using RNA as an analyte, the detection of early pancreatic cancer or a pancreatic cancer precursor lesion (cells) in a subject can comprise, for example, the following steps (a), (b), and (c):

(a) a step of binding RNA prepared from a sample from the subject or complementary polynucleotides (cDNAs) transcribed from the RNA to a polynucleotide(s) in the kit or the device of the present invention;

(b) a step of quantitatively or qualitatively measuring the sample-derived RNA or the cDNAs synthesized from the RNA, which is/are bound to the polynucleotide(s), by hybridization using the polynucleotide(s) as a nucleic acid probe(s), by use of a sequencer for polynucleotide sequencing, or by quantitative RT-PCR using the polynucleotide(s) as a primer(s); and (c) a step of evaluating in vitro whether or not the subject has early pancreatic cancer or pancreatic cancer precursor lesion through comparison with a control on the basis of the measurement results of the step (b), to detect the presence or absence of early pancreatic cancer or a pancreatic cancer precursor lesion (or early pancreatic cancer- or pancreatic cancer precursor lesion-derived gene expression) in the subject.

For example, various hybridization methods can be used for detecting, examining, evaluating, or diagnosing early pancreatic cancer or a pancreatic cancer precursor lesion (or pancreatic cancer-derived gene expression) in vitro according to the present invention. For example, Northern blot, Southern blot, RT-PCR, DNA chip analysis, in situ hybridization, Northern hybridization, Southern hybridization, or a polynucleotide sequencing technique using a sequencer or the like can be used as such a hybridization method.

In the case of using the Northern blot, the presence or absence of expression of each gene or the expression level thereof in the RNA can be detected or measured by use of the nucleic acid probe(s) that can be used in the present invention. Specific examples thereof can include a method which comprises labeling the nucleic acid probe (or a complementary strand) with a radioisotope ($^{32}P$, $^{33}P$, $^{35}S$, etc.), a fluorescent material, or the like, hybridizing the labeled product with the living tissue-derived RNA from a subject, which is transferred to a nylon membrane or the like according to a routine method, and then detecting and measuring a signal derived from the label (radioisotope or fluorescent material) on the formed DNA/RNA duplex using a radiation detector (examples thereof can include BAS-1800 II (Fujifilm Corp., Japan)) or a fluorescence detector (examples thereof can include STORM 865 (GE Healthcare Japan Corp.)).

In the case of using the quantitative RT-PCR, the presence or absence of expression of each gene or the expression level thereof in the RNA can be detected or measured by use of the primer that can be used in the present invention. Specific examples thereof can include a method which comprises preparing cDNAs from the living tissue-derived RNA of a subject according to a routine method, hybridizing a pair of primers (consisting of a plus strand and a reverse strand binding to the cDNA) prepared from the composition for detection of the present invention with the cDNA and performing PCR according to a routine method such that the region of each target gene can be amplified with the cDNA as a template, and thereby detecting the obtained double-stranded DNA. The method for detecting the double-stranded DNA can include a method of performing the PCR using the primers labeled in advance with a radioisotope or a fluorescent material, a method of electrophoresing the PCR product on an agarose gel and staining the double-stranded DNA with ethidium bromide or the like for detection, and a method of transferring the produced double-stranded DNA to a nylon membrane or the like according to a routine method and hybridizing the double-stranded DNA to a labeled nucleic acid probe for detection.

In the case of using the sequencer, the presence or absence of expression of each gene or the expression level thereof in the RNA can be detected or measured from the number of reads by use of the primer that can be used in the present invention. Specific examples thereof can include a method which comprises preparing cDNAs from the living tissue-derived RNA of a subject according to a routine method, hybridizing a pair of primers (consisting of a plus strand and a reverse strand binding to the cDNA) prepared from the composition for detection of the present invention with the cDNA and performing PCR according to a routine method such that the region of each target gene can be amplified with the cDNA as a template, and detecting or measuring the amplified DNA using a sequencer such as HiSeq 2500 (Illumina, Inc.) or Ion Proton® System (Thermo Fisher Scientific Inc.). Another specific example thereof can include a method which comprises detecting or measuring the living tissue-derived RNA of a subject using PacBio RS II (Pacific Biosciences of California, Inc.) without PCR amplification.

In the case of using the nucleic acid array technique (or analysis), an RNA chip or a DNA chip on which the composition for detection of the present invention is attached as nucleic acid probes (single-stranded or double-stranded) to a substrate (solid phase) is used. Regions having the attached nucleic acid probes are referred to as probe spots, and regions having no attached nucleic acid probe are referred to as blank spots. A substrate on which a group of genes are immobilized is generally called a nucleic acid chip, a nucleic acid array, a microarray, or the like. The DNA or RNA array includes a DNA or RNA macroarray and a DNA or RNA microarray. In the present specification, the term "chip" includes these arrays. 3D-Gene® Human miRNA Oligo chip (Toray Industries, Inc.) can be used as the DNA chip, though the DNA chip is not limited thereto.

Examples of the measurement using the DNA chip can include, but are not limited to, a method of detecting and measuring a signal derived from the label of the composition for detection using an image detector (examples thereof can include Typhoon 9410 (GE Healthcare) and 3D-Gene® scanner (Toray Industries, Inc.)).

The "stringent conditions" used herein are, as mentioned above, conditions under which a nucleic acid probe hybridizes to its target sequence to a detectably larger extent (e.g., a measurement value equal to or larger than "(a mean of background measurement values)+(a standard error of the background measurement values)×2") than that for other sequences.

The stringent conditions are defined by hybridization and subsequent washing. Examples of the hybridization conditions include, but not limited to, 30° C. to 60° C. for 1 to 24 hours in a solution containing SSC, a surfactant, formamide, dextran sulfate, a blocking agent(s), etc. In this context, 1×SSC is an aqueous solution (pH 7.0) containing 150 mM sodium chloride and 15 mM sodium citrate. The surfactant includes, for example, SDS (sodium dodecyl sulfate), Triton, or Tween. The hybridization conditions more preferably comprise 3-10×SSC and 0.1-1% SDS. Furthermore, examples of the conditions for the washing, following the hybridization, which is another condition to define the stringent conditions, can include conditions comprising sequential washing at 30° C. in a solution containing 0.5× SSC and 0.1% SDS, at 30° C. in a solution containing 0.2×SSC and 0.1% SDS, and at 30° C. in a 0.05×SSC solution. It is desirable that the complementary strand should maintain its hybridized state with a target plus strand even during washing under such conditions. Specifically, examples of such a complementary strand can include a strand consisting of a nucleotide sequence in a completely complementary relationship with the nucleotide sequence of the target plus strand, and a strand consisting of a nucleotide sequence having at least 80%, preferably at least 85%, more preferably at least 90% or at least 95%, for example, at least 98% or at least 99% identity to the strand.

Other examples of the "stringent conditions" for the hybridization are described in, for example, Sambrook, J. & Russel, D., Molecular Cloning, A LABORATORY MANUAL, Cold Spring Harbor Laboratory Press, published on Jan. 15, 2001, Vol. 1, 7.42 to 7.45 and Vol. 2, 8.9 to 8.17, and can be used in the present invention.

Examples of the conditions for carrying out PCR using polynucleotide fragments in the kit of the present invention as primers include treatment for approximately 15 seconds to 1 minute at a Tm value+5-10° C., wherein the Tm value is calculated from the sequences of the primers, using a PCR buffer having composition such as 10 mM Tris-HCL (pH 8.3), 50 mM KCL, and 1 to 2 mM $MgCl_2$. Examples of the method for calculating such a Tm value include Tm value=2×(the number of adenine residues+the number of thymine residues)+4×(the number of guanine residues+the number of cytosine residues).

In the case of using the quantitative RT-PCR, a commercially available kit for measurement specially designed for quantitatively measuring miRNA, such as TaqMan® MicroRNA Assays (Life Technologies Corp.), LNA®-based MicroRNA PCR (Exiqon), or Ncode® miRNA qRT-PCT kit (Invitrogen Corp.) may be used.

For the calculation of gene expression levels, statistical processing described in, for example, Statistical analysis of gene expression microarray data (Speed T., Chapman and Hall/CRC), and A beginner's guide Microarray gene expression data analysis (Causton H. C. et al., Blackwell publishing) can be used in the present invention, though the calculation method is not limited thereto. For example, twice, preferably 3 times, more preferably 6 times the standard deviation of the measurement values of the blank spots are added to the average measurement value of the blank spots on the DNA chip, and probe spots having a signal value equal to or larger than the resulting value can be defined as detection spots. Furthermore, the average measurement value of the blank spots can be considered as a background and can be subtracted from the measurement values of the probe spots to determine the resulting value as gene expression levels. A missing value for a gene expression level can be excluded from the analyte, preferably replaced with the smallest value of the gene expression level in each DNA chip, or more preferably replaced with a value obtained by subtracting 0.1 from a logarithmic value of the smallest value of the gene expression level. In order to exclude low-signal genes, only a gene having a gene expression level of $2^6$, preferably $2^8$, more preferably $2^{10}$ or larger in 20% or more, preferably 50% or more, more preferably 80% or more of the number of measurement samples can be selected as the analyte. Examples of the normalization of the gene expression level include, but are not limited to, global normalization and quantile normalization (Bolstad, B. M. et al., 2003, Bioinformatics, Vol. 19, p. 185-193).

The present invention also provides a method for detecting (or assisting in the detection of) early pancreatic cancer or a pancreatic cancer precursor lesion in a subject, comprising measuring expression levels of target genes in a sample from the subject using the polynucleotides, the kit, or the device (e.g., chip) for diagnosis of the present invention, or a combination thereof, and assigning the expression levels of the target genes in the sample from the subject to a discriminant (discriminant function) to evaluate the presence or absence of early pancreatic cancer or a pancreatic cancer precursor lesion, wherein the discriminant is prepared with gene expression levels in a sample from a subject (or a patient) known to have early pancreatic cancer or a pancreatic cancer precursor lesion and gene expression levels in a sample from a healthy subject as supervising samples and is capable of discriminating an early pancreatic cancer or pancreatic cancer precursor lesion patient from a healthy subject.

The present invention further provides the method comprising: a first step of measuring in vitro expression levels of target genes in a plurality of samples from subjects known to have early pancreatic cancer or a pancreatic cancer precursor lesion and/or to have neither early pancreatic cancer nor a pancreatic cancer precursor lesion, using the polynucleotides, the kit, or the device (e.g., chip) for diagnosis of the present invention, or a combination thereof; a second step of preparing a discriminant with the measurement values of the expression levels of the target genes obtained in the first step as supervising samples; a third step of measuring in vitro expression levels of the target genes in a sample derived from a subject in the same way as in the first step; and a fourth step of assigning the measurement values of the expression levels of the target genes obtained in the third step to the discriminant obtained in the second step, and determining or evaluating the presence or absence of early pancreatic cancer or a pancreatic cancer precursor lesion in the subject on the basis of the results obtained from the discriminant, wherein the target genes can be detected using the polynucleotides, the polynucleotides contained in the kit or the device (e.g., chip), variants thereof, or fragments thereof.

As used herein, the discriminant can be prepared by use of any discriminant analysis method that can prepare a discriminant for discriminating an early pancreatic cancer or pancreatic cancer precursor lesion patient from a healthy subject, for example, Fisher's discriminant analysis, nonlinear discriminant analysis based on Mahalanobis' distance, neural network, or Support Vector Machine (SVM), though the method is not limited thereto.

When a clustering boundary is a straight line or a hyperplane, the linear discriminant analysis is a method for determining the belonging of a cluster using Formula 1 as a discriminant. In Formula 1, x represents an explanatory variable, w represents a coefficient of the explanatory variable, and $w_0$ represents a constant term.

$$f(x) = w_0 + \sum_{i=1}^{n} w_i x_i \qquad \text{Formula 1}$$

Values obtained from the discriminant are referred to as discriminant scores. The measurement values of a newly offered dataset can be assigned as explanatory variables to the discriminant to determine clusters by the signs (+ or −) of the discriminant scores.

The Fisher's discriminant analysis, one type of linear discriminant analysis, is a dimensionality reduction method for selecting a dimension suitable for discriminating classes, and constructs a highly discriminating synthetic variable by focusing on the variance of the synthetic variables and minimizing the variance of data having the same label (Venables, W. N. et al., Modern Applied Statistics with S. Fourth edition. Springer, 2002). In the Fisher's discriminant analysis, projection direction w is determined so as to maximize Formula 2. In this formula, t represents an average input, $n_g$ represents the number of data belonging to class g, and g represents an average input of the data belonging to class g. The numerator and the denominator are the interclass variance and the intraclass variance, respectively, when each data is projected in the direction of the vector w. Discriminant coefficient $w_i$ is determined by maximizing this ratio (Takafumi Kanamori et al., "Pattern Recognition", Kyoritsu Shuppan Co., Ltd., (Tokyo, Japan) (2009); and Richard O. et al., Pattern Classification Second Edition., Wiley-Interscience, 2000).

$$J(w) = \frac{\sum_{g=1}^{G} n_g (w^T \mu_g - w^T \mu)(w^T \mu_g - w^T \mu)^T}{\sum_{g=1}^{G} \sum_{i:y_i=g} (w^T x_i - w^T \mu_g)(w^T x_i - w^T \mu_g)} \qquad \text{Formula 2}$$

$$\text{subject to } \mu = \sum_{i=1}^{n} \frac{x_i}{n}, \mu_g = \sum_{i:u_i=g}^{n} \frac{x_i}{n_g}$$

The Mahalanobis' distance is calculated according to Formula 3 in consideration of data correlation and can be used as nonlinear discriminant analysis for determining a cluster to which a data point belongs, based on the smallest Mahalanobis' distance between the data point and each cluster. In Formula 3, μ represents a central vector of each cluster, and $S^{-1}$ represents an inverse matrix of the variance-covariance matrix of the cluster. The central vector is calculated from explanatory variable x, and an average vector, a median value vector, or the like can be used.

$$D(x, \mu) = \{(x - \mu)^t S^{-1} (x - \mu)\}^{\frac{1}{2}} \qquad \text{Formula 3}$$

SVM is a discriminant analysis method devised by V. Vapnik (The Nature of Statistical Leaning Theory, Springer, 1995). Particular data points of a dataset having known classes are defined as explanatory variables, and classes are defined as objective variables. A boundary plane called hyperplane for correctly classifying the dataset into the known classes is determined, and a discriminant for data classification is determined using the boundary plane. Then, the measurement values of a newly offered dataset can be assigned as explanatory variables to the discriminant to determine classes. In this respect, the result of the discriminant analysis may be classes, may be a probability of being classified into correct classes, or may be the distance from the hyperplane. In SVM, a method of nonlinearly converting a feature vector to a high dimension and performing linear discriminant analysis in the space is known as a method for tackling nonlinear problems. An expression in which an inner product of two factors in a nonlinearly mapped space is expressed only by inputs in their original spaces is called kernel. Examples of the kernel can include a linear kernel, a RBF (Radial Basis Function) kernel, and a Gaussian kernel. While highly dimensional mapping is performed according to the kernel, the optimum discriminant, i.e., a discriminant, can be actually constructed by mere calculation according to the kernel, which avoids calculating features in the mapped space (e.g., Hideki Aso et al., Frontier of Statistical Science 6 "Statistics of pattern recognition and learning—New concepts and approaches", Iwanami Shoten, Publishers, (Tokyo, Japan) (2004); Nello Cristianini et al., Introduction to SVM, Kyoritsu Shuppan Co., Ltd., (Tokyo, Japan) (2008)).

C-support vector classification (C-SVC), one type of SVM, comprises preparing a hyperplane by supervision according to a dataset with the explanatory variables of two groups and classifying an unknown dataset into either of the groups (C. Cortes et al., 1995, Machine Learning, Vol. 20, p. 273-297).

Exemplary calculation of the C-SVC discriminant that can be used in the method of the present invention will be given below. First, all subjects are divided into two groups, i.e., an early pancreatic cancer or pancreatic cancer precursor lesion patient group and a healthy subject group. For example, pancreatic tissue examination can be used for a reference under which each subject is confirmed either as an early pancreatic cancer or pancreatic cancer precursor lesion patient or as a healthy subject.

Next, a dataset consisting of comprehensive gene expression levels of serum-derived samples of the two divided groups (hereinafter, this dataset is referred to as a training cohort) is prepared, and a C-SVC discriminant is determined by using genes found to differ clearly in their gene expression levels between the two groups as explanatory variables and this grouping as objective variables (e.g., −1 and +1). An optimizing objective function is represented by Formula 4 wherein e represents all input vectors, y represents an objective variable, a represents a Lagrange multiplier vector, Q represents a positive definite matrix, and C represents a parameter for adjusting constrained conditions.

$$\min_{a} \frac{1}{2} a^T Q a - e^T a \quad \text{Formula 4}$$

subject to $y^T a = 0$, $0 \le a_i \le C$, $i = 1, \ldots, l$,

Formula 5 is a finally obtained discriminant, and a group to which the data point belongs to can be determined on the basis of the sign of a value obtained according to the discriminant. In this formula, x represents a support vector, y represents a label indicating the belonging of a group, a represents the corresponding coefficient, b represents a constant term, and K represents a kernel function.

$$f(x) = \mathrm{sgn}\left(\sum_{i=1}^{l} y_i a_i K(x_i, x) + b\right) \quad \text{Formula 5}$$

For example, a RBF kernel defined by Formula 6 can be used as the kernel function. In this formula, x represents a support vector, and γ represents a kernel parameter for adjusting the complexity of the hyperplane.

$$K(x_i, x_j) = \exp(-r\|x_i - x_j\|^2), \; r < 0 \quad \text{Formula 6}$$

In addition, an approach such as neural network, k-nearest neighbor algorithms, decision trees, or logistic regression analysis can be selected as a method for determining or evaluating the presence and/or absence of an early pancreatic cancer or pancreatic cancer precursor lesion in a subject, or for evaluating the expression level thereof by comparison with a control derived from a healthy subject.

The method of the present invention can comprise, for example, the following steps (a), (b), and (c):

(a) a step of measuring an expression level(s) of a target gene(s) in samples already known to be derived from early pancreatic cancer or pancreatic cancer precursor lesion patients and to be derived from healthy subjects or subjects having neither early pancreatic cancer nor a pancreatic cancer precursor lesion, using the polynucleotide(s), the kit, or the device (e.g., DNA chip) for detection according to the present invention;

(b) a step of preparing the discriminants of Formulas 1 to 3, 5, and 6 described above from the measurement values of the expression level measured in the step (a); and (c) a step of measuring an expression level(s) of the target gene(s) in a sample derived from a subject using the polynucleotide(s), the kit, or the device (e.g., DNA chip) for diagnosis (detection) according to the present invention, assigning the obtained measurement value(s) to the discriminants prepared in the step (b), and determining or evaluating the presence or absence of early pancreatic cancer or a pancreatic cancer precursor lesion in the subject, or evaluating early pancreatic cancer- or pancreatic cancer precursor lesion-derived expression levels by comparison with a healthy subject-derived control, on the basis of the obtained results.

In this context, in the discriminants of Formulas 1 to 3, 5, and 6, x represents an explanatory variable and includes a value obtained by measuring a polynucleotide(s) selected from the polynucleotides or the like described in Section 2 above, or any fragment thereof. Specifically, the explanatory variable for discriminating an early pancreatic cancer or pancreatic cancer precursor lesion patient from a healthy subject according to the present invention is a gene expression level(s) selected from, for example, the following expression levels (1) to (2):

(1) a gene expression level(s) in the serum of an early pancreatic cancer or pancreatic cancer precursor lesion patient and a healthy subject measured by any of RNAs or DNAs comprising 15 or more consecutive nucleotides in a nucleotide sequence represented by any of SEQ ID NOs: 1 to 83, 227 to 229, 246, 248, and 250 or a complementary sequence thereof, or nucleotides derived from the nucleotides by the replacement of u with t;

(2) a gene expression level(s) in the serum of an early pancreatic cancer or pancreatic cancer precursor lesion patient and a healthy subject measured by any of RNAs or DNAs comprising 15 or more consecutive nucleotides in a nucleotide sequence represented by any of SEQ ID NOs: 84 to 226, 230 to 245, 247, and 249 or a complementary sequence thereof, or nucleotides derived from the nucleotides by the replacement of u with t; and As described above, for the method for determining or evaluating whether or not a subject has early pancreatic cancer or a pancreatic cancer precursor lesion as to a sample derived from the subject, the preparation of a discriminant requires a discriminant prepared from a training cohort. For enhancing the discrimination accuracy of the discriminant, it is necessary to use genes having clear difference in their expression level between two groups consisting of an early pancreatic cancer or pancreatic cancer precursor lesion patient group and a healthy subject group in the training cohort when preparing the discriminant.

Each gene that is used for an explanatory variable in a discriminant is preferably determined as follows. First, comprehensive gene expression levels of an early pancreatic cancer or pancreatic cancer precursor lesion patient group and comprehensive gene expression levels of a healthy subject group, both of which are in a training cohort, are used as a dataset, and the degree of difference in the expression level of each gene between the two groups is determined through the use of, for example, the P value of t test, which is parametric analysis, or the P value of Mann-Whitney's U test or Wilcoxon test, which is nonparametric analysis.

The degree of difference in the expression level can be considered as being statistically significant when the critical rate (significance level) as the P value obtained by the test is smaller than, for example, 5%, 1%, or 0.01%.

In order to correct an increased probability of type I error attributed to the repetition of a test, a method known in the art, for example, Bonferroni or Holm method, can be used for the correction (e.g., Yasushi Nagata et al., "Basics of statistical multiple comparison methods", Scientist Press Co., Ltd. (Tokyo, Japan) (2007)). As an example of the Bonferroni correction, for example, the P value obtained by a test is multiplied by the number of repetitions of the test, i.e., the number of genes used in the analysis, and the obtained value can be compared with a desired significance level to reduce a probability of causing type I error in the whole test.

Instead of the test, the absolute value (fold change) of an expression ratio of a median value of each gene expression level between gene expression levels of an early pancreatic cancer or pancreatic cancer precursor lesion patient group and gene expression levels of a healthy subject group may be calculated to select a gene that is used for an explanatory variable in a discriminant. Alternatively, ROC curves may be prepared using gene expression levels of an early pancreatic cancer or pancreatic cancer precursor lesion patient group and a healthy subject group, and a gene that is used for an explanatory variable in a discriminant can be selected on the basis of an AUROC value.

Next, a discriminant that can be calculated by various methods described above is prepared using any number of genes having large difference in their gene expression levels determined here. Examples of the method for constructing a discriminant that produces the largest discrimination accuracy include a method of constructing a discriminant in every combination of genes that satisfy the significance level for P value, and a method of repetitively evaluating the genes for use in the preparation of a discriminant while increasing the number of genes one by one in a descending order of difference in gene expression level (Furey T S. et al., 2000, Bioinformatics., Vol. 16, p. 906-14). A gene expression level of another independent early pancreatic cancer or pancreatic cancer precursor lesion patient or healthy subject is assigned as an explanatory variable to this discriminant to calculate discrimination results of the group to which this independent early pancreatic cancer or pancreatic cancer precursor lesion patient or healthy subject belongs. Specifically, the identified gene set for diagnosis and the discriminant constructed using the gene set for diagnosis can be evaluated with an independent sample cohort to identify a more universal gene set for diagnosis capable of detecting early pancreatic cancer or a pancreatic cancer precursor lesion and a more universal method for discriminating early pancreatic cancer or a pancreatic cancer precursor lesion.

Split-sample method is preferably used for evaluating the discrimination performance (generalization) of the discriminant. Specifically, a dataset is divided into a training cohort and a validation cohort, and gene selection by a statistical test and discriminant preparation are performed using the training cohort. Accuracy, sensitivity, and specificity are calculated using a result of discriminating a validation cohort according to the discriminant, and a true group to which the validation cohort belongs, to evaluate the discrimination performance of the discriminant. On the other hand, instead of dividing a dataset, the gene selection by a statistical test and discriminant preparation may be performed using all of samples, and accuracy, sensitivity, and specificity can be calculated by discriminating a newly prepared sample with the discriminant for evaluation of the discrimination performance of the discriminant.

The present invention provides polynucleotides for disease diagnosis useful in the diagnosis and treatment of early pancreatic cancer or a pancreatic cancer precursor lesion, a method for detecting early pancreatic cancer or a pancreatic cancer precursor lesion using the polynucleotide(s), and a kit and a device for the detection of early pancreatic cancer or a pancreatic cancer precursor lesion, comprising the polynucleotide(s). Particularly, in order to select a gene(s) for diagnosis and prepare a discriminant so as to exhibit accuracy beyond the early pancreatic cancer or pancreatic cancer precursor lesion diagnosis methods using the existing tumor markers CEA and CA19-9, a gene set for diagnosis and a discriminant for the method of the present invention can be constructed, which exhibit accuracy beyond CEA and CA19-9, for example, by comparing expressed genes in serum from a patient confirmed to be negative using CEA and CA19-9 but finally found to have early pancreatic cancer or a pancreatic cancer precursor lesion by detailed examination such as computed tomography using a contrast medium, with genes expressed in serum from a patient having no early pancreatic cancer or pancreatic cancer precursor lesion.

For example, the gene set for diagnosis is determined as any combination selected from one or two or more of the polynucleotides based on a nucleotide sequence represented by any of SEQ ID NOs: 1 to 83, 227 to 229, 246, 248, and 250 or a nucleotide sequence derived from the nucleotide sequence by the replacement of u with t, or a complementary sequence thereof as described above; and optionally one or two or more of the polynucleotides based on a nucleotide sequence represented by any of SEQ ID NOs: 84 to 226, 230 to 245, 247, and 249 or a nucleotide sequence derived from the nucleotide sequence by the replacement of u with t, or a complementary sequence thereof; and optionally one or two or more of the polynucleotides based on a nucleotide sequence represented by any of SEQ ID NOs: 227 to 245 or a nucleotide sequence derived from the nucleotide sequence by the replacement of u with t, or a complementary sequence thereof. Further, a discriminant is constructed using expression levels of the gene set for diagnosis in samples from class I early pancreatic cancer or pancreatic cancer precursor lesion patients as a result of tissue diagnosis and samples from class II healthy subjects and/or other cancers and/or benign diseases as a result of tissue diagnosis. As a result, the presence or absence of early pancreatic cancer or a pancreatic cancer precursor lesion in a subject from which an unknown sample is derived can be determined with 100% accuracy at the maximum by measuring expression levels of the gene set for diagnosis in the unknown sample.

EXAMPLES

Hereinafter, the present invention will be described further specifically with reference to Examples below. However, the scope of the present invention is not intended to be limited by these Examples.

Reference Example 1

<Collection of Samples of Early Pancreatic Cancer or Pancreatic Cancer Precursor Lesion Patient and Healthy Subject>

Sera were collected using VENOJECT II vacuum blood collecting tube VP-AS109K60 (Terumo Corp., Japan) from each of 21 pancreatic cancer precursor lesion patients (4 cases with IPMA low grade, 5 cases with IPMA high grade, and 12 cases with IPMC) confirmed to have no cancer in organs, 31 early pancreatic cancer patients (9 cases with stage IIA and 22 cases with stage IIB) confirmed to have no cancer in organs other than the pancreas, and 123 healthy subjects after obtainment of informed consent, and used as a training cohort. Likewise, sera were collected using VENOJECT II vacuum blood collecting tube VP-AS109K60 (Terumo Corp.) from each of 12 pancreatic cancer precursor lesion patients (3 cases with IPMA low grade, 3 cases with IPMA high grade, and 6 cases with IPMC) confirmed to have no cancer in organs, 13 early pancreatic cancer patients (3 cases with stage IIA and 10 cases with stage IIB) confirmed to have no cancer in organs other than the pancreas, and 61 healthy subjects after obtainment of informed consent, and used as a validation cohort.

<Extraction of Total RNA>

Total RNA was obtained using a reagent for RNA extraction in 3D-Gene® RNA extraction reagent from liquid sample kit (Toray Industries, Inc., Japan) according to the protocol provided by the manufacturer from 300 μL of the serum sample obtained from each of 261 persons in total of 33 pancreatic cancer precursor lesion patients, 184 healthy subjects, and 44 early pancreatic cancer patients included in the training cohort and the validation cohort.

<Measurement of Gene Expression Level> miRNAs in the total RNA obtained from sera of each of the 261 persons in total of the 33 pancreatic cancer precursor lesion patients, the 184 healthy subjects, and the 44 early pancreatic cancer patients included in the training cohort and the validation cohort were fluorescently labeled using 3D-Gene® miRNA Labeling kit (Toray Industries, Inc.) according to the protocol (ver 2.20) provided by the manufacturer. The oligo DNA chip used was 3D-Gene® Human miRNA Oligo chip (Toray Industries, Inc.) with attached probes having sequences complementary to 2,555 miRNAs among the miRNAs registered in miRBase Release 20. Hybridization under stringent conditions and washing following the hybridization were performed according to the protocol provided by the manufacturer. The DNA chip was scanned using 3D-Gene® scanner (Toray Industries, Inc.) to obtain images. Fluorescence intensity was digitized using 3D-Gene® Extraction (Toray Industries, Inc.). The digitized fluorescence intensity was converted to a logarithmic value having a base of 2 and used as a gene expression level, from which a blank value was subtracted. A missing value was replaced with a value obtained by subtracting 0.1 from a logarithmic value of the smallest value of the gene expression level in each DNA chip. As a result, the comprehensive gene expression levels of the miRNAs in the sera were obtained from each of the 261 persons in total of the 33 pancreatic cancer precursor lesion patients, the 184 healthy subjects, and the 46 early pancreatic cancer patients. Calculation and statistical analysis using the digitized gene expression levels of the miRNAs were carried out using R language 3.0.2 (R Development Core Team (2013). R: A language and environment for statistical computing. R Foundation for Statistical Computing, URL http://www.R-project.org/.) and MASS package 7.3-30 (Venables, W. N. & Ripley, B. D. (2002) Modern Applied Statistics with S. Fourth Edition. Springer, New York. ISBN 0-387-95457-0).

Reference Example 2

<Collection of Samples of Other Cancers and Benign Diseases>

Sera were collected using VENOJECT II vacuum blood collecting tube VP-AS109K60 (Terumo Corp.) from each of 61 advanced pancreatic cancer patients, 66 bile duct cancer patients, 31 colorectal cancer patients, 32 stomach cancer patients, 34 esophageal cancer patients, 38 liver cancer patients, and 15 benign pancreatic disease patients confirmed to have no cancer in other organs after obtainment of informed consent. Also, data on 51 breast cancer patients, 35 prostate cancer patients, and 26 benign prostatic disease patients was extracted from the data set under Accession No. GSE73002 of a gene expression information database Gene Expression Omnibus (http://www.ncbi.nlm.nih.gov/geo/). These samples were used as a training cohort together with the samples of 21 pancreatic cancer precursor lesion patients (4 cases with IPMA low grade, 5 cases with IPMA high grade, and 12 cases with IPMC), 31 early pancreatic cancer patients (8 cases with stage IIA and 22 cases with stage IIB), and 128 healthy subjects of Reference Example 1. Likewise, sera were collected using VENOJECT II vacuum blood collecting tube VP-AS109K60 (Terumo Corp.) from each of 39 advanced pancreatic cancer patients, 32 bile duct cancer patients, 19 colorectal cancer patients, 18 stomach cancer patients, 16 esophageal cancer patients, 14 liver cancer patients, and 9 benign pancreatic disease patients confirmed to have no cancer in other organs after obtainment of informed consent. Also, data on 23 breast cancer patients, 17 prostate cancer patients, and 15 benign prostatic disease patients was extracted from the dataset under Accession No. GSE73002 of a gene expression information database Gene Expression Omnibus (http://www.ncbi.nlm.nih.gov/geo/). These samples were used as a validation cohort together with the samples of 12 pancreatic cancer precursor lesion patients (3 cases with IPMA low grade, 3 cases with IPMA high grade, and 6 cases with IPMC), 13 early pancreatic cancer patients (3 cases with stage IIA and 10 cases with stage IIB), and 56 healthy subjects of Reference Example 1. Subsequent extraction of total RNA and measurement and analysis of gene expression levels were conducted in the same way as in Reference Example 1.

Example 1

<Selection of Gene Markers Using Samples of the Training Cohort, and Method for Evaluating Early Pancreatic Cancer or Pancreatic Cancer Precursor Lesion Discriminant Performance of the Single Gene Marker Using the Validation Cohort>

In this Example, a gene marker for discriminating an early pancreatic cancer or pancreatic cancer precursor lesion patient as a positive control group from a healthy subject as a negative control group was selected from the training cohort and studied in samples of the validation cohort independent of the training cohort.

Specifically, first, the miRNA expression levels of the training cohort and the validation cohort obtained in the preceding Reference Examples were combined and normalized by global normalization.

Next, genes for diagnosis were selected using the training cohort. Here, in order to acquire diagnostic markers with higher reliability, only genes having the expression level of $2^6$ or higher in 50% or more of the samples in either of the early pancreatic cancer or pancreatic cancer precursor lesion patient group of the training cohort or the healthy subject group of the training cohort were selected. In order to further acquire statistically significant genes for discriminating an early pancreatic cancer or pancreatic cancer precursor lesion patient group from a healthy subject group, the P value obtained by two-tailed t-test assuming equal variance as to each gene expression level was corrected by the Bonferroni method, and genes that satisfied p<0.01 were acquired as gene markers for use in explanatory variables of a discriminant and described in Table 2.

In this way, hsa-miR-6784-5p, hsa-miR-1181, hsa-miR-671-5p, hsa-miR-6857-5p, hsa-miR-4276, hsa-miR-1914-3p, hsa-miR-149-3p, hsa-miR-937-5p, hsa-miR-4675, hsa-miR-6795-5p, hsa-miR-4731-5p, hsa-miR-5090, hsa-miR-3620-5p, hsa-miR-1343-5p, hsa-miR-6717-5p, hsa-miR-6825-5p, hsa-miR-6738-5p, hsa-miR-6769a-5p, hsa-miR-4728-5p, hsa-miR-652-5p, hsa-miR-4257, hsa-miR-6785-5p, hsa-miR-7110-5p, hsa-miR-6887-5p, hsa-miR-887-3p, hsa-miR-1228-5p, hsa-miR-5572, hsa-miR-6782-5p, hsa-miR-4298, hsa-miR-6786-5p, hsa-miR-5010-5p, hsa-miR-6087, hsa-miR-6765-5p, hsa-miR-6732-5p, hsa-miR-6787-5p, hsa-miR-6737-5p, hsa-miR-128-2-5p, hsa-miR-4270, hsa-miR-6861-5p, hsa-miR-6756-5p, hsa-miR-1229-5p, hsa-miR-6891-5p, hsa-miR-6848-5p, hsa-miR-1237-5p, hsa-miR-30c-1-3p, hsa-miR-1233-5p, hsa-miR-211-3p, hsa-miR-4758-5p, hsa-miR-614, hsa-miR-6746-5p, hsa-miR- 1915-5p, hsa-miR-4688, hsa-miR-3917, hsa-miR-5787, hsa-miR-4632-5p, hsa-miR-6126, hsa-miR-135a-3p, hsa-miR-8063, hsa-miR-5698, hsa-miR-6089, hsa-miR-498, hsa-miR-296-3p, hsa-miR-4419b, hsa-miR-6802-5p, hsa-miR-6829-5p, hsa-miR-6803-5p, hsa-miR-1199-5p, hsa-miR-6840-3p, hsa-miR-6752-5p, hsa-miR-6798-5p, hsa-miR-6131, hsa-miR-4667-5p, hsa-miR-6510-5p, hsa-miR-4690-5p, hsa-miR-920, hsa-miR-23b-3p, hsa-miR-4448, hsa-miR-2110, hsa-miR-4706, hsa-miR-7845-5p, hsa-miR-6808-5p, hsa-miR-4447, hsa-miR-6869-5p, hsa-miR-1908-5p, hsa-miR-6729-5p, hsa-miR-5195-3p, hsa-miR-638, hsa-miR-6125, hsa-miR-3178, hsa-miR-3196, hsa-miR-8069, hsa-miR-4723-5p, hsa-miR-4746-3p, hsa-miR-4689, hsa-miR-6816-5p, hsa-miR-6757-5p, hsa-miR-7109-5p, hsa-miR-6724-5p, hsa-miR-1225-3p, hsa-miR-6875-5p, hsa-miR-7108-5p, hsa-miR-4508, hsa-miR-6085, hsa-miR-6779-5p, hsa-miR-642a-3p, hsa-miR-4695-5p, hsa-miR-7847-3p, hsa-miR-3197, hsa-miR-6769b-5p, hsa-miR-7641, hsa-miR-187-5p, hsa-miR-3185, hsa-miR-2861, hsa-miR-3940-5p, hsa-miR-1203, hsa-miR-615-5p, hsa-miR-4787-5p, hsa-miR-1343-3p, hsa-miR-6813-5p, hsa-miR-1225-5p, hsa-miR-602, hsa-miR-4488, hsa-miR-125a-3p, hsa-miR-5100, hsa-miR-4294, hsa-miR-1231, hsa-miR-6765-3p, hsa-miR-4442, hsa-miR-718, hsa-miR-6780b-5p, hsa-miR-6090, hsa-miR-6845-5p, hsa-miR-4741, hsa-miR-4467, hsa-miR-4707-5p, hsa-miR-4271, hsa-miR-4673, hsa-miR-3184-5p, hsa-miR-1469, hsa-miR-4640-5p, hsa-miR-663a, hsa-miR-6791-5p, hsa-miR-6826-5p, hsa-miR-4433b-3p, hsa-miR-1915-3p, hsa-miR-4417, hsa-miR-4449, hsa-miR-4707-3p, hsa-miR-3180-3p, hsa-miR-5585-3p, hsa-miR-1268a, hsa-miR-8072, hsa-miR-296-5p, hsa-miR-204-3p, hsa-miR-4454, hsa-miR-6722-3p, hsa-miR-1290, hsa-miR-3622a-5p, hsa-miR-939-5p, hsa-miR-675-5p, hsa-miR-3131, hsa-miR-4648, hsa-miR-1268b, hsa-miR-6741-5p, hsa-miR-6893-5p, hsa-miR-3162-5p, hsa-miR-642b-3p, hsa-miR-4734, hsa-miR-150-3p, hsa-miR-8089, hsa-miR-6805-3p, hsa-miR-7113-3p, hsa-miR-6850-5p, hsa-miR-6799-5p, hsa-miR-6768-5p, hsa-miR-92b-5p, hsa-miR-3679-5p, hsa-miR-4792, hsa-miR-3656, hsa-miR-92a-2-5p, hsa-miR-4466, hsa-miR-4513, hsa-miR-6781-5p, hsa-miR-4649-5p, hsa-miR-6775-5p, hsa-miR-4651, hsa-miR-3195, hsa-miR-6726-5p, hsa-miR-6872-3p, hsa-miR-371a-5p, hsa-miR-6777-5p, hsa-miR-6789-5p, hsa-miR-7975, hsa-miR-6821-5p, hsa-miR-4534, hsa-miR-619-5p, hsa-miR-7107-5p, hsa-miR-1228-3p, hsa-miR-6774-5p, hsa-miR-6805-5p, hsa-miR-23a-3p, hsa-miR-4665-5p, hsa-miR-4505, hsa-miR-4638-5p, hsa-miR-24-3p, hsa-miR-3135b, hsa-miR-4745-5p, hsa-miR-128-1-5p, hsa-miR-4476, hsa-miR-4687-3p, hsa-miR-3665, hsa-miR-6806-5p, hsa-miR-3937, hsa-miR-711, hsa-miR-3141, hsa-miR-3188, hsa-miR-4281, hsa-miR-5196-5p, hsa-miR-6880-5p, hsa-miR-3960, hsa-miR-3648, hsa-miR-6721-5p, hsa-miR-4492, hsa-miR-744-5p, hsa-miR-7704, and hsa-miR-4749-5p genes, and the nucleotide sequences of SEQ ID NOs: 1 to 226 related thereto were identified.

A discriminant for determining the presence or absence of early pancreatic cancer or a pancreatic cancer precursor lesion was further prepared by Fisher's discriminant analysis with the expression levels of these genes as indicators. Specifically, any newly found expression level measurement values of polynucleotide consisting of a nucleotide sequence represented by any of SEQ ID NOs: 1 to 83 among the 226 genes selected in the training cohort was input to Formula 2 above to prepare a discriminant. Calculated accuracy, sensitivity, and specificity are shown in Table 3. In this respect, a discriminant coefficient and a constant term are shown in Table 4.

Figure 2:
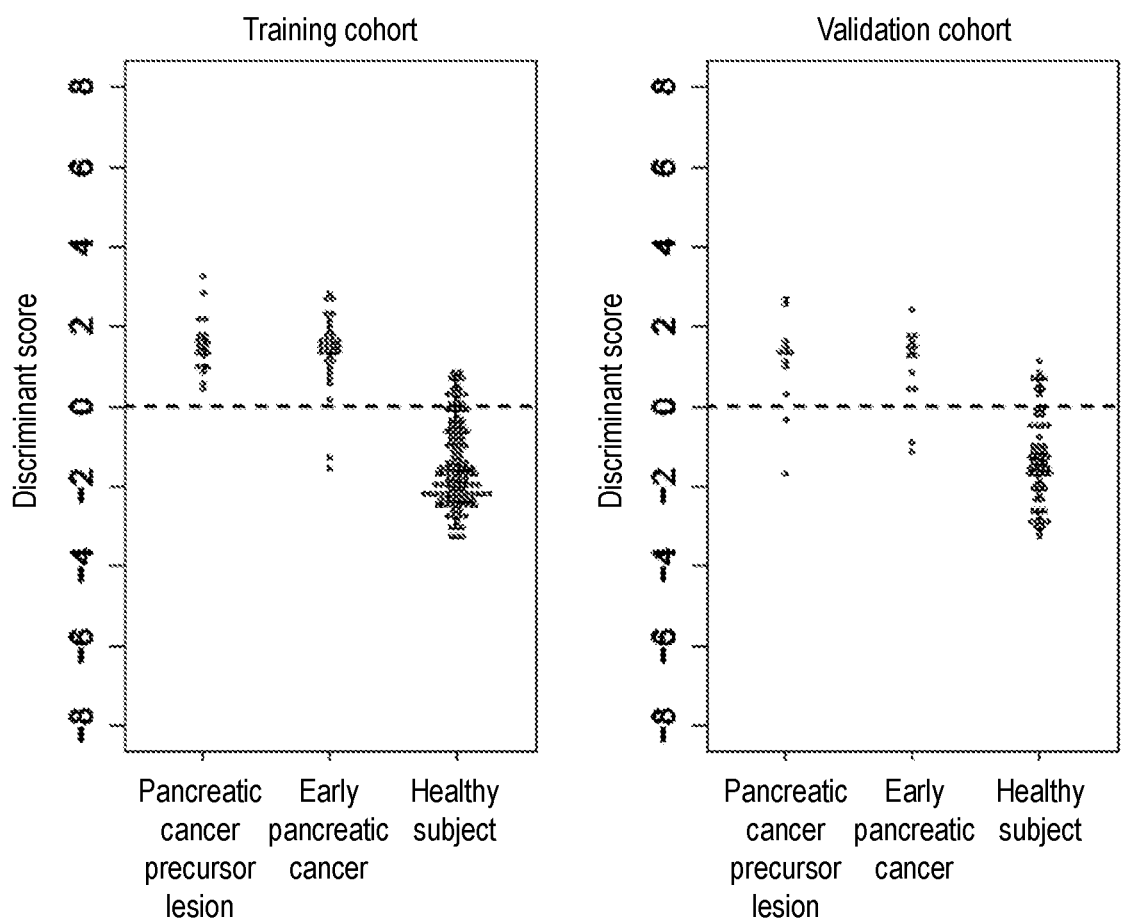
FIG. 2 In the left diagram of FIG. 2, a discriminant (3.10×hsa-miR-miR-6784-5p−39.85) was prepared by use of Fisher's discriminant analysis from the expression level measurement values of hsa-miR-6784-5p (SEQ ID NO: 1) in pancreatic cancer precursor lesion patients (21 persons), early pancreatic cancer patients (31 persons), and healthy subjects (123 persons) selected as a training cohort, and discriminant scores obtained with the discriminant are plotted on the vertical axis with the cohort plotted on the horizontal axis. The dotted line in the diagram depicts a discriminant boundary on which the discriminant score is 0 and by which the two groups are discriminated. In the right diagram of FIG. 2, the vertical axis plots discriminant scores for the expression level measurement values of hsa-miR-6784-5p (SEQ ID NO: 1) in pancreatic cancer precursor lesion patients (12 persons), early pancreatic cancer patients (13 persons), and healthy subjects (61 persons) selected as a validation cohort, wherein the discriminant scores are obtained with the discriminant prepared from the training cohort, and the horizontal axis plots the cohort. The dotted line in the diagram depicts the discriminant boundary on which the discriminant score is 0 and by which the two groups are discriminated.

Next, accuracy, sensitivity, and specificity in the validation cohort were calculated using the discriminant thus prepared, and the discriminant performance of the selected polynucleotides was validated using independent samples (Table 3). For example, the discriminant score obtained by use of Fisher's discriminant analysis from the expression level measurement value of the nucleotide sequence represented by SEQ ID NO: 1 was compared between the pancreatic cancer precursor lesion patients (21 persons) or the early pancreatic cancer patients (31 persons) and the healthy subjects in the training cohort. As a result, the discriminant score in the training cohort was found to be significantly higher in the early pancreatic cancer or pancreatic cancer precursor lesion group than in the healthy subject group (see the left diagram of FIG. 2). These results were also reproducible in the validation cohort (see the right diagram of FIG. 2). Likewise, the results obtained about the other polynucleotides shown in SEQ ID NOs: 1 to 226 showed that the gene expression level measurement values were significantly lower (decrease) or higher (increase) in the early pancreatic cancer or pancreatic cancer precursor lesion patient group than in the healthy subject group (Table 2). These results were able to be validated in the validation cohort. For example, as for this nucleotide sequence represented by SEQ ID NO: 1, the number of correctly or incorrectly identified samples in the detection of early pancreatic cancer or a pancreatic cancer precursor lesion in the validation cohort was calculated using the threshold (0) that was set in the training cohort for discriminating the two groups. As a result, 22 true positives, 52 true negatives, 9 false positives, and 4 false negatives were obtained. From these values, 85.1% accuracy, 84.6% sensitivity, and 85.2% specificity were obtained as the detection performance. In this way, the detection performance was calculated as to all of the polynucleotides shown in SEQ ID NOs: 1 to 83, and described in Table 3. Among the polynucleotides consisting of the nucleotide sequences represented by SEQ ID NOs: 1 to 83 shown in Table 2, for example, 26 polynucleotides consisting of the nucleotide sequences represented by SEQ ID NOs: 2, 3, 18, 12, 20, 1, 15, 50, 63, 72, 5, 24, 10, 52, 9, 11, 19, 39, 61, 7, 17, 22, 26, 74, 21, and 28 exhibited sensitivity of 100%, 92.3%, 92.3%, 76.9%, 80.8%, 84.6%, 76.9%, 84.6%, 73.1%, 80.8%, 88.5%, 88.5%, 88.5%, 73.1%, 73.1%, 76.9%, 61.5%, 65.4%, 84.6%, 92.3%, 73.1%, 61.5%, 76.9%, 73.1%, 80.8%, and 92.3%, respectively, in the validation cohort (Table 3). As seen from Comparative Examples mentioned later, the existing markers CEA and CA19-9 had sensitivity of 20% and 68%, respectively, in the validation cohort (Table 5-2), demonstrating that, for example, the 26 polynucleotides consisting of the nucleotide sequences represented by SEQ ID NOs: 2, 3, 18, 12, 20, 1, 15, 50, 63, 72, 5, 24, 10, 52, 9, 11, 19, 39, 61, 7, 17, 22, 26, 74, 21, and 28 can discriminate, each alone, early pancreatic cancer or a pancreatic cancer precursor lesion in the validation cohort with sensitivity beyond or equivalent to CA19-9.

Example 2

<Method a for Evaluating Early Pancreatic Cancer or Pancreatic Cancer Precursor Lesion Discriminant Performance by Combination of Plurality of Gene Markers Using Samples in the Validation Cohort>

In this Example, a method for evaluating early pancreatic cancer or a pancreatic cancer precursor lesion discriminant performance by a combination of the gene markers selected in Example 1 was studied.

Figure 3:
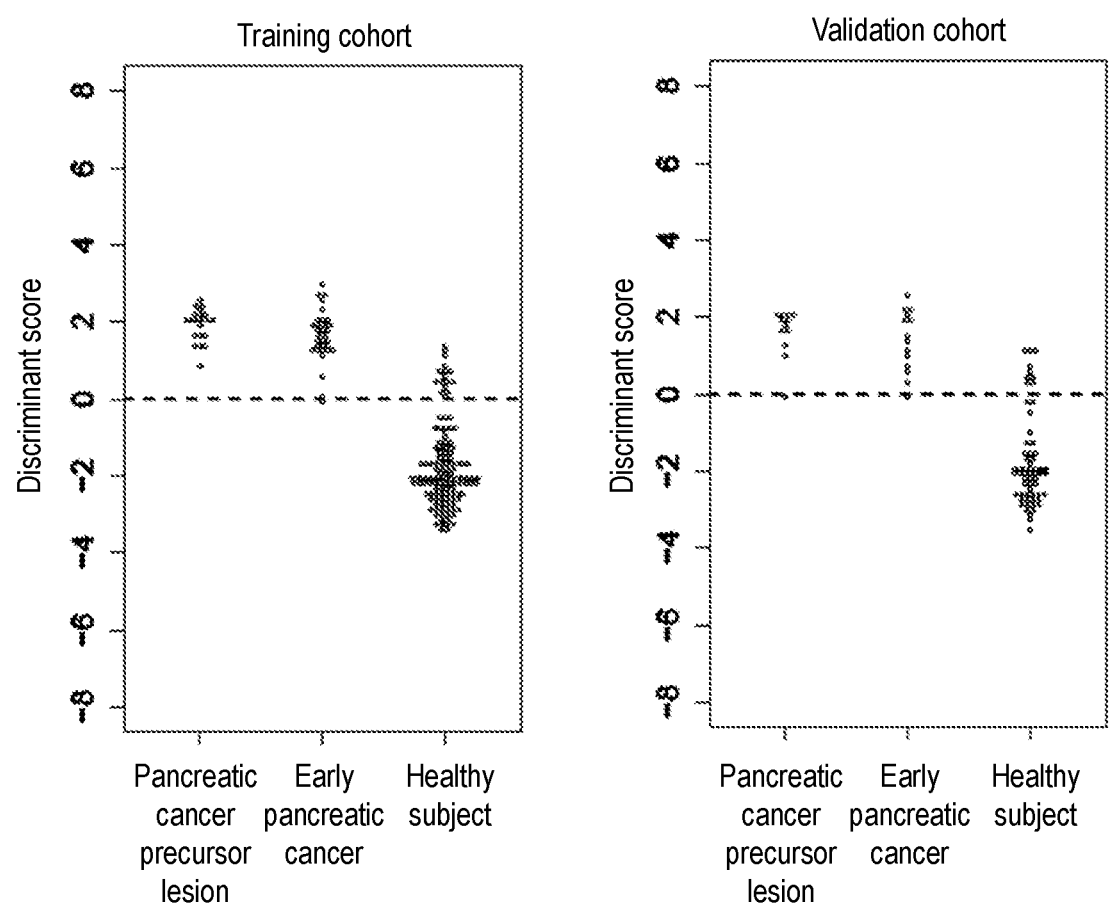
FIG. 3 In the left diagram of FIG. 3, a discriminant (1.90×hsa-miR-6784-5p+1.72×hsa-miR-1181−34.50) was prepared by use of Fisher's discriminant analysis from the expression level measurement values of hsa-miR-6784-5p (SEQ ID NO: 1) and hsa-miR-1181 (SEQ ID NO: 2) in pancreatic cancer precursor lesion patients (21 persons), early pancreatic cancer patients (31 persons), and healthy subjects (123 persons) selected as a training cohort, and discriminant scores obtained with the discriminant are plotted on the vertical axis with the cohort plotted on the horizontal axis. The dotted line in the diagram depicts a discriminant boundary on which the discriminant score is 0 and by which the two groups are discriminated. In the right diagram of FIG. 3, the vertical axis plots discriminant scores for the expression level measurement values of hsa-miR-6784-5p (SEQ ID NO: 1) and hsa-miR-1181 (SEQ ID NO: 2) in pancreatic cancer precursor lesion patients (12 persons), early pancreatic cancer patients (13 persons), and healthy subjects (61 persons) selected as a validation cohort, wherein the discriminant scores are obtained with the discriminant prepared from the training cohort, and the horizontal axis plots the cohort. The dotted line in the diagram depicts a discriminant boundary on which the discriminant score is 0 and by which the two groups are discriminated.

Specifically, Fisher's discriminant analysis was conducted as to 15,272 combinations of two expression level measurement values comprising at least one or more of the expression level measurement values of the newly found polynucleotides consisting of the nucleotide sequences represented by SEQ ID NOs: 1 to 83 among the polynucleotides consisting of the nucleotide sequences represented by SEQ ID NOs: 1 to 226 selected in Example 1, to construct a discriminant for determining the presence or absence of early pancreatic cancer or a pancreatic cancer precursor lesion. Next, accuracy, sensitivity, and specificity in the validation cohort were calculated using the discriminant thus prepared, and the discriminant performance of the selected polynucleotides was validated using independent samples. For example, the expression level measurement values of the nucleotide sequences represented by SEQ ID NO: 1 and SEQ ID NO: 2 were compared between the pancreatic cancer precursor lesion patients (21 persons) or the early pancreatic cancer patients (31 persons) and the healthy subjects (123 persons) in the training cohort. As a result, a scatter diagram that significantly separated the expression level measurement values of the early pancreatic cancer or pancreatic cancer precursor lesion patient group from those of the healthy subject group was obtained in the training cohort. These results were also reproducible in the validation cohort. Likewise, a scatter diagram that significantly separated the gene expression level measurement values of the early pancreatic cancer or pancreatic cancer precursor lesion patient group from those of the healthy subject group was also obtained as to the other combinations of two expression level measurement values comprising at least one of the expression level measurement values of the newly found polynucleotides consisting of the nucleotide sequences represented by SEQ ID NOs: 1 to 83 among the polynucleotides consisting of the nucleotide sequences represented by SEQ ID NOs: 1 to 226. These results were able to be validated in the validation cohort. For example, as for these nucleotide sequences represented by SEQ ID NO: 1 and SEQ ID NO: 2, the number of correctly or incorrectly identified samples in the detection of early pancreatic cancer or a pancreatic cancer precursor lesion was calculated using the threshold (0=1.90×hsa-miR-6784-5p+1.72×hsa-miR-1181−34.50) that was set in the training cohort for discriminating the two groups. As a result, 52 true positives, 107 true negatives, 16 false positives, and 1 false negative were obtained in the training cohort. From these values, 90.3% accuracy, 98.1% sensitivity, and 87% specificity were obtained as the detection performance (see the left diagram of FIG. 3). These results were also reproducible in the validation cohort (see the right diagram of FIG. 3). In this way, the detection performance was calculated for all of the combinations of two expression level measurement values comprising at least one of the expression level measurement values of the newly found polynucleotides consisting of the nucleotide sequences represented by SEQ ID NOs: 1 to 83 among the polynucleotides consisting of the nucleotide sequences represented by SEQ ID NOs: 1 to 226. Among them, 225 combinations comprising the expression level measurement value of the polynucleotide consisting of the nucleotide sequence represented by SEQ ID NO: 1, and the detection performance thereof are described in Table 6 as an example. In Table 6, "SEQ ID NO" indicates the combinations of a plurality of polynucleotides used by SEQ ID NO (the same applies to the tables mentioned later herein). For example, the combinations of the expression level measurement values of the polynucleotides consisting of the nucleotide sequences represented by SEQ ID NO: 1 and SEQ ID NO: 2, SEQ ID NO: 1 and SEQ ID NO: 3, SEQ ID NO: 1 and SEQ ID NO: 4, and SEQ ID NO: 1 and SEQ ID NO: 5 showed sensitivity of 92.3%, 88.5%, 84.6%, 88.5%, and 84.6%, respectively, in the validation cohort (Table 6). Further, the combinations of two polynucleotides consisting of nucleotide sequences other than SEQ ID NO: 1 are shown in Table 7 as an example. For example, the combinations of SEQ ID NOs: 2 and 18, SEQ ID NOs: 2 and 53, SEQ ID NOs: 2 and 20, SEQ ID NOs: 2 and 3, SEQ ID NOs: 2 and 50, SEQ ID NOs: 85 and 3, SEQ ID NOs: 84 and 3, SEQ ID NOs: 90 and 3, SEQ ID NOs: 87 and 3, SEQ ID NOs: 90 and 18, SEQ ID NOs: 87 and 18, SEQ ID NOs: 89 and 18, SEQ ID NOs: 84 and 18, SEQ ID NOs: 85 and 12, SEQ ID NOs: 85 and 20, SEQ ID NOs: 84 and 20, SEQ ID NOs: 90 and 20, SEQ ID NOs: 87 and 20, SEQ ID NOs: 87 and 15, SEQ ID NOs: 85 and 15, SEQ ID NOs: 2 and 15, SEQ ID NOs: 85 and 50, SEQ ID NOs: 87 and 50, SEQ ID NOs: 84 and 50, SEQ ID NOs: 106 and 50, SEQ ID NOs: 90 and 50, SEQ ID NOs: 2 and 63, SEQ ID NOs: 85 and 63, SEQ ID NOs: 90 and 63, SEQ ID NOs: 87 and 63, SEQ ID NOs: 84 and 72, SEQ ID NOs: 85 and 72, SEQ ID NOs: 88 and 72, SEQ ID NOs: 87 and 72, SEQ ID NOs: 85 and 5, SEQ ID NOs: 87 and 5, SEQ ID NOs: 84 and 5, SEQ ID NOs: 85 and 10, SEQ ID NOs: 90 and 10, SEQ ID NOs: 85 and 52, SEQ ID NOs: 88 and 52, SEQ ID NOs: 87 and 52, SEQ ID NOs: 98 and 52, SEQ ID NOs: 84 and 52, SEQ ID NOs: 87 and 9, SEQ ID NOs: 85 and 9, SEQ ID NOs: 117 and 9, SEQ ID NOs: 88 and 9, SEQ ID NOs: 87 and 11, SEQ ID NOs: 85 and 11, SEQ ID NOs: 102 and 11, SEQ ID NOs: 84 and 11, SEQ ID NOs: 85 and 19, SEQ ID NOs: 87 and 19, SEQ ID NOs: 88 and 19, SEQ ID NOs: 89 and 19, SEQ ID NOs: 87 and 39, SEQ ID NOs: 85 and 39, SEQ ID NOs: 2 and 39, SEQ ID NOs: 87 and 61, SEQ ID NOs: 85 and 61, SEQ ID NOs: 88 and 61, SEQ ID NOs: 88 and 7, SEQ ID NOs: 85 and 7, SEQ ID NOs: 87 and 7, SEQ ID NOs: 91 and 7, SEQ ID NOs: 85 and 17, SEQ ID NOs: 87 and 17, SEQ ID NOs: 85 and 22, SEQ ID NOs: 87 and 22, SEQ ID NOs: 117 and 22, SEQ ID NOs: 85 and 26, SEQ ID NOs: 87 and 26, SEQ ID NOs: 84 and 26, SEQ ID NOs: 85 and 74, SEQ ID NOs: 2 and 74, SEQ ID NOs: 87 and 74, SEQ ID NOs: 84 and 74, SEQ ID NOs: 88 and 74, SEQ ID NOs: 85 and 28, and SEQ ID NOs: 84 and 28 as specific combinations of two polynucleotides showed sensitivity of 95% or higher to discriminate early pancreatic cancer or pancreatic cancer precursor lesion patients from healthy subjects in both of the training cohort and the validation cohort. In this way, the 14,079 combinations of the expression level measurement values of the polynucleotides having sensitivity beyond the existing marker CA19-9 (68% from Table 5-2) were obtained in the validation cohort. All of the nucleotide sequences 1 to 226 described in Table 2 obtained in Example 1 were employed at least once in these combinations. These results demonstrated that the combinations of two expression level measurement values comprising at least one of the expression level measurement values of the polynucleotides consisting of the nucleotide sequences represented by SEQ ID NOs: 1 to 226 detect early pancreatic cancer or a pancreatic cancer precursor lesion with sensitivity beyond CA19-9 in the validation cohort.

Thus, markers capable of detecting early pancreatic cancer or a pancreatic cancer precursor lesion with excellent sensitivity are obtained even if 3, 4, 5, 6, 7, 8, 9, 10 or more of the expression level measurement values of the polynucleotides consisting of the nucleotide sequences represented by SEQ ID NOs: 1 to 226 are combined. For example, the polynucleotides consisting of the nucleotide sequences represented by SEQ ID NOs: 1 to 226 selected in Example 1 were ranked in the descending order of their P values which indicate statistical significance, and detection performance was calculated using combinations of one or more miRNAs to which the miRNAs were added one by one from the top to the bottom according to the rank. As a result, the sensitivity in the validation cohort was 69.2% for 2 miRNAs, 80.8% for 5 miRNAs, 92.3% for 10 miRNAs, 96.2% for 20 miRNAs, 100% for 100 miRNAs, and 100% for 226 miRNAs. These values of the sensitivity were higher than the sensitivity of the existing tumor marker in blood, demonstrating that even combinations of a plurality of the miRNAs can serve as excellent markers for the detection of early pancreatic cancer or a pancreatic cancer precursor lesion. In this context, the combinations of a plurality of the miRNAs are not limited to the combinations of the miRNAs added in the order of statistically significant difference as described above, and any combination of a plurality of the miRNAs can be used in the detection of early pancreatic cancer or a pancreatic cancer precursor lesion.

From these results, it can be concluded that all of the polynucleotides consisting of the nucleotide sequences represented by SEQ ID NOs: 1 to 226 serve as excellent diagnostic markers.

Tables 2, 3, 4, 5, 6, and 7 mentioned above are as follows.

TABLE 2

| SEQ ID NO: | Gene name | P value after Bonferroni correction | Change in expression level in early pancreatic cancer and pancreatic cancer precursor lesion patient relative to healthy subject |
|---|---|---|---|
| 1 | hsa-miR-6784-5p | 8.01E−38 | Increase |
| 2 | hsa-miR-1181 | 1.56E−37 | Increase |
| 3 | hsa-miR-671-5p | 4.06E−32 | Decrease |
| 4 | hsa-miR-6857-5p | 1.70E−31 | Increase |
| 5 | hsa-miR-4276 | 2.59E−29 | Increase |
| 6 | hsa-miR-1914-3p | 5.13E−28 | Decrease |
| 7 | hsa-miR-149-3p | 6.76E−25 | Decrease |
| 8 | hsa-miR-937-5p | 1.08E−24 | Decrease |
| 9 | hsa-miR-4675 | 8.93E−24 | Decrease |
| 10 | hsa-miR-6795-5p | 3.80E−23 | Decrease |
| 11 | hsa-miR-4731-5p | 5.78E−23 | Decrease |
| 12 | hsa-miR-5090 | 9.07E−23 | Decrease |
| 13 | hsa-miR-3620-5p | 5.97E−22 | Increase |
| 14 | hsa-miR-1343-5p | 3.10E−21 | Increase |
| 15 | hsa-miR-6717-5p | 1.26E−20 | Decrease |
| 16 | hsa-miR-6825-5p | 3.53E−20 | Increase |
| 17 | hsa-miR-6738-5p | 5.73E−20 | Decrease |
| 18 | hsa-miR-6769a-5p | 6.03E−20 | Decrease |
| 19 | hsa-miR-4728-5p | 6.45E−20 | Decrease |
| 20 | hsa-miR-652-5p | 6.72E−20 | Decrease |
| 21 | hsa-miR-4257 | 9.04E−20 | Decrease |
| 22 | hsa-miR-6785-5p | 1.42E−19 | Decrease |
| 23 | hsa-miR-7110-5p | 2.12E−19 | Increase |
| 24 | hsa-miR-6887-5p | 2.20E−19 | Decrease |
| 25 | hsa-miR-887-3p | 3.36E−19 | Increase |
| 26 | hsa-miR-1228-5p | 8.56E−19 | Increase |
| 27 | hsa-miR-5572 | 3.16E−18 | Increase |
| 28 | hsa-miR-6782-5p | 2.24E−17 | Decrease |
| 29 | hsa-miR-4298 | 2.85E−17 | Decrease |
| 30 | hsa-miR-6786-5p | 1.52E−16 | Increase |
| 31 | hsa-miR-5010-5p | 2.17E−16 | Decrease |
| 32 | hsa-miR-6087 | 9.02E−16 | Increase |
| 33 | hsa-miR-6765-5p | 2.35E−15 | Increase |
| 34 | hsa-miR-6732-5p | 4.15E−15 | Increase |
| 35 | hsa-miR-6787-5p | 9.05E−15 | Decrease |
| 36 | hsa-miR-6737-5p | 9.97E−15 | Increase |
| 37 | hsa-miR-128-2-5p | 1.76E−14 | Decrease |
| 38 | hsa-miR-4270 | 2.27E−14 | Decrease |
| 39 | hsa-miR-6861-5p | 2.90E−14 | Decrease |
| 40 | hsa-miR-6756-5p | 8.32E−14 | Decrease |
| 41 | hsa-miR-1229-5p | 4.69E−13 | Decrease |
| 42 | hsa-miR-6891-5p | 7.35E−13 | Decrease |

TABLE 2-continued

| SEQ ID NO: | Gene name | P value after Bonferroni correction | Change in expression level in early pancreatic cancer and pancreatic cancer precursor lesion patient relative to healthy subject |
|---|---|---|---|
| 43 | hsa-miR-6848-5p | 1.26E−12 | Increase |
| 44 | hsa-miR-1237-5p | 9.08E−12 | Increase |
| 45 | hsa-miR-30c-1-3p | 1.04E−11 | Decrease |
| 46 | hsa-miR-1233-5p | 2.45E−11 | Decrease |
| 47 | hsa-miR-211-3p | 3.35E−11 | Decrease |
| 48 | hsa-miR-4758-5p | 4.39E−11 | Decrease |
| 49 | hsa-miR-614 | 5.53E−11 | Decrease |
| 50 | hsa-miR-6746-5p | 9.72E−11 | Decrease |
| 51 | hsa-miR-1915-5p | 1.53E−10 | Decrease |
| 52 | hsa-miR-4688 | 1.67E−10 | Decrease |
| 53 | hsa-miR-3917 | 2.52E−10 | Decrease |
| 54 | hsa-miR-5787 | 2.64E−10 | Increase |
| 55 | hsa-miR-4632-5p | 2.94E−10 | Increase |
| 56 | hsa-miR-6126 | 3.79E−10 | Increase |
| 57 | hsa-miR-135a-3p | 7.42E−10 | Increase |
| 58 | hsa-miR-8063 | 1.29E−09 | Decrease |
| 59 | hsa-miR-5698 | 3.21E−09 | Decrease |
| 60 | hsa-miR-6089 | 2.31E−08 | Increase |
| 61 | hsa-miR-498 | 2.38E−08 | Decrease |
| 62 | hsa-miR-296-3p | 5.37E−08 | Decrease |
| 63 | hsa-miR-4419b | 1.02E−07 | Decrease |
| 64 | hsa-miR-6802-5p | 1.69E−07 | Decrease |
| 65 | hsa-miR-6829-5p | 2.31E−07 | Decrease |
| 66 | hsa-miR-6803-5p | 3.54E−07 | Increase |
| 67 | hsa-miR-1199-5p | 5.49E−07 | Decrease |
| 68 | hsa-miR-6840-3p | 7.30E−07 | Decrease |
| 69 | hsa-miR-6752-5p | 3.97E−06 | Increase |
| 70 | hsa-miR-6798-5p | 1.85E−05 | Increase |
| 71 | hsa-miR-6131 | 4.80E−05 | Decrease |
| 72 | hsa-miR-4667-5p | 9.09E−05 | Decrease |
| 73 | hsa-miR-6510-5p | 1.04E−04 | Decrease |
| 74 | hsa-miR-4690-5p | 1.22E−04 | Decrease |
| 75 | hsa-miR-920 | 1.49E−04 | Decrease |
| 76 | hsa-miR-23b-3p | 1.85E−04 | Decrease |
| 77 | hsa-miR-4448 | 2.38E−04 | Increase |
| 78 | hsa-miR-2110 | 3.99E−04 | Decrease |
| 79 | hsa-miR-4706 | 5.83E−04 | Decrease |
| 80 | hsa-miR-7845-5p | 2.34E−03 | Increase |
| 81 | hsa-miR-6808-5p | 4.82E−03 | Decrease |
| 82 | hsa-miR-4447 | 5.38E−03 | Decrease |
| 83 | hsa-miR-6869-5p | 6.71E−03 | Increase |
| 84 | hsa-miR-1908-5p | 3.48E−50 | Increase |
| 85 | hsa-miR-6729-5p | 1.20E−47 | Increase |
| 86 | hsa-miR-5195-3p | 4.85E−45 | Decrease |
| 87 | hsa-miR-638 | 6.56E−44 | Increase |
| 88 | hsa-miR-6125 | 2.97E−42 | Increase |
| 89 | hsa-miR-3178 | 3.76E−41 | Increase |
| 90 | hsa-miR-3196 | 2.70E−39 | Increase |
| 91 | hsa-miR-8069 | 3.80E−36 | Increase |
| 92 | hsa-miR-4723-5p | 3.97E−36 | Decrease |
| 93 | hsa-miR-4746-3p | 1.24E−35 | Increase |
| 94 | hsa-miR-4689 | 2.84E−35 | Decrease |
| 95 | hsa-miR-6816-5p | 3.48E−35 | Increase |
| 96 | hsa-miR-6757-5p | 1.20E−34 | Decrease |
| 97 | hsa-miR-7109-5p | 1.21E−34 | Decrease |
| 98 | hsa-miR-6724-5p | 2.96E−34 | Increase |
| 99 | hsa-miR-1225-3p | 2.03E−33 | Increase |
| 100 | hsa-miR-6875-5p | 5.61E−33 | Increase |
| 101 | hsa-miR-7108-5p | 4.48E−32 | Increase |
| 102 | hsa-miR-4508 | 1.03E−31 | Increase |
| 103 | hsa-miR-6085 | 7.30E−30 | Decrease |
| 104 | hsa-miR-6779-5p | 7.94E−30 | Decrease |
| 105 | hsa-miR-642a-3p | 1.28E−28 | Decrease |
| 106 | hsa-miR-4695-5p | 1.37E−28 | Increase |
| 107 | hsa-miR-7847-3p | 1.49E−28 | Decrease |
| 108 | hsa-miR-3197 | 1.08E−27 | Increase |
| 109 | hsa-miR-6769b-5p | 1.82E−27 | Decrease |
| 110 | hsa-miR-7641 | 3.73E−27 | Decrease |
| 111 | hsa-miR-187-5p | 1.45E−26 | Decrease |
| 112 | hsa-miR-3185 | 1.98E−26 | Increase |
| 113 | hsa-miR-2861 | 4.70E−26 | Increase |
| 114 | hsa-miR-3940-5p | 2.68E−25 | Increase |
| 115 | hsa-miR-1203 | 3.13E−25 | Increase |

TABLE 2-continued

| SEQ ID NO: | Gene name | P value after Bonferroni correction | Change in expression level in early pancreatic cancer and pancreatic cancer precursor lesion patient relative to healthy subject |
|---|---|---|---|
| 116 | hsa-miR-615-5p | 9.78E-25 | Decrease |
| 117 | hsa-miR-4787-5p | 4.84E-24 | Increase |
| 118 | hsa-miR-1343-3p | 7.76E-24 | Decrease |
| 119 | hsa-miR-6813-5p | 9.50E-24 | Decrease |
| 120 | hsa-miR-1225-5p | 2.32E-22 | Increase |
| 121 | hsa-miR-602 | 3.00E-22 | Increase |
| 122 | hsa-miR-4488 | 5.30E-22 | Increase |
| 123 | hsa-miR-125a-3p | 1.08E-21 | Decrease |
| 124 | hsa-miR-5100 | 1.58E-21 | Increase |
| 125 | hsa-miR-4294 | 2.49E-21 | Decrease |
| 126 | hsa-miR-1231 | 3.00E-21 | Increase |
| 127 | hsa-miR-6765-3p | 5.05E-21 | Decrease |
| 128 | hsa-miR-4442 | 8.24E-21 | Decrease |
| 129 | hsa-miR-718 | 1.55E-20 | Increase |
| 130 | hsa-miR-6780b-5p | 3.10E-20 | Increase |
| 131 | hsa-miR-6090 | 1.16E-19 | Increase |
| 132 | hsa-miR-6845-5p | 1.52E-19 | Increase |
| 133 | hsa-miR-4741 | 1.58E-19 | Increase |
| 134 | hsa-miR-4467 | 3.00E-19 | Increase |
| 135 | hsa-miR-4707-5p | 3.49E-19 | Increase |
| 136 | hsa-miR-4271 | 1.16E-18 | Decrease |
| 137 | hsa-miR-4673 | 1.20E-18 | Increase |
| 138 | hsa-miR-3184-5p | 1.69E-18 | Increase |
| 139 | hsa-miR-1469 | 1.98E-18 | Increase |
| 140 | hsa-miR-4640-5p | 2.13E-18 | Increase |
| 141 | hsa-miR-663a | 3.70E-18 | Increase |
| 142 | hsa-miR-6791-5p | 9.89E-18 | Increase |
| 143 | hsa-miR-6826-5p | 5.46E-17 | Decrease |
| 144 | hsa-miR-4433b-3p | 1.49E-16 | Increase |
| 145 | hsa-miR-1915-3p | 1.61E-16 | Increase |
| 146 | hsa-miR-4417 | 3.24E-16 | Increase |
| 147 | hsa-miR-4449 | 6.68E-16 | Increase |
| 148 | hsa-miR-4707-3p | 9.83E-16 | Increase |
| 149 | hsa-miR-3180-3p | 1.06E-15 | Increase |
| 150 | hsa-miR-5585-3p | 3.68E-15 | Increase |
| 151 | hsa-miR-1268a | 4.67E-15 | Increase |
| 152 | hsa-miR-8072 | 8.29E-15 | Increase |
| 153 | hsa-miR-296-5p | 1.70E-14 | Decrease |
| 154 | hsa-miR-204-3p | 2.59E-14 | Decrease |
| 155 | hsa-miR-4454 | 2.97E-14 | Decrease |
| 156 | hsa-miR-6722-3p | 3.47E-14 | Increase |
| 157 | hsa-miR-1290 | 5.12E-14 | Increase |
| 158 | hsa-miR-3622a-5p | 5.86E-14 | Decrease |
| 159 | hsa-miR-939-5p | 9.18E-14 | Increase |
| 160 | hsa-miR-675-5p | 1.25E-13 | Decrease |
| 161 | hsa-miR-3131 | 1.26E-13 | Decrease |
| 162 | hsa-miR-4648 | 1.93E-13 | Increase |
| 163 | hsa-miR-1268b | 2.06E-13 | Increase |
| 164 | hsa-miR-6741-5p | 2.25E-13 | Decrease |
| 165 | hsa-miR-6893-5p | 5.59E-13 | Decrease |
| 166 | hsa-miR-3162-5p | 1.01E-12 | Decrease |
| 167 | hsa-miR-642b-3p | 1.51E-12 | Decrease |
| 168 | hsa-miR-4734 | 7.47E-12 | Increase |
| 169 | hsa-miR-150-3p | 3.02E-11 | Decrease |
| 170 | hsa-miR-8089 | 3.88E-11 | Decrease |
| 171 | hsa-miR-6805-3p | 4.65E-11 | Increase |
| 172 | hsa-miR-7113-3p | 6.07E-11 | Increase |
| 173 | hsa-miR-6850-5p | 1.45E-10 | Increase |
| 174 | hsa-miR-6799-5p | 2.02E-10 | Decrease |
| 175 | hsa-miR-6768-5p | 2.10E-10 | Increase |
| 176 | hsa-miR-92b-5p | 2.27E-10 | Increase |
| 177 | hsa-miR-3679-5p | 3.05E-10 | Increase |
| 178 | hsa-miR-4792 | 4.13E-10 | Increase |
| 179 | hsa-miR-3656 | 8.02E-10 | Increase |
| 180 | hsa-miR-92a-2-5p | 9.84E-10 | Increase |
| 181 | hsa-miR-4466 | 1.70E-09 | Increase |
| 182 | hsa-miR-4513 | 1.79E-09 | Decrease |
| 183 | hsa-miR-6781-5p | 2.02E-09 | Increase |
| 184 | hsa-miR-4649-5p | 3.34E-09 | Decrease |
| 185 | hsa-miR-6775-5p | 7.94E-09 | Increase |
| 186 | hsa-miR-4651 | 2.08E-08 | Decrease |
| 187 | hsa-miR-3195 | 4.19E-08 | Increase |
| 188 | hsa-miR-6726-5p | 4.45E-08 | Decrease |
| 189 | hsa-miR-6872-3p | 7.91E-08 | Decrease |
| 190 | hsa-miR-371a-5p | 1.32E-07 | Decrease |
| 191 | hsa-miR-6777-5p | 2.82E-07 | Decrease |
| 192 | hsa-miR-6789-5p | 5.95E-07 | Increase |
| 193 | hsa-miR-7975 | 1.00E-06 | Decrease |
| 194 | hsa-miR-6821-5p | 1.36E-06 | Decrease |
| 195 | hsa-miR-4534 | 5.94E-06 | Decrease |
| 196 | hsa-miR-619-5p | 6.51E-06 | Increase |
| 197 | hsa-miR-7107-5p | 1.06E-05 | Decrease |
| 198 | hsa-miR-1228-3p | 1.07E-05 | Increase |
| 199 | hsa-miR-6774-5p | 1.08E-05 | Decrease |
| 200 | hsa-miR-6805-5p | 1.10E-05 | Increase |
| 201 | hsa-miR-23a-3p | 2.26E-05 | Decrease |
| 202 | hsa-miR-4665-5p | 3.25E-05 | Decrease |
| 203 | hsa-miR-4505 | 7.17E-05 | Increase |
| 204 | hsa-miR-4638-5p | 7.59E-05 | Decrease |
| 205 | hsa-miR-24-3p | 8.75E-05 | Decrease |
| 206 | hsa-miR-3135b | 1.20E-04 | Decrease |
| 207 | hsa-miR-4745-5p | 1.24E-04 | Increase |
| 208 | hsa-miR-128-1-5p | 1.45E-04 | Increase |
| 209 | hsa-miR-4476 | 1.81E-04 | Decrease |
| 210 | hsa-miR-4687-3p | 1.94E-04 | Decrease |
| 211 | hsa-miR-3665 | 2.61E-04 | Increase |
| 212 | hsa-miR-6806-5p | 3.17E-04 | Decrease |
| 213 | hsa-miR-3937 | 3.45E-04 | Increase |
| 214 | hsa-miR-711 | 6.28E-04 | Increase |
| 215 | hsa-miR-3141 | 6.80E-04 | Increase |
| 216 | hsa-miR-3188 | 6.88E-04 | Increase |
| 217 | hsa-miR-4281 | 9.34E-04 | Decrease |
| 218 | hsa-miR-5196-5p | 1.33E-03 | Decrease |
| 219 | hsa-miR-6880-5p | 1.48E-03 | Increase |
| 220 | hsa-miR-3960 | 2.60E-03 | Increase |
| 221 | hsa-miR-3648 | 3.23E-03 | Increase |
| 222 | hsa-miR-6721-5p | 3.69E-03 | Increase |
| 223 | hsa-miR-4492 | 4.89E-03 | Increase |
| 224 | hsa-miR-744-5p | 8.59E-03 | Increase |
| 225 | hsa-miR-7704 | 8.95E-03 | Increase |
| 226 | hsa-miR-4749-5p | 8.96E-03 | Increase |

TABLE 3

| | Training cohort | | | Validation cohort | | |
|---|---|---|---|---|---|---|
| SEQ ID NO: | Accuracy (%) | Sensitivity (%) | Specificity (%) | Accuracy (%) | Sensitivity (%) | Specificity (%) |
| 1 | 89.8 | 96.2 | 87 | 85.1 | 84.6 | 85.2 |
| 2 | 89.8 | 96.2 | 87 | 89.7 | 100 | 85.2 |
| 3 | 87.5 | 86.8 | 87.8 | 94.3 | 92.3 | 95.1 |
| 4 | 88.1 | 96.2 | 84.6 | 90.8 | 92.3 | 90.2 |
| 5 | 88.6 | 94.3 | 86.2 | 85.1 | 88.5 | 83.6 |
| 6 | 88.6 | 86.8 | 89.4 | 89.7 | 84.6 | 91.8 |
| 7 | 84.1 | 86.8 | 82.9 | 92 | 92.3 | 91.8 |

TABLE 3-continued

| | Training cohort | | | Validation cohort | | |
|---|---|---|---|---|---|---|
| SEQ ID NO: | Accuracy (%) | Sensitivity (%) | Specificity (%) | Accuracy (%) | Sensitivity (%) | Specificity (%) |
| 8 | 85.8 | 79.2 | 88.6 | 89.7 | 88.5 | 90.2 |
| 9 | 84.1 | 84.9 | 83.7 | 79.3 | 73.1 | 82 |
| 10 | 85.8 | 84.9 | 86.2 | 86.2 | 88.5 | 85.2 |
| 11 | 84.7 | 88.7 | 82.9 | 81.6 | 76.9 | 83.6 |
| 12 | 86.9 | 92.5 | 84.6 | 83.9 | 76.9 | 86.9 |
| 13 | 85.8 | 94.3 | 82.1 | 83.9 | 88.5 | 82 |
| 14 | 84.7 | 79.2 | 87 | 74.7 | 61.5 | 80.3 |
| 15 | 84.1 | 84.9 | 83.7 | 80.5 | 76.9 | 82 |
| 16 | 83 | 83 | 82.9 | 78.2 | 73.1 | 80.3 |
| 17 | 83 | 77.4 | 85.4 | 80.5 | 73.1 | 83.6 |
| 18 | 85.2 | 90.6 | 82.9 | 85.1 | 92.3 | 82 |
| 19 | 81.2 | 83 | 80.5 | 79.3 | 61.5 | 86.9 |
| 20 | 84.7 | 84.9 | 84.6 | 82.8 | 80.8 | 83.6 |
| 21 | 86.9 | 80.8 | 89.4 | 85.1 | 80.8 | 86.9 |
| 22 | 81.8 | 73.6 | 85.4 | 74.7 | 61.5 | 80.3 |
| 23 | 79.5 | 83 | 78 | 74.7 | 76.9 | 73.8 |
| 24 | 86.9 | 81.1 | 89.4 | 80.5 | 88.5 | 77 |
| 25 | 84.1 | 94.3 | 79.7 | 81.6 | 88.5 | 78.7 |
| 26 | 79.5 | 81.1 | 78.9 | 78.2 | 76.9 | 78.7 |
| 27 | 80.1 | 86.8 | 77.2 | 74.7 | 73.1 | 75.4 |
| 28 | 83 | 81.1 | 83.7 | 89.7 | 92.3 | 88.5 |
| 29 | 78.4 | 75.5 | 79.7 | 79.1 | 61.5 | 86.7 |
| 30 | 78.4 | 73.6 | 80.5 | 83.9 | 80.8 | 85.2 |
| 31 | 79.5 | 83 | 78 | 86.2 | 96.2 | 82 |
| 32 | 79 | 94.3 | 72.4 | 83.9 | 100 | 77 |
| 33 | 80.1 | 81.1 | 79.7 | 77 | 80.8 | 75.4 |
| 34 | 77.8 | 86.8 | 74 | 81.6 | 80.8 | 82 |
| 35 | 79.5 | 84.9 | 77.2 | 82.8 | 88.5 | 80.3 |
| 36 | 81.2 | 84.9 | 79.7 | 79.3 | 76.9 | 80.3 |
| 37 | 77.3 | 71.7 | 79.7 | 75.9 | 61.5 | 82 |
| 38 | 75.6 | 79.2 | 74 | 73.6 | 73.1 | 73.8 |
| 39 | 76.7 | 75.5 | 77.2 | 70.1 | 65.4 | 72.1 |
| 40 | 75 | 75.5 | 74.8 | 74.7 | 80.8 | 72.1 |
| 41 | 73.9 | 71.7 | 74.8 | 83.9 | 92.3 | 80.3 |
| 42 | 79.5 | 69.8 | 83.7 | 75.9 | 73.1 | 77 |
| 43 | 80.7 | 81.1 | 80.5 | 83.9 | 69.2 | 90.2 |
| 44 | 75.6 | 79.2 | 74 | 74.7 | 80.8 | 72.1 |
| 45 | 77.8 | 75.5 | 78.9 | 78.2 | 69.2 | 82 |
| 46 | 75.6 | 77.4 | 74.8 | 67.8 | 61.5 | 70.5 |
| 47 | 76.1 | 86.8 | 71.5 | 72.4 | 65.4 | 75.4 |
| 48 | 75 | 77.4 | 74 | 69 | 69.2 | 68.9 |
| 49 | 74.4 | 71.7 | 75.6 | 69 | 57.7 | 73.8 |
| 50 | 79 | 83 | 77.2 | 79.3 | 84.6 | 77 |
| 51 | 77.8 | 77.4 | 78 | 77 | 76.9 | 77 |
| 52 | 73.9 | 81.1 | 70.7 | 74.7 | 73.1 | 75.4 |
| 53 | 71 | 81.1 | 66.7 | 71.3 | 69.2 | 72.1 |
| 54 | 73.9 | 67.9 | 76.4 | 79.3 | 73.1 | 82 |
| 55 | 78.4 | 62.3 | 85.4 | 74.7 | 61.5 | 80.3 |
| 56 | 73.9 | 67.9 | 76.4 | 72.4 | 73.1 | 72.1 |
| 57 | 77.3 | 86.8 | 73.2 | 74.7 | 80.8 | 72.1 |
| 58 | 73.9 | 73.6 | 74 | 69 | 57.7 | 73.8 |
| 59 | 71.6 | 81.1 | 67.5 | 78.2 | 73.1 | 80.3 |
| 60 | 76.1 | 71.7 | 78 | 77 | 69.2 | 80.3 |
| 61 | 72.7 | 75.5 | 71.5 | 78.2 | 84.6 | 75.4 |
| 62 | 69.9 | 71.7 | 69.1 | 73.6 | 73.1 | 73.8 |
| 63 | 74.4 | 86.8 | 69.1 | 72.4 | 73.1 | 72.1 |
| 64 | 71.6 | 75.5 | 69.9 | 66.7 | 80.8 | 60.7 |
| 65 | 69.9 | 67.9 | 70.7 | 67.8 | 73.1 | 65.6 |
| 66 | 67.6 | 62.3 | 69.9 | 73.6 | 69.2 | 75.4 |
| 67 | 72.2 | 73.6 | 71.5 | 66.7 | 69.2 | 65.6 |
| 68 | 72.2 | 71.7 | 72.4 | 63.2 | 57.7 | 65.6 |
| 69 | 68.2 | 79.2 | 63.4 | 72.4 | 80.8 | 68.9 |
| 70 | 68.8 | 75.5 | 65.9 | 62.1 | 65.4 | 60.7 |
| 71 | 71 | 62.3 | 74.8 | 73.3 | 68 | 75.4 |
| 72 | 67 | 75.5 | 63.4 | 70.1 | 80.8 | 65.6 |
| 73 | 68.8 | 62.3 | 71.5 | 70.1 | 69.2 | 70.5 |
| 74 | 68.8 | 69.8 | 68.3 | 66.7 | 73.1 | 63.9 |
| 75 | 69.3 | 66 | 70.7 | 74.7 | 80.8 | 72.1 |
| 76 | 72.7 | 69.8 | 74 | 73.6 | 57.7 | 80.3 |
| 77 | 64.8 | 73.6 | 61 | 58.6 | 73.1 | 52.5 |
| 78 | 65.9 | 66 | 65.9 | 73.6 | 73.1 | 73.8 |

TABLE 3-continued

| | Training cohort | | | Validation cohort | | |
|---|---|---|---|---|---|---|
| SEQ ID NO: | Accuracy (%) | Sensitivity (%) | Specificity (%) | Accuracy (%) | Sensitivity (%) | Specificity (%) |
| 79 | 72.7 | 83 | 68.3 | 60.9 | 46.2 | 67.2 |
| 80 | 64.8 | 69.8 | 62.6 | 64.4 | 53.8 | 68.9 |
| 81 | 64.2 | 69.8 | 61.8 | 66.7 | 76.9 | 62.3 |
| 82 | 66.5 | 69.8 | 65 | 69 | 76.9 | 65.6 |
| 83 | 60.8 | 52.8 | 64.2 | 70.1 | 65.4 | 72.1 |

TABLE 4

| SEQ ID NO: | Discriminant coefficient | Constant term |
|---|---|---|
| 1 | 3.10 | 39.85 |
| 2 | 2.84 | 16.65 |
| 3 | 2.22 | 13.44 |
| 4 | 1.76 | 10.14 |
| 5 | 2.75 | 16.32 |
| 6 | 3.19 | 22.93 |
| 7 | 6.93 | 64.26 |
| 8 | 3.85 | 31.55 |
| 9 | 2.35 | 17.01 |
| 10 | 2.72 | 16.12 |
| 11 | 3.83 | 24.06 |
| 12 | 3.64 | 27.80 |
| 13 | 3.40 | 27.68 |
| 14 | 3.50 | 36.83 |
| 15 | 1.68 | 9.99 |
| 16 | 2.03 | 13.73 |
| 17 | 2.79 | 19.34 |
| 18 | 2.79 | 17.67 |
| 19 | 3.46 | 23.85 |
| 20 | 2.16 | 12.27 |
| 21 | 1.69 | 11.03 |
| 22 | 2.22 | 19.50 |
| 23 | 1.82 | 14.51 |
| 24 | 2.08 | 13.00 |
| 25 | 2.36 | 17.76 |
| 26 | 4.24 | 50.31 |
| 27 | 2.19 | 15.19 |
| 28 | 2.97 | 17.23 |
| 29 | 2.73 | 15.72 |
| 30 | 4.77 | 60.37 |
| 31 | 2.88 | 16.50 |
| 32 | 3.36 | 40.40 |
| 33 | 4.45 | 47.32 |
| 34 | 3.10 | 26.84 |
| 35 | 2.73 | 22.91 |
| 36 | 3.64 | 26.76 |
| 37 | 2.04 | 21.42 |
| 38 | 3.84 | 30.11 |
| 39 | 2.80 | 20.07 |
| 40 | 3.78 | 31.18 |
| 41 | 3.93 | 28.97 |
| 42 | 3.87 | 27.95 |
| 43 | 3.61 | 27.20 |
| 44 | 4.63 | 58.85 |
| 45 | 1.91 | 10.91 |
| 46 | 2.27 | 24.74 |
| 47 | 2.57 | 15.29 |
| 48 | 5.47 | 46.73 |
| 49 | 1.56 | 10.17 |
| 50 | 1.61 | 10.45 |
| 51 | 1.31 | 7.87 |
| 52 | 3.03 | 21.43 |
| 53 | 1.93 | 11.42 |
| 54 | 3.60 | 47.33 |
| 55 | 2.26 | 18.49 |
| 56 | 2.73 | 29.67 |
| 57 | 1.87 | 14.47 |
| 58 | 2.21 | 18.13 |
| 59 | 2.26 | 13.31 |
| 60 | 5.71 | 76.75 |
| 61 | 2.63 | 15.46 |
| 62 | 1.12 | 6.78 |
| 63 | 1.37 | 8.50 |
| 64 | 3.59 | 30.25 |
| 65 | 2.51 | 15.04 |
| 66 | 4.85 | 54.20 |
| 67 | 2.42 | 15.94 |
| 68 | 2.46 | 21.44 |
| 69 | 3.86 | 43.50 |
| 70 | 2.76 | 28.72 |
| 71 | 1.34 | 13.78 |
| 72 | 2.57 | 15.69 |
| 73 | 2.33 | 14.12 |
| 74 | 2.22 | 13.04 |
| 75 | 1.22 | 6.90 |
| 76 | 1.12 | 6.52 |
| 77 | 1.35 | 7.66 |
| 78 | 2.49 | 14.91 |
| 79 | 2.22 | 17.09 |
| 80 | 2.59 | 17.43 |
| 81 | 2.64 | 17.94 |
| 82 | 1.95 | 11.84 |
| 83 | 3.21 | 44.93 |

TABLE 5-1

| | Training cohort | | | |
|---|---|---|---|---|
| Sample name | Disease | Stage of progression | CEA (ng/mL) | CA19-9 (U/mL) |
| IP013 | IPMC | | 4.6 | 66.6 |
| IP023 | IPMC | | 4.7 | 8 |
| IP063 | IPMC | | 3 | 193.4 |
| IP147 | IPMC | | 3.2 | 183.3 |
| IP148 | IPMC | | 11.9 | 1158 |
| IP149 | IPMA | high grade | 3.6 | 35.6 |
| IP151 | IPMA | high grade | 2.3 | 0.1 |
| IP153 | IPMA | low grade | 3.5 | 4.4 |
| IP154 | IPMA | low grade | 1.8 | 7.2 |
| IP157 | IPMA | high grade | 4 | 0.1 |
| IP159 | IPMC | | 6.1 | 22.8 |
| IP160 | IPMC | | 2.8 | 26.1 |
| IP161 | IPMC | | 2.7 | 16.8 |
| IP166 | IPMA | low grade | 1.1 | 2.9 |
| IP167 | IPMA | high grade | 4.5 | 0.6 |
| IP168 | IPMA | low grade | 2.4 | 17 |
| IP172 | IPMC | | 6.2 | 60.2 |
| IP175 | IPMC | | 7.5 | 2246 |
| IP178 | IPMC | | 1.9 | 30 |
| IP182 | IPMA | high grade | | |
| IP205 | IPMC | | | |
| P_06 | Early pancreatic cancer | 2b | 1.7 | 435.1 |
| P_07 | | 2b | 1 | 149.8 |
| P_09 | | 2b | 3.5 | 22100 |
| P_10 | | 2b | 0.8 | 62 |
| P_11 | | 2a | 2.7 | 0.4 |
| P_13 | | 2a | 4.6 | 66.6 |
| P_15 | | 2a | 2.4 | 735 |
| P_18 | | 2a | 1.9 | 33.6 |
| P_19 | | 2b | 8.9 | 47.1 |
| P_20 | | 2b | 1.7 | 30.3 |

TABLE 5-1-continued

Training cohort

| Sample name | Disease | Stage of progression | CEA (ng/mL) | CA19-9 (U/mL) |
|---|---|---|---|---|
| P_21 | | 2b | 14.8 | 22.3 |
| P_25 | | 2b | 12.1 | 3274 |
| P_27 | | 2b | 4.6 | 282.8 |
| P_29 | | 2a | 1.5 | 37.8 |
| P_30 | | 2a | 1.7 | 20.9 |
| P_31 | | 2a | 2.1 | 387.9 |
| P_32 | | 2a | 1.1 | 15.4 |
| P_33 | | 2b | 3.1 | 160.6 |
| P_35 | | 2b | 0.3 | 9.9 |
| P_40 | | 2b | 1.4 | 221.5 |
| P_42 | | 2b | 34.6 | 168.8 |
| P_45 | | 2b | 9.1 | 569 |
| P_46 | | 2b | 3.3 | 80.5 |
| P_47 | | 2b | 1.8 | 97.5 |
| P_48 | | 2b | 3.1 | 405.7 |
| P_50 | | 2b | 0.9 | 8.1 |
| P_51 | | 2a | 2.3 | 2118 |
| P_54 | | 2b | 1.9 | 250.4 |
| P_56 | | 2b | 3.3 | 1870 |
| P_59 | | 2b | 2.1 | 95.1 |
| P_60 | | 2b | 3.4 | 79.2 |
| Sensitivity (%) | | | 18 | 58 |

TABLE 5-2

Validation cohort

| Sample name | Disease | Stage of progression | CEA (ng/mL) | CA19-9 (U/mL) |
|---|---|---|---|---|
| IP008 | IPMC | | 1.8 | 19.5 |
| IP155 | IPMA | low grade | 1.9 | 18.6 |
| IP156 | IPMA | high grade | 0.7 | 8.8 |
| IP162 | IPMA | high grade | 1.5 | 10.9 |
| IP163 | IPMC | | 3 | 103.4 |
| IP164 | IPMA | high grade | 3.5 | 122.9 |
| IP165 | IPMC | | 5.6 | 401.7 |
| IP169 | IPMC | | 3.1 | 1143 |
| IP170 | IPMA | low grade | 1 | 7.1 |
| IP173 | IPMC | | 2.7 | 51.3 |
| IP174 | IPMC | | 3.9 | 23.2 |
| IP176 | IPMA | low grade | 2.2 | 28.3 |
| P_01 | Early pancreatic cancer | 2b | 4.5 | 55.9 |
| P_02 | | 2b | 2.6 | 327.6 |
| P_04 | | 2b | 4.1 | 950 |
| P_14 | | 2b | 3.2 | 137.8 |
| P_28 | | 2a | 3.8 | 348.8 |
| P_36 | | 2b | 5.2 | 1251 |
| P_52 | | 2b | 2.8 | 41.6 |
| P_53 | | 2b | 4 | 279.9 |
| P_55 | | 2a | 6.4 | 2848 |
| P_57 | | 2b | 5.9 | 454.3 |
| P_58 | | 2a | 2.1 | 0.1 |
| P_61 | | 2b | 10.3 | 283.5 |
| P_62 | | 2b | 4.2 | 268 |
| Sensitivity (%) | | | 20 | 68 |

TABLE 6

| | Training cohort | | | Validation cohort | | |
|---|---|---|---|---|---|---|
| SEQ ID NO: | Accuracy (%) | Sensitivity (%) | Specificity (%) | Accuracy (%) | Sensitivity (%) | Specificity (%) |
| 1_2 | 90.3 | 98.1 | 87 | 87.4 | 92.3 | 85.2 |
| 1_3 | 96.6 | 96.2 | 96.7 | 94.3 | 88.5 | 96.7 |
| 1_4 | 90.3 | 96.2 | 87.8 | 85.1 | 84.6 | 85.2 |
| 1_5 | 92.6 | 96.2 | 91.1 | 87.4 | 88.5 | 86.9 |
| 1_6 | 89.8 | 96.2 | 87 | 83.9 | 84.6 | 83.6 |
| 1_7 | 90.9 | 94.3 | 89.4 | 86.2 | 88.5 | 85.2 |
| 1_8 | 93.2 | 96.2 | 91.9 | 89.7 | 84.6 | 91.8 |
| 1_9 | 89.8 | 96.2 | 87 | 85.1 | 80.8 | 86.9 |
| 1_10 | 93.2 | 94.3 | 92.7 | 88.5 | 88.5 | 88.5 |
| 1_11 | 93.8 | 96.2 | 92.7 | 87.4 | 84.6 | 88.5 |
| 1_12 | 89.8 | 96.2 | 87 | 86.2 | 84.6 | 86.9 |
| 1_13 | 90.3 | 96.2 | 87.8 | 85.1 | 84.6 | 85.2 |
| 1_14 | 89.8 | 96.2 | 87 | 83.9 | 80.8 | 85.2 |
| 1_15 | 94.3 | 92.5 | 95.1 | 90.8 | 80.8 | 95.1 |
| 1_16 | 89.8 | 96.2 | 87 | 85.1 | 84.6 | 85.2 |
| 1_17 | 92 | 96.2 | 90.2 | 83.9 | 84.6 | 83.6 |
| 1_18 | 95.5 | 94.3 | 95.9 | 89.7 | 84.6 | 91.8 |
| 1_19 | 92.6 | 94.3 | 91.9 | 88.5 | 88.5 | 88.5 |
| 1_20 | 95.5 | 94.3 | 95.9 | 93.1 | 88.5 | 95.1 |
| 1_21 | 93.7 | 90.4 | 95.1 | 94.3 | 88.5 | 96.7 |
| 1_22 | 89.2 | 94.3 | 87 | 81.6 | 76.9 | 83.6 |
| 1_23 | 90.3 | 96.2 | 87.8 | 85.1 | 84.6 | 85.2 |
| 1_24 | 95.5 | 94.3 | 95.9 | 90.8 | 88.5 | 91.8 |
| 1_25 | 90.9 | 96.2 | 88.6 | 83.9 | 84.6 | 83.6 |
| 1_26 | 90.9 | 94.3 | 89.4 | 83.9 | 80.8 | 85.2 |
| 1_27 | 90.3 | 96.2 | 87.8 | 85.1 | 84.6 | 85.2 |
| 1_28 | 94.3 | 94.3 | 94.3 | 95.4 | 96.2 | 95.1 |
| 1_29 | 89.8 | 96.2 | 87 | 86 | 80.8 | 88.3 |
| 1_30 | 90.3 | 96.2 | 87.8 | 85.1 | 84.6 | 85.2 |
| 1_31 | 90.9 | 96.2 | 88.6 | 87.4 | 84.6 | 88.5 |
| 1_32 | 89.2 | 96.2 | 86.2 | 85.1 | 84.6 | 85.2 |
| 1_33 | 90.3 | 96.2 | 87.8 | 85.1 | 84.6 | 85.2 |
| 1_34 | 89.8 | 96.2 | 87 | 85.1 | 84.6 | 85.2 |
| 1_35 | 92 | 94.3 | 91.1 | 87.4 | 88.5 | 86.9 |
| 1_36 | 89.8 | 96.2 | 87 | 85.1 | 84.6 | 85.2 |
| 1_37 | 88.6 | 96.2 | 85.4 | 85.1 | 84.6 | 85.2 |
| 1_38 | 89.8 | 96.2 | 87 | 85.1 | 84.6 | 85.2 |
| 1_39 | 93.2 | 94.3 | 92.7 | 85.1 | 80.8 | 86.9 |

TABLE 6-continued

| SEQ ID NO: | Training cohort ||| Validation cohort |||
| --- | --- | --- | --- | --- | --- | --- |
| | Accuracy (%) | Sensitivity (%) | Specificity (%) | Accuracy (%) | Sensitivity (%) | Specificity (%) |
| 1_40 | 92.6 | 94.3 | 91.9 | 83.9 | 80.8 | 85.2 |
| 1_41 | 89.8 | 96.2 | 87 | 83.9 | 88.5 | 82 |
| 1_42 | 90.3 | 96.2 | 87.8 | 88.5 | 88.5 | 88.5 |
| 1_43 | 89.8 | 96.2 | 87 | 85.1 | 84.6 | 85.2 |
| 1_44 | 90.3 | 96.2 | 87.8 | 85.1 | 84.6 | 85.2 |
| 1_45 | 89.2 | 96.2 | 86.2 | 83.9 | 84.6 | 83.6 |
| 1_46 | 91.5 | 96.2 | 89.4 | 85.1 | 84.6 | 85.2 |
| 1_47 | 90.9 | 94.3 | 89.4 | 82.8 | 80.8 | 83.6 |
| 1_48 | 92 | 94.3 | 91.1 | 82.8 | 80.8 | 83.6 |
| 1_49 | 90.3 | 96.2 | 87.8 | 85.1 | 84.6 | 85.2 |
| 1_50 | 94.3 | 92.5 | 95.1 | 90.8 | 84.6 | 93.4 |
| 1_51 | 89.2 | 96.2 | 86.2 | 85.1 | 84.6 | 85.2 |
| 1_52 | 92 | 94.3 | 91.1 | 85.1 | 84.6 | 85.2 |
| 1_53 | 93.2 | 94.3 | 92.7 | 88.5 | 84.6 | 90.2 |
| 1_54 | 91.5 | 96.2 | 89.4 | 85.1 | 84.6 | 85.2 |
| 1_55 | 89.2 | 96.2 | 86.2 | 85.1 | 84.6 | 85.2 |
| 1_56 | 90.3 | 96.2 | 87.8 | 85.1 | 84.6 | 85.2 |
| 1_57 | 89.8 | 96.2 | 87 | 82.8 | 84.6 | 82 |
| 1_58 | 90.3 | 96.2 | 87.8 | 85.1 | 84.6 | 85.2 |
| 1_59 | 90.9 | 94.3 | 89.4 | 85.1 | 84.6 | 85.2 |
| 1_60 | 90.3 | 96.2 | 87.8 | 85.1 | 84.6 | 85.2 |
| 1_61 | 93.2 | 94.3 | 92.7 | 89.7 | 84.6 | 91.8 |
| 1_62 | 93.8 | 92.5 | 94.3 | 93.1 | 88.5 | 95.1 |
| 1_63 | 94.9 | 94.3 | 95.1 | 89.7 | 80.8 | 93.4 |
| 1_64 | 91.5 | 94.3 | 90.2 | 82.8 | 80.8 | 83.6 |
| 1_65 | 92.6 | 94.3 | 91.9 | 89.7 | 84.6 | 91.8 |
| 1_66 | 89.2 | 96.2 | 86.2 | 85.1 | 84.6 | 85.2 |
| 1_67 | 89.2 | 96.2 | 86.2 | 85.1 | 84.6 | 85.2 |
| 1_68 | 89.8 | 96.2 | 87 | 85.1 | 84.6 | 85.2 |
| 1_69 | 93.2 | 94.3 | 92.7 | 87.4 | 84.6 | 88.5 |
| 1_70 | 89.8 | 94.3 | 87.8 | 85.1 | 84.6 | 85.2 |
| 1_71 | 89.8 | 96.2 | 87 | 84.9 | 84 | 85.2 |
| 1_72 | 93.2 | 94.3 | 92.7 | 90.8 | 84.6 | 93.4 |
| 1_73 | 89.8 | 96.2 | 87 | 83.9 | 84.6 | 83.6 |
| 1_74 | 92 | 94.3 | 91.1 | 87.4 | 88.5 | 86.9 |
| 1_75 | 92 | 96.2 | 90.2 | 83.9 | 76.9 | 86.9 |
| 1_76 | 90.3 | 96.2 | 87.8 | 85.1 | 84.6 | 85.2 |
| 1_77 | 91.5 | 96.2 | 89.4 | 83.9 | 84.6 | 83.6 |
| 1_78 | 90.9 | 96.2 | 88.6 | 83.9 | 84.6 | 83.6 |
| 1_79 | 89.8 | 96.2 | 87 | 83.9 | 84.6 | 83.6 |
| 1_80 | 91.5 | 96.2 | 89.4 | 85.1 | 84.6 | 85.2 |
| 1_81 | 93.2 | 94.3 | 92.7 | 87.4 | 84.6 | 88.5 |
| 1_82 | 94.3 | 94.3 | 94.3 | 86.2 | 80.8 | 88.5 |
| 1_83 | 91.5 | 96.2 | 89.4 | 85.1 | 84.6 | 85.2 |
| 1_84 | 95.5 | 100 | 93.5 | 90.8 | 96.2 | 88.5 |
| 1_85 | 97.2 | 100 | 95.9 | 97.7 | 100 | 96.7 |
| 1_86 | 96.6 | 96.2 | 96.7 | 93.1 | 84.6 | 96.7 |
| 1_87 | 96.6 | 100 | 95.1 | 95.4 | 100 | 93.4 |
| 1_88 | 96.6 | 98.1 | 95.9 | 93.1 | 92.3 | 93.4 |
| 1_89 | 96 | 98.1 | 95.1 | 89.7 | 88.5 | 90.2 |
| 1_90 | 92.6 | 100 | 89.4 | 92 | 100 | 88.5 |
| 1_91 | 94.9 | 96.2 | 94.3 | 90.8 | 88.5 | 91.8 |
| 1_92 | 94.9 | 92.5 | 95.9 | 95.4 | 96.2 | 95.1 |
| 1_93 | 93.2 | 96.2 | 91.9 | 88.5 | 84.6 | 90.2 |
| 1_94 | 94.3 | 96.2 | 93.5 | 90.8 | 84.6 | 93.4 |
| 1_95 | 89.2 | 96.2 | 86.2 | 85.1 | 84.6 | 85.2 |
| 1_96 | 94.3 | 92.5 | 95.1 | 90.8 | 84.6 | 93.4 |
| 1_97 | 94.3 | 96.2 | 93.5 | 90.8 | 96.2 | 88.5 |
| 1_98 | 95.5 | 96.2 | 95.1 | 93.1 | 88.5 | 95.1 |
| 1_99 | 92 | 96.2 | 90.2 | 85.1 | 88.5 | 83.6 |
| 1_100 | 89.2 | 96.2 | 86.2 | 85.1 | 84.6 | 85.2 |
| 1_101 | 90.3 | 96.2 | 87.8 | 88.5 | 88.5 | 88.5 |
| 1_102 | 96 | 98.1 | 95.1 | 90.8 | 92.3 | 90.2 |
| 1_103 | 92 | 96.2 | 90.2 | 87.4 | 84.6 | 88.5 |
| 1_104 | 94.3 | 94.3 | 94.3 | 87.4 | 80.8 | 90.2 |
| 1_105 | 94.9 | 94.3 | 95.1 | 94.3 | 88.5 | 96.7 |
| 1_106 | 88.6 | 96.2 | 85.4 | 87.2 | 88 | 86.9 |
| 1_107 | 94.3 | 94.3 | 94.3 | 85.1 | 76.9 | 88.5 |
| 1_108 | 89.2 | 96.2 | 86.2 | 83.9 | 80.8 | 85.2 |
| 1_109 | 96 | 94.3 | 96.7 | 94.3 | 88.5 | 96.7 |
| 1_110 | 88.6 | 96.2 | 85.4 | 85.1 | 84.6 | 85.2 |
| 1_111 | 93.8 | 96.2 | 92.7 | 89.7 | 80.8 | 93.4 |
| 1_112 | 90.3 | 96.2 | 87.8 | 86.2 | 80.8 | 88.5 |
| 1_113 | 92 | 96.2 | 90.2 | 87.4 | 88.5 | 86.9 |
| 1_114 | 90.3 | 96.2 | 87.8 | 85.1 | 84.6 | 85.2 |

TABLE 6-continued

| | Training cohort | | | Validation cohort | | |
|---|---|---|---|---|---|---|
| SEQ ID NO: | Accuracy (%) | Sensitivity (%) | Specificity (%) | Accuracy (%) | Sensitivity (%) | Specificity (%) |
| 1_115 | 93.8 | 96.2 | 92.7 | 92 | 96.2 | 90.2 |
| 1_116 | 92 | 96.2 | 90.2 | 88.5 | 80.8 | 91.8 |
| 1_117 | 96.6 | 96.2 | 96.7 | 88.5 | 88.5 | 88.5 |
| 1_118 | 93.2 | 94.3 | 92.7 | 87.4 | 88.5 | 86.9 |
| 1_119 | 89.8 | 96.2 | 87 | 87.4 | 84.6 | 88.5 |
| 1_120 | 89.8 | 96.2 | 87 | 85.1 | 84.6 | 85.2 |
| 1_121 | 93.8 | 94.3 | 93.5 | 92 | 96.2 | 90.2 |
| 1_122 | 92 | 96.2 | 90.2 | 85.1 | 88.5 | 83.6 |
| 1_123 | 90.3 | 94.3 | 88.6 | 89.7 | 84.6 | 91.8 |
| 1_124 | 88.6 | 96.2 | 85.4 | 83.9 | 84.6 | 83.6 |
| 1_125 | 96 | 92.5 | 97.6 | 92 | 92.3 | 91.8 |
| 1_126 | 89.2 | 96.2 | 86.2 | 86.2 | 88.5 | 85.2 |
| 1_127 | 92 | 94.3 | 91.1 | 83.9 | 80.8 | 85.2 |
| 1_128 | 88.6 | 96.2 | 85.4 | 85.1 | 84.6 | 85.2 |
| 1_129 | 94.9 | 100 | 92.7 | 94.3 | 96.2 | 93.4 |
| 1_130 | 89.2 | 96.2 | 86.2 | 86.2 | 88.5 | 85.2 |
| 1_131 | 90.9 | 96.2 | 88.6 | 87.4 | 88.5 | 86.9 |
| 1_132 | 91.5 | 94.3 | 90.2 | 87.4 | 88.5 | 86.9 |
| 1_133 | 92 | 96.2 | 90.2 | 87.4 | 88.5 | 86.9 |
| 1_134 | 91.5 | 96.2 | 89.4 | 85.1 | 84.6 | 85.2 |
| 1_135 | 90.9 | 96.2 | 88.6 | 88.5 | 88.5 | 88.5 |
| 1_136 | 88.1 | 96.2 | 84.6 | 83.9 | 84.6 | 83.6 |
| 1_137 | 90.9 | 96.2 | 88.6 | 88.5 | 84.6 | 90.2 |
| 1_138 | 89.2 | 96.2 | 86.2 | 85.1 | 84.6 | 85.2 |
| 1_139 | 90.3 | 96.2 | 87.8 | 86.2 | 88.5 | 85.2 |
| 1_140 | 92.6 | 96.2 | 91.1 | 87.4 | 88.5 | 86.9 |
| 1_141 | 96 | 100 | 94.3 | 92 | 96.2 | 90.2 |
| 1_142 | 92 | 96.2 | 90.2 | 85.1 | 84.6 | 85.2 |
| 1_143 | 93.8 | 94.3 | 93.5 | 92 | 84.6 | 95.1 |
| 1_144 | 89.8 | 94.3 | 87.8 | 85.1 | 84.6 | 85.2 |
| 1_145 | 92.6 | 94.3 | 91.9 | 86.2 | 84.6 | 86.9 |
| 1_146 | 90.3 | 96.2 | 87.8 | 85.1 | 84.6 | 85.2 |
| 1_147 | 92.6 | 96.2 | 91.1 | 89.7 | 96.2 | 86.9 |
| 1_148 | 89.8 | 96.2 | 87 | 85.1 | 84.6 | 85.2 |
| 1_149 | 89.2 | 96.2 | 86.2 | 85.1 | 84.6 | 85.2 |
| 1_150 | 92.6 | 94.3 | 91.9 | 86.2 | 88.5 | 85.2 |
| 1_151 | 90.3 | 96.2 | 87.8 | 85.1 | 84.6 | 85.2 |
| 1_152 | 93.2 | 96.2 | 91.9 | 89.7 | 88.5 | 90.2 |
| 1_153 | 89.8 | 96.2 | 87 | 87.4 | 84.6 | 88.5 |
| 1_154 | 89.2 | 96.2 | 86.2 | 85.1 | 88.5 | 83.6 |
| 1_155 | 91.4 | 96.2 | 89.3 | 85.1 | 84.6 | 85.2 |
| 1_156 | 89.2 | 96.2 | 86.2 | 85.1 | 84.6 | 85.2 |
| 1_157 | 91.5 | 96.2 | 89.4 | 83.9 | 84.6 | 83.6 |
| 1_158 | 90.3 | 94.3 | 88.6 | 85.1 | 88.5 | 83.6 |
| 1_159 | 89.8 | 96.2 | 87 | 85.1 | 84.6 | 85.2 |
| 1_160 | 92 | 94.3 | 91.1 | 85.1 | 80.8 | 86.9 |
| 1_161 | 96 | 94.3 | 96.7 | 92 | 88.5 | 93.4 |
| 1_162 | 89.8 | 96.2 | 87 | 85.1 | 84.6 | 85.2 |
| 1_163 | 90.3 | 96.2 | 87.8 | 85.1 | 84.6 | 85.2 |
| 1_164 | 93.8 | 94.3 | 93.5 | 90.8 | 84.6 | 93.4 |
| 1_165 | 90.3 | 96.2 | 87.8 | 85.1 | 84.6 | 85.2 |
| 1_166 | 94.3 | 92.5 | 95.1 | 90.8 | 84.6 | 93.4 |
| 1_167 | 89.8 | 96.2 | 87 | 85.1 | 84.6 | 85.2 |
| 1_168 | 93.2 | 96.2 | 91.9 | 88.5 | 88.5 | 88.5 |
| 1_169 | 89.8 | 96.2 | 87 | 85.1 | 88.5 | 83.6 |
| 1_170 | 89.8 | 96.2 | 87 | 82.8 | 84.6 | 82 |
| 1_171 | 89.8 | 96.2 | 87 | 85.1 | 84.6 | 85.2 |
| 1_172 | 90.3 | 96.2 | 87.8 | 85.1 | 84.6 | 85.2 |
| 1_173 | 92 | 96.2 | 90.2 | 86.2 | 88.5 | 85.2 |
| 1_174 | 91.4 | 96.2 | 89.4 | 86.2 | 88.5 | 85.2 |
| 1_175 | 89.8 | 96.2 | 87 | 85.1 | 84.6 | 85.2 |
| 1_176 | 89.2 | 96.2 | 86.2 | 85.1 | 84.6 | 85.2 |
| 1_177 | 90.3 | 96.2 | 87.8 | 86.2 | 88.5 | 85.2 |
| 1_178 | 92.6 | 94.3 | 91.9 | 85.1 | 84.6 | 85.2 |
| 1_179 | 91.5 | 96.2 | 89.4 | 87.4 | 88.5 | 86.9 |
| 1_180 | 90.3 | 94.3 | 88.6 | 83.9 | 84.6 | 83.6 |
| 1_181 | 92 | 96.2 | 90.2 | 86.2 | 88.5 | 85.2 |
| 1_182 | 91.5 | 94.3 | 90.2 | 87.4 | 88.5 | 86.9 |
| 1_183 | 89.8 | 96.2 | 87 | 85.1 | 84.6 | 85.2 |
| 1_184 | 89.2 | 96.2 | 86.2 | 85.1 | 84.6 | 85.2 |
| 1_185 | 89.8 | 96.2 | 87 | 85.1 | 84.6 | 85.2 |
| 1_186 | 88.6 | 96.2 | 85.4 | 85.1 | 84.6 | 85.2 |
| 1_187 | 90.3 | 94.3 | 88.6 | 85.1 | 84.6 | 85.2 |
| 1_188 | 88.6 | 96.2 | 85.4 | 85.1 | 84.6 | 85.2 |
| 1_189 | 89.2 | 94.3 | 87 | 82.8 | 80.8 | 83.6 |

TABLE 6-continued

| | Training cohort | | | Validation cohort | | |
|---|---|---|---|---|---|---|
| SEQ ID NO: | Accuracy (%) | Sensitivity (%) | Specificity (%) | Accuracy (%) | Sensitivity (%) | Specificity (%) |
| 1_190 | 93.2 | 94.3 | 92.7 | 88.5 | 84.6 | 90.2 |
| 1_191 | 89.8 | 92.5 | 88.6 | 86.2 | 88.5 | 85.2 |
| 1_192 | 94.3 | 96.2 | 93.5 | 89.7 | 88.5 | 90.2 |
| 1_193 | 88.6 | 94.3 | 86.2 | 83.9 | 84.6 | 83.6 |
| 1_194 | 92.6 | 92.5 | 92.7 | 90.8 | 84.6 | 93.4 |
| 1_195 | 94.3 | 96.2 | 93.5 | 86.2 | 76.9 | 90.2 |
| 1_196 | 92 | 94.3 | 91.1 | 86.2 | 88.5 | 85.2 |
| 1_197 | 89.8 | 96.2 | 87 | 82.8 | 84.6 | 82 |
| 1_198 | 89.8 | 96.2 | 87 | 85.1 | 84.6 | 85.2 |
| 1_199 | 92.6 | 96.2 | 91.1 | 90.8 | 80.8 | 95.1 |
| 1_200 | 90.3 | 96.2 | 87.8 | 85.1 | 84.6 | 85.2 |
| 1_201 | 90.9 | 96.2 | 88.6 | 85.1 | 84.6 | 85.2 |
| 1_202 | 89.8 | 96.2 | 87 | 85.1 | 84.6 | 85.2 |
| 1_203 | 89.8 | 96.2 | 87 | 85.1 | 80.8 | 86.9 |
| 1_204 | 91.5 | 96.2 | 89.4 | 85.1 | 84.6 | 85.2 |
| 1_205 | 93.2 | 92.5 | 93.5 | 89.7 | 88.5 | 90.2 |
| 1_206 | 89.2 | 96.2 | 86.2 | 85.1 | 84.6 | 85.2 |
| 1_207 | 92 | 96.2 | 90.2 | 89.7 | 84.6 | 91.8 |
| 1_208 | 89.8 | 94.3 | 87.8 | 85.1 | 84.6 | 85.2 |
| 1_209 | 89.2 | 96.2 | 86.2 | 82.8 | 84.6 | 82 |
| 1_210 | 93.2 | 96.2 | 91.9 | 88.5 | 84.6 | 90.2 |
| 1_211 | 90.9 | 96.2 | 88.6 | 85.1 | 84.6 | 85.2 |
| 1_212 | 90.9 | 96.2 | 88.6 | 85.1 | 84.6 | 85.2 |
| 1_213 | 89.8 | 96.2 | 87 | 85.1 | 84.6 | 85.2 |
| 1_214 | 89.2 | 94.3 | 87 | 85.1 | 84.6 | 85.2 |
| 1_215 | 89.8 | 96.2 | 87 | 85.1 | 84.6 | 85.2 |
| 1_216 | 89.1 | 96.2 | 86.2 | 85.1 | 84.6 | 85.2 |
| 1_217 | 88.6 | 96.2 | 85.4 | 83.9 | 84.6 | 83.6 |
| 1_218 | 89.8 | 96.2 | 87 | 85.1 | 84.6 | 85.2 |
| 1_219 | 90.3 | 96.2 | 87.8 | 85.1 | 84.6 | 85.2 |
| 1_220 | 90.3 | 96.2 | 87.8 | 85.1 | 84.6 | 85.2 |
| 1_221 | 93.8 | 94.3 | 93.5 | 86.2 | 84.6 | 86.9 |
| 1_222 | 89.8 | 94.3 | 87.8 | 85.1 | 84.6 | 85.2 |
| 1_223 | 91.4 | 96.2 | 89.3 | 85.1 | 84.6 | 85.2 |
| 1_224 | 88.6 | 96.2 | 85.4 | 85.1 | 84.6 | 85.2 |
| 1_225 | 90.9 | 96.2 | 88.6 | 85.1 | 84.6 | 85.2 |
| 1_226 | 91.5 | 96.2 | 89.4 | 85.1 | 84.6 | 85.2 |

TABLE 7

| | Training cohort | | | Validation cohort | | |
|---|---|---|---|---|---|---|
| SEQ ID NO: | Accuracy (%) | Sensitivity (%) | Specificity (%) | Accuracy (%) | Sensitivity (%) | Specificity (%) |
| 2_18 | 98.9 | 100 | 98.4 | 97.7 | 100 | 96.7 |
| 2_53 | 98.9 | 98.1 | 99.2 | 97.7 | 100 | 96.7 |
| 2_20 | 98.9 | 96.2 | 100 | 98.9 | 100 | 98.4 |
| 2_3 | 98.3 | 98.1 | 98.4 | 98.9 | 100 | 98.4 |
| 2_50 | 98.3 | 98.1 | 98.4 | 98.9 | 100 | 98.4 |
| 85_3 | 98.9 | 100 | 98.4 | 100 | 100 | 100 |
| 84_3 | 98.9 | 98.1 | 99.2 | 97.7 | 100 | 96.7 |
| 90_3 | 98.3 | 100 | 97.6 | 98.9 | 100 | 98.4 |
| 87_3 | 97.7 | 100 | 96.7 | 98.9 | 100 | 98.4 |
| 3_137 | 97.7 | 94.3 | 99.2 | 100 | 100 | 100 |
| 90_18 | 99.4 | 100 | 99.2 | 97.7 | 100 | 96.7 |
| 87_18 | 98.9 | 98.1 | 99.2 | 98.9 | 100 | 98.4 |
| 89_18 | 98.3 | 96.2 | 99.2 | 98.9 | 100 | 98.4 |
| 18_137 | 98.3 | 94.3 | 100 | 98.9 | 96.2 | 100 |
| 84_18 | 97.7 | 98.1 | 97.6 | 96.6 | 100 | 95.1 |
| 86_12 | 97.2 | 96.2 | 97.6 | 97.7 | 92.3 | 100 |
| 109_12 | 97.2 | 96.2 | 97.6 | 96.6 | 92.3 | 98.4 |
| 85_12 | 96.6 | 100 | 95.1 | 97.7 | 100 | 96.7 |
| 88_12 | 96.6 | 100 | 95.1 | 94.3 | 92.3 | 95.1 |
| 105_12 | 96.6 | 98.1 | 95.9 | 97.7 | 92.3 | 100 |
| 85_20 | 98.3 | 100 | 97.6 | 100 | 100 | 100 |
| 84_20 | 98.3 | 98.1 | 98.4 | 97.7 | 100 | 96.7 |
| 106_20 | 98.3 | 98.1 | 98.4 | 97.7 | 92 | 100 |
| 90_20 | 97.7 | 100 | 96.7 | 98.9 | 100 | 98.4 |
| 87_20 | 97.7 | 98.1 | 97.6 | 96.6 | 100 | 95.1 |
| 87_15 | 98.9 | 100 | 98.4 | 98.9 | 100 | 98.4 |
| 85_15 | 98.3 | 96.2 | 99.2 | 100 | 100 | 100 |

TABLE 7-continued

| SEQ ID NO: | Training cohort | | | Validation cohort | | |
| --- | --- | --- | --- | --- | --- | --- |
| | Accuracy (%) | Sensitivity (%) | Specificity (%) | Accuracy (%) | Sensitivity (%) | Specificity (%) |
| 2_15 | 97.7 | 98.1 | 97.6 | 97.7 | 100 | 96.7 |
| 88_15 | 97.2 | 94.3 | 98.4 | 100 | 100 | 100 |
| 15_137 | 97.2 | 94.3 | 98.4 | 97.7 | 96.2 | 98.4 |
| 85_50 | 98.3 | 98.1 | 98.4 | 100 | 100 | 100 |
| 87_50 | 97.7 | 100 | 96.7 | 97.7 | 100 | 96.7 |
| 84_50 | 97.7 | 98.1 | 97.6 | 97.7 | 100 | 96.7 |
| 106_50 | 97.7 | 96.2 | 98.4 | 98.8 | 96 | 100 |
| 90_50 | 97.2 | 98.1 | 96.7 | 97.7 | 100 | 96.7 |
| 2_63 | 98.3 | 98.1 | 98.4 | 100 | 100 | 100 |
| 85_63 | 97.7 | 100 | 96.7 | 100 | 100 | 100 |
| 90_63 | 97.7 | 100 | 96.7 | 97.7 | 100 | 96.7 |
| 84_63 | 97.7 | 98.1 | 97.6 | 94.3 | 92.3 | 95.1 |
| 87_63 | 97.2 | 100 | 95.9 | 97.7 | 100 | 96.7 |
| 84_72 | 98.3 | 100 | 97.6 | 97.7 | 100 | 96.7 |
| 85_72 | 97.7 | 100 | 96.7 | 100 | 100 | 100 |
| 88_72 | 97.7 | 100 | 96.7 | 97.7 | 96.2 | 98.4 |
| 87_72 | 97.7 | 98.1 | 97.6 | 98.9 | 100 | 98.4 |
| 93_72 | 97.7 | 98.1 | 97.6 | 94.3 | 92.3 | 95.1 |
| 94_5 | 98.3 | 96.2 | 99.2 | 94.3 | 92.3 | 95.1 |
| 85_5 | 97.7 | 98.1 | 97.6 | 97.7 | 100 | 96.7 |
| 87_5 | 97.2 | 100 | 95.9 | 94.3 | 100 | 91.8 |
| 5_107 | 97.2 | 94.3 | 98.4 | 93.1 | 84.6 | 96.7 |
| 84_5 | 96.6 | 100 | 95.1 | 93.1 | 96.2 | 91.8 |
| 85_24 | 97.2 | 94.3 | 98.4 | 100 | 100 | 100 |
| 87_24 | 96.6 | 94.3 | 97.6 | 97.7 | 100 | 96.7 |
| 89_24 | 96.6 | 94.3 | 97.6 | 96.6 | 92.3 | 98.4 |
| 90_24 | 96.6 | 92.5 | 98.4 | 98.9 | 100 | 98.4 |
| 102_24 | 96.6 | 92.5 | 98.4 | 97.7 | 100 | 96.7 |
| 85_10 | 97.7 | 96.2 | 98.4 | 100 | 100 | 100 |
| 87_10 | 97.7 | 94.3 | 99.2 | 98.9 | 100 | 98.4 |
| 90_10 | 97.2 | 96.2 | 97.6 | 96.6 | 96.2 | 96.7 |
| 88_10 | 97.2 | 92.5 | 99.2 | 100 | 100 | 100 |
| 2_10 | 96.6 | 94.3 | 97.6 | 96.6 | 96.2 | 96.7 |
| 85_52 | 98.3 | 100 | 97.6 | 97.7 | 100 | 96.7 |
| 88_52 | 98.3 | 100 | 97.6 | 100 | 100 | 100 |
| 87_52 | 97.7 | 100 | 96.7 | 94.3 | 100 | 91.8 |
| 98_52 | 97.7 | 98.1 | 97.6 | 96.6 | 96.2 | 96.7 |
| 84_52 | 97.2 | 98.1 | 96.7 | 94.3 | 96.2 | 93.4 |
| 87_9 | 98.3 | 100 | 97.6 | 95.4 | 100 | 93.4 |
| 89_9 | 97.7 | 100 | 96.7 | 93.1 | 92.3 | 93.4 |
| 85_9 | 97.2 | 100 | 95.9 | 96.6 | 96.2 | 96.7 |
| 117_9 | 97.2 | 98.1 | 96.7 | 97.7 | 100 | 96.7 |
| 88_9 | 96.6 | 98.1 | 95.9 | 94.3 | 96.2 | 93.4 |
| 87_11 | 98.3 | 100 | 97.6 | 95.4 | 100 | 93.4 |
| 85_11 | 98.3 | 98.1 | 98.4 | 98.9 | 100 | 98.4 |
| 89_11 | 98.3 | 98.1 | 98.4 | 93.1 | 92.3 | 93.4 |
| 102_11 | 98.3 | 98.1 | 98.4 | 98.9 | 100 | 98.4 |
| 84_11 | 97.7 | 98.1 | 97.6 | 94.3 | 96.2 | 93.4 |
| 85_19 | 98.9 | 100 | 98.4 | 98.9 | 96.2 | 100 |
| 87_19 | 98.3 | 100 | 97.6 | 97.7 | 100 | 96.7 |
| 88_19 | 98.3 | 100 | 97.6 | 98.9 | 96.2 | 100 |
| 89_19 | 97.7 | 100 | 96.7 | 97.7 | 96.2 | 98.4 |
| 106_19 | 97.2 | 98.1 | 96.7 | 95.3 | 92 | 96.7 |
| 87_39 | 98.9 | 100 | 98.4 | 98.9 | 100 | 98.4 |
| 85_39 | 97.7 | 98.1 | 97.6 | 98.9 | 96.2 | 100 |
| 88_39 | 97.2 | 96.2 | 97.6 | 96.6 | 92.3 | 98.4 |
| 84_39 | 96.6 | 98.1 | 95.9 | 94.3 | 92.3 | 95.1 |
| 2_39 | 96.6 | 98.1 | 95.9 | 97.7 | 100 | 96.7 |
| 87_61 | 97.2 | 100 | 95.9 | 98.9 | 100 | 98.4 |
| 85_61 | 96.6 | 98.1 | 95.9 | 100 | 100 | 100 |
| 88_61 | 96.6 | 98.1 | 95.9 | 100 | 100 | 100 |
| 108_61 | 96 | 94.3 | 96.7 | 86.2 | 73.1 | 91.8 |
| 93_61 | 96 | 92.5 | 97.6 | 94.3 | 84.6 | 98.4 |
| 88_7 | 97.7 | 100 | 96.7 | 100 | 100 | 100 |
| 85_7 | 97.2 | 100 | 95.9 | 100 | 100 | 100 |
| 87_7 | 97.2 | 100 | 95.9 | 97.7 | 100 | 96.7 |
| 86_7 | 97.2 | 96.2 | 97.6 | 97.7 | 92.3 | 100 |
| 91_7 | 96.6 | 96.2 | 96.7 | 98.9 | 100 | 98.4 |
| 85_17 | 98.3 | 100 | 97.6 | 97.7 | 100 | 96.7 |
| 87_17 | 97.7 | 100 | 96.7 | 95.4 | 100 | 93.4 |
| 89_17 | 96.6 | 94.3 | 97.6 | 94.3 | 88.5 | 96.7 |
| 102_17 | 96.6 | 94.3 | 97.6 | 97.7 | 96.2 | 98.4 |
| 84_17 | 96 | 100 | 94.3 | 93.1 | 92.3 | 93.4 |
| 85_22 | 98.9 | 100 | 98.4 | 97.7 | 96.2 | 98.4 |
| 87_22 | 98.9 | 100 | 98.4 | 98.9 | 100 | 98.4 |

TABLE 7-continued

| | Training cohort | | | Validation cohort | | |
|---|---|---|---|---|---|---|
| SEQ ID NO: | Accuracy (%) | Sensitivity (%) | Specificity (%) | Accuracy (%) | Sensitivity (%) | Specificity (%) |
| 102_22 | 97.7 | 96.2 | 98.4 | 94.3 | 84.6 | 98.4 |
| 89_22 | 97.2 | 98.1 | 96.7 | 93.1 | 88.5 | 95.1 |
| 117_22 | 97.2 | 96.2 | 97.6 | 95.4 | 96.2 | 95.1 |
| 85_26 | 98.9 | 100 | 98.4 | 96.6 | 96.2 | 96.7 |
| 87_26 | 98.3 | 100 | 97.6 | 96.6 | 100 | 95.1 |
| 88_26 | 97.2 | 100 | 95.9 | 95.4 | 92.3 | 96.7 |
| 84_26 | 96 | 100 | 94.3 | 95.4 | 100 | 93.4 |
| 94_26 | 96 | 98.1 | 95.1 | 90.8 | 88.5 | 91.8 |
| 85_74 | 98.9 | 100 | 98.4 | 100 | 100 | 100 |
| 2_74 | 97.7 | 100 | 96.7 | 97.7 | 100 | 96.7 |
| 87_74 | 97.2 | 100 | 95.9 | 97.7 | 100 | 96.7 |
| 84_74 | 96.6 | 96.2 | 96.7 | 95.4 | 100 | 93.4 |
| 88_74 | 96.6 | 96.2 | 96.7 | 97.7 | 100 | 96.7 |
| 90_21 | 97.1 | 94.2 | 98.4 | 98.9 | 100 | 98.4 |
| 2_21 | 97.1 | 94.2 | 98.4 | 97.7 | 96.2 | 98.4 |
| 106_21 | 97.1 | 92.3 | 99.2 | 97.7 | 92 | 100 |
| 84_21 | 96.6 | 94.2 | 97.6 | 96.6 | 100 | 95.1 |
| 85_21 | 96.6 | 92.3 | 98.4 | 100 | 100 | 100 |
| 85_28 | 97.7 | 98.1 | 97.6 | 100 | 100 | 100 |
| 84_28 | 97.2 | 96.2 | 97.6 | 96.6 | 100 | 95.1 |
| 86_28 | 96.6 | 94.3 | 97.6 | 96.6 | 92.3 | 98.4 |
| 87_28 | 96.6 | 94.3 | 97.6 | 98.9 | 100 | 98.4 |
| 93_28 | 96.6 | 92.5 | 98.4 | 100 | 100 | 100 |

Example 3

<Selection of Gene Markers Using all Samples and Method for Evaluating Early Pancreatic Cancer or Pancreatic Cancer Precursor Lesion Discriminant Performance of Acquired Gene Markers>

In this Example, the samples of the training cohort and the validation cohort used in Examples 1 and 2 were integrated, and selection of a gene marker and evaluation of its early pancreatic cancer or pancreatic cancer precursor lesion discriminant performance were conducted using all of the samples.

Specifically, the miRNA expression levels in the sera of the pancreatic cancer precursor lesion patients (33 persons), early pancreatic cancer patients (44 persons) and the healthy subjects (184 persons) obtained in the preceding Reference Examples were normalized by global normalization. In order to acquire diagnosis markers with higher reliability, only genes having a gene expression level of $2^6$ or higher in 50% or more of the samples in either of the early pancreatic cancer or pancreatic cancer precursor lesion patient group or the healthy subject group were selected in the gene marker selection. In order to further acquire statistical significance for discriminating an early pancreatic cancer or pancreatic cancer precursor lesion patient group from a healthy subject group, the P value obtained by two-tailed t-test assuming equal variance as to each gene expression level was corrected by the Bonferroni method, and genes that satisfied p<0.01 were selected as gene markers for use in explanatory variables of a discriminant and described in Table 8. In this way, hsa-miR-6794-5p, hsa-miR-6511a-5p, hsa-miR-6824-5p, hsa-miR-762, hsa-miR-6836-3p, hsa-miR-6727-5p, hsa-miR-4739, hsa-miR-7977, hsa-miR-4484, hsa-miR-6515-3p, hsa-miR-373-5p, hsa-miR-4258, hsa-miR-4674, hsa-miR-3180, hsa-miR-6076, hsa-miR-1238-5p, hsa-miR-4463, hsa-miR-4486, and hsa-miR-4730 genes, and the nucleotide sequences of SEQ ID NOs: 227 to 245 related thereto were found in addition to the genes described in Table 2. As with the nucleotide sequences of SEQ ID NOs: 1 to 226, the results obtained about the polynucleotides shown in SEQ ID NOs: 227 to 245 also showed that the measurement values were significantly lower (decrease) or higher (increase) in the early pancreatic cancer or pancreatic cancer precursor lesion patient group than in the healthy subject group (Table 8). These results were able to be validated in the validation cohort. Thus, the presence or absence of early pancreatic cancer or pancreatic cancer precursor lesion in the newly obtained samples can be determined by the methods described in Examples 1 and 2 by using, alone or in combination, the gene expression level measurement values described in Table 8.

TABLE 8

| SEQ ID NO: | Gene name | P value after Bonferroni correction | Change in expression level in early pancreatic cancer and pancreatic cancer precursor lesion patient relative to healthy subject |
|---|---|---|---|
| 227 | hsa-miR-6794-5p | 1.19E–03 | Decrease |
| 228 | hsa-miR-6511a-5p | 1.44E–03 | Decrease |
| 229 | hsa-miR-6824-5p | 2.18E–03 | Decrease |
| 230 | hsa-miR-762 | 2.05E–07 | Increase |
| 231 | hsa-miR-6836-3p | 9.60E–07 | Increase |
| 232 | hsa-miR-6727-5p | 1.30E–06 | Increase |
| 233 | hsa-miR-4739 | 5.12E–06 | Increase |
| 234 | hsa-miR-7977 | 1.01E–05 | Decrease |
| 235 | hsa-miR-4484 | 1.38E–05 | Increase |
| 236 | hsa-miR-6515-3p | 4.31E–04 | Decrease |
| 237 | hsa-miR-373-5p | 6.79E–04 | Increase |
| 238 | hsa-miR-4258 | 9.00E–04 | Increase |
| 239 | hsa-miR-4674 | 9.95E–04 | Increase |
| 240 | hsa-miR-3180 | 1.43E–03 | Increase |
| 241 | hsa-miR-6076 | 2.65E–03 | Decrease |
| 242 | hsa-miR-1238-5p | 2.77E–03 | Decrease |
| 243 | hsa-miR-4463 | 3.16E–03 | Increase |
| 244 | hsa-miR-4486 | 6.37E–03 | Increase |
| 245 | hsa-miR-4730 | 9.34E–03 | Increase |

Example 4

<Method for Evaluating Early Pancreatic Cancer or Pancreatic Cancer Precursor Lesion-Specific Discriminant Performance by Combination of Plurality of Gene Markers Using Samples of Validation Cohort>

In this Example, gene expression levels of miRNAs in sera were compared between a pancreatic cancer precursor lesion patient group and an early pancreatic cancer patient group as positive control groups and a healthy subject group, an advanced pancreatic cancer patient group, a bile duct cancer patient group, a breast cancer patient group, a prostate cancer patient group, a colorectal cancer patient group, a stomach cancer patient group, an esophageal cancer patient group, a liver cancer patient group, a benign pancreatic disease patient group, and a benign prostatic disease patient group as negative control groups in the same way as the method described in Example 1 with respect to the training cohort as the sample group described in Reference Example 2 to select an additional gene marker for diagnosis. The additional gene marker for diagnosis (SEQ ID NOs: 246 to 247) thus selected was combined with the gene markers selected in Example 1 to study a method for evaluating early pancreatic cancer or pancreatic cancer precursor lesion-specific discriminant performance.

Specifically, first, the miRNA expression levels of the training cohort and the validation cohort obtained in Reference Example 2 mentioned above were combined and normalized by global normalization. Next, Fisher's discriminant analysis was conducted as to combinations of 1 to 5 expression level measurement values comprising at least one of the expression level measurement values of the newly found polynucleotides consisting of the nucleotide sequences represented by SEQ ID NOs: 1 to 83, 227 to 229, 246, 248, and 250 among the polynucleotides consisting of the nucleotide sequences represented by SEQ ID NOs: 1 to 250, to construct a discriminant for determining the presence or absence of early pancreatic cancer or a pancreatic cancer precursor lesion. Next, accuracy, sensitivity, and specificity in the validation cohort were calculated using the discriminant thus prepared, with the pancreatic cancer precursor lesion patient group and the early pancreatic cancer patient group as positive control groups and the healthy subject group, the advanced pancreatic cancer patient group, the bile duct cancer patient group, the breast cancer patient group, the prostate cancer patient group, the colorectal cancer patient group, the stomach cancer patient group, the esophageal cancer patient group, the liver cancer patient group, the benign pancreatic disease patient group, and the benign prostatic disease patient group as negative sample groups. The discriminant performance of the selected polynucleotides was validated using independent samples.

Most of polynucleotides consisting of the nucleotide sequences represented by these SEQ ID NOs (SEQ ID NOs: 1 to 250 corresponding to the miRNA markers of Table 1) or complementary sequences thereof mentioned above were able to provide relatively high accuracy, sensitivity, and specificity in the determination of the presence or absence of early pancreatic cancer or a pancreatic cancer precursor lesion, and furthermore, were able to specifically discriminate early pancreatic cancer or a pancreatic cancer precursor lesion from the other cancers and benign diseases. For example, among the combinations of multiple polynucleotides selected from the group consisting of polynucleotides consisting of the nucleotide sequences represented by SEQ ID NOs: 119, 12, 28, 105, 137, 121, 109, 87, 5, 140, 106, 2, 175, 90, 237, 247, 103, 97, 124, 92, 100, 32, 1, 246, 84, 13, 85, 153, 111, 86, 141, 54, and 24 or complementary sequences thereof (the cancer type-specific polynucleotide group 1) as polynucleotides capable of specifically binding to target markers, combinations comprising at least one polynucleotides preferably selected from the group consisting of polynucleotides consisting of the nucleotide sequences represented by SEQ ID NOs: 119, 12, 28, 105, 137, 121, 109, 87, 5, 140, 106, 2, 175, 90, 237, and 247 or complementary sequences thereof (the cancer type-specific polynucleotide group 2) included in the cancer type-specific polynucleotide group 1 were able to specifically discriminate early pancreatic cancer or a pancreatic cancer precursor lesion from the other cancers and benign diseases with high accuracy.

The number of the polynucleotides with cancer type specificity in the combination mentioned above can be 1, 2, 3, 4, 5, 6, 7, 8, 9, 10 or more for the combination. The combinations of 4 or more of these polynucleotides were able to exhibit discrimination accuracy of 92% or higher or 95% or higher.

The probes used in the measurement were the above-defined nucleic acids capable of specifically binding to each polynucleotide as a target marker.

Specifically, the discrimination results of the measurement using the polynucleotide consisting of the nucleotide sequence represented by SEQ ID NO: 12 or a complementary sequence thereof as a target marker are shown in Table 9-1. The measurement using one polynucleotide consisting of the nucleotide sequence represented by SEQ ID NO: 12 or a complementary sequence thereof exhibited accuracy of 82.6% in the training cohort and accuracy of 82% in the validation cohort. Also, for example, the measurement using the combination of two polynucleotides comprising one polynucleotide consisting of the nucleotide sequence represented by SEQ ID NO: 12 or a complementary sequence thereof exhibited accuracy of 87% in the training cohort and accuracy of 88% in the validation cohort. Furthermore, for example, the measurement using the combination of three polynucleotides comprising one polynucleotide consisting of the nucleotide sequence represented by SEQ ID NO: 12 or a complementary sequence thereof exhibited accuracy of 91.4% in the training cohort and accuracy of 86.6% in the validation cohort. Furthermore, for example, the measurement using the combination of four polynucleotides comprising one polynucleotide consisting of the nucleotide sequence represented by SEQ ID NO: 12 or a complementary sequence thereof exhibited accuracy of 95.6% in the training cohort and accuracy of 95.1% in the validation cohort. Furthermore, for example, the measurement using the combination of five polynucleotides comprising one polynucleotide consisting of the nucleotide sequence represented by SEQ ID NO: 12 or a complementary sequence thereof exhibited the highest accuracy of 98.8% in the training cohort and the highest accuracy of 98.9% in the validation cohort.

Specifically, the discrimination results of the measurement using the polynucleotide consisting of the nucleotide sequence represented by SEQ ID NO: 28 or a complementary sequence thereof as a target marker are shown in Table 9-2. The measurement using one polynucleotide consisting of the nucleotide sequence represented by SEQ ID NO: 28 or a complementary sequence thereof exhibited accuracy of 81.6% in the training cohort and accuracy of 81.7% in the validation cohort. Also, for example, the measurement using the combination of two polynucleotides comprising one polynucleotide consisting of the nucleotide sequence represented by SEQ ID NO: 28 or a complementary sequence thereof exhibited accuracy of 84.9% in the training cohort and accuracy of 85.6% in the validation cohort. Furthermore, for example, the measurement using the combination of three polynucleotides comprising one polynucleotide consisting of the nucleotide sequence represented by SEQ ID NO: 28 or a complementary sequence thereof exhibited accuracy of 88.8% in the training cohort and accuracy of 86.3% in the validation cohort. Furthermore, for example, the measurement using the combination of four polynucleotides comprising one polynucleotide consisting of the nucleotide sequence represented by SEQ ID NO: 28 or a complementary sequence thereof exhibited accuracy of 92.4% in the training cohort and accuracy of 93.6% in the validation cohort. Furthermore, for example, the measurement using the combination of five polynucleotides comprising one polynucleotide consisting of the nucleotide sequence represented by SEQ ID NO: 28 or a complementary sequence thereof exhibited the highest accuracy of 97.7% in the training cohort and the highest accuracy of 98.6% in the validation cohort.

Specifically, the discrimination results of the measurement using the polynucleotide consisting of the nucleotide sequence represented by SEQ ID NO: 5 or a complementary sequence thereof as a target marker are shown in Table 9-3. The measurement using one polynucleotide consisting of the nucleotide sequence represented by SEQ ID NO: 5 or a complementary sequence thereof exhibited accuracy of 84% in the training cohort and accuracy of 87% in the validation cohort. Also, for example, the measurement using the combination of two polynucleotides comprising one polynucleotide consisting of the nucleotide sequence represented by SEQ ID NO: 5 or a complementary sequence thereof exhibited accuracy of 87.9% in the training cohort and accuracy of 88.4% in the validation cohort. Furthermore, for example, the measurement using the combination of three polynucleotides comprising one polynucleotide consisting of the nucleotide sequence represented by SEQ ID NO: 5 or a complementary sequence thereof exhibited accuracy of 90.4% in the training cohort and accuracy of 90.5% in the validation cohort. Furthermore, for example, the measurement using the combination of four polynucleotides comprising one polynucleotide consisting of the nucleotide sequence represented by SEQ ID NO: 5 or a complementary sequence thereof exhibited accuracy of 93.2% in the training cohort and accuracy of 93.7% in the validation cohort. Furthermore, for example, the measurement using the combination of five polynucleotides comprising one polynucleotide consisting of the nucleotide sequence represented by SEQ ID NO: 5 or a complementary sequence thereof exhibited the highest accuracy of 97.7% in the training cohort and the highest accuracy of 98.2% in the validation cohort.

Specifically, the discrimination results of the measurement using the polynucleotide consisting of the nucleotide sequence represented by SEQ ID NO: 2 or a complementary sequence thereof as a target marker are shown in Table 9-4. The measurement using one polynucleotide consisting of the nucleotide sequence represented by SEQ ID NO: 2 or a complementary sequence thereof exhibited accuracy of 86.8% in the training cohort and accuracy of 90.5% in the validation cohort. Also, for example, the measurement using the combination of two polynucleotides comprising one polynucleotide consisting of the nucleotide sequence represented by SEQ ID NO: 2 or a complementary sequence thereof exhibited accuracy of 88.4% in the training cohort and accuracy of 90.1% in the validation cohort. Furthermore, for example, the measurement using the combination of three polynucleotides comprising one polynucleotide consisting of the nucleotide sequence represented by SEQ ID NO: 2 or a complementary sequence thereof exhibited accuracy of 90.9% in the training cohort and accuracy of 92.6% in the validation cohort. Furthermore, for example, the measurement using the combination of four polynucleotides comprising one polynucleotide consisting of the nucleotide sequence represented by SEQ ID NO: 2 or a complementary sequence thereof exhibited accuracy of 93% in the training cohort and accuracy of 92.6% in the validation cohort. Furthermore, for example, the measurement using the combination of five polynucleotides comprising one polynucleotide consisting of the nucleotide sequence represented by SEQ ID NO: 2 or a complementary sequence thereof exhibited the highest accuracy of 97.7% in the training cohort and the highest accuracy of 98.2% in the validation cohort.

Specifically, the discrimination results of the measurement using the polynucleotides consisting of the nucleotide sequences represented by SEQ ID NOs: 12 and 28 or complementary sequences thereof as target markers are shown in Table 9-5. The measurement using the combination of two polynucleotides comprising the polynucleotides consisting of the nucleotide sequences represented by SEQ ID NOs: 12 and 28 or complementary sequences thereof exhibited accuracy of 90% in the training cohort and accuracy of 92.6% in the validation cohort. Also, for example, the measurement using the combination of three polynucleotides comprising the polynucleotides consisting of the nucleotide sequences represented by SEQ ID NOs: 12 and 28 or complementary sequences thereof exhibited accuracy of 92.3% in the training cohort and accuracy of 93.3% in the validation cohort. Furthermore, for example, the measurement using the combination of four polynucleotides comprising the polynucleotides consisting of the nucleotide sequences represented by SEQ ID NOs: 12 and 28 or complementary sequences thereof exhibited accuracy of 93.9% in the training cohort and accuracy of 93.7% in the validation cohort. Furthermore, for example, the measurement using the combination of five polynucleotides comprising the polynucleotides consisting of the nucleotide sequences represented by SEQ ID NOs: 12 and 28 or complementary sequences thereof exhibited the highest accuracy of 97.9% in the training cohort and the highest accuracy of 97.9% in the validation cohort.

Specifically, the discrimination results of the measurement using the polynucleotides consisting of the nucleotide sequences represented by SEQ ID NOs: 12 and 5 or complementary sequences thereof as target markers are shown in Table 9-6. The measurement using the combination of two polynucleotides comprising the polynucleotides consisting of the nucleotide sequences represented by SEQ ID NOs: 12 and 5 or complementary sequences thereof exhibited accuracy of 91.2% in the training cohort and accuracy of 89.4% in the validation cohort. Also, for example, the measurement using the combination of three polynucleotides comprising the polynucleotides consisting of the nucleotide sequences represented by SEQ ID NOs: 12 and 5 or complementary sequences thereof exhibited accuracy of 93% in the training cohort and accuracy of 92.6% in the validation cohort. Furthermore, for example, the measurement using the combination of four polynucleotides comprising the polynucleotides consisting of the nucleotide sequences represented by SEQ ID NOs: 12 and 5 or complementary sequences thereof exhibited accuracy of 95.1% in the training cohort and accuracy of 93% in the validation cohort. Furthermore, for example, the measurement using the combination of five polynucleotides comprising the polynucleotides consisting of the nucleotide sequences represented by SEQ ID NOs: 12 and 5 or complementary sequences thereof exhibited the highest accuracy of 98.1% in the training cohort and the highest accuracy of 97.9% in the validation cohort.

Specifically, the discrimination results of the measurement using the polynucleotides consisting of the nucleotide sequences represented by SEQ ID NOs: 12 and 2 or complementary sequences thereof as target markers are shown in Table 9-7. The measurement using the combination of two polynucleotides comprising the polynucleotides consisting of the nucleotide sequences represented by SEQ ID NOs: 12 and 2 or complementary sequences thereof exhibited accuracy of 91.2% in the training cohort and accuracy of 90.1% in the validation cohort. Also, for example, the measurement using the combination of three polynucleotides comprising the polynucleotides consisting of the nucleotide sequences represented by SEQ ID NOs: 12 and 2 or complementary sequences thereof exhibited accuracy of 93.9% in the training cohort and accuracy of 92.6% in the validation cohort. Furthermore, for example, the measurement using the combination of four polynucleotides comprising the polynucleotides consisting of the nucleotide sequences represented by SEQ ID NOs: 12 and 2 or complementary sequences thereof exhibited accuracy of 94.6% in the training cohort and accuracy of 93.3% in the validation cohort. Furthermore, for example, the measurement using the combination of five polynucleotides comprising the polynucleotides consisting of the nucleotide sequences represented by SEQ ID NOs: 12 and 2 or complementary sequences thereof exhibited the highest accuracy of 98.1% in the training cohort and the highest accuracy of 97.9% in the validation cohort.

Specifically, the discrimination results of the measurement using the polynucleotides consisting of the nucleotide sequences represented by SEQ ID NOs: 5 and 2 or complementary sequences thereof as target markers are shown in Table 9-8. The measurement using the combination of two polynucleotides comprising the polynucleotides consisting of the nucleotide sequences represented by SEQ ID NOs: 5 and 2 or complementary sequences thereof exhibited accuracy of 89.8% in the training cohort and accuracy of 92.3% in the validation cohort. Also, for example, the measurement using the combination of three polynucleotides comprising the polynucleotides consisting of the nucleotide sequences represented by SEQ ID NOs: 5 and 2 or complementary sequences thereof exhibited accuracy of 92.1% in the training cohort and accuracy of 94% in the validation cohort. Furthermore, for example, the measurement using the combination of four polynucleotides comprising the polynucleotides consisting of the nucleotide sequences represented by SEQ ID NOs: 5 and 2 or complementary sequences thereof exhibited accuracy of 93.9% in the training cohort and accuracy of 95.1% in the validation cohort. Furthermore, for example, the measurement using the combination of five polynucleotides comprising the polynucleotides consisting of the nucleotide sequences represented by SEQ ID NOs: 5 and 2 or complementary sequences thereof exhibited the highest accuracy of 97.2% in the training cohort and the highest accuracy of 97.9% in the validation cohort.

Specifically, the discrimination results of the measurement using the polynucleotides consisting of the nucleotide sequences represented by SEQ ID NOs: 12, 28, and 5 or complementary sequences thereof as target markers are shown in Table 9-9. The measurement using the combination of three polynucleotides comprising the polynucleotides consisting of the nucleotide sequences represented by SEQ ID NOs: 12, 28, and 5 or complementary sequences thereof exhibited accuracy of 93.3% in the training cohort and accuracy of 94.4% in the validation cohort. Also, for example, the measurement using the combination of four polynucleotides comprising the polynucleotides consisting of the nucleotide sequences represented by SEQ ID NOs: 12, 28, and 5 or complementary sequences thereof exhibited accuracy of 94.6% in the training cohort and accuracy of 96.5% in the validation cohort. Furthermore, for example, the measurement using the combination of five polynucleotides comprising the polynucleotides consisting of the nucleotide sequences represented by SEQ ID NOs: 12, 28, and 5 or complementary sequences thereof exhibited accuracy of 97.5% in the training cohort and accuracy of 96.8% in the validation cohort.

Figure 4:
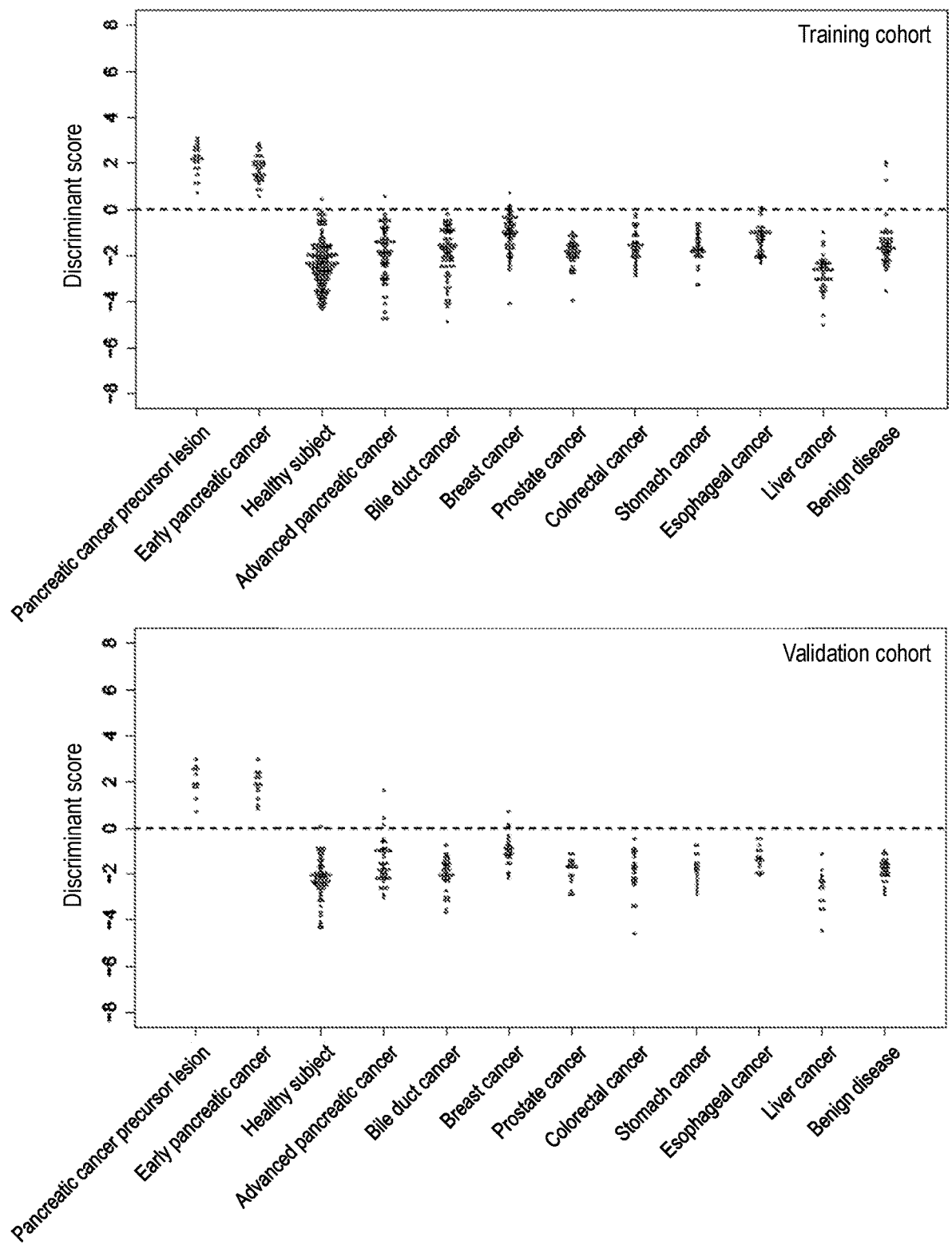
FIG. 4 In the top diagram of FIG. 4, a discriminant (0.48×hsa-miR-4695-5p−1.75×hsa-miR-5090+1.31×hsa-miR-4673−0.98×hsa-miR-6813-5p−1.16×hsa-miR-642a-3p+15.39) was prepared by use of Fisher's discriminant analysis from the expression level measurement values of hsa-miR-4695-5p (SEQ ID NO: 106), hsa-miR-5090 (SEQ ID NO: 12), hsa-miR-4673 (SEQ ID NO: 137), hsa-miR-6813-5p (SEQ ID NO: 119), and hsa-miR-642a-3p (SEQ ID NO: 105) in 21 pancreatic cancer precursor lesion patients, 31 early pancreatic cancer patients, 128 healthy subjects, 61 advanced pancreatic cancer patients, 66 bile duct cancer patients, 51 breast cancer patients, 35 prostate cancer patients, 31 colorectal cancer patients, 32 stomach cancer patients, 34 esophageal cancer patients, 38 liver cancer patients, 15 benign pancreatic disease patients, and 26 benign prostatic disease patients selected as a training cohort, and discriminant scores obtained with the discriminant are plotted on the vertical axis with the cohort plotted on the horizontal axis. The dotted line in the diagram depicts a discriminant boundary on which the discriminant score is 0 and by which the two groups are discriminated. In the bottom diagram of FIG. 4, the vertical axis plots discriminant scores for the expression level measurement values of hsa-miR-4695-5p (SEQ ID NO: 106), hsa-miR-5090 (SEQ ID NO: 12), hsa-miR-4673 (SEQ ID NO: 137), hsa-miR-6813-5p (SEQ ID NO: 119), and hsa-miR-642a-3p (SEQ ID NO: 105) in 12 pancreatic cancer precursor lesion patients, 13 early pancreatic cancer patients, 56 healthy subjects, 39 advanced pancreatic cancer patients, 32 bile duct cancer patients, 23 breast cancer patients, 17 prostate cancer patients, 19 colorectal cancer patients, 18 stomach cancer patients, 16 esophageal cancer patients, 14 liver cancer patients, and 24 benign pancreatic and prostatic disease patients selected as a validation cohort, wherein the discriminant scores are obtained with the discriminant prepared from the training cohort, and the horizontal axis plots the cohort. The dotted line in the diagram depicts a discriminant boundary on which the discriminant score is 0 and by which the two groups are discriminated.

The expression level measurement values of the nucleotide sequences represented by SEQ ID NOs: 106, 12, 137, 119, and 105 were compared among 21 pancreatic cancer precursor lesion patients, 31 early pancreatic cancer patients, 128 healthy subjects, 61 advanced pancreatic cancer patients, 66 bile duct cancer patients, 51 breast cancer patients, 35 prostate cancer patients, 31 colorectal cancer patients, 32 stomach cancer patients, 34 esophageal cancer patients, 38 liver cancer patients, 15 benign pancreatic disease patients, and 26 benign prostatic disease patients in the training cohort. As a result, a scatter diagram that significantly separated the discriminant score of the early pancreatic cancer or pancreatic cancer precursor lesion patient group from the discriminant scores of the other groups was obtained in the training cohort (see the upper diagram of FIG. 4). These results were also reproducible in the validation cohort (see the lower diagram of FIG. 4).

TABLE 9-1

| SEQ ID NO: | Training cohort | | | Validation cohort | | |
|---|---|---|---|---|---|---|
| | Accuracy (%) | Sensitivity (%) | Specificity (%) | Accuracy (%) | Sensitivity (%) | Specificity (%) |
| 12 | 82.6 | 90.6 | 81.8 | 82 | 76.9 | 82.6 |
| 12_237 | 87 | 96.2 | 86.1 | 88 | 92.3 | 87.6 |
| 12_85_13 | 91.4 | 100 | 90.5 | 86.6 | 84.6 | 86.8 |
| 90_12_97_140 | 95.6 | 100 | 95.2 | 95.1 | 96.2 | 95 |
| 12_137_119_105_237 | 98.4 | 100 | 98.3 | 97.9 | 100 | 97.7 |
| 87_12_137_119_105 | 98.2 | 100 | 98.1 | 97.5 | 100 | 97.3 |
| 12_103_137_105_247 | 98.2 | 100 | 98.1 | 98.6 | 100 | 98.4 |
| 12_137_119_92_105 | 98.2 | 100 | 98.1 | 97.9 | 100 | 97.7 |
| 12_137_119_105_121 | 98.2 | 100 | 98.1 | 98.2 | 100 | 98.1 |
| 12_137_1_119_105 | 98.1 | 100 | 97.9 | 97.9 | 100 | 97.7 |
| 12_137_119_124_105 | 98.1 | 100 | 97.9 | 97.9 | 100 | 97.7 |
| 12_137_119_105_32 | 98.1 | 100 | 97.9 | 98.2 | 100 | 98.1 |
| 12_137_119_105_100 | 98.1 | 100 | 97.9 | 97.9 | 100 | 97.7 |
| 12_137_119_105_86 | 98.1 | 100 | 97.9 | 97.9 | 100 | 97.7 |
| 12_137_119_105_153 | 98.1 | 100 | 97.9 | 98.6 | 100 | 98.4 |
| 12_137_119_105_141 | 98.1 | 100 | 97.9 | 97.5 | 100 | 97.3 |

TABLE 9-1-continued

| | Training cohort | | | Validation cohort | | |
|---|---|---|---|---|---|---|
| SEQ ID NO: | Accuracy (%) | Sensitivity (%) | Specificity (%) | Accuracy (%) | Sensitivity (%) | Specificity (%) |
| 12_137_105_246_153 | 98.1 | 100 | 97.9 | 97.2 | 100 | 96.9 |
| 12_97_137_105_153 | 97.9 | 100 | 97.7 | 96.8 | 100 | 96.5 |
| 12_103_137_119_105 | 97.9 | 100 | 97.7 | 97.9 | 100 | 97.7 |
| 12_137_119_105_246 | 97.9 | 100 | 97.7 | 98.2 | 100 | 98.1 |
| 12_137_92_105_247 | 97.9 | 100 | 97.7 | 98.2 | 100 | 98.1 |
| 12_137_124_105_153 | 97.9 | 100 | 97.7 | 97.5 | 100 | 97.3 |
| 12_137_105_32_153 | 97.9 | 100 | 97.7 | 97.5 | 100 | 97.3 |
| 12_137_105_13_121 | 97.9 | 100 | 97.7 | 97.5 | 100 | 97.3 |
| 106_12_137_119_105 | 98.8 | 100 | 98.6 | 97.5 | 100 | 97.3 |
| 12_137_119_105_13 | 98.6 | 100 | 98.4 | 97.9 | 100 | 97.7 |
| 12_137_119_105_140 | 98.6 | 100 | 98.4 | 97.9 | 100 | 97.7 |
| 12_137_119_105_247 | 98.6 | 100 | 98.4 | 98.9 | 100 | 98.8 |
| 12_137_119_105_109 | 98.4 | 100 | 98.3 | 97.5 | 100 | 97.3 |
| 12_137_105_109_121 | 98.1 | 100 | 97.9 | 97.5 | 100 | 97.3 |
| 12_103_137_105_121 | 97.9 | 100 | 97.7 | 97.9 | 100 | 97.7 |
| 12_137_105_32_121 | 97.9 | 100 | 97.7 | 97.9 | 100 | 97.7 |
| 12_137_124_105_247 | 98.1 | 100 | 97.9 | 97.5 | 100 | 97.3 |
| 12_137_105_246_247 | 98.1 | 100 | 97.9 | 97.2 | 100 | 96.9 |
| 12_137_105_153_247 | 98.1 | 100 | 97.9 | 97.5 | 100 | 97.3 |
| 12_137_105_247_141 | 98.1 | 100 | 97.9 | 97.2 | 100 | 96.9 |
| 12_137_105_247 | 97.9 | 100 | 97.7 | 97.2 | 100 | 96.9 |
| 12_137_105_140_247 | 98.1 | 100 | 97.9 | 97.9 | 100 | 97.7 |
| 12_119_124_105_140 | 98.1 | 100 | 97.9 | 97.5 | 100 | 97.3 |
| 12_119_105_100_140 | 98.1 | 100 | 97.9 | 96.8 | 96.2 | 96.9 |
| 90_12_119_105_140 | 97.7 | 100 | 97.5 | 97.9 | 100 | 97.7 |
| 90_12_137_119_105 | 97.9 | 100 | 97.7 | 98.2 | 100 | 98.1 |
| 90_12_137_105_32 | 97.9 | 100 | 97.7 | 97.2 | 100 | 96.9 |
| 90_12_137_105_153 | 97.9 | 100 | 97.7 | 96.8 | 100 | 96.5 |
| 90_12_119_105_100 | 97.7 | 100 | 97.5 | 97.2 | 96.2 | 97.3 |
| 90_12_119_109_140 | 97.7 | 100 | 97.5 | 97.2 | 100 | 96.9 |
| 87_12_137_105_247 | 97.7 | 100 | 97.5 | 97.2 | 100 | 96.9 |
| 90_12_109_140_237 | 97.9 | 100 | 97.7 | 96.1 | 96.2 | 96.1 |
| 12_137_105_109_153 | 97.9 | 100 | 97.7 | 97.2 | 100 | 96.9 |
| 12_137_105_109_247 | 97.9 | 100 | 97.7 | 97.9 | 100 | 97.7 |
| 12_137_109_140_247 | 97.9 | 98.1 | 97.9 | 96.1 | 96.2 | 96.1 |
| 12_137_109_121_237 | 97.9 | 98.1 | 97.9 | 96.8 | 100 | 96.5 |
| 12_137_119_105_175 | 98.1 | 100 | 97.9 | 97.9 | 100 | 97.7 |
| 12_137_109_175_121 | 97.5 | 100 | 97.3 | 97.5 | 100 | 97.3 |
| 87_12_119_105_175 | 97.4 | 100 | 97.1 | 97.5 | 100 | 97.3 |
| 12_137_119_105_111 | 98.2 | 100 | 98.1 | 97.9 | 100 | 97.7 |
| 12_137_119_105_24 | 98.2 | 100 | 98.1 | 97.9 | 100 | 97.7 |
| 12_137_105_32_247 | 98.2 | 100 | 98.1 | 98.2 | 100 | 98.1 |
| 90_12_137_105_237 | 98.1 | 100 | 97.9 | 96.5 | 100 | 96.1 |
| 12_84_137_119_105 | 98.1 | 100 | 97.9 | 97.9 | 100 | 97.7 |
| 12_97_137_105_247 | 98.1 | 100 | 97.9 | 97.9 | 100 | 97.7 |
| 87_12_137_105_237 | 97.2 | 100 | 96.9 | 96.5 | 100 | 96.1 |
| 87_12_100_109_237 | 97.2 | 100 | 96.9 | 95.8 | 100 | 95.3 |
| 87_12_100_109_237 | 97.2 | 100 | 96.9 | 95.8 | 100 | 95.3 |
| 106_12_137_105_86 | 97.9 | 100 | 97.7 | 97.2 | 100 | 96.9 |
| 106_12_137_105_247 | 97.9 | 100 | 97.7 | 97.5 | 100 | 97.3 |
| 106_12_119_105_100 | 97.9 | 100 | 97.7 | 95.7 | 96 | 95.7 |
| 106_12_137_105_121 | 97.7 | 100 | 97.5 | 97.5 | 100 | 97.3 |

TABLE 9-2

| | Training cohort | | | Validation cohort | | |
|---|---|---|---|---|---|---|
| SEQ ID NO: | Accuracy (%) | Sensitivity (%) | Specificity (%) | Accuracy (%) | Sensitivity (%) | Specificity (%) |
| 28 | 81.6 | 83 | 81.4 | 81.7 | 96.2 | 80.2 |
| 103_28 | 84.9 | 84.9 | 84.9 | 85.6 | 96.2 | 84.5 |
| 105_28_109 | 88.8 | 88.7 | 88.8 | 86.3 | 96.2 | 85.3 |
| 84_105_28_100 | 92.4 | 94.3 | 92.2 | 93.6 | 100 | 93 |
| 137_119_105_28_237 | 97.7 | 98.1 | 97.7 | 98.6 | 100 | 100 |
| 87_106_119_28_121 | 97.4 | 100 | 97.1 | 97.5 | 100 | 100 |
| 106_137_119_28_121 | 97.4 | 100 | 97.1 | 97.5 | 100 | 100 |
| 90_119_105_28_237 | 97.4 | 98.1 | 97.3 | 97.9 | 100 | 100 |

TABLE 9-3

| SEQ ID NO: | Training cohort | | | Validation cohort | | |
|---|---|---|---|---|---|---|
| | Accuracy (%) | Sensitivity (%) | Specificity (%) | Accuracy (%) | Sensitivity (%) | Specificity (%) |
| 5 | 84 | 88.7 | 83.6 | 87 | 88.5 | 86.8 |
| 5__84 | 87.9 | 92.5 | 87.4 | 88.4 | 92.3 | 88 |
| 5__137__85 | 90.4 | 98.1 | 89.6 | 90.5 | 96.2 | 89.9 |
| 5__97__237__247 | 93.2 | 94.3 | 93 | 93.7 | 100 | 93 |
| 90__5__137__119__105 | 97.7 | 100 | 97.5 | 98.2 | 100 | 100 |
| 5__137__119__105__237 | 97.7 | 98.1 | 97.7 | 98.2 | 100 | 100 |
| 5__137__119__105__32 | 97.5 | 98.1 | 97.5 | 97.9 | 100 | 100 |

TABLE 9-4

| SEQ ID NO: | Training cohort | | | Validation cohort | | |
|---|---|---|---|---|---|---|
| | Accuracy (%) | Sensitivity (%) | Specificity (%) | Accuracy (%) | Sensitivity (%) | Specificity (%) |
| 2 | 86.8 | 96.2 | 85.9 | 90.5 | 96.2 | 89.9 |
| 2__1 | 88.4 | 98.1 | 87.4 | 90.1 | 96.2 | 89.5 |
| 2__87__111 | 90.9 | 100 | 89.9 | 92.6 | 100 | 91.9 |
| 2__87__90__103 | 93 | 98.1 | 92.5 | 92.6 | 100 | 91.9 |
| 2__137__119__105__237 | 97.7 | 98.1 | 97.7 | 98.2 | 100 | 100 |
| 2__87__137__119__105 | 97.4 | 100 | 97.1 | 97.9 | 100 | 100 |
| 2__137__119__105__13 | 97.4 | 100 | 97.1 | 98.2 | 100 | 100 |
| 2__137__119__105__121 | 97.4 | 100 | 97.1 | 98.2 | 100 | 100 |
| 2__137__119__105__247 | 97.4 | 98.1 | 97.3 | 97.9 | 100 | 100 |
| 2__87__119__109__247 | 97.2 | 100 | 96.9 | 97.5 | 100 | 100 |
| 2__90__137__119__105 | 97.2 | 100 | 96.9 | 97.5 | 100 | 100 |
| 2__137__119__105__140 | 97.2 | 100 | 96.9 | 98.2 | 100 | 100 |
| 2__87__119__105__237 | 97.2 | 100 | 96.9 | 96.8 | 100 | 100 |

TABLE 9-5

| SEQ ID NO: | Training cohort | | | Validation cohort | | |
|---|---|---|---|---|---|---|
| | Accuracy (%) | Sensitivity (%) | Specificity (%) | Accuracy (%) | Sensitivity (%) | Specificity (%) |
| 12__28 | 90 | 92.5 | 89.7 | 92.6 | 88.5 | 93 |
| 12__28__32 | 92.3 | 96.2 | 91.9 | 93.3 | 92.3 | 93.4 |
| 12__137__28__32 | 93.9 | 100 | 93.2 | 93.7 | 100 | 93 |
| 12__137__105__28__247 | 97.9 | 98.1 | 97.9 | 97.5 | 100 | 100 |
| 12__137__119__105__28 | 97.7 | 100 | 97.5 | 97.9 | 100 | 100 |
| 12__103__137__105__28 | 97.5 | 100 | 97.3 | 96.8 | 100 | 100 |
| 12__84__28__140__121 | 97.5 | 98.1 | 97.5 | 96.5 | 92.3 | 92.3 |
| 12__137__28__109__121 | 97.5 | 98.1 | 97.5 | 97.5 | 100 | 100 |
| 12__1__28__121__247 | 97.5 | 98.1 | 97.5 | 96.1 | 96.2 | 96.2 |
| 12__119__28__100__121 | 97.5 | 98.1 | 97.5 | 97.2 | 100 | 100 |
| 12__92__28__100__247 | 97.5 | 98.1 | 97.5 | 97.2 | 100 | 100 |
| 12__28__100__140__247 | 97.5 | 98.1 | 97.5 | 97.5 | 96.2 | 96.2 |
| 12__137__28__109__247 | 97.5 | 94.3 | 97.9 | 95.8 | 92.3 | 92.3 |
| 12__84__28__109__121 | 97.4 | 98.1 | 97.3 | 95.8 | 96.2 | 96.2 |
| 12__103__1__28__121 | 97.4 | 98.1 | 97.3 | 95.4 | 100 | 100 |
| 12__1__28__32__121 | 97.4 | 98.1 | 97.3 | 95.8 | 100 | 100 |
| 12__1__28__100__121 | 97.4 | 98.1 | 97.3 | 95.1 | 96.2 | 96.2 |
| 12__1__28__175__121 | 97.4 | 98.1 | 97.3 | 95.8 | 100 | 100 |

TABLE 9-6

| SEQ ID NO: | Training cohort | | | Validation cohort | | |
|---|---|---|---|---|---|---|
| | Accuracy (%) | Sensitivity (%) | Specificity (%) | Accuracy (%) | Sensitivity (%) | Specificity (%) |
| 5__12 | 91.2 | 98.1 | 90.5 | 89.4 | 84.6 | 89.9 |
| 5__12__92 | 93 | 98.1 | 92.5 | 92.6 | 96.2 | 92.2 |

TABLE 9-6-continued

| | Training cohort | | | Validation cohort | | |
|---|---|---|---|---|---|---|
| SEQ ID NO: | Accuracy (%) | Sensitivity (%) | Specificity (%) | Accuracy (%) | Sensitivity (%) | Specificity (%) |
| 5_12_105_13 | 95.1 | 98.1 | 94.8 | 93 | 92.3 | 93 |
| 5_12_137_119_105 | 97.9 | 100 | 97.7 | 97.9 | 100 | 100 |
| 90_5_12_119_105 | 97.7 | 100 | 97.5 | 96.8 | 100 | 100 |
| 5_12_137_105_121 | 97.7 | 100 | 97.5 | 97.5 | 100 | 100 |
| 5_12_119_92_121 | 97.7 | 100 | 97.5 | 96.1 | 100 | 100 |
| 90_5_12_109_247 | 97.7 | 98.1 | 97.7 | 95.8 | 96.2 | 96.2 |
| 5_12_137_109_121 | 97.7 | 98.1 | 97.7 | 97.5 | 100 | 100 |
| 5_12_137_109_247 | 97.7 | 96.2 | 97.9 | 97.9 | 100 | 100 |
| 90_5_106_12_109 | 97.5 | 100 | 97.3 | 95.4 | 96 | 96 |
| 90_5_12_137_105 | 97.5 | 100 | 97.3 | 96.8 | 100 | 100 |
| 90_5_12_119_109 | 97.5 | 100 | 97.3 | 96.1 | 100 | 100 |
| 90_5_12_105_109 | 97.5 | 100 | 97.3 | 96.1 | 100 | 100 |
| 5_12_137_105_153 | 97.5 | 100 | 97.3 | 97.5 | 100 | 100 |
| 5_12_119_105_54 | 97.5 | 100 | 97.3 | 97.5 | 96.2 | 96.2 |
| 87_5_106_12_109 | 97.4 | 100 | 97.1 | 96.1 | 96 | 96 |
| 87_5_12_137_105 | 97.4 | 100 | 97.1 | 96.1 | 100 | 100 |
| 90_5_12_1_105 | 97.4 | 100 | 97.1 | 95.4 | 96.2 | 96.2 |
| 90_5_12_109_86 | 97.4 | 100 | 97.1 | 95.4 | 96.2 | 96.2 |
| 5_12_137_105_247 | 98.1 | 100 | 97.9 | 97.5 | 100 | 100 |
| 90_5_12_109_175 | 97.5 | 100 | 97.3 | 95.1 | 100 | 100 |
| 5_12_100_109_121 | 97.9 | 100 | 97.7 | 96.1 | 96.2 | 96.2 |

TABLE 9-7

| | Training cohort | | | Validation cohort | | |
|---|---|---|---|---|---|---|
| SEQ ID NO: | Accuracy (%) | Sensitivity (%) | Specificity (%) | Accuracy (%) | Sensitivity (%) | Specificity (%) |
| 2_12 | 91.2 | 100 | 90.3 | 90.1 | 92.3 | 89.9 |
| 2_12_121 | 93.9 | 100 | 93.2 | 92.6 | 92.3 | 92.6 |
| 2_12_1_121 | 94.6 | 100 | 94 | 93.3 | 96.2 | 93 |
| 2_12_137_119_105 | 97.9 | 100 | 97.7 | 97.2 | 100 | 100 |
| 2_12_137_105_153 | 97.9 | 100 | 97.7 | 96.5 | 100 | 100 |
| 2_12_137_105_121 | 97.5 | 100 | 97.3 | 96.5 | 100 | 100 |
| 2_12_109_121_247 | 97.4 | 100 | 97.1 | 95.4 | 96.2 | 96.2 |
| 2_90_12_119_105 | 97.2 | 100 | 96.9 | 96.8 | 100 | 100 |
| 2_90_12_109_140 | 97.2 | 100 | 96.9 | 96.1 | 96.2 | 96.2 |
| 2_12_100_109_121 | 97.2 | 100 | 96.9 | 95.8 | 96.2 | 96.2 |
| 2_12_109_175_121 | 97.2 | 100 | 96.9 | 95.8 | 96.2 | 96.2 |
| 2_12_97_105_247 | 97.2 | 98.1 | 97.1 | 95.1 | 96.2 | 96.2 |
| 2_12_137_105_247 | 98.1 | 100 | 97.9 | 96.8 | 100 | 100 |
| 2_12_137_109_121 | 97.9 | 100 | 97.7 | 97.9 | 100 | 100 |

TABLE 9-8

| | Training cohort | | | Validation cohort | | |
|---|---|---|---|---|---|---|
| SEQ ID NO: | Accuracy (%) | Sensitivity (%) | Specificity (%) | Accuracy (%) | Sensitivity (%) | Specificity (%) |
| 2_5 | 89.8 | 100 | 88.8 | 92.3 | 100 | 91.5 |
| 2_5_247 | 92.1 | 98.1 | 91.5 | 94 | 100 | 93.4 |
| 2_5_97_153 | 93.9 | 98.1 | 93.4 | 95.1 | 100 | 94.6 |
| 2_90_5_119_105 | 97.2 | 100 | 96.9 | 97.9 | 100 | 100 |
| 2_5_119_109_121 | 97.2 | 100 | 96.9 | 97.9 | 100 | 100 |
| 2_5_119_86_121 | 97.2 | 100 | 96.9 | 96.5 | 100 | 100 |

TABLE 9-9

| | Training cohort | | | Validation cohort | | |
|---|---|---|---|---|---|---|
| SEQ ID NO: | Accuracy (%) | Sensitivity (%) | Specificity (%) | Accuracy (%) | Sensitivity (%) | Specificity (%) |
| 5_12_28 | 93.3 | 96.2 | 93 | 94.4 | 96.2 | 94.2 |
| 5_12_119_28 | 94.6 | 98.1 | 94.2 | 96.5 | 100 | 96.1 |
| 5_12_1_28_121 | 97.5 | 98.1 | 97.5 | 96.8 | 100 | 100 |

Example 5

<Method for Evaluating Early Pancreatic Cancer or Pancreatic Cancer Precursor Lesion Discriminant Performance by Combination of Multiple Gene Markers Using Samples in the Validation Cohort>

Example 2 showed that discriminant performance was improved by using a combination of the multiple gene markers selected in Example 1, as compared with using one of the gene marker. Thus, in this Example, even the gene markers that were not selected in Example 1 were studied as to whether high early pancreatic cancer or pancreatic cancer precursor lesion discriminant performance is obtained by combinations with the gene markers selected in Example 1.

Specifically, among the genes having a gene expression level of $2^6$ or higher in 50% or more of the samples in either of the early pancreatic cancer or pancreatic cancer precursor lesion patient group in the training cohort or the healthy subject group in the training cohort, genes that showed statistical significance for discriminating an early pancreatic cancer or pancreatic cancer precursor lesion patient group from a healthy subject group with the P value smaller than 0.05 calculated by two-tailed t-test assuming equal variance as to each gene expression level and corrected by the Bonferroni method, were examined. As a result, 248 genes containing the 226 genes selected in Example 1 were found. Fisher's discriminant analysis was conducted as to 30,876 combinations using one or two of these 248 genes, to construct a discriminant for determining the presence or absence of early pancreatic cancer or a pancreatic cancer precursor lesion. The discriminant performance of the selected combinations of 1 or 2 of the genes was validated in the same way as the method of Example 2.

As a result, some combinations of these genes exhibited accuracy of 85% or higher in both of the training cohort and the validation cohort and are shown in Table 10. For example, the newly found polynucleotide consisting of the nucleotide sequence represented by SEQ ID NO: 248 to 250 discriminated the early pancreatic cancer or pancreatic cancer precursor lesion patients from the healthy subjects with high discriminant performance when used in combination of at least two polynucleotides comprising any of the polynucleotides consisting of the nucleotide sequences represented by SEQ ID NOs: 1 to 226. More specifically, the polynucleotides consisting of the nucleotide sequences represented by SEQ ID NO: 248 to 250 was able to exhibit discrimination accuracy of 85% or higher between the early pancreatic cancer or pancreatic cancer precursor lesion patients and the healthy subjects in both of the training cohort and the validation cohort when used in combination of at least two polynucleotides comprising any of the polynucleotides consisting of the nucleotide sequences represented by SEQ ID NOs: 2, 3, 18, 12, 20, 1, 15, 50, 63, 72, 5, 24, 10, 52, 9, 11, 19, 39, 61, 7, 17, 22, 26, 74, 21, and 28. Examples of such combinations of two genes include combinations of SEQ ID NOs: 2 and 248, SEQ ID NOs: 3 and 249, SEQ ID NOs: 2 and 250, SEQ ID NOs: 1 and 249, SEQ ID NOs: 5 and 250, SEQ ID NOs: 3 and 248, SEQ ID NOs: 3 and 250, SEQ ID NOs: 1 and 250, SEQ ID NOs: 2 and 249, SEQ ID NOs: 21 and 248, SEQ ID NOs: 10 and 248, SEQ ID NOs: 5 and 248, SEQ ID NOs: 11 and 249, SEQ ID NOs: 9 and 250, SEQ ID NOs: 17 and 250, SEQ ID NOs: 21 and 249, SEQ ID NOs: 7 and 250, SEQ ID NOs: 15 and 248, SEQ ID NOs: 5 and 249, SEQ ID NOs: 12 and 248, SEQ ID NOs: 10 and 249, SEQ ID NOs: 28 and 250, SEQ ID NOs: 7 and 249, SEQ ID NOs: 18 and 249, SEQ ID NOs: 15 and 249, SEQ ID NOs: 20 and 249, SEQ ID NOs: 24 and 249, SEQ ID NOs: 11 and 250, and SEQ ID NOs: 18 and 248.

As one example, an attempt was made to discriminate the early pancreatic cancer or pancreatic cancer precursor lesion patients from the healthy subjects using the expression level measurement values of the nucleotide sequences represented by SEQ ID NO: 2 and SEQ ID NO: 248. As a result, discriminant performance as high as 93.2% accuracy, 96.2% sensitivity, and 91.9% specificity in the training cohort and 95.4% accuracy, 100% sensitivity, and 93.4% specificity in the validation cohort was obtained.

From these results, it can be concluded that all of the polynucleotides consisting of the nucleotide sequences represented by SEQ ID NOs: 248 to 250 are also excellent diagnostic markers.

Table 10 mentioned above is as follows.

TABLE 10

| SEQ ID NO: | Training cohort | | | Validation cohort | | |
| --- | --- | --- | --- | --- | --- | --- |
| | Accuracy (%) | Sensitivity (%) | Specificity (%) | Accuracy (%) | Sensitivity (%) | Specificity (%) |
| 2_248 | 93.2 | 96.2 | 91.9 | 95.4 | 100 | 93.4 |
| 3_249 | 91.5 | 86.8 | 93.5 | 96.6 | 100 | 95.1 |
| 2_250 | 90.9 | 98.1 | 87.8 | 88.5 | 100 | 83.6 |
| 1_249 | 90.3 | 94.3 | 88.6 | 86.2 | 88.5 | 85.2 |
| 5_250 | 90.3 | 92.5 | 89.4 | 87.4 | 84.6 | 88.5 |
| 3_248 | 90.3 | 90.6 | 90.2 | 93.1 | 92.3 | 93.4 |
| 3_250 | 90.3 | 88.7 | 91.1 | 94.3 | 92.3 | 95.1 |
| 1_250 | 89.8 | 96.2 | 87 | 85.1 | 84.6 | 85.2 |
| 2_249 | 89.8 | 96.2 | 87 | 89.7 | 100 | 85.2 |
| 21_248 | 89.7 | 78.8 | 94.3 | 89.7 | 76.9 | 95.1 |
| 10_248 | 88.6 | 88.7 | 88.6 | 86.2 | 88.5 | 85.2 |
| 5_248 | 87.5 | 90.6 | 86.2 | 89.7 | 92.3 | 88.5 |
| 11_249 | 87.5 | 90.6 | 86.2 | 89.7 | 88.5 | 90.2 |
| 9_250 | 87.5 | 88.7 | 87 | 89.7 | 84.6 | 91.8 |
| 17_250 | 87.5 | 84.9 | 88.6 | 85.1 | 84.6 | 85.2 |
| 21_249 | 87.4 | 80.8 | 90.2 | 86.2 | 80.8 | 88.5 |
| 7_250 | 86.9 | 90.6 | 85.4 | 90.8 | 96.2 | 88.5 |

TABLE 10-continued

| SEQ ID NO: | Training cohort | | | Validation cohort | | |
| --- | --- | --- | --- | --- | --- | --- |
| | Accuracy (%) | Sensitivity (%) | Specificity (%) | Accuracy (%) | Sensitivity (%) | Specificity (%) |
| 15_248 | 86.9 | 81.1 | 89.4 | 90.8 | 88.5 | 91.8 |
| 5_249 | 86.4 | 90.6 | 84.6 | 85.1 | 92.3 | 82 |
| 12_248 | 86.4 | 90.6 | 84.6 | 88.5 | 84.6 | 90.2 |
| 10_249 | 86.4 | 84.9 | 87 | 92 | 92.3 | 91.8 |
| 28_250 | 86.4 | 84.9 | 87 | 87.4 | 84.6 | 88.5 |
| 7_249 | 85.8 | 88.7 | 84.6 | 92 | 92.3 | 91.8 |
| 18_249 | 85.8 | 88.7 | 84.6 | 87.4 | 92.3 | 85.2 |
| 15_249 | 85.8 | 83 | 87 | 85.1 | 80.8 | 86.9 |
| 20_249 | 85.8 | 81.1 | 87.8 | 88.5 | 88.5 | 88.5 |
| 24_249 | 85.8 | 81.1 | 87.8 | 88.5 | 96.2 | 85.2 |
| 11_250 | 85.2 | 90.6 | 82.9 | 86.2 | 92.3 | 83.6 |
| 18_248 | 85.2 | 86.8 | 84.6 | 86.2 | 88.5 | 85.2 |

Comparative Example 1

<Early Pancreatic Cancer or Pancreatic Cancer Precursor Lesion Discriminant Performance of Existing Tumor Markers in Blood>

The concentrations of the existing tumor markers CEA and CA19-9 in blood were measured in the training cohort and the validation cohort obtained in the preceding Reference Examples. In principle, when the concentrations of these tumor markers in blood are higher than the reference values described in Non-Patent Literature 3 above (CEA: 5 ng/mL, CA19-9: 37 U/mL), subjects are usually suspected of having cancer. Thus, whether or not the concentrations of CEA and CA19-9 in blood exceeded their reference values was examined for each sample to decide whether early pancreatic cancer or pancreatic cancer precursor lesion patients were determined as early pancreatic cancer or pancreatic cancer precursor lesion patients, and the sensitivity of each existing marker was thereby calculated for the training cohort and validation cohort. The results are shown in Tables 5-1 and 5-2. The sensitivity of CEA and CA19-9 was as low as 18% and 58%, respectively, in the training cohort, and was as low as 20% and 68%, respectively, in the validation cohort, demonstrating that neither of the markers are useful in the detection of early pancreatic cancer or a pancreatic cancer precursor lesion (Tables 5-1 and 5-2). Furthermore, CEA and CA19-9 were totally unable to detect IPMA low grade, one type of pancreatic cancer precursor lesion with a low malignancy, in the training cohort and the validation cohort (Tables 5-1 and 5-2).

On the other hand, as shown above in Tables 3 and 6 of Examples 1 and 2, it can be concluded that in all of the polynucleotides consisting of the nucleotide sequences represented by SEQ ID NOs: 1 to 226, combinations of 1, 2 or more polynucleotides exhibiting sensitivity beyond the existing early pancreatic cancer or pancreatic cancer precursor lesion markers are present, and thus such polynucleotides serve as excellent diagnosis markers.

Comparative Example 2

<Performance of Existing Pancreatic Cancer miRNA Markers in Blood for Early Pancreatic Cancer or Pancreatic Cancer Precursor Lesion>

Combinations of one or more miRNAs selected from hsa-miR-4294 (SEQ ID NO: 125), hsa-miR-6836-3p (SEQ ID NO: 231), and hsa-miR-6880-5p (SEQ ID NO: 219) included in the present invention among hsa-miR-6075, hsa-miR-4294, hsa-miR-6836-3p, hsa-miR-4530, and hsa-miR-6880-5p described in Patent Literature 2 as being capable of specifically discriminating a pancreatic cancer patient group from other cancer patient groups were evaluated for their early pancreatic cancer or pancreatic cancer precursor lesion discriminant performance in the training cohort and the validation cohort obtained in the preceding Reference Examples. For example, the combination of the polynucleotides consisting of the nucleotide sequences represented by SEQ ID NOs: 219, 125, and 231 or complementary sequences thereof showed excellent accuracy of 93% in both of the training cohort and the validation cohort, but had sensitivity of 50% and specificity of 94.7% in the training cohort and sensitivity of 72.7% and specificity of 93.8% in the validation cohort and tended to differ in sensitivity between the training cohort and the validation cohort (Table 11).

TABLE 11

| SEQ ID NO: | Training cohort | | | Validation cohort | | |
| --- | --- | --- | --- | --- | --- | --- |
| | Accuracy (%) | Sensitivity (%) | Specificity (%) | Accuracy (%) | Sensitivity (%) | Specificity (%) |
| 219_125_231 | 93 | 50 | 94.7 | 93 | 72.7 | 93.8 |

On the other hand, as shown in Tables 9-1 to 9-9 in Example 4, for example, the measurement using the combination of three polynucleotides comprising at least one polynucleotide selected from the group consisting of the polynucleotides consisting of the nucleotide sequences represented by SEQ ID NOs: 119, 12, 28, 105, 137, 121, 109, 87, 5, 140, 106, 2, 175, 90, 237, and 247 or complementary sequences thereof had the highest sensitivity of 100%, the lowest sensitivity of 88.7%, the highest specificity of 93.2%, and the lowest specificity of 88.8% in the training cohort and the highest sensitivity of 100%, the lowest sensitivity of 84.6%, the highest specificity of 94.2%, and the lowest specificity of 85.3% in the validation cohort and thus showed equivalently high sensitivity and specificity between the training cohort and the validation cohort. From these results, it can be concluded that the combination of two or more, preferably three or more, more preferably four or more or five or more polynucleotides comprising at least one polynucleotide selected from the group consisting of the polynucleotides consisting of the nucleotide sequences represented by SEQ ID NOs: 119, 12, 28, 105, 137, 121, 109, 87, 5, 140, 106, 2, 175, 90, 237, and 247 or complementary sequences thereof exhibits higher discriminant performance than that of the combination of existing pancreatic cancer miRNA markers in blood and serves as excellent diagnostic markers.

Comparative Example 3

<<Performance of Existing Pancreatic Cancer miRNA Markers in Blood for Early Pancreatic Cancer or Pancreatic Cancer Precursor Lesion>> hsa-miR-145-5p (SEQ ID NO: 813), hsa-let-7f-5p (SEQ ID NO: 814), hsa-miR-146a-5p (SEQ ID NO: 815), hsa-let-7d-5p (SEQ ID NO: 816), and hsa-let-7a-5p (SEQ ID NO: 817) having 3.0 or more fold change in their gene expression levels in a pancreatic cancer precursor lesion patient group relative to a healthy subject group were selected from among top 30 miRNAs that had statistically significant difference in their expression levels between a healthy subject group and an IPMN patient group in Patent Literature 5 and evaluated for their early pancreatic cancer or pancreatic cancer precursor lesion discriminant performance in the training cohort and the validation cohort obtained in the preceding Reference Examples. The combination of the polynucleotides consisting of the nucleotide sequences represented by SEQ ID NOs: 813 to 817 or complementary sequences thereof had sensitivity of 63.6% and specificity of 74.5% in the training cohort and sensitivity of 54.5% and specificity of 74.7% in the validation cohort (Table 12).

TABLE 12

| | Training cohort | | | Validation cohort | | |
| --- | --- | --- | --- | --- | --- | --- |
| SEQ ID NO: | Accuracy (%) | Sensitivity (%) | Specificity (%) | Accuracy (%) | Sensitivity (%) | Specificity (%) |
| 813_814_815_816_817 | 74 | 63.6 | 74.5 | 73.9 | 54.5 | 74.7 |

On the other hand, as shown in Tables 9-1 to 9-9 in Example 4 described above, for example, the measurement using the combination of five polynucleotides comprising at least one polynucleotide selected from the group consisting of the polynucleotides consisting of the nucleotide sequences represented by SEQ ID NOs: 119, 12, 28, 105, 137, 121, 109, 87, 5, 140, 106, 2, 175, 90, 237, and 247 or complementary sequences thereof showed the highest sensitivity of 100%, the lowest sensitivity of 94.3%, the highest specificity of 98.6%, and the lowest specificity of 96.9% in the training cohort and the highest sensitivity of 100%, the lowest sensitivity of 92.3%, the highest specificity of 100%, and the lowest specificity of 92.3% in the validation cohort. From these results, it can be concluded that the combination of two or more, preferably three or more, more preferably four or more or five or more polynucleotides comprising at least one polynucleotide selected from the group consisting of the polynucleotides consisting of the nucleotide sequences represented by SEQ ID NOs: 119, 12, 28, 105, 137, 121, 109, 87, 5, 140, 106, 2, 175, 90, 237, and 247 or complementary sequences thereof exhibits higher discriminant performance than that of the combination of existing pancreatic cancer and pancreatic cancer precursor lesion miRNA markers in blood and serves as excellent diagnostic markers.

As shown in these Examples and Comparative Examples, the kit and the method of the present invention can detect early pancreatic cancer or a pancreatic cancer precursor lesion with higher sensitivity and specificity than the existing tumor markers and therefore permit early treatment and early decision to carry out the surgical resection of a cancer site. As a result, improvement in 5-year survival rate and reduction in the rate of recurrence can be achieved.

INDUSTRIAL APPLICABILITY

According to the present invention, early pancreatic cancer or a pancreatic cancer precursor lesion can be detected in a subject with much higher sensitivity, specificity, and accuracy than conventional methods. This enables early detection, diagnosis and treatment of early pancreatic cancer or a pancreatic cancer precursor lesion. According to the present invention, early pancreatic cancer or a pancreatic cancer precursor lesion can be detected with limited invasiveness using the blood of a subject. This allows early pancreatic cancer or a pancreatic cancer precursor lesion to be determined conveniently, rapidly, and inexpensively.

All publications, patents, and patent applications cited herein are incorporated herein by reference in their entirety.

The invention claimed is:

1. A method for detecting and then treating or diagnosing pancreatic cancer in a human subject, comprising:
   measuring an expression level of hsa-miR-6089 in a blood sample from the subject;
   comparing the measured expression level of hsa-miR-6089 to a control expression level of hsa-miR-6089 obtained from a blood sample from a healthy subject;
   detecting increased level of hsa-miR-6089 in the blood sample from the subject as compared to the control expression level of hsa-miR-6089 obtained from the blood sample from the healthy human subject;
   wherein the increased level of hsa-miR-6089 indicates that the subject has pancreatic cancer; and
   treating the subject for the pancreatic cancer or performing a diagnostic procedure on the subject with pancreatic cancer;
   wherein the treatment comprises surgery, radiotherapy, chemotherapy, or a combination thereof, and wherein the diagnostic procedure comprises abdominal ultrasonography, CT scanning, endoscopic retrograde cholangiopancreatography, endoscopic ultrasonography, or a combination thereof.

2. The method according to claim 1, wherein the pancreatic cancer is early pancreatic cancer.

* * * * *

SEQUENCE LISTING

```
<160> NUMBER OF SEQ ID NOS: 817

<210> SEQ ID NO 1
<211> LENGTH: 20
<212> TYPE: RNA
<213> ORGANISM: Homo sapiens

<400> SEQUENCE: 1
gccggggcuu ugggugaggg                                           20

<210> SEQ ID NO 2
<211> LENGTH: 21
<212> TYPE: RNA
<213> ORGANISM: Homo sapiens

<400> SEQUENCE: 2
ccgucgccgc cacccgagcc g                                         21

<210> SEQ ID NO 3
<211> LENGTH: 23
<212> TYPE: RNA
<213> ORGANISM: Homo sapiens

<400> SEQUENCE: 3
aggaagcccu ggaggggcug gag                                       23

<210> SEQ ID NO 4
<211> LENGTH: 22
<212> TYPE: RNA
<213> ORGANISM: Homo sapiens

<400> SEQUENCE: 4
uuggggauug ggucaggcca gu                                        22

<210> SEQ ID NO 5
<211> LENGTH: 17
<212> TYPE: RNA
<213> ORGANISM: Homo sapiens

<400> SEQUENCE: 5
cucagugacu caugugc                                              17

<210> SEQ ID NO 6
<211> LENGTH: 22
<212> TYPE: RNA
<213> ORGANISM: Homo sapiens

<400> SEQUENCE: 6
ggaggggucc cgcacuggga gg                                        22

<210> SEQ ID NO 7
<211> LENGTH: 21
<212> TYPE: RNA
<213> ORGANISM: Homo sapiens

<400> SEQUENCE: 7
agggagggac gggggcugug c                                         21

<210> SEQ ID NO 8
<211> LENGTH: 20
<212> TYPE: RNA
<213> ORGANISM: Homo sapiens

<400> SEQUENCE: 8
```

| | |
|---|---|
| gugagucagg gugggcugg | 20 |

<210> SEQ ID NO 9
<211> LENGTH: 22
<212> TYPE: RNA
<213> ORGANISM: Homo sapiens

<400> SEQUENCE: 9

| | |
|---|---|
| ggggcuguga uugaccagca gg | 22 |

<210> SEQ ID NO 10
<211> LENGTH: 24
<212> TYPE: RNA
<213> ORGANISM: Homo sapiens

<400> SEQUENCE: 10

| | |
|---|---|
| uggggggaca ggaugagagg cugu | 24 |

<210> SEQ ID NO 11
<211> LENGTH: 22
<212> TYPE: RNA
<213> ORGANISM: Homo sapiens

<400> SEQUENCE: 11

| | |
|---|---|
| ugcuggggc cacaugagug ug | 22 |

<210> SEQ ID NO 12
<211> LENGTH: 23
<212> TYPE: RNA
<213> ORGANISM: Homo sapiens

<400> SEQUENCE: 12

| | |
|---|---|
| ccggggcaga uugguguagg gug | 23 |

<210> SEQ ID NO 13
<211> LENGTH: 22
<212> TYPE: RNA
<213> ORGANISM: Homo sapiens

<400> SEQUENCE: 13

| | |
|---|---|
| gugggcuggg cugggcuggg cc | 22 |

<210> SEQ ID NO 14
<211> LENGTH: 22
<212> TYPE: RNA
<213> ORGANISM: Homo sapiens

<400> SEQUENCE: 14

| | |
|---|---|
| uggggagcgg cccccgggug gg | 22 |

<210> SEQ ID NO 15
<211> LENGTH: 22
<212> TYPE: RNA
<213> ORGANISM: Homo sapiens

<400> SEQUENCE: 15

| | |
|---|---|
| aggcgaugug gggauguaga ga | 22 |

<210> SEQ ID NO 16
<211> LENGTH: 22
<212> TYPE: RNA
<213> ORGANISM: Homo sapiens

```
<400> SEQUENCE: 16
ugggagggug uggagucagc au                                            22

<210> SEQ ID NO 17
<211> LENGTH: 23
<212> TYPE: RNA
<213> ORGANISM: Homo sapiens

<400> SEQUENCE: 17 cgaggguag aagagcacag ggg                                            23

<210> SEQ ID NO 18
<211> LENGTH: 21
<212> TYPE: RNA
<213> ORGANISM: Homo sapiens

<400> SEQUENCE: 18
agguggguau ggaggagccc u                                             21

<210> SEQ ID NO 19
<211> LENGTH: 23
<212> TYPE: RNA
<213> ORGANISM: Homo sapiens

<400> SEQUENCE: 19
ugggagggga gaggcagcaa gca                                           23

<210> SEQ ID NO 20
<211> LENGTH: 25
<212> TYPE: RNA
<213> ORGANISM: Homo sapiens

<400> SEQUENCE: 20
caacccuagg agagggugcc auuca                                         25

<210> SEQ ID NO 21
<211> LENGTH: 18
<212> TYPE: RNA
<213> ORGANISM: Homo sapiens

<400> SEQUENCE: 21
ccagaggugg ggacugag                                                 18

<210> SEQ ID NO 22
<211> LENGTH: 22
<212> TYPE: RNA
<213> ORGANISM: Homo sapiens

<400> SEQUENCE: 22
ugggagggcg uggaugaugg ug                                            22

<210> SEQ ID NO 23
<211> LENGTH: 21
<212> TYPE: RNA
<213> ORGANISM: Homo sapiens

<400> SEQUENCE: 23 uggggugug gggagagaga g                                              21

<210> SEQ ID NO 24
<211> LENGTH: 23
<212> TYPE: RNA
<213> ORGANISM: Homo sapiens
```

```
-continued

<400> SEQUENCE: 24 ugggggaca gauggagagg aca                                            23

<210> SEQ ID NO 25
<211> LENGTH: 22
<212> TYPE: RNA
<213> ORGANISM: Homo sapiens

<400> SEQUENCE: 25
gugaacgggc gccaucccga gg                                            22

<210> SEQ ID NO 26
<211> LENGTH: 21
<212> TYPE: RNA
<213> ORGANISM: Homo sapiens

<400> SEQUENCE: 26
gugggcgggg gcaggugugu g                                             21

<210> SEQ ID NO 27
<211> LENGTH: 21
<212> TYPE: RNA
<213> ORGANISM: Homo sapiens

<400> SEQUENCE: 27
guuggggugc aggggucugc u                                             21

<210> SEQ ID NO 28
<211> LENGTH: 25
<212> TYPE: RNA
<213> ORGANISM: Homo sapiens

<400> SEQUENCE: 28 uaggggugg ggaauucagg ggugu                                          25

<210> SEQ ID NO 29
<211> LENGTH: 22
<212> TYPE: RNA
<213> ORGANISM: Homo sapiens

<400> SEQUENCE: 29
cugggacagg aggaggaggc ag                                            22

<210> SEQ ID NO 30
<211> LENGTH: 21
<212> TYPE: RNA
<213> ORGANISM: Homo sapiens

<400> SEQUENCE: 30 gcggugggc cggaggggcg u                                              21

<210> SEQ ID NO 31
<211> LENGTH: 22
<212> TYPE: RNA
<213> ORGANISM: Homo sapiens

<400> SEQUENCE: 31 aggggaugg cagagcaaaa uu                                             22

<210> SEQ ID NO 32
<211> LENGTH: 18
<212> TYPE: RNA
```

<213> ORGANISM: Homo sapiens

<400> SEQUENCE: 32
ugaggcgggg gggcgagc                                              18

<210> SEQ ID NO 33
<211> LENGTH: 25
<212> TYPE: RNA
<213> ORGANISM: Homo sapiens

<400> SEQUENCE: 33
gugaggcggg gccaggaggg ugugu                                      25

<210> SEQ ID NO 34
<211> LENGTH: 20
<212> TYPE: RNA
<213> ORGANISM: Homo sapiens

<400> SEQUENCE: 34 uaggggugg caggcuggcc                                             20

<210> SEQ ID NO 35
<211> LENGTH: 22
<212> TYPE: RNA
<213> ORGANISM: Homo sapiens

<400> SEQUENCE: 35
uggcgggggu agagcuggcu gc                                         22

<210> SEQ ID NO 36
<211> LENGTH: 21
<212> TYPE: RNA
<213> ORGANISM: Homo sapiens

<400> SEQUENCE: 36 uuggggugu cggcccugga g                                           21

<210> SEQ ID NO 37
<211> LENGTH: 23
<212> TYPE: RNA
<213> ORGANISM: Homo sapiens

<400> SEQUENCE: 37
gggggccgau acacuguacg aga                                        23

<210> SEQ ID NO 38
<211> LENGTH: 20
<212> TYPE: RNA
<213> ORGANISM: Homo sapiens

<400> SEQUENCE: 38
ucagggaguc aggggagggc                                            20

<210> SEQ ID NO 39
<211> LENGTH: 22
<212> TYPE: RNA
<213> ORGANISM: Homo sapiens

<400> SEQUENCE: 39
acuggguagg uggggcucca gg                                         22

<210> SEQ ID NO 40
<211> LENGTH: 23

```
<212> TYPE: RNA
<213> ORGANISM: Homo sapiens

<400> SEQUENCE: 40 agggugggc uggagguggg gcu                                                23

<210> SEQ ID NO 41
<211> LENGTH: 24
<212> TYPE: RNA
<213> ORGANISM: Homo sapiens

<400> SEQUENCE: 41
guggguaggg uuuggggag agcg                                               24

<210> SEQ ID NO 42
<211> LENGTH: 19
<212> TYPE: RNA
<213> ORGANISM: Homo sapiens

<400> SEQUENCE: 42
uaaggagggg gaugagggg                                                    19

<210> SEQ ID NO 43
<211> LENGTH: 23
<212> TYPE: RNA
<213> ORGANISM: Homo sapiens

<400> SEQUENCE: 43 uggggcugg gaugggccau ggu                                                23

<210> SEQ ID NO 44
<211> LENGTH: 21
<212> TYPE: RNA
<213> ORGANISM: Homo sapiens

<400> SEQUENCE: 44
cgggggcggg gccgaagcgc g                                                 21

<210> SEQ ID NO 45
<211> LENGTH: 22
<212> TYPE: RNA
<213> ORGANISM: Homo sapiens

<400> SEQUENCE: 45
cugggagagg guuguuuacu cc                                                22

<210> SEQ ID NO 46
<211> LENGTH: 22
<212> TYPE: RNA
<213> ORGANISM: Homo sapiens

<400> SEQUENCE: 46
agugggaggc cagggcacgg ca                                                22

<210> SEQ ID NO 47
<211> LENGTH: 21
<212> TYPE: RNA
<213> ORGANISM: Homo sapiens

<400> SEQUENCE: 47
gcagggacag caaaggggug c                                                 21

<210> SEQ ID NO 48
```

```
<211> LENGTH: 23
<212> TYPE: RNA
<213> ORGANISM: Homo sapiens

<400> SEQUENCE: 48
gugaguggga gccgugggg cug                                              23

<210> SEQ ID NO 49
<211> LENGTH: 23
<212> TYPE: RNA
<213> ORGANISM: Homo sapiens

<400> SEQUENCE: 49
gaacgccugu ucuugccagg ugg                                             23

<210> SEQ ID NO 50
<211> LENGTH: 22
<212> TYPE: RNA
<213> ORGANISM: Homo sapiens

<400> SEQUENCE: 50
ccgggagaag gagguggccu gg                                              22

<210> SEQ ID NO 51
<211> LENGTH: 22
<212> TYPE: RNA
<213> ORGANISM: Homo sapiens

<400> SEQUENCE: 51
accuugccuu gcugcccggg cc                                              22

<210> SEQ ID NO 52
<211> LENGTH: 22
<212> TYPE: RNA
<213> ORGANISM: Homo sapiens

<400> SEQUENCE: 52
uaggggcagc agaggaccug gg                                              22

<210> SEQ ID NO 53
<211> LENGTH: 20
<212> TYPE: RNA
<213> ORGANISM: Homo sapiens

<400> SEQUENCE: 53
gcucggacug agcagguggg                                                 20

<210> SEQ ID NO 54
<211> LENGTH: 20
<212> TYPE: RNA
<213> ORGANISM: Homo sapiens

<400> SEQUENCE: 54
gggcuggggc gcgggaggu                                                  20

<210> SEQ ID NO 55
<211> LENGTH: 23
<212> TYPE: RNA
<213> ORGANISM: Homo sapiens

<400> SEQUENCE: 55
gagggcagcg uggguguggc gga                                             23
```

```
<210> SEQ ID NO 56
<211> LENGTH: 18
<212> TYPE: RNA
<213> ORGANISM: Homo sapiens

<400> SEQUENCE: 56
gugaaggccc ggcggaga                                             18

<210> SEQ ID NO 57
<211> LENGTH: 22
<212> TYPE: RNA
<213> ORGANISM: Homo sapiens

<400> SEQUENCE: 57
uauagggauu ggagccgugg cg                                        22

<210> SEQ ID NO 58
<211> LENGTH: 22
<212> TYPE: RNA
<213> ORGANISM: Homo sapiens

<400> SEQUENCE: 58
ucaaaaucag gagucggggc uu                                        22

<210> SEQ ID NO 59
<211> LENGTH: 22
<212> TYPE: RNA
<213> ORGANISM: Homo sapiens

<400> SEQUENCE: 59 uggggagug cagugauugu gg                                         22

<210> SEQ ID NO 60
<211> LENGTH: 24
<212> TYPE: RNA
<213> ORGANISM: Homo sapiens

<400> SEQUENCE: 60
ggaggccggg gugggcggg gcgg                                       24

<210> SEQ ID NO 61
<211> LENGTH: 23
<212> TYPE: RNA
<213> ORGANISM: Homo sapiens

<400> SEQUENCE: 61
uuucaagcca gggggcguuu uuc                                       23

<210> SEQ ID NO 62
<211> LENGTH: 22
<212> TYPE: RNA
<213> ORGANISM: Homo sapiens

<400> SEQUENCE: 62 gagguugg uggaggcucu cc                                          22

<210> SEQ ID NO 63
<211> LENGTH: 18
<212> TYPE: RNA
<213> ORGANISM: Homo sapiens

<400> SEQUENCE: 63
gaggcugaag gaagaugg                                             18
```

```
<210> SEQ ID NO 64
<211> LENGTH: 20
<212> TYPE: RNA
<213> ORGANISM: Homo sapiens

<400> SEQUENCE: 64
cuaggugggg ggcuugaagc                                               20

<210> SEQ ID NO 65
<211> LENGTH: 20
<212> TYPE: RNA
<213> ORGANISM: Homo sapiens

<400> SEQUENCE: 65
ugggcugcug agaaggggca                                               20

<210> SEQ ID NO 66
<211> LENGTH: 22
<212> TYPE: RNA
<213> ORGANISM: Homo sapiens

<400> SEQUENCE: 66 cuggggugg ggggcugggc gu                                             22

<210> SEQ ID NO 67
<211> LENGTH: 20
<212> TYPE: RNA
<213> ORGANISM: Homo sapiens

<400> SEQUENCE: 67
ccugagcccg ggccgcgcag                                               20

<210> SEQ ID NO 68
<211> LENGTH: 22
<212> TYPE: RNA
<213> ORGANISM: Homo sapiens

<400> SEQUENCE: 68
gcccaggacu uugugcgggg ug                                            22

<210> SEQ ID NO 69
<211> LENGTH: 22
<212> TYPE: RNA
<213> ORGANISM: Homo sapiens

<400> SEQUENCE: 69 gggggugug gagccagggg gc                                             22

<210> SEQ ID NO 70
<211> LENGTH: 23
<212> TYPE: RNA
<213> ORGANISM: Homo sapiens

<400> SEQUENCE: 70 ccaggggau gggcgagcuu ggg                                            23

<210> SEQ ID NO 71
<211> LENGTH: 19
<212> TYPE: RNA
<213> ORGANISM: Homo sapiens

<400> SEQUENCE: 71
ggcuggucag augggagug                                                19
```

```
<210> SEQ ID NO 72
<211> LENGTH: 22
<212> TYPE: RNA
<213> ORGANISM: Homo sapiens

<400> SEQUENCE: 72 acugggagc agaaggagaa cc                                          22

<210> SEQ ID NO 73
<211> LENGTH: 22
<212> TYPE: RNA
<213> ORGANISM: Homo sapiens

<400> SEQUENCE: 73
cagcagggga gagagaggag uc                                         22

<210> SEQ ID NO 74
<211> LENGTH: 22
<212> TYPE: RNA
<213> ORGANISM: Homo sapiens

<400> SEQUENCE: 74
gagcaggcga ggcugggcug aa                                         22

<210> SEQ ID NO 75
<211> LENGTH: 20
<212> TYPE: RNA
<213> ORGANISM: Homo sapiens

<400> SEQUENCE: 75
ggggagcugu ggaagcagua                                            20

<210> SEQ ID NO 76
<211> LENGTH: 21
<212> TYPE: RNA
<213> ORGANISM: Homo sapiens

<400> SEQUENCE: 76
aucacauugc cagggauuac c                                          21

<210> SEQ ID NO 77
<211> LENGTH: 20
<212> TYPE: RNA
<213> ORGANISM: Homo sapiens

<400> SEQUENCE: 77
ggcuccuugg ucuaggggua                                            20

<210> SEQ ID NO 78
<211> LENGTH: 22
<212> TYPE: RNA
<213> ORGANISM: Homo sapiens

<400> SEQUENCE: 78
uuggggaaac ggccgcugag ug                                         22

<210> SEQ ID NO 79
<211> LENGTH: 25
<212> TYPE: RNA
<213> ORGANISM: Homo sapiens

<400> SEQUENCE: 79
```
agcggggagg aagugggcgc ugcuu      25

<210> SEQ ID NO 80
<211> LENGTH: 21
<212> TYPE: RNA
<213> ORGANISM: Homo sapiens

<400> SEQUENCE: 80
aagggacagg gagggucgug g      21

<210> SEQ ID NO 81
<211> LENGTH: 22
<212> TYPE: RNA
<213> ORGANISM: Homo sapiens

<400> SEQUENCE: 81
caggcaggga ggugggacca ug      22

<210> SEQ ID NO 82
<211> LENGTH: 17
<212> TYPE: RNA
<213> ORGANISM: Homo sapiens

<400> SEQUENCE: 82 gguggggcu guuguuu      17

<210> SEQ ID NO 83
<211> LENGTH: 22
<212> TYPE: RNA
<213> ORGANISM: Homo sapiens

<400> SEQUENCE: 83
gugaguagug gcgcgcggcg gc      22

<210> SEQ ID NO 84
<211> LENGTH: 21
<212> TYPE: RNA
<213> ORGANISM: Homo sapiens

<400> SEQUENCE: 84
cggcggggac ggcgauuggu c      21

<210> SEQ ID NO 85
<211> LENGTH: 22
<212> TYPE: RNA
<213> ORGANISM: Homo sapiens

<400> SEQUENCE: 85
ugggcgaggg cggcugagcg gc      22

<210> SEQ ID NO 86
<211> LENGTH: 21
<212> TYPE: RNA
<213> ORGANISM: Homo sapiens

<400> SEQUENCE: 86
auccaguucu cugaggggc u      21

<210> SEQ ID NO 87
<211> LENGTH: 25
<212> TYPE: RNA
<213> ORGANISM: Homo sapiens

<400> SEQUENCE: 87
agggaucgcg ggcggguggc ggccu          25

<210> SEQ ID NO 88
<211> LENGTH: 20
<212> TYPE: RNA
<213> ORGANISM: Homo sapiens

<400> SEQUENCE: 88
gcggaaggcg gagcggcgga                20

<210> SEQ ID NO 89
<211> LENGTH: 17
<212> TYPE: RNA
<213> ORGANISM: Homo sapiens

<400> SEQUENCE: 89
ggggcgcggc cggaucg                   17

<210> SEQ ID NO 90
<211> LENGTH: 18
<212> TYPE: RNA
<213> ORGANISM: Homo sapiens

<400> SEQUENCE: 90
cggggcggca ggggccuc                  18

<210> SEQ ID NO 91
<211> LENGTH: 23
<212> TYPE: RNA
<213> ORGANISM: Homo sapiens

<400> SEQUENCE: 91
ggaugguugg gggcggucgg cgu            23

<210> SEQ ID NO 92
<211> LENGTH: 24
<212> TYPE: RNA
<213> ORGANISM: Homo sapiens

<400> SEQUENCE: 92 uggggggagcc augagauaag agca          24

<210> SEQ ID NO 93
<211> LENGTH: 21
<212> TYPE: RNA
<213> ORGANISM: Homo sapiens

<400> SEQUENCE: 93
agcggugcuc cugcgggccg a              21

<210> SEQ ID NO 94
<211> LENGTH: 22
<212> TYPE: RNA
<213> ORGANISM: Homo sapiens

<400> SEQUENCE: 94
uugaggagac augguggggg cc             22

<210> SEQ ID NO 95
<211> LENGTH: 21
<212> TYPE: RNA
<213> ORGANISM: Homo sapiens

```
<400> SEQUENCE: 95 ugggggcgggg cagguecccug c                                            21

<210> SEQ ID NO 96
<211> LENGTH: 22
<212> TYPE: RNA
<213> ORGANISM: Homo sapiens

<400> SEQUENCE: 96 uagggaugggg aggccaggau ga                                            22

<210> SEQ ID NO 97
<211> LENGTH: 21
<212> TYPE: RNA
<213> ORGANISM: Homo sapiens

<400> SEQUENCE: 97
cuggggggag gagacccugc u                                              21

<210> SEQ ID NO 98
<211> LENGTH: 23
<212> TYPE: RNA
<213> ORGANISM: Homo sapiens

<400> SEQUENCE: 98
cugggcccgc ggcgggcgug ggg                                            23

<210> SEQ ID NO 99
<211> LENGTH: 22
<212> TYPE: RNA
<213> ORGANISM: Homo sapiens

<400> SEQUENCE: 99
ugagccccug ugccgccccc ag                                             22

<210> SEQ ID NO 100
<211> LENGTH: 21
<212> TYPE: RNA
<213> ORGANISM: Homo sapiens

<400> SEQUENCE: 100
ugagggaccc aggacaggag a                                              21

<210> SEQ ID NO 101
<211> LENGTH: 21
<212> TYPE: RNA
<213> ORGANISM: Homo sapiens

<400> SEQUENCE: 101
guguggccgg caggcgggug g                                              21

<210> SEQ ID NO 102
<211> LENGTH: 17
<212> TYPE: RNA
<213> ORGANISM: Homo sapiens

<400> SEQUENCE: 102
gcggggcugg gcgcgcg                                                   17

<210> SEQ ID NO 103
<211> LENGTH: 19
<212> TYPE: RNA
<213> ORGANISM: Homo sapiens
```

```
<400> SEQUENCE: 103 aagggggcugg gggagcaca                                               19

<210> SEQ ID NO 104
<211> LENGTH: 21
<212> TYPE: RNA
<213> ORGANISM: Homo sapiens

<400> SEQUENCE: 104
cugggagggg cuggguuugg c                                             21

<210> SEQ ID NO 105
<211> LENGTH: 22
<212> TYPE: RNA
<213> ORGANISM: Homo sapiens

<400> SEQUENCE: 105
agacacauuu ggagagggaa cc                                            22

<210> SEQ ID NO 106
<211> LENGTH: 22
<212> TYPE: RNA
<213> ORGANISM: Homo sapiens

<400> SEQUENCE: 106
caggaggcag ugggcgagca gg                                            22

<210> SEQ ID NO 107
<211> LENGTH: 21
<212> TYPE: RNA
<213> ORGANISM: Homo sapiens

<400> SEQUENCE: 107
cguggaggac gaggaggagg c                                             21

<210> SEQ ID NO 108
<211> LENGTH: 23
<212> TYPE: RNA
<213> ORGANISM: Homo sapiens

<400> SEQUENCE: 108
ggaggcgcag gcucggaaag gcg                                           23

<210> SEQ ID NO 109
<211> LENGTH: 23
<212> TYPE: RNA
<213> ORGANISM: Homo sapiens

<400> SEQUENCE: 109
uggugggugg ggaggagaag ugc                                           23

<210> SEQ ID NO 110
<211> LENGTH: 19
<212> TYPE: RNA
<213> ORGANISM: Homo sapiens

<400> SEQUENCE: 110
uugaucucgg aagcuaagc                                                19

<210> SEQ ID NO 111
<211> LENGTH: 22
<212> TYPE: RNA
```

```
<213> ORGANISM: Homo sapiens

<400> SEQUENCE: 111
ggcuacaaca caggacccgg gc                                              22

<210> SEQ ID NO 112
<211> LENGTH: 23
<212> TYPE: RNA
<213> ORGANISM: Homo sapiens

<400> SEQUENCE: 112
agaagaaggc ggucggucug cgg                                             23

<210> SEQ ID NO 113
<211> LENGTH: 19
<212> TYPE: RNA
<213> ORGANISM: Homo sapiens

<400> SEQUENCE: 113
ggggccuggc ggugggcgg                                                  19

<210> SEQ ID NO 114
<211> LENGTH: 20
<212> TYPE: RNA
<213> ORGANISM: Homo sapiens

<400> SEQUENCE: 114
guggguuggg gcgggcucug                                                 20

<210> SEQ ID NO 115
<211> LENGTH: 21
<212> TYPE: RNA
<213> ORGANISM: Homo sapiens

<400> SEQUENCE: 115
cccggagcca ggaugcagcu c                                               21

<210> SEQ ID NO 116
<211> LENGTH: 22
<212> TYPE: RNA
<213> ORGANISM: Homo sapiens

<400> SEQUENCE: 116
gggggucccc ggugcucgga uc                                              22

<210> SEQ ID NO 117
<211> LENGTH: 22
<212> TYPE: RNA
<213> ORGANISM: Homo sapiens

<400> SEQUENCE: 117 gcggggugg cggcggcauc cc                                               22

<210> SEQ ID NO 118
<211> LENGTH: 22
<212> TYPE: RNA
<213> ORGANISM: Homo sapiens

<400> SEQUENCE: 118 cuccugggc ccgcacucuc gc                                               22

<210> SEQ ID NO 119
<211> LENGTH: 23
```

```
<212> TYPE: RNA
<213> ORGANISM: Homo sapiens

<400> SEQUENCE: 119
caggggcugg gguuucaggu ucu                                            23

<210> SEQ ID NO 120
<211> LENGTH: 22
<212> TYPE: RNA
<213> ORGANISM: Homo sapiens

<400> SEQUENCE: 120
guggguacgg cccagugggg gg                                             22

<210> SEQ ID NO 121
<211> LENGTH: 23
<212> TYPE: RNA
<213> ORGANISM: Homo sapiens

<400> SEQUENCE: 121
gacacgggcg acagcugcgg ccc                                            23

<210> SEQ ID NO 122
<211> LENGTH: 18
<212> TYPE: RNA
<213> ORGANISM: Homo sapiens

<400> SEQUENCE: 122 aggggggcggg cuccggcg                                                 18

<210> SEQ ID NO 123
<211> LENGTH: 22
<212> TYPE: RNA
<213> ORGANISM: Homo sapiens

<400> SEQUENCE: 123
acaggugagg uucuugggag cc                                             22

<210> SEQ ID NO 124
<211> LENGTH: 22
<212> TYPE: RNA
<213> ORGANISM: Homo sapiens

<400> SEQUENCE: 124
uucagauccc agcggugccu cu                                             22

<210> SEQ ID NO 125
<211> LENGTH: 17
<212> TYPE: RNA
<213> ORGANISM: Homo sapiens

<400> SEQUENCE: 125
gggagucuac agcaggg                                                   17

<210> SEQ ID NO 126
<211> LENGTH: 20
<212> TYPE: RNA
<213> ORGANISM: Homo sapiens

<400> SEQUENCE: 126
gugucugggc ggacagcugc                                                20

<210> SEQ ID NO 127
```

```
<211> LENGTH: 21
<212> TYPE: RNA
<213> ORGANISM: Homo sapiens

<400> SEQUENCE: 127
ucaccuggcu ggcccgccca g                                              21

<210> SEQ ID NO 128
<211> LENGTH: 17
<212> TYPE: RNA
<213> ORGANISM: Homo sapiens

<400> SEQUENCE: 128
gccggacaag agggagg                                                   17

<210> SEQ ID NO 129
<211> LENGTH: 21
<212> TYPE: RNA
<213> ORGANISM: Homo sapiens

<400> SEQUENCE: 129
cuuccgcccc gccgggcguc g                                              21

<210> SEQ ID NO 130
<211> LENGTH: 23
<212> TYPE: RNA
<213> ORGANISM: Homo sapiens

<400> SEQUENCE: 130 ugggaaggc uuggcaggga aga                                             23

<210> SEQ ID NO 131
<211> LENGTH: 19
<212> TYPE: RNA
<213> ORGANISM: Homo sapiens

<400> SEQUENCE: 131
ggggagcgag gggcggggc                                                 19

<210> SEQ ID NO 132
<211> LENGTH: 19
<212> TYPE: RNA
<213> ORGANISM: Homo sapiens

<400> SEQUENCE: 132
cggggccaga gcagagagc                                                 19

<210> SEQ ID NO 133
<211> LENGTH: 23
<212> TYPE: RNA
<213> ORGANISM: Homo sapiens

<400> SEQUENCE: 133
cgggcugucc ggaggggucg gcu                                            23

<210> SEQ ID NO 134
<211> LENGTH: 22
<212> TYPE: RNA
<213> ORGANISM: Homo sapiens

<400> SEQUENCE: 134
uggcggcggu aguuaugggc uu                                             22
```

```
<210> SEQ ID NO 135
<211> LENGTH: 23
<212> TYPE: RNA
<213> ORGANISM: Homo sapiens

<400> SEQUENCE: 135
gccccggcgc gggcggguuc ugg                                           23

<210> SEQ ID NO 136
<211> LENGTH: 19
<212> TYPE: RNA
<213> ORGANISM: Homo sapiens

<400> SEQUENCE: 136
gggggaagaa aaggugggg                                                19

<210> SEQ ID NO 137
<211> LENGTH: 22
<212> TYPE: RNA
<213> ORGANISM: Homo sapiens

<400> SEQUENCE: 137
uccaggcagg agccggacug ga                                            22

<210> SEQ ID NO 138
<211> LENGTH: 24
<212> TYPE: RNA
<213> ORGANISM: Homo sapiens

<400> SEQUENCE: 138
ugaggggccu cagaccgagc uuuu                                          24

<210> SEQ ID NO 139
<211> LENGTH: 22
<212> TYPE: RNA
<213> ORGANISM: Homo sapiens

<400> SEQUENCE: 139
cucggcgcgg ggcgcgggcu cc                                            22

<210> SEQ ID NO 140
<211> LENGTH: 23
<212> TYPE: RNA
<213> ORGANISM: Homo sapiens

<400> SEQUENCE: 140
ugggccaggg agcagcuggu ggg                                           23

<210> SEQ ID NO 141
<211> LENGTH: 22
<212> TYPE: RNA
<213> ORGANISM: Homo sapiens

<400> SEQUENCE: 141
aggcggggcg ccgcgggacc gc                                            22

<210> SEQ ID NO 142
<211> LENGTH: 22
<212> TYPE: RNA
<213> ORGANISM: Homo sapiens

<400> SEQUENCE: 142
ccccuggggc ugggcaggcg ga                                            22
```

```
<210> SEQ ID NO 143
<211> LENGTH: 23
<212> TYPE: RNA
<213> ORGANISM: Homo sapiens

<400> SEQUENCE: 143
ucaauaggaa agagguggga ccu                                               23

<210> SEQ ID NO 144
<211> LENGTH: 21
<212> TYPE: RNA
<213> ORGANISM: Homo sapiens

<400> SEQUENCE: 144 caggagugggg ggguggggacg u                                               21

<210> SEQ ID NO 145
<211> LENGTH: 20
<212> TYPE: RNA
<213> ORGANISM: Homo sapiens

<400> SEQUENCE: 145
ccccagggcg acgcggcggg                                                   20

<210> SEQ ID NO 146
<211> LENGTH: 18
<212> TYPE: RNA
<213> ORGANISM: Homo sapiens

<400> SEQUENCE: 146 gguggggcuuc ccggaggg                                                    18

<210> SEQ ID NO 147
<211> LENGTH: 22
<212> TYPE: RNA
<213> ORGANISM: Homo sapiens

<400> SEQUENCE: 147
cgucccgggg cugcgcgagg ca                                                22

<210> SEQ ID NO 148
<211> LENGTH: 22
<212> TYPE: RNA
<213> ORGANISM: Homo sapiens

<400> SEQUENCE: 148
agcccgcccc agccgagguu cu                                                22

<210> SEQ ID NO 149
<211> LENGTH: 22
<212> TYPE: RNA
<213> ORGANISM: Homo sapiens

<400> SEQUENCE: 149
uggggcggag cuuccggagg cc                                                22

<210> SEQ ID NO 150
<211> LENGTH: 22
<212> TYPE: RNA
<213> ORGANISM: Homo sapiens

<400> SEQUENCE: 150
cugaauagcu gggacuacag gu                                                22
```

```
<210> SEQ ID NO 151
<211> LENGTH: 18
<212> TYPE: RNA
<213> ORGANISM: Homo sapiens

<400> SEQUENCE: 151
cgggcguggu gguggggg                                                 18

<210> SEQ ID NO 152
<211> LENGTH: 20
<212> TYPE: RNA
<213> ORGANISM: Homo sapiens

<400> SEQUENCE: 152
ggcggcgggg agguaggcag                                               20

<210> SEQ ID NO 153
<211> LENGTH: 21
<212> TYPE: RNA
<213> ORGANISM: Homo sapiens

<400> SEQUENCE: 153
agggcccccc cucaauccug u                                             21

<210> SEQ ID NO 154
<211> LENGTH: 21
<212> TYPE: RNA
<213> ORGANISM: Homo sapiens

<400> SEQUENCE: 154
gcugggaagg caaagggacg u                                             21

<210> SEQ ID NO 155
<211> LENGTH: 20
<212> TYPE: RNA
<213> ORGANISM: Homo sapiens

<400> SEQUENCE: 155
ggauccgagu cacggcacca                                               20

<210> SEQ ID NO 156
<211> LENGTH: 22
<212> TYPE: RNA
<213> ORGANISM: Homo sapiens

<400> SEQUENCE: 156
ugcagggguc gguguggcca gg                                            22

<210> SEQ ID NO 157
<211> LENGTH: 19
<212> TYPE: RNA
<213> ORGANISM: Homo sapiens

<400> SEQUENCE: 157
uggauuuuug gaucaggga                                                19

<210> SEQ ID NO 158
<211> LENGTH: 22
<212> TYPE: RNA
<213> ORGANISM: Homo sapiens

<400> SEQUENCE: 158
```
caggcacggg agcucaggug ag                                                    22

<210> SEQ ID NO 159
<211> LENGTH: 24
<212> TYPE: RNA
<213> ORGANISM: Homo sapiens

<400> SEQUENCE: 159 ugggagcug aggcucuggg ggug                                                   24

<210> SEQ ID NO 160
<211> LENGTH: 23
<212> TYPE: RNA
<213> ORGANISM: Homo sapiens

<400> SEQUENCE: 160
uggugcggag agggcccaca gug                                                   23

<210> SEQ ID NO 161
<211> LENGTH: 23
<212> TYPE: RNA
<213> ORGANISM: Homo sapiens

<400> SEQUENCE: 161
ucgaggacug guggaagggc cuu                                                   23

<210> SEQ ID NO 162
<211> LENGTH: 20
<212> TYPE: RNA
<213> ORGANISM: Homo sapiens

<400> SEQUENCE: 162
ugugggacug caaaugggag                                                       20

<210> SEQ ID NO 163
<211> LENGTH: 20
<212> TYPE: RNA
<213> ORGANISM: Homo sapiens

<400> SEQUENCE: 163
cgggcguggu gguggggug                                                        20

<210> SEQ ID NO 164
<211> LENGTH: 22
<212> TYPE: RNA
<213> ORGANISM: Homo sapiens

<400> SEQUENCE: 164
gugggugcug gugggagccg ug                                                    22

<210> SEQ ID NO 165
<211> LENGTH: 21
<212> TYPE: RNA
<213> ORGANISM: Homo sapiens

<400> SEQUENCE: 165
caggcaggug uaggguggag c                                                     21

<210> SEQ ID NO 166
<211> LENGTH: 23
<212> TYPE: RNA
<213> ORGANISM: Homo sapiens

<400> SEQUENCE: 166
uuagggagua aaggguggg gag 23

<210> SEQ ID NO 167
<211> LENGTH: 22
<212> TYPE: RNA
<213> ORGANISM: Homo sapiens

<400> SEQUENCE: 167
agacacauuu ggagagggac cc 22

<210> SEQ ID NO 168
<211> LENGTH: 22
<212> TYPE: RNA
<213> ORGANISM: Homo sapiens

<400> SEQUENCE: 168
gcugcgggcu gcggucaggg cg 22

<210> SEQ ID NO 169
<211> LENGTH: 22
<212> TYPE: RNA
<213> ORGANISM: Homo sapiens

<400> SEQUENCE: 169
cugguacagg ccuggggac ag 22

<210> SEQ ID NO 170
<211> LENGTH: 24
<212> TYPE: RNA
<213> ORGANISM: Homo sapiens

<400> SEQUENCE: 170
ccuggggaca ggggauuggg gcag 24

<210> SEQ ID NO 171
<211> LENGTH: 23
<212> TYPE: RNA
<213> ORGANISM: Homo sapiens

<400> SEQUENCE: 171
uugcucugcu cccccgcccc cag 23

<210> SEQ ID NO 172
<211> LENGTH: 23
<212> TYPE: RNA
<213> ORGANISM: Homo sapiens

<400> SEQUENCE: 172
ccucccugcc cgccucucug cag 23

<210> SEQ ID NO 173
<211> LENGTH: 22
<212> TYPE: RNA
<213> ORGANISM: Homo sapiens

<400> SEQUENCE: 173
gugcggaacg cuggccgggg cg 22

<210> SEQ ID NO 174
<211> LENGTH: 20
<212> TYPE: RNA
<213> ORGANISM: Homo sapiens

```
<400> SEQUENCE: 174
ggggaggugu gcagggcugg                                              20

<210> SEQ ID NO 175
<211> LENGTH: 23
<212> TYPE: RNA
<213> ORGANISM: Homo sapiens

<400> SEQUENCE: 175
cacacaggaa aagcggggcc cug                                          23

<210> SEQ ID NO 176
<211> LENGTH: 22
<212> TYPE: RNA
<213> ORGANISM: Homo sapiens

<400> SEQUENCE: 176
agggacggga cgcggugcag ug                                           22

<210> SEQ ID NO 177
<211> LENGTH: 23
<212> TYPE: RNA
<213> ORGANISM: Homo sapiens

<400> SEQUENCE: 177
ugaggauaug gcagggaagg gga                                          23

<210> SEQ ID NO 178
<211> LENGTH: 18
<212> TYPE: RNA
<213> ORGANISM: Homo sapiens

<400> SEQUENCE: 178
cggugagcgc ucgcuggc                                                18

<210> SEQ ID NO 179
<211> LENGTH: 17
<212> TYPE: RNA
<213> ORGANISM: Homo sapiens

<400> SEQUENCE: 179
ggcgggugcg ggggugg                                                 17

<210> SEQ ID NO 180
<211> LENGTH: 22
<212> TYPE: RNA
<213> ORGANISM: Homo sapiens

<400> SEQUENCE: 180 gggugggau uuguugcauu ac                                            22

<210> SEQ ID NO 181
<211> LENGTH: 18
<212> TYPE: RNA
<213> ORGANISM: Homo sapiens

<400> SEQUENCE: 181
gggugcgggc cggcgggg                                                18

<210> SEQ ID NO 182
<211> LENGTH: 22
<212> TYPE: RNA
<213> ORGANISM: Homo sapiens
```

-continued

```
<400> SEQUENCE: 182
agacugacgg cuggaggccc au                                           22

<210> SEQ ID NO 183
<211> LENGTH: 21
<212> TYPE: RNA
<213> ORGANISM: Homo sapiens

<400> SEQUENCE: 183
cgggccggag gucaagggcg u                                            21

<210> SEQ ID NO 184
<211> LENGTH: 24
<212> TYPE: RNA
<213> ORGANISM: Homo sapiens

<400> SEQUENCE: 184
ugggcgaggg gugggcucuc agag                                         24

<210> SEQ ID NO 185
<211> LENGTH: 25
<212> TYPE: RNA
<213> ORGANISM: Homo sapiens

<400> SEQUENCE: 185
ucggggcaug ggggagggag gcugg                                        25

<210> SEQ ID NO 186
<211> LENGTH: 20
<212> TYPE: RNA
<213> ORGANISM: Homo sapiens

<400> SEQUENCE: 186
cggggugggu gaggucgggc                                              20

<210> SEQ ID NO 187
<211> LENGTH: 17
<212> TYPE: RNA
<213> ORGANISM: Homo sapiens

<400> SEQUENCE: 187
cgcgccgggc ccggguu                                                 17

<210> SEQ ID NO 188
<211> LENGTH: 21
<212> TYPE: RNA
<213> ORGANISM: Homo sapiens

<400> SEQUENCE: 188
cgggagcugg ggucugcagg u                                            21

<210> SEQ ID NO 189
<211> LENGTH: 21
<212> TYPE: RNA
<213> ORGANISM: Homo sapiens

<400> SEQUENCE: 189
cccaugccuc cugccgcggu c                                            21

<210> SEQ ID NO 190
<211> LENGTH: 20
<212> TYPE: RNA
```

<210> SEQ ID NO 190 (context continued)
<213> ORGANISM: Homo sapiens

<400> SEQUENCE: 190
acucaaacug uggggggcacu                                          20

<210> SEQ ID NO 191
<211> LENGTH: 23
<212> TYPE: RNA
<213> ORGANISM: Homo sapiens

<400> SEQUENCE: 191
acggggaguc aggcaguggu gga                                       23

<210> SEQ ID NO 192
<211> LENGTH: 24
<212> TYPE: RNA
<213> ORGANISM: Homo sapiens

<400> SEQUENCE: 192
guaggggcgu cccgggcgcg cggg                                      24

<210> SEQ ID NO 193
<211> LENGTH: 18
<212> TYPE: RNA
<213> ORGANISM: Homo sapiens

<400> SEQUENCE: 193
auccuaguca cggcacca                                             18

<210> SEQ ID NO 194
<211> LENGTH: 23
<212> TYPE: RNA
<213> ORGANISM: Homo sapiens

<400> SEQUENCE: 194
gugcguggug gcucgaggcg ggg                                       23

<210> SEQ ID NO 195
<211> LENGTH: 17
<212> TYPE: RNA
<213> ORGANISM: Homo sapiens

<400> SEQUENCE: 195
ggauggagga ggggucu                                              17

<210> SEQ ID NO 196
<211> LENGTH: 22
<212> TYPE: RNA
<213> ORGANISM: Homo sapiens

<400> SEQUENCE: 196
gcugggauua caggcaugag cc                                        22

<210> SEQ ID NO 197
<211> LENGTH: 22
<212> TYPE: RNA
<213> ORGANISM: Homo sapiens

<400> SEQUENCE: 197
ucggccuggg gaggaggaag gg                                        22

<210> SEQ ID NO 198
<211> LENGTH: 20

```
<212> TYPE: RNA
<213> ORGANISM: Homo sapiens

<400> SEQUENCE: 198
ucacaccugc cucgccccc                                              20

<210> SEQ ID NO 199
<211> LENGTH: 25
<212> TYPE: RNA
<213> ORGANISM: Homo sapiens

<400> SEQUENCE: 199
acuugggcag gagggacccu guaug                                       25

<210> SEQ ID NO 200
<211> LENGTH: 22
<212> TYPE: RNA
<213> ORGANISM: Homo sapiens

<400> SEQUENCE: 200 uaggggcgg cuuguggagu gu                                           22

<210> SEQ ID NO 201
<211> LENGTH: 21
<212> TYPE: RNA
<213> ORGANISM: Homo sapiens

<400> SEQUENCE: 201
aucacauugc cagggauuuc c                                           21

<210> SEQ ID NO 202
<211> LENGTH: 23
<212> TYPE: RNA
<213> ORGANISM: Homo sapiens

<400> SEQUENCE: 202 cuggggacg cgugagcgcg agc                                          23

<210> SEQ ID NO 203
<211> LENGTH: 18
<212> TYPE: RNA
<213> ORGANISM: Homo sapiens

<400> SEQUENCE: 203
aggcugggcu gggacgga                                               18

<210> SEQ ID NO 204
<211> LENGTH: 21
<212> TYPE: RNA
<213> ORGANISM: Homo sapiens

<400> SEQUENCE: 204
acucggcugc gguggacaag u                                           21

<210> SEQ ID NO 205
<211> LENGTH: 22
<212> TYPE: RNA
<213> ORGANISM: Homo sapiens

<400> SEQUENCE: 205
uggcucaguu cagcaggaac ag                                          22

<210> SEQ ID NO 206
```

-continued

```
<211> LENGTH: 22
<212> TYPE: RNA
<213> ORGANISM: Homo sapiens

<400> SEQUENCE: 206
ggcuggagcg agugcagugg ug                                            22

<210> SEQ ID NO 207
<211> LENGTH: 23
<212> TYPE: RNA
<213> ORGANISM: Homo sapiens

<400> SEQUENCE: 207
ugaguggggc ucccgggacg gcg                                           23

<210> SEQ ID NO 208
<211> LENGTH: 23
<212> TYPE: RNA
<213> ORGANISM: Homo sapiens

<400> SEQUENCE: 208
cggggccgua gcacugucug aga                                           23

<210> SEQ ID NO 209
<211> LENGTH: 22
<212> TYPE: RNA
<213> ORGANISM: Homo sapiens

<400> SEQUENCE: 209
caggaaggau uuagggacag gc                                            22

<210> SEQ ID NO 210
<211> LENGTH: 21
<212> TYPE: RNA
<213> ORGANISM: Homo sapiens

<400> SEQUENCE: 210
uggcuguugg aggggggcagg c                                            21

<210> SEQ ID NO 211
<211> LENGTH: 18
<212> TYPE: RNA
<213> ORGANISM: Homo sapiens

<400> SEQUENCE: 211
agcaggugcg gggcggcg                                                 18

<210> SEQ ID NO 212
<211> LENGTH: 24
<212> TYPE: RNA
<213> ORGANISM: Homo sapiens

<400> SEQUENCE: 212
uguaggcaug aggcagggcc cagg                                          24

<210> SEQ ID NO 213
<211> LENGTH: 23
<212> TYPE: RNA
<213> ORGANISM: Homo sapiens

<400> SEQUENCE: 213
acaggcggcu guagcaaugg ggg                                           23
```

```
<210> SEQ ID NO 214
<211> LENGTH: 22
<212> TYPE: RNA
<213> ORGANISM: Homo sapiens

<400> SEQUENCE: 214
gggacccagg gagagacgua ag                                              22

<210> SEQ ID NO 215
<211> LENGTH: 19
<212> TYPE: RNA
<213> ORGANISM: Homo sapiens

<400> SEQUENCE: 215
gagggcgggu ggaggagga                                                  19

<210> SEQ ID NO 216
<211> LENGTH: 23
<212> TYPE: RNA
<213> ORGANISM: Homo sapiens

<400> SEQUENCE: 216
agaggcuuug ugcggauacg ggg                                             23

<210> SEQ ID NO 217
<211> LENGTH: 18
<212> TYPE: RNA
<213> ORGANISM: Homo sapiens

<400> SEQUENCE: 217
gggucccggg gaggggggg                                                  18

<210> SEQ ID NO 218
<211> LENGTH: 22
<212> TYPE: RNA
<213> ORGANISM: Homo sapiens

<400> SEQUENCE: 218
agggaagggg acgaggguug gg                                              22

<210> SEQ ID NO 219
<211> LENGTH: 22
<212> TYPE: RNA
<213> ORGANISM: Homo sapiens

<400> SEQUENCE: 219
ugguggagga agagggcagc uc                                              22

<210> SEQ ID NO 220
<211> LENGTH: 20
<212> TYPE: RNA
<213> ORGANISM: Homo sapiens

<400> SEQUENCE: 220
ggcggcggcg gaggcggggg                                                 20

<210> SEQ ID NO 221
<211> LENGTH: 21
<212> TYPE: RNA
<213> ORGANISM: Homo sapiens

<400> SEQUENCE: 221
agccgcgggg aucgccgagg g                                               21
```

```
<210> SEQ ID NO 222
<211> LENGTH: 23
<212> TYPE: RNA
<213> ORGANISM: Homo sapiens

<400> SEQUENCE: 222
ugggcagggg cuuauuguag gag                                            23

<210> SEQ ID NO 223
<211> LENGTH: 17
<212> TYPE: RNA
<213> ORGANISM: Homo sapiens

<400> SEQUENCE: 223
ggggcugggc gcgcgcc                                                   17

<210> SEQ ID NO 224
<211> LENGTH: 22
<212> TYPE: RNA
<213> ORGANISM: Homo sapiens

<400> SEQUENCE: 224
ugcggggcua gggcuaacag ca                                             22

<210> SEQ ID NO 225
<211> LENGTH: 19
<212> TYPE: RNA
<213> ORGANISM: Homo sapiens

<400> SEQUENCE: 225
cggggucggc ggcgacgug                                                 19

<210> SEQ ID NO 226
<211> LENGTH: 22
<212> TYPE: RNA
<213> ORGANISM: Homo sapiens

<400> SEQUENCE: 226
ugcggggaca ggccagggca uc                                             22

<210> SEQ ID NO 227
<211> LENGTH: 20
<212> TYPE: RNA
<213> ORGANISM: Homo sapiens

<400> SEQUENCE: 227 caggggacu gggggugagc                                                 20

<210> SEQ ID NO 228
<211> LENGTH: 23
<212> TYPE: RNA
<213> ORGANISM: Homo sapiens

<400> SEQUENCE: 228
caggcagaag uggggcugac agg                                            23

<210> SEQ ID NO 229
<211> LENGTH: 22
<212> TYPE: RNA
<213> ORGANISM: Homo sapiens

<400> SEQUENCE: 229
guaggggagg uugggccagg ga                                             22
```

```
<210> SEQ ID NO 230
<211> LENGTH: 22
<212> TYPE: RNA
<213> ORGANISM: Homo sapiens

<400> SEQUENCE: 230
ggggcugggg ccggggccga gc                                            22

<210> SEQ ID NO 231
<211> LENGTH: 21
<212> TYPE: RNA
<213> ORGANISM: Homo sapiens

<400> SEQUENCE: 231
augccucccc cggccccgca g                                             21

<210> SEQ ID NO 232
<211> LENGTH: 23
<212> TYPE: RNA
<213> ORGANISM: Homo sapiens

<400> SEQUENCE: 232
cucggggcag gcggcuggga gcg                                           23

<210> SEQ ID NO 233
<211> LENGTH: 25
<212> TYPE: RNA
<213> ORGANISM: Homo sapiens

<400> SEQUENCE: 233
aagggaggag gagcggaggg gcccu                                         25

<210> SEQ ID NO 234
<211> LENGTH: 18
<212> TYPE: RNA
<213> ORGANISM: Homo sapiens

<400> SEQUENCE: 234
uucccagcca acgcacca                                                 18

<210> SEQ ID NO 235
<211> LENGTH: 20
<212> TYPE: RNA
<213> ORGANISM: Homo sapiens

<400> SEQUENCE: 235
aaaaggcggg agaagcccca                                               20

<210> SEQ ID NO 236
<211> LENGTH: 20
<212> TYPE: RNA
<213> ORGANISM: Homo sapiens

<400> SEQUENCE: 236
ucucuucauc uaccccccag                                               20

<210> SEQ ID NO 237
<211> LENGTH: 22
<212> TYPE: RNA
<213> ORGANISM: Homo sapiens

<400> SEQUENCE: 237
```

```
acucaaaaug ggggcgcuuu cc                                             22

<210> SEQ ID NO 238
<211> LENGTH: 17
<212> TYPE: RNA
<213> ORGANISM: Homo sapiens

<400> SEQUENCE: 238
ccccgccacc gccuugg                                                   17

<210> SEQ ID NO 239
<211> LENGTH: 21
<212> TYPE: RNA
<213> ORGANISM: Homo sapiens

<400> SEQUENCE: 239
cugggcucgg gacgcgcggc u                                              21

<210> SEQ ID NO 240
<211> LENGTH: 19
<212> TYPE: RNA
<213> ORGANISM: Homo sapiens

<400> SEQUENCE: 240 ugggcggag cuuccggag                                                  19

<210> SEQ ID NO 241
<211> LENGTH: 21
<212> TYPE: RNA
<213> ORGANISM: Homo sapiens

<400> SEQUENCE: 241
agcaugacag aggagaggug g                                              21

<210> SEQ ID NO 242
<211> LENGTH: 23
<212> TYPE: RNA
<213> ORGANISM: Homo sapiens

<400> SEQUENCE: 242
gugaguggga gccccagugu gug                                            23

<210> SEQ ID NO 243
<211> LENGTH: 17
<212> TYPE: RNA
<213> ORGANISM: Homo sapiens

<400> SEQUENCE: 243
gagacugggg ugggggcc                                                  17

<210> SEQ ID NO 244
<211> LENGTH: 17
<212> TYPE: RNA
<213> ORGANISM: Homo sapiens

<400> SEQUENCE: 244
gcugggcgag gcuggca                                                   17

<210> SEQ ID NO 245
<211> LENGTH: 23
<212> TYPE: RNA
<213> ORGANISM: Homo sapiens

<400> SEQUENCE: 245
```

```
cuggcggagc ccauuccaug cca                                              23

<210> SEQ ID NO 246
<211> LENGTH: 22
<212> TYPE: RNA
<213> ORGANISM: Homo sapiens

<400> SEQUENCE: 246
ugauugucuu cccccacccu ca                                               22

<210> SEQ ID NO 247
<211> LENGTH: 17
<212> TYPE: RNA
<213> ORGANISM: Homo sapiens

<400> SEQUENCE: 247
accccacucc ugguacc                                                     17

<210> SEQ ID NO 248
<211> LENGTH: 23
<212> TYPE: RNA
<213> ORGANISM: Homo sapiens

<400> SEQUENCE: 248
caggcagaag uggggcugac agg                                              23

<210> SEQ ID NO 249
<211> LENGTH: 25
<212> TYPE: RNA
<213> ORGANISM: Homo sapiens

<400> SEQUENCE: 249
aagggaggag gagcggaggg gcccu                                            25

<210> SEQ ID NO 250
<211> LENGTH: 22
<212> TYPE: RNA
<213> ORGANISM: Homo sapiens

<400> SEQUENCE: 250
ucgggccugg gguuggggga gc                                               22

<210> SEQ ID NO 251
<211> LENGTH: 67
<212> TYPE: RNA
<213> ORGANISM: Homo sapiens

<400> SEQUENCE: 251
uacaggccgg ggcuuugggu gagggacccc cggagucugu cacggucuca ccccaacucu      60
gccccag                                                                67

<210> SEQ ID NO 252
<211> LENGTH: 81
<212> TYPE: RNA
<213> ORGANISM: Homo sapiens

<400> SEQUENCE: 252
uccacugcug ccgccgucgc cgccacccga gccggagcgg gcugggccgc caaggcaaga      60
ugguggacua cagcgugugg g                                                81

<210> SEQ ID NO 253
```

```
<211> LENGTH: 118
<212> TYPE: RNA
<213> ORGANISM: Homo sapiens

<400> SEQUENCE: 253
gcaggugaac uggcaggcca ggaagaggag gaagcccugg aggggcugga ggugauggau      60 guuuccucc gguucucagg gcuccaccuc uuucgggccg uagagccagg gcuggugc        118

<210> SEQ ID NO 254
<211> LENGTH: 93
<212> TYPE: RNA
<213> ORGANISM: Homo sapiens

<400> SEQUENCE: 254 gcuguuggg gauuggguca ggccagugun caagggcccc uccucuagua cucccuguuu      60
guguucugcc acugacugag cuucuccca cag                                   93

<210> SEQ ID NO 255
<211> LENGTH: 70
<212> TYPE: RNA
<213> ORGANISM: Homo sapiens

<400> SEQUENCE: 255
cacagucuga cucagugacu caugugcugg cagguggccac guaaauagag cuacuguguc    60
ugaaagcaau                                                            70

<210> SEQ ID NO 256
<211> LENGTH: 80
<212> TYPE: RNA
<213> ORGANISM: Homo sapiens

<400> SEQUENCE: 256
cgugugagcc cgcccugugc ccggcccacu ucugcuuccu cuuagcgcag gaggggucc     60 gcacugggag gggcccucac                                                 80

<210> SEQ ID NO 257
<211> LENGTH: 89
<212> TYPE: RNA
<213> ORGANISM: Homo sapiens

<400> SEQUENCE: 257
gccggcgccc gagcucuggc uccgugucuu cacucccgug cuuguccgag gagggaggga    60
gggacggggg cugugcuggg gcagcugga                                       89

<210> SEQ ID NO 258
<211> LENGTH: 86
<212> TYPE: RNA
<213> ORGANISM: Homo sapiens

<400> SEQUENCE: 258
agcacugccc ccggugaguc agggguggc uggccccug cuucgugccc auccgcgcuc       60
ugacucucug cccaccugca ggagcu                                          86

<210> SEQ ID NO 259
<211> LENGTH: 77
<212> TYPE: RNA
<213> ORGANISM: Homo sapiens

<400> SEQUENCE: 259
caugagaaau ccugcugguc aaccauagcc cuggucagac ucuccggggc ugugauugac     60
```
cagcaggacu ucucaug                                                    77

<210> SEQ ID NO 260
<211> LENGTH: 68
<212> TYPE: RNA
<213> ORGANISM: Homo sapiens

<400> SEQUENCE: 260
aggguugggg ggacaggaug agaggcuguc uucauucccu cuugaccacc ccucguuucu    60
ucccccag                                                              68

<210> SEQ ID NO 261
<211> LENGTH: 70
<212> TYPE: RNA
<213> ORGANISM: Homo sapiens

<400> SEQUENCE: 261
cccugccagu gcuggggggcc acaugagugu gcagucaucc acacacaagu ggcccccaac    60
acuggcaggg                                                            70

<210> SEQ ID NO 262
<211> LENGTH: 85
<212> TYPE: RNA
<213> ORGANISM: Homo sapiens

<400> SEQUENCE: 262
ucugagguac ccggggcaga uugguguagg gugcaaagcc ugcccgcccc cuaagccuuc    60
ugcccccaac uccagccugu cagga                                           85

<210> SEQ ID NO 263
<211> LENGTH: 79
<212> TYPE: RNA
<213> ORGANISM: Homo sapiens

<400> SEQUENCE: 263 gugaggugg ggccagcagg gagugggcug ggcugggcug ggccaagguua caaggccuca    60 cccugcaucc cgcacccag                                                  79

<210> SEQ ID NO 264
<211> LENGTH: 84
<212> TYPE: RNA
<213> ORGANISM: Homo sapiens

<400> SEQUENCE: 264
gcuggcgucg gugcugggga gcggcccccg ggugggccuc ugcucuggcc ccuccugggg    60
cccgcacucu cgcucugggc ccgc                                            84

<210> SEQ ID NO 265
<211> LENGTH: 73
<212> TYPE: RNA
<213> ORGANISM: Homo sapiens

<400> SEQUENCE: 265
cugguguuug aggcgaugug gggauguaga gacaacuucc cagucucauu uccucauccu    60
gccaggccac cau                                                        73

<210> SEQ ID NO 266
<211> LENGTH: 66
<212> TYPE: RNA

```
<213> ORGANISM: Homo sapiens

<400> SEQUENCE: 266
gggcaugggg aggugugggag ucagcauggg gcuaggaggc cccgcgcuga cccgccuucu    60
ccgcag                                                                66

<210> SEQ ID NO 267
<211> LENGTH: 64
<212> TYPE: RNA
<213> ORGANISM: Homo sapiens

<400> SEQUENCE: 267
gaaggcgagg gguagaagag cacagggguu cugauaaacc cuucugccug cauucuacuc    60
ccag                                                                  64

<210> SEQ ID NO 268
<211> LENGTH: 73
<212> TYPE: RNA
<213> ORGANISM: Homo sapiens

<400> SEQUENCE: 268
aggccaggug gguauggagg agcccucaua uggcaguugg cgagggccca gugagcsccu    60
cucugcucuc cag                                                        73

<210> SEQ ID NO 269
<211> LENGTH: 67
<212> TYPE: RNA
<213> ORGANISM: Homo sapiens

<400> SEQUENCE: 269
gugggagggg agaggcagca agcacacagg gccugggacu agcaugcuga ccucccuccu    60
gccccag                                                               67

<210> SEQ ID NO 270
<211> LENGTH: 98
<212> TYPE: RNA
<213> ORGANISM: Homo sapiens

<400> SEQUENCE: 270
acgaauggcu augcacugca cacccuagg agaggugcc auucacauag acuauaauug      60
aauggcgcca cuaggguugu gcagugcaca accuacac                             98

<210> SEQ ID NO 271
<211> LENGTH: 86
<212> TYPE: RNA
<213> ORGANISM: Homo sapiens

<400> SEQUENCE: 271
ggcuuagaaa cagucccuag guaggauuug gggaggagcu aagaagcccc uacagggccc    60
agaggugggg acugagccuu aguugg                                          86

<210> SEQ ID NO 272
<211> LENGTH: 81
<212> TYPE: RNA
<213> ORGANISM: Homo sapiens

<400> SEQUENCE: 272
cucccuggga gggcguggau gauggugggga gaggagcccc acuguggaag ucugaccccc    60
acaucgcccc accuucccca g                                               81
```

<210> SEQ ID NO 273
<211> LENGTH: 86
<212> TYPE: RNA
<213> ORGANISM: Homo sapiens

<400> SEQUENCE: 273
ggggcugggg guguggggag agagagugca cagccagcuc agggauuaaa gcucuuucuc    60
ucucucucuc ucccacuucc cugcag                                        86

<210> SEQ ID NO 274
<211> LENGTH: 65
<212> TYPE: RNA
<213> ORGANISM: Homo sapiens

<400> SEQUENCE: 274
gagaaugggg ggacagaugg agaggacaca ggcuggcacu gagguccccu ccacuuuccu    60
ccuag                                                               65

<210> SEQ ID NO 275
<211> LENGTH: 79
<212> TYPE: RNA
<213> ORGANISM: Homo sapiens

<400> SEQUENCE: 275
gugcagaucc uugggagccc uguuagacuc uggauuuuac acuuggagug aacgggcgcc    60
aucccgaggc uuugcacag                                                79

<210> SEQ ID NO 276
<211> LENGTH: 73
<212> TYPE: RNA
<213> ORGANISM: Homo sapiens

<400> SEQUENCE: 276
gugggcgggg gcaggugugu gguggugggu ggccugcggu gagcagggcc cucacaccug    60
ccucgccccc cag                                                      73

<210> SEQ ID NO 277
<211> LENGTH: 137
<212> TYPE: RNA
<213> ORGANISM: Homo sapiens

<400> SEQUENCE: 277
agccagacaa gagggucaug gggagucacu gucaacccag agcaggcacu gccccugcga    60
ccagccuggg gcaucgguug gggugcaggg gucugcuggu gaugcuuucc aucucuuugc   120
uuuguccuga uuguagc                                                 137

<210> SEQ ID NO 278
<211> LENGTH: 69
<212> TYPE: RNA
<213> ORGANISM: Homo sapiens

<400> SEQUENCE: 278 uggguaggg gugggggaau cagggggugu cgaacucaug gcugccaccu uugucccc      60 auccugcag                                                           69

<210> SEQ ID NO 279
<211> LENGTH: 73
<212> TYPE: RNA

<213> ORGANISM: Homo sapiens

<400> SEQUENCE: 279
ggggagguac cuggacagg aggaggaggc agccuugccu cagaaaccaa acugucaaaa  60
guguagguuc cac                                                    73

<210> SEQ ID NO 280
<211> LENGTH: 113
<212> TYPE: RNA
<213> ORGANISM: Homo sapiens

<400> SEQUENCE: 280
gccggguggg gcggggcggc cucaggaggg gcccagcucc ccuggaugug cugcgguggg  60
gccggagggg cgucacgugc acccaaguga cgccccuucu gauucugccu cag         113

<210> SEQ ID NO 281
<211> LENGTH: 120
<212> TYPE: RNA
<213> ORGANISM: Homo sapiens

<400> SEQUENCE: 281
gauccaggga acccuagagc aggggaaugg cagagcaaaa uucauggccu acagcugccu  60
cuugccaaac ugcacuggau uugugucuc ccauucccca gagcugucug aggugcuuug  120

<210> SEQ ID NO 282
<211> LENGTH: 49
<212> TYPE: RNA
<213> ORGANISM: Homo sapiens

<400> SEQUENCE: 282
ggugaggcgg gggggcgagc ccugaggggc ucucgcuucu ggcgccaag              49

<210> SEQ ID NO 283
<211> LENGTH: 87
<212> TYPE: RNA
<213> ORGANISM: Homo sapiens

<400> SEQUENCE: 283
gugaggcggg gccaggaggg uguguggcgu gggugcugcg gggccgucag ggugccugcg  60
ggacgcucac cuggcuggcc cgcccag                                     87

<210> SEQ ID NO 284
<211> LENGTH: 60
<212> TYPE: RNA
<213> ORGANISM: Homo sapiens

<400> SEQUENCE: 284
aggccuaggg gguggcaggc uggccaucag uguggcuaa cccuguccuc ucccucccag   60

<210> SEQ ID NO 285
<211> LENGTH: 61
<212> TYPE: RNA
<213> ORGANISM: Homo sapiens

<400> SEQUENCE: 285
ucggcuggcg ggggguagagc uggcugcagg cccggcccu cucagcugcu gcccucucca  60
g                                                                 61

<210> SEQ ID NO 286
<211> LENGTH: 70

```
<212> TYPE: RNA
<213> ORGANISM: Homo sapiens

<400> SEQUENCE: 286
uuggguuggg guggucggcc cuggaggggg uuuguuugcu uauuccccuc ugugcuucac    60
cccuacccag                                                          70

<210> SEQ ID NO 287
<211> LENGTH: 84
<212> TYPE: RNA
<213> ORGANISM: Homo sapiens

<400> SEQUENCE: 287
ugugcagugg aaggggggc cgauacacug uacgagagug aguagcaggu cucacaguga    60
accggucucu uucccuacug uguc                                          84

<210> SEQ ID NO 288
<211> LENGTH: 70
<212> TYPE: RNA
<213> ORGANISM: Homo sapiens

<400> SEQUENCE: 288
acaaauagcu ucagggaguc aggggagggc agaaauagau ggccuucccc ugcugggaag    60
aaaguggguc                                                          70

<210> SEQ ID NO 289
<211> LENGTH: 64
<212> TYPE: RNA
<213> ORGANISM: Homo sapiens

<400> SEQUENCE: 289
gaggcacugg guagguggg cuccagggcu ccugacaccu ggaccucucc uccccaggcc    60
caca                                                                64

<210> SEQ ID NO 290
<211> LENGTH: 63
<212> TYPE: RNA
<213> ORGANISM: Homo sapiens

<400> SEQUENCE: 290
acccuagggu gggcuggag gugggcuga ggcugagucu ccuccccuu ccucccugcc       60 cag                                                                 63

<210> SEQ ID NO 291
<211> LENGTH: 69
<212> TYPE: RNA
<213> ORGANISM: Homo sapiens

<400> SEQUENCE: 291 gugggguaggg uuuggggag agcgugggcu gggguucagg gacacccucu caccacugcc   60
cucccacag                                                           69

<210> SEQ ID NO 292
<211> LENGTH: 93
<212> TYPE: RNA
<213> ORGANISM: Homo sapiens

<400> SEQUENCE: 292
guaaggaggg ggaugagggg ucauaucucu ucucagggaa agcaggagcc cuucagcagg   60
```

```
gucagggccc cucaucuucc ccuccuuucc cag                                93
```

<210> SEQ ID NO 293
<211> LENGTH: 70
<212> TYPE: RNA
<213> ORGANISM: Homo sapiens

<400> SEQUENCE: 293

```
gucccugggg gcugggaugg gccauggugu gcucugaucc cccugggguc ucuuggcccc    60
caggaacucc                                                          70
```

<210> SEQ ID NO 294
<211> LENGTH: 102
<212> TYPE: RNA
<213> ORGANISM: Homo sapiens

<400> SEQUENCE: 294

```
gugggagggc ccaggcgcgg gcaggggugg ggguggcaga gcgcuguccc gggggcgggg    60
ccgaagcgcg gcgaccguaa cuccuucugc uccgucccc ag                      102
```

<210> SEQ ID NO 295
<211> LENGTH: 89
<212> TYPE: RNA
<213> ORGANISM: Homo sapiens

<400> SEQUENCE: 295

```
accaugcugu agugugugua aacauccuac acucucagcu gugagcucaa gguggcuggg    60 agagggguugu uuacuccuuc ugccaugga                                    89
```

<210> SEQ ID NO 296
<211> LENGTH: 82
<212> TYPE: RNA
<213> ORGANISM: Homo sapiens

<400> SEQUENCE: 296

```
gugaguggga ggccagggca cggcagggg agcugcaggg cuaugggagg ggccccagcg    60
ucugagcccu guccucccgc ag                                            82
```

<210> SEQ ID NO 297
<211> LENGTH: 82
<212> TYPE: RNA
<213> ORGANISM: Homo sapiens

<400> SEQUENCE: 297

```
gugaguggga ggccagggca cggcagggg agcugcaggg cuaugggagg ggccccagcg    60
ucugagcccu guccucccgc ag                                            82
```

<210> SEQ ID NO 298
<211> LENGTH: 110
<212> TYPE: RNA
<213> ORGANISM: Homo sapiens

<400> SEQUENCE: 298

```
ucaccuggcc augugacuug ugggcuuccc uuugucaucc uucgccuagg gcucugagca    60
gggcagggac agcaaagggg ugcucaguug ucacuuccca cagcacggag              110
```

<210> SEQ ID NO 299
<211> LENGTH: 71
<212> TYPE: RNA
<213> ORGANISM: Homo sapiens

<400> SEQUENCE: 299
ggugaguggg agccgguggg gcuggaguaa gggcacgccc gggcugccc caccugcuga    60 ccacccuccc c    71

<210> SEQ ID NO 300
<211> LENGTH: 90
<212> TYPE: RNA
<213> ORGANISM: Homo sapiens

<400> SEQUENCE: 300
ucuaagaaac gcaguggucu cugaagccug caggggcagg ccagcccugc acugaacgcc    60
uguucuugcc agguggcaga agguugcugc    90

<210> SEQ ID NO 301
<211> LENGTH: 63
<212> TYPE: RNA
<213> ORGANISM: Homo sapiens

<400> SEQUENCE: 301
cuugcccggg agaaggaggu ggccuggaga gcugcugucu ccagccgccg ccugucucca    60
cag    63

<210> SEQ ID NO 302
<211> LENGTH: 80
<212> TYPE: RNA
<213> ORGANISM: Homo sapiens

<400> SEQUENCE: 302
ugagaggccg caccuugccu ugcugcccgg gccgugcacc cgugggcccc agggcgacgc    60
ggcgggggcg gcccuagcga    80

<210> SEQ ID NO 303
<211> LENGTH: 83
<212> TYPE: RNA
<213> ORGANISM: Homo sapiens

<400> SEQUENCE: 303
gucuacuccc agggugccaa gcuguuucgu guucccuccc uaggggaucc cagguagggg    60
cagcagagga ccugggccug gac    83

<210> SEQ ID NO 304
<211> LENGTH: 93
<212> TYPE: RNA
<213> ORGANISM: Homo sapiens

<400> SEQUENCE: 304
ggcgcuuuug ugcgcgcccg ggucuguugg ugcucagagu guggucaggc ggcucggacu    60
gagcaggugg gugcggggcu cggaggaggc ggc    93

<210> SEQ ID NO 305
<211> LENGTH: 55
<212> TYPE: RNA
<213> ORGANISM: Homo sapiens

<400> SEQUENCE: 305
gggggcuggg gcgcggggag gugcuagguc ggccucggcu cccgcgccgc acccc    55

<210> SEQ ID NO 306

```
<211> LENGTH: 61
<212> TYPE: RNA
<213> ORGANISM: Homo sapiens

<400> SEQUENCE: 306
gagggcagcg uggguguggc ggaggcaggc gugaccguuu gccgcccucu cgcugcucua        60
g                                                                      61

<210> SEQ ID NO 307
<211> LENGTH: 89
<212> TYPE: RNA
<213> ORGANISM: Homo sapiens

<400> SEQUENCE: 307
agccugyggg aaagagaaga gcagggcagg gugaaggccc ggcggagaca cucugcccac        60
cccacacccu gccuauggcc cacacagcu                                         89

<210> SEQ ID NO 308
<211> LENGTH: 90
<212> TYPE: RNA
<213> ORGANISM: Homo sapiens

<400> SEQUENCE: 308
aggccucgcu guucucuaug gcuuuuauu ccaugugau ucuacugcuc acucauauag          60
ggauuggagc cguggcgcac ggcggggaca                                        90

<210> SEQ ID NO 309
<211> LENGTH: 81
<212> TYPE: RNA
<213> ORGANISM: Homo sapiens

<400> SEQUENCE: 309
uagaggcagu uucaacagau guguagacuu uugauaugag aaauugguuu caaaaucagg        60
agucggggcu uuacugcuuu u                                                 81

<210> SEQ ID NO 310
<211> LENGTH: 72
<212> TYPE: RNA
<213> ORGANISM: Homo sapiens

<400> SEQUENCE: 310
cugugcaccu gggggagugc agugauugug gaaugcaaag ucccacaauc acuguacucc        60
ccaggugcac ag                                                           72

<210> SEQ ID NO 311
<211> LENGTH: 64
<212> TYPE: RNA
<213> ORGANISM: Homo sapiens

<400> SEQUENCE: 311
ccccgggccc ggcguucccu cccuucccgu gcgccagugg aggccggggu ggggcgggc         60 gggg                                                                    64

<210> SEQ ID NO 312
<211> LENGTH: 64
<212> TYPE: RNA
<213> ORGANISM: Homo sapiens

<400> SEQUENCE: 312
ccccgggccc ggcguucccu cccuucccgu gcgccagugg aggccggggu ggggcgggc         60
``` gggg                                                                    64

<210> SEQ ID NO 313
<211> LENGTH: 124
<212> TYPE: RNA
<213> ORGANISM: Homo sapiens

<400> SEQUENCE: 313
aacccuccuu gggaagugaa gcucaggcug ugauuucaag ccaggggcg uuuuucuaua        60 acuggaugaa aagcaccucc agagcuugaa gcucacaguu ugagagcaau cgucuaagga      120
aguu                                                                   124

<210> SEQ ID NO 314
<211> LENGTH: 80
<212> TYPE: RNA
<213> ORGANISM: Homo sapiens

<400> SEQUENCE: 314
aggacccuuc cagagggccc ccccucaauc cuguugugcc uaauucagag gguugggugg       60
aggcucuccu gaagggcucu                                                   80

<210> SEQ ID NO 315
<211> LENGTH: 68
<212> TYPE: RNA
<213> ORGANISM: Homo sapiens

<400> SEQUENCE: 315
cucaggcuca guggugcaug cuuauagucc cagccacucu ggaggcugaa ggaagauggc       60
uugagccu                                                                68

<210> SEQ ID NO 316
<211> LENGTH: 65
<212> TYPE: RNA
<213> ORGANISM: Homo sapiens

<400> SEQUENCE: 316
gagggcuagg uggggggcuu gaagccccga gaugccucac gcuucaccc cucucaccua        60 agcag                                                                   65

<210> SEQ ID NO 317
<211> LENGTH: 67
<212> TYPE: RNA
<213> ORGANISM: Homo sapiens

<400> SEQUENCE: 317
cagcgugggc ugcugagaag gggcagggguc cuccagcuca uccuccugc cuccuccgug       60 gccucag                                                                 67

<210> SEQ ID NO 318
<211> LENGTH: 65
<212> TYPE: RNA
<213> ORGANISM: Homo sapiens

<400> SEQUENCE: 318
cuccucuggg ggugggggc ugggcguggu ggacagcgau gcaucccucg ccuucucacc        60
cucag                                                                   65

<210> SEQ ID NO 319

```
<211> LENGTH: 119
<212> TYPE: RNA
<213> ORGANISM: Homo sapiens

<400> SEQUENCE: 319
agccugcgcc ggagccgggg ccugagcccg ggccgcgcag gccgugaacu cgucgagcug    60
cgcgugcggc cggugcucaa ccugccgggu ccuggccccg cgcucccgcg cgcccugga   119

<210> SEQ ID NO 320
<211> LENGTH: 71
<212> TYPE: RNA
<213> ORGANISM: Homo sapiens

<400> SEQUENCE: 320
ugaccacccc cgggcaaaga ccugcagauc cccuguuaga cgggccca ggacuuugug     60 cggggugccc a                                                       71

<210> SEQ ID NO 321
<211> LENGTH: 71
<212> TYPE: RNA
<213> ORGANISM: Homo sapiens

<400> SEQUENCE: 321 auggagggg guguggagcc aggggcccca ggucuacagc uucuccccgc ucccugcccc    60
cauacuccca g                                                       71

<210> SEQ ID NO 322
<211> LENGTH: 67
<212> TYPE: RNA
<213> ORGANISM: Homo sapiens

<400> SEQUENCE: 322
ggcagccagg gggauggggcg agcuugggcc cauuccuuuc cuuacccuac cccccauccc    60
ccuguag                                                            67

<210> SEQ ID NO 323
<211> LENGTH: 109
<212> TYPE: RNA
<213> ORGANISM: Homo sapiens

<400> SEQUENCE: 323
ucccgcauuc ccucugcuuu ggucaggugg ugcccuccuu ccaugggguag agccagagau   60 ggugggucu ggcuggucag augggagugg acagagaccc ggggguccuc                109

<210> SEQ ID NO 324
<211> LENGTH: 66
<212> TYPE: RNA
<213> ORGANISM: Homo sapiens

<400> SEQUENCE: 324
ugacugggga gcagaaggag aacccaagaa aagcugacuu ggaggucccu ccuucuguccc   60 ccacag                                                             66

<210> SEQ ID NO 325
<211> LENGTH: 54
<212> TYPE: RNA
<213> ORGANISM: Homo sapiens

<400> SEQUENCE: 325
agcagcaggg gagagagagg aguccucuag acaccgacuc ugucuccugc agau          54
```

<210> SEQ ID NO 326
<211> LENGTH: 60
<212> TYPE: RNA
<213> ORGANISM: Homo sapiens

<400> SEQUENCE: 326
gagcaggcga ggcugggcug aacccguggg ugaggagugc agcccagcug aggccucugc    60

<210> SEQ ID NO 327
<211> LENGTH: 75
<212> TYPE: RNA
<213> ORGANISM: Homo sapiens

<400> SEQUENCE: 327
guaguuguuc uacagaagac cuggaugugu aggagcuaag acacaucca ggggagcugu    60 ggaagcagua acacg                                                    75

<210> SEQ ID NO 328
<211> LENGTH: 97
<212> TYPE: RNA
<213> ORGANISM: Homo sapiens

<400> SEQUENCE: 328
cucaggugcu cuggcugcuu ggguuccugg caugcugauu ugugacuuaa gauuaaaauc    60
acauugccag ggauuaccac gcaaccacga ccuuggc                            97

<210> SEQ ID NO 329
<211> LENGTH: 86
<212> TYPE: RNA
<213> ORGANISM: Homo sapiens

<400> SEQUENCE: 329
aggagugacc aaaagacaag agugcgagcc uucuauuaug cccagacagg gccaccagag    60
ggcuccuugg ucuaggggua augcca                                        86

<210> SEQ ID NO 330
<211> LENGTH: 75
<212> TYPE: RNA
<213> ORGANISM: Homo sapiens

<400> SEQUENCE: 330
caggggunug gggaaacggc cgcugaguga ggcgucggcu uguuucuca ccgcggucuu    60 uuccucccac ucuug                                                    75

<210> SEQ ID NO 331
<211> LENGTH: 82
<212> TYPE: RNA
<213> ORGANISM: Homo sapiens

<400> SEQUENCE: 331
gcuacgggga gcggggagga agugggcgcu gcuucugcgu uaucuggaag gagcagccca    60
cuccuguccu gggcucugug gu                                            82

<210> SEQ ID NO 332
<211> LENGTH: 99
<212> TYPE: RNA
<213> ORGANISM: Homo sapiens

<400> SEQUENCE: 332

```
gcaagggaca gggagggucg uggcgacacu cgcgccagcu cccgggacgg cugggcucgg    60
gcuggucgcc gaccuccgac ccuccacuag augccuggc                           99

<210> SEQ ID NO 333
<211> LENGTH: 59
<212> TYPE: RNA
<213> ORGANISM: Homo sapiens

<400> SEQUENCE: 333
ggggccaggc agggaggugg gaccaugggg gccuugcugu ugaccaccg uuccugcag      59

<210> SEQ ID NO 334
<211> LENGTH: 91
<212> TYPE: RNA
<213> ORGANISM: Homo sapiens

<400> SEQUENCE: 334
guucuagagc augguuucuc aucauuugca cuacugauac uuggggucag auaauuguuu    60 guggugggg cuguuguuug cauuguagga u                                    91

<210> SEQ ID NO 335
<211> LENGTH: 62
<212> TYPE: RNA
<213> ORGANISM: Homo sapiens

<400> SEQUENCE: 335
gugaguagug gcgcgcggcg gcucggagua ccucugccgc cgcgcgcauc ggcucagcau    60
gc                                                                   62

<210> SEQ ID NO 336
<211> LENGTH: 80
<212> TYPE: RNA
<213> ORGANISM: Homo sapiens

<400> SEQUENCE: 336
cgggaaugcc gcggcgggga cggcgauugg uccguaugug ugugccacc ggccgccggc     60 uccgccccgg cccccgcccc                                                80

<210> SEQ ID NO 337
<211> LENGTH: 65
<212> TYPE: RNA
<213> ORGANISM: Homo sapiens

<400> SEQUENCE: 337
gagggugggc gagggcggcu gagcggcucc auccccggc cugcucaucc cccucgcccu    60
cucag                                                                65

<210> SEQ ID NO 338
<211> LENGTH: 115
<212> TYPE: RNA
<213> ORGANISM: Homo sapiens

<400> SEQUENCE: 338
gagcaaaaac cagagaacaa caugggagcg uuccuaaccc cuaaggcaac uggaugggag    60
accugaccca uccaguucuc ugaggggcu cuugugueuu cuacaagguu guuca         115

<210> SEQ ID NO 339
<211> LENGTH: 100
<212> TYPE: RNA
<213> ORGANISM: Homo sapiens
```

<400> SEQUENCE: 339
gugagcgggc gcggcaggga ucgcgggcgg guggcggccu agggcgcgga gggcggaccg    60
ggaauggcgc gccgugcgcc gccggcguaa cugcggcgcu                         100

<210> SEQ ID NO 340
<211> LENGTH: 96
<212> TYPE: RNA
<213> ORGANISM: Homo sapiens

<400> SEQUENCE: 340
gcucuggggc gugccgccgc cgucgcugcc accuccccua ccgcuagugg aagaagaugg    60
cggaaggcgg agcggcggau cuggacaccc agcggu                             96

<210> SEQ ID NO 341
<211> LENGTH: 84
<212> TYPE: RNA
<213> ORGANISM: Homo sapiens

<400> SEQUENCE: 341
gaggcugggc ggggcgcggc cggaucgguc gagagcgucc uggcugauga cggucucccg    60
ugcccacgcc ccaaacgcag ucuc                                          84

<210> SEQ ID NO 342
<211> LENGTH: 64
<212> TYPE: RNA
<213> ORGANISM: Homo sapiens

<400> SEQUENCE: 342 ggguggggc ggggcggcag gggccucccc cagugccagg ccccauucug cuucucuccc     60
agcu                                                                64

<210> SEQ ID NO 343
<211> LENGTH: 86
<212> TYPE: RNA
<213> ORGANISM: Homo sapiens

<400> SEQUENCE: 343
cgccugagcg ugcagcagga caucuuccug accugguaau aauuagguga gaaggauggu    60 uggggcggu cggcguaacu caggga                                         86

<210> SEQ ID NO 344
<211> LENGTH: 86
<212> TYPE: RNA
<213> ORGANISM: Homo sapiens

<400> SEQUENCE: 344
cgccugagcg ugcagcagga caucuuccug accugguaau aauuagguga gaaggauggu    60 uggggcggu cggcguaacu caggga                                         86

<210> SEQ ID NO 345
<211> LENGTH: 81
<212> TYPE: RNA
<213> ORGANISM: Homo sapiens

<400> SEQUENCE: 345
aguugguggg ggagccauga gauaagagca ccuccuagag aauguugaac uaaaggugcc    60
cucucuggcu ccuccccaaa g                                             81

<210> SEQ ID NO 346
<211> LENGTH: 71
<212> TYPE: RNA
<213> ORGANISM: Homo sapiens

<400> SEQUENCE: 346
gugucugugc cggucccagg agaaccugca gaggcaucgg gucagcggug cuccugcggg    60
ccgacacuca c                                                        71

<210> SEQ ID NO 347
<211> LENGTH: 70
<212> TYPE: RNA
<213> ORGANISM: Homo sapiens

<400> SEQUENCE: 347
gguuucuccu ugaggagaca uggugggggc cggucaggca gcccaugcca uguguccuca    60
uggagaggcc                                                          70

<210> SEQ ID NO 348
<211> LENGTH: 66
<212> TYPE: RNA
<213> ORGANISM: Homo sapiens

<400> SEQUENCE: 348
ccgagugggg cggggcaggu cccugcaggg acugugacac ugaaggaccu gcaccuucgc    60
ccacag                                                              66

<210> SEQ ID NO 349
<211> LENGTH: 69
<212> TYPE: RNA
<213> ORGANISM: Homo sapiens

<400> SEQUENCE: 349
gggcuuaggg augggaggcc aggaugaaga uuaaucccua auccccaaca cuggccuugc    60
uaucccag                                                            69

<210> SEQ ID NO 350
<211> LENGTH: 65
<212> TYPE: RNA
<213> ORGANISM: Homo sapiens

<400> SEQUENCE: 350
gucuccuggg gggaggagac ccugcucucc cuggcagcaa gccucccug cccuuccaga    60 uuagc                                                               65

<210> SEQ ID NO 351
<211> LENGTH: 92
<212> TYPE: RNA
<213> ORGANISM: Homo sapiens

<400> SEQUENCE: 351
cgcugcgcuu cugggcccgc ggcgggcgug gggcugcccg ggccggucga ccagcgcgcc    60
guagcucccg aggcccgagc cgcgacccgc gg                                  92

<210> SEQ ID NO 352
<211> LENGTH: 92
<212> TYPE: RNA
<213> ORGANISM: Homo sapiens

<400> SEQUENCE: 352

```
cgcugcgcuu cugggcccgc ggcgggcgug gggcugcccg ggccggucga ccagcgcgcc    60
guagcucccg aggcccgagc cgcgacccgc gg                                  92

<210> SEQ ID NO 353
<211> LENGTH: 92
<212> TYPE: RNA
<213> ORGANISM: Homo sapiens

<400> SEQUENCE: 353
cgcugcgcuu cugggcccgc ggcgggcgug gggcugcccg ggccggucga ccagcgcgcc    60
guagcucccg aggcccgagc cgcgacccgc gg                                  92

<210> SEQ ID NO 354
<211> LENGTH: 92
<212> TYPE: RNA
<213> ORGANISM: Homo sapiens

<400> SEQUENCE: 354
cgcugcgcuu cugggcccgc ggcgggcgug gggcugcccg ggccggucga ccagcgcgcc    60
guagcucccg aggcccgagc cgcgacccgc gg                                  92

<210> SEQ ID NO 355
<211> LENGTH: 90
<212> TYPE: RNA
<213> ORGANISM: Homo sapiens

<400> SEQUENCE: 355 gugguacgg cccagugggg gggagaggga cacgcccugg gcucugccca gggugcagcc    60
ggacugacug agccccugug ccgccccag                                      90

<210> SEQ ID NO 356
<211> LENGTH: 72
<212> TYPE: RNA
<213> ORGANISM: Homo sapiens

<400> SEQUENCE: 356
gagucugagg gacccaggac aggagaaggc cuauggugau uugcauucuu ccugcccugg    60
cuccauccuc ag                                                        72

<210> SEQ ID NO 357
<211> LENGTH: 87
<212> TYPE: RNA
<213> ORGANISM: Homo sapiens

<400> SEQUENCE: 357
guguggccgg caggcgggug ggcggggcg gccgguggga accccgcccc gccccgcgcc     60
cgcacucacc cgcccgucuc cccacag                                        87

<210> SEQ ID NO 358
<211> LENGTH: 70
<212> TYPE: RNA
<213> ORGANISM: Homo sapiens

<400> SEQUENCE: 358
aggacccagc ggggcugggc gcgcggagca gcgcugggug cagcgccugc gccggcagcu    60
gcaagggccg                                                           70

<210> SEQ ID NO 359
```

```
<211> LENGTH: 110
<212> TYPE: RNA
<213> ORGANISM: Homo sapiens

<400> SEQUENCE: 359
gcuuaccagg uguggccca gcuuuacaua guucaugcug aggccgggau uucaugcaga    60
aaacugguug caaaaggugc ugaaggggcu gggggagcac aagggagaag              110

<210> SEQ ID NO 360
<211> LENGTH: 64
<212> TYPE: RNA
<213> ORGANISM: Homo sapiens

<400> SEQUENCE: 360
gagcucuggg aggggcuggg uuuggcagga caguuuccaa gcccugucuc cucccaucuu    60
ccag                                                                64

<210> SEQ ID NO 361
<211> LENGTH: 97
<212> TYPE: RNA
<213> ORGANISM: Homo sapiens

<400> SEQUENCE: 361
aucugaguug ggagggucccc ucuccaaaug ugucuugggg uggggauca agacacauuu    60 ggagagggaa ccucccaacu cggccucugc caucauu                             97

<210> SEQ ID NO 362
<211> LENGTH: 74
<212> TYPE: RNA
<213> ORGANISM: Homo sapiens

<400> SEQUENCE: 362
ccugcaggag gcagugggcg agcaggcggg gcagcccaau gccaugggcc ugaucucacc    60
gcugccuccu uccc                                                     74

<210> SEQ ID NO 363
<211> LENGTH: 103
<212> TYPE: RNA
<213> ORGANISM: Homo sapiens

<400> SEQUENCE: 363
gugucggcug uggcgugacu gucccucugu guccccacu aggcccacug cucaguggag    60
cguggaggac gaggaggagg ccguccacga gcaaugccag cau                    103

<210> SEQ ID NO 364
<211> LENGTH: 73
<212> TYPE: RNA
<213> ORGANISM: Homo sapiens

<400> SEQUENCE: 364
ggcgagggga ggcgcaggcu cggaaaggcg cgcgaggcuc caggcuccuu cccgauccac    60
cgcucuccuc gcu                                                      73

<210> SEQ ID NO 365
<211> LENGTH: 62
<212> TYPE: RNA
<213> ORGANISM: Homo sapiens

<400> SEQUENCE: 365
cuuccuggug ggugggagg agaagugccg uccucaugag ccccucucug ucccacccau    60
```

```
ag                                                                          62

<210> SEQ ID NO 366
<211> LENGTH: 61
<212> TYPE: RNA
<213> ORGANISM: Homo sapiens

<400> SEQUENCE: 366
ucucguuuga ucucggaagc uaagcagggu ugggccuggu aguacuugg augggaaacu            60
u                                                                          61

<210> SEQ ID NO 367
<211> LENGTH: 53
<212> TYPE: RNA
<213> ORGANISM: Homo sapiens

<400> SEQUENCE: 367
guuugaucuc ggaagcuaag caggucggg ccugguuagu acuuggaugg gag                   53

<210> SEQ ID NO 368
<211> LENGTH: 109
<212> TYPE: RNA
<213> ORGANISM: Homo sapiens

<400> SEQUENCE: 368
ggucgggcuc accaugacac agugugagac cucgggcuac aacacaggac ccgggcgcug           60
cucugacccc ucgugucuug uguugcagcc ggagggacgc agguccgca                      109

<210> SEQ ID NO 369
<211> LENGTH: 68
<212> TYPE: RNA
<213> ORGANISM: Homo sapiens

<400> SEQUENCE: 369
gaauggaaga agaaggcggu cggucugcgg gagccaggcc gcagagccau ccgccuucug           60
uccauguc                                                                   68

<210> SEQ ID NO 370
<211> LENGTH: 90
<212> TYPE: RNA
<213> ORGANISM: Homo sapiens

<400> SEQUENCE: 370
ggcgccucug cagcuccggc uccccuggc cucucgggaa cuacaagucc caggggccu            60
ggcggugggc ggcgggcgga agaggcgggg                                           90

<210> SEQ ID NO 371
<211> LENGTH: 102
<212> TYPE: RNA
<213> ORGANISM: Homo sapiens

<400> SEQUENCE: 371
gcuuaucgag gaaaagaucg aggugggguug gggcgggcuc uggggauuug gucucacagc         60
ccggauccca gcccacuuac cuugguuacu cuccuuccuu cu                            102

<210> SEQ ID NO 372
<211> LENGTH: 85
<212> TYPE: RNA
<213> ORGANISM: Homo sapiens
```

-continued

```
<400> SEQUENCE: 372
uccuccccgg agccaggaug cagcucaagc cacagcaggg uguuuagcgc ucuucagugg    60
cuccagauug uggcgcuggu gcagg                                         85

<210> SEQ ID NO 373
<211> LENGTH: 96
<212> TYPE: RNA
<213> ORGANISM: Homo sapiens

<400> SEQUENCE: 373
cucgggaggg gcgggagggg gguccccggu gcucggaucu cgagggugcu uauuguucgg    60
uccgagccug ggucucccuc uuccccccaa cccccc                             96

<210> SEQ ID NO 374
<211> LENGTH: 84
<212> TYPE: RNA
<213> ORGANISM: Homo sapiens

<400> SEQUENCE: 374
cgguccagac guggcggggg uggcggcggc aucccggacg gccugugagg gaugcgccgc    60
ccacugcccc gcgccgccug accg                                          84

<210> SEQ ID NO 375
<211> LENGTH: 84
<212> TYPE: RNA
<213> ORGANISM: Homo sapiens

<400> SEQUENCE: 375
gcuggcgucg gugcugggga gcggcccccg gguggccuc ugcucuggcc ccuccugggg     60
cccgcacucu cgcucugggc ccgc                                          84

<210> SEQ ID NO 376
<211> LENGTH: 56
<212> TYPE: RNA
<213> ORGANISM: Homo sapiens

<400> SEQUENCE: 376
guaggcaggg gcugggguuu cagguucuca gucagaaccu uggccccucu ccccag        56

<210> SEQ ID NO 377
<211> LENGTH: 90
<212> TYPE: RNA
<213> ORGANISM: Homo sapiens

<400> SEQUENCE: 377 gugg guacgg cccagugggg gggagaggga cacgcccugg gcucugccca gggugcagcc   60
ggacugacug agcccugugu ccgcccccag                                    90

<210> SEQ ID NO 378
<211> LENGTH: 98
<212> TYPE: RNA
<213> ORGANISM: Homo sapiens

<400> SEQUENCE: 378
uucucacccc cgccugacac gggcgacagc ugcggcccgc uguguucacu cgggccgagu    60
gcgucuccug ucaggcaagg gagagcagag cccccug                            98

<210> SEQ ID NO 379
<211> LENGTH: 62
```

```
<212> TYPE: RNA
<213> ORGANISM: Homo sapiens

<400> SEQUENCE: 379
gguagggggc gggcuccggc gcugggaccc cacuaggguc gcgccuuggc cccgccccgc    60
cc                                                                   62

<210> SEQ ID NO 380
<211> LENGTH: 86
<212> TYPE: RNA
<213> ORGANISM: Homo sapiens

<400> SEQUENCE: 380
ugccagucuc uagguccccug agacccuuua accugugagg acauccaggg ucacagguga    60
gguucuuggg agccuggcgu cuggcc                                         86

<210> SEQ ID NO 381
<211> LENGTH: 119
<212> TYPE: RNA
<213> ORGANISM: Homo sapiens

<400> SEQUENCE: 381
ccaugaggag cuggcagugg gauggccugg ggguaggagc guggcuucug gagcuagacc    60
acaugggunc agaucccagc ggugccucua acuggccaca ggaccuuggg cagucagcu    119

<210> SEQ ID NO 382
<211> LENGTH: 76
<212> TYPE: RNA
<213> ORGANISM: Homo sapiens

<400> SEQUENCE: 382
ccgaugccuc gggagucuac agcagggcca ugucugugag ggcccaaggg ugcaugguc     60 ucccagguuu cggugc                                                    76

<210> SEQ ID NO 383
<211> LENGTH: 92
<212> TYPE: RNA
<213> ORGANISM: Homo sapiens

<400> SEQUENCE: 383
gucagugucu gggcggacag cugcaggaaa gggaagacca aggcuugcug ucuguccagu    60
cugccacccu acccugucug uucuugccac ag                                  92

<210> SEQ ID NO 384
<211> LENGTH: 87
<212> TYPE: RNA
<213> ORGANISM: Homo sapiens

<400> SEQUENCE: 384
gugaggcggg gccaggaggg uguguggcgu gggugcugcg gggccgucag ggugccugcg    60
ggacgcucac cuggcuggcc cgcccag                                        87

<210> SEQ ID NO 385
<211> LENGTH: 67
<212> TYPE: RNA
<213> ORGANISM: Homo sapiens

<400> SEQUENCE: 385
gcgcccuccc ucucuccccg gugugcaaau gugugugugc ggguguuaugc cggacaagag    60
```

```
ggaggug                                                              67

<210> SEQ ID NO 386
<211> LENGTH: 70
<212> TYPE: RNA
<213> ORGANISM: Homo sapiens

<400> SEQUENCE: 386
ggccgcggcg cgcaagaugg cggcgggccc gggcaccgcc ccuuccgccc cgccgggcgu    60
cgcacgaggc                                                           70

<210> SEQ ID NO 387
<211> LENGTH: 79
<212> TYPE: RNA
<213> ORGANISM: Homo sapiens

<400> SEQUENCE: 387
cagccugggg aaggcuuggc agggaagaca caugagcagu gccuccacuu cacgccucuc    60 ccugucucc uuucccuag                                                  79

<210> SEQ ID NO 388
<211> LENGTH: 60
<212> TYPE: RNA
<213> ORGANISM: Homo sapiens

<400> SEQUENCE: 388 cgcuggqucc gcgcgcccug ggccgggcga uguccgcuug ggggagcgag gggcggggcg    60

<210> SEQ ID NO 389
<211> LENGTH: 61
<212> TYPE: RNA
<213> ORGANISM: Homo sapiens

<400> SEQUENCE: 389
aacugcgggg ccagagcaga gagcccuugc acaccaccag ccucuccucc cugugcccca    60
g                                                                    61

<210> SEQ ID NO 390
<211> LENGTH: 90
<212> TYPE: RNA
<213> ORGANISM: Homo sapiens

<400> SEQUENCE: 390 cgggcgggc gguccggcc gccuccgagc ccggccggca gccccggcc uuaaagcgcg       60 ggcuguccgg aggggucggc uuucccaccg                                     90

<210> SEQ ID NO 391
<211> LENGTH: 63
<212> TYPE: RNA
<213> ORGANISM: Homo sapiens

<400> SEQUENCE: 391
ugguggcggc gguaguuaug ggcuucucuu ucucaccagc agccccuggg ccgccgccuc    60
ccu                                                                  63

<210> SEQ ID NO 392
<211> LENGTH: 80
<212> TYPE: RNA
<213> ORGANISM: Homo sapiens

<400> SEQUENCE: 392
```

```
gguuccggag cccCggcgcg ggcggguucu gggguguaga cgcugcuggc cagcccgccc    60
cagccgaggu ucucggcacc                                               80
```

<210> SEQ ID NO 393
<211> LENGTH: 67
<212> TYPE: RNA
<213> ORGANISM: Homo sapiens

<400> SEQUENCE: 393

```
aaaucucucu ccauaucuuu ccugcagccc ccaggugggg gggaagaaaa gguggggaau    60
uagauuc                                                             67
```

<210> SEQ ID NO 394
<211> LENGTH: 59
<212> TYPE: RNA
<213> ORGANISM: Homo sapiens

<400> SEQUENCE: 394

```
guccaggcag gagccggacu ggaccucagg gaagaggcug acccggcccc ucuugcggc     59
```

<210> SEQ ID NO 395
<211> LENGTH: 75
<212> TYPE: RNA
<213> ORGANISM: Homo sapiens

<400> SEQUENCE: 395

```
aagcaagacu gaggggccuc agaccgagcu uuuggaaaau agaaaagucu cgcucucugc    60
cccucagccu aacuu                                                    75
```

<210> SEQ ID NO 396
<211> LENGTH: 47
<212> TYPE: RNA
<213> ORGANISM: Homo sapiens

<400> SEQUENCE: 396

```
cucggcgcgg ggcgcgggcu ccggguuggg gcgagccaac gccgggg                 47
```

<210> SEQ ID NO 397
<211> LENGTH: 90
<212> TYPE: RNA
<213> ORGANISM: Homo sapiens

<400> SEQUENCE: 397

```
cugugggcug ggccagggag cagcuggugg gugggaagua agaucugacc uggacuccau    60
cccacccacc cccuguuucc uggcccacag                                    90
```

<210> SEQ ID NO 398
<211> LENGTH: 93
<212> TYPE: RNA
<213> ORGANISM: Homo sapiens

<400> SEQUENCE: 398

```
ccuuccggcg ucccaggcgg ggcgccgcgg gaccgcccuc gugucugugg cgguqggauc    60 ccgcggccgu guuuuccugg uggcccggcc aug                                93
```

<210> SEQ ID NO 399
<211> LENGTH: 67
<212> TYPE: RNA
<213> ORGANISM: Homo sapiens

<400> SEQUENCE: 399
ccagaccccu ggggcugggc aggcggaaag aggucugaac ugccucugcc uccuuggucu    60
ccggcag                                                              67

<210> SEQ ID NO 400
<211> LENGTH: 98
<212> TYPE: RNA
<213> ORGANISM: Homo sapiens

<400> SEQUENCE: 400
cuuggucaau aggaaagagg ugggaccucc uggcuuuucc ucugcagcau ggcucggacc    60
uagugcaaug uuuaagcucc ccucucuuuc cguucag                             98

<210> SEQ ID NO 401
<211> LENGTH: 102
<212> TYPE: RNA
<213> ORGANISM: Homo sapiens

<400> SEQUENCE: 401
uguguucccu auccuccuua ugucccaccc ccacuccugu uugaauauuu caccagaaac    60
aggagugggg ggugggacgu aaggaggaug ggggaaagaa ca                      102

<210> SEQ ID NO 402
<211> LENGTH: 80
<212> TYPE: RNA
<213> ORGANISM: Homo sapiens

<400> SEQUENCE: 402
ugagaggccg caccuugccu ugcugcccgg gccgugcacc cgugggcccc agggcgacgc    60
ggcgggggcg gcccuagcga                                                80

<210> SEQ ID NO 403
<211> LENGTH: 73
<212> TYPE: RNA
<213> ORGANISM: Homo sapiens

<400> SEQUENCE: 403
gaaaacaacc aggugggcuu cccggagggc ggaacaccca gccccagcau ccagggcuca    60
ccuaccacgu uug                                                       73

<210> SEQ ID NO 404
<211> LENGTH: 66
<212> TYPE: RNA
<213> ORGANISM: Homo sapiens

<400> SEQUENCE: 404
agcagcccuc ggcggcccgg ggggcgggcg gcggugcccg ucccggggcu gcgcgaggca    60
caggcg                                                               66

<210> SEQ ID NO 405
<211> LENGTH: 80
<212> TYPE: RNA
<213> ORGANISM: Homo sapiens

<400> SEQUENCE: 405 gguccggag cccccgcgcg ggcggguucu gggguguaga cgcugcuggc cagcccgccc     60
cagccgaggu ucucggcacc                                                80

```
<210> SEQ ID NO 406
<211> LENGTH: 94
<212> TYPE: RNA
<213> ORGANISM: Homo sapiens

<400> SEQUENCE: 406
cagugcgacg ggcggagcuu ccagacgcuc cgccccacgu cgcaugcgcc ccgggaaagc      60
guggggcgga gcuuccggag gccccgcccu gcug                                  94

<210> SEQ ID NO 407
<211> LENGTH: 88
<212> TYPE: RNA
<213> ORGANISM: Homo sapiens

<400> SEQUENCE: 407
gcgacgggcg gagcuuccag acgcuccgcc ccacgucgca ugcgcccccgg gaaagcgugg     60 ggcggagcuu ccggaggccc cgcccugc                                         88

<210> SEQ ID NO 408
<211> LENGTH: 94
<212> TYPE: RNA
<213> ORGANISM: Homo sapiens

<400> SEQUENCE: 408
cagugcgacg ggcggagcuu ccagacgcuc cgccccacgu cgcaugcgcc ccgggaaagc      60
guggggcgga gcuuccggag gccccgcccu gcug                                  94

<210> SEQ ID NO 409
<211> LENGTH: 59
<212> TYPE: RNA
<213> ORGANISM: Homo sapiens

<400> SEQUENCE: 409
ugaaguacca gcuacucgag aggucagagg auugcuccug aauagcuggg acuacaggu       59

<210> SEQ ID NO 410
<211> LENGTH: 52
<212> TYPE: RNA
<213> ORGANISM: Homo sapiens

<400> SEQUENCE: 410
uagccgggcg ugguggugggg ggccuguggu cccagcuacu uuggaggcug ag              52

<210> SEQ ID NO 411
<211> LENGTH: 80
<212> TYPE: RNA
<213> ORGANISM: Homo sapiens

<400> SEQUENCE: 411
gcgucaagau ggcggcgggg agguaggcag agcaggacgc cgcugcugcc gccgccaccg      60
ccgccuccgc uccagucgcc                                                  80

<210> SEQ ID NO 412
<211> LENGTH: 80
<212> TYPE: RNA
<213> ORGANISM: Homo sapiens

<400> SEQUENCE: 412
aggacccuuc cagagggccc ccccucaauc cuguugugcc uaauucagag gguuggguug      60
aggcucuccu gaagggcucu                                                  80
```

<210> SEQ ID NO 413
<211> LENGTH: 110
<212> TYPE: RNA
<213> ORGANISM: Homo sapiens

<400> SEQUENCE: 413
ggcuacaguc uuucuucaug ugacucgugg acuucccuuu gucauccuau gccugagaau    60
auaugaagga ggcugggaag gcaaagggac guucaauugu caucacuggc              110

<210> SEQ ID NO 414
<211> LENGTH: 55
<212> TYPE: RNA
<213> ORGANISM: Homo sapiens

<400> SEQUENCE: 414
ccggauccga gucacggcac caaauuucau gcguguccgu gugaagagac cacca         55

<210> SEQ ID NO 415
<211> LENGTH: 78
<212> TYPE: RNA
<213> ORGANISM: Homo sapiens

<400> SEQUENCE: 415
ggccucaggc aggcgcaccc gaccacaugc auggcuggug gcggcugca ggggucgggu     60 gggccaggcu gugggggcg                                                 78

<210> SEQ ID NO 416
<211> LENGTH: 78
<212> TYPE: RNA
<213> ORGANISM: Homo sapiens

<400> SEQUENCE: 416
gagcgucacg uugacacuca aaaguuuca gauuuuggaa cauuucggau uuuggauuuu     60
uggaucaggg augcucaa                                                  78

<210> SEQ ID NO 417
<211> LENGTH: 83
<212> TYPE: RNA
<213> ORGANISM: Homo sapiens

<400> SEQUENCE: 417
aauagagggu gcacaggcac gggagcucag gugaggcagg gagcugagcu caccugaccu    60
cccaugccug ugcacccucu auu                                            83

<210> SEQ ID NO 418
<211> LENGTH: 82
<212> TYPE: RNA
<213> ORGANISM: Homo sapiens

<400> SEQUENCE: 418
ugugggcagg gcccugggga gcugaggcuc uggggguggc cggggcugac ccugggccuc    60
ugcuccccag ugucugaccg cg                                             82

<210> SEQ ID NO 419
<211> LENGTH: 73
<212> TYPE: RNA
<213> ORGANISM: Homo sapiens

<400> SEQUENCE: 419
cccagggucu ggugcggaga gggcccacag uggacuuggu gacgcuguau gcccucaccg    60

-continued cucagccccu ggg                                                    73

<210> SEQ ID NO 420
<211> LENGTH: 63
<212> TYPE: RNA
<213> ORGANISM: Homo sapiens

<400> SEQUENCE: 420
gagucgagga cugguggaag ggccuuuccc cucagaccaa ggcccuggcc ccagcuucuu    60
cuc                                                                63

<210> SEQ ID NO 421
<211> LENGTH: 72
<212> TYPE: RNA
<213> ORGANISM: Homo sapiens

<400> SEQUENCE: 421
ugugggacug caaaugggag cucagcaccu gccugccacc cacgcagacc agcccugcu    60 cuguucccac ag                                                      72

<210> SEQ ID NO 422
<211> LENGTH: 50
<212> TYPE: RNA
<213> ORGANISM: Homo sapiens

<400> SEQUENCE: 422
acccgggcgu ggugguggg gugggugccu guaauuccag cuaguuggga              50

<210> SEQ ID NO 423
<211> LENGTH: 63
<212> TYPE: RNA
<213> ORGANISM: Homo sapiens

<400> SEQUENCE: 423
aauggguggg ugcugguggg agccgugccc uggccacuca uucggcucuc ucccucaccc    60
uag                                                                63

<210> SEQ ID NO 424
<211> LENGTH: 69
<212> TYPE: RNA
<213> ORGANISM: Homo sapiens

<400> SEQUENCE: 424
ccgggcaggc agguguaggg uggagcccac ugugccuccu gacucagccc ugcugccuuc    60
accugccag                                                          69

<210> SEQ ID NO 425
<211> LENGTH: 82
<212> TYPE: RNA
<213> ORGANISM: Homo sapiens

<400> SEQUENCE: 425
cugacuuuuu uagggaguag aagggugggg agcaugaaca auguuucuca cucccuaccc    60
cuccacuccc caaaaaaguc ag                                            82

<210> SEQ ID NO 426
<211> LENGTH: 77
<212> TYPE: RNA
<213> ORGANISM: Homo sapiens

```
<400> SEQUENCE: 426
gaguugggag guucccucuc caaaugugug uugaucccccc accccaagac acauuuggag    60
agggacccuc ccaacuc                                                    77

<210> SEQ ID NO 427
<211> LENGTH: 70
<212> TYPE: RNA
<213> ORGANISM: Homo sapiens

<400> SEQUENCE: 427
cucgggcccg accgcgccgg cccgcaccuc ccggcccgga gcugcgggcu gcggucaggg    60
cgaucccggg                                                            70

<210> SEQ ID NO 428
<211> LENGTH: 84
<212> TYPE: RNA
<213> ORGANISM: Homo sapiens

<400> SEQUENCE: 428
cuccccaugg cccugucucc caacccuugu accagugcug ggcucagacc cugguacagg    60 ccuggggac agggaccugg ggac                                             84

<210> SEQ ID NO 429
<211> LENGTH: 82
<212> TYPE: RNA
<213> ORGANISM: Homo sapiens

<400> SEQUENCE: 429
aaggagcacu cacuccaauu ucccuggacu gggggcaggc ugccaccucc uggggacagg    60
ggauuggggc aggauguucc ag                                              82

<210> SEQ ID NO 430
<211> LENGTH: 62
<212> TYPE: RNA
<213> ORGANISM: Homo sapiens

<400> SEQUENCE: 430
uggccuaggg ggcggcuugu ggagguauag ggcugagccu ugcucugcuc ccccgccccc    60
ag                                                                    62

<210> SEQ ID NO 431
<211> LENGTH: 59
<212> TYPE: RNA
<213> ORGANISM: Homo sapiens

<400> SEQUENCE: 431
cuccagggag acagugugug aggccucuug ccauggccuc ccugcccgcc ucucugcag     59

<210> SEQ ID NO 432
<211> LENGTH: 61
<212> TYPE: RNA
<213> ORGANISM: Homo sapiens

<400> SEQUENCE: 432
gugcggaacg cuggccgggg cgggaggggga agggacgccc ggccggaacg ccgcacucac    60
g                                                                     61

<210> SEQ ID NO 433
<211> LENGTH: 69
```

```
<212> TYPE: RNA
<213> ORGANISM: Homo sapiens

<400> SEQUENCE: 433
gaggagggga ggugugcagg gcuggggguca cugacucugc uuccccugcc cugcauggug    60
uccccacag                                                             69

<210> SEQ ID NO 434
<211> LENGTH: 72
<212> TYPE: RNA
<213> ORGANISM: Homo sapiens

<400> SEQUENCE: 434
ccaggcacac aggaaaagcg gggcccuggg uucggcugcu accccaaagg ccacauucuc    60
cugugcacac ag                                                         72

<210> SEQ ID NO 435
<211> LENGTH: 96
<212> TYPE: RNA
<213> ORGANISM: Homo sapiens

<400> SEQUENCE: 435
cgggccccgg gcgggcggga gggacgggac gcggugcagu guuguuuuuu cccccgccaa    60
uauugcacuc gucccggccu ccggccccc cggccc                                96

<210> SEQ ID NO 436
<211> LENGTH: 68
<212> TYPE: RNA
<213> ORGANISM: Homo sapiens

<400> SEQUENCE: 436
cguggugagg auauggcagg gaaggggagu uucccucuau ucccuucccc ccaguaaucu    60
ucaucaug                                                              68

<210> SEQ ID NO 437
<211> LENGTH: 74
<212> TYPE: RNA
<213> ORGANISM: Homo sapiens

<400> SEQUENCE: 437
gcagcccggu gagcgcucgc uggccuggca gucgucgga agaacagggc gggugggcc     60 gcgcacaucu cugc                                                       74

<210> SEQ ID NO 438
<211> LENGTH: 69
<212> TYPE: RNA
<213> ORGANISM: Homo sapiens

<400> SEQUENCE: 438
cuuucggcca gcgggacggc auccgaggug ggcuaggcuc gggcccgugg cgggugcggg    60
gguggagg                                                              69

<210> SEQ ID NO 439
<211> LENGTH: 75
<212> TYPE: RNA
<213> ORGANISM: Homo sapiens

<400> SEQUENCE: 439
ucaucccugg gugggauuu guugcauuac uuguguucua uauaaaguau ugcacuuguc    60
```
ccggccugug gaaga 75

<210> SEQ ID NO 440
<211> LENGTH: 54
<212> TYPE: RNA
<213> ORGANISM: Homo sapiens

<400> SEQUENCE: 440
acgcgggugc gggccggcgg gguagaagcc acccggcccg gcccggcccg gcga 54

<210> SEQ ID NO 441
<211> LENGTH: 86
<212> TYPE: RNA
<213> ORGANISM: Homo sapiens

<400> SEQUENCE: 441
auucuaggug gggagacuga cggcuggagg cccauaagcu gucuaaaacu ucggccccca 60
gauuucuggu cucccacuu cagaac 86

<210> SEQ ID NO 442
<211> LENGTH: 64
<212> TYPE: RNA
<213> ORGANISM: Homo sapiens

<400> SEQUENCE: 442
aaccccgggc cggaggucaa gggcgucgcu ucucccuaau guugccucuu uuccacggcc 60
ucag 64

<210> SEQ ID NO 443
<211> LENGTH: 64
<212> TYPE: RNA
<213> ORGANISM: Homo sapiens

<400> SEQUENCE: 443
ucugggcgag ggguggcuc ucagagggc uggcaguacu gcucugaggc cugccucuc 60 ccag 64

<210> SEQ ID NO 444
<211> LENGTH: 69
<212> TYPE: RNA
<213> ORGANISM: Homo sapiens

<400> SEQUENCE: 444
gaaccucggg gcauggggga gggaggcugg acaggagagg gcucacccag gcccuguccu 60
cugccccag 69

<210> SEQ ID NO 445
<211> LENGTH: 73
<212> TYPE: RNA
<213> ORGANISM: Homo sapiens

<400> SEQUENCE: 445
cggcgacggc ggggugggug aggucgggcc ccaagacucg ggguugccg ggcgccucag 60 uucaccgcgg ccg 73

<210> SEQ ID NO 446
<211> LENGTH: 84
<212> TYPE: RNA
<213> ORGANISM: Homo sapiens

<400> SEQUENCE: 446

-continued

```
ccgcagccgc cgcgccgggc ccggguuggc cgcugacccc cgcggggccc ccggcggccg      60 gggcggggc gggggcugcc ccgg                                              84

<210> SEQ ID NO 447
<211> LENGTH: 61
<212> TYPE: RNA
<213> ORGANISM: Homo sapiens

<400> SEQUENCE: 447
gggggcggga gcuggggucu gcagguucgc acugaugccu gcucgcccug ucucccgcua      60
g                                                                      61

<210> SEQ ID NO 448
<211> LENGTH: 62
<212> TYPE: RNA
<213> ORGANISM: Homo sapiens

<400> SEQUENCE: 448
gugggucucg caucaggagg caaggccagg acccgcugac ccaugccucc ugccgcgguc      60
ag                                                                     62

<210> SEQ ID NO 449
<211> LENGTH: 67
<212> TYPE: RNA
<213> ORGANISM: Homo sapiens

<400> SEQUENCE: 449
guggcacuca aacuguggggg gcacuuucug cucucuggug aaagugccgc caucuuuuga    60
guguuac                                                                67

<210> SEQ ID NO 450
<211> LENGTH: 66
<212> TYPE: RNA
<213> ORGANISM: Homo sapiens

<400> SEQUENCE: 450
ucaagacggg gagucaggca gugguggaga uggagagccc ugagccucca cucuccuggc     60
ccccag                                                                 66

<210> SEQ ID NO 451
<211> LENGTH: 98
<212> TYPE: RNA
<213> ORGANISM: Homo sapiens

<400> SEQUENCE: 451
cgagguaggg gcgucccggg cgcgcgggcg ggucccaggc ugggcccuc ggaggccggg      60 ugcucacugc cccgucccgg cgcccgeguc uccuccag                              98

<210> SEQ ID NO 452
<211> LENGTH: 68
<212> TYPE: RNA
<213> ORGANISM: Homo sapiens

<400> SEQUENCE: 452
gugcaaagag caggaggaca ggggauuuau cucccaaggg aggucccug auccaguca       60 cggcacca                                                               68

<210> SEQ ID NO 453
```

```
<211> LENGTH: 74
<212> TYPE: RNA
<213> ORGANISM: Homo sapiens

<400> SEQUENCE: 453
gugcguggug gcucgaggcg ggggugggggg ccucgcccug cuugggcccu cccugaccuc    60
uccgcuccgc acag                                                      74

<210> SEQ ID NO 454
<211> LENGTH: 60
<212> TYPE: RNA
<213> ORGANISM: Homo sapiens

<400> SEQUENCE: 454
ugugaaugac ccccuuccag agccaaaauc accagggaug gaggaggggu cuggguacu     60

<210> SEQ ID NO 455
<211> LENGTH: 99
<212> TYPE: RNA
<213> ORGANISM: Homo sapiens

<400> SEQUENCE: 455
cgcccaccuc agcucccaa aaugcuggga uuacaggcau gagccacugc ggucgaccau     60
gaccuggaca uguuugugcc caguacuguc aguuugcag                           99

<210> SEQ ID NO 456
<211> LENGTH: 80
<212> TYPE: RNA
<213> ORGANISM: Homo sapiens

<400> SEQUENCE: 456
ugccgucggc cugggagga ggaagggcaa guccaaaggu auacaguugg ucguucauu      60 cucucuuuuu ggccuacaag                                                80

<210> SEQ ID NO 457
<211> LENGTH: 73
<212> TYPE: RNA
<213> ORGANISM: Homo sapiens

<400> SEQUENCE: 457
gugggcgggg gcaggugugu gguggguggu ggccugcggu gagcagggcc cucacaccug    60
ccucgccccc cag                                                       73

<210> SEQ ID NO 458
<211> LENGTH: 70
<212> TYPE: RNA
<213> ORGANISM: Homo sapiens

<400> SEQUENCE: 458
ugugcacuug ggcaggaggg acccuguaug ucuccccgca gcaccgucau cgucccccuc    60
uuguccacag                                                           70

<210> SEQ ID NO 459
<211> LENGTH: 62
<212> TYPE: RNA
<213> ORGANISM: Homo sapiens

<400> SEQUENCE: 459
uggccuaggg ggcggcuugu ggaguguaug ggcugagccu ugcucugcuc ccccgccccc    60
ag                                                                   62
```

```
<210> SEQ ID NO 460
<211> LENGTH: 73
<212> TYPE: RNA
<213> ORGANISM: Homo sapiens

<400> SEQUENCE: 460
ggccggcugg gguuccuggg gaugggauuu gcuuccuguc acaaaucaca uugccaggga    60
uuuccaaccg acc                                                      73

<210> SEQ ID NO 461
<211> LENGTH: 79
<212> TYPE: RNA
<213> ORGANISM: Homo sapiens

<400> SEQUENCE: 461
cucgaggugc uggggacgc gugagcgcga gccgcuuccu cacggcucgg ccgcggcgcg    60 uagccccgc cacaucggg                                                 79

<210> SEQ ID NO 462
<211> LENGTH: 73
<212> TYPE: RNA
<213> ORGANISM: Homo sapiens

<400> SEQUENCE: 462
ggaggcuggg cuggacgga cacccggccu ccacuuucug uggcagguac cuccuccaug    60
ucggcccgcc uug                                                      73

<210> SEQ ID NO 463
<211> LENGTH: 68
<212> TYPE: RNA
<213> ORGANISM: Homo sapiens

<400> SEQUENCE: 463
gacucggcug cgguggacaa guccggcucc agaaccugga caccgcucag ccggccgcgg    60
cagggguc                                                            68

<210> SEQ ID NO 464
<211> LENGTH: 68
<212> TYPE: RNA
<213> ORGANISM: Homo sapiens

<400> SEQUENCE: 464
cuccggugcc uacugagcug auaucaguuc ucauuuuaca cacuggcuca guucagcagg    60
aacaggag                                                            68

<210> SEQ ID NO 465
<211> LENGTH: 73
<212> TYPE: RNA
<213> ORGANISM: Homo sapiens

<400> SEQUENCE: 465
cucugccucc cgugccuacu gagcugaaac acaguugguu uguguacacu ggcucaguuc    60
agcaggaaca ggg                                                      73

<210> SEQ ID NO 466
<211> LENGTH: 68
<212> TYPE: RNA
<213> ORGANISM: Homo sapiens
```

```
<400> SEQUENCE: 466
ugcccaggcu ggagcgagug caguggugca gucaguccua gcucacugca gccucgaacu      60
ccugggcu                                                              68

<210> SEQ ID NO 467
<211> LENGTH: 62
<212> TYPE: RNA
<213> ORGANISM: Homo sapiens

<400> SEQUENCE: 467 gugaguggggg cucccgggac ggcgcccgcc cuggcccugg cccggcgacg ucucacgguc     60
cc                                                                    62

<210> SEQ ID NO 468
<211> LENGTH: 82
<212> TYPE: RNA
<213> ORGANISM: Homo sapiens

<400> SEQUENCE: 468
ugagcuguug gauucggggc cguagcacug ucugagaggu uuacauuucu cacagugaac     60
cggucucuuu uucagcugcu uc                                              82

<210> SEQ ID NO 469
<211> LENGTH: 70
<212> TYPE: RNA
<213> ORGANISM: Homo sapiens

<400> SEQUENCE: 469
aaaagccugu cccuaagucc cucccagccu uccagaguug gugccaggaa ggauuuaggg     60
acaggcuuug                                                            70

<210> SEQ ID NO 470
<211> LENGTH: 80
<212> TYPE: RNA
<213> ORGANISM: Homo sapiens

<400> SEQUENCE: 470
accugaggag ccagcccucc uccgcaccc aaacuuggag cacuugaccu uuggcuguug      60 gaggggggcag gcucgcgggu                                                80

<210> SEQ ID NO 471
<211> LENGTH: 105
<212> TYPE: RNA
<213> ORGANISM: Homo sapiens

<400> SEQUENCE: 471
gcgggcggcg gcggcggcag cagcagcagg ugcggggcgg cggccgcgcu ggccgcucga     60
cuccgcagcu gcucguucug cuucuccagc uugcgcacca gcucc                    105

<210> SEQ ID NO 472
<211> LENGTH: 64
<212> TYPE: RNA
<213> ORGANISM: Homo sapiens

<400> SEQUENCE: 472
ugcucuguag gcaugaggca gggcccaggu uccaugugau gcugaagcuc ugacauuccu     60
gcag                                                                  64
```

```
<210> SEQ ID NO 473
<211> LENGTH: 106
<212> TYPE: RNA
<213> ORGANISM: Homo sapiens

<400> SEQUENCE: 473
agaagaaugc ccaaccagcc cucaguugcu acaguucccu guuguuucag cucgacaaca      60
acaggcggcu guagcaaugg ggggcuggau gggcaucuca augugc                    106

<210> SEQ ID NO 474
<211> LENGTH: 76
<212> TYPE: RNA
<213> ORGANISM: Homo sapiens

<400> SEQUENCE: 474
acugacuuug agucucuccu cagggugcug caggcaaagc uggggaccca gggagagacg      60
uaagugaggg gagaug                                                      76

<210> SEQ ID NO 475
<211> LENGTH: 61
<212> TYPE: RNA
<213> ORGANISM: Homo sapiens

<400> SEQUENCE: 475
ucacccggug agggcgggug gaggaggagg gucccacca ucagccuuca cugggacggg       60
a                                                                      61

<210> SEQ ID NO 476
<211> LENGTH: 85
<212> TYPE: RNA
<213> ORGANISM: Homo sapiens

<400> SEQUENCE: 476
ggcgccuccu gcucugcugu gccgccaggg ccuccccuag cgcgccuucu ggagaggcuu      60
ugugcggaua cggggcugga ggccu                                            85

<210> SEQ ID NO 477
<211> LENGTH: 62
<212> TYPE: RNA
<213> ORGANISM: Homo sapiens

<400> SEQUENCE: 477
gcuggggguc ccccgacagu guggagcugg ggccgggucc cggggagggg gguucgggc       60 ag                                                                     62

<210> SEQ ID NO 478
<211> LENGTH: 115
<212> TYPE: RNA
<213> ORGANISM: Homo sapiens

<400> SEQUENCE: 478
ucugaggaga ccugggcugu cagaggccag ggaaggggac gagggguugg gaacaggugg      60
uuagcacuuc auccucgucu cccucccagg uuagaagggc cccccucucu gaagg           115

<210> SEQ ID NO 479
<211> LENGTH: 62
<212> TYPE: RNA
<213> ORGANISM: Homo sapiens

<400> SEQUENCE: 479
```

```
gaggguggug gaggaagagg gcagcuccca ugacugccug accgccuucu cuccucccc      60 ag                                                                    62

<210> SEQ ID NO 480
<211> LENGTH: 91
<212> TYPE: RNA
<213> ORGANISM: Homo sapiens

<400> SEQUENCE: 480
ggcgccccgg cucccgcgc ccccgaucgg ggccgccgcu aguaguggcg gcggcggagg      60
cgggggcagc ggcggcggcg gcggaggcgc c                                    91

<210> SEQ ID NO 481
<211> LENGTH: 180
<212> TYPE: RNA
<213> ORGANISM: Homo sapiens

<400> SEQUENCE: 481
cgcgacugcg gcggcggugg uggggggagc cgcggggauc gccgagggcc ggucggccgc      60
cccgggugcc gcgcggugcc gccggcggcg gugaggcccc gcgcgugugu cccggcugcg     120
gucggccgcg cucgaggggu ccccguggcg uccccuuccc cgccggccgc cuuucucgcg     180

<210> SEQ ID NO 482
<211> LENGTH: 180
<212> TYPE: RNA
<213> ORGANISM: Homo sapiens

<400> SEQUENCE: 482
cgcgacugcg gcggcggugg uggggggagc cgcggggauc gccgagggcc ggucggccgc      60
cccgggugcc gcgcggugcc gccggcggcg gugaggcccc gcgcgugugu cccggcugcg     120
gucggccgcg cucgaggggu ccccguggcg uccccuuccc cgccggccgc cuuucucgcg     180

<210> SEQ ID NO 483
<211> LENGTH: 87
<212> TYPE: RNA
<213> ORGANISM: Homo sapiens

<400> SEQUENCE: 483
cccucaucuc ugggcagggg cuuauuguag gagucucuga agagagcugu ggacugaccu      60
gcuuuaaccc uuccccaggu ucccauu                                         87

<210> SEQ ID NO 484
<211> LENGTH: 80
<212> TYPE: RNA
<213> ORGANISM: Homo sapiens

<400> SEQUENCE: 484
cugcagcgug cuucuccagg ccccgcgcgc ggacagacac acggacaagu cccgccaggg      60
gcugggcgcg cgccagccgg                                                 80

<210> SEQ ID NO 485
<211> LENGTH: 98
<212> TYPE: RNA
<213> ORGANISM: Homo sapiens

<400> SEQUENCE: 485
uugggcaagg ugcggggcua gggcuaacag cagucuuacu gaagguuucc uggaaaccac      60
gcacaugcug uugccacuaa ccucaaccuu acucgguc                             98
```

<210> SEQ ID NO 486
<211> LENGTH: 59
<212> TYPE: RNA
<213> ORGANISM: Homo sapiens

<400> SEQUENCE: 486
cggggucggc ggcgacgugc ucagcuuggc acccaaguuc ugccgcuccg acgcccggc    59

<210> SEQ ID NO 487
<211> LENGTH: 61
<212> TYPE: RNA
<213> ORGANISM: Homo sapiens

<400> SEQUENCE: 487
ccugcgggga caggccaggg caucuaggcu gugcacagug acgcccccucc ugccccaca   60 g                                                                   61

<210> SEQ ID NO 488
<211> LENGTH: 68
<212> TYPE: RNA
<213> ORGANISM: Homo sapiens

<400> SEQUENCE: 488
gggcgcaggg ggacuggggg ugagcaggcc cagaacccag cucgugcuca cucucaguccc   60 cucccuag                                                            68

<210> SEQ ID NO 489
<211> LENGTH: 67
<212> TYPE: RNA
<213> ORGANISM: Homo sapiens

<400> SEQUENCE: 489
ccugcaggca gaaguggggc ugacagggca gagggguugcg ccccucacc aucccuucug   60 ccugcag                                                             67

<210> SEQ ID NO 490
<211> LENGTH: 67
<212> TYPE: RNA
<213> ORGANISM: Homo sapiens

<400> SEQUENCE: 490
ccugcaggca gaaguggggc ugacagggca gagggguugcg ccccucacc aucccuucug   60 ccugcag                                                             67

<210> SEQ ID NO 491
<211> LENGTH: 67
<212> TYPE: RNA
<213> ORGANISM: Homo sapiens

<400> SEQUENCE: 491
ccugcaggca gaaguggggc ugacagggca gagggguugcg ccccucacc aucccuucug   60 ccugcag                                                             67

<210> SEQ ID NO 492
<211> LENGTH: 67
<212> TYPE: RNA
<213> ORGANISM: Homo sapiens

<400> SEQUENCE: 492

```
ccugcaggca aaguggggc ugacagggca gagguugcg cccccucacc aucccuucug    60
ccugcag                                                           67
```

<210> SEQ ID NO 493
<211> LENGTH: 63
<212> TYPE: RNA
<213> ORGANISM: Homo sapiens

<400> SEQUENCE: 493

```
gagguguagg ggagguuggg ccagggaugc cuucacugug ucucucuggu cuugccaccc   60
cag                                                                63
```

<210> SEQ ID NO 494
<211> LENGTH: 83
<212> TYPE: RNA
<213> ORGANISM: Homo sapiens

<400> SEQUENCE: 494

```
ggcccggcuc cggucucgg cccguacagu ccggccggcc augcuggcgg ggcuggggcc    60
ggggccgagc ccgcggcggg gcc                                          83
```

<210> SEQ ID NO 495
<211> LENGTH: 63
<212> TYPE: RNA
<213> ORGANISM: Homo sapiens

<400> SEQUENCE: 495

```
ggcuccgcag ggcccuggcg caggcaucca gacagcgggc gaaugccucc cccggccccg   60
cag                                                                63
```

<210> SEQ ID NO 496
<211> LENGTH: 65
<212> TYPE: RNA
<213> ORGANISM: Homo sapiens

<400> SEQUENCE: 496

```
gggugcucgg ggcaggcggc ugggagcggc ccucacauug auggcuccug ccaccuccuc   60
cgcag                                                              65
```

<210> SEQ ID NO 497
<211> LENGTH: 74
<212> TYPE: RNA
<213> ORGANISM: Homo sapiens

<400> SEQUENCE: 497

```
ggaggaaga agggaggagg agcggagggg cccuugucuu cccagagccu cucccuuccu    60 ccccucccc uccc                                                     74
```

<210> SEQ ID NO 498
<211> LENGTH: 49
<212> TYPE: RNA
<213> ORGANISM: Homo sapiens

<400> SEQUENCE: 498

```
uucccagcca acgcaccaaa aaugauaugg gucuguuguc uggagaaac               49
```

<210> SEQ ID NO 499
<211> LENGTH: 83
<212> TYPE: RNA
<213> ORGANISM: Homo sapiens

```
<400> SEQUENCE: 499
ggguuuccuc ugccuuuuuu uccaaugaaa auaacgaaac cuguuauuuc ccauugaggg      60
ggaaaaaggc gggagaagcc cca                                            83

<210> SEQ ID NO 500
<211> LENGTH: 57
<212> TYPE: RNA
<213> ORGANISM: Homo sapiens

<400> SEQUENCE: 500
cauuggaggg uguggaagac aucugggcca acucugaucu cuucaucuac cccccag       57

<210> SEQ ID NO 501
<211> LENGTH: 69
<212> TYPE: RNA
<213> ORGANISM: Homo sapiens

<400> SEQUENCE: 501
gggauacuca aaaugggggc gcuuuccuuu uugucuguac ugggaagugc uucgauuuug    60
ggugucccc                                                            69

<210> SEQ ID NO 502
<211> LENGTH: 91
<212> TYPE: RNA
<213> ORGANISM: Homo sapiens

<400> SEQUENCE: 502
acgccccccg ccccgccacc gccuuggagg cugaccucuu acuuucgguc ggucuucuuc    60
ccugggcuug guuuggggc gggggagugu c                                    91

<210> SEQ ID NO 503
<211> LENGTH: 87
<212> TYPE: RNA
<213> ORGANISM: Homo sapiens

<400> SEQUENCE: 503
cccaggcgcc cgcucccgac ccacgccgcg ccgccggguc ccuccucccc ggagaggcug    60
ggcucgggac gcgcggcuca gcucggg                                        87

<210> SEQ ID NO 504
<211> LENGTH: 153
<212> TYPE: RNA
<213> ORGANISM: Homo sapiens

<400> SEQUENCE: 504
gcuccgcccc acgucgcaug cgccccggga acgcguggg cggagcuucc ggaggccccg     60
cucugcugcc gacccugugg agcggagggu gaagccuccg gaugccaguc ccucaucgcu   120
ggccuggucg cgcuguggcg aaggggggcgg agc                                153

<210> SEQ ID NO 505
<211> LENGTH: 153
<212> TYPE: RNA
<213> ORGANISM: Homo sapiens

<400> SEQUENCE: 505
gcuccgcccc acgucgcaug cgccccggga acgcguggg cggagcuucc ggaggccccg     60
cccugcugcc gacccugugg agcggagggu gaagccuccg gaugccaguc ccucaucgcu   120
```

```
ggcccggucg cgcuguggcg aaggggcgg agc                               153
```

<210> SEQ ID NO 506
<211> LENGTH: 113
<212> TYPE: RNA
<213> ORGANISM: Homo sapiens

<400> SEQUENCE: 506

```
agcaugacag aggagaggug gagguaggcg agaguaauau aauuucucca ggagaacauc    60
ugagagggga aguugcuuuc cugcccuggc ccuuucaccc uccugaguuu ggg          113
```

<210> SEQ ID NO 507
<211> LENGTH: 83
<212> TYPE: RNA
<213> ORGANISM: Homo sapiens

<400> SEQUENCE: 507

```
gugaguggga gcccagugu gugguuggg ccauggcggg ugggcagccc agccucugag      60
ccuuccucgu cugucugccc cag                                            83
```

<210> SEQ ID NO 508
<211> LENGTH: 67
<212> TYPE: RNA
<213> ORGANISM: Homo sapiens

<400> SEQUENCE: 508

```
aauagauuau uggucaccac cuccaguuuc ugaauugug agacugggu ggggccugag      60 aauuugc                                                              67
```

<210> SEQ ID NO 509
<211> LENGTH: 63
<212> TYPE: RNA
<213> ORGANISM: Homo sapiens

<400> SEQUENCE: 509

```
gcaugcuggg cgaggcuggc aucuagcaca ggcgguagau gcuugcucuu gccauugcaa    60
uga                                                                  63
```

<210> SEQ ID NO 510
<211> LENGTH: 76
<212> TYPE: RNA
<213> ORGANISM: Homo sapiens

<400> SEQUENCE: 510

```
cgcaggccuc uggcggagcc cauuccaugc cagaugcuga gcgauggcug gugugugcug    60
cuccacaggc cuggug                                                    76
```

<210> SEQ ID NO 511
<211> LENGTH: 72
<212> TYPE: RNA
<213> ORGANISM: Homo sapiens

<400> SEQUENCE: 511

```
augagcgggu gggagcagau cuuauugaga guuccuucuc cugcuccuga uugucuuccc    60
ccacccucac ag                                                        72
```

<210> SEQ ID NO 512
<211> LENGTH: 93
<212> TYPE: RNA
<213> ORGANISM: Homo sapiens -continued

```
<400> SEQUENCE: 512
uacuuauggc accccacucc ugguaccaua gucauaaguu aggagauguu agagcuguga    60
guaccaugac uuaagugugg uggcuuaaac aug                                93

<210> SEQ ID NO 513
<211> LENGTH: 67
<212> TYPE: RNA
<213> ORGANISM: Homo sapiens

<400> SEQUENCE: 513
ccugcaggca aagugggc ugacagggca gagggguugcg ccccucacc aucccuucug     60 ccugcag                                                              67

<210> SEQ ID NO 514
<211> LENGTH: 67
<212> TYPE: RNA
<213> ORGANISM: Homo sapiens

<400> SEQUENCE: 514
ccugcaggca gaagugggc ugacagggca gagggguugcg ccccucacc aucccuucug    60 ccugcag                                                              67

<210> SEQ ID NO 515
<211> LENGTH: 67
<212> TYPE: RNA
<213> ORGANISM: Homo sapiens

<400> SEQUENCE: 515
ccugcaggca gaagugggc ugacagggca gagggguugcg ccccucacc aucccuucug    60 ccugcag                                                              67

<210> SEQ ID NO 516
<211> LENGTH: 67
<212> TYPE: RNA
<213> ORGANISM: Homo sapiens

<400> SEQUENCE: 516
ccugcaggca gaagugggc ugacagggca gagggguugcg ccccucacc aucccuucug    60 ccugcag                                                              67

<210> SEQ ID NO 517
<211> LENGTH: 74
<212> TYPE: RNA
<213> ORGANISM: Homo sapiens

<400> SEQUENCE: 517
gggaggaaga agggaggagg agcggagggg cccuugucuu cccagagccu cucccuuccu   60 ccccucccc uccc                                                       74

<210> SEQ ID NO 518
<211> LENGTH: 69
<212> TYPE: RNA
<213> ORGANISM: Homo sapiens

<400> SEQUENCE: 518
ggcccucggg ccuggggguug ggggagcucu guccugcucu acucauugcu ccuccccugc  60
cuggcccag                                                            69
```

```
<210> SEQ ID NO 519
<211> LENGTH: 26
<212> TYPE: RNA
<213> ORGANISM: Homo sapiens

<400> SEQUENCE: 519
caagauggug gacuacagcg uguggg                                    26

<210> SEQ ID NO 520
<211> LENGTH: 15
<212> TYPE: RNA
<213> ORGANISM: Homo sapiens

<400> SEQUENCE: 520
aggcaagaug gugga                                                15

<210> SEQ ID NO 521
<211> LENGTH: 25
<212> TYPE: RNA
<213> ORGANISM: Homo sapiens

<400> SEQUENCE: 521
aggaagcccu ggaggggcug gaggu                                     25

<210> SEQ ID NO 522
<211> LENGTH: 15
<212> TYPE: RNA
<213> ORGANISM: Homo sapiens

<400> SEQUENCE: 522
aggaagagga ggaag                                                15

<210> SEQ ID NO 523
<211> LENGTH: 23
<212> TYPE: RNA
<213> ORGANISM: Homo sapiens

<400> SEQUENCE: 523
aggagggguc ccgcacuggg agg                                       23

<210> SEQ ID NO 524
<211> LENGTH: 15
<212> TYPE: RNA
<213> ORGANISM: Homo sapiens

<400> SEQUENCE: 524
ugggaggggc ccuca                                                15

<210> SEQ ID NO 525
<211> LENGTH: 23
<212> TYPE: RNA
<213> ORGANISM: Homo sapiens

<400> SEQUENCE: 525
gagggaggga cggggcugu gcu                                        23

<210> SEQ ID NO 526
<211> LENGTH: 15
<212> TYPE: RNA
<213> ORGANISM: Homo sapiens

<400> SEQUENCE: 526
gaggagggag ggagg                                                15
```

```
<210> SEQ ID NO 527
<211> LENGTH: 21
<212> TYPE: RNA
<213> ORGANISM: Homo sapiens

<400> SEQUENCE: 527
gugagucagg gugggggcugg c                                             21

<210> SEQ ID NO 528
<211> LENGTH: 21
<212> TYPE: RNA
<213> ORGANISM: Homo sapiens

<400> SEQUENCE: 528
gugagucagg gugggggcugg c                                             21

<210> SEQ ID NO 529
<211> LENGTH: 21
<212> TYPE: RNA
<213> ORGANISM: Homo sapiens

<400> SEQUENCE: 529 ugcuggggggc cacaugagug u                                             21

<210> SEQ ID NO 530
<211> LENGTH: 20
<212> TYPE: RNA
<213> ORGANISM: Homo sapiens

<400> SEQUENCE: 530 gcuggggggcc acaugagugu                                               20

<210> SEQ ID NO 531
<211> LENGTH: 24
<212> TYPE: RNA
<213> ORGANISM: Homo sapiens

<400> SEQUENCE: 531
cccggggcag auugguguag ggug                                           24

<210> SEQ ID NO 532
<211> LENGTH: 17
<212> TYPE: RNA
<213> ORGANISM: Homo sapiens

<400> SEQUENCE: 532
cggggcagau uggugua                                                   17

<210> SEQ ID NO 533
<211> LENGTH: 23
<212> TYPE: RNA
<213> ORGANISM: Homo sapiens

<400> SEQUENCE: 533
gugggcuggg cugggcuggg cca                                            23

<210> SEQ ID NO 534
<211> LENGTH: 15
<212> TYPE: RNA
<213> ORGANISM: Homo sapiens

<400> SEQUENCE: 534
```

-continued gggcugggcu gggcu                                                                                         15

<210> SEQ ID NO 535
<211> LENGTH: 21
<212> TYPE: RNA
<213> ORGANISM: Homo sapiens

<400> SEQUENCE: 535
gaggcgaugu ggggauguag a                                                                                  21

<210> SEQ ID NO 536
<211> LENGTH: 20
<212> TYPE: RNA
<213> ORGANISM: Homo sapiens

<400> SEQUENCE: 536
cccagucuca uuuccucauc                                                                                    20

<210> SEQ ID NO 537
<211> LENGTH: 22
<212> TYPE: RNA
<213> ORGANISM: Homo sapiens

<400> SEQUENCE: 537
ugggagggga gaggcagcaa gc                                                                                 22

<210> SEQ ID NO 538
<211> LENGTH: 22
<212> TYPE: RNA
<213> ORGANISM: Homo sapiens

<400> SEQUENCE: 538
ugggagggga gaggcagcaa gc                                                                                 22

<210> SEQ ID NO 539
<211> LENGTH: 26
<212> TYPE: RNA
<213> ORGANISM: Homo sapiens

<400> SEQUENCE: 539
acaacccuag gagagggugc cauuca                                                                             26

<210> SEQ ID NO 540
<211> LENGTH: 15
<212> TYPE: RNA
<213> ORGANISM: Homo sapiens

<400> SEQUENCE: 540
acaacccuag gagag                                                                                         15

<210> SEQ ID NO 541
<211> LENGTH: 27
<212> TYPE: RNA
<213> ORGANISM: Homo sapiens

<400> SEQUENCE: 541
gugaacgggc gccaucccga ggcuuug                                                                            27

<210> SEQ ID NO 542
<211> LENGTH: 16
<212> TYPE: RNA
<213> ORGANISM: Homo sapiens

<400> SEQUENCE: 542
gugaacgggc gccauc                                                    16

<210> SEQ ID NO 543
<211> LENGTH: 22
<212> TYPE: RNA
<213> ORGANISM: Homo sapiens

<400> SEQUENCE: 543
gugggcgggg gcaggugugu gg                                             22

<210> SEQ ID NO 544
<211> LENGTH: 15
<212> TYPE: RNA
<213> ORGANISM: Homo sapiens

<400> SEQUENCE: 544
cgggggcagg ugugu                                                     15

<210> SEQ ID NO 545
<211> LENGTH: 16
<212> TYPE: RNA
<213> ORGANISM: Homo sapiens

<400> SEQUENCE: 545
accagccugg ggcauc                                                    16

<210> SEQ ID NO 546
<211> LENGTH: 16
<212> TYPE: RNA
<213> ORGANISM: Homo sapiens

<400> SEQUENCE: 546
accagccugg ggcauc                                                    16

<210> SEQ ID NO 547
<211> LENGTH: 15
<212> TYPE: RNA
<213> ORGANISM: Homo sapiens

<400> SEQUENCE: 547
aggaggagga ggcag                                                     15

<210> SEQ ID NO 548
<211> LENGTH: 15
<212> TYPE: RNA
<213> ORGANISM: Homo sapiens

<400> SEQUENCE: 548
aggaggagga ggcag                                                     15

<210> SEQ ID NO 549
<211> LENGTH: 24
<212> TYPE: RNA
<213> ORGANISM: Homo sapiens

<400> SEQUENCE: 549 caggggaug gcagagcaaa auuc                                            24

<210> SEQ ID NO 550
<211> LENGTH: 17
<212> TYPE: RNA
<213> ORGANISM: Homo sapiens

```
<400> SEQUENCE: 550
aggggauggg cagagca                                            17

<210> SEQ ID NO 551
<211> LENGTH: 26
<212> TYPE: RNA
<213> ORGANISM: Homo sapiens

<400> SEQUENCE: 551
gaggggcucu cgcuucuggc gccaag                                  26

<210> SEQ ID NO 552
<211> LENGTH: 15
<212> TYPE: RNA
<213> ORGANISM: Homo sapiens

<400> SEQUENCE: 552
ggugaggcgg ggggg                                              15

<210> SEQ ID NO 553
<211> LENGTH: 23
<212> TYPE: RNA
<213> ORGANISM: Homo sapiens

<400> SEQUENCE: 553
gggggccgau acacuguacg aga                                     23

<210> SEQ ID NO 554
<211> LENGTH: 20
<212> TYPE: RNA
<213> ORGANISM: Homo sapiens

<400> SEQUENCE: 554
gggggccgau acacuguacg                                         20

<210> SEQ ID NO 555
<211> LENGTH: 15
<212> TYPE: RNA
<213> ORGANISM: Homo sapiens

<400> SEQUENCE: 555
uggcagagcg cuguc                                              15

<210> SEQ ID NO 556
<211> LENGTH: 15
<212> TYPE: RNA
<213> ORGANISM: Homo sapiens

<400> SEQUENCE: 556
uggcagagcg cuguc                                              15

<210> SEQ ID NO 557
<211> LENGTH: 27
<212> TYPE: RNA
<213> ORGANISM: Homo sapiens

<400> SEQUENCE: 557
caagguggcu gggagagggu uguuuac                                 27

<210> SEQ ID NO 558
<211> LENGTH: 15
<212> TYPE: RNA
<213> ORGANISM: Homo sapiens
```

-continued

```
<400> SEQUENCE: 558
gugagcucaa ggugg                                                    15

<210> SEQ ID NO 559
<211> LENGTH: 19
<212> TYPE: RNA
<213> ORGANISM: Homo sapiens

<400> SEQUENCE: 559
agugggaggc cagggcacg                                                19

<210> SEQ ID NO 560
<211> LENGTH: 15
<212> TYPE: RNA
<213> ORGANISM: Homo sapiens

<400> SEQUENCE: 560 aggggagcu gcagg                                                     15

<210> SEQ ID NO 561
<211> LENGTH: 22
<212> TYPE: RNA
<213> ORGANISM: Homo sapiens

<400> SEQUENCE: 561
ggcagggaca gcaaaggggu gc                                            22

<210> SEQ ID NO 562
<211> LENGTH: 18
<212> TYPE: RNA
<213> ORGANISM: Homo sapiens

<400> SEQUENCE: 562
gcagggacag caaagggg                                                 18

<210> SEQ ID NO 563
<211> LENGTH: 24
<212> TYPE: RNA
<213> ORGANISM: Homo sapiens

<400> SEQUENCE: 563
gugaguggga gccggugggg cugg                                          24

<210> SEQ ID NO 564
<211> LENGTH: 15
<212> TYPE: RNA
<213> ORGANISM: Homo sapiens

<400> SEQUENCE: 564
ggggcuggag uaagg                                                    15

<210> SEQ ID NO 565
<211> LENGTH: 17
<212> TYPE: RNA
<213> ORGANISM: Homo sapiens

<400> SEQUENCE: 565
ugcaggggca ggccagc                                                  17

<210> SEQ ID NO 566
<211> LENGTH: 15
<212> TYPE: RNA
```

```
<213> ORGANISM: Homo sapiens

<400> SEQUENCE: 566
ccuguucuug ccagg                                                    15

<210> SEQ ID NO 567
<211> LENGTH: 23
<212> TYPE: RNA
<213> ORGANISM: Homo sapiens

<400> SEQUENCE: 567
caccuugccu ugcugcccgg gcc                                           23

<210> SEQ ID NO 568
<211> LENGTH: 22
<212> TYPE: RNA
<213> ORGANISM: Homo sapiens

<400> SEQUENCE: 568
caccuugccu ugcugcccgg gc                                            22

<210> SEQ ID NO 569
<211> LENGTH: 23
<212> TYPE: RNA
<213> ORGANISM: Homo sapiens

<400> SEQUENCE: 569
uaggggcagc agaggaccug ggc                                           23

<210> SEQ ID NO 570
<211> LENGTH: 20
<212> TYPE: RNA
<213> ORGANISM: Homo sapiens

<400> SEQUENCE: 570
uaggggcagc agaggaccug                                               20

<210> SEQ ID NO 571
<211> LENGTH: 29
<212> TYPE: RNA
<213> ORGANISM: Homo sapiens

<400> SEQUENCE: 571
ggucaggcgg cucggacuga gcagguggg                                     29

<210> SEQ ID NO 572
<211> LENGTH: 15
<212> TYPE: RNA
<213> ORGANISM: Homo sapiens

<400> SEQUENCE: 572
agaguguggu caggc                                                    15

<210> SEQ ID NO 573
<211> LENGTH: 15
<212> TYPE: RNA
<213> ORGANISM: Homo sapiens

<400> SEQUENCE: 573
ggcgcgggga ggugc                                                    15

<210> SEQ ID NO 574
<211> LENGTH: 15
```

```
<212> TYPE: RNA
<213> ORGANISM: Homo sapiens

<400> SEQUENCE: 574
ggcgcgggga ggugc                                               15

<210> SEQ ID NO 575
<211> LENGTH: 21
<212> TYPE: RNA
<213> ORGANISM: Homo sapiens

<400> SEQUENCE: 575
gagggcagcg uggugugggc g                                        21

<210> SEQ ID NO 576
<211> LENGTH: 21
<212> TYPE: RNA
<213> ORGANISM: Homo sapiens

<400> SEQUENCE: 576
gagggcagcg uggugugggc g                                        21

<210> SEQ ID NO 577
<211> LENGTH: 16
<212> TYPE: RNA
<213> ORGANISM: Homo sapiens

<400> SEQUENCE: 577
gugaaggccc ggcgga                                              16

<210> SEQ ID NO 578
<211> LENGTH: 15
<212> TYPE: RNA
<213> ORGANISM: Homo sapiens

<400> SEQUENCE: 578
gugaaggccc ggcgg                                               15

<210> SEQ ID NO 579
<211> LENGTH: 22
<212> TYPE: RNA
<213> ORGANISM: Homo sapiens

<400> SEQUENCE: 579
auauagggau uggagccgug gc                                       22

<210> SEQ ID NO 580
<211> LENGTH: 20
<212> TYPE: RNA
<213> ORGANISM: Homo sapiens

<400> SEQUENCE: 580
auauagggau uggagccgug                                          20

<210> SEQ ID NO 581
<211> LENGTH: 24
<212> TYPE: RNA
<213> ORGANISM: Homo sapiens

<400> SEQUENCE: 581 uggggagug cagugauugu ggaa                                      24

<210> SEQ ID NO 582
```

-continued

<211> LENGTH: 19
<212> TYPE: RNA
<213> ORGANISM: Homo sapiens

<400> SEQUENCE: 582 uggggagug cagugauug                                                    19

<210> SEQ ID NO 583
<211> LENGTH: 16
<212> TYPE: RNA
<213> ORGANISM: Homo sapiens

<400> SEQUENCE: 583
cgggcccggc guuccc                                                      16

<210> SEQ ID NO 584
<211> LENGTH: 15
<212> TYPE: RNA
<213> ORGANISM: Homo sapiens

<400> SEQUENCE: 584
ccgggcccgg cguuc                                                       15

<210> SEQ ID NO 585
<211> LENGTH: 23
<212> TYPE: RNA
<213> ORGANISM: Homo sapiens

<400> SEQUENCE: 585
uuucaagcca gggggcguuu uuc                                              23

<210> SEQ ID NO 586
<211> LENGTH: 18
<212> TYPE: RNA
<213> ORGANISM: Homo sapiens

<400> SEQUENCE: 586
uuucaagcca gggggcgu                                                    18

<210> SEQ ID NO 587
<211> LENGTH: 22
<212> TYPE: RNA
<213> ORGANISM: Homo sapiens

<400> SEQUENCE: 587
gaggguuggg uggaggcucu cc                                               22

<210> SEQ ID NO 588
<211> LENGTH: 15
<212> TYPE: RNA
<213> ORGANISM: Homo sapiens

<400> SEQUENCE: 588
gaggguuggg uggag                                                       15

<210> SEQ ID NO 589
<211> LENGTH: 18
<212> TYPE: RNA
<213> ORGANISM: Homo sapiens

<400> SEQUENCE: 589
gaggcugaag gaagaugg                                                    18

```
<210> SEQ ID NO 590
<211> LENGTH: 15
<212> TYPE: RNA
<213> ORGANISM: Homo sapiens

<400> SEQUENCE: 590
gaggcugaag gaaga                                                     15

<210> SEQ ID NO 591
<211> LENGTH: 20
<212> TYPE: RNA
<213> ORGANISM: Homo sapiens

<400> SEQUENCE: 591
ggcuggucag augggagugg                                                20

<210> SEQ ID NO 592
<211> LENGTH: 20
<212> TYPE: RNA
<213> ORGANISM: Homo sapiens

<400> SEQUENCE: 592
ggcuggucag augggagugg                                                20

<210> SEQ ID NO 593
<211> LENGTH: 24
<212> TYPE: RNA
<213> ORGANISM: Homo sapiens

<400> SEQUENCE: 593
ugacugggga gcagaaggag aacc                                           24

<210> SEQ ID NO 594
<211> LENGTH: 15
<212> TYPE: RNA
<213> ORGANISM: Homo sapiens

<400> SEQUENCE: 594
gacuggggag cagaa                                                     15

<210> SEQ ID NO 595
<211> LENGTH: 21
<212> TYPE: RNA
<213> ORGANISM: Homo sapiens

<400> SEQUENCE: 595
cagcagggga gagagaggag u                                              21

<210> SEQ ID NO 596
<211> LENGTH: 20
<212> TYPE: RNA
<213> ORGANISM: Homo sapiens

<400> SEQUENCE: 596
cagcagggga gagagaggag                                                20

<210> SEQ ID NO 597
<211> LENGTH: 19
<212> TYPE: RNA
<213> ORGANISM: Homo sapiens

<400> SEQUENCE: 597
gcaggcgagg cugggcuga                                                 19
```

<210> SEQ ID NO 598
<211> LENGTH: 16
<212> TYPE: RNA
<213> ORGANISM: Homo sapiens

<400> SEQUENCE: 598
aggcgaggcu gggcug                                           16

<210> SEQ ID NO 599
<211> LENGTH: 26
<212> TYPE: RNA
<213> ORGANISM: Homo sapiens

<400> SEQUENCE: 599
aaaaucacau ugccagggau uaccac                                26

<210> SEQ ID NO 600
<211> LENGTH: 15
<212> TYPE: RNA
<213> ORGANISM: Homo sapiens

<400> SEQUENCE: 600
aaucacauug ccagg                                            15

<210> SEQ ID NO 601
<211> LENGTH: 20
<212> TYPE: RNA
<213> ORGANISM: Homo sapiens

<400> SEQUENCE: 601
ggcuccuugg ucuaggggua                                       20

<210> SEQ ID NO 602
<211> LENGTH: 15
<212> TYPE: RNA
<213> ORGANISM: Homo sapiens

<400> SEQUENCE: 602
cuuggucuag gggua                                            15

<210> SEQ ID NO 603
<211> LENGTH: 28
<212> TYPE: RNA
<213> ORGANISM: Homo sapiens

<400> SEQUENCE: 603
uuggggaaac ggccgcugag ugaggcgu                              28

<210> SEQ ID NO 604
<211> LENGTH: 15
<212> TYPE: RNA
<213> ORGANISM: Homo sapiens

<400> SEQUENCE: 604
ggggaaacgg ccgcu                                            15

<210> SEQ ID NO 605
<211> LENGTH: 25
<212> TYPE: RNA
<213> ORGANISM: Homo sapiens

<400> SEQUENCE: 605
agcggggagg aagugggcgc ugcuu                                 25

-continued

<210> SEQ ID NO 606
<211> LENGTH: 21
<212> TYPE: RNA
<213> ORGANISM: Homo sapiens

<400> SEQUENCE: 606
agcggggagg aagugggcgc u                                               21

<210> SEQ ID NO 607
<211> LENGTH: 15
<212> TYPE: RNA
<213> ORGANISM: Homo sapiens

<400> SEQUENCE: 607
ggcgcgcggc ggcuc                                                      15

<210> SEQ ID NO 608
<211> LENGTH: 15
<212> TYPE: RNA
<213> ORGANISM: Homo sapiens

<400> SEQUENCE: 608
ggcgcgcggc ggcuc                                                      15

<210> SEQ ID NO 609
<211> LENGTH: 22
<212> TYPE: RNA
<213> ORGANISM: Homo sapiens

<400> SEQUENCE: 609
cgcggcgggg acggcgauug gu                                              22

<210> SEQ ID NO 610
<211> LENGTH: 17
<212> TYPE: RNA
<213> ORGANISM: Homo sapiens

<400> SEQUENCE: 610
cggcggggac ggcgauu                                                    17

<210> SEQ ID NO 611
<211> LENGTH: 21
<212> TYPE: RNA
<213> ORGANISM: Homo sapiens

<400> SEQUENCE: 611
auccaguucu cugaggggc u                                                21

<210> SEQ ID NO 612
<211> LENGTH: 21
<212> TYPE: RNA
<213> ORGANISM: Homo sapiens

<400> SEQUENCE: 612
auccaguucu cugaggggc u                                                21

<210> SEQ ID NO 613
<211> LENGTH: 16
<212> TYPE: RNA
<213> ORGANISM: Homo sapiens

<400> SEQUENCE: 613

```
ggcgcggagg gcggac                                           16

<210> SEQ ID NO 614
<211> LENGTH: 15
<212> TYPE: RNA
<213> ORGANISM: Homo sapiens

<400> SEQUENCE: 614
ggcgcggagg gcgga                                            15

<210> SEQ ID NO 615
<211> LENGTH: 23
<212> TYPE: RNA
<213> ORGANISM: Homo sapiens

<400> SEQUENCE: 615
cuaguggaag aagauggcgg aag                                   23

<210> SEQ ID NO 616
<211> LENGTH: 15
<212> TYPE: RNA
<213> ORGANISM: Homo sapiens

<400> SEQUENCE: 616
uaguggaaga agaug                                            15

<210> SEQ ID NO 617
<211> LENGTH: 24
<212> TYPE: RNA
<213> ORGANISM: Homo sapiens

<400> SEQUENCE: 617
gaucggucga gagcguccug gcug                                  24

<210> SEQ ID NO 618
<211> LENGTH: 15
<212> TYPE: RNA
<213> ORGANISM: Homo sapiens

<400> SEQUENCE: 618
gcugggcggg gcgcg                                            15

<210> SEQ ID NO 619
<211> LENGTH: 17
<212> TYPE: RNA
<213> ORGANISM: Homo sapiens

<400> SEQUENCE: 619
gcggggcggc aggggcc                                          17

<210> SEQ ID NO 620
<211> LENGTH: 15
<212> TYPE: RNA
<213> ORGANISM: Homo sapiens

<400> SEQUENCE: 620
gggggcgggg cggca                                            15

<210> SEQ ID NO 621
<211> LENGTH: 25
<212> TYPE: RNA
<213> ORGANISM: Homo sapiens

<400> SEQUENCE: 621
```

```
gggggagcca ugagauaaga gcacc                                              25

<210> SEQ ID NO 622
<211> LENGTH: 20
<212> TYPE: RNA
<213> ORGANISM: Homo sapiens

<400> SEQUENCE: 622 uggggagcc augagauaag                                                     20

<210> SEQ ID NO 623
<211> LENGTH: 21
<212> TYPE: RNA
<213> ORGANISM: Homo sapiens

<400> SEQUENCE: 623
uugaggagac auggugggg c                                                   21

<210> SEQ ID NO 624
<211> LENGTH: 15
<212> TYPE: RNA
<213> ORGANISM: Homo sapiens

<400> SEQUENCE: 624
uugaggagac auggu                                                         15

<210> SEQ ID NO 625
<211> LENGTH: 25
<212> TYPE: RNA
<213> ORGANISM: Homo sapiens

<400> SEQUENCE: 625
uucugggccc gcggcgggcg ugggg                                              25

<210> SEQ ID NO 626
<211> LENGTH: 15
<212> TYPE: RNA
<213> ORGANISM: Homo sapiens

<400> SEQUENCE: 626
cgcggcgggc guggg                                                         15

<210> SEQ ID NO 627
<211> LENGTH: 18
<212> TYPE: RNA
<213> ORGANISM: Homo sapiens

<400> SEQUENCE: 627
cagcggggcu gggcgcgc                                                      18

<210> SEQ ID NO 628
<211> LENGTH: 15
<212> TYPE: RNA
<213> ORGANISM: Homo sapiens

<400> SEQUENCE: 628
cagcggggcu gggcg                                                         15

<210> SEQ ID NO 629
<211> LENGTH: 24
<212> TYPE: RNA
<213> ORGANISM: Homo sapiens
```

```
<400> SEQUENCE: 629
agacacauuu ggagagggaa ccuc                                        24

<210> SEQ ID NO 630
<211> LENGTH: 16
<212> TYPE: RNA
<213> ORGANISM: Homo sapiens

<400> SEQUENCE: 630
agacacauuu ggagag                                                 16

<210> SEQ ID NO 631
<211> LENGTH: 21
<212> TYPE: RNA
<213> ORGANISM: Homo sapiens

<400> SEQUENCE: 631
aggaggcagu gggcgagcag g                                           21

<210> SEQ ID NO 632
<211> LENGTH: 21
<212> TYPE: RNA
<213> ORGANISM: Homo sapiens

<400> SEQUENCE: 632
aggaggcagu gggcgagcag g                                           21

<210> SEQ ID NO 633
<211> LENGTH: 23
<212> TYPE: RNA
<213> ORGANISM: Homo sapiens

<400> SEQUENCE: 633
ggaggcgcag gcucggaaag gcg                                         23

<210> SEQ ID NO 634
<211> LENGTH: 15
<212> TYPE: RNA
<213> ORGANISM: Homo sapiens

<400> SEQUENCE: 634
gcaggcucgg aaagg                                                  15

<210> SEQ ID NO 635
<211> LENGTH: 23
<212> TYPE: RNA
<213> ORGANISM: Homo sapiens

<400> SEQUENCE: 635
ggcuacaaca caggacccgg gcg                                         23

<210> SEQ ID NO 636
<211> LENGTH: 21
<212> TYPE: RNA
<213> ORGANISM: Homo sapiens

<400> SEQUENCE: 636
ggcuacaaca caggacccgg g                                           21

<210> SEQ ID NO 637
<211> LENGTH: 23
<212> TYPE: RNA
<213> ORGANISM: Homo sapiens
```

-continued

<400> SEQUENCE: 637
agaagaaggc ggucggucug cgg                                       23

<210> SEQ ID NO 638
<211> LENGTH: 21
<212> TYPE: RNA
<213> ORGANISM: Homo sapiens

<400> SEQUENCE: 638
aagaaggcgg ucggucugcg g                                         21

<210> SEQ ID NO 639
<211> LENGTH: 16
<212> TYPE: RNA
<213> ORGANISM: Homo sapiens

<400> SEQUENCE: 639
ggcggugggc ggcggg                                               16

<210> SEQ ID NO 640
<211> LENGTH: 15
<212> TYPE: RNA
<213> ORGANISM: Homo sapiens

<400> SEQUENCE: 640
ggccucucgg gaacu                                                15

<210> SEQ ID NO 641
<211> LENGTH: 19
<212> TYPE: RNA
<213> ORGANISM: Homo sapiens

<400> SEQUENCE: 641
guggguuggg gcgggcucu                                            19

<210> SEQ ID NO 642
<211> LENGTH: 19
<212> TYPE: RNA
<213> ORGANISM: Homo sapiens

<400> SEQUENCE: 642
guggguuggg gcgggcucu                                            19

<210> SEQ ID NO 643
<211> LENGTH: 23
<212> TYPE: RNA
<213> ORGANISM: Homo sapiens

<400> SEQUENCE: 643
gggggucccc ggugcucgga ucu                                       23

<210> SEQ ID NO 644
<211> LENGTH: 16
<212> TYPE: RNA
<213> ORGANISM: Homo sapiens

<400> SEQUENCE: 644
ucgggagggg cgggag                                               16

<210> SEQ ID NO 645
<211> LENGTH: 21
<212> TYPE: RNA

```
<213> ORGANISM: Homo sapiens

<400> SEQUENCE: 645 ggcggggguq gcggcggcau c                                             21

<210> SEQ ID NO 646
<211> LENGTH: 15
<212> TYPE: RNA
<213> ORGANISM: Homo sapiens

<400> SEQUENCE: 646
gguggcggcg gcauc                                                    15

<210> SEQ ID NO 647
<211> LENGTH: 23
<212> TYPE: RNA
<213> ORGANISM: Homo sapiens

<400> SEQUENCE: 647
cuccuggggc ccgcacucuc gcu                                           23

<210> SEQ ID NO 648
<211> LENGTH: 18
<212> TYPE: RNA
<213> ORGANISM: Homo sapiens

<400> SEQUENCE: 648
cuccuggggc ccgcacuc                                                 18

<210> SEQ ID NO 649
<211> LENGTH: 19
<212> TYPE: RNA
<213> ORGANISM: Homo sapiens

<400> SEQUENCE: 649 aggggcggg cuccggcgc                                                 19

<210> SEQ ID NO 650
<211> LENGTH: 15
<212> TYPE: RNA
<213> ORGANISM: Homo sapiens

<400> SEQUENCE: 650 guaggggcg ggcuc                                                     15

<210> SEQ ID NO 651
<211> LENGTH: 23
<212> TYPE: RNA
<213> ORGANISM: Homo sapiens

<400> SEQUENCE: 651
cacaggugag guucuuggga gcc                                           23

<210> SEQ ID NO 652
<211> LENGTH: 15
<212> TYPE: RNA
<213> ORGANISM: Homo sapiens

<400> SEQUENCE: 652
acaggugagg uucuu                                                    15

<210> SEQ ID NO 653
<211> LENGTH: 17
```

```
<212> TYPE: RNA
<213> ORGANISM: Homo sapiens

<400> SEQUENCE: 653
gaucccagcg gugccuc                                              17

<210> SEQ ID NO 654
<211> LENGTH: 15
<212> TYPE: RNA
<213> ORGANISM: Homo sapiens

<400> SEQUENCE: 654
gaucccagcg gugcc                                                15

<210> SEQ ID NO 655
<211> LENGTH: 20
<212> TYPE: RNA
<213> ORGANISM: Homo sapiens

<400> SEQUENCE: 655
cuccccggug ugcaaaugug                                           20

<210> SEQ ID NO 656
<211> LENGTH: 15
<212> TYPE: RNA
<213> ORGANISM: Homo sapiens

<400> SEQUENCE: 656
cccucccucu cuccc                                                15

<210> SEQ ID NO 657
<211> LENGTH: 15
<212> TYPE: RNA
<213> ORGANISM: Homo sapiens

<400> SEQUENCE: 657
ggcggcgggc ccggg                                                15

<210> SEQ ID NO 658
<211> LENGTH: 15
<212> TYPE: RNA
<213> ORGANISM: Homo sapiens

<400> SEQUENCE: 658
ggcggcgggc ccggg                                                15

<210> SEQ ID NO 659
<211> LENGTH: 26
<212> TYPE: RNA
<213> ORGANISM: Homo sapiens

<400> SEQUENCE: 659
gcgggcuguc cggagggguc ggcuuu                                    26

<210> SEQ ID NO 660
<211> LENGTH: 16
<212> TYPE: RNA
<213> ORGANISM: Homo sapiens

<400> SEQUENCE: 660
gcuguccgga gggguc                                               16

<210> SEQ ID NO 661
```

```
<211> LENGTH: 25
<212> TYPE: RNA
<213> ORGANISM: Homo sapiens

<400> SEQUENCE: 661
uggcggcggu aguuaugggc uucuc                                         25

<210> SEQ ID NO 662
<211> LENGTH: 25
<212> TYPE: RNA
<213> ORGANISM: Homo sapiens

<400> SEQUENCE: 662
uggcggcggu aguuaugggc uucuc                                         25

<210> SEQ ID NO 663
<211> LENGTH: 23
<212> TYPE: RNA
<213> ORGANISM: Homo sapiens

<400> SEQUENCE: 663
gccccggcgc gggcggguuc ugg                                           23

<210> SEQ ID NO 664
<211> LENGTH: 16
<212> TYPE: RNA
<213> ORGANISM: Homo sapiens

<400> SEQUENCE: 664
ggagccccgg cgcggg                                                   16

<210> SEQ ID NO 665
<211> LENGTH: 16
<212> TYPE: RNA
<213> ORGANISM: Homo sapiens

<400> SEQUENCE: 665
ugggggggaa gaaaag                                                   16

<210> SEQ ID NO 666
<211> LENGTH: 16
<212> TYPE: RNA
<213> ORGANISM: Homo sapiens

<400> SEQUENCE: 666
ugggggggaa gaaaag                                                   16

<210> SEQ ID NO 667
<211> LENGTH: 24
<212> TYPE: RNA
<213> ORGANISM: Homo sapiens

<400> SEQUENCE: 667
caggcaggag ccggacugga ccuc                                          24

<210> SEQ ID NO 668
<211> LENGTH: 21
<212> TYPE: RNA
<213> ORGANISM: Homo sapiens

<400> SEQUENCE: 668
uccaggcagg agccggacug g                                             21
```

-continued

```
<210> SEQ ID NO 669
<211> LENGTH: 25
<212> TYPE: RNA
<213> ORGANISM: Homo sapiens

<400> SEQUENCE: 669
cugggccagg gagcagcugg uggau                                         25

<210> SEQ ID NO 670
<211> LENGTH: 20
<212> TYPE: RNA
<213> ORGANISM: Homo sapiens

<400> SEQUENCE: 670
ugggccaggg agcagcuggu                                               20

<210> SEQ ID NO 671
<211> LENGTH: 26
<212> TYPE: RNA
<213> ORGANISM: Homo sapiens

<400> SEQUENCE: 671 cgguggauc ccgcggccgu guuuuc                                         26

<210> SEQ ID NO 672
<211> LENGTH: 15
<212> TYPE: RNA
<213> ORGANISM: Homo sapiens

<400> SEQUENCE: 672
ggggcgccgc gggac                                                    15

<210> SEQ ID NO 673
<211> LENGTH: 20
<212> TYPE: RNA
<213> ORGANISM: Homo sapiens

<400> SEQUENCE: 673
ccccagggcg acgcggcggg                                               20

<210> SEQ ID NO 674
<211> LENGTH: 15
<212> TYPE: RNA
<213> ORGANISM: Homo sapiens

<400> SEQUENCE: 674
cgcggcgggg gcggc                                                    15

<210> SEQ ID NO 675
<211> LENGTH: 18
<212> TYPE: RNA
<213> ORGANISM: Homo sapiens

<400> SEQUENCE: 675 gguggcuuc ccggaggg                                                  18

<210> SEQ ID NO 676
<211> LENGTH: 15
<212> TYPE: RNA
<213> ORGANISM: Homo sapiens

<400> SEQUENCE: 676 gguggcuuc ccgga                                                     15
```

```
<210> SEQ ID NO 677
<211> LENGTH: 26
<212> TYPE: RNA
<213> ORGANISM: Homo sapiens

<400> SEQUENCE: 677
gucccggggc ugcgcgaggc acaggc                                          26

<210> SEQ ID NO 678
<211> LENGTH: 15
<212> TYPE: RNA
<213> ORGANISM: Homo sapiens

<400> SEQUENCE: 678
ggcccggggg gcggg                                                      15

<210> SEQ ID NO 679
<211> LENGTH: 23
<212> TYPE: RNA
<213> ORGANISM: Homo sapiens

<400> SEQUENCE: 679
cagcccgccc cagccgaggu ucu                                             23

<210> SEQ ID NO 680
<211> LENGTH: 17
<212> TYPE: RNA
<213> ORGANISM: Homo sapiens

<400> SEQUENCE: 680
agcccgcccc agccgag                                                    17

<210> SEQ ID NO 681
<211> LENGTH: 23
<212> TYPE: RNA
<213> ORGANISM: Homo sapiens

<400> SEQUENCE: 681
uggggcggag cuuccggagg ccc                                             23

<210> SEQ ID NO 682
<211> LENGTH: 15
<212> TYPE: RNA
<213> ORGANISM: Homo sapiens

<400> SEQUENCE: 682
gccccgggaa agcgu                                                      15

<210> SEQ ID NO 683
<211> LENGTH: 22
<212> TYPE: RNA
<213> ORGANISM: Homo sapiens

<400> SEQUENCE: 683
cugaauagcu gggacuacag gu                                              22

<210> SEQ ID NO 684
<211> LENGTH: 15
<212> TYPE: RNA
<213> ORGANISM: Homo sapiens

<400> SEQUENCE: 684
ccugaauagc uggga                                                      15
```

```
<210> SEQ ID NO 685
<211> LENGTH: 21
<212> TYPE: RNA
<213> ORGANISM: Homo sapiens

<400> SEQUENCE: 685
gccgggcgug guggugggg c                                              21

<210> SEQ ID NO 686
<211> LENGTH: 15
<212> TYPE: RNA
<213> ORGANISM: Homo sapiens

<400> SEQUENCE: 686
uagccgggcg uggug                                                    15

<210> SEQ ID NO 687
<211> LENGTH: 23
<212> TYPE: RNA
<213> ORGANISM: Homo sapiens

<400> SEQUENCE: 687
gagggccccc ccucaauccu guu                                           23

<210> SEQ ID NO 688
<211> LENGTH: 15
<212> TYPE: RNA
<213> ORGANISM: Homo sapiens

<400> SEQUENCE: 688 agggccccccc cucaa                                                   15

<210> SEQ ID NO 689
<211> LENGTH: 24
<212> TYPE: RNA
<213> ORGANISM: Homo sapiens

<400> SEQUENCE: 689
gaggcuggga aggcaaaggg acgu                                          24

<210> SEQ ID NO 690
<211> LENGTH: 15
<212> TYPE: RNA
<213> ORGANISM: Homo sapiens

<400> SEQUENCE: 690
gaaggaggcu gggaa                                                    15

<210> SEQ ID NO 691
<211> LENGTH: 21
<212> TYPE: RNA
<213> ORGANISM: Homo sapiens

<400> SEQUENCE: 691
cggauccgag ucacggcacc a                                             21

<210> SEQ ID NO 692
<211> LENGTH: 15
<212> TYPE: RNA
<213> ORGANISM: Homo sapiens

<400> SEQUENCE: 692
```

| | |
|---|---|
| ggauccgagu cacgg | 15 |

<210> SEQ ID NO 693
<211> LENGTH: 20
<212> TYPE: RNA
<213> ORGANISM: Homo sapiens

<400> SEQUENCE: 693

| | |
|---|---|
| ggauuuuugg aucagggaug | 20 |

<210> SEQ ID NO 694
<211> LENGTH: 15
<212> TYPE: RNA
<213> ORGANISM: Homo sapiens

<400> SEQUENCE: 694

| | |
|---|---|
| auuuuuggau caggg | 15 |

<210> SEQ ID NO 695
<211> LENGTH: 22
<212> TYPE: RNA
<213> ORGANISM: Homo sapiens

<400> SEQUENCE: 695

| | |
|---|---|
| caggcacggg agcucaggug ag | 22 |

<210> SEQ ID NO 696
<211> LENGTH: 17
<212> TYPE: RNA
<213> ORGANISM: Homo sapiens

<400> SEQUENCE: 696

| | |
|---|---|
| caggcacggg agcucag | 17 |

<210> SEQ ID NO 697
<211> LENGTH: 24
<212> TYPE: RNA
<213> ORGANISM: Homo sapiens

<400> SEQUENCE: 697

| | |
|---|---|
| uggggagcug aggcucuggg ggug | 24 |

<210> SEQ ID NO 698
<211> LENGTH: 15
<212> TYPE: RNA
<213> ORGANISM: Homo sapiens

<400> SEQUENCE: 698

| | |
|---|---|
| ggcccugggg agcug | 15 |

<210> SEQ ID NO 699
<211> LENGTH: 23
<212> TYPE: RNA
<213> ORGANISM: Homo sapiens

<400> SEQUENCE: 699

| | |
|---|---|
| uggugcggag agggcccaca gug | 23 |

<210> SEQ ID NO 700
<211> LENGTH: 15
<212> TYPE: RNA
<213> ORGANISM: Homo sapiens

<400> SEQUENCE: 700
gggucuggug cggag 15

<210> SEQ ID NO 701
<211> LENGTH: 24
<212> TYPE: RNA
<213> ORGANISM: Homo sapiens

<400> SEQUENCE: 701
ucgaggacug guggaagggc cuuu 24

<210> SEQ ID NO 702
<211> LENGTH: 16
<212> TYPE: RNA
<213> ORGANISM: Homo sapiens

<400> SEQUENCE: 702
ucgaggacug guggaa 16

<210> SEQ ID NO 703
<211> LENGTH: 22
<212> TYPE: RNA
<213> ORGANISM: Homo sapiens

<400> SEQUENCE: 703
ugugggacug caaaugggag cu 22

<210> SEQ ID NO 704
<211> LENGTH: 22
<212> TYPE: RNA
<213> ORGANISM: Homo sapiens

<400> SEQUENCE: 704
ugugggacug caaaugggag cu 22

<210> SEQ ID NO 705
<211> LENGTH: 24
<212> TYPE: RNA
<213> ORGANISM: Homo sapiens

<400> SEQUENCE: 705
cgggcguggu gguggggug ggug 24

<210> SEQ ID NO 706
<211> LENGTH: 15
<212> TYPE: RNA
<213> ORGANISM: Homo sapiens

<400> SEQUENCE: 706
cgggcguggu ggugg 15

<210> SEQ ID NO 707
<211> LENGTH: 23
<212> TYPE: RNA
<213> ORGANISM: Homo sapiens

<400> SEQUENCE: 707
agggaguaga aggguggga gca 23

<210> SEQ ID NO 708
<211> LENGTH: 16
<212> TYPE: RNA
<213> ORGANISM: Homo sapiens

```
<400> SEQUENCE: 708
uagggaguag aagggu                                                    16

<210> SEQ ID NO 709
<211> LENGTH: 20
<212> TYPE: RNA
<213> ORGANISM: Homo sapiens

<400> SEQUENCE: 709
aagacacauu uggagaggga                                                20

<210> SEQ ID NO 710
<211> LENGTH: 16
<212> TYPE: RNA
<213> ORGANISM: Homo sapiens

<400> SEQUENCE: 710
agacacauuu ggagag                                                    16

<210> SEQ ID NO 711
<211> LENGTH: 25
<212> TYPE: RNA
<213> ORGANISM: Homo sapiens

<400> SEQUENCE: 711
gcugcgggcu gcggucaggg cgauc                                          25

<210> SEQ ID NO 712
<211> LENGTH: 20
<212> TYPE: RNA
<213> ORGANISM: Homo sapiens

<400> SEQUENCE: 712
gcugcgggcu gcggucaggg                                                20

<210> SEQ ID NO 713
<211> LENGTH: 24
<212> TYPE: RNA
<213> ORGANISM: Homo sapiens

<400> SEQUENCE: 713
cugguacagg ccuggggac aggg                                            24

<210> SEQ ID NO 714
<211> LENGTH: 18
<212> TYPE: RNA
<213> ORGANISM: Homo sapiens

<400> SEQUENCE: 714
cugguacagg ccuggggg                                                  18

<210> SEQ ID NO 715
<211> LENGTH: 26
<212> TYPE: RNA
<213> ORGANISM: Homo sapiens

<400> SEQUENCE: 715
agggacggga cgcggugcag uguugu                                         26

<210> SEQ ID NO 716
<211> LENGTH: 15
<212> TYPE: RNA
<213> ORGANISM: Homo sapiens
```

-continued

<400> SEQUENCE: 716
ggcgggcggg aggga                                                    15

<210> SEQ ID NO 717
<211> LENGTH: 23
<212> TYPE: RNA
<213> ORGANISM: Homo sapiens

<400> SEQUENCE: 717
ugaggauaug gcagggaagg gga                                           23

<210> SEQ ID NO 718
<211> LENGTH: 19
<212> TYPE: RNA
<213> ORGANISM: Homo sapiens

<400> SEQUENCE: 718
ugaggauaug gcagggaag                                                19

<210> SEQ ID NO 719
<211> LENGTH: 17
<212> TYPE: RNA
<213> ORGANISM: Homo sapiens

<400> SEQUENCE: 719
ggugagcgcu cgcuggc                                                  17

<210> SEQ ID NO 720
<211> LENGTH: 15
<212> TYPE: RNA
<213> ORGANISM: Homo sapiens

<400> SEQUENCE: 720
cggugagcgc ucgcu                                                    15

<210> SEQ ID NO 721
<211> LENGTH: 19
<212> TYPE: RNA
<213> ORGANISM: Homo sapiens

<400> SEQUENCE: 721
uggcgggugc gggggugggg                                               19

<210> SEQ ID NO 722
<211> LENGTH: 15
<212> TYPE: RNA
<213> ORGANISM: Homo sapiens

<400> SEQUENCE: 722
uggcgggugc ggggg                                                    15

<210> SEQ ID NO 723
<211> LENGTH: 25
<212> TYPE: RNA
<213> ORGANISM: Homo sapiens

<400> SEQUENCE: 723
ggguggggau uuguugcauu acuug                                         25

<210> SEQ ID NO 724
<211> LENGTH: 20
<212> TYPE: RNA

```
<213> ORGANISM: Homo sapiens

<400> SEQUENCE: 724
ggguggggau uuguugcauu                                              20

<210> SEQ ID NO 725
<211> LENGTH: 19
<212> TYPE: RNA
<213> ORGANISM: Homo sapiens

<400> SEQUENCE: 725
gggugcgggc cggcggggu                                               19

<210> SEQ ID NO 726
<211> LENGTH: 15
<212> TYPE: RNA
<213> ORGANISM: Homo sapiens

<400> SEQUENCE: 726
ugcgggccgg cgggg                                                   15

<210> SEQ ID NO 727
<211> LENGTH: 18
<212> TYPE: RNA
<213> ORGANISM: Homo sapiens

<400> SEQUENCE: 727
ucuaggnggg gagacuga                                                18

<210> SEQ ID NO 728
<211> LENGTH: 16
<212> TYPE: RNA
<213> ORGANISM: Homo sapiens

<400> SEQUENCE: 728 gugggagac ugacgg                                                   16

<210> SEQ ID NO 729
<211> LENGTH: 15
<212> TYPE: RNA
<213> ORGANISM: Homo sapiens

<400> SEQUENCE: 729
ucugggcgag gggug                                                   15

<210> SEQ ID NO 730
<211> LENGTH: 15
<212> TYPE: RNA
<213> ORGANISM: Homo sapiens

<400> SEQUENCE: 730
ucugggcgag gggug                                                   15

<210> SEQ ID NO 731
<211> LENGTH: 23
<212> TYPE: RNA
<213> ORGANISM: Homo sapiens

<400> SEQUENCE: 731
ggugggugag gucgggcccc aag                                          23

<210> SEQ ID NO 732
<211> LENGTH: 20
```

```
<212> TYPE: RNA
<213> ORGANISM: Homo sapiens

<400> SEQUENCE: 732
cggggugggu gaggucgggc                                               20

<210> SEQ ID NO 733
<211> LENGTH: 17
<212> TYPE: RNA
<213> ORGANISM: Homo sapiens

<400> SEQUENCE: 733
ggggcggggg cgggggc                                                  17

<210> SEQ ID NO 734
<211> LENGTH: 15
<212> TYPE: RNA
<213> ORGANISM: Homo sapiens

<400> SEQUENCE: 734
cgcgccgggc ccggg                                                    15

<210> SEQ ID NO 735
<211> LENGTH: 22
<212> TYPE: RNA
<213> ORGANISM: Homo sapiens

<400> SEQUENCE: 735
acucaaacug uggggcacu uu                                             22

<210> SEQ ID NO 736
<211> LENGTH: 19
<212> TYPE: RNA
<213> ORGANISM: Homo sapiens

<400> SEQUENCE: 736
acucaaacug uggggcac                                                 19

<210> SEQ ID NO 737
<211> LENGTH: 17
<212> TYPE: RNA
<213> ORGANISM: Homo sapiens

<400> SEQUENCE: 737
uccuagucac ggcacca                                                  17

<210> SEQ ID NO 738
<211> LENGTH: 17
<212> TYPE: RNA
<213> ORGANISM: Homo sapiens

<400> SEQUENCE: 738
uccuagucac ggcacca                                                  17

<210> SEQ ID NO 739
<211> LENGTH: 28
<212> TYPE: RNA
<213> ORGANISM: Homo sapiens

<400> SEQUENCE: 739
cagccuccca aaaugcuggg auuacagg                                      28

<210> SEQ ID NO 740
```

```
<211> LENGTH: 15
<212> TYPE: RNA
<213> ORGANISM: Homo sapiens

<400> SEQUENCE: 740
gcccaccuca gccuc                                              15

<210> SEQ ID NO 741
<211> LENGTH: 22
<212> TYPE: RNA
<213> ORGANISM: Homo sapiens

<400> SEQUENCE: 741
ccucacaccu gccucgcccc cc                                      22

<210> SEQ ID NO 742
<211> LENGTH: 15
<212> TYPE: RNA
<213> ORGANISM: Homo sapiens

<400> SEQUENCE: 742
ucacaccugc cucgc                                              15

<210> SEQ ID NO 743
<211> LENGTH: 27
<212> TYPE: RNA
<213> ORGANISM: Homo sapiens

<400> SEQUENCE: 743
aucacauugc cagggauuuc caaccga                                 27

<210> SEQ ID NO 744
<211> LENGTH: 15
<212> TYPE: RNA
<213> ORGANISM: Homo sapiens

<400> SEQUENCE: 744
aaucacauug ccagg                                              15

<210> SEQ ID NO 745
<211> LENGTH: 23
<212> TYPE: RNA
<213> ORGANISM: Homo sapiens

<400> SEQUENCE: 745 cuggggacg cgugagcgcg agc                                      23

<210> SEQ ID NO 746
<211> LENGTH: 21
<212> TYPE: RNA
<213> ORGANISM: Homo sapiens

<400> SEQUENCE: 746 cuggggacg cgugagcgcg a                                        21

<210> SEQ ID NO 747
<211> LENGTH: 30
<212> TYPE: RNA
<213> ORGANISM: Homo sapiens

<400> SEQUENCE: 747
gcugggcugg gacggacacc cggccuccac                              30
```

```
<210> SEQ ID NO 748
<211> LENGTH: 19
<212> TYPE: RNA
<213> ORGANISM: Homo sapiens

<400> SEQUENCE: 748
gaggcugggc ugggacgga                                              19

<210> SEQ ID NO 749
<211> LENGTH: 22
<212> TYPE: RNA
<213> ORGANISM: Homo sapiens

<400> SEQUENCE: 749
acucggcugc gguggacaag uc                                          22

<210> SEQ ID NO 750
<211> LENGTH: 20
<212> TYPE: RNA
<213> ORGANISM: Homo sapiens

<400> SEQUENCE: 750
acucggcugc gguggacaag                                             20

<210> SEQ ID NO 751
<211> LENGTH: 24
<212> TYPE: RNA
<213> ORGANISM: Homo sapiens

<400> SEQUENCE: 751
acuggcucag uucagcagga acag                                        24

<210> SEQ ID NO 752
<211> LENGTH: 15
<212> TYPE: RNA
<213> ORGANISM: Homo sapiens

<400> SEQUENCE: 752
uggcucaguu cagca                                                  15

<210> SEQ ID NO 753
<211> LENGTH: 21
<212> TYPE: RNA
<213> ORGANISM: Homo sapiens

<400> SEQUENCE: 753
cccaggcugg agcgagugca g                                           21

<210> SEQ ID NO 754
<211> LENGTH: 15
<212> TYPE: RNA
<213> ORGANISM: Homo sapiens

<400> SEQUENCE: 754
agcucacugc agccu                                                  15

<210> SEQ ID NO 755
<211> LENGTH: 20
<212> TYPE: RNA
<213> ORGANISM: Homo sapiens

<400> SEQUENCE: 755 ugagugggc ucccgggacg                                              20
```

```
<210> SEQ ID NO 756
<211> LENGTH: 20
<212> TYPE: RNA
<213> ORGANISM: Homo sapiens

<400> SEQUENCE: 756 ugagugggggc ucccgggacg                                          20

<210> SEQ ID NO 757
<211> LENGTH: 23
<212> TYPE: RNA
<213> ORGANISM: Homo sapiens

<400> SEQUENCE: 757
cggggccgua gcacugucug aga                                       23

<210> SEQ ID NO 758
<211> LENGTH: 20
<212> TYPE: RNA
<213> ORGANISM: Homo sapiens

<400> SEQUENCE: 758
cggggccgua gcacugucug                                           20

<210> SEQ ID NO 759
<211> LENGTH: 25
<212> TYPE: RNA
<213> ORGANISM: Homo sapiens

<400> SEQUENCE: 759
caggaaggau uuagggacag gcuuu                                     25

<210> SEQ ID NO 760
<211> LENGTH: 19
<212> TYPE: RNA
<213> ORGANISM: Homo sapiens

<400> SEQUENCE: 760
caggaaggau uuagggaca                                            19

<210> SEQ ID NO 761
<211> LENGTH: 20
<212> TYPE: RNA
<213> ORGANISM: Homo sapiens

<400> SEQUENCE: 761
uggcuguugg aggggggcagg                                          20

<210> SEQ ID NO 762
<211> LENGTH: 15
<212> TYPE: RNA
<213> ORGANISM: Homo sapiens

<400> SEQUENCE: 762 ggaggggggca ggcuc                                               15

<210> SEQ ID NO 763
<211> LENGTH: 18
<212> TYPE: RNA
<213> ORGANISM: Homo sapiens

<400> SEQUENCE: 763
gcggcggcgg cggcagca                                             18
```

-continued

<210> SEQ ID NO 764
<211> LENGTH: 15
<212> TYPE: RNA
<213> ORGANISM: Homo sapiens

<400> SEQUENCE: 764
gcgggcggcg gcggc                                                   15

<210> SEQ ID NO 765
<211> LENGTH: 16
<212> TYPE: RNA
<213> ORGANISM: Homo sapiens

<400> SEQUENCE: 765
ggacccaggg agagac                                                  16

<210> SEQ ID NO 766
<211> LENGTH: 16
<212> TYPE: RNA
<213> ORGANISM: Homo sapiens

<400> SEQUENCE: 766
ggacccaggg agagac                                                  16

<210> SEQ ID NO 767
<211> LENGTH: 19
<212> TYPE: RNA
<213> ORGANISM: Homo sapiens

<400> SEQUENCE: 767
gagggcgggu ggaggagga                                               19

<210> SEQ ID NO 768
<211> LENGTH: 15
<212> TYPE: RNA
<213> ORGANISM: Homo sapiens

<400> SEQUENCE: 768
gcggguggag gagga                                                   15

<210> SEQ ID NO 769
<211> LENGTH: 26
<212> TYPE: RNA
<213> ORGANISM: Homo sapiens

<400> SEQUENCE: 769
ccuucuggag aggcuuugug cggaua                                       26

<210> SEQ ID NO 770
<211> LENGTH: 15
<212> TYPE: RNA
<213> ORGANISM: Homo sapiens

<400> SEQUENCE: 770
ccuucuggag aggcu                                                   15

<210> SEQ ID NO 771
<211> LENGTH: 16
<212> TYPE: RNA
<213> ORGANISM: Homo sapiens

<400> SEQUENCE: 771 cuggggucc cccgac                                                      16

<210> SEQ ID NO 772
<211> LENGTH: 15
<212> TYPE: RNA
<213> ORGANISM: Homo sapiens

<400> SEQUENCE: 772
guguggagcu ggggc                                                      15

<210> SEQ ID NO 773
<211> LENGTH: 25
<212> TYPE: RNA
<213> ORGANISM: Homo sapiens

<400> SEQUENCE: 773
gggacgaggg uuggggaaca ggugg                                           25

<210> SEQ ID NO 774
<211> LENGTH: 15
<212> TYPE: RNA
<213> ORGANISM: Homo sapiens

<400> SEQUENCE: 774
uggggaacag guggu                                                      15

<210> SEQ ID NO 775
<211> LENGTH: 18
<212> TYPE: RNA
<213> ORGANISM: Homo sapiens

<400> SEQUENCE: 775
cuccccgcgc ccccgauc                                                   18

<210> SEQ ID NO 776
<211> LENGTH: 15
<212> TYPE: RNA
<213> ORGANISM: Homo sapiens

<400> SEQUENCE: 776
gcuccccgcg ccccc                                                      15

<210> SEQ ID NO 777
<211> LENGTH: 29
<212> TYPE: RNA
<213> ORGANISM: Homo sapiens

<400> SEQUENCE: 777
gggagccgcg gggaucgccg agggccggu                                       29

<210> SEQ ID NO 778
<211> LENGTH: 15
<212> TYPE: RNA
<213> ORGANISM: Homo sapiens

<400> SEQUENCE: 778
ggcggcggug guggg                                                      15

<210> SEQ ID NO 779
<211> LENGTH: 25
<212> TYPE: RNA
<213> ORGANISM: Homo sapiens

<400> SEQUENCE: 779
ugggcagggg cuuauuguag gaguc                                            25

<210> SEQ ID NO 780
<211> LENGTH: 19
<212> TYPE: RNA
<213> ORGANISM: Homo sapiens

<400> SEQUENCE: 780
ugggcagggg cuuauugua                                                   19

<210> SEQ ID NO 781
<211> LENGTH: 17
<212> TYPE: RNA
<213> ORGANISM: Homo sapiens

<400> SEQUENCE: 781
aggggcuggg cgcgcgc                                                     17

<210> SEQ ID NO 782
<211> LENGTH: 15
<212> TYPE: RNA
<213> ORGANISM: Homo sapiens

<400> SEQUENCE: 782
caggggcugg gcgcg                                                       15

<210> SEQ ID NO 783
<211> LENGTH: 25
<212> TYPE: RNA
<213> ORGANISM: Homo sapiens

<400> SEQUENCE: 783
ugcggggcua gggcuaacag caguc                                            25

<210> SEQ ID NO 784
<211> LENGTH: 15
<212> TYPE: RNA
<213> ORGANISM: Homo sapiens

<400> SEQUENCE: 784
ugcggggcua gggcu                                                       15

<210> SEQ ID NO 785
<211> LENGTH: 24
<212> TYPE: RNA
<213> ORGANISM: Homo sapiens

<400> SEQUENCE: 785
cugcggggac aggccagggc aucu                                             24

<210> SEQ ID NO 786
<211> LENGTH: 20
<212> TYPE: RNA
<213> ORGANISM: Homo sapiens

<400> SEQUENCE: 786
cugcggggac aggccagggc                                                  20

<210> SEQ ID NO 787
<211> LENGTH: 25
<212> TYPE: RNA
<213> ORGANISM: Homo sapiens

```
<400> SEQUENCE: 787
ugcaggcaga agugggcug acagg                                          25

<210> SEQ ID NO 788
<211> LENGTH: 20
<212> TYPE: RNA
<213> ORGANISM: Homo sapiens

<400> SEQUENCE: 788
cugcaggcag aagugggcu                                                20

<210> SEQ ID NO 789
<211> LENGTH: 23
<212> TYPE: RNA
<213> ORGANISM: Homo sapiens

<400> SEQUENCE: 789
aagggaggag gagcggaggg gcc                                           23

<210> SEQ ID NO 790
<211> LENGTH: 15
<212> TYPE: RNA
<213> ORGANISM: Homo sapiens

<400> SEQUENCE: 790
gggaggagga gcgga                                                    15

<210> SEQ ID NO 791
<211> LENGTH: 22
<212> TYPE: RNA
<213> ORGANISM: Homo sapiens

<400> SEQUENCE: 791
gaaaaaggcg ggagaagccc ca                                            22

<210> SEQ ID NO 792
<211> LENGTH: 15
<212> TYPE: RNA
<213> ORGANISM: Homo sapiens

<400> SEQUENCE: 792
gaaaaaggcg ggaga                                                    15

<210> SEQ ID NO 793
<211> LENGTH: 21
<212> TYPE: RNA
<213> ORGANISM: Homo sapiens

<400> SEQUENCE: 793
caacucugau cucuucaucu a                                             21

<210> SEQ ID NO 794
<211> LENGTH: 20
<212> TYPE: RNA
<213> ORGANISM: Homo sapiens

<400> SEQUENCE: 794
ucucuucauc uaccccccag                                               20

<210> SEQ ID NO 795
<211> LENGTH: 22
<212> TYPE: RNA
<213> ORGANISM: Homo sapiens
```

<400> SEQUENCE: 795
acucaaaaug ggggcgcuuu cc                                                22

<210> SEQ ID NO 796
<211> LENGTH: 22
<212> TYPE: RNA
<213> ORGANISM: Homo sapiens

<400> SEQUENCE: 796
acucaaaaug ggggcgcuuu cc                                                22

<210> SEQ ID NO 797
<211> LENGTH: 22
<212> TYPE: RNA
<213> ORGANISM: Homo sapiens

<400> SEQUENCE: 797
cugggcucgg gacgcgcggc uc                                                22

<210> SEQ ID NO 798
<211> LENGTH: 19
<212> TYPE: RNA
<213> ORGANISM: Homo sapiens

<400> SEQUENCE: 798
cugggcucgg gacgcgcgg                                                    19

<210> SEQ ID NO 799
<211> LENGTH: 23
<212> TYPE: RNA
<213> ORGANISM: Homo sapiens

<400> SEQUENCE: 799 ugggggcggag cuuccggagg ccc                                              23

<210> SEQ ID NO 800
<211> LENGTH: 16
<212> TYPE: RNA
<213> ORGANISM: Homo sapiens

<400> SEQUENCE: 800
aucgcuggcc uggucg                                                       16

<210> SEQ ID NO 801
<211> LENGTH: 18
<212> TYPE: RNA
<213> ORGANISM: Homo sapiens

<400> SEQUENCE: 801
gagacugggg uggggccu                                                     18

<210> SEQ ID NO 802
<211> LENGTH: 16
<212> TYPE: RNA
<213> ORGANISM: Homo sapiens

<400> SEQUENCE: 802
agacuggggu ggggcc                                                       16

<210> SEQ ID NO 803
<211> LENGTH: 19
<212> TYPE: RNA

```
<213> ORGANISM: Homo sapiens

<400> SEQUENCE: 803
gcugggcgag gcuggcauc                                                19

<210> SEQ ID NO 804
<211> LENGTH: 17
<212> TYPE: RNA
<213> ORGANISM: Homo sapiens

<400> SEQUENCE: 804
gcugggcgag gcuggca                                                  17

<210> SEQ ID NO 805
<211> LENGTH: 22
<212> TYPE: RNA
<213> ORGANISM: Homo sapiens

<400> SEQUENCE: 805
uggcggagcc cauuccaugc ca                                            22

<210> SEQ ID NO 806
<211> LENGTH: 21
<212> TYPE: RNA
<213> ORGANISM: Homo sapiens

<400> SEQUENCE: 806
cuggcggagc ccauuccaug c                                             21

<210> SEQ ID NO 807
<211> LENGTH: 22
<212> TYPE: RNA
<213> ORGANISM: Homo sapiens

<400> SEQUENCE: 807
accccacucc ugguaccaua gu                                            22

<210> SEQ ID NO 808
<211> LENGTH: 15
<212> TYPE: RNA
<213> ORGANISM: Homo sapiens

<400> SEQUENCE: 808
accccacucc uggua                                                    15

<210> SEQ ID NO 809
<211> LENGTH: 25
<212> TYPE: RNA
<213> ORGANISM: Homo sapiens

<400> SEQUENCE: 809
ugcaggcaga agugggcug acagg                                          25

<210> SEQ ID NO 810
<211> LENGTH: 20
<212> TYPE: RNA
<213> ORGANISM: Homo sapiens

<400> SEQUENCE: 810
cugcaggcag aagugggcu                                                20

<210> SEQ ID NO 811
<211> LENGTH: 23
```

```
<212> TYPE: RNA
<213> ORGANISM: Homo sapiens

<400> SEQUENCE: 811
aagggaggag gagcggaggg gcc                                               23

<210> SEQ ID NO 812
<211> LENGTH: 15
<212> TYPE: RNA
<213> ORGANISM: Homo sapiens

<400> SEQUENCE: 812
gggaggagga gcgga                                                        15

<210> SEQ ID NO 813
<211> LENGTH: 23
<212> TYPE: RNA
<213> ORGANISM: Homo sapiens

<400> SEQUENCE: 813
guccaguuuu cccaggaauc ccu                                               23

<210> SEQ ID NO 814
<211> LENGTH: 22
<212> TYPE: RNA
<213> ORGANISM: Homo sapiens

<400> SEQUENCE: 814
ugagguagua gauuguauag uu                                                22

<210> SEQ ID NO 815
<211> LENGTH: 22
<212> TYPE: RNA
<213> ORGANISM: Homo sapiens

<400> SEQUENCE: 815
ugagaacuga auuccauggg uu                                                22

<210> SEQ ID NO 816
<211> LENGTH: 22
<212> TYPE: RNA
<213> ORGANISM: Homo sapiens

<400> SEQUENCE: 816
agagguagua gguugcauag uu                                                22

<210> SEQ ID NO 817
<211> LENGTH: 22
<212> TYPE: RNA
<213> ORGANISM: Homo sapiens

<400> SEQUENCE: 817
ugagguagua gguuguauag uu                                                22
```